US011970525B2

(12) United States Patent
Siegel et al.

(10) Patent No.: US 11,970,525 B2
(45) Date of Patent: Apr. 30, 2024

(54) TREATMENT OF CANCER USING GFR ALPHA-4 CHIMERIC ANTIGEN RECEPTOR

(71) Applicants: THE TRUSTEES OF THE UNIVERSITY OF PENNSYLVANIA, Philadelphia, PA (US); NOVARTIS AG, Basel (CH); THE SCRIPPS RESEARCH INSTITUTE, La Jolla, CA (US)

(72) Inventors: Donald L. Siegel, Lansdale, PA (US); Michael C. Milone, Cherry Hill, NJ (US); Vijay Bhoj, Philadelphia, PA (US); Christoph Rader, Jupiter, FL (US)

(73) Assignees: The Trustees of the University of Pennsylvania, Philadelphia, PA (US); Novartis AG, Basel (CH); The Scripps Research Institute, La Jolla, CA (US)

(*) Notice: Subject to any disclaimer, the term of this patent is extended or adjusted under 35 U.S.C. 154(b) by 567 days.

(21) Appl. No.: 17/078,903

(22) Filed: Oct. 23, 2020

(65) Prior Publication Data

US 2021/0079059 A1 Mar. 18, 2021

Related U.S. Application Data

(62) Division of application No. 15/503,971, filed as application No. PCT/US2015/045349 on Aug. 14, 2015, now Pat. No. 10,851,149.

(60) Provisional application No. 62/037,383, filed on Aug. 14, 2014.

(51) Int. Cl.

| | |
|---|---|
| ***C07K 14/725*** | (2006.01) |
| ***C07K 14/705*** | (2006.01) |
| ***C07K 14/71*** | (2006.01) |
| ***C07K 16/28*** | (2006.01) |
| ***C07K 16/30*** | (2006.01) |
| *A61K 38/00* | (2006.01) |
| *A61K 39/00* | (2006.01) |

(52) U.S. Cl.

CPC .... *C07K 14/7051* (2013.01); *C07K 14/70517* (2013.01); *C07K 14/70578* (2013.01); *C07K 14/71* (2013.01); *C07K 16/2863* (2013.01); *C07K 16/30* (2013.01); *A61K 38/00* (2013.01); *A61K 2039/505* (2013.01); *A61K 2039/5156* (2013.01); *C07K 2317/24* (2013.01); *C07K 2317/33* (2013.01); *C07K 2317/55* (2013.01); *C07K 2317/622* (2013.01); *C07K 2317/73* (2013.01); *C07K 2319/00* (2013.01); *C07K 2319/03* (2013.01); *C07K 2319/30* (2013.01); *C07K 2319/50* (2013.01); *C07K 2319/70* (2013.01)

(58) Field of Classification Search

None

See application file for complete search history.

(56) References Cited

U.S. PATENT DOCUMENTS

| | | | |
|---|---|---|---|
| 5,199,942 A | 4/1993 | Gillis et al. | |
| 5,350,674 A | 9/1994 | Boenisch et al. | |
| 5,399,346 A | 3/1995 | Anderson et al. | |
| 5,565,332 A | 10/1996 | Hoogenboom et al. | |
| 5,573,905 A | 11/1996 | Lerner et al. | |
| 5,580,859 A | 12/1996 | Felgner et al. | |
| 5,585,362 A | 12/1996 | Wilson et al. | |
| 5,589,466 A | 12/1996 | Felgner et al. | |
| 6,120,766 A | 9/2000 | Hale et al. | |
| 6,326,193 B1 | 12/2001 | Liu et al. | |
| 2004/0101519 A1 | 5/2004 | June et al. | |
| 2006/0034810 A1 | 2/2006 | Riley et al. | |
| 2013/0266551 A1* | 10/2013 | Campana | A61K 39/0011 435/328 |
| 2015/0210769 A1 | 7/2015 | Freeman et al. | |

FOREIGN PATENT DOCUMENTS

| | | |
|---|---|---|
| WO | 0129058 A1 | 4/2001 |
| WO | 0162795 A1 | 8/2001 |
| WO | 0196584 A2 | 12/2001 |
| WO | 2011157275 A1 | 12/2011 |
| WO | 2012079000 A1 | 6/2012 |
| WO | 2012138475 A1 | 10/2012 |
| WO | 2013019615 A2 | 2/2013 |
| WO | 2014190273 A1 | 11/2014 |

OTHER PUBLICATIONS

Lloyd et al.(Protein Engineering, Design & Selection, 22:159-168, 2009).*
Edwards et al.(J Mol Biol, 14;334(1):103-118, 2003).*
Gussow et al. (Methods in Enzymology. 1991; 203: 99-121).*
Muyldermans, Serge (ARB, 82:775-797, 2013).*
Australian Patent Application No. 2015301460—First Examination Report dated Apr. 16, 2020.
European Patent Application No. 15757371.8—Office Action dated Jul. 15, 2019.
European Patent Application No. 15757371.8—Official Communication dated Aug. 6, 2018.
GenBank Accession No. AAA62478.2 dated Mar. 5, 1999.
GenBank Accession No. BAG36664.1 dated Jan. 11, 2008.
GenBank/NCBI Accession No. NF_022139.3, dated May 19, 2006.
International Search Report and Written Opinion dated Nov. 17, 2015—PCT/US2015/045349.
Japanese Patent Application No. 2017-508037—Notice of Reasons for Rejection dated Sep. 9, 2019.
Japanese Patent Application No. 2017-508039—Decision of Rejection dispatched Aug. 24, 2020.

(Continued)

*Primary Examiner* — Brad Duffy

(74) *Attorney, Agent, or Firm* — Saul Ewing LLP; Kathryn Doyle

(57) ABSTRACT

The present invention relates to compositions and methods for treating diseases, disorders or conditions associated with the expression of the Glycosyl-phosphatidylinositol (GPI)-linked GDNF family α-receptor 4 (GFRα4).

20 Claims, 29 Drawing Sheets

Specification includes a Sequence Listing.

(56) References Cited

OTHER PUBLICATIONS

NCBI Reference Sequence NM_000734.3, dated Jan. 31, 2008.
UniProt Accession Q9GZZ7, dated Apr. 23, 2003.
"Human GFR[alpha]- 4/GDNF R-[alpha]- 4 Antibody", Monoclonal Mouse IgG1 Clone #215725; R&D Systems Catalog No. MAB1439.
Airaksinen , et al., "GDNF Family Neurotrophic Factor Signaling: Four Masters, One Servant?", Molecular and Cellular Neuroscience 13, 313-325 (1999).
Barrett , et al., "Chimeric Antigen Receptor Therapy for Cancer", Annu Rev Med. 2014 ; 65: 333-347.
Bird , et al., "Single-Chain Antigen-Binding Proteins", 1988, Science 242(4877):423-426.
Bruggermann , et al., "Designer Mice: The Production of Human Antibody Repertoires in Transgenic Animals.", Year in Immunol., 7:33-40 (1993).
Carpenito , et al., "Control of large, established tumor xenografts with genetically retargeted human T cells containing CD28 and CD137 domains.", 2009, PNAS 106(9):3360-3365.
Carter , et al., "Humanization of an anti-p185HER2 antibody for human cancer therapy.", 1992, Proc Natl Acad Sci USA 89:4285-4289.
Chothia , et al., "Canonical structures for the hypervariable regions of immunoglobulins.", J Mol Biol. Aug. 20, 1987;196(4):901-17. (Abstract).
Clackson , et al., "Making antibody fragments using phage display libraries.", 1991, Nature 352:624-628.
Duchosal , et al., "Immunization of hu-PBL-SCID mice and the rescue of human monoclonal Fab fragments through combinatorial libraries.", 1992, Nature 355:258-262.
Essand , et al., "Genetically engineered T cells for the treatment of cancer.", 2013, J Intern Med 273:166-181.
Fernandez-Quintero , et al., "Antibody humanization—the Influence of the antibody framework on the CDR-H3 loop ensemble in solution.", 2019, Protein Engineering, Design and Selection 32(9):411-422.
Fujiwara , et al., "Impact of scFv structure in chimeric antigen receptor on receptor expression efficiency and antigen recognition properties.", Biochemical and Biophysical Research Communications, https://doi.org/10.1016/j.obrc_2020.03.071—Feb. 25, 2020.
Griffiths , et al., "Human anti-self antibodies with high specificity from phage display libraries.", The EMBO Journal vol. 12, No. 2, pp. 725-734, 1993.
Gussow , et al., "Humanization of Monoclonal Antibodies.", Methods in Enzymology 203:99-121.
Hofer , et al., "Chimeric Rabbit/Human Fab and IgG Specific for Members of the Nogo-66 Receptor Family Selected for Species Cross-Reactivity with an Improved Phage Display Vector", J Immunol Methods. Jan. 10, 2007; 318(1-2): 75-87.
Holliger , et al., "Engineered antibody fragments and the rise of single domains.", 2005, Nature Biotechnology 23(9):1126-36.
Hoogenboom , et al., "By-passing immunization. Human antibodies from synthetic repertoires of germline VH gene segments rearranged in vitro", J. Mol. Biol. 227, 1991, 381-388 (Abstract Only).
Hooijberg , et al., "NFAT-controlled expression of GFP permits visualization and isolation of antigen-stimulated primary human T cells.", 2000, Blood 96(2):459-466.
Huston , "Protein engineering of antibody binding sites: Recovery of specific activity in an anti-digoxin single-chain Fv analogue produced in *Escherichia coli*.", 1988, Proc. Natl. Acad. Sci. USA 85:5879-5883.
Jakobovits , et al., "Analysis of homozygous mutant chimeric mice: Deletion of the immunoglobulin heavy-chain joining region blocks B-cell development and antibody production", Proc. Natl. Acad. Sci. 90, 1993, 2551-2555.
Jakobovits , et al., "Germ-line transmission and expression of a human-derived yeast artificial chromosome", Nature, 362:255-258 (1993).
Jena , et al., "Chimeric Antigen Receptor (CAR)-Specific Monoclonal Antibody to Detect CD19-Specific T Cells in Clinical Trials." 2013, PLoS One 8(3):e57838.
Johnson , et al., "Human antibody engnieering.", 1993, Current Opinion in Structural Biology 3:564-571.
Jones , et al., "Replacing the complementarity-determining regions in a human antibody with those from a mouse", Nature, 321:522-525 (1986).
June , et al., "Engineering lymphocyte subsets: tools, trials and tribulations.", Nat Rev Immunol, 9:, 2009, 704-16.
Lim , et al., "The Principles of Engineering Immune Cells to Treat Cancer", 2017, Cell 168(4):724-740 (Feb. 9, 2017).
Lin , et al., "The tyrosine phosphatase CD148 is excluded from the immunologic synapse and down-regulates prolonged T cell signaling", The Journal of Cell Biology, vol. 162, No. 4, Aug. 18, 2003 673-682.
Lindahal , et al., "Human Glial Cell Line-derived Neurotrophic Factor Receptor alpha-4 Is the Receptor for Persephin and Is Predominantly Expressed in Normal and Malignant Thyroid Medullary Cells.", 2001, J Biol Chem 276(12):9344-9351.
Lindahl , et al., "Human Glial Cell Line-derived Neurotrophic Factor Receptor alpha-4 Is the Receptor for Persephin and Is Predominantly Expressed in Normal and Malignant Thyroid Medullary Cells*", J. Biol. Chem. 2001, 276:9344-9351.
Lonberg , et al., "Human antibodies from transgenic mice.", Int. Rev. Immunol., 13:65-93 (1995).
Mariuzza , et al., "The Structural Basis of Antigen-Antibody Recognition.", 1987, Ann Rev Biophys Biophys Chem 16:139-159.
Marks , et al., "By-passing immunization. Human antibodies from V-gene libraries displayed on phage", J. Mol. Biol. 222:581-597 (1991).
McCafferty , et al., "Phage antibodies: filamentous phage displaying antibody variable domains", Nature, 348:552-553 (1990)93).
Milone , et al., "Chimeric receptors containing CD137 signal transduction domains mediate enhanced survival of T cells and increased antileukemic efficacy in vivo", Mol Ther 17(8):, 2009, 1453-64.
Padlan , "A possible procedure for reducing the immunogenicity of antibody variable domains while preserving their ligand-binding properties", 1991, Molecular Immunology, 28(4/5): 489-498.
Parry , et al., "CD28 and Inducible Costimulatory Protein Src Homology 2 Binding Domains Show Distinct Regulation of Phosphatidylinositol 3-Kinase, Bcl-x L, and IL-2 Expression in Primary Human CD4 T Lymphocytes", J Immunol 2003; 171:166-174.
Plaza Menacho , et al., "RET-Familial Medullary Thyroid Carcinoma Mutants Y791F and S891A Activate a Src/JAK/STAT3 Pathway, Independent of Glial Cell Line-Derived Neurotrophic Factor", Cancer Res 2005; 65(5): 1729-37.
Presta , "Antibody engineering", Current Opinion in Biotechnology 3, 1992, 394-398.
Presta , et al., "Humanization of an antibody directed against IgE", J. Immunol., 151:2623-32 (1993).
Reichmann , et al., "Reshaping Human Antibodies for Therapy", Nature. 332(6162), 1988, 323-327.
Roder , et al., "The EBV-hybridoma technique", Methods Enzymol., 121:140-167 (1986).
Roguska , et al., "A comparison of two murine monoclonal antibodies humanized by CDR-grafting and variable domain resurfacing", Protein Eng., 9(10):895-904 (1996).
Rosenberg , et al., "Use of Tumor-Infiltrating Lymphocytes and Interleukin-2 in the Immunotherapy of Patients with Metastatic Melanoma", New Eng. J. of Med. 319:1676-1680, 1988.
Sela-Culang , et al., "The structural basis of antibody-antigen recognition.", Oct. 2013, Frontiers in Immunology vol. 4, Article 302—pp. 1-13.
Sims , et al., "A humanized CD18 antibody can block function without cell destruction", J. Immunol., 151:2296-2308 (1993).
Skerra , et al., "Assembly of a Functional Immunoglobulin Fv Fragment in *Escherichia coli*", Science, 240, 1988, 1038-1041.
Song , et al., "CD27 costimulation augments the survival and antitumor activity of redirected human T cells in vivo", Blood 119(3), 2012, 696-706.

(56) References Cited

OTHER PUBLICATIONS

Studnicka , et al., “Human-engineered monoclonal antibodies retain full specific binding activity by preserving non-CDR complementarity-modulating residues”, Protein Engineering, 7(6):805-814 (1994).
Vaughan , et al., “Human antibodies with sub-nanomolar affinities isolated from a large non-immunized phage display library”, Nature Biotech., 14:309-14 (1996) (abstract).
Ward , et al., “Binding activities of a repertoire of single immunoglobulin variable domains secreted from *Escherichia coli*”, Nature 341, 1989, 544-546.
Winkler , et al., “Chaning the Antigen Binding Specificity by Single Point Mutations of an Anti-p24 (HIV-1) Antibody.”. 2000, J Immunol 165:4505-4514.
Wu , et al., “Humanization of a murine monoclonal antibody by simultaneous optimization of framework and CDR residues.”, J. Mol. Biol., 294:151-162 (1999).

* cited by examiner

```
        10        20        30        40        50        60        70        80
NRCVDAAEACTADARCQRLRSEYVAQCLGRAAQGGCPRARCRRALRRFFARGPPALTHALLFCPCAGPACAERRRQTFVP

        90       100       110       120       130       140       150       160
SCAFSGPGPAPPSCLEPLNFCERSRVCRPRLLAFQVSCTPAPSAPDGCLLDQGARCLRAYAGLVGTAVTPNYVDNVSARV

       170       180       190       200       210       220       230       240
APWCDCGASGNRREDCEAFRGLFTRNRCLDGAIQAFASGWPPVLLDQLNPQGDPEHSLLQVSIEGRMDPKSCDKTHTCPP

       250       260       270       280       290       300       310       320
CPAPEAEGAPSVFLFPPKPKDTLMISRTPEVTCVVVDVSHEDPEVKFNWYVDGVEVHNAKTKPREEQYNSTYRVVSVLTV

       330       340       350       360       370       380       390       400
LHQDWLNGKEYKCKVSNKALPAPIEKTISKAKGQPREPQVYTLPPSRDELTKNQVSLTCLVKGFYPSDIAVEWESNGQPE

       410       420       430       440       450       460
NNYKATPPVLDSDGSFFLYSKLTVDKSRWQQGNVFSCSVMHEALHNHYTQKSLSLSPGKHHHHHH   (SEQ ID NO:212)
```

Amino acid location:
1 – 222: GFRα 4a fragment
223 – 228: Factor Xa cleavage site
229 – 459: human IgG1 Fc domain fragment
460 – 465: 6 x His

Figure 1

```
        10         20         30         40         50         60         70         80
NRCVDAAEACTADARCQRLRSEYVAQCLGRAAQGGCPRARCRRALRRFFARGPPALTHALLFCPCAGPACAERRRQTFVP

        90        100        110        120        130        140        150        160
SCAFSGPGPAPPSCLEPLNFCERSRVCRCARAAAGPWRGWGRGLSPAHRPPAAQASPPGLSGLVHPSAQRPRRLPAGPGR

       170        180        190        200        210        220        230        240
PLPARLRGPRGVPAGTAVTPNYVDNVSARVAPWCDCGASGNRREDCEAFRGLFTRNRCLDGAIQAFASGWPPVLLDQLNP

       250        260        270        280        290        300        310        320
QGDPEHSLLQVGGGENLYFQGGGGGAGGGGDKTHTCPPCPAPELLGGPSVFLFPPKPKDTLMISRTPEVTCVVVDVSHED

       330        340        350        360        370        380        390        400
PEVKFNWYVDGVEVHNAKTKPREEQYNSTYRVVSVLTVLHQDWLNGKEYKCKVSNKALPAPIEKTISKAKGQPREPQVYT

       410        420        430        440        450        460        470        480
LPPSRDELTKNQVSLTCLVKGFYPSDIAVEWESNGQPENNYKTTPPVLDSDGSFFLYSKLTVDKSRWQQGNVFSCSVMHE

       490
ALHNHYTQKSLSLSPGK
```

(SEQ ID NO:213)

Amino acid location:

1 – 251: GFRα 4b fragment

252 – 270: TEV cleavage site and linker

271 – 497: human IgG1 Fc domain fragment

Figure 2

Figure 6
(SEQ ID NO: 56)
(SEQ ID NO: 57)
P4-6 scFv construct
P4-6 scFv codon optimized

NTD IV
BLI
Day post TT cell injection p410bbz
BLI
Day post TT cell injection

BLI
Day post TT cell injection
NTD
p410bbz

TREATMENT OF CANCER USING GFR ALPHA-4 CHIMERIC ANTIGEN RECEPTOR

CROSS-REFERENCE TO RELATED APPLICATION

This application is a divisional of U.S. patent application Ser. No. 15/503,971 filed Feb. 14, 2017, which is a 35 U.S.C. § 371 national phase application from, and claims priority to, International Application No. PCT/US2015/045349, filed Aug. 14, 2015, which claims priority under 35 U.S.C. § 119(e) to U.S. Provisional Application No. 62/037,383, filed Aug. 14, 2014, all of which applications are incorporated herein by reference in their entireties.

FIELD OF THE INVENTION

The present invention relates generally to the use of immune effector cells (e.g., T cells or NK cells) engineered to express a Chimeric Antigen Receptor (CAR) to treat a disease associated with expression of a glial cell line-derived neurotrophic factor (GDNF) family alpha receptor (also referred to herein as GFRalpha or GFRa).

BACKGROUND OF THE INVENTION

Thyroid cancer is one of the few cancers that has increased in incidence over recent years with the incidence of new cases rising on average 5.5% each year from 2002-2011. It is the most common endocrine cancer with an expected incidence of ~60,000 new cases this year and about 2,000 deaths. Papillary and follicular thyroid carcinomas comprise 80-90% of all thyroid cancers while medullary and anaplastic comprise 5-10% and 1-2% respectively (Pacini et al., Ann Oncol 23 (suppl 7), 2012; Howlader et al., SEER Cancer Statistics Review, 1975-2011, National Cancer Institute). While thyroid cancer has a good prognosis overall, this is not necessarily the case for the medullary and anaplastic forms if they are not treated early before they spread beyond the thyroid gland.

Medullary Thyroid Cancer (also referred to herein as medullary thyroid carcinoma) (MTC) is a type of thyroid cancer that develops from the parafollicular cells of the thyroid that are not related with the main function of the thyroid gland, i.e. production and secretion of thyroid hormone. Rather, these cells are involved in the production of calcitonin, a calcium-regulatory hormone apparently unimportant to humans for maintaining calcium homeostasis. Approximately 25% of MTC is genetic in nature caused by a mutation in the proto-oncogene receptor tyrosine kinase RET (Pacini et al., Clin Oncol, 22(6):475-85, 2010; Roy et al., Oncologist, 18(10):1093-100, 2013). MTC can also coexist with tumors of the parathyroid gland and adrenal gland (pheochromocytoma) in a syndrome known as multiple endocrine neoplasia type 2 (MEN2). Calcitonin doubling time (CDT) can be used as a prognostic marker; e.g. when the CDT is <6 months, 5-year survival is <25%. Surgery and radiation therapy are used for MTC, though risk of recurrence remains high due to the fact that 50% of patients have metastasis to regional lymph nodes at the time of diagnosis. Tyrosine kinase inhibitors such as vandetanib (Caprelsa) and cabozantinib (Cometriq) were approved by the FDA in April, 2011 and November, 2012, respectively, for treatment of late-stage metastatic MTC, though only 10-30% of patients show clear evidence of response.

The GDNF family of neurotrophic factors includes four members: glial cell line-derived neurotrophic factor (GDNF), neurturin, artemin, and persephin (PSPN). GDNF family ligands signal through receptors consisting of a GPI-linked GFRα subunit and the transmembrane receptor tyrosine kinase RET. In order to activate the transmembrane receptor tyrosine kinase RET, each of the GDNF family neurotrophic factors binds preferentially to one of the glycosyl-phosphatidylinositol (GPI)-linked GDNF family α-receptors (GFRα1-4) (Airaksinen et al., Mol Cell Neurosci.; 13(5):313-25, 1999). GDNF signals via GFRα1, neurturin via GFRα2, artemin via GFRα3: however, the mammalian GFRα receptor for persephin (PSPN) and the biological role of GFRα4 (also referred to herein as GFRalpha-4 or GFRα4) has so far remained unclear. In adult humans, GFRα4 is restricted to normal and malignant thyroid medullary cells (Lindahl et al., J. Biol. Chem. 276:9344-51, 2001), although it may be expressed elsewhere during fetal development. GFRα1, GFRα2, and GFRα3 appear to be expressed in non-thyroid tissues of the human body that may include brain.

Thus, the relative specific expressions of GFRα4 on the cell surface of malignant parafollicular cells of the thyroid tissues make it an attractive target for MTC tumor diagnosis and therapy. Although generic anti-GFRα4 antibodies were previously identified (WO2001062795A1—patent application Ser. No. 10/203,639), GFRα4-specific T bodies, particularly the GFRα4-specific scFv as targeting moieties, remain unexplored.

There is a need in the art for the development of therapies to treat medullary thyroid carcinoma. The present invention addresses this need.

SUMMARY OF THE INVENTION

As described below, the present invention includes compositions and methods relating to antibodies and fragments thereof that bind to a thyroid cell antigen specific for medullary thyroid carcinoma (MTC). In one embodiment, the antibodies and fragments thereof bind to Glycosyl-phosphatidylinositol (GPI)-linked GDNF family α-receptor 4 (GFRα4) cell-surface receptor. Additional disclosed herein are chimeric antigen receptors that comprise an antigen binding domain that binds to GFRα4 (also referred to herein as GFRalpha-4 or GFRα4).

In an aspect, the invention features an isolated nucleic acid molecule encoding a chimeric antigen receptor (CAR), wherein the CAR comprises an antigen binding domain, a transmembrane domain, and an intracellular signaling domain, and wherein the antigen binding domain binds to a Glycosyl-phosphatidylinositol (GPI)-linked GDNF family α-receptor 4 (GFRα4) cell-surface receptor. In an embodiment, the GFRα4 cell-surface receptor is chosen from GFRα4a or GFRα4b.

In an embodiment, the encoded antigen binding domain comprises an antibody or an antigen-binding fragment thereof. In an embodiment, the antigen-binding fragment is a Fab, a single-chain variable fragment (scFv) or a single-domain antibody. In an embodiment, the antibody or antigen-binding fragment is a human antibody or a humanized antibody or a fragment thereof.

In an embodiment, the encoded antigen binding domain comprises a heavy chain complementary determining region 1 (HC CDR1), a heavy chain complementary determining region 2 (HC CDR2), and a heavy chain complementary determining region 3 (HC CDR3) of any heavy chain binding domain amino acid sequence listed in Table 2. In an embodiment, the encoded antigen binding domain further comprises a light chain complementary determining region 1 (LC CDR1), a light chain complementary determining region 2 (LC CDR2), and a light chain complementary determining region 3 (LC CDR3) of any light chain binding domain amino acid sequence listed in Table 2.

In an embodiment, the isolated nucleic acid molecule encodes a CAR comprising: (i) the amino acid sequence of any light chain variable region listed in Table 2; (ii) an amino acid sequence having at least one, two or three modifications but not more than 20 or 10 modifications of the amino acid sequence of any of the light chain variable regions provided in Table 2; or (iii) an amino acid sequence with 95-99% identity to the amino acid sequence of any of the light chain variable regions provided in Table 2.

In an embodiment, the isolated nucleic acid molecule encodes a CAR comprising: (i) the amino acid sequence of any heavy chain variable region listed in Table 2; (ii) an amino acid sequence having at least one, two or three modifications but not more than 20 or 10 modifications of the amino acid sequence of any of the heavy chain variable regions provided in Table 2: or (iii) an amino acid sequence with 95-99% identity to the amino acid sequence of any of the heavy chain variable regions provided in Table 2.

In an embodiment, the isolated nucleic acid molecule encodes a CAR comprising the amino acid sequence of any light chain variable region listed in Table 2, and the amino acid sequence of any heavy chain variable region listed Table 2.

In an embodiment, the encoded antigen binding domain (e.g., the scFv) comprises: (i) the amino acid sequence selected from SEQ ID NO: 59, SEQ ID NO: 79, SEQ ID NO: 41; SEQ ID NO: 49; SEQ ID NO: 61; or SEQ ID NO: 69; (ii) an amino acid sequence having at least one, two or three modifications but not more than 30, 20 or 10 modifications to SEQ ID NO: 59, SEQ ID NO: 79, SEQ ID NO: 41; SEQ ID NO: 49; SEQ ID NO: 61; or SEQ ID NO: 69; or (iii) an amino acid sequence with 95-99% identity to SEQ ID NO: 59, SEQ ID NO: 79, SEQ ID NO: 41; SEQ ID NO: 49; SEQ ID NO: 61; or SEQ ID NO: 69.

In an embodiment, the nucleic acid sequence of the antigen binding domain (e.g., the scFv) comprises a nucleotide sequence selected from SEQ ID NOs:56, 57, 76, or 77, or a sequence with 95-99% identity thereof.

In an embodiment, the encoded CAR includes a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154.

In an embodiment, the encoded transmembrane domain comprises (i) the amino acid sequence of SEQ ID NO: 6, or an amino acid sequence comprises at least one, two or three modifications but not more than 5 modifications of the amino acid sequence of SEQ ID NO:6, or a sequence with 95-99% identity to the amino acid sequence of SEQ ID NO:6; or (ii) the nucleic acid sequence encoding the transmembrane domain comprises the nucleotide sequence of SEQ ID NO:17, or a sequence with 95-99% identity thereof.

In an embodiment, the encoded antigen binding domain is connected to the transmembrane domain by a hinge region. In an embodiment, the encoded hinge region comprises (i) the amino acid sequence of SEQ ID NO:2, or a sequence with 95-99% identity thereof; or (ii) the nucleic acid sequence encoding the hinge region comprises the nucleotide sequence of SEQ ID NO: 13, or a sequence with 95-99% identity thereof.

In an embodiment, the encoded intracellular signaling domain comprises a functional signaling domain from a protein selected from the group consisting of an MHC class I molecule, a TNF receptor protein, an Immunoglobulin-like protein, a cytokine receptor, an integrin, a signaling lymphocytic activation molecule (SLAM protein), an activating NK cell receptor, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

In an embodiment, the encoded intracellular signaling domain comprises the amino acid sequence of SEQ ID NO:7, or an amino acid sequence having at least one, two or three modifications but not more than 10 or 5 modifications of the amino acid sequence of SEQ ID NO:7, or an amino acid sequence with 95-99% identity to the amino acid sequence of SEQ ID NO:7. In an embodiment, the nucleic acid sequence encoding the intracellular signaling domain comprises the nucleotide sequence of SEQ ID NO:18, or a sequence with 95-99% identity thereof. In an embodiment, the encoded intracellular signaling domain comprises a functional signaling domain of 4-1BB and/or a functional signaling domain of CD3 zeta.

In an embodiment, the encoded intracellular signaling domain comprises the amino acid sequence of SEQ ID NO: 7 and/or the sequence of SEQ ID NO:9 or SEQ ID NO:10; or an amino acid sequence having at least one, two or three modifications but not more than 10 or 5 modifications of the amino acid sequence of SEQ ID NO:7 and/or the amino acid sequence of SEQ ID NO:9 or SEQ ID NO:10; or a sequence with 95-99% identity to the amino acid sequence of SEQ ID NO:7 and/or the amino acid sequence of SEQ ID NO:9 or SEQ ID NO:10. In an embodiment, the encoded intracellular signaling domain comprises the amino acid sequence of SEQ ID NO:7 and the amino acid sequence of SEQ ID NO:9 or SEQ ID NO:10, wherein the amino acid sequences comprising the intracellular signaling domains are expressed as a single polypeptide chain. In an embodiment, the nucleic acid sequence encoding the intracellular signaling domain comprises the nucleotide sequence of SEQ ID NO:18, or a sequence with 95-99% identity thereof, and/or the nucleotide sequence of SEQ ID NO:20 or SEQ ID NO:21, or a sequence with 95-99% identity thereof.

In an embodiment, the nucleic acid molecule further comprises a leader sequence which encodes the amino acid sequence of SEQ ID NO:1.

In an embodiment, the nucleic acid molecule encodes a CAR comprising: (i) the amino acid sequence of any of SEQ ID NOs:85, 86, 90, 92, 94, 96, 98, 100, 102, or 104; (ii) an amino acid sequence having at least one, two or three modifications but not more than 30, 20 or 10 modifications to any of SEQ ID NOs: 85, 86, 90, 92, 94, 96, 98, 100, 102, or 104; or (iii) an amino acid sequence with 95-99% identity to any of SEQ ID NOs: 85, 86, 90, 92, 94, 96, 98, 100, 102, or 104.

In an embodiment, the nucleic acid molecule comprises the nucleotide sequence of any of SEQ ID NOs: 89, 91, 93, 95, 97, 99, 101, or 103, or a nucleotide sequence with 95-99% identity to any of SEQ ID NOs: 89, 91, 93, 95, 97, 99, 101, or 103.

In another aspect, the invention features an isolated chimeric antigen receptor (CAR) polypeptide comprising an antigen binding domain, a transmembrane domain, an intracellular signaling domain, wherein the antigen binding domain binds to a Glycosyl-phosphatidylinositol (GPI)-linked GDNF family α-receptor 4 (GFRα4) cell-surface receptor. In an embodiment, the GFRα4 cell-surface receptor is chosen from GFRα4a or GFRα4b. In an embodiment, the antigen binding domain is an antibody or an antigen-binding fragment thereof. In an embodiment, the antigen-binding fragment is chosen from a Fab, a scFv, or a single-domain antibody. In an embodiment, the antibody or antigen-binding fragment is a human antibody or a humanized antibody or a fragment thereof.

In an embodiment, the antigen binding domain comprises a heavy chain complementary determining region 1 (HC CDR1), a heavy chain complementary determining region 2 (HC CDR2), and a heavy chain complementary determining region 3 (HC CDR3) of any heavy chain binding domain amino acid sequence listed in Table 2. In an embodiment, the antigen binding domain further comprises a light chain complementary determining region 1 (LC CDR1), a light chain complementary determining region 2 (LC CDR2), and a light chain complementary determining region 3 (LC CDR3) of any heavy chain binding domain amino acid sequence listed in Table 2.

In an embodiment, the isolated CAR polypeptide encodes a CAR comprising:
(i) the amino acid sequence of any light chain variable region listed in Table 2;
(ii) an amino acid sequence having at least one, two or three modifications but not more than 20 or 10 modifications of the amino acid sequence of any of the light chain variable regions provided in Table 2; or (iii) an amino acid sequence with 95-99% identity to the amino acid sequence of any of the light chain variable regions provided in Table 2.

In an embodiment, the isolated CAR polypeptide encodes a CAR comprising:
(i) the amino acid sequence of any heavy chain variable region listed in Table 2;
(ii) an amino acid sequence having at least one, two or three modifications but not more than 20 or 10 modifications of the amino acid sequence of any of the heavy chain variable regions provided in Table 2: or (iii) an amino acid sequence with 95-99% identity to the amino acid sequence of any of the heavy chain variable regions provided in Table 2. In an embodiment, the isolated CAR polypeptide encodes a CAR comprising the amino acid sequence of any light chain variable region listed in Table 2, and the amino acid sequence of any light chain variable region listed Table 2.

In an embodiment, the antigen binding domain comprises: (i) the amino acid sequence selected from SEQ ID NO: 59, SEQ ID NO: 79, SEQ ID NO: 41; SEQ ID NO: 49; SEQ ID NO: 61; or SEQ ID NO: 69; (ii) an amino acid sequence having at least one, two or three modifications but not more than 30, 20 or 10 modifications to SEQ ID NO: 59, SEQ ID NO: 79, SEQ ID NO: 41; SEQ ID NO: 49; SEQ ID NO: 61; or SEQ ID NO: 69; or (iii) an amino acid sequence with 95-99% identity to SEQ ID NO: 59, SEQ ID NO: 79, SEQ ID NO: 41; SEQ ID NO: 49; SEQ ID NO: 61; or SEQ ID NO: 69.

In an embodiment, the transmembrane domain comprises a transmembrane domain from a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In an embodiment, the transmembrane domain comprises: (i) the amino acid sequence of SEQ ID NO: 6, (ii) an amino acid sequence comprising at least one, two or three modifications but not more than 5 modifications of the amino acid sequence of SEQ ID NO:6, or (iii) a sequence with 95-99% identity to the amino acid sequence of SEQ ID NO:6.

In an embodiment, the antigen binding domain is connected to the transmembrane domain by a hinge region. In an embodiment, the hinge region comprises the amino acid sequence of SEQ ID NO:2, or a sequence with 95-99% identity thereof.

In an embodiment, the intracellular signaling domain comprises a functional signaling domain from a protein selected from the group consisting of an MHC class I molecule, a TNF receptor protein, an Immunoglobulin-like protein, a cytokine receptor, an integrin, a signaling lymphocytic activation molecule (SLAM protein), an activating NK cell receptor, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

In an embodiment, the intracellular signaling domain comprises the amino acid sequence of SEQ ID NO:7, or an amino acid sequence having at least one, two or three modifications but not more than 10 or 5 modifications of the amino acid sequence of SEQ ID NO:7, or a sequence with 95-99% identity to the amino acid sequence of SEQ ID NO:7. In an embodiment, the intracellular signaling domain comprises a functional signaling domain of 4-1BB and/or a functional signaling domain of CD3 zeta. In an embodiment, the intracellular signaling domain comprises the amino acid sequence of SEQ ID NO: 7 and/or the sequence of SEQ ID NO:9 or SEQ ID NO:10; or an amino acid sequence having at least one, two or three modifications but not more than 10 or 5 modifications of the amino acid sequence of SEQ ID NO:7 and/or the amino acid sequence of SEQ ID NO:9 or SEQ ID NO:10; or a sequence with 95-99% identity to the amino acid sequence of SEQ ID NO:7 and/or the amino acid sequence of SEQ ID NO:9 or SEQ ID NO:10. In an embodiment, the intracellular signaling domain comprises the sequence of SEQ ID NO:7 and the sequence of SEQ ID NO:9 or SEQ ID NO:10, wherein the sequences comprising the intracellular signaling domain are expressed as a single polypeptide chain.

In an embodiment, the isolated CAR polypeptide further comprises a leader sequence which comprises the amino acid sequence of SEQ ID NO:1.

In an embodiment, the isolated CAR polypeptide comprises: (i) the amino acid sequence of any of SEQ ID NOs: 85, 86, 90, 92, 94, 96, 98, 100, 102, or 104; (ii) an amino acid sequence having at least one, two or three modifications but not more than 30, 20 or 10 modifications to any of SEQ ID NOs: 85, 86, 90, 92, 94, 96, 98, 100, 102, or 104; or (iii) an amino acid sequence with 95-99% identity to any of SEQ ID NOs: 85, 86, 90, 92, 94, 96, 98, 100, 102, or 104.

In an embodiment, the isolated CAR polypeptide is encoded by the nucleic acid molecule described herein.

In an aspect, the invention features a vector comprising a nucleic acid molecule comprising the nucleic acid molecule of the invention, or a nucleic acid molecule encoding the CAR polypeptide of the invention, wherein the vector is selected from the group consisting of a DNA vector, an RNA vector, an mRNA, a plasmid, a lentivirus vector, an adenoviral vector, and a retrovirus vector.

In an embodiment, the vector further comprises an EF-1 promoter comprising the sequence of SEQ ID NO: 11.

In an aspect, the invention provides a cell comprising the nucleic acid molecule encoding a CAR of the invention, the CAR polypeptide of the invention, or the vector comprising a nucleic acid molecule comprising the nucleic acid molecule of the invention, or a nucleic acid molecule encoding the CAR polypeptide of the invention. In an embodiment, the cell is selected from the group consisting of a T cell, a natural killer (NK) cell, a cytotoxic T lymphocyte (CTL), and a regulatory T cell.

In an aspect, the invention provides a method of making a cell, e.g., an immune effector cell, comprising transducing an immune effector cell with a vector comprising a nucleic acid molecule comprising the nucleic acid molecule of the invention, or a nucleic acid molecule encoding the CAR polypeptide of the invention.

In an aspect, the invention provides a method of generating a population of RNA-engineered cells, comprising introducing an in vitro transcribed RNA or synthetic RNA into a cell, where the RNA comprises a nucleic acid encoding a CAR polypeptide of the invention.

In another aspect, the invention provides method for stimulating a T cell-mediated immune response to a thyroid cell population in a mammal, the method comprising administering to a mammal an effective amount of a cell, e.g., a population of immune effector cells, comprising the CAR nucleic acid molecule of the invention, or the CAR polypeptide of the invention.

In another aspect, the invention provides a method of providing an anti-tumor immunity in a mammal, comprising administering to the mammal an effective amount of a cell, e.g., a population of immune effector cells, comprising the CAR nucleic acid of the invention, or the CAR polypeptide of the invention.

In another aspect, the invention provides a method of treating a mammal having a disease associated with expression of a GFRα4 cell-surface receptor. The method comprises administering to the mammal an effective amount of a cell, e.g., a population of immune effector cells, comprising the CAR nucleic acid molecule of the invention, or the CAR polypeptide of the invention. In one embodiment, the GFRα4 cell-surface receptor is chosen from GFRα4a or GFRα4b.

In one embodiment, the cell, e.g., the population of immune effector cells, is administered in combination with one or more of: (i) an agent that increases the efficacy of the cell comprising the CAR nucleic acid or the CAR polypeptide; (ii) an agent that ameliorates one or more side effects associated with administration of the cell comprising the CAR nucleic acid or the CAR polypeptide; or (iii) an agent that treats the disease associated with a GFRα4 cell surface receptor.

In one embodiment, the method further comprises administering an antitumor vaccine. In one embodiment, the cell and the antitumor vaccine are co-administered to the mammal or administered separately.

In one embodiment, the disease associated with expression of a GFRα4 cell-surface receptor is a cancer. In one embodiment, the cancer is medullary thyroid carcinoma (MTC) or a metastasis resulting from MTC.

In any of the methods of the invention, the mammal is a human.

In embodiments, the invention provides the isolated nucleic acid molecule of the invention, the isolated CAR polypeptide molecule of the invention, the vector of the invention, or the cell of the invention for use as a medicament.

In embodiments, the invention provides the isolated CAR nucleic acid molecule of the invention, the isolated CAR polypeptide molecule of the invention, the vector of the invention, or the cell of the invention for use in the treatment of a disease associated with expression of a thyroid cell antigen, e.g., GFRα4.

In embodiments, the invention provides the cell, e.g., a population of immune effector cells, of the invention, further expressing an inhibitory molecule that comprises a first polypeptide that comprises at least a portion of an inhibitory molecule, associated with a second polypeptide that comprises a positive signal from an intracellular signaling domain. In one embodiment, the first polypeptide comprises at least a portion of PD-1 and the second polypeptide comprising a costimulatory domain and a primary signaling domain.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting. Headings, sub-headings or numbered or lettered elements, e.g., (a), (b), (i) etc, are presented merely for ease of reading. The use of headings or numbered or lettered elements in this document does not require the steps or elements be performed in alphabetical order or that the steps or elements are necessarily discrete from one another. Other features, objects, and advantages of the invention will be apparent from the description and drawings, and from the claims.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1 displays the amino acid sequence of the fragment of GFRα4 isoform a (SEQ ID NO: 212) expressed as a human Fc bivalent fusion protein used for selection of anti-GFRα4 antibodies and for stimulating CAR-transduced Jurkat reporter cells. The fragment comprises Asn24-Ser245 of the native full-length protein (UniProt accession Q9GZZ7-2), a Factor Xa cleavage site, a human IgG1 Fc domain fragment, and a 6×His sequence for purification.

FIG. 2 displays the amino acid sequence of the fragment of GFRα4 isoform b (SEQ ID NO: 213) expressed as a human Fc bivalent fusion protein used for selection of anti-GFRα4 antibodies and for stimulating CAR-transduced Jurkat reporter cells. The fragment comprises Asn24-Va1274 of the native full-length protein (UniProt accession Q9GZZ7-1), a tobacco etch virus (TEV) protease cleavage site and linker, and a human IgG1 Fc domain fragment.

FIG. 4, comprising FIG. 4A shows the nucleotide sequence alignments of P4-6 scFv (SEQ ID NO: 56) with P4-6 $V_H$ (SEQ ID NO: 40) and P4-6 $V_L$ (SEQ ID NO: 48) and FIG. 4B shows the amino acid alignments of P4-6 scFv (SEQ ID NO: 58) with P4-6 $V_H$ (SEQ ID NO: 41) and P4-6 $V_L$ (SEQ ID NO: 49).

FIG. 5, comprising FIG. 5A shows the nucleotide sequence alignments P4-10 scFv (SEQ ID NO: 76) with P4-10 $V_H$ (SEQ ID NO: 60) and P4-10 $V_L$ (SEQ ID NO: 68) and FIG. 5B shows the amino acid alignments P4-10 scFv (SEQ ID NO: 78) with P4-10 $V_H$ (SEQ ID NO: 61) and P4-10 $V_L$ (SEQ ID NO: 69).

FIG. 18, comprising

FIG. 19, comprising

FIG. 20, comprising

FIG. 21, comprising

FIG. 22, comprising FIG. 22A shows the mean with standard error of the mean of tumor volume over time. Arrows indicate times of T cell injection. FIG. 22B shows tumor size of individual mice at day 38 for each group (P=0.0008 by Mann-Whitney test). Mean and standard error of the mean are indicated for each group.

FIG. 23, comprising FIG. 23A shows the mean with standard error of the mean of tumor volume over time. The arrow indicates time of T cell injection. FIG. 23B shows tumor size of individual mice at day 27 for each group (P=0.0093 by Mann-Whitney test).

FIG. 24, comprising FIG. 24C shows the mean with standard deviation of BLI over time.

DETAILED DESCRIPTION

Definitions

Figure 3:
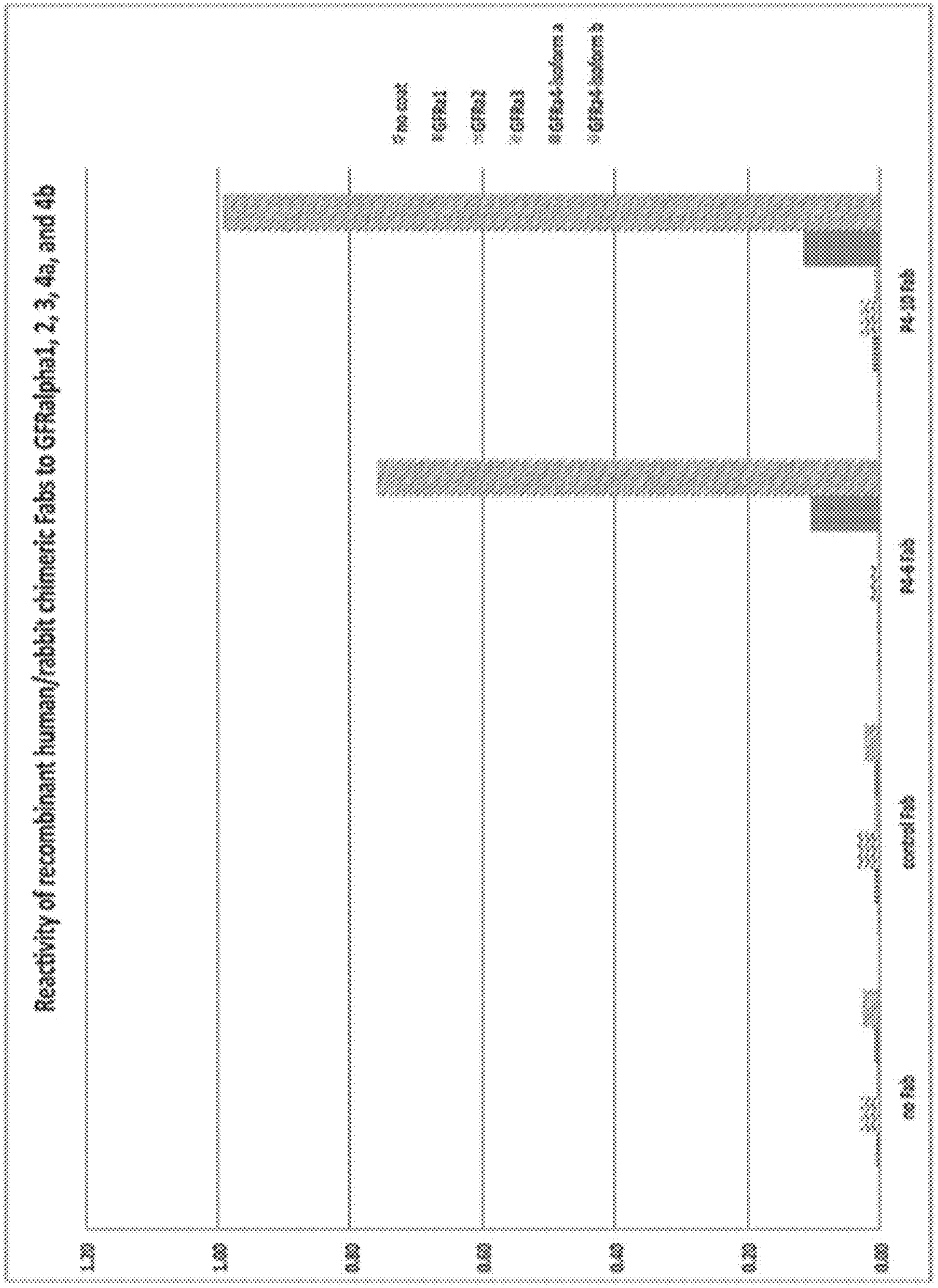
FIG. 3 is a graph depicting the reactivity of recombinant human/rabbit chimeric Fabs against the GFRα1, GFRα2, GFRα3, GFRα4a and GFRα4b, and demonstrates that 2 antibodies to GFRα4, P4-6 and P4-10, isolated by antibody phage display, crossreact with GFRα4a and GFRα4b, but do not show binding to GFRα1, GFRα2, and GFRα3 above the background binding seen with only secondary antibody reagent (HRP-anti human Fab, "no Fab") or binding with an irrelevant recombinant human/rabbit chimeric lambda light chain-containing Fab ("control Fab").

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "Chimeric Antigen Receptor" or alternatively a "CAR" refers to a recombinant polypeptide construct comprising at least an extracellular antigen binding domain, a transmembrane domain and a cytoplasmic signaling domain (also referred to herein as "an intracellular signaling domain") comprising a functional signaling domain derived from a stimulatory molecule as defined below. In some embodiments, the domains in the CAR polypeptide construct are in the same polypeptide chain, e.g., comprise a chimeric fusion protein. In some embodiments, the domains in the CAR polypeptide construct are not contiguous with each other, e.g., are in different polypeptide chains, e.g., as provided in an RCAR as described herein.

In one aspect, the stimulatory molecule is the zeta chain associated with the T cell receptor complex. In one aspect, the cytoplasmic signaling domain further comprises one or more functional signaling domains derived from at least one costimulatory molecule as defined below. In one aspect, the costimulatory molecule is chosen from 4-1BB (i.e., CD137), CD27, ICOS, and/or CD28. In one aspect, the CAR comprises a chimeric fusion protein comprising an extracellular antigen recognition domain, a transmembrane domain and an intracellular signaling domain comprising a functional signaling domain derived from a stimulatory molecule. In one aspect, the CAR comprises a chimeric fusion protein comprising an extracellular antigen recognition domain, a transmembrane domain and an intracellular signaling domain comprising a functional signaling domain derived from a co-stimulatory molecule and a functional signaling domain derived from a stimulatory molecule. In one aspect, the CAR comprises a chimeric fusion protein comprising an extracellular antigen recognition domain, a transmembrane domain and an intracellular signaling domain comprising two functional signaling domains derived from one or more co-stimulatory molecule(s) and a functional signaling domain derived from a stimulatory molecule. In one aspect, the CAR comprises a chimeric fusion protein comprising an extracellular antigen recognition domain, a transmembrane domain and an intracellular signaling domain comprising at least two functional signaling domains derived from one or more co-stimulatory molecule(s) and a functional signaling domain derived from a stimulatory molecule. In one aspect the CAR comprises an optional leader sequence at the amino-terminus (N-ter) of the CAR fusion protein. In one aspect, the CAR further comprises a leader sequence at the N-terminus of the extracellular antigen recognition domain, wherein the leader sequence is optionally cleaved from the antigen recognition domain (e.g., aa scFv) during cellular processing and localization of the CAR to the cellular membrane.

A CAR that comprises an antigen binding domain (e.g., a scFv, a single domain antibody, or TCR (e.g., a TCR alpha binding domain or TCR beta binding domain)) that specifically binds a specific tumor marker X, wherein X can be a tumor marker as described herein, is also referred to as XCAR. For example, a CAR that comprises an antigen binding domain that specifically binds GFRα receptor, e.g., GFRα4, is referred to as GFRα CAR, e.g., GFRα4 CAR The CAR can be expressed in any cell, e.g., an immune effector cell as described herein (e.g., a T cell or an NK cell).

The term "signaling domain" refers to the functional portion of a protein which acts by transmitting information within the cell to regulate cellular activity via defined signaling pathways by generating second messengers or functioning as effectors by responding to such messengers.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies can be typically tetramers of immunoglobulin molecules. Tetramers may be naturally occurring or reconstructed from single chain antibodies or antibody fragments. Antibodies also include dimers that may be naturally occurring or constructed from single chain antibodies or antibody fragments. The antibodies in the present invention may exist in a variety of forms including, for example, polyclonal antibodies, monoclonal antibodies, Fv, Fab and $F(ab')_2$, as well as single chain antibodies (scFv), humanized antibodies, and human antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, NY; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', $F(ab')_2$, and Fv fragments, linear antibodies, scFv antibodies, single-domain antibodies such as sdAb (either VL or VH), such as camelid antibodies (Riechmann, 1999, Journal of Immunological Methods 231:25-38), camelid VHH domains, composed of either a $V_L$ or a $V_H$ domain which exhibit sufficient affinity for the target, and multispecific antibodies formed from antibody fragments such as a bivalent fragment comprising two Fab fragments linked by a disulfide brudge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (Fn3)(see U.S. Pat. No. 6,703,199, which describes fibronectin polypeptide minibodies). The antibody fragment also includes a human antibody or a humanized antibody or a portion of a human antibody or a humanized antibody.

The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The term "complementarity determining region" or "CDR," as used herein, refers to the sequences of amino acids within antibody variable regions which confer antigen specificity and binding affinity. For example, in general, there are three CDRs in each heavy chain variable region (e.g., HCDR1, HCDR2, and HCDR3) and three CDRs in each light chain variable region (LCDR1, LCDR2, and LCDR3). The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273, 927-948 ("Chothia" numbering scheme), or a combination thereof. Under the Kabat numbering scheme, in some embodiments, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under the Chothia numbering scheme, in some embodiments, the CDR amino acids in the VH are numbered 26-32 (HCDR1), 52-56 (HCDR2), and 95-102 (HCDR3); and the CDR amino acid residues in the VL are numbered 26-32 (LCDR1), 50-52 (LCDR2), and 91-96 (LCDR3). In a combined Kabat and Chothia numbering scheme, in some embodiments, the CDRs correspond to the amino acid residues that are part of a Kabat CDR, a Chothia CDR, or both. For instance, in some embodiments, the CDRs correspond to amino acid residues 26-35 (HCDR1), 50-65 (HCDR2), and 95-102 (HCDR3) in a VH, e.g., a mammalian VH, e.g., a human VH; and amino acid residues 24-34 (LCDR1), 50-56 (LCDR2), and 89-97 (LCDR3) in a VL, e.g., a mammalian VL, e.g., a human VL.

The portion of the CAR composition of the invention comprising an antibody or antibody fragment thereof may exist in a variety of forms where the antigen binding domain is expressed as part of a contiguous polypeptide chain including, for example, a single domain antibody fragment (sdAb), a single chain antibody (scFv) and a humanized or human antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, NY; Houston et al., 1988, Proc. Natl. Acad. Sci. USA 85:5879-5883; Bird et al., 1988, Science 242:423-426). In one aspect, the antigen binding domain of a CAR composition of the invention comprises an antibody fragment. In a further aspect, the CAR comprises an antibody fragment that comprises a scFv.

As used herein, the term "binding domain" or "antibody molecule" (also referred to herein as "anti-target (e.g., GFRα4) binding domain") refers to a protein, e.g., an immunoglobulin chain or fragment thereof, comprising at least one immunoglobulin variable domain sequence. The term "binding domain" or "antibody molecule" encompasses antibodies and antibody fragments. In an embodiment, an antibody molecule is a multispecific antibody molecule, e.g., it comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" or "recombinant antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a fluid with other biological components.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "apheresis" as used herein refers to the art-recognized extracorporeal process by which the blood of a donor or patient is removed from the donor or patient and passed through an apparatus that separates out selected particular constituent(s) and returns the remainder to the circulation of the donor or patient, e.g., by retransfusion. Thus, in the context of "an apheresis sample" refers to a sample obtained using apheresis.

The term "combination" refers to either a fixed combination in one dosage unit form, or a combined administration where a compound of the present invention and a combination partner (e.g. another drug as explained below, also referred to as "therapeutic agent" or "co-agent") may be administered independently at the same time or separately within time intervals, especially where these time intervals allow that the combination partners show a cooperative, e.g. synergistic effect. The single components may be packaged in a kit or separately. One or both of the components (e.g., powders or liquids) may be reconstituted or diluted to a desired dose prior to administration.

The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g. a compound of the present invention and a combination partner, are both administered to a patient simultaneously in the form of a single entity or dosage. The term "non-fixed combination" means that the active ingredients, e.g. a compound of the present invention and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. The terms "tumor" and "cancer" are used interchangeably herein, e.g., both terms encompass solid and liquid, e.g., diffuse or circulating, tumors. As used herein, the term "cancer" or "tumor" includes premalignant, as well as malignant cancers and tumors. In certain embodiments, the cancer is medullary thyroid carcinoma.

"Derived from" as that term is used herein, indicates a relationship between a first and a second molecule. It generally refers to structural similarity between the first molecule and a second molecule and does not connotate or include a process or source limitation on a first molecule that is derived from a second molecule. For example, in the case of an intracellular signaling domain that is derived from a CD3zeta molecule, the intracellular signaling domain retains sufficient CD3zeta structure such that is has the required function, namely, the ability to generate a signal under the appropriate conditions. It does not connotate or include a limitation to a particular process of producing the intracellular signaling domain, e.g., it does not mean that, to provide the intracellular signaling domain, one must start with a CD3zeta sequence and delete unwanted sequence, or impose mutations, to arrive at the intracellular signaling domain.

The phrase "disease associated with expression of GFRα" as used herein includes but is not limited to, a disease associated with expression of GFRα or condition associated with cells which express GFRα including, e.g., a proliferative disease such as a cancer or malignancy or a precancerous condition; or a noncancer related indication associated with cells which express GFRα. In one aspect, a cancer associated with expression of GFRα is medullary thyroid cancer (MTC). Further disease associated with expression of GFRα expression include, but are not limited to, e.g., atypical and/or non-classical cancers, malignancies, precancerous conditions or proliferative diseases associated with expression of GFRα. Non-cancer related indications associated with expression of GFRα may also be included.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for the ability to bind GFRα4 using the functional assays described herein.

The term "stimulation," refers to a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

The term "stimulatory molecule," refers to a molecule expressed by a T cell that provides the primary cytoplasmic signaling sequence(s) that regulate primary activation of the TCR complex in a stimulatory way for at least some aspect of the T cell signaling pathway. In one aspect, the primary signal is initiated by, for instance, binding of a TCR/CD3 complex with an MEW molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or ITAM. Examples of an ITAM containing primary cytoplasmic signaling sequence that is of particular use in the invention includes, but is not limited to, those derived from TCR zeta, FcR gamma, FcR beta, CD3 gamma, CD3 delta, CD3 epsilon, CD5, CD22, CD79a, CD79b, CD278 (also known as "ICOS"), FcεRI, CD66d, DAP10, and DAP12. In a specific CAR of the invention, the intracellular signaling domain in any one or more CARS of the invention comprises an intracellular signaling sequence, e.g., a primary signaling sequence of CD3-zeta. In a specific CAR of the invention, the primary signaling sequence of CD3-zeta is the sequence provided as SEQ ID NO:9, or the equivalent residues from a non-human species, e.g., mouse, rodent, monkey, ape and the like. In a specific CAR of the invention, the primary signaling sequence of CD3-zeta is the sequence as provided in SEQ ID NO:10, or the equivalent residues from a non-human species, e.g., mouse, rodent, monkey, ape and the like.

The term "antigen presenting cell" or "APC" refers to an immune system cell such as an accessory cell (e.g., a B-cell, a dendritic cell, and the like) that displays a foreign antigen complexed with major histocompatibility complexes (MHC's) on its surface. T-cells may recognize these complexes using their T-cell receptors (TCRs). APCs process antigens and present them to T-cells.

An "intracellular signaling domain," as the term is used herein, refers to an intracellular portion of a molecule. The intracellular signaling domain generates a signal that promotes an immune effector function of the CAR containing cell, e.g., a CART cell. Examples of immune effector function, e.g., in a CART cell, include cytolytic activity and helper activity, including the secretion of cytokines. In embodiments, the intracellular signal domain transduces the effector function signal and directs the cell to perform a specialized function. While the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation. For example, in the case of a CART, a primary intracellular signaling domain can comprise a cytoplasmic sequence of a T cell receptor, and a costimulatory intracellular signaling domain can comprise cytoplasmic sequence from co-receptor or costimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, FcR gamma, FcR beta, CD3 gamma, CD3 delta, CD3 epsilon, CD5, CD22, CD79a, CD79b, CD278 (also known as "ICOS"), FcεRI, CD66d, DAP10, and DAP12.

The term "zeta" or alternatively "zeta chain", "CD3-zeta" or "TCR-zeta" is defined as the protein provided as GenBan Acc. No. BAG36664.1, or the equivalent residues from a non-human species, e.g., mouse, rodent, monkey, ape and the like, and a "zeta stimulatory domain" or alternatively a "CD3-zeta stimulatory domain" or a "TCR-zeta stimulatory domain" is defined as the amino acid residues from the cytoplasmic domain of the zeta chain that are sufficient to functionally transmit an initial signal necessary for T cell activation. In one aspect the cytoplasmic domain of zeta comprises residues 52 through 164 of GenBank Acc. No. BAG36664.1 or the equivalent residues from a non-human species, e.g., mouse, rodent, monkey, ape and the like, that are functional orthologs thereof. In one aspect, the "zeta stimulatory domain" or a "CD3-zeta stimulatory domain" is the sequence provided as SEQ ID NO:9. In one aspect, the "zeta stimulatory domain" or a "CD3-zeta stimulatory domain" is the sequence provided as SEQ ID NO:10.

The term "costimulatory molecule" refers to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are required for an efficient immune response. Costimulatory molecules include, but are not limited to an a MEW class I molecule, a TNF receptor protein, an Immunoglobulin-like protein, a cytokine receptor, an integrin, a signaling lymphocytic activation molecule (SLAM protein), an activating NK cell receptor, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

A costimulatory intracellular signaling domain refers to the intracellular portion of a costimulatory molecule.

The intracellular signaling domain can comprise the entire intracellular portion, or the entire native intracellular signaling domain, of the molecule from which it is derived, or a functional fragment thereof.

The term "4-1BB" refers to a member of the TNFR superfamily with an amino acid sequence provided as GenBank Acc. No. AAA62478.2, or the equivalent residues from a non-human species, e.g., mouse, rodent, monkey, ape and the like; and a "4-1BB costimulatory domain" is defined as amino acid residues 214-255 of GenBank Acc. No. AAA62478.2, or the equivalent residues from a non-human species, e.g., mouse, rodent, monkey, ape and the like. In one aspect, the "4-1BB costimulatory domain" is the sequence provided as SEQ ID NO:7 or the equivalent residues from a non-human species, e.g., mouse, rodent, monkey, ape and the like.

"Co-stimulatory ligand", as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

"Immune effector cell," as that term is used herein, refers to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NKT) cells, mast cells, and myeloic-derived phagocytes.

"Immune effector function or immune effector response," as that term is used herein, refers to function or response, e.g., of an immune effector cell, that enhances or promotes an immune attack of a target cell. E.g., an immune effector function or response refers a property of a T or NK cell that promotes killing or the inhibition of growth or proliferation, of a target cell. In the case of a T cell, primary stimulation and co-stimulation are examples of immune effector function or response.

The term "dysregulated" when used in the context of the level of expression or activity of GFRα4 refers to the level of expression or activity that is different from the expression level or activity of GFRα4 in an otherwise identical healthy animal, organism, tissue, cell or component thereof. The term "dysregulated" also refers to the altered regulation of the level of expression and activity of GFRα4 compared to the regulation in an otherwise identical healthy animal, organism, tissue, cell or component thereof.

The term "effector function" refers to a specialized function of a cell. Effector function of a T cell, for example, may be cytolytic activity or helper activity including the secretion of cytokines.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

The term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include but are not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

As used herein, the terms "GDNF family receptor alpha 4" and "GFRα4", are used interchangeably, and include variants, isoforms and species homologs of human GFRα4. Isoforms of GFRα4 include GFRα4a and GFRα4b. Accordingly, human antibodies of this disclosure may, in certain cases, cross-react with GFRα4 from species other than human. In certain embodiments, the antibodies may be completely specific for one or more human GFRα4 proteins and may not exhibit species or other types of non-human cross-reactivity. The complete amino acid sequence of an exemplary human GFRα4 has Genbank/NCBI accession number: NM 022139.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The term "nucleic acid" or "polynucleotide" as used herein "refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. As used herein, polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

The term "flexible polypeptide linker" or "linker" as used in the context of a scFv refers to a peptide linker that consists of amino acids such as glycine and/or serine residues used alone or in combination, to link variable heavy and variable light chain regions together. In one embodiment, the flexible polypeptide linker is a Gly/Ser linker and comprises the amino acid sequence $(Gly-Gly-Gly-Ser)_n$ (SEQ ID NO: 38), where n is a positive integer equal to or greater than 1. For example, n=1, n=2, n=3. n=4, n=5 and n=6, n=7, n=8, n=9 and n=10 In one embodiment, the flexible polypeptide linkers include, but are not limited to, $(Gly_4\ Ser)_4$ (SEQ ID NO:27) or $(Gly_4\ Ser)_3$ (SEQ ID NO:28). In another embodiment, the linkers include multiple repeats of $(Gly_2Ser)$, (GlySer) or $(Gly_3Ser)$ (SEQ ID NO:29). Also included within the scope of the invention are linkers described in WO2012/138475, incorporated herein by reference.

As used herein, a 5' cap (also termed an RNA cap, an RNA 7-methylguanosine cap or an RNA $m^7G$ cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "in vitro transcribed RNA" refers to RNA, preferably mRNA, that has been synthesized in vitro. Generally, the in vitro transcribed RNA is generated from an in vitro transcription vector. The in vitro transcription vector comprises a template that is used to generate the in vitro transcribed RNA.

As used herein, a "poly(A)" is a series of adenosines attached by polyadenylation to the mRNA. In the preferred embodiment of a construct for transient expression, the polyA is between 50 and 5000 (SEQ ID NO: 30), preferably greater than 64, more preferably greater than 100, most preferably greater than 300 or 400. poly(A) sequences can be modified chemically or enzymatically to modulate mRNA functionality such as localization, stability or efficiency of translation.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

As used herein, the terms "treat", "treatment" and "treating" refer to the reduction or amelioration of the progression, severity and/or duration of a proliferative disorder, or the amelioration of one or more symptoms (preferably, one or more discernible symptoms) of a proliferative disorder resulting from the administration of one or more therapies (e.g., one or more therapeutic agents such as a CAR of the invention). In specific embodiments, the terms "treat", "treatment" and "treating" refer to the amelioration of at least one measurable physical parameter of a proliferative disorder, such as growth of a tumor, not necessarily discernible by the patient. In other embodiments the terms "treat", "treatment" and "treating"-refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell. An example of a "cell surface receptor" is human GFRα4.

"Single chain antibodies" refer to antibodies formed by recombinant DNA techniques in which immunoglobulin heavy and light chain fragments are linked to each other using an engineered span of amino acids to recapitulate the Fv region of an antibody as a single polypeptide. Various methods of generating single chain antibodies are known, including those described in U.S. Pat. No. 4,694,778; Bird (1988) Science 242:423-442; Huston et al. (1988) Proc. Natl. Acad. Sci. USA 85:5879-5883; Ward et al. (1989) Nature 334:54454; Skerra et al. (1988) Science 242:1038-1041.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "prophylaxis" as used herein means the prevention of or protective treatment for a disease or disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

By the term "specifically binds," as used herein, is meant an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell and/or on a tumor cell.

A "stimulatory ligand," as used herein, means a ligand that when present on an antigen presenting cell (e.g., an aAPC, a dendritic cell, a B-cell, and the like) or a tumor cell, can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MEW Class I molecule loaded with a peptide, an anti-CD3 antibody, a superagonist anti-CD28 antibody, and a superagonist anti-CD2 antibody.

"Regulatable chimeric antigen receptor (RCAR)," as used herein, refers to a set of polypeptides, typically two in the simplest embodiments, which when in an immune effector cell, provides the cell with specificity for a target cell, typically a cancer cell, and with regulatable intracellular signal generation. In some embodiments, an RCAR comprises at least an extracellular antigen binding domain, a transmembrane and a cytoplasmic signaling domain (also referred to herein as "an intracellular signaling domain") comprising a functional signaling domain derived from a stimulatory molecule and/or costimulatory molecule as defined herein in the context of a CAR molecule. In some embodiments, the set of polypeptides in the RCAR are not contiguous with each other, e.g., are in different polypeptide chains. In some embodiments, the RCAR includes a dimerization switch that, upon the presence of a dimerization molecule, can couple the polypeptides to one another, e.g., can couple an antigen binding domain to an intracellular signaling domain. In some embodiments, the RCAR is expressed in a cell (e.g., an immune effector cell) as described herein, e.g., an RCAR-expressing cell (also referred to herein as "RCARX cell"). In an embodiment the RCARX cell is a T cell, and is referred to as a RCART cell. In an embodiment the RCARX cell is an NK cell, and is referred to as a RCARN cell. The RCAR can provide the RCAR-expressing cell with specificity for a target cell, typically a cancer cell, and with regulatable intracellular signal generation or proliferation, which can optimize an immune effector property of the RCAR-expressing cell. In embodiments, an RCAR cell relies at least in part, on an antigen binding domain to provide specificity to a target cell that comprises the antigen bound by the antigen binding domain.

"Membrane anchor" or "membrane tethering domain", as that term is used herein, refers to a polypeptide or moiety, e.g., a myristoyl group, sufficient to anchor an extracellular or intracellular domain to the plasma membrane.

"Switch domain," as that term is used herein, e.g., when referring to an RCAR, refers to an entity, typically a polypeptide-based entity, that, in the presence of a dimerization molecule, associates with another switch domain. The association results in a functional coupling of a first entity linked to, e.g., fused to, a first switch domain, and a second entity linked to, e.g., fused to, a second switch domain. A first and second switch domain are collectively referred to as a dimerization switch. In embodiments, the first and second switch domains are the same as one another, e.g., they are polypeptides having the same primary amino acid sequence, and are referred to collectively as a homodimerization switch. In embodiments, the first and second switch domains are different from one another, e.g., they are polypeptides having different primary amino acid sequences, and are referred to collectively as a heterodimerization switch. In embodiments, the switch is intracellular. In embodiments, the switch is extracellular. In embodiments, the switch domain is a polypeptide-based entity, e.g., FKBP or FRB-based, and the dimerization molecule is small molecule, e.g., a rapalogue. In embodiments, the switch domain is a polypeptide-based entity, e.g., an scFv that binds a myc peptide, and the dimerization molecule is a polypeptide, a fragment thereof, or a multimer of a polypeptide, e.g., a myc ligand or multimers of a myc ligand that bind to one or more myc scFvs. In embodiments, the switch domain is a polypeptide-based entity, e.g., myc receptor, and the dimerization molecule is an antibody or fragments thereof, e.g., myc antibody.

"Dimerization molecule," as that term is used herein, e.g., when referring to an RCAR, refers to a molecule that promotes the association of a first switch domain with a second switch domain. In embodiments, the dimerization molecule does not naturally occur in the subject, or does not occur in concentrations that would result in significant dimerization. In embodiments, the dimerization molecule is a small molecule, e.g., rapamycin or a rapalogue, e.g, RAD001.

The term "bioequivalent" refers to an amount of an agent other than the reference compound (e.g., RAD001), required to produce an effect equivalent to the effect produced by the reference dose or reference amount of the reference compound (e.g., RAD001). In an embodiment the effect is the level of mTOR inhibition, e.g., as measured by P70 S6 kinase inhibition, e.g., as evaluated in an in vivo or in vitro assay, e.g., as measured by an assay described herein, e.g., the Boulay assay, or measurement of phosphorylated S6 levels by western blot. In an embodiment, the effect is alteration of the ratio of PD-1 positive/PD-1 negative T cells, as measured by cell sorting. In an embodiment a bioequivalent amount or dose of an mTOR inhibitor is the amount or dose that achieves the same level of P70 S6 kinase inhibition as does the reference dose or reference amount of a reference compound. In an embodiment, a bioequivalent amount or dose of an mTOR inhibitor is the amount or dose that achieves the same level of alteration in the ratio of PD-1 positive/PD-1 negative T cells as does the reference dose or reference amount of a reference compound.

The term "low, immune enhancing, dose" when used in conjuction with an mTOR inhibitor, e.g., an allosteric mTOR inhibitor, e.g., RAD001 or rapamycin, or a catalytic mTOR inhibitor, refers to a dose of mTOR inhibitor that partially, but not fully, inhibits mTOR activity, e.g., as measured by the inhibition of P70 S6 kinase activity. Methods for evaluating mTOR activity, e.g., by inhibition of P70 S6 kinase, are discussed herein. The dose is insufficient to result in complete immune suppression but is sufficient to enhance the immune response. In an embodiment, the low, immune enhancing, dose of mTOR inhibitor results in a decrease in the number of PD-1 positive T cells and/or an increase in the number of PD-1 negative T cells, or an increase in the ratio of PD-1 negative T cells/PD-1 positive T cells. In an embodiment, the low, immune enhancing, dose of mTOR inhibitor results in an increase in the number of naive T cells. In an embodiment, the low, immune enhancing, dose of mTOR inhibitor results in one or more of the following:

an increase in the expression of one or more of the following markers: $CD62L^{high}$, $CD127^{high}$, $CD27^{+}$, and BCL2, e.g., on memory T cells, e.g., memory T cell precursors;

a decrease in the expression of KLRG1, e.g., on memory T cells, e.g., memory T cell precursors; and an increase in the number of memory T cell precursors, e.g., cells with any one or combination of the following characteristics: increased $CD62L^{high}$, increased $CD127^{high}$, increased $CD27^{+}$, decreased KLRG1, and increased BCL2;

wherein any of the changes described above occurs, e.g., at least transiently, e.g., as compared to a non-treated subject.

"Refractory" as used herein refers to a disease, e.g., cancer, that does not respond to a treatment. In embodiments, a refractory cancer can be resistant to a treatment before or at the beginning of the treatment. In other embodiments, the refractory cancer can become resistant during a treatment. A refractory cancer is also called a resistant cancer.

"Relapsed" or a "relapse" as used herein refers to the reappearance of a disease (e.g., cancer) or the signs and symptoms of a disease such as cancer after a period of improvement or responsiveness, e.g., after prior treatment of a therapy, e.g., cancer therapy. For example, the period of responsiveness may involve the level of cancer cells falling below a certain threshold, e.g., below 20%, 1%, 10%, 5%, 4%, 3%, 2%, or 1%. The reappearance may involve the level of cancer cells rising above a certain threshold, e.g., above 20%, 1%, 10%, 5%, 4%, 3%, 2%, or 1%.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

In one aspect, the present invention provides isolated antibodies that bind specifically to GFRα4. In certain embodiments, the antibodies of the invention comprise particular structural features such as CDR regions comprising particular amino acid sequences. The invention also provides methods of making such antibodies.

In one embodiment, a peptide containing amino acids of human GFRα4 was used to screen a phage display library to isolate single-chain variable fragment (scFv) against GFRα4. In a particular embodiment, the isolated scFv targets GFRα4 isoform "a" (SEQ ID NOs: 212). In another embodiment, the isolated scFv targets GFRα4 isoform "b" (SEQ ID NOs: 213).

In one embodiment, the scFv antibodies of the invention can be used for diagnosing the presence of GFRα4 in a biological sample. In one embodiment, the scFv antibodies of the invention can be used for diagnosing the presence of GFRα4 in a tumor cell.

In one embodiment, the scFv antibodies of the invention can be used for therapy against a disease, disorder or condition associated with normal or dysregulated expression of GFRα4. The level of expression of GFRα4 on the surface of medullary cancer cells may be considered the same as on normal thyroid C-cells. That said, should a different cell type (e.g. adrenal cells, neuronal cells) exhibit a pathology that is the result of dysregulated GFRα4, the present invention may be useful in targeting these cells to relieve the pathology.

In one embodiment, the scFv antibodies of the invention can be used for cancer therapy against cancers associated with normal or dysregulated expression of GFRα4. In another embodiment, the scFv antibodies of the invention can be used for cancer therapy against thyroid cancers. In yet another embodiment, the scFv antibodies of the invention can be used for cancer therapy against Medullary Thyroid Cancer (MTC).

The present invention relates generally to the treatment of a patient having a cancer associated with the expression of GFRα4, or at risk of having a cancer associated with the expression of GFRα4, using cellular infusion. In one embodiment, lymphocyte infusion, preferably autologous lymphocyte infusion is used in the treatment. In another embodiment, the cancer associated with expression of GFRα4 is a thyroid cancer. In yet another embodiment, the cancer associated with expression of GFRα4 is MTC.

In one embodiment, peripheral blood mononuclear cells (PBMCs) are collected from a patient in need of treatment and T cells therefrom are engineered and expanded using the methods described herein and then infused back into the patient. In another embodiment, autologous or heterologous NK cells or NK cell lines are engineered and expanded using the methods described herein and then infused back into the patient. The invention should not be limited to a particular cell or cell type. Rather, any cell or cell type can be engineered and expanded using the methods described herein and then infused back into the patient.

In one embodiment, the scFv antibodies of the invention can be cloned into vectors that allow expression in cis with cellular cytotoxins. The combination of the scFv antibodies with cellular cytotoxins can be used for transarterial infusion into patients in need thereof. The antibodies of the invention can be incorporated into an immunoconjugate, a chimeric antigen receptor (CAR), a pharmaceutical composition, and the like. In one embodiment, the immunoconjugates of the invention may be therapeutic agents, for example, cytotoxins or radioactive isotopes. Accordingly, the present invention provides compositions and methods for treating, among other diseases, cancer or any malignancy or autoimmune disease in which expression of GFRα4 is expressed on the cell surface.

The present invention also relates generally to the use of immune effector cells, e.g., T cells or NK cells, engineered to express a Chimeric Antigen Receptor (CAR). CARs combine an antigen binding domain of a specific antibody with an intracellular signaling molecule. For example, the intracellular signaling molecule can include but is not limited to CD3-zeta chain, 4-1BB and CD28 signaling modules and combinations thereof. Preferably, the antigen binding domain binds to GFRα4, e.g., GFRα4a or GFRα4b. In some instances, the antigen binding domain comprises an anti-GFRα4 antibody, e.g., an antibody fragment or scFv, described herein. Accordingly, the invention provides a GFRα4-CAR engineered into an immune effector cell, e.g., a T cell or a NK cell, and methods of their use for adoptive therapy.

In one embodiment, the invention includes autologous cells that are transfected with a vector comprising a GFRα4 CAR transgene. Preferably, the vector is a retroviral vector. More preferably, the vector is a self-inactivating lentiviral vector as described elsewhere herein.

In one embodiment, the GFRα 4-CAR T cells of the invention can be generated by introducing a lentiviral vector comprising a GFRα4 binding domain, a glycine-serine linker and transmembrane domain, and a CD3zeta signaling domain into the cells. In another embodiment, the GFRα 4-CAR T cells of the invention can be generated by introducing a lentiviral vector comprising a GFRα4 binding domain, CD8a hinge and transmembrane domain, and a CD3zeta signaling domain into the cells. In some instances, the vector further comprises the signaling domain of 4-1BB, CD28, or a combination of both. This is because the present invention is partly based on the discovery that CAR-mediated T-cell responses can be further enhanced with the addition of costimulatory domains. For example, inclusion of the CD28 signaling domain significantly increased antitumor activity and in vivo persistence of CAR T cells compared to an otherwise identical CAR T cell not engineered to express CD28.

In one embodiment, the CAR-modified T cells of the invention are expected to replicate in vivo resulting in long-term persistence that can lead to sustained tumor control.

Antibodies

Anti-GFRα4 Antibodies

The antibodies of the invention are characterized by particular functional features or properties of the antibodies. For example, the antibodies specifically bind to human GFRα4. Preferably, the antibodies of the invention bind to GFRα4 with high affinity. Preferably, the antibodies of the invention specifically recognize naturally expressed hGFRα4 protein on a cell and do not cross-react to other surface molecules.

In one embodiment, the antibodies of the invention are human antibodies designated as P4-6 or P4-10. The $V_H$ amino acid sequences of P4-6 or P4-10 are shown in SEQ ID NOs: 41 and 61, respectively (Table 2). The $V_L$ amino acid sequences of P4-6 or P4-10 are shown in SEQ ID NOs: 49 and 69, respectively (Table 2).

In one embodiment, the antibody contains heavy chain variable regions (Table 2) having CDRs 1, 2 and 3 consisting of the amino acid sequences set forth in SEQ ID NOs: in any of the following (a) to (b):

(a) SEQ ID NOs: 43, 45 and 47 (P4-6), (b) SEQ ID NOs: 63, 65 and 67 (P4-10).

In one embodiment, the antibody contains light chain variable regions (Table 2) having CDRs 1, 2 and 3 consisting of the amino acid sequences set forth in SEQ ID NOs: in any of the following (c) to (d):

(c) SEQ ID NOs: 51, 53 and 55 (P4-6), (d) SEQ ID NOs: 71, 73 and 75 (P4-10).

Given that each of these antibodies binds to GFRα4, the $V_H$ and $V_L$ sequences can be "mixed and matched" to create other anti-GFRα4 binding molecules of the invention. GFRα4 binding of such "mixed and matched" antibodies can be tested using the binding assays described herein, in the art, for example, in the Examples section (e.g., ELISAs). Preferably, when VH and VL chains are mixed and matched, a VH sequence from a particular VH/VL pairing is replaced with a structurally similar VH sequence. Likewise, preferably a VL sequence from a particular VH/VL pairing is replaced with a structurally similar VL sequence. It will be readily apparent to the ordinary skilled artisan that novel VH and VL sequences can be created by substituting one or more VH and/or VL CDR region sequences with structurally similar sequences from the CDR sequences disclosed herein.

In one embodiment, the invention includes antibodies that comprise the heavy chain and light chain (CDR1s, CDR2s, and CDR3s) of P4-6 and P4-10, or combinations thereof. In one embodiment, the antibody comprise the heavy chain and/or light chain (CDR1s, CDR2s, and CDR3s) of P4-6 and P4-10 or a sequence substantially identical thereto (e.g., a CDR sequence having 5, 4, 3, 2, or 1 modifications, e.g., conservative modifications).

In one embodiment, the antibody of the invention comprises heavy and light chain variable regions comprising amino acid sequences that are identical to the amino acid sequences of the preferred antibodies described herein, and wherein the antibodies retain the desired functional properties of the anti-GFRα4 antibodies of the invention.

For example, the invention includes an isolated antibody, or antigen binding portion thereof, comprising a heavy chain variable region and a light chain variable region, wherein: (a) the heavy chain variable region comprises an amino acid sequence that is at least 80%, 85%, 90%, 95% or 99% identical to an amino acid sequence selected from the group consisting of SEQ ID NOs: 41 and 61, (b) the light chain variable region comprises an amino acid sequence that is at least 80%, 85%, 90%, 95% or 99% identical to an amino acid sequence selected from the group consisting of SEQ ID NOs: 49 and 69.

In certain embodiments, an antibody of the invention comprises a heavy chain variable region comprising CDR1 and CDR2 sequences and a light chain variable region comprising CDR1 and CDR2 sequences, wherein one or more of these CDR sequences comprise specified amino acid sequences based on the preferred antibodies described herein (e.g., P4-6 and P4-10), or conservative modifications thereof, and wherein the antibodies retain the desired functional properties of the anti-GFRα4 antibodies of the invention. Accordingly, the invention provides an isolated antibody (e.g., scFv), or antigen binding portion thereof, comprising a heavy chain variable region comprising CDR1, CDR2, and CDR3 sequences and a light chain variable region comprising CDR1, CDR2, and CDR3 sequences, wherein: (a) the heavy chain variable region CDR3 sequence comprises an amino acid sequence selected from the group consisting of amino acid sequences of SEQ ID NOs: 43, 45, 47, 63, 65 and 67, and one or more conservative modifications thereof (e.g., 30, 20, 10 or less conservative modifications); (b) the light chain variable region CDR3 sequence comprises an amino acid sequence selected from the group consisting of amino acid sequence of SEQ ID NOs: 51, 53, 55, 71, 73 and 75, and one or more conservative modifications thereof e.g., 30, 20, 10 or less conservative modifications).

In another embodiment, the invention includes antibodies that bind to the same epitope on human GFRα4 as any of the GFRα4 antibodies of the invention (i.e., antibodies that have the ability to cross-compete for binding to GFRα4 with any of the antibodies of the invention). In a preferred embodiment, the reference antibody for cross-competition studies can be one of the antibodies described herein (e.g., P4-6 and P4-10). For example, Biacore analysis, ELISA assays or flow cytometry may be used to demonstrate cross-competition with the antibodies of the current invention. The ability of a test antibody to inhibit the binding of, for example, P4-6 and P4-10, to human GFRα4 demonstrates that the test antibody can compete with P4-6 and P4-10 for binding to human GFRα4 and thus is considered to bind to the same epitope on human GFRα4 as P4-6 and P4-10.

An antibody of the invention is prepared using an antibody having one or more of the VH and/or VL sequences disclosed herein as a starting material to engineer a modified antibody, which modified antibody may have altered properties as compared with the starting antibody. An antibody can be engineered by modifying one or more amino acids within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

Table 1 below provides the corresponding SEQ ID NOs for the amino acid and nucleotide sequences for the GFRα4 scFV.

TABLE 1

Summary of the sequence identifiers for anti-GFRα4 scFV

| SEQ ID NO: # | Description |
|---|---|
| SEQ ID NO: 40 | P4-6; heavy chain (nucleic acid) |
| SEQ ID NO: 41 | P4-6; heavy chain (amino acid) |
| SEQ ID NO: 42 | P4-6; CDR1 heavy chain (nucleic acid) |
| SEQ ID NO: 43 | P4-6; CDR1 heavy chain (amino acid) |
| SEQ ID NO: 44 | P4-6; CDR2 heavy chain (nucleic acid) |
| SEQ ID NO: 45 | P4-6; CDR2 heavy chain (amino acid) |
| SEQ ID NO: 46 | P4-6; CDR3 heavy chain (nucleic acid) |
| SEQ ID NO: 47 | P4-6; CDR3 heavy chain (amino acid) |
| SEQ ID NO: 48 | P4-6; light chain (nucleic acid) |
| SEQ ID NO: 49 | P4-6; light chain (amino acid) |
| SEQ ID NO: 50 | P4-6; CDR1 light chain (nucleic acid) |
| SEQ ID NO: 51 | P4-6; CDR1 light chain (amino acid) |
| SEQ ID NO: 52 | P4-6; CDR2 light chain (nucleic acid) |

TABLE 1-continued

Summary of the sequence identifiers for anti-GFRα4 scFV

| SEQ ID NO: # | Description |
|---|---|
| SEQ ID NO: 53 | P4-6; CDR2 light chain (amino acid) |
| SEQ ID NO: 54 | P4-6; CDR3 light chain (nucleic acid) |
| SEQ ID NO: 55 | P4-6; CDR3 light chain (amino acid) |
| SEQ ID NO: 60 | P4-10; heavy chain (nucleic acid) |
| SEQ ID NO: 61 | P4-10; heavy chain (amino acid) |
| SEQ ID NO: 62 | P4-10; CDR1 heavy chain (nucleic acid) |
| SEQ ID NO: 63 | P4-10; CDR1 heavy chain (amino acid) |
| SEQ ID NO: 64 | P4-10; CDR2 heavy chain (nucleic acid) |
| SEQ ID NO: 65 | P4-10; CDR2 heavy chain (amino acid) |
| SEQ ID NO: 66 | P4-10; CDR3 heavy chain (nucleic acid) |
| SEQ ID NO: 67 | P4-10; CDR3 heavy chain (amino acid) |
| SEQ ID NO: 68 | P4-10; light chain (nucleic acid) |
| SEQ ID NO: 69 | P4-10; light chain (amino acid) |
| SEQ ID NO: 70 | P4-10; CDR1 light chain (nucleic acid) |
| SEQ ID NO: 71 | P4-10; CDR1 light chain (amino acid) |
| SEQ ID NO: 72 | P4-10; CDR2 light chain (nucleic acid) |
| SEQ ID NO: 73 | P4-10; CDR2 light chain (amino acid) |
| SEQ ID NO: 74 | P4-10; CDR3 light chain (nucleic acid) |
| SEQ ID NO: 75 | P4-10; CDR3 light chain (amino acid) |

The amino acid and nucleotide sequences for the CDRs, heavy chain variable region (VH), light chain variable region (VL), and scFv sequences are provided in the table below. "NT" designates the nucleotide sequences, and "AA" designates the amino acid sequences.

The nucleotide and amino acid sequences of P4-6 and P4-10 single chain antibody (scFv) constructs derived from the $V_H$ and $V_L$ sequences of recombinant human/rabbit Fabs. The scFv constructs position the heavy and light chain variable regions in the order $V_H$-linker-$V_L$ with the linker comprising nucleotides to encode a 15-amino acid glycine/serine rich peptide. Each nucleotide sequence begins and ends with a restriction site (BamH1 and Nhe1, respectively) for subsequent cloning into CAR plasmids. The nucleotide sequences depicted here are before human codon optimization. They include: Nucleotide sequence of P4-6 scFv construct (SEQ ID NO: 56 and 57); Amino acid sequence of P4-6 scFv construct (SEQ ID NO: 58 and 59); Nucleotide sequence of P4-10 scFv construct (SEQ ID NO: 76 and 77); and Amino acid sequence of P4-10 scFv construct with and without restriction sites (SEQ ID NO: 78 and 79, respectively).

TABLE 2

GFRα4 Antibody Sequences

| Name/ Description | SEQ ID NO: | Sequence |
|---|---|---|
| P4-6 VH-NT | 40 | GAGCAGCTGAAGGAGTCCGGGGGAGGTCTCTTCAAGCCAACGG ATACCCTGACACTCACCTGCACAGTCTCTGGATTCTCCCTCAGT TACTATGGAGTGAACTGGGTCCGCCAGGCTCCAGGGAACGGGC TGGAATGGATCGGAACCATTGGTGGTAGTGGTGACACATACTA CGCGAGCTGGGCGAAGAGCCGATCCACCATCATCAGAAACACC AACGAGAACACGGTGACTCTGAAAATGACCAGTCTGACAGCCG CGGACACGGCCACCTATTTCTGTGTGAGATATGCTAATATTGGT TATGAGTACTTTAACGTCTGGGGTCCAGGCACCCTGGTCACCGT CTCTTCA |
| P4-6 VH-AA | 41 | EQLKESGGGLFKPTDTLTLTCTVSGFSLSYYGVNWVRQAPGNGLE WIGTIGGSGDTYYASWAKSRSTIIRNTNENTVTLKMTSLTAADTAT YFCVRYANIGYEYFNVWGPGTLVTVSS |
| P4-6 HC CDR1-NT | 42 | GGATTCTCCCTCAGTTACTATGGA |
| P4-6 HC CDR1-AA | 43 | GFSLSYYG |

TABLE 2-continued

GFRα4 Antibody Sequences

| Name/ Description | SEQ ID NO: | Sequence |
|---|---|---|
| P4-6 HC CDR2-NT | 44 | ATTGGTGGTAGTGGTGACACA |
| P4-6 HC CDR2-AA | 45 | IGGSGDT |
| P4-6 HC CDR3-NT | 46 | GTGAGATATGCTAATATTGGTTATGAGTACTTTAACGTC |
| P4-6 HC CDR3-AA | 47 | VRYANIGYEYFNV |
| P4-6 VL-NT | 48 | CAGTTTGTGCTGACTCAGTCGCCCTCTGCATCTGCTGCCCTGGG<br>AGCCTCGGCCAAGCTCACCTGCACCCTGAGCAGTGCCCACAAG<br>ACCTACACCATTGACTGGTATCAGCAGCAGAAAGGGAAGGCCC<br>CTCGCTACCTGATACAAGTTAAGAGTGATGGAACCTACACCAA<br>GGCGACCGGGGTCCCTGATCGCTTCTCGGGCTCCAGCTCTGGGG<br>CTGACCGCTACCTGATCATCCCCAGCGTCCAGGCTGATGACGAA<br>GCCGACTACTATTGTGGTACAGATTATACCGGTGGGTATGTGTT<br>CGGCGGGGGGACCCAGCTGACCGTCACA |
| P4-6 VL-AA | 49 | QFVLTQSPSASAALGASAKLTCTLSSAHKTYTIDWYQQQKGKAPR<br>YLIQVKSDGTYTKATGVPDRFSGSSSGADRYLIIPSVQADDEADYY<br>CGTDYTGGYVFGGGTQLTVT |
| P4-6 LC CDR1-NT | 50 | AGTGCCCACAAGACCTACACC |
| P4-6 LC CDR1-AA | 51 | SAHKTYT |
| P4-6 LC CDR2-NT | 52 | GTTAAGAGTGATGGAACCTAC |
| P4-6 LC CDR2-AA | 53 | VKSDGTY |
| P4-6 LC CDR3-NT | 54 | GGTACAGATTATACCGGTGGGTATGTG |
| P4-6 LC CDR3-AA | 55 | GTDYTGGYV |
| P4-6 scFv-NT (with restric- tion sites, rabbit codon usage) | 56 | GGATCCGAGCAGCTGAAGGAGTCCGGGGGAGGTCTCTTCAAGC<br>CAACGGATACCCTGACACTCACCTGCACAGTCTCTGGATTCTCC<br>CTCAGTTACTATGGAGTGAACTGGGTCCGCCAGGCTCCAGGGA<br>ACGGGCTGGAATGGATCGGAACCATTGGTGGTAGTGGTGACAC<br>ATACTACGCGAGCTGGGCGAAGAGCCGATCCACCATCATCAGA<br>AACACCAACGAGAACACGGTGACTCTGAAAATGACCAGTCTGA<br>CAGCCGCGGACACGGCCACCTATTTCTGTGTGAGATATGCTAAT<br>ATTGGTTATGAGTACTTTAACGTCTGGGGTCCAGGCACCCTGGT<br>CAC<br>CGTCTCTTCAGGTGGAGGCGGTTCAGGCGGCGGTGGCTCTAGCG<br>GTGGTGGATCGCAGTTTGTGCTGACTCAGTCGCCCTCTGCATCT<br>GCTGCCCTGGGAGCCTCGGCCAAGCTCACCTGCACCCTGAGCA<br>GTGCCCACAAGACCTACACCATTGACTGGTATCAGCAGCAGAA<br>AGGGAAGGCCCCTCGCTACCTGATACAAGTTAAGAGTGATGGA<br>ACCTACACCAAGGCGACCGGGGTCCCTGATCGCTTCTCGGGCTC<br>CAGCTCTGGGGCTGACCGCTACCTGATCATCCCCAGCGTCCAGG<br>CTGATGACGAAGCCGACTACTATTGTGGTACAGATTATACCGGT<br>GGGTATGTGTTCGGCGGGGGGACCCAGCTGACCGTCACAGCTA<br>GC |
| P4-6 scFv-NT (with restric- tion sites, human optimized codon) | 57 | GGATCCGAGCAGCTGAAGGAGTCCGGCGGAGGCCTGTTTAAGC<br>CCACCGACACCCTGACACTGACCTGCACAGTGTCCGGCTTCAGC<br>CTGAGCTACTATGGCGTGAACTGGGTGAGACAGGCCCCTGGCA<br>ACGGACTGGAGTGGATCGGCACCATTGGCGGCAGCGGAGACAC<br>CTACTACGCCAGCTGGGCCAAGTCCAGGAGCACCATCATCAGA<br>AACACCAACGAGAACACCGTGACCCTGAAGATGACCTCCCTGA<br>CAGCCGCCGACACCGCCACCTACTTCTGCGTGAGGTACGCCAAC<br>ATCGGCTACGAGTACTTCAACGTGTGGGGCCCTGGCACCCTGGT<br>GACAGTGTCCAGCGGCGGAGGAGGAAGCGGCGGCGGCGGCTCC<br>AGCGGAGGCGGCAGCCAGTTTGTGCTGACCCAGAGCCCTAGCG<br>CTTCCGCCGCCCTGGGCGCCAGCGCCAAGCTCACCTGTACCCTG |

TABLE 2-continued

GFRα4 Antibody Sequences

| Name/ Description | SEQ ID NO: | Sequence |
|---|---|---|
| | | AGCAGCGCCCACAAGACCTATACCATCGACTGGTACCAGCAGC AGAAGGGCAAGGCCCCCAGGTACCTGATCCAGGTGAAGTCCGA CGGCACCTACACCAAAGCCACCGGCGTGCCCGACAGATTTAGC GGCAGCAGCTCCGGCGCCGACAGGTATCTGATCATCCCTTCCGT GCAGGCCGACGACGAGGCCGACTACTACTGCGGAACCGACTAC ACCGGCGGATACGTGTTCGGAGGCGGCACCCAGCTGACCGTGA CCGCTAGC |
| P4-6 scFv-AA (with restric-tion sites) | 58 | GSEQLKESGGGLFKPTDTLTLTCTVSGFSLSYYGVNWVRQAPGNG LEWIGTIGGSGDTYYASWAKSRSTIIRNTNENTVTLKMTSLTAADT ATYFCVRYANIGYEYFNVWGPGTLVTVSSGGGGSGGGGSSGGGS QFVLTQSPSASAALGASAKLTCTLSSAHKTYTIDWYQQQKGKAPR YLIQVKSDGTYTKATGVPDRFSGSSSGADRYLIIPSVQADDEADYY CGTDYTGGYVFGGGTQLTVTAS |
| P4-6 scFv-AA (without restric - tion sites) | 59 | EQLKESGGGLFKPTDTLTLTCTVSGFSLSYYGVNWVRQAPGNGLE WIGTIGGSGDTYYASWAKSRSTIIRNTNENTVTLKMTSLTAADTAT YFCVRYANIGYEYFNVWGPGTLVTVSSGGGGSGGGGSSGGGSQF VLTQSPSASAALGASAKLTCTLSSAHKTYTIDWYQQQKGKAPRYL IQVKSDGTYTKATGVPDRFSGSSSGADRYLIIPSVQADDEADYYCG TDYTGGYVFGGGTQLTVT |
| P4-10 VH-NT | 60 | CAGTCAGTGAAGGAGTCCGAGGGAGGTCTCTTCAAGCCAACGG ATACCCTGACACTCACCTGCACGGTCTCTGGATTCTCCCTCAGT AGACATGCACTGACCTGGGTCCGCCAGGCTCCAGGGAACGGGC TGGAATGGATCGGAGCCATTGATAACGCTGGTACCACATACTA CGCGAGCTGGGCGAAAAGCCGCTCCACCATCACCAGAAACACC GACCTGCACACGGTGACTCTGAAAATGACCAGTCTGACAGCCT CGGACACGGCTACCTATTTCTGTGCGAGAGTCTTTTATGATATT AATAGTGGTTATTATCTGGACGGCATGGACCTCTGGGGCCCAGG GACCCTCGTCACCGTCTCTTCA |
| P4-10 VH-AA | 61 | QSVKESEGGLFKPTDTLTLTCTVSGFSLSRHALTWVRQAPGNGLE WIGAIDNAGTTYYASWAKSRSTITRNTDLHTVTLKMTSLTASDTA TYFCARVFYDINSGYYLDGMDLWGPGTLVTVSS |
| P4-10 HC CDR1-NT | 62 | GGATTCTCCCTCAGTAGACATGCA |
| P4-10 HC CDR1-AA | 63 | GFSLSRHA |
| P4-10 HC CDR2-NT | 64 | ATTGATAACGCTGGTACCACA |
| P4-10 HC CDR2-AA | 65 | IDNAGTT |
| P4-10 HC CDR3-NT | 66 | GCGAGAGTCTTTTATGATATTAATAGTGGTTATTATCTGGACGG CATGGACCTC |
| P4-10 HC CDR3-AA | 67 | ARVFYDINSGYYLDGMDL |
| P4-10 VL-NT | 68 | CAGTTTGTGCTGACTCAGTCGCCCTCTGTGTCTGCCGCCCTGGG AGCCTCTGCCAAGCTCACCTGCACCCTGAGCAGTGCCCACAAG ACCTACACCATTGACTGGTATCAGCAGCAGCAAGGGGAGGCCC CTCGGTACCTGATGCAAGTTAAGAGTGATGGAAGCTACACCAA GGGGACCGGGGTCCCTGATCGCTTCTCGGGCTCCAGCTCTGGGG CTGACCGCTACTTGATCATCCCCAGCGTCCAGGCTGATGACGAA GCCGGCTACGTTTGTGGTGCAGATGATAACGGTGGGTATGTGTT CGGCGGAGGGACCCAGCTGACCGTCACA |
| P4-10 VL-AA | 69 | QFVLTQSPSVSAALGASAKLTCTLSSAHKTYTIDWYQQQQGEAPR YLMQVKSDGSYTKGTGVPDRFSGSSSGADRYLIIPSVQADDEAGY VCGADDNGGYVFGGGTQLTVT |
| P4-10 LC CDR1-NT | 70 | AGTGCCCACAAGACCTACACC |
| P4-10 LC CDR1-AA | 71 | SAHKTYT |
| P4-10 LC CDR2-NT | 72 | GTTAAGAGTGATGGAAGCTAC |

TABLE 2-continued

GFRα4 Antibody Sequences

| Name/Description | SEQ ID NO: | Sequence |
|---|---|---|
| P4-10 LC CDR2-AA | 73 | VKSDGSY |
| P4-10 LC CDR3-NT | 74 | GGTGCAGATGATAACGGTGGGTATGTG |
| P4-10 LC CDR3-AA | 75 | GADDNGGYV |
| P4-10 scFv- NT (with restriction sites, rabbit codon usage) | 76 | GGATCCCAGTCAGTGAAGGAGTCCGAGGGAGGTCTCTTCAAGC CAACGGATACCCTGACACTCACCTGCACGGTCTCTGGATTCTCC CTCAGTAGACATGCACTGACCTGGGTCCGCCAGGCTCCAGGGA ACGGGCTGGAATGGATCGGAGCCATTGATAACGCTGGTACCAC ATACTACGCGAGCTGGGCGAAAAGCCGCTCCACCATCACCAGA AACACCGACCTGCACACGGTGACTCTGAAAATGACCAGTCTGA CAGCCTCGGACACGGCTACCTATTTCTGTGCGAGAGTCTTTTAT GATATTAATAGTGGTTATTATCTGGACGGCATGGACCTCTGGGG CCCAGGGACCCTCGTCACCGTCTCTTCAGGTGGAGGCGGTTCAG GCGGCGGTGGCTCTAGCGGTGGTGGATCGCAGTTTGTGCTGACT CAGTCGCCCTCTGTGTCTGCCGCCCTGGGAGCCTCTGCCAAGCT CACCTGCACCCTGAGCAGTGCCCACAAGACCTACACCATTGACT GGTATCAGCAGCAGCAAGGGGAGGCCCCTCGGTACCTGATGCA AGTTAAGAGTGATGGAAGCTACACCAAGGGGACCGGGGTCCCT GATCGCTTCTCGGGCTCCAGCTCTGGGGCTGACCGCTACTTGAT CATCCCCAGCGTCCAGGCTGATGACGAAGCCGGCTACGTTTGTG GTGCAGATGATAACGGTGGGTATGTGTTCGGCGGAGGGACCCA GCTGACCGTCACAGCTAGC |
| P4-10 scFv-NT (with restriction sites, human optimized codon) | 77 | GGATCCCAGTCCGTGAAGGAGAGCGAGGGCGGCCTGTTCAAGC CCACCGACACCCTGACCCTGACCTGCACAGTGAGCGGCTTCAGC CTGTCCAGACACGCCCTGACATGGGTGAGACAGGCCCCTGGCA ACGGCCTGGAATGGATCGGCGCCATCGACAACGCCGGCACCAC CTACTACGCCAGCTGGGCCAAGTCCAGGTCCACCATCACCAGG AACACCGACCTCCACACCGTGACCCTGAAGATGACAAGCCTGA CCGCCTCCGACACCGCCACCTACTTCTGCGCCAGGGTGTTCTAC GACATCAACAGCGGCTACTACCTGGATGGCATGGACCTGTGGG GACCTGGCACACTGGTGACCGTGAGCAGCGGAGGCGGCGGCAG CGGCGGCGGCGGCAGCAGCGGCGGCGGAAGCCAGTTCGTGCTG ACACAGAGCCCTAGCGTGAGCGCCGCCCTGGGAGCCTCCGCTA AACTGACCTGCACCCTGAGCAGCGCCCACAAGACCTACACCAT CGACTGGTACCAACAGCAGCAGGGCGAGGCCCCCAGGTATCTG ATGCAGGTGAAGTCCGACGGCAGCTACACCAAAGGCACCGGCG TGCCTGACAGGTTCAGCGGCAGCTCCAGCGGAGCCGACAGGTA CCTGATCATCCCCTCCGTGCAGGCCGACGACGAGGCTGGCTACG TGTGTGGCGCCGACGACAATGGCGGCTACGTGTTCGGAGGCGG CACCCAGCTGACCGTGACAGCTAGC |
| P4-10 scFv- AA (with restriction sites) | 78 | GSQSVKESEGGLFKPTDTLTLTCTVSGFSLSRHALTWVRQAPGNGL EWIGAIDNAGTTYYASWAKSRSTITRNTDLHTVTLKMTSLTASDT ATYFCARVFYDINSGYYLDGMDLWGPGTLVTVSSGGGGSGGGGS SGGGSQFVLTQSPSVSAALGASAKLTCTLSSAHKTYTIDWYQQQQ GEAPRYLMQVKSDGSYTKGTGVPDRFSGSSSGADRYLIIPSVQADD EAGYVCGADDNGGYVFGGGTQLTVTAS |
| P4-10 scFv-AA (without restriction sites) | 79 | QSVKESEGGLFKPTDTLTLTCTVSGFSLSRHALTWVRQAPGNGLE WIGAIDNAGTTYYASWAKSRSTITRNTDLHTVTLKMTSLTASDTA TYFCARVFYDINSGYYLDGMDLWGPGTLVTVSSGGGGSGGGGSS GGGSQFVLTQSPSVSAALGASAKLTCTLSSAHKTYTIDWYQQQQG EAPRYLMQVKSDGSYTKGTGVPDRFSGSSSGADRYLIIPSVQADDE AGYVCGADDNGGYVFGGGTQLTVT |

Humanized Antibodies

For in vivo use of antibodies in humans, it may be preferable to use human antibodies. Completely human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety. A human antibody can also be an antibody wherein the heavy and light chains are encoded by a nucleotide sequence derived from one or more sources of human DNA.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Anti-GFRα4 antibodies directed against the human GFRα4 antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For an overview of this technology for producing human antibodies, see, Lonberg and Huszar (Int. Rev. Immunol., 13:65-93 (1995)). For a detailed discussion of this technology for producing human antibodies and human monoclonal antibodies and protocols for producing such antibodies, see, e.g., PCT Publication Nos. WO 98/24893, WO 96/34096, and WO 96/33735; and U.S. Pat. Nos. 5,413,923; 5,625,126; 5,633,425; 5,569,825; 5,661,016; 5,545,806; 5,814,318; and 5,939,598, each of which is incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above. For a specific discussion of transfer of a human germ-line immunoglobulin gene array in germ-line mutant mice that will result in the production of human antibodies upon antigen challenge see, e.g., Jakobovits et al., Proc. Natl. Acad. Sci. USA, 90:2551 (1993); Jakobovits et al., Nature, 362:255-258 (1993); Bruggermann et al., Year in Immunol., 7:33 (1993); and Duchosal et al., Nature, 355:258 (1992).

Human antibodies can also be derived from phage-display libraries (Hoogenboom et al., J. Mol. Biol., 227:381 (1991); Marks et al., J. Mol. Biol., 222:581-597 (1991); Vaughan et al., Nature Biotech., 14:309 (1996)). Phage display technology (McCafferty et al., Nature, 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of unimmunized mice. A repertoire of V genes from unimmunized human donors can be constructed and antibodies to a diverse array of antigens (including self-antigens) can be isolated essentially following the techniques described by Marks et al., J. Mol. Biol., 222:581-597 (1991), or Griffith et al., EMBO J., 12:725-734 (1993). See, also, U.S. Pat. Nos. 5,565,332 and 5,573,905, each of which is incorporated herein by reference in its entirety.

Human antibodies may also be generated by in vitro activated B cells (see, U.S. Pat. Nos. 5,567,610 and 5,229,275, each of which is incorporated herein by reference in its entirety). Human antibodies may also be generated in vitro using hybridoma techniques such as, but not limited to, that described by Roder et al. (Methods Enzymol., 121:140-167 (1986)).

Alternatively, in some embodiments, a non-human antibody is humanized, where specific sequences or regions of the antibody are modified to increase similarity to an antibody naturally produced in a human. For instance, in the present invention, the GFRα4 antibody comprises a rabbit scFv. In one embodiment, the antigen binding domain portion is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, preferably improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some framework (FR) residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

In some instances, a human scFv may also be derived from a yeast display library.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993), the contents of which are incorporated herein by reference herein in their entirety).

Antibodies can be humanized with retention of high affinity for the target antigen and other favorable biological properties. According to one aspect of the invention, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

A humanized antibody retains a similar antigenic specificity as the original antibody, i.e., in the rabbit scFv of the present invention, the ability to bind human GFRα4. However, using certain methods of humanization, the affinity and/or specificity of binding of the antibody for human GFRα4 may be increased using methods of "directed evolution," as described by Wu et al., J. Mol. Biol., 294:151 (1999), the contents of which are incorporated herein by reference herein in their entirety.

Rabbit Antibody

Notwithstanding the above, it is contemplated that the rabbit antibody disclosed herein may be equally useful as a therapeutic antibody in the methods of the invention without humanization.

Chimeric Antigen Receptor (CAR)

The present invention encompasses a recombinant DNA construct comprising sequences of the antibody of the invention that specifically binds to human GFRα4, wherein the sequence of the antibody or a fragment thereof is operably linked to the nucleic acid sequence of an intracellular domain. The intracellular domain or otherwise the cytoplasmic domain comprises, a costimulatory signaling region and/or a zeta chain portion. The costimulatory signaling region refers to a portion of the CAR comprising the intracellular domain of a costimulatory molecule. Costimulatory molecules are cell surface molecules other than antigens receptors or their ligands that are required for an efficient response of lymphocytes to antigen.

The present invention therefore encompasses a recombinant DNA construct comprising sequences of a fully human CAR, wherein the sequence comprises the nucleic acid sequence of a GFRα4 binding domain operably linked to the nucleic acid sequence of an intracellular domain. An exemplary intracellular domain that can be used in the CAR includes but is not limited to the intracellular domain of CD3-zeta, CD28, 4-1BB, CD27, and the like. In some instances, the CAR can comprise any combination of CD3-zeta, CD28, 4-1BB, CD27, and the like.

Between the extracellular domain and the transmembrane domain of the CAR, or between the cytoplasmic domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than as cloned molecules. In one embodiment, the CAR of the invention comprises a target-specific binding element otherwise referred to as an antigen binding moiety as described elsewhere herein. Examples of cell surface markers that may act as ligands for the antigen moiety domain in the CAR of the invention include those associated with viral, bacterial and parasitic infections, autoimmune disease and cancer cells.

In one embodiment, the CAR-mediated T-cell response can be directed to an antigen of interest by way of engineering a desired antigen into the CAR.

In some instances, it is beneficial for the antigen binding domain to be derived from the same species in which the CAR will ultimately be used in. For example, for use in humans, it may be beneficial for the antigen binding domain of the CAR to comprise a human antibody or a fragment thereof.

In one embodiment, the antigen binding domain of the CAR includes a nucleic acid sequence encoding an antibody as described elsewhere herein.

In an embodiment, the antigen binding domain portion of the CAR targets GFRα4, preferably human GFRα4.

Antigen Binding Domain

The CARs of the present invention comprise a target-specific binding domain. The choice of moiety depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen binding domain in a CAR of the invention include those associated with viral, bacterial and parasitic infections, autoimmune disease and cancer cells.

In one aspect, the CAR-mediated T-cell response can be directed to an antigen of interest by way of engineering an antigen binding domain that specifically binds a desired antigen into the CAR.

In one aspect, the CAR of the present invention comprises a binding domain that specifically binds GFRα4. In one aspect, the antigen binding domain specifically binds human GFRα4.

The antigen binding domain can be any domain that binds to the antigen including but not limited to a monoclonal antibody, a polyclonal antibody, a recombinant antibody, a human antibody, a humanized antibody, and a functional fragment thereof, including but not limited to a single-domain antibody such as a heavy chain variable domain (VH), a light chain variable domain (VL) and a variable domain (VHH) of camelid derived nanobody, and to an alternative scaffold known in the art to function as antigen binding domain, such as a recombinant fibronectin domain, and the like. In some instances, it is beneficial for the antigen binding domain to be derived from the same species in which the CAR will ultimately be used in. For example, for use in humans, it may be beneficial for the antigen binding domain of the CAR to comprise human or humanized residues for the antigen binding domain of an antibody or antibody fragment.

In some instances, it is beneficial for the antigen binding domain to be derived from the same species in which the CAR will ultimately be used in. For example, for use in humans, it may be beneficial for the antigen binding domain of the CAR to comprise human or humanized residues for the antigen binding domain of an antibody or antibody fragment. Thus, in one aspect, the antigen binding domain comprises a human antibody or an antibody fragment.

In one embodiment, GFRα4 binding domain comprises one or more (e.g., all three) light chain complementary determining region 1 (LC CDR1), light chain complementary determining region 2 (LC CDR2), and light chain complementary determining region 3 (LC CDR3) of a GFRα4 binding domain described herein, and/or one or more (e.g., all three) heavy chain complementary determining region 1 (HC CDR1), heavy chain complementary determining region 2 (HC CDR2), and heavy chain complementary determining region 3 (HC CDR3) of a GFRα4 binding domain described herein, e.g., a GFRα4 binding domain comprising one or more, e.g., all three, LC CDRs and one or more, e.g., all three, HC CDRs. In one embodiment, the GFRα4 binding domain comprises one or more (e.g., all three) heavy chain complementary determining region 1 (HC CDR1), heavy chain complementary determining region 2 (HC CDR2), and heavy chain complementary determining region 3 (HC CDR3) of a GFRα4 binding domain described herein, e.g., the GFRα4 binding domain has two variable heavy chain regions, each comprising a HC CDR1, a HC CDR2 and a HC CDR3 described herein. In an embodiment, the GFRα4 binding domain comprises one or more (e.g., all three) light chain complementary determining regions (LC CDRs) having at least one, two or three modifications (e.g., substitutions, e.g., conservative substitutions) but not more than 5 modifications (e.g., substitutions, e.g., conservative substitutions) of each CDR or combination of CDRs. In another embodiment, the GFRα4 binding domain comprises one or more (e.g., all three) heavy chain complementary determining regions (HC CDRs) having at least one, two or three modifications (e.g., substitutions, e.g., conservative substitutions) but not more than 5 modifications (e.g., substitutions, e.g., conservative substitutions) of each CDR or combination of CDRs.

In one embodiment, the GFRα4 binding domain comprises a light chain variable region described herein (e.g., in Table 2) and/or a heavy chain variable region described herein (e.g., in Table 2). In one embodiment, the GFRα4 binding domain comprises a human heavy chain variable region described herein (e.g., in Table 2), e.g., at least two heavy chain variable regions described herein (e.g., in Table 2). In one embodiment, the GFRα4 binding domain is a scFv comprising a light chain and a heavy chain of an amino acid sequence of Table 2. In an embodiment, the GFRα4 binding domain (e.g., an scFv) comprises: a light chain variable region comprising an amino acid sequence having at least one, two or three modifications (e.g., substitutions, e.g., conservative substitutions) but not more than 30, 20 or 10 modifications (e.g., substitutions, e.g., conservative substitutions) of an amino acid sequence of a light chain variable region provided in Table 2, or a sequence with 95-99% identity with an amino acid sequence of Table 2; and/or a heavy chain variable region comprising an amino acid sequence having at least one, two or three modifications (e.g., substitutions, e.g., conservative substitutions) but not more than 30, 20 or 10 modifications (e.g., substitutions, e.g., conservative substitutions) of an amino acid sequence of a heavy chain variable region provided in Table 2, or a sequence with 95-99% identity to an amino acid sequence of Table 2. In one embodiment, the GFRα4 binding domain comprises a sequence selected SEQ ID NO: 59 or 79, or a sequence with 95-99% identity thereof. In one embodiment, the nucleic acid sequence encoding the human GFRα4 binding domain comprises a sequence selected from a group consisting of SEQ ID NO:56, 57, 76, and 77, or a sequence with 95-99% identity thereof. In one embodiment, the GFRα4 binding domain is a scFv, and a light chain variable region comprising an amino acid sequence described herein, e.g., in Table 2, is attached to a heavy chain variable region comprising an amino acid sequence described herein, e.g., in Table 2, via a linker, e.g., a linker described herein. In one embodiment, the GFRα4 binding domain includes a $(Gly_4$-$Ser)n$ linker, wherein n is 1, 2, 3, 4, 5, or 6, preferably 3 or 4 (SEQ ID NO:26). The light chain variable region and heavy chain variable region of a scFv can be, e.g., in any of the following orientations: light chain variable region-linker-heavy chain variable region or heavy chain variable region-linker-light chain variable region.

In one aspect, the antigen binding domain portion comprises SEQ ID NO: 59 or 79. In one aspect the CAR is selected from one or more sequence selected from SEQ ID NOs: 85, 86, 90, 92, 94, 96, 98, 100, 102, or 104.

In one aspect, the GFRα4 binding domain is characterized by particular functional features or properties of an antibody or antibody fragment. For example, in one aspect, the portion of a CAR composition of the invention that comprises an antigen binding domain specifically binds human GFRα4, e.g., GFRα4a and/or GFRα4b.

In one aspect, the invention relates to an antigen binding domain comprising an antibody or antibody fragment, wherein the antibody binding domain specifically binds to a GFRα4 protein or fragment thereof, wherein the antibody or antibody fragment comprises a variable light chain and/or a variable heavy chain that includes an amino acid sequence of SEQ ID NO: 59 or 79. In one aspect, the antigen binding domain comprises an amino acid sequence of an scFv selected from SEQ ID NOs: 59 or 79. In certain aspects, the scFv is contiguous with and in the same reading frame as a leader sequence. In one aspect the leader sequence is the polypeptide sequence provided as SEQ ID NO:1.

In one aspect, GFRα4 binding domain is a fragment, e.g., a single chain variable fragment (scFv). In one aspect, the human GFRα4 binding domain is a Fv, a Fab, a (Fab')2, or a bi-functional (e.g. bi-specific) hybrid antibody (e.g., Lanzavecchia et al., Eur. J. Immunol. 17, 105 (1987)). In one aspect, the antibodies and fragments thereof of the invention binds a GFRα4 protein or a fragment thereof with wild-type or enhanced affinity.

In some instances a human scFv be derived from a display library. A display library is a collection of entities; each entity includes an accessible polypeptide component and a recoverable component that encodes or identifies the polypeptide component. The polypeptide component is varied so that different amino acid sequences are represented. The polypeptide component can be of any length, e.g. from three amino acids to over 300 amino acids. A display library entity can include more than one polypeptide component, for example, the two polypeptide chains of a Fab. In one exemplary embodiment, a display library can be used to identify a GFRα4 binding domain. In a selection, the polypeptide component of each member of the library is probed with GFRα4, or a fragment there, and if the polypeptide component binds to GFRα4, the display library member is identified, typically by retention on a support.

Retained display library members are recovered from the support and analyzed. The analysis can include amplification and a subsequent selection under similar or dissimilar conditions. For example, positive and negative selections can be alternated. The analysis can also include determining the amino acid sequence of the polypeptide component, i.e., the GFRα4 binding domain, and purification of the polypeptide component for detailed characterization.

A variety of formats can be used for display libraries. Examples include the phage display. In phage display, the protein component is typically covalently linked to a bacteriophage coat protein. The linkage results from translation of a nucleic acid encoding the protein component fused to the coat protein. The linkage can include a flexible peptide linker, a protease site, or an amino acid incorporated as a result of suppression of a stop codon. Phage display is described, for example, in U.S. Pat. No. 5,223,409; Smith (1985) Science 228:1315-1317; WO 92/18619; WO 91/17271; WO 92/20791; WO 92/15679; WO 93/01288; WO 92/01047; WO 92/09690; WO 90/02809; de Haard et al. (1999) *J. Biol. Chem* 274:18218-30; Hoogenboom et al. (1998) *Immunotechnology* 4:1-20; Hoogenboom et al. (2000) Immunol Today 2:371-8 and Hoet et al. (2005) *Nat Biotechnol.* 23(3)344-8. Bacteriophage displaying the protein component can be grown and harvested using standard phage preparatory methods, e.g. PEG precipitation from growth media. After selection of individual display phages, the nucleic acid encoding the selected protein components can be isolated from cells infected with the selected phages or from the phage themselves, after amplification. Individual colonies or plaques can be picked, the nucleic acid isolated and sequenced.

Other display formats include cell based display (see, e.g., WO 03/029456), protein-nucleic acid fusions (see, e.g., U.S. Pat. No. 6,207,446), ribosome display (See, e.g., Mattheakis et al. (1994) *Proc. Natl. Acad. Sci. USA* 91:9022 and Hanes et al. (2000) *Nat Biotechnol.* 18:1287-92; Hanes et al. (2000) *Methods Enzymol.* 328:404-30; and Schaffitzel et al. (1999) *J Immunol Methods.* 231(1-2):119-35), and *E. coli* periplasmic display (2005 Nov. 22; PMID: 16337958).

In some instances, scFvs can be prepared according to method known in the art (see, for example, Bird et al., (1988) Science 242:423-426 and Huston et al., (1988) Proc. Natl. Acad. Sci. USA 85:5879-5883). ScFv molecules can be produced by linking VH and VL regions together using flexible polypeptide linkers. The scFv molecules comprise a linker (e.g., a Ser-Gly linker) with an optimized length and/or amino acid composition. The linker length can greatly affect how the variable regions of a scFv fold and interact. In fact, if a short polypeptide linker is employed (e.g., between 5-10 amino acids) intrachain folding is prevented. Interchain folding is also required to bring the two variable regions together to form a functional epitope binding site. For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, is incorporated herein by reference.

An scFv can comprise a linker of at least 1, 2, 3, 4, 5, 6, 7, 8, 9, 10, 11, 12, 13, 14, 15, 16, 17, 18, 19, 20, 25, 30, 35, 40, 45, 50, or more amino acid residues between its VL and VH regions. The linker sequence may comprise any naturally occurring amino acid. In some embodiments, the linker sequence comprises amino acids glycine and serine. In another embodiment, the linker sequence comprises sets of glycine and serine repeats such as $(Gly_4Ser)n$, where n is a positive integer equal to or greater than 1 (SEQ ID NO:25). In one embodiment, the linker can be $(Gly_4Ser)_4$ (SEQ ID NO:27) or $(Gly_4Ser)_3$ (SEQ ID NO:28). Variation in the linker length may retain or enhance activity, giving rise to superior efficacy in activity studies.

Exemplary GFRα4 CAR Constructs and Antigen Binding Domains

Exemplary GFRα4 CAR constructs disclose herein comprise an scFv (e.g., a human scFv as disclosed in Tables 2 herein, optionally preceded with an optional leader sequence (e.g., SEQ ID NO:1 and SEQ ID NO:12 for exemplary leader amino acid and nucleotide sequences, respectively). The sequences of the human scFv fragments (amino acid sequences of SEQ ID NOs:58, 59, 78, or 79, and nucleotide sequences of SEQ ID NOs:56, 57, 76, or 77) are provided herein in Table 2. The GFRα4 CAR construct can further include an optional hinge domain, e.g., a CD8 hinge domain (e.g., including the amino acid sequence of SEQ ID NO: 2 or encoded by a nucleic acid sequence of SEQ ID NO:13); a transmembrane domain, e.g., a CD8 transmembrane domain (e.g., including the amino acid sequence of SEQ ID NO: 6 or encoded by the nucleotide sequence of SEQ ID NO: 17); an intracellular domain, e.g., a 4-1BB intracellular domain (e.g., including the amino acid sequence of SEQ ID NO: 7 or encoded by the nucleotide sequence of SEQ ID NO: 18; and a functional signaling domain, e.g., a CD3 zeta domain (e.g., including amino acid sequence of SEQ ID NO: 9 or 10, or encoded by the nucleotide sequence of SEQ ID NO: 20 or 21). In certain embodiments, the domains are contiguous with and in the same reading frame to form a single fusion protein. In other embodiments, the domain are in separate polypeptides, e.g., as in an RCAR molecule as described herein.

In certain embodiments, the full length GFRα4 CAR molecule includes the amino acid sequence of, or is encoded by the nucleotide sequence provided in Table 2, or a sequence substantially (e.g., 95-99%) identical thereto.

In certain embodiments, the GFRα4 CAR molecule, or the GFRα4 antigen binding domain, includes the scFv amino acid sequence provided in Table 2; or or is encoded by the nucleotide sequence provided in Table 2, or a sequence substantially identical (e.g., 95-99% identical, or up to 20, 15, 10, 8, 6, 5, 4, 3, 2, or 1 amino acid changes, e.g., substitutions (e.g., conservative substitutions)) to any of the aforesaid sequences.

In certain embodiments, the GFRα4 CAR molecule, or the GFRα4 antigen binding domain, includes the heavy chain variable region and/or the light chain variable region provided in Table 2, or a sequence substantially identical (e.g., 95-99% identical, or up to 20, 15, 10, 8, 6, 5, 4, 3, 2, or 1 amino acid changes, e.g., substitutions (e.g., conservative substitutions)) to any of the aforesaid sequences.

In certain embodiments, the GFRα4 molecule, or the GFRα4 antigen binding domain, includes one, two or three CDRs from the heavy chain variable region (e.g., HCDR1, HCDR2 and/or HCDR3) provided in Table 2; and/or one, two or three CDRs from the light chain variable region (e.g., LCDR1, LCDR2 and/or LCDR3) provided in Table 2; or a sequence substantially identical (e.g., 95-99% identical, or up to 5, 4, 3, 2, or 1 amino acid changes, e.g., substitutions (e.g., conservative substitutions)) to any of the aforesaid sequences.

The amino acid and nucleic acid sequences of the GFRα4 scFv domains are provided in Table 2. The amino acid sequences for the variable heavy chain and variable light chain for each scFv is also provided in Table 2. It is noted that the scFv fragments (SEQ ID NOs: 59 or 79) or CAR molecules with a leader sequence (e.g., the amino acid sequence of SEQ ID NO: 1 or the nucleotide sequence of SEQ ID NO: 12) are also encompassed by the present invention. Amino acid sequences of exemplary GFRα4 CAR molecules (SEQ ID NOs: 85, 86, 90, 92, 94, 96, 98, 100, 102, and 104) and nucleic acid sequences of exemplary GFRα4 CAR molecules (SEQ ID NOs: 89, 91, 93, 95, 97, 99, 101, and 103) are also provided herein.

The following sequences can be used to construct a CAR molecule comprising a GFRα4 antigen binding domain of the present invention.

```
Leader (amino acid sequence)
                                        (SEQ ID NO: 1)
MALPVTALLLPLALLLHAARP
```

-continued

```
Leader (nucleic acid sequence)
                                        (SEQ ID NO: 12)
ATGGCCCTGCCTGTGACAGCCCTGCTGCTGCCTCTGGCTCTGCTGCTGCA

TGCCGCTAGACCC

CD8 hinge (amino acid sequence)
                                        (SEQ ID NO: 2)
TTTPAPRPPTPAPTIASQPLSLRPEACRPAAGGAVHTRGLDFACD

CD8 hinge (nucleic acid sequence)
                                        (SEQ ID NO: 13)
ACCACGACGCCAGCGCCGCGACCACCAACACCGGCGCCCACCATCGCGTC

GCAGCCCCTGTCCCTGCGCCCAGAGGCGTGCCGGCCAGCGGCGGGGGGCG

CAGTGCACACGAGGGGGCTGGACTTCGCCTGTGA

CD8 transmembrane (amino acid sequence)
                                        (SEQ ID NO: 6)
IYIWAPLAGTCGVLLLSLVITLYC

CD8 transmembrane (nucleic acid sequence)
                                        (SEQ ID NO: 17)
ATCTACATCTGGGCGCCCTTGGCCGGGACTTGTGGGGTCCTTCTCCTGTC

ACTGGTTATCACCCTTTACTGC

4-1BB Intracellular domain (amino acid sequence)
                                        (SEQ ID NO: 7)
KRGRKKLLYIFKQPFMRPVQTTQEEDGCSCRFPEEEEGGCEL

4-1BB Intracellular domain (nucleic acid sequence)
                                        (SEQ ID NO: 18)
AAACGGGGCAGAAAGAAACTCCTGTATATATTCAAACAACCATTTATGAG

ACCAGTACAAACTACTCAAGAGGAAGATGGCTGTAGCTGCCGATTTCCAG

AAGAAGAAGAAGGAGGATGTGAACTG

CD28 Intracellular domain (amino acid sequence)
(SEQ ID NO: 80)
                                        (SEQ ID NO: 80)
RSKRSRLLHSDYMNMTPRRPGPTRKHYQPYAPPRDFAAYRS

CD28 Intracellular domain (nucleotide sequence)
(SEQ ID NO: 81)
                                        (SEQ ID NO: 81)
AGGAGTAAGAGGAGCAGGCTCCTGCACAGTGACTACATGAACATGACTCC

CCGCCGCCCCGGGCCCACCCGCAAGCATTACCAGCCCTATGCCCCACCAC

GCGACTTCGCAGCCTATCGCTCC

ICOS Intracellular domain (amino acid sequence)
(SEQ ID NO: 82)
                                        (SEQ ID NO: 82)
T K K K Y S S S V H D P N G E Y M F M R A V N T A

K K S R L T D V T L

ICOS Intracellular domain (nucleotide sequence)
(SEQ ID NO: 83)
                                        (SEQ ID NO: 83)
ACAAAAAAGAAGTATTCATCCAGTGTGCACGACCCTAACGGTGAATACAT

GTTCATGAGAGCAGTGAACACAGCCAAAAAATCCAGACTCACAGATGTGA

CCCTA

CD3 zeta domain (amino acid sequence)
                                        (SEQ ID NO: 9)
RVKFSRSADAPAYKQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR
```

-continued

CD3 zeta (nucleic acid sequence)
(SEQ ID NO: 20)
AGAGTGAAGTTCAGCAGGAGCGCAGACGCCCCCGCGTACAAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGC

CD3 zeta domain (amino acid sequence; NCBI Reference Sequence NM_000734.3)
(SEQ ID NO: 10)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

CD3 zeta (nucleic acid sequence; NCBI Reference Sequence NM_000734.3);
(SEQ ID NO: 21)
AGAGTGAAGTTCAGCAGGAGCGCAGACGCCCCCGCGTACCAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGC

IgG4 Hinge (amino acid sequence)
(SEQ ID NO: 36)
ESKYGPPCPPCPAPEFLGGPSVFLEPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGKM

IgG4 Hinge (nucleotide sequence)
(SEQ ID NO: 37)
GAGAGCAAGTACGGCCCTCCCTGCCCCCCTTGCCCTGCCCCCGAGTTCCT

GGGCGGACCCAGCGTGTTCCTGTTCCCCCCCAAGCCCAAGGACACCCTGA

TGATCAGCCGGACCCCCGAGGTGACCTGTGTGGTGGTGGACGTGTCCCAG

GAGGACCCCGAGGTCCAGTTCAACTGGTACGTGGACGGCGTGGAGGTGCA

CAACGCCAAGACCAAGCCCCGGGAGGAGCAGTTCAATAGCACCTACCGGG

TGGTGTCCGTGCTGACCGTGCTGCACCAGGACTGGCTGAACGGCAAGGAA

TACAAGTGTAAGGTGTCCAACAAGGGCCTGCCCAGCAGCATCGAGAAAAC

CATCAGCAAGGCCAAGGGCCAGCCTCGGGAGCCCCAGGTGTACACCCTGC

CCCCTAGCCAAGAGGAGATGACCAAGAACCAGGTGTCCCTGACCTGCCTG

GTGAAGGGCTTCTACCCCAGCGACATCGCCGTGGAGTGGGAGAGCAACGG

CCAGCCCGAGAACAACTACAAGACCACCCCCCCTGTGCTGGACAGCGACG

GCAGCTTCTTCCTGTACAGCCGGCTGACCGTGGACAAGAGCCGGTGGCAG

-continued

GAGGGCAACGTCTTTAGCTGCTCCGTGATGCACGAGGCCCTGCACAACCA

CTACACCCAGAAGAGCCTGAGCCTGTCCCTGGGCAAGATG

In embodiments, the CAR scFv fragments can be cloned into lentiviral vectors to create a full length CAR construct in a single coding frame, and using the EF1 alpha promoter for expression (SEQ ID NO: 11).

EF1 alpha promoter
CGTGAGGCTCCGGTGCCCGTCAGTGGGCAGAGCGCACATCGCCCACAGTC

CCCGAGAAGTTGGGGGGAGGGGTCGGCAATTGAACCGGTGCCTAGAGAAG

GTGGCGCGGGGTAAACTGGGAAAGTGATGTCGTGTACTGGCTCCGCCTTT

TTCCCGAGGGTGGGGGAGAACCGTATATAAGTGCAGTAGTCGCCGTGAAC

GTTCTTTTTCGCAACGGGTTTGCCGCCAGAACACAGGTAAGTGCCGTGTG

TGGTTCCCGCGGGCCTGGCCTCTTTACGGGTTATGGCCCTTGCGTGCCTT

GAATTACTTCCACCTGGCTGCAGTACGTGATTCTTGATCCCGAGCTTCGG

GTTGGAAGTGGGTGGGAGAGTTCGAGGCCTTGCGCTTAAGGAGCCCCTTC

GCCTCGTGCTTGAGTTGAGGCCTGGCCTGGGCGCTGGGGCCGCCGCGTGC

GAATCTGGTGGCACCTTCGCGCCTGTCTCGCTGCTTTCGATAAGTCTCTA

GCCATTTAAAATTTTTGATGACCTGCTGCGACGCTTTTTTTCTGGCAAGA

TAGTCTTGTAAATGCGGGCCAAGATCTGCACACTGGTATTTCGGTTTTTG

GGGCCGCGGGCGGCGACGGGGCCCGTGCGTCCCAGCGCACATGTTCGGCG

AGGCGGGGCCTGCGAGCGCGGCCACCGAGAATCGGACGGGGGTAGTCTCA

AGCTGGCCGGCCTGCTCTGGTGCCTGGCCTCGCGCCGCCGTGTATCGCCC

CGCCCTGGGCGGCAAGGCTGGCCCGGTCGGCACCAGTTGCGTGAGCGGAA

AGATGGCCGCTTCCCGGCCCTGCTGCAGGGAGCTCAAAATGGAGGACGCG

GCGCTCGGGAGAGCGGGCGGGTGAGTCACCCACACAAAGGAAAAGGGCCT

TTCCGTCCTCAGCCGTCGCTTCATGTGACTCCACGGAGTACCGGGCGCCG

TCCAGGCACCTCGATTAGTTCTCGAGCTTTTGGAGTACGTCGTCTTTAGG

TTGGGGGGAGGGGTTTTATGCGATGGAGTTTCCCCACACTGAGTGGGTGG

AGACTGAAGTTAGGCCAGCTTGGCACTTGATGTAATTCTCCTTGGAATTT

GCCCTTTTTGAGTTTGGATCTTGGTTCATTCTCAAGCCTCAGACAGTGGT

TCAAAGTTTTTTTCTTCCATTTCAGGTGTCGTGA

Gly/Ser (SEQ ID NO: 25)
GGGGS

Gly/Ser (SEQ ID NO: 26):
This sequence may encompass 1-6 "Gly Gly Gly Gly Ser" repeating units
GGGGSGGGGS GGGGSGGGGS GGGGSGGGGS Gly/Ser (SEQ ID NO: 27)
GGGGSGGGGS GGGGSGGGGS Gly/Ser (SEQ ID NO: 28)
GGGGSGGGGS GGGGS Gly/Ser (SEQ ID NO: 29)
GGGS PolyA: $(A)_{5000}$ (SEQ ID NO: 30)
This sequence may encompass 50-5000 adenines.

-continued

PolyA: $(T)_{100}$ (SEQ ID NO: 31)

PolyA: $(T)_{5000}$ (SEQ ID NO: 32)

This sequence may encompass 50-5000 thymines.
PolyA: $(A)_{5000}$ (SEQ ID NO: 33)

This sequence may encompass 100-5000 adenines.
PolyA: $(A)_{400}$ (SEQ ID NO: 34)

PolyA: $(A)_{2000}$ (SEQ ID NO: 35)

Gly/Ser (SEQ ID NO: 38):
This sequence may encompass 1-10 "Gly Gly Gly Ser" repeating units
GGGSGGGSGG GSGGGSGGGS GGGSGGGSGG GSGGGSGGGS The CAR construct can include a Gly/Ser linker having one or more of the following sequences: GGGGS (SEQ ID NO:25); encompassing 1-6 "Gly Gly Gly Gly Ser" repeating units, e.g., GGGGSGGGGS GGGGSGGGGS GGGGSGGGGS (SEQ ID NO:26); GGGGSGGGGS GGGGSGGGGS (SEQ ID NO:27); GGGGSGGGGS GGGGS (SEQ ID NO:28); GGGS (SEQ ID NO:29); or encompassing 1-10 "Gly Gly Gly Ser" repeating units, e.g., GGGSGGGSGG GSGGGSGGGS GGGSGGGSGG GSGGGSGGGS (SEQ ID NO:38).

In embodiments, the CAR construct include a poly A sequence, e.g., a sequence encompassing 50-5000 or 100-5000 adenines (e.g., SEQ ID NO:30, SEQ ID NO:33, SEQ ID NO:34 or SEQ ID NO:35), or a sequence encompassing 50-5000 thymines (e.g., SEQ ID NO:31, SEQ ID NO:32). Alternatively, the CAR construct can include, for example, a linker including the sequence GSTSGSGKPGSGEGSTKG (SEQ ID NO: 84)

In embodiments, the CAR constructs provided below contained a Q/K residue change in the signal domain of the co-stimulatory domain derived from CD3zeta chain NVS-P4-6-CAR - amino acid sequence
(SEQ ID NO: 85)
MALPVTALLLPLALLLHAARPEQLKESGGGLFKPTDTLTLTCTVSGFSLS

YYGVNWVRQAPGNGLEWIGTIGGSGDTYYASWAKSRSTIIRNTNENTVTL

KMTSLTAADTATYFCVRYANIGYEYFNVWGPGTLVTVSSGGGGSGGGGSG

GGGSQFVLTQSPSASAALGASAKLTCTLSSAHKTYTIDWYQQQKGKAPRY

LIQVKSDGTYTKATGVPDRFSGSSSGADRYLIIPSVQADDEADYYCGTDY

TGGYVFGGGTQLTVTTTTPAPRPPTPAPTIASQPLSLRPEACRPAAGGAV

HTRGLDFACDIYIWAPLAGTCGVLLLSLVITLYCKRGRKKLLYIFKQPFM

RPVQTTQEEDGCSCRFPEEEEGGCELRVKFSRSADAPAYKQGQNQLYNEL

NLGRREEYDVLDKRRGRDPEMGGKPRRKNPQEGLYNELQKDKMAEAYSEI

GMKGERRRGKGHDGLYQGLSTATKDTYDALHMQALPPR

NVS-P4-10-CAR - amino acid sequence
(SEQ ID NO: 86)
MALPVTALLLPLALLLHAARPQSVKESEGGLFKPTDTLTLTCTVSGFSLS

RHALTWVRQAPGNGLEWIGAIDNAGTTYYASWAKSRSTITRNTDLHTVTL

KMTSLTASDTATYFCARVFYDINSGYYLDGMDLWGPGTLVTVSSGGGGSG

GGGSGGGGSQFVLTQSPSVSAALGASAKLTCTLSSAHKTYTIDWYQQQQG

EAPRYLMQVKSDGSYTKGTGVPDRFSGSSSGADRYLIIPSVQADDEAGYV

-continued

CGADDNGGYVFGGGTQLTVTTTTPAPRPPTPAPTIASQPLSLRPEACRPA

AGGAVHTRGLDFACDIYIWAPLAGTCGVLLLSLVITLYCKRGRKKLLYIF

KQPFMRPVQTTQEEDGCSCRFPEEEEGGCELRVKFSRSADAPAYKQGQNQ

LYNELNLGRREEYDVLDKRRGRDPEMGGKPRRKNPQEGLYNELQKDKMAE

AYSEIGMKGERRRGKGHDGLYQGLSTATKDTYDALHMQALPPR

Additional CAR constructs are provided below. In some embodiments, the CAR constructs can comprise a signal recognition peptide (SRP) N-terminal to the antigen binding domain, e.g., scFv. In an embodiment, the SRP comprises the amino acid sequence MEFGLSWLFLVAILKGVQC (SEQ ID NO: 87) or is encoded by the nucleotide sequence ATGGAGTTTGGGCTGAGCTGGCTTTTTCTTGTGGCTATTTTAAAAGGTGTCCAGTG C (SEQ ID NO: 88).

P4-6-gs-bbz CAR - nucleotide sequence (underlined is p4-6 scFv, double underlined is GGGGSx2 hinge, thick underline is human CD8alpha transmembrane domain)
(SEQ ID NO: 89)
GGATCCGAGCAGCTGAAGGAGTCCGGGGGAGGTCTCTTCAAGCCAACGGA

TACCCTGACACTCACCTGCACAGTCTCTGGATTCTCCCTCAGTTACTATG

GAGTGAACTGGGTCCGCCAGGCTCCAGGGAACGGGCTGGAATGGATCGGA

ACCATTGGTGGTAGTGGTGACACATACTACGCGAGCTGGGCGAAGAGCCG

ATCCACCATCATCAGAAACACCAACGAGAACACGGTGACTCTGAAAATGA

CCAGTCTGACAGCCGCGGACACGGCCACCTATTTCTGTGTGAGATATGCT

AATATTGGTTATGAGTACTTTAACGTCTGGGGTCCAGGCACCCTGGTCAC

CGTCTCTTCAGGTGGAGGCGGTTCAGGCGGCGGTGGCTCTAGCGGTGGTG

GATCGCAGTTTGTGCTGACTCAGTCGCCCTCTGCATCTGCTGCCCTGGGA

GCCTCGGCCAAGCTCACCTGCACCCTGAGCAGTGCCCACAAGACCTACAC

CATTGACTGGTATCAGCAGCAGAAAGGGAAGGCCCCTCGCTACCTGATAC

AAGTTAAGAGTGATGGAACCTACACCAAGGCGACCGGGGTCCCTGATCGC

TTCTCGGGCTCCAGCTCTGGGGCTGACCGCTACCTGATCATCCCCAGCGT

CCAGGCTGATGACGAAGCCGACTACTATTGTGGTACAGATTATACCGGTG

GGTATGTGTTCGGCGGGGGGACCCAGCTGACCGTCACAGCTAGCGGTGGC

GGAGGTTCTGGAGGTGGAGGTTCCTCCGGA

ATCTACATCTGGGCCCCTCTGGCCGGCACCTGTGGCGT

GCTGCTGCTGTCCCTGGTCATCACCCTGTACTGCAAG

CGGGGCAGAAAGAAGCTGCTGTACATCTTCAAGCAGCCCTTCATGCGGCC

TGTGCAGACCACACAGGAAGAGGACGGCTGTAGCTGTAGATTCCCCGAGG

AAGAGGAAGGCGGCTGCGAGCTGAGAGTGAAGTTCAGCAGAAGCGCCGAC

GCCCCTGCCTATCAGCAGGGCCAGAACCAGCTGTACAACGAGCTGAACCT

GGGCAGACGGGAGGAATACGACGTGCTGGACAAGAGAAGAGGCCGGGACC

CTGAGATGGGCGGCAAGCCCAGACGGAAGAACCCCCAGGAAGGCCTGTAT

AACGAACTGCAGAAAGACAAGATGGCCGAGGCCTACAGCGAGATCGGCAT

-continued

GAAGGGCGAGCGGAGAAGAGGCAAGGGCCATGACGGCCTGTACCAGGGCC

TGAGCACCGCCACCAAGGACACCTACGACGCCCTGCACATGCAGGCCCTG

CCTCCAAGATGA

P4-6-gs-bbz CAR- amino acid sequence (underlined is p4-6 scFv, double underlined is GGGGSx2 hinge, thick underline is human CD8alpha transmembrane domain)

(SEQ ID NO: 90)

GSEQLKESGGGLFKPTDTLTLTCTVSGFSLSYYGVNWVRQAPGNGLEWIG

TIGGSGDTYYASWAKSRSTIIRNTNENTVTLKMTSLTAADTATYFCVRYA

NIGYEYFNVWGPGTLVTVSSGGGGSGGGGSSGGGSQFVLTQSPSASAALG

ASAKLTCTLSSAHKTYTIDWYQQQKGKAPRYLIQVKSDGTYTKATGVPDR

FSGSSSGADRYLIIPSVQADDEADYYCGTDYTGGYVFGGGTQLTVTAS

GGGGSGGGGSSGIYIWAPLAGTCGVLLLSLVITLYCK

RGRKKLLYIFKQPFMRPVQTTQEEDGCSCRFPEEEEGGCELRVKFSRSAD

APAYQQGQNQLYNELNLGRREEYDVLDKRRGRDPEMGGKPRRKNPQEGLY

NELQKDKMAEAYSEIGMKGERRRGKGHDGLYQGLSTATKDTYDALHMQAL

PPR

P4-10-gs-bbz - nucleotide sequence (underlined is p4-10 s cFv, double underlined is GGGGSx2 hinge, thick underline is human CD8alpha transmembrane domain)

(SEQ ID NO: 91)

GGATCCCAGTCAGTGAAGGAGTCCGAGGGAGGTCTCTTCAAGCCAACGGA

TACCCTGACACTCACCTGCACGGTCTCTGGATTCTCCCTCAGTAGACATG

CACTGACCTGGGTCCGCCAGGCTCCAGGGAACGGGCTGGAATGGATCGGA

GCCATTGATAACGCTGGTACCACATACTACGCGAGCTGGGCGAAAAGCCG

CTCCACCATCACCAGAAACACCGACCTGCACACGGTGACTCTGAAAATGA

CCAGTCTGACAGCCTCGGACACGGCTACCTATTTCTGTGCGAGAGTCTTT

TATGATATTAATAGTGGTTATTATCTGGACGGCATGGACCTCTGGGGCCC

AGGGACCCTCGTCACCGTCTCTTCAGGTGGAGGCGGTTCAGGCGGCGGTG

GCTCTAGCGGTGGTGGATCGCAGTTTGTGCTGACTCAGTCGCCCTCTGTG

TCTGCCGCCCTGGGAGCCTCTGCCAAGCTCACCTGCACCCTGAGCAGTGC

CCACAAGACCTACACCATTGACTGGTATCAGCAGCAGCAAGGGGAGGCCC

CTCGGTACCTGATGCAAGTTAAGAGTGATGGAAGCTACACCAAGGGGACC

GGGGTCCCTGATCGCTTCTCGGGCTCCAGCTCTGGGGCTGACCGCTACTT

GATCATCCCCAGCGTCCAGGCTGATGACGAAGCCGGCTACGTTTGTGGTG

CAGATGATAACGGTGGGTATGTGTTCGGCGGAGGGACCCAGCTGACCGTC

ACAGCTAGCGGTGGCGGAGGTTCTGGAGGTGGAGGTTCCTCCGGA

CCGGCACCTGTGGCGTGCTGC

TGCTGTCCCTGGTCATCACCCTGTACTGCAAG

CGGGGCAGAAAGAAGCTGCTGTACATCTTCAAGCAGCCCTTCATGCGGCC

TGTGCAGACCACACAGGAAGAGGACGGCTGTAGCTGTAGATTCCCCGAGG

AAGAGGAAGGCGGCTGCGAGCTGAGAGTGAAGTTCAGCAGAAGCGCCGAC

GCCCCTGCCTATCAGCAGGGCCAGAACCAGCTGTACAACGAGCTGAACCT

GGGCAGACGGGAGGAATACGACGTGCTGGACAAGAGAAGAGGCCGGGACC

-continued

CTGAGATGGGCGGCAAGCCCAGACGGAAGAACCCCCAGGAAGGCCTGTAT

AACGAACTGCAGAAAGACAAGATGGCCGAGGCCTACAGCGAGATCGGCAT

GAAGGGCGAGCGGAGAAGAGGCAAGGGCCATGACGGCCTGTACCAGGGCC

TGAGCACCGCCACCAAGGACACCTACGACGCCCTGCACATGCAGGCCCTG

CCTCCAAGATGA

P4-10-gs-bbz - amino acid sequence (underlined is p4-10 scFv, double underlined is GGGGSx2 hinge, thick underline is human CD8alpha transmembrane domain)

(SEQ ID NO: 92)

GSQSVKESEGGLFKPTDTLTLTCTVSGFSLSRHALTWVRQAPGNGLEWIG

AIDNAGTTYYASWAKSRSTITRNTDLHTVTLKMTSLTASDTATYFCARVF

YDINSGYYLDGMDLWGPGTLVTVSSGGGGSGGGGSSGGGSQFVLTQSPSV

SAALGASAKLTCTLSSAHKTYTIDWYQQQGEAPRYLMQVKSDGSYTKGT

GVPDRFSGSSSGADRYLIIPSVQADDEAGYVCGADDNGGYVFGGGTQLTV

TASGGGGSGGGGSSGIYIWAPLAGTCGVLLLSLVITLYCK

RGRKKLLYIFKQPFMRPVQTTQEEDGCSCRFPEEEEGGCELRVKFSRSAD

APAYQQGQNQLYNELNLGRREEYDVLDKRRGRDPEMGGKPRRKNPQEGLY

NELQKDKMAEAYSEIGMKGERRRGKGHDGLYQGLSTATKDTYDALHMQAL

PPR

P4-6-cd8-bbz - nucleotide sequence (underlined is p4-6scFv, double underlined is human CD8alpha hinge, thick underline is human CD8alpha transmembrane domain)

(SEQ ID NO: 93)

GGATCCGAGCAGCTGAAGGAGTCCGGGGGAGGTCTCTTCAAGCCAACGGA

TACCCTGACACTCACCTGCACAGTCTCTGGATTCTCCCTCAGTTACTATG

GAGTGAACTGGGTCCGCCAGGCTCCAGGGAACGGGCTGGAATGGATCGGA

ACCATTGGTGGTAGTGGTGACACATACTACGCGAGCTGGGCGAAGAGCCG

ATCCACCATCATCAGAAACACCAACGAGAACACGGTGACTCTGAAAATGA

CCAGTCTGACAGCCGCGGACACGGCCACCTATTTCTGTGTGAGATATGCT

AATATTGGTTATGAGTACTTTAACGTCTGGGGTCCAGGCACCCTGGTCAC

CGTCTCTTCAGGTGGAGGCGGTTCAGGCGGCGGTGGCTCTAGCGGTGGTG

GATCGCAGTTTGTGCTGACTCAGTCGCCCTCTGCATCTGCTGCCCTGGGA

GCCTCGGCCAAGCTCACCTGCACCCTGAGCAGTGCCCACAAGACCTACAC

CATTGACTGGTATCAGCAGCAGAAAGGGAAGGCCCCTCGCTACCTGATAC

AAGTTAAGAGTGATGGAACCTACACCAAGGCGACCGGGGTCCCTGATCGC

TTCTCGGGCTCCAGCTCTGGGGCTGACCGCTACCTGATCATCCCCAGCGT

CCAGGCTGATGACGAAGCCGACTACTATTGTGGTACAGATTATACCGGTG

GGTATGTGTTCGGCGGGGGGACCCAGCTGACCGTCACAGCTAGCACCACG

ACGCCAGCGCCGCGACCACCAACACCGGCGCCCACCATCGCGTCGCAGCC

CCTGTCCCTGCGCCCAGAGGCGTGCCGGCCAGCGGCGGGGGGCGCAGTGC

ACACGAGGGGGCTGGACTTCGCCTGTGATTCCGGA

ATCTACATCTGGGCCCCTCTGGCCGGCACCTGTGGCGTGC

TGCTGCTGTCCCTGGTCATCACCCTGTACTGCAAG

-continued

CGGGGCAGAAAGAAGCTGCTGTACATCTTCAAGCAGCCCTTCATGCGGCC
TGTGCAGACCACACAGGAAGAGGACGGCTGTAGCTGTAGATTCCCCGAGG
AAGAGGAAGGCGGCTGCGAGCTGAGAGTGAAGTTCAGCAGAAGCGCCGAC
GCCCCTGCCTATCAGCAGGGCCAGAACCAGCTGTACAACGAGCTGAACCT
GGGCAGACGGGAGGAATACGACGTGCTGGACAAGAGAAGAGGCCGGGACC
CTGAGATGGGCGGCAAGCCCAGACGGAAGAACCCCCAGGAAGGCCTGTAT
AACGAACTGCAGAAAGACAAGATGGCCGAGGCCTACAGCGAGATCGGCAT
GAAGGGCGAGCGGAGAAGAGGCAAGGGCCATGACGGCCTGTACCAGGGCC
TGAGCACCGCCACCAAGGACACCTACGACGCCCTGCACATGCAGGCCCTG
CCTCCAAGATGA

P4-6-cd8-bbz - amino acid sequence (underlined is p4-6scFv, double underlined is human CD8alpha hinge, thick underline is human CD8alpha transmembrane domain)

(SEQ ID NO: 94)

GSEQLKESGGGLFKPTDTLTLTCTVSGFSLSYYGVNWVRQAPGNGLEWIG
TIGGSGDTYYASWAKSRSTIIRNTNENTVTLKMTSLTAADTATYFCVRYA
NIGYEYFNVWGPGTLVTVSSGGGGSGGGGSSGGGSQFVLTQSPSASAALG
ASAKLTCTLSSAHKTYTIDWYQQQKGKAPRYLIQVKSDGTYTKATGVPDR
FSGSSSGADRYLIIPSVQADDEADYYCGTDYTGGYVFGGGTQLTVTASTT
TPAPRPPTPAPTIASQPLSLRPEACRPAAGGAVHTRGLDFACDSG
IYIWAPLAGTCGVLLLSLVITLYCKRGRKKLLYIFKQPFMRPVQTTQE
EDGCSCRFPEEEEGGCELRVKFSRSADAPAYQQGQNQLYNELNLGRREEY
DVLDKRRGRDPEMGGKPRRKNPQEGLYNELQKDKMAEAYSEIGMKGERRR
GKGHDGLYQGLSTATKDTYDALHMQALPPR

P4-10-cd8-bbz - nucleotide sequence (underlined is p4-10scFv, double underlined is human CD8alpha hinge, thick underline is human CD8alpha transmembrane domain)

(SEQ ID NO: 95)

GGATCCCAGTCAGTGAAGGAGTCCGAGGGAGGTCTCTTCAAGCCAACGGA
TACCCTGACACTCACCTGCACGGTCTCTGGATTCTCCCTCAGTAGACATG
CACTGACCTGGGTCCGCCAGGCTCCAGGGAACGGGCTGGAATGGATCGGA
GCCATTGATAACGCTGGTACCACATACTACGCGAGCTGGGCGAAAAGCCG
CTCCACCATCACCAGAAACACCGACCTGCACACGGTGACTCTGAAAATGA
CCAGTCTGACAGCCTCGGACACGGCTACCTATTTCTGTGCGAGAGTCTTT
TATGATATTAATAGTGGTTATTATCTGGACGGCATGGACCTCTGGGGCCC
AGGGACCCTCGTCACCGTCTCTTCAGGTGGAGGCGGTTCAGGCGGCGGTG
GCTCTAGCGGTGGTGGATCGCAGTTTGTGCTGACTCAGTCGCCCTCTGTG
TCTGCCGCCCTGGGAGCCTCTGCCAAGCTCACCTGCACCCTGAGCAGTGC
CCACAAGACCTACACCATTGACTGGTATCAGCAGCAGCAAGGGGAGGCCC
CTCGGTACCTGATGCAAGTTAAGAGTGATGGAAGCTACACCAAGGGGACC
GGGGTCCCTGATCGCTTCTCGGGCTCCAGCTCTGGGGCTGACCGCTACTT
GATCATCCCCAGCGTCCAGGCTGATGACGAAGCCGGCTACGTTTGTGGTG
CAGATGATAACGGTGGGTATGTGTTCGGCGGAGGGACCCAGCTGACCGTC
ACAGCTAGCACCACGACGCCAGCGCCGCGACCACCAACACCGGCGCCCAC
CATCGCGTCGCAGCCCCTGTCCCTGCGCCCAGAGGCGTGCCGGCCAGCGG
CGGGGGGCGCAGTGCACACGAGGGGGCTGGACTTCGCCTGTGATTCCGGA
ATCTACATCTGGGCCCCTCTGGCCGGCACCTGTGGCGTGCTGC
TGCTGTCCCTGGTCATCACCCTGTACTGCAAG
CGGGGCAGAAAGAAGCTGCTGTACATCTTCAAGCAGCCCTTCATGCGGCC
TGTGCAGACCACACAGGAAGAGGACGGCTGTAGCTGTAGATTCCCCGAGG
AAGAGGAAGGCGGCTGCGAGCTGAGAGTGAAGTTCAGCAGAAGCGCCGAC
GCCCCTGCCTATCAGCAGGGCCAGAACCAGCTGTACAACGAGCTGAACCT
GGGCAGACGGGAGGAATACGACGTGCTGGACAAGAGAAGAGGCCGGGACC
CTGAGATGGGCGGCAAGCCCAGACGGAAGAACCCCCAGGAAGGCCTGTAT
AACGAACTGCAGAAAGACAAGATGGCCGAGGCCTACAGCGAGATCGGCAT
GAAGGGCGAGCGGAGAAGAGGCAAGGGCCATGACGGCCTGTACCAGGGCC
TGAGCACCGCCACCAAGGACACCTACGACGCCCTGCACATGCAGGCCCTG
CCTCCAAGATGA

P4-10-cd8-bbz - amino acid sequence (underlined is p4-10scFv, double underlined is human CD8alpha hinge, thick underline is human CD8alpha transmembrane domain)

(SEQ ID NO: 96)

GSQSVKESEGGLFKPTDTLTLTCTVSGFSLSRHALTWVRQAPGNGLEWIG
AIDNAGTTYYASWAKSRSTITRNTDLHTVTLKMTSLTASDTATYFCARVF
YDINSGYYLDGMDLWGPGTLVTVSSGGGGSGGGGSSGGGSQFVLTQSPSV
SAALGASAKLTCTLSSAHKTYTIDWYQQQQGEAPRYLMQVKSDGSYTKGT
GVPDRFSGSSSGADRYLIIPSVQADDEAGYVCGADDNGGYVFGGGTQLTV
TASTTTPAPRPPTPAPTIASQPLSLRPEACRPAAGGAVHTRGLDFACDSG
IYIWAPLAGTCGVLLLSLVITLYCKRGRKKLLYIFKQPFM
RPVQTTQEEDGCSCRFPEEEEGGCELRVKFSRSADAPAYQQGQNQLYNEL
NLGRREEYDVLDKRRGRDPEMGGKPRRKNPQEGLYNELQKDKMAEAYSEI
GMKGERRRGKGHDGLYQGLSTATKDTYDALHMQALPPR

P4-6-gs-28z - nucleotide sequence (underlined is p4-6 scFv)

(SEQ ID NO: 97)

GGATCCGAGCAGCTGAAGGAGTCCGGGGGAGGTCTCTTCAAGCCAACGGA
TACCCTGACACTCACCTGCACAGTCTCTGGATTCTCCCTCAGTTACTATG
GAGTGAACTGGGTCCGCCAGGCTCCAGGGAACGGGCTGGAATGGATCGGA
ACCATTGGTGGTAGTGGTGACACATACTACGCGAGCTGGGCGAAGAGCCG
ATCCACCATCATCAGAAACACCAACGAGAACACGGTGACTCTGAAAATGA
CCAGTCTGACAGCCGCGGACACGGCCACCTATTTCTGTGTGAGATATGCT
AATATTGGTTATGAGTACTTTAACGTCTGGGGTCCAGGCACCCTGGTCAC
CGTCTCTTCAGGTGGAGGCGGTTCAGGCGGCGGTGGCTCTAGCGGTGGTG
GATCGCAGTTTGTGCTGACTCAGTCGCCCTCTGCATCTGCTGCCCTGGGA
GCCTCGGCCAAGCTCACCTGCACCCTGAGCAGTGCCCACAAGACCTACAC
CATTGACTGGTATCAGCAGCAGAAAGGGAAGGCCCCTCGCTACCTGATAC
AAGTTAAGAGTGATGGAACCTACACCAAGGCGACCGGGGTCCCTGATCGC

-continued

TTCTCGGGCTCCAGCTCTGGGGCTGACCGCTACCTGATCATCCCCAGCGT
CCAGGCTGATGACGAAGCCGACTACTATTGTGGTACAGATTATACCGGTG
GGTATGTGTTCGGCGGGGGGACCCAGCTGACCGTCACAGCTAGCGGTGGC
GGAGGTTCTGGAGGTGGAGGTTCCTCCGGATTTTGGGTGCTGGTGGTGGT
TGGTGGAGTCCTGGCTTGCTATAGCTTGCTAGTAACAGTGGCCTTTATTA
TTTTCTGGGTGAGGAGTAAGAGGAGCAGGCTCCTGCACAGTGACTACATG
AACATGACTCCCCGCCGCCCCGGGCCCACCCGCAAGCATTACCAGCCCTA
TGCCCCACCACGCGACTTCGCAGCCTATCGCTCCCTGAGAGTGAAGTTCA
GCAGGAGCGCAGACGCCCCCGCGTACCAGCAGGGCCAGAACCAGCTCTAT
AACGAGCTCAATCTAGGACGAAGAGAGGAGTACGATGTTTTGGACAAGAG
ACGTGGCCGGGACCCTGAGATGGGGGGAAAGCCGAGAAGGAAGAACCCTC
AGGAAGGCCTGTACAATGAACTGCAGAAAGATAAGATGGCGGAGGCCTAC
AGTGAGATTGGGATGAAAGGCGAGCGCCGGAGGGGCAAGGGGCACGATGG
CCTTTACCAGGGTCTCAGTACAGCCACCAAGGACACCTACGACGCCCTTC
ACATGCAGGCCCTGCCCCCTCGCTAATAA

P4-6-gs-28z - amino acid sequence (underlined is p4-6 scFv)

(SEQ ID NO: 98)

GSEQLKESGGGLFKPTDTLTLTCTVSGFSLSYYGVNWVRQAPGNGLEWIG
TIGGSGDTYYASWAKSRSTIIRNTNENTVTLKMTSLTAADTATYFCVRYA
NIGYEYFNVWGPGTLVTVSSGGGGSGGGGSSGGGSQFVLTQSPSASAALG
ASAKLTCTLSSAHKTYTIDWYQQQKGKAPRYLIQVKSDGTYTKATGVPDR
FSGSSSGADRYLIIPSVQADDEADYYCGTDYTGGYVFGGGTQLTVTASGG
GGSGGGGSSGFWVLVVVGGVLACYSLLVTVAFIIFWVRSKRSRLLHSDYM
NMTPRRPGPTRKHYQPYAPPRDFAAYRSLRVKFSRSADAPAYQQGQNQLY
NELNLGRREEYDVLDKRRGRDPEMGGKPRRKNPQEGLYNELQKDKMAEAY
SEIGMKGERRRGKGHDGLYQGLSTATKDTYDALHMQALPPR

P4-10-gs-28z - nucleotide sequence (underlined is p4-10 scFv)

(SEQ ID NO: 99)

GGATCCCAGTCAGTGAAGGAGTCCGAGGGAGGTCTCTTCAAGCCAACGGA
TACCCTGACACTCACCTGCACGGTCTCTGGATTCTCCCTCAGTAGACATG
CACTGACCTGGGTCCGCCAGGCTCCAGGGAACGGGCTGGAATGGATCGGA
GCCATTGATAACGCTGGTACCACATACTACGCGAGCTGGGCGAAAAGCCG
CTCCACCATCACCAGAAACACCGACCTGCACACGGTGACTCTGAAAATGA
CCAGTCTGACAGCCTCGGACACGGCTACCTATTTCTGTGCGAGAGTCTTT
TATGATATTAATAGTGGTTATTATCTGGACGGCATGGACCTCTGGGGCCC
AGGGACCCTCGTCACCGTCTCTTCAGGTGGAGGCGGTTCAGGCGGCGGTG
GCTCTAGCGGTGGTGGATCGCAGTTTGTGCTGACTCAGTCGCCCTCTGTG
TCTGCCGCCCTGGGAGCCTCTGCCAAGCTCACCTGCACCCTGAGCAGTGC
CCACAAGACCTACACCATTGACTGGTATCAGCAGCAGCAAGGGGAGGCCC
CTCGGTACCTGATGCAAGTTAAGAGTGATGGAAGCTACACCAAGGGGACC
GGGGTCCCTGATCGCTTCTCGGGCTCCAGCTCTGGGGCTGACCGCTACTT
GATCATCCCCAGCGTCCAGGCTGATGACGAAGCCGGCTACGTTTGTGGTG
CAGATGATAACGGTGGGTATGTGTTCGGCGGAGGGACCCAGCTGACCGTC
ACAGCTAGCGGTGGCGGAGGTTCTGGAGGTGGAGGTTCCTCCGGATTTTG
GGTGCTGGTGGTGGTTGGTGGAGTCCTGGCTTGCTATAGCTTGCTAGTAA
CAGTGGCCTTTATTATTTTCTGGGTGAGGAGTAAGAGGAGCAGGCTCCTG
CACAGTGACTACATGAACATGACTCCCCGCCGCCCCGGGCCCACCCGCAA
GCATTACCAGCCCTATGCCCCACCACGCGACTTCGCAGCCTATCGCTCCC
TGAGAGTGAAGTTCAGCAGGAGCGCAGACGCCCCCGCGTACCAGCAGGGC
CAGAACCAGCTCTATAACGAGCTCAATCTAGGACGAAGAGAGGAGTACGA
TGTTTTGGACAAGAGACGTGGCCGGGACCCTGAGATGGGGGGAAAGCCGA
GAAGGAAGAACCCTCAGGAAGGCCTGTACAATGAACTGCAGAAAGATAAG
ATGGCGGAGGCCTACAGTGAGATTGGGATGAAAGGCGAGCGCCGGAGGGG
CAAGGGGCACGATGGCCTTTACCAGGGTCTCAGTACAGCCACCAAGGACA
CCTACGACGCCCTTCACATGCAGGCCCTGCCCCCTCGCTAATAA

P4-10-gs-28z - amino acid sequence (underlined is p4-10 scFv)

(SEQ ID NO: 100)

GSQSVKESEGGLFKPTDTLTLTCTVSGFSLSRHALTWVRQAPGNGLEWIG
AIDNAGTTYYASWAKSRSTITRNTDLHTVTLKMTSLTASDTATYFCARVF
YDINSGYYLDGMDLWGPGTLVTVSSGGGGSGGGGSSGGGSQFVLTQSPSV
SAALGASAKLTCTLSSAHKTYTIDWYQQQQGEAPRYLMQVKSDGSYTKGT
GVPDRFSGSSSGADRYLIIPSVQADDEAGYVCGADDNGGYVFGGGTQLTV
TASGGGGSGGGGSSGFWVLVVVGGVLACYSLLVTVAFIIFWVRSKRSRLL
HSDYMNMTPRRPGPTRKHYQPYAPPRDFAAYRSLRVKFSRSADAPAYQQG
QNQLYNELNLGRREEYDVLDKRRGRDPEMGGKPRRKNPQEGLYNELQKDK
MAEAYSEIGMKGERRRGKGHDGLYQGLSTATKDTYDALHMQALPPR

Dap12 - T2A - P4-6-gs-KIRS2 - nucleotide sequence (thick underlined is Dap12 and T2A sequence; italicized is the CD8 SRP; underlined is the P4-6 scFv, double underline is the KIR2DS2 fragment)

(SEQ ID NO: 101)

ATGGGGGGACTTGAACCCTGCAGCAGGTTCCTGCTCC
TGCCTCTCCTGCTGGCTGTAAGTGGTCTCCGTCCTGTC
CAGGTCCAGGCCCAGAGCGATTGCAGTTGCTCTAC
GGTGAGCCCGGGCGTGCTG
AGACCTGGTGCTGACAGTGCTCATTGCCCTGGCCGTGTA
CTTCCTGGGCCGGCTGGTCCCTCGGGGGCGAGGG
GCTGCGGAGGCAGCGACCCGGAAACAGCGTATCACTG
AGACCGAGTCGCCTTATCAGGAGCTCCAGGGTCAGA
GGTCGGATGTCTACAGCGACCTCAACACACAGAGG
CCGTATTACAAAGTCGAGGGCGGCGGAGAGGGCAGA
GGAAGTCTTCTAACATGCGGTGACGTGGAGGAGAATCCCGGC
CCTAGG*ATGGCCTTACCAGTGACCGCCTTGCTCCTGCCGCTGGCCTTGCT*
*GCTCCACGCCGCCAGGCCG*GGATCCGAGCAGCTGAAGGAGTCCGGGGGAG
GTCTCTTCAAGCCAACGGATACCCTGACACTCACCTGCACAGTCTCTGGA

-continued

TTCTCCCTCAGTTACTATGGAGTGAACTGGGTCCGCCAGGCTCCAGGGAA

CGGGCTGGAATGGATCGGAACCATTGGTGGTAGTGGTGACACATACTACG

CGAGCTGGGCGAAGAGCCGATCCACCATCATCAGAAACACCAACGAGAAC

ACGGTGACTCTGAAAATGACCAGTCTGACAGCCGCGGACACGGCCACCTA

TTTCTGTGTGAGATATGCTAATATTGGTTATGAGTACTTTAACGTCTGGG

GTCCAGGCACCCTGGTCACCGTCTCTTCAGGTGGAGGCGGTTCAGGCGGC

GGTGGCTCTAGCGGTGGTGGATCGCAGTTTGTGCTGACTCAGTCGCCCTC

TGCATCTGCTGCCCTGGGAGCCTCGGCCAAGCTCACCTGCACCCTGAGCA

GTGCCCACAAGACCTACACCATTGACTGGTATCAGCAGCAGAAAGGGAAG

GCCCCTCGCTACCTGATACAAGTTAAGAGTGATGGAACCTACACCAAGGC

GACCGGGGTCCCTGATCGCTTCTCGGGCTCCAGCTCTGGGGCTGACCGCT

ACCTGATCATCCCCAGCGTCCAGGCTGATGACGAAGCCGACTACTATTGT

GGTACAGATTATACCGGTGGGTATGTGTTCGGCGGGGGGACCCAGCTGAC

CGTCACAGCTAGCGGTGGCGGAGGTTCTGGAGGTGGGGGTTCCTCACCCA

CTGAACCAAGCTCCAAAACCGGTAACCCCAGACACCTGCATGTTCTGATT

GGGACCTCAGTGGTCAAAATCCCTTTCACCATCCTCCTCTTCTTTCTCCT

TCATCGCTGGTGCTCCAACAAAAAAAATGCTGCTGTAATGGACCAAGAGC

CTGCAGGGAACAGAACAGTGAACAGCGAGGATTCTGATGAACAAGACCAT

CAGGAGGTGTCATACGCATAA

Dap12 - T2A - P4-6-gs-KIRS2 - amino acid sequence (thick underlined is Dap12 and T2A sequence; italicized is the CD8 SRP; underlined is the P4-6 scFv, double underline is the KIR2DS2 fragment)

(SEQ ID NO: 102)

MGGLEPCSRFLLLPLLLAVSGLRPVQVQAQSDCSCST

VSPGVLAGIVMGDLVLTVLIALAVYFLGRLVPRGRGAAE

AATRKQRITETESPYQELQGQRSDVYSDLNTQRPYYK

VEGGGEGRGSLLTCGDVEENPGPR*MALPVTALLLPLALLLHAARP*

GSEQLKESGGGLFKPTDTLTLTCTVSGFSLSYYGVNWVRQAPGNGLEWIG

TIGGSGDTYYASWAKSRSTIIRNTNENTVTLKMTSLTAADTATYFCVRYA

NIGYEYFNVWGPGTLVTVSSGGGGSGGGGSSGGGSQFVLTQSPSASAALG

ASAKLTCTLSSAHKTYTIDWYQQQKGKAPRYLIQVKSDGTYTKATGVPDR

FSGSSSGADRYLIIPSVQADDEADYYCGTDYTGGYVFGGGTQLTVTASGG

GGSGGGGSSPTEPSSKTGNPRHLHVLIGTSVVKIPFTILLFFLLHRWCSN

KKNAAVMDQEPAGNRTVNSEDSDEQDHQEVSYA

Dap12 - T2A - P4-10-gs-KIRS2 - nucleotide sequence (Thick underlined is Dap12 and T2A sequence; italicized is the CD8 SRP; underlined is the P4-10 scFv, double underline is KIR2DS2 fragment)

(SEQ ID NO: 103)

ATGGGGGGACTTGAACCCTGCAGCAGGTTCCTGCTCCT

GCCTCTCCTGCTGGCTGTAAGTGGTCTCCGTCC

AGGTCCAGGCCCAGAGCGATTGCAGTTGCTCTAC

GGTGAGCCCGGGCGTGCTGGCAGGGATCGTGATGGG

AGACCTGGTGCTGACAGTGCTCATTGCCCTGGCCGTGT

ACTTCCTGGGCCGGCTGGTCCCTCGGGGGCGAGGG

GCTGCGGAGGCAGCGACCCGGAAACAGCGTATCACT

GAGACCGAGTCGCCTTATCAGGAGCTCCAGGGTCAGA

GGTCGGATGTCTACAGCGACCTCAACACACAGAGG

CCGTATTACAAAGTCGAGGGCGGCGGAGAGGGCAGA

GGAAGTCTTCTAACATGCGGTGACGTGGAGGAGAATCCCGGC

CCTAGG*ATGGCCTTACCAGTGACCGCCTTGCTCCTGCCGCTGGCCTTGCT*

*GCTCCACGCCGCCAGGCCG*GGATCCCAGTCAGTGAAGGAGTCCGAGGGAG

GTCTCTTCAAGCCAACGGATACCCTGACACTCACCTGCACGGTCTCTGGA

TTCTCCCTCAGTAGACATGCACTGACCTGGGTCCGCCAGGCTCCAGGGAA

CGGGCTGGAATGGATCGGAGCCATTGATAACGCTGGTACCACATACTACG

CGAGCTGGGCGAAAAGCCGCTCCACCATCACCAGAAACACCGACCTGCAC

ACGGTGACTCTGAAAATGACCAGTCTGACAGCCTCGGACACGGCTACCTA

TTTCTGTGCGAGAGTCTTTTATGATATTAATAGTGGTTATTATCTGGACG

GCATGGACCTCTGGGGCCCAGGGACCCTCGTCACCGTCTCTTCAGGTGGA

GGCGGTTCAGGCGGCGGTGGCTCTAGCGGTGGTGGATCGCAGTTTGTGCT

GACTCAGTCGCCCTCTGTGTCTGCCGCCCTGGGAGCCTCTGCCAAGCTCA

CCTGCACCCTGAGCAGTGCCCACAAGACCTACACCATTGACTGGTATCAG

CAGCAGCAAGGGGAGGCCCCTCGGTACCTGATGCAAGTTAAGAGTGATGG

AAGCTACACCAAGGGGACCGGGGTCCCTGATCGCTTCTCGGGCTCCAGCT

CTGGGGCTGACCGCTACTTGATCATCCCCAGCGTCCAGGCTGATGACGAA

GCCGGCTACGTTTGTGGTGCAGATGATAACGGTGGGTATGTGTTCGGCGG

AGGGACCCAGCTGACCGTCACAGCTAGCGGTGGCGGAGGTTCTGGAGGTG

GGGGTTCCTCACCCACTGAACCAAGCTCCAAAACCGGTAACCCCAGACAC

CTGCATGTTCTGATTGGGACCTCAGTGGTCAAAATCCCTTTCACCATCCT

CCTCTTCTTTCTCCTTCATCGCTGGTGCTCCAACAAAAAAAATGCTGCTG

TAATGGACCAAGAGCCTGCAGGGAACAGAACAGTGAACAGCGAGGATTCT

GATGAACAAGACCATCAGGAGGTGTCATACGCATAA

Dap12 - T2A - P4-10-gs-KIRS2 - amino acid sequence (Thick underlined is Dap12 and T2A sequence; italicized is the CD8 SRP; underlined is the P4-10 scFv, double underline is KIR2DS2 fragment)

(SEQ ID NO: 104)

MGGLEPCSRFLLLPLLLAVSGLRPVQVQAQSDCSCSTV

SPGVLAGIVMGDLVLTVLIALAVYFLGRLVPRGRGAA

EAATRKQRITETESPYQELQGQRSDVYSDLNTQRPYYK

VEGGGEGRGSLLTCGDVEENPGPR*MALPVTALLTPLALLLHAARP*

GSQSVKESEGGLFKPTDTLTLTCTVSGFSLSRHALTWVRQAPGNGLEWIG

AIDNAGTTYYASWAKSRSTITRNTDLHTVTLKMTSLTASDTATYFCARVF

YDINSGYYLDGMDLWGPGTLVTVSSGGGGSGGGGSSGGGSQFVLTQSPSV

-continued

SAALGASAKLTCTLSSAHKTYTIDWYQQQQGEAPRYLMQVKSDGSYTKGT

GVPDRFSGSSSGADRYLIIPSVQADDEAGYVCGADDNGGYVFGGGTQLTV

-continued

TASGGGGSGGGGSSPTEPSSKTGNPRHLHVLIGTSVVKIPFTILLFFLLH

RWCSNKKNAAVMDQEPAGNRTVNSEDSDEQDHQEVSYA

Vectors encoding CAR constructs are provided below:

Vector P4-6gs encoding CAR (SEQ ID NO: 105)

GTGCACGAGTGGGTTACATCGAACTGGATCTCAACAGCGGTAAGATCCTTGAGAGTTTTCGCCCCGAAGAACGTTTTCCAATGATGAGCA

CTTTTAAAGTTCTGCTATGTGGCGCGGTATTATCCCGTATTGACGCCGGGCAAGAGCAACTCGGTCGCCGCATACACTATTCTCAGAATG

ACTTGGTTGAGTACTCACCAGTCACAGAAAAGCATCTTACGGATGGCATGACAGTAAGAGAATTATGCAGTGCTGCCATAACCATGAGTG

ATAACACTGCGGCCAACTTACTTCTGACAACGATCGGAGGACCGAAGGAGCTAACCGCTTTTTTGCACAACATGGGGGATCATGTAACTC

GCCTTGATCGTTGGGAACCGGAGCTGAATGAAGCCATACCAAACGACGAGCGTGACACCACGATGCCTGTAGCAATGGCAACAACGTTGC

GCAAACTATTAACTGGCGAACTACTTACTCTAGCTTCCCGGCAACAATTAATAGACTGGATGGAGGCGGATAAAGTTGCAGGACCACTTC

TGCGCTCGGCCCTTCCGGCTGGCTGGTTTATTGCTGATAAATCTGGAGCCGGTGAGCGTGGGTCTCGCGGTATCATTGCAGCACTGGGGC

CAGATGGTAAGCCCTCCCGTATCGTAGTTATCTACACGACGGGGAGTCAGGCAACTATGGATGAACGAAATAGACAGATCGCTGAGATAG

GTGCCTCACTGATTAAGCATTGGTAACTGTCAGACCAAGTTTACTCATATATACTTTAGATTGATTTAAAACTTCATTTTTAATTTAAAA

GGATCTAGGTGAAGATCCTTTTTGATAATCTCATGACCAAAATCCCTTAACGTGAGTTTTCGTTCCACTGAGCGTCAGACCCCGTAGAAA

AGATCAAAGGATCTTCTTGAGATCCTTTTTTTCTGCGCGTAATCTGCTGCTTGCAAACAAAAAAACCACCGCTACCAGCGGTGGTTTGTT

TGCCGGATCAAGAGCTACCAACTCTTTTTCCGAAGGTAACTGGCTTCAGCAGAGCGCAGATACCAAATACTGTTCTTCTAGTGTAGCCGT

AGTTAGGCCACCACTTCAAGAACTCTGTAGCACCGCCTACATACCTCGCTCTGCTAATCCTGTTACCAGTGGCTGCTGCCAGTGGCGATA

AGTCGTGTCTTACCGGGTTGGACTCAAGACGATAGTTACCGGATAAGGCGCAGCGGTCGGGCTGAACGGGGGGTTCGTGCACACAGCCCA

GCTTGGAGCGAACGACCTACACCGAACTGAGATACCTACAGCGTGAGCTATGAGAAAGCGCCACGCTTCCCGAAGGGAGAAAGGCGGACA

GGTATCCGGTAAGCGGCAGGGTCGGAACAGGAGAGCGCACGAGGGAGCTTCCAGGGGGAAACGCCTGGTATCTTTATAGTCCTGTCGGGT

TTCGCCACCTCTGACTTGAGCGTCGATTTTTGTGATGCTCGTCAGGGGGGCGGAGCCTATGGAAAAACGCCAGCAACGCGGCCTTTTTAC

GGTTCCTGGCCTTTTGCTGGCCTTTTGCTCACATGTTCTTTCCTGCGTTATCCCCTGATTCTGTGGATAACCGTATTACCGCCTTTGAGT

GAGCTGATACCGCTCGCCGCAGCCGAACGACCGAGCGCAGCGAGTCAGTGAGCGAGGAAGCGGAAGAGCGCCCAATACGCAAACCGCCTC

TCCCCGCGCGTTGGCCGATTCATTAATGCAGCTGGCACGACAGGTTTCCCGACTGGAAAGCGGGCAGTGAGCGCAACGCAATTAATGTGA

GTTAGCTCACTCATTAGGCACCCCAGGCTTTACACTTTATGCTTCCGGCTCGTATGTTGTGTGGAATTGTGAGCGGATAACAATTTCACA

CAGGAAACAGCTATGACCATGATTACGCCAAGCGCGCAATTAACCCTCACTAAAGGGAACAAAAGCTGGAGCTGCAAGCTTAATGTAGTC

TTATGCAATACTCTTGTAGTCTTGCAACATGGTAACGATGAGTTAGCAACATGCCTTACAAGGAGAGAAAAAGCACCGTGCATGCCGATT

GGTGGAAGTAAGGTGGTACGATCGTGCCTTATTAGGAAGGCAACAGACGGGTCTGACATGGATTGGACGAACCACTGAATTGCCGCATTG

CAGAGATATTGTATTTAAGTGCCTAGCTCGATACATAAACGGGTCTCTCTGGTTAGACCAGATCTGAGCCTGGGAGCTCTCTGGCTAACT

AGGGAACCCACTGCTTAAGCCTCAATAAAGCTTGCCTTGAGTGCTTCAAGTAGTGTGTGCCCGTCTGTTGTGTGACTCTGGTAACTAGAG

ATCCCTCAGACCCTTTTAGTCAGTGTGGAAAATCTCTAGCAGTGGCGCCCGAACAGGGACTTGAAAGCGAAAGGGAAACCAGAGGAGCTC

TCTCGACGCAGGACTCGGCTTGCTGAAGCGCGCACGGCAAGAGGCGAGGGGCGGCGACTGGTGAGTACGCCAAAAATTTTGACTAGCGGA

GGCTAGAAGGAGAGAGATGGGTGCGAGAGCGTCAGTATTAAGCGGGGGAGAATTAGATCGCGATGGGAAAAAATTCGGTTAAGGCCAGGG

GGAAAGAAAAAATATAAATTAAAACATATAGTATGGGCAAGCAGGGAGCTAGAACGATTCGCAGTTAATCCTGGCCTGTTAGAAACATCA

GAAGGCTGTAGACAAATACTGGGACAGCTACAACCATCCCTTCAGACAGGATCAGAAGAACTTAGATCATTATATAATACAGTAGCAACC

CTCTATTGTGTGCATCAAAGGATAGAGATAAAAGACACCAAGGAAGCTTTAGACAAGATAGAGGAAGAGCAAAACAAAAGTAAGACCACC

GCACAGCAAGCGGCCGCTGATCTTCAGACCTGGAGGAGGAGATATGAGGGACAATTGGAGAAGTGAATTATATAAATATAAAGTAGTAAA

AATTGAACCATTAGGAGTAGCACCCACCAAGGCAAAGAGAAGAGTGGTGCAGAGAGAAAAAAGAGCAGTGGGAATAGGAGCTTTGTTCCT

TGGGTTCTTGGGAGCAGCAGGAAGCACTATGGGCGCAGCGTCAATGACGCTGACGGTACAGGCCAGACAATTATTGTCTGGTATAGTGCA

-continued

```
GCAGCAGAACAATTTGCTGAGGGCTATTGAGGCGCAACAGCATCTGTTGCAACTCACAGTCTGGGGCATCAAGCAGCTCCAGGCAAGAAT
CCTGGCTGTGGAAAGATACCTAAAGGATCAACAGCTCCTGGGGATTTGGGGTTGCTCTGGAAAACTCATTTGCACCACTGCTGTGCCTTG
GAATGCTAGTTGGAGTAATAAATCTCTGGAACAGATTTGGAATCACACGACCTGGATGGAGTGGGACAGAGAAATTAACAATTACACAAG
CTTAATACACTCCTTAATTGAAGAATCGCAAAACCAGCAAGAAAAGAATGAACAAGAATTATTGGAATTAGATAAATGGGCAAGTTTGTG
GAATTGGTTTAACATAACAAATTGGCTGTGGTATATAAAATTATTCATAATGATAGTAGGAGGCTTGGTAGGTTTAAGAATAGTTTTTGC
TGTACTTTCTATAGTGAATAGAGTTAGGCAGGGATATTCACCATTATCGTTTCAGACCCACCTCCCAACCCCGAGGGGACCCGACAGGCC
CGAAGGAATAGAAGAAGAAGGTGGAGAGAGAGACAGAGACAGATCCATTCGATTAGTGAACGGATCTCGACGGTATCGATTAGACTGTAG
CCCAGGAATATGGCAGCTAGATTGTACACATTTAGAAGGAAAAGTTATCTTGGTAGCAGTTCATGTAGCCAGTGGATATATAGAAGCAGA
AGTAATTCCAGCAGAGACAGGGCAAGAAACAGCATACTTCCTCTTAAAATTAGCAGGAAGATGGCCAGTAAAAACAGTACATACAGACAA
TGGCAGCAATTTCACCAGTACTACAGTTAAGGCCGCCTGTTGGTGGGCGGGGATCAAGCAGGAATTTGGCATTCCCTACAATCCCCAAAG
TCAAGGAGTAATAGAATCTATGAATAAAGAATTAAAGAAAATTATAGGACAGGTAAGAGATCAGGCTGAACATCTTAAGACAGCAGTACA
AATGGCAGTATTCATCCACAATTTTAAAAGAAAAGGGGGGATTGGGGGGTACAGTGCAGGGGAAAGAATAGTAGACATAATAGCAACAGA
CATACAAACTAAAGAATTACAAAAACAAATTACAAAAATTCAAAATTTTCGGGTTTATTACAGGGACAGCAGAGATCCAGTTTGGCTGCA
TACGCGTCGTGAGGCTCCGGTGCCCGTCAGTGGGCAGAGCGCACATCGCCCACAGTCCCCGAGAAGTTGGGGGGAGGGGTCGGCAATTGA
ACCGGTGCCTAGAGAAGGTGGCGCGGGGTAAACTGGGAAAGTGATGTCGTGTACTGGCTCCGCCTTTTTCCCGAGGGTGGGGGAGAACCG
TATATAAGTGCAGTAGTCGCCGTGAACGTTCTTTTTCGCAACGGGTTTGCCGCCAGAACACAGGTAAGTGCCGTGTGTGGTTCCCGCGGG
CCTGGCCTCTTTACGGGTTATGGCCCTTGCGTGCCTTGAATTACTTCCACCTGGCTGCAGTACGTGATTCTTGATCCCGAGCTTCGGGTT
GGAAGTGGGTGGGAGAGTTCGAGGCCTTGCGCTTAAGGAGCCCCTTCGCCTCGTGCTTGAGTTGAGGCCTGGCCTGGGCGCTGGGGCCGC
CGCGTGCGAATCTGGTGGCACCTTCGCGCCTGTCTCGCTGCTTTCGATAAGTCTCTAGCCATTTAAAATTTTTGATGACCTGCTGCGACG
CTTTTTTTCTGGCAAGATAGTCTTGTAAATGCGGGCCAAGATCTGCACACTGGTATTTCGGTTTTTGGGGCCGCGGGCGGCGACGGGGCC
CGTGCGTCCCAGCGCACATGTTCGGCGAGGCGGGGCCTGCGAGCGCGGCCACCGAGAATCGGACGGGGGTAGTCTCAAGCTGGCCGGCCT
GCTCTGGTGCCTGGCCTCGCGCCGCCGTGTATCGCCCCGCCCTGGGCGGCAAGGCTGGCCCGGTCGGCACCAGTTGCGTGAGCGGAAAGA
TGGCCGCTTCCCGGCCCTGCTGCAGGGAGCTCAAAATGGAGGACGCGGCGCTCGGGAGAGCGGGCGGGTGAGTCACCCACACAAAGGAAA
AGGGCCTTTCCGTCCTCAGCCGTCGCTTCATGTGACTCCACTGAGTACCGGGCGCCGTCCAGGCACCTCGATTAGTTCTCGTGCTTTTGG
AGTACGTCGTCTTTAGGTTGGGGGGAGGGGTTTTATGCGATGGAGTTTCCCCACACTGAGTGGGTGGAGACTGAAGTTAGGCCAGCTTGG
CACTTGATGTAATTCTCCTTGGAATTTGCCCTTTTTGAGTTTGGATCTTGGTTCATTCTCAAGCCTCAGACAGTGGTTCAAAGTTTTTTT
CTTCCATTTCAGGTGTCGTGAGCTAGAGCCACCATGGAGTTTGGGCTGAGCTGGCTTTTTCTTGTGGCTATTTTAAAAGGTGTCCAGTGC
GGATCCGAGCAGCTGAAGGAGTCCGGGGGAGGTCTCTTCAAGCCAACGGATACCCTGACACTCACCTGCACAGTCTCTGGATTCTCCCTC
AGTTACTATGGAGTGAACTGGGTCCGCCAGGCTCCAGGGAACGGGCTGGAATGGATCGGAACCATTGGTGGTAGTGGTGACACATACTAC
GCGAGCTGGGCGAAGAGCCGATCCACCATCATCAGAAACACCAACGAGAACACGGTGACTCTGAAAATGACCAGTCTGACAGCCGCGGAC
ACGGCCACCTATTTCTGTGTGAGATATGCTAATATTGGTTATGAGTACTTTAACGTCTGGGGTCCAGGCACCCTGGTCACCGTCTCTTCA
GGTGGAGGCGGTTCAGGCGGCGGTGGCTCTAGCGGTGGTGGATCGCAGTTTGTGCTGACTCAGTCGCCCTCTGCATCTGCTGCCCTGGGA
GCCTCGGCCAAGCTCACCTGCACCCTGAGCAGTGCCCACAAGACCTACACCATTGACTGGTATCAGCAGCAGAAAGGGAAGGCCCCTCGC
TACCTGATACAAGTTAAGAGTGATGGAACCTACACCAAGGCGACCGGGGTCCCTGATCGCTTCTCGGGCTCCAGCTCTGGGGCTGACCGC
TACCTGATCATCCCCAGCGTCCAGGCTGATGACGAAGCCGACTACTATTGTGGTACAGATTATACCGGTGGGTATGTGTTCGGCGGGGGG
ACCCAGCTGACCGTCACAGCTAGCGGTGGCGGAGGTTCTGGAGGTGGAGGTTCCTCCGGAATCTACATCTGGGCCCCTCTGGCCGGCACC
TGTGGCGTGCTGCTGCTGTCCCTGGTCATCACCCTGTACTGCAAGCGGGGCAGAAAGAAGCTGCTGTACATCTTCAAGCAGCCCTTCATG
CGGCCTGTGCAGACCACACAGGAAGAGGACGGCTGTAGCTGTAGATTCCCCGAGGAAGAGGAAGGCGGCTGCGAGCTGAGAGTGAAGTTC
AGCAGAAGCGCCGACGCCCCTGCCTATCAGCAGGGCCAGAACCAGCTGTACAACGAGCTGAACCTGGGCAGACGGGAGGAATACGACGTG
CTGGACAAGAGAAGAGGCCGGGACCCTGAGATGGGCGGCAAGCCCAGACGGAAGAACCCCCAGGAAGGCCTGTATAACGAACTGCAGAAA
GACAAGATGGCCGAGGCCTACAGCGAGATCGGCATGAAGGGCGAGCGGAGAAGAGGCAAGGGCCATGACGGCCTGTACCAGGGCCTGAGC
```

-continued

ACCGCCACCAAGGACACCTACGACGCCCTGCACATGCAGGCCCTGCCTCCAAGATGAGTCGACAATCAACCTCTGGATTACAAAATTTGT

GAAAGATTGACTGGTATTCTTAACTATGTTGCTCCTTTTACGCTATGTGGATACGCTGCTTTAATGCCTTTGTATCATGCTATTGCTTCC

CGTATGGCTTTCATTTTCTCCTCCTTGTATAAATCCTGGTTGCTGTCTCTTTATGAGGAGTTGTGGCCCGTTGTCAGGCAACGTGGCGTG

GTGTGCACTGTGTTTGCTGACGCAACCCCCACTGGTTGGGGCATTGCCACCACCTGTCAGCTCCTTTCCGGGACTTTCGCTTTCCCCCTC

CCTATTGCCACGGCGGAACTCATCGCCGCCTGCCTTGCCCGCTGCTGGACAGGGGCTCGGCTGTTGGGCACTGACAATTCCGTGGTGTTG

TCGGGGAAGCTGACGTCCTTTCCTTGGCTGCTCGCCTGTGTTGCCACCTGGATTCTGCGCGGGACGTCCTTCTGCTACGTCCCTTCGGCC

CTCAATCCAGCGGACCTTCCTTCCCGCGGCCTGCTGCCGGCTCTGCGGCCTCTTCCGCGTCTTCGCCTTCGCCCTCAGACGAGTCGGATC

TCCCTTTGGGCCGCCTCCCCGCCTGGAATTCGAGCTCGGTACCTTTAAGACCAATGACTTACAAGGCAGCTGTAGATCTTAGCCACTTTT

TAAAAGAAAAGGGGGGACTGGAAGGGCTAATTCACTCCCAACGAAGACAAGATCTGCTTTTTGCTTGTACTGGGTCTCTCTGGTTAGACC

AGATCTGAGCCTGGGAGCTCTCTGGCTAACTAGGGAACCCACTGCTTAAGCCTCAATAAAGCTTGCCTTGAGTGCTTCAAGTAGTGTGTG

CCCGTCTGTTGTGTGACTCTGGTAACTAGAGATCCCTCAGACCCTTTTAGTCAGTGTGGAAAATCTCTAGCAGTAGTAGTTCATGTCATC

TTATTATTCAGTATTTATAACTTGCAAAGAAATGAATATCAGAGAGTGAGAGGAACTTGTTTATTGCAGCTTATAATGGTTACAAATAAA

GCAATAGCATCACAAATTTCACAAATAAAGCATTTTTTTCACTGCATTCTAGTTGTGGTTTGTCCAAACTCATCAATGTATCTTATCATG

TCTGGCTCTAGCTATCCCGCCCCTAACTCCGCCCAGTTCCGCCCATTCTCCGCCCCATGGCTGACTAATTTTTTTTATTTATGCAGAGGC

CGAGGCCGCCTCGGCCTCTGAGCTATTCCAGAAGTAGTGAGGAGGCTTTTTTGGAGGCCTAGCTAGGGACGTACCCAATTCGCCCTATAG

TGAGTCGTATTACGCGCGCTCACTGGCCGTCGTTTTACAACGTCGTGACTGGGAAAACCCTGGCGTTACCCAACTTAATCGCCTTGCAGC

ACATCCCCCTTTCGCCAGCTGGCGTAATAGCGAAGAGGCCCGCACCGATCGCCCTTCCCAACAGTTGCGCAGCCTGAATGGCGAATGGGA

CGCGCCCTGTAGCGGCGCATTAAGCGCGGCGGGTGTGGTGGTTACGCGCAGCGTGACCGCTACACTTGCCAGCGCCCTAGCGCCCGCTCC

TTTCGCTTTCTTCCCTTCCTTTCTCGCCACGTTCGCCGGCTTTCCCCGTCAAGCTCTAAATCGGGGGCTCCCTTTAGGGTTCCGATTTAG

TGCTTTACGGCACCTCGACCCCAAAAAACTTGATTAGGGTGATGGTTCACGTAGTGGGCCATCGCCCTGATAGACGGTTTTTCGCCCTTT

GACGTTGGAGTCCACGTTCTTTAATAGTGGACTCTTGTTCCAAACTGGAACAACACTCAACCCTATCTCGGTCTATTCTTTTGATTTATA

AGGGATTTTGCCGATTTCGGCCTATTGGTTAAAAAATGAGCTGATTTAACAAAAATTTAACGCGAATTTTAACAAAATATTAACGCTTAC

AATTTAGGTGGCACTTTTCGGGGAAATGTGCGCGGAACCCCTATTTGTTTATTTTTCTAAATACATTCAAATATGTATCCGCTCATGAGA

CAATAACCCTGATAAATGCTTCAATAATATTGAAAAAGGAAGAGTATGAGTATTCAACATTTCCGTGTCGCCCTTATTCCCTTTTTTGCG

GCATTTTGCCTTCCTGTTTTTGCTCACCCAGAAACGCTGGTGAAAGTAAAAGATGCTGAAGATCAGTTGG

Vector P4-10gs encoding CAR (SEQ ID NO: 106)

GTGCACGAGTGGGTTACATCGAACTGGATCTCAACAGCGGTAAGATCCTTGAGAGTTTTCGCCCCGAAGAACGTTTTCCAATGATGAGCA

CTTTTAAAGTTCTGCTATGTGGCGCGGTATTATCCCGTATTGACGCCGGGCAAGAGCAACTCGGTCGCCGCATACACTATTCTCAGAATG

ACTTGGTTGAGTACTCACCAGTCACAGAAAAGCATCTTACGGATGGCATGACAGTAAGAGAATTATGCAGTGCTGCCATAACCATGAGTG

ATAACACTGCGGCCAACTTACTTCTGACAACGATCGGAGGACCGAAGGAGCTAACCGCTTTTTTGCACAACATGGGGGATCATGTAACTC

GCCTTGATCGTTGGGAACCGGAGCTGAATGAAGCCATACCAAACGACGAGCGTGACACCACGATGCCTGTAGCAATGGCAACAACGTTGC

GCAAACTATTAACTGGCGAACTACTTACTCTAGCTTCCCGGCAACAATTAATAGACTGGATGGAGGCGGATAAAGTTGCAGGACCACTTC

TGCGCTCGGCCCTTCCGGCTGGCTGGTTTATTGCTGATAAATCTGGAGCCGGTGAGCGTGGGTCTCGCGGTATCATTGCAGCACTGGGGC

CAGATGGTAAGCCCTCCCGTATCGTAGTTATCTACACGACGGGGAGTCAGGCAACTATGGATGAACGAAATAGACAGATCGCTGAGATAG

GTGCCTCACTGATTAAGCATTGGTAACTGTCAGACCAAGTTTACTCATATATACTTTAGATTGATTTAAAACTTCATTTTTAATTTAAAA

GGATCTAGGTGAAGATCCTTTTTGATAATCTCATGACCAAAATCCCTTAACGTGAGTTTTCGTTCCACTGAGCGTCAGACCCCGTAGAAA

AGATCAAAGGATCTTCTTGAGATCCTTTTTTTCTGCGCGTAATCTGCTGCTTGCAAACAAAAAAACCACCGCTACCAGCGGTGGTTTGTT

TGCCGGATCAAGAGCTACCAACTCTTTTTCCGAAGGTAACTGGCTTCAGCAGAGCGCAGATACCAAATACTGTTCTTCTAGTGTAGCCGT

AGTTAGGCCACCACTTCAAGAACTCTGTAGCACCGCCTACATACCTCGCTCTGCTAATCCTGTTACCAGTGGCTGCTGCCAGTGGCGATA

AGTCGTGTCTTACCGGGTTGGACTCAAGACGATAGTTACCGGATAAGGCGCAGCGGTCGGGCTGAACGGGGGGTTCGTGCACACAGCCCA

-continued

GCTTGGAGCGAACGACCTACACCGAACTGAGATACCTACAGCGTGAGCTATGAGAAAGCGCCACGCTTCCCGAAGGGAGAAAGGCGGACA

GGTATCCGGTAAGCGGCAGGGTCGGAACAGGAGAGCGCACGAGGGAGCTTCCAGGGGGAAACGCCTGGTATCTTTATAGTCCTGTCGGGT

TTCGCCACCTCTGACTTGAGCGTCGATTTTTGTGATGCTCGTCAGGGGGGCGGAGCCTATGGAAAAACGCCAGCAACGCGGCCTTTTTAC

GGTTCCTGGCCTTTTGCTGGCCTTTTGCTCACATGTTCTTTCCTGCGTTATCCCCTGATTCTGTGGATAACCGTATTACCGCCTTTGAGT

GAGCTGATACCGCTCGCCGCAGCCGAACGACCGAGCGCAGCGAGTCAGTGAGCGAGGAAGCGGAAGAGCGCCCAATACGCAAACCGCCTC

TCCCCGCGCGTTGGCCGATTCATTAATGCAGCTGGCACGACAGGTTTCCCGACTGGAAAGCGGGCAGTGAGCGCAACGCAATTAATGTGA

GTTAGCTCACTCATTAGGCACCCCAGGCTTTACACTTTATGCTTCCGGCTCGTATGTTGTGTGGAATTGTGAGCGGATAACAATTTCACA

CAGGAAACAGCTATGACCATGATTACGCCAAGCGCGCAATTAACCCTCACTAAAGGGAACAAAAGCTGGAGCTGCAAGCTTAATGTAGTC

TTATGCAATACTCTTGTAGTCTTGCAACATGGTAACGATGAGTTAGCAACATGCCTTACAAGGAGAGAAAAAGCACCGTGCATGCCGATT

GGTGGAAGTAAGGTGGTACGATCGTGCCTTATTAGGAAGGCAACAGACGGGTCTGACATGGATTGGACGAACCACTGAATTGCCGCATTG

CAGAGATATTGTATTTAAGTGCCTAGCTCGATACATAAACGGGTCTCTCTGGTTAGACCAGATCTGAGCCTGGGAGCTCTCTGGCTAACT

AGGGAACCCACTGCTTAAGCCTCAATAAAGCTTGCCTTGAGTGCTTCAAGTAGTGTGTGCCCGTCTGTTGTGTGACTCTGGTAACTAGAG

ATCCCTCAGACCCTTTTAGTCAGTGTGGAAAATCTCTAGCAGTGGCGCCCGAACAGGGACTTGAAAGCGAAAGGGAAACCAGAGGAGCTC

TCTCGACGCAGGACTCGGCTTGCTGAAGCGCGCACGGCAAGAGGCGAGGGGCGGCGACTGGTGAGTACGCCAAAAATTTTGACTAGCGGA

GGCTAGAAGGAGAGAGATGGGTGCGAGAGCGTCAGTATTAAGCGGGGGAGAATTAGATCGCGATGGGAAAAAATTCGGTTAAGGCCAGGG

GGAAAGAAAAAATATAAATTAAAACATATAGTATGGGCAAGCAGGGAGCTAGAACGATTCGCAGTTAATCCTGGCCTGTTAGAAACATCA

GAAGGCTGTAGACAAATACTGGGACAGCTACAACCATCCCTTCAGACAGGATCAGAAGAACTTAGATCATTATATAATACAGTAGCAACC

CTCTATTGTGTGCATCAAAGGATAGAGATAAAAGACACCAAGGAAGCTTTAGACAAGATAGAGGAAGAGCAAAACAAAAGTAAGACCACC

GCACAGCAAGCGGCCGCTGATCTTCAGACCTGGAGGAGGAGATATGAGGGACAATTGGAGAAGTGAATTATATAAATATAAAGTAGTAAA

AATTGAACCATTAGGAGTAGCACCCACCAAGGCAAAGAGAAGAGTGGTGCAGAGAGAAAAAAGAGCAGTGGGAATAGGAGCTTTGTTCCT

TGGGTTCTTGGGAGCAGCAGGAAGCACTATGGGCGCAGCGTCAATGACGCTGACGGTACAGGCCAGACAATTATTGTCTGGTATAGTGCA

GCAGCAGAACAATTTGCTGAGGGCTATTGAGGCGCAACAGCATCTGTTGCAACTCACAGTCTGGGGCATCAAGCAGCTCCAGGCAAGAAT

CCTGGCTGTGGAAAGATACCTAAAGGATCAACAGCTCCTGGGGATTTGGGGTTGCTCTGGAAAACTCATTTGCACCACTGCTGTGCCTTG

GAATGCTAGTTGGAGTAATAAATCTCTGGAACAGATTTGGAATCACACGACCTGGATGGAGTGGGACAGAGAAATTAACAATTACACAAG

CTTAATACACTCCTTAATTGAAGAATCGCAAAACCAGCAAGAAAAGAATGAACAAGAATTATTGGAATTAGATAAATGGGCAAGTTTGTG

GAATTGGTTTAACATAACAAATTGGCTGTGGTATATAAAATTATTCATAATGATAGTAGGAGGCTTGGTAGGTTTAAGAATAGTTTTTGC

TGTACTTTCTATAGTGAATAGAGTTAGGCAGGGATATTCACCATTATCGTTTCAGACCCACCTCCCAACCCCGAGGGGACCCGACAGGCC

CGAAGGAATAGAAGAAGAAGGTGGAGAGAGAGACAGAGACAGATCCATTCGATTAGTGAACGGATCTCGACGGTATCGATTAGACTGTAG

CCCAGGAATATGGCAGCTAGATTGTACACATTTAGAAGGAAAAGTTATCTTGGTAGCAGTTCATGTAGCCAGTGGATATATAGAAGCAGA

AGTAATTCCAGCAGAGACAGGGCAAGAAACAGCATACTTCCTCTTAAAATTAGCAGGAAGATGGCCAGTAAAAACAGTACATACAGACAA

TGGCAGCAATTTCACCAGTACTACAGTTAAGGCCGCCTGTTGGTGGGCGGGGATCAAGCAGGAATTTGGCATTCCCTACAATCCCCAAAG

TCAAGGAGTAATAGAATCTATGAATAAAGAATTAAAGAAAATTATAGGACAGGTAAGAGATCAGGCTGAACATCTTAAGACAGCAGTACA

AATGGCAGTATTCATCCACAATTTTAAAAGAAAAGGGGGGATTGGGGGGTACAGTGCAGGGGAAAGAATAGTAGACATAATAGCAACAGA

CATACAAACTAAAGAATTACAAAAACAAATTACAAAAATTCAAAATTTTCGGGTTTATTACAGGGACAGCAGAGATCCAGTTTGGCTGCA

TACGCGTCGTGAGGCTCCGGTGCCCGTCAGTGGGCAGAGCGCACATCGCCCACAGTCCCCGAGAAGTTGGGGGGAGGGGTCGGCAATTGA

ACCGGTGCCTAGAGAAGGTGGCGCGGGGTAAACTGGGAAAGTGATGTCGTGTACTGGCTCCGCCTTTTTCCCGAGGGTGGGGGAGAACCG

TATATAAGTGCAGTAGTCGCCGTGAACGTTCTTTTTCGCAACGGGTTTGCCGCCAGAACACAGGTAAGTGCCGTGTGTGGTTCCCGCGGG

CCTGGCCTCTTTACGGGTTATGGCCCTTGCGTGCCTTGAATTACTTCCACCTGGCTGCAGTACGTGATTCTTGATCCCGAGCTTCGGGTT

GGAAGTGGGTGGGAGAGTTCGAGGCCTTGCGCTTAAGGAGCCCCTTCGCCTCGTGCTTGAGTTGAGGCCTGGCCTGGGCGCTGGGGCCGC

CGCGTGCGAATCTGGTGGCACCTTCGCGCCTGTCTCGCTGCTTTCGATAAGTCTCTAGCCATTTAAAATTTTTGATGACCTGCTGCGACG

CTTTTTTTCTGGCAAGATAGTCTTGTAAATGCGGGCCAAGATCTGCACACTGGTATTTCGGTTTTTGGGGCCGCGGGCGGCGACGGGGCC

-continued

CGTGCGTCCCAGCGCACATGTTCGGCGAGGCGGGGCCTGCGAGCGCGGCCACCGAGAATCGGACGGGGGTAGTCTCAAGCTGGCCGGCCT

GCTCTGGTGCCTGGCCTCGCGCCGCCGTGTATCGCCCCGCCCTGGGCGGCAAGGCTGGCCCGGTCGGCACCAGTTGCGTGAGCGGAAAGA

TGGCCGCTTCCCGGCCCTGCTGCAGGGAGCTCAAAATGGAGGACGCGGCGCTCGGGAGAGCGGGCGGGTGAGTCACCCACACAAAGGAAA

AGGGCCTTTCCGTCCTCAGCCGTCGCTTCATGTGACTCCACTGAGTACCGGGCGCCGTCCAGGCACCTCGATTAGTTCTCGTGCTTTTGG

AGTACGTCGTCTTTAGGTTGGGGGGAGGGGTTTTATGCGATGGAGTTTCCCCACACTGAGTGGGTGGAGACTGAAGTTAGGCCAGCTTGG

CACTTGATGTAATTCTCCTTGGAATTTGCCCTTTTTGAGTTTGGATCTTGGTTCATTCTCAAGCCTCAGACAGTGGTTCAAAGTTTTTTT

CTTCCATTTCAGGTGTCGTGAGCTAGAGCCACCATGGAGTTTGGGCTGAGCTGGCTTTTTCTTGTGGCTATTTTAAAAGGTGTCCAGTGC

GGATCCCAGTCAGTGAAGGAGTCCGAGGGAGGTCTCTTCAAGCCAACGGATACCCTGACACTCACCTGCACGGTCTCTGGATTCTCCCTC

AGTAGACATGCACTGACCTGGGTCCGCCAGGCTCCAGGGAACGGGCTGGAATGGATCGGAGCCATTGATAACGCTGGTACCACATACTAC

GCGAGCTGGGCGAAAAGCCGCTCCACCATCACCAGAAACACCGACCTGCACACGGTGACTCTGAAAATGACCAGTCTGACAGCCTCGGAC

ACGGCTACCTATTTCTGTGCGAGAGTCTTTTATGATATTAATAGTGGTTATTATCTGGACGGCATGGACCTCTGGGGCCCAGGGACCCTC

GTCACCGTCTCTTCAGGTGGAGGCGGTTCAGGCGGCGGTGGCTCTAGCGGTGGTGGATCGCAGTTTGTGCTGACTCAGTCGCCCTCTGTG

TCTGCCGCCCTGGGAGCCTCTGCCAAGCTCACCTGCACCCTGAGCAGTGCCCACAAGACCTACACCATTGACTGGTATCAGCAGCAGCAA

GGGGAGGCCCCTCGGTACCTGATGCAAGTTAAGAGTGATGGAAGCTACACCAAGGGGACCGGGGTCCCTGATCGCTTCTCGGGCTCCAGC

TCTGGGGCTGACCGCTACTTGATCATCCCCAGCGTCCAGGCTGATGACGAAGCCGGCTACGTTTGTGGTGCAGATGATAACGGTGGGTAT

GTGTTCGGCGGAGGGACCCAGCTGACCGTCACAGCTAGCGGTGGCGGAGGTTCTGGAGGTGGAGGTTCCTCCGGAATCTACATCTGGGCC

CCTCTGGCCGGCACCTGTGGCGTGCTGCTGCTGTCCCTGGTCATCACCCTGTACTGCAAGCGGGGCAGAAAGAAGCTGCTGTACATCTTC

AAGCAGCCCTTCATGCGGCCTGTGCAGACCACACAGGAAGAGGACGGCTGTAGCTGTAGATTCCCCGAGGAAGAGGAAGGCGGCTGCGAG

CTGAGAGTGAAGTTCAGCAGAAGCGCCGACGCCCCTGCCTATCAGCAGGGCCAGAACCAGCTGTACAACGAGCTGAACCTGGGCAGACGG

GAGGAATACGACGTGCTGGACAAGAGAAGAGGCCGGGACCCTGAGATGGGCGGCAAGCCCAGACGGAAGAACCCCCAGGAAGGCCTGTAT

AACGAACTGCAGAAAGACAAGATGGCCGAGGCCTACAGCGAGATCGGCATGAAGGGCGAGCGGAGAAGAGGCAAGGGCCATGACGGCCTG

TACCAGGGCCTGAGCACCGCCACCAAGGACACCTACGACGCCCTGCACATGCAGGCCCTGCCTCCAAGATGAGTCGACAATCAACCTCTG

GATTACAAAATTTGTGAAAGATTGACTGGTATTCTTAACTATGTTGCTCCTTTTACGCTATGTGGATACGCTGCTTTAATGCCTTTGTAT

CATGCTATTGCTTCCCGTATGGCTTTCATTTTCTCCTCCTTGTATAAATCCTGGTTGCTGTCTCTTTATGAGGAGTTGTGGCCCGTTGTC

AGGCAACGTGGCGTGGTGTGCACTGTGTTTGCTGACGCAACCCCCACTGGTTGGGGCATTGCCACCACCTGTCAGCTCCTTTCCGGGACT

TTCGCTTTCCCCCTCCCTATTGCCACGGCGGAACTCATCGCCGCCTGCCTTGCCCGCTGCTGGACAGGGGCTCGGCTGTTGGGCACTGAC

AATTCCGTGGTGTTGTCGGGGAAGCTGACGTCCTTTCCTTGGCTGCTCGCCTGTGTTGCCACCTGGATTCTGCGCGGGACGTCCTTCTGC

TACGTCCCTTCGGCCCTCAATCCAGCGGACCTTCCTTCCCGCGGCCTGCTGCCGGCTCTGCGGCCTCTTCCGCGTCTTCGCCTTCGCCCT

CAGACGAGTCGGATCTCCCTTTGGGCCGCCTCCCCGCCTGGAATTCGAGCTCGGTACCTTTAAGACCAATGACTTACAAGGCAGCTGTAG

ATCTTAGCCACTTTTTAAAAGAAAAGGGGGGACTGGAAGGGCTAATTCACTCCCAACGAAGACAAGATCTGCTTTTTGCTTGTACTGGGT

CTCTCTGGTTAGACCAGATCTGAGCCTGGGAGCTCTCTGGCTAACTAGGGAACCCACTGCTTAAGCCTCAATAAAGCTTGCCTTGAGTGC

TTCAAGTAGTGTGTGCCCGTCTGTTGTGTGACTCTGGTAACTAGAGATCCCTCAGACCCTTTTAGTCAGTGTGGAAAATCTCTAGCAGTA

GTAGTTCATGTCATCTTATTATTCAGTATTTATAACTTGCAAAGAAATGAATATCAGAGAGTGAGAGGAACTTGTTTATTGCAGCTTATA

ATGGTTACAAATAAAGCAATAGCATCACAAATTTCACAAATAAAGCATTTTTTTCACTGCATTCTAGTTGTGGTTTGTCCAAACTCATCA

ATGTATCTTATCATGTCTGGCTCTAGCTATCCCGCCCCTAACTCCGCCCAGTTCCGCCCATTCTCCGCCCCATGGCTGACTAATTTTTTT

TATTTATGCAGAGGCCGAGGCCGCCTCGGCCTCTGAGCTATTCCAGAAGTAGTGAGGAGGCTTTTTTGGAGGCCTAGCTAGGGACGTACC

CAATTCGCCCTATAGTGAGTCGTATTACGCGCGCTCACTGGCCGTCGTTTTACAACGTCGTGACTGGGAAAACCCTGGCGTTACCCAACT

TAATCGCCTTGCAGCACATCCCCCTTTCGCCAGCTGGCGTAATAGCGAAGAGGCCCGCACCGATCGCCCTTCCCAACAGTTGCGCAGCCT

GAATGGCGAATGGGACGCGCCCTGTAGCGGCGCATTAAGCGCGGCGGGTGTGGTGGTTACGCGCAGCGTGACCGCTACACTTGCCAGCGC

CCTAGCGCCCGCTCCTTTCGCTTTCTTCCCTTCCTTTCTCGCCACGTTCGCCGGCTTTCCCCGTCAAGCTCTAAATCGGGGGCTCCCTTT

-continued

AGGGTTCCGATTTAGTGCTTTACGGCACCTCGACCCCAAAAAACTTGATTAGGGTGATGGTTCACGTAGTGGGCCATCGCCCTGATAGAC

GGTTTTTCGCCCTTTGACGTTGGAGTCCACGTTCTTTAATAGTGGACTCTTGTTCCAAACTGGAACAACACTCAACCCTATCTCGGTCTA

TTCTTTTGATTTATAAGGGATTTTGCCGATTTCGGCCTATTGGTTAAAAAATGAGCTGATTTAACAAAAATTTAACGCGAATTTTAACAA

AATATTAACGCTTACAATTTAGGTGGCACTTTTCGGGGAAATGTGCGCGGAACCCCTATTTGTTTATTTTTCTAAATACATTCAAATATG

TATCCGCTCATGAGACAATAACCCTGATAAATGCTTCAATAATATTGAAAAAGGAAGAGTATGAGTATTCAACATTTCCGTGTCGCCCTT

ATTCCCTTTTTTGCGGCATTTTGCCTTCCTGTTTTTGCTCACCCAGAAACGCTGGTGAAAGTAAAAGATGCTGAAGATCAGTTGG

Vector P4-6cd8 encoding CAR (SEQ ID NO: 107)

GTGCACGAGTGGGTTACATCGAACTGGATCTCAACAGCGGTAAGATCCTTGAGAGTTTTCGCCCCGAAGAACGTTTTCCAATGATGAGCA

CTTTTAAAGTTCTGCTATGTGGCGCGGTATTATCCCGTATTGACGCCGGGCAAGAGCAACTCGGTCGCCGCATACACTATTCTCAGAATG

ACTTGGTTGAGTACTCACCAGTCACAGAAAAGCATCTTACGGATGGCATGACAGTAAGAGAATTATGCAGTGCTGCCATAACCATGAGTG

ATAACACTGCGGCCAACTTACTTCTGACAACGATCGGAGGACCGAAGGAGCTAACCGCTTTTTTGCACAACATGGGGGATCATGTAACTC

GCCTTGATCGTTGGGAACCGGAGCTGAATGAAGCCATACCAAACGACGAGCGTGACACCACGATGCCTGTAGCAATGGCAACAACGTTGC

GCAAACTATTAACTGGCGAACTACTTACTCTAGCTTCCCGGCAACAATTAATAGACTGGATGGAGGCGGATAAAGTTGCAGGACCACTTC

TGCGCTCGGCCCTTCCGGCTGGCTGGTTTATTGCTGATAAATCTGGAGCCGGTGAGCGTGGGTCTCGCGGTATCATTGCAGCACTGGGGC

CAGATGGTAAGCCCTCCCGTATCGTAGTTATCTACACGACGGGGAGTCAGGCAACTATGGATGAACGAAATAGACAGATCGCTGAGATAG

GTGCCTCACTGATTAAGCATTGGTAACTGTCAGACCAAGTTTACTCATATATACTTTAGATTGATTTAAAACTTCATTTTTAATTTAAAA

GGATCTAGGTGAAGATCCTTTTTGATAATCTCATGACCAAAATCCCTTAACGTGAGTTTTCGTTCCACTGAGCGTCAGACCCCGTAGAAA

AGATCAAAGGATCTTCTTGAGATCCTTTTTTTCTGCGCGTAATCTGCTGCTTGCAAACAAAAAAACCACCGCTACCAGCGGTGGTTTGTT

TGCCGGATCAAGAGCTACCAACTCTTTTTCCGAAGGTAACTGGCTTCAGCAGAGCGCAGATACCAAATACTGTTCTTCTAGTGTAGCCGT

AGTTAGGCCACCACTTCAAGAACTCTGTAGCACCGCCTACATACCTCGCTCTGCTAATCCTGTTACCAGTGGCTGCTGCCAGTGGCGATA

AGTCGTGTCTTACCGGGTTGGACTCAAGACGATAGTTACCGGATAAGGCGCAGCGGTCGGGCTGAACGGGGGGTTCGTGCACACAGCCCA

GCTTGGAGCGAACGACCTACACCGAACTGAGATACCTACAGCGTGAGCTATGAGAAAGCGCCACGCTTCCCGAAGGGAGAAAGGCGGACA

GGTATCCGGTAAGCGGCAGGGTCGGAACAGGAGAGCGCACGAGGGAGCTTCCAGGGGGAAACGCCTGGTATCTTTATAGTCCTGTCGGGT

TTCGCCACCTCTGACTTGAGCGTCGATTTTTGTGATGCTCGTCAGGGGGGCGGAGCCTATGGAAAAACGCCAGCAACGCGGCCTTTTTAC

GGTTCCTGGCCTTTTGCTGGCCTTTTGCTCACATGTTCTTTCCTGCGTTATCCCCTGATTCTGTGGATAACCGTATTACCGCCTTTGAGT

GAGCTGATACCGCTCGCCGCAGCCGAACGACCGAGCGCAGCGAGTCAGTGAGCGAGGAAGCGGAAGAGCGCCCAATACGCAAACCGCCTC

TCCCCGCGCGTTGGCCGATTCATTAATGCAGCTGGCACGACAGGTTTCCCGACTGGAAAGCGGGCAGTGAGCGCAACGCAATTAATGTGA

GTTAGCTCACTCATTAGGCACCCCAGGCTTTACACTTTATGCTTCCGGCTCGTATGTTGTGTGGAATTGTGAGCGGATAACAATTTCACA

CAGGAAACAGCTATGACCATGATTACGCCAAGCGCGCAATTAACCCTCACTAAAGGGAACAAAAGCTGGAGCTGCAAGCTTAATGTAGTC

TTATGCAATACTCTTGTAGTCTTGCAACATGGTAACGATGAGTTAGCAACATGCCTTACAAGGAGAGAAAAAGCACCGTGCATGCCGATT

GGTGGAAGTAAGGTGGTACGATCGTGCCTTATTAGGAAGGCAACAGACGGGTCTGACATGGATTGGACGAACCACTGAATTGCCGCATTG

CAGAGATATTGTATTTAAGTGCCTAGCTCGATACATAAACGGGTCTCTCTGGTTAGACCAGATCTGAGCCTGGGAGCTCTCTGGCTAACT

AGGGAACCCACTGCTTAAGCCTCAATAAAGCTTGCCTTGAGTGCTTCAAGTAGTGTGTGCCCGTCTGTTGTGTGACTCTGGTAACTAGAG

ATCCCTCAGACCCTTTTAGTCAGTGTGGAAAATCTCTAGCAGTGGCGCCCGAACAGGGACTTGAAAGCGAAAGGGAAACCAGAGGAGCTC

TCTCGACGCAGGACTCGGCTTGCTGAAGCGCGCACGGCAAGAGGCGAGGGGCGGCGACTGGTGAGTACGCCAAAAATTTTGACTAGCGGA

GGCTAGAAGGAGAGAGATGGGTGCGAGAGCGTCAGTATTAAGCGGGGGAGAATTAGATCGCGATGGGAAAAAATTCGGTTAAGGCCAGGG

GGAAAGAAAAAATATAAATTAAAACATATAGTATGGGCAAGCAGGGAGCTAGAACGATTCGCAGTTAATCCTGGCCTGTTAGAAACATCA

GAAGGCTGTAGACAAATACTGGGACAGCTACAACCATCCCTTCAGACAGGATCAGAAGAACTTAGATCATTATATAATACAGTAGCAACC

CTCTATTGTGTGCATCAAAGGATAGAGATAAAAGACACCAAGGAAGCTTTAGACAAGATAGAGGAAGAGCAAAACAAAAGTAAGACCACC

GCACAGCAAGCGGCCGCTGATCTTCAGACCTGGAGGAGGAGATATGAGGGACAATTGGAGAAGTGAATTATATAAATATAAAGTAGTAAA

AATTGAACCATTAGGAGTAGCACCCACCAAGGCAAAGAGAAGAGTGGTGCAGAGAGAAAAAAGAGCAGTGGGAATAGGAGCTTTGTTCCT

-continued

TGGGTTCTTGGGAGCAGCAGGAAGCACTATGGGCGCAGCGTCAATGACGCTGACGGTACAGGCCAGACAATTATTGTCTGGTATAGTGCA

GCAGCAGAACAATTTGCTGAGGGCTATTGAGGCGCAACAGCATCTGTTGCAACTCACAGTCTGGGGCATCAAGCAGCTCCAGGCAAGAAT

CCTGGCTGTGGAAAGATACCTAAAGGATCAACAGCTCCTGGGGATTTGGGGTTGCTCTGGAAAACTCATTTGCACCACTGCTGTGCCTTG

GAATGCTAGTTGGAGTAATAAATCTCTGGAACAGATTTGGAATCACACGACCTGGATGGAGTGGGACAGAGAAATTAACAATTACACAAG

CTTAATACACTCCTTAATTGAAGAATCGCAAAACCAGCAAGAAAAGAATGAACAAGAATTATTGGAATTAGATAAATGGGCAAGTTTGTG

GAATTGGTTTAACATAACAAATTGGCTGTGGTATATAAAATTATTCATAATGATAGTAGGAGGCTTGGTAGGTTTAAGAATAGTTTTTGC

TGTACTTTCTATAGTGAATAGAGTTAGGCAGGGATATTCACCATTATCGTTTCAGACCCACCTCCCAACCCCGAGGGGACCCGACAGGCC

CGAAGGAATAGAAGAAGAAGGTGGAGAGAGAGACAGAGACAGATCCATTCGATTAGTGAACGGATCTCGACGGTATCGATTAGACTGTAG

CCCAGGAATATGGCAGCTAGATTGTACACATTTAGAAGGAAAAGTTATCTTGGTAGCAGTTCATGTAGCCAGTGGATATATAGAAGCAGA

AGTAATTCCAGCAGAGACAGGGCAAGAAACAGCATACTTCCTCTTAAAATTAGCAGGAAGATGGCCAGTAAAAACAGTACATACAGACAA

TGGCAGCAATTTCACCAGTACTACAGTTAAGGCCGCCTGTTGGTGGGCGGGGATCAAGCAGGAATTTGGCATTCCCTACAATCCCCAAAG

TCAAGGAGTAATAGAATCTATGAATAAAGAATTAAAGAAAATTATAGGACAGGTAAGAGATCAGGCTGAACATCTTAAGACAGCAGTACA

AATGGCAGTATTCATCCACAATTTTAAAAGAAAAGGGGGGATTGGGGGGTACAGTGCAGGGGAAAGAATAGTAGACATAATAGCAACAGA

CATACAAACTAAAGAATTACAAAAACAAATTACAAAAATTCAAAATTTTCGGGTTTATTACAGGGACAGCAGAGATCCAGTTTGGCTGCA

TACGCGTCGTGAGGCTCCGGTGCCCGTCAGTGGGCAGAGCGCACATCGCCCACAGTCCCCGAGAAGTTGGGGGGAGGGGTCGGCAATTGA

ACCGGTGCCTAGAGAAGGTGGCGCGGGGTAAACTGGGAAAGTGATGTCGTGTACTGGCTCCGCCTTTTTCCCGAGGGTGGGGGAGAACCG

TATATAAGTGCAGTAGTCGCCGTGAACGTTCTTTTTCGCAACGGGTTTGCCGCCAGAACACAGGTAAGTGCCGTGTGTGGTTCCCGCGGG

CCTGGCCTCTTTACGGGTTATGGCCCTTGCGTGCCTTGAATTACTTCCACCTGGCTGCAGTACGTGATTCTTGATCCCGAGCTTCGGGTT

GGAAGTGGGTGGGAGAGTTCGAGGCCTTGCGCTTAAGGAGCCCCTTCGCCTCGTGCTTGAGTTGAGGCCTGGCCTGGGCGCTGGGGCCGC

CGCGTGCGAATCTGGTGGCACCTTCGCGCCTGTCTCGCTGCTTTCGATAAGTCTCTAGCCATTTAAAATTTTTGATGACCTGCTGCGACG

CTTTTTTTCTGGCAAGATAGTCTTGTAAATGCGGGCCAAGATCTGCACACTGGTATTTCGGTTTTTGGGGCCGCGGGCGGCGACGGGGCC

CGTGCGTCCCAGCGCACATGTTCGGCGAGGCGGGGCCTGCGAGCGCGGCCACCGAGAATCGGACGGGGGTAGTCTCAAGCTGGCCGGCCT

GCTCTGGTGCCTGGCCTCGCGCCGCCGTGTATCGCCCCGCCCTGGGCGGCAAGGCTGGCCCGGTCGGCACCAGTTGCGTGAGCGGAAAGA

TGGCCGCTTCCCGGCCCTGCTGCAGGGAGCTCAAAATGGAGGACGCGGCGCTCGGGAGAGCGGGCGGGTGAGTCACCCACACAAAGGAAA

AGGGCCTTTCCGTCCTCAGCCGTCGCTTCATGTGACTCCACTGAGTACCGGGCGCCGTCCAGGCACCTCGATTAGTTCTCGTGCTTTTGG

AGTACGTCGTCTTTAGGTTGGGGGGAGGGGTTTTATGCGATGGAGTTTCCCCACACTGAGTGGGTGGAGACTGAAGTTAGGCCAGCTTGG

CACTTGATGTAATTCTCCTTGGAATTTGCCCTTTTTGAGTTTGGATCTTGGTTCATTCTCAAGCCTCAGACAGTGGTTCAAAGTTTTTTT

CTTCCATTTCAGGTGTCGTGAGCTAGAGCCACCATGGAGTTTGGGCTGAGCTGGCTTTTTCTTGTGGCTATTTTAAAAGGTGTCCAGTGC

GGATCCGAGCAGCTGAAGGAGTCCGGGGGAGGTCTCTTCAAGCCAACGGATACCCTGACACTCACCTGCACAGTCTCTGGATTCTCCCTC

AGTTACTATGGAGTGAACTGGGTCCGCCAGGCTCCAGGGAACGGGCTGGAATGGATCGGAACCATTGGTGGTAGTGGTGACACATACTAC

GCGAGCTGGGCGAAGAGCCGATCCACCATCATCAGAAACACCAACGAGAACACGGTGACTCTGAAAATGACCAGTCTGACAGCCGCGGAC

ACGGCCACCTATTTCTGTGTGAGATATGCTAATATTGGTTATGAGTACTTTAACGTCTGGGGTCCAGGCACCCTGGTCACCGTCTCTTCA

GGTGGAGGCGGTTCAGGCGGCGGTGGCTCTAGCGGTGGTGGATCGCAGTTTGTGCTGACTCAGTCGCCCTCTGCATCTGCTGCCCTGGGA

GCCTCGGCCAAGCTCACCTGCACCCTGAGCAGTGCCCACAAGACCTACACCATTGACTGGTATCAGCAGCAGAAAGGGAAGGCCCCTCGC

TACCTGATACAAGTTAAGAGTGATGGAACCTACACCAAGGCGACCGGGGTCCCTGATCGCTTCTCGGGCTCCAGCTCTGGGGCTGACCGC

TACCTGATCATCCCCAGCGTCCAGGCTGATGACGAAGCCGACTACTATTGTGGTACAGATTATACCGGTGGGTATGTGTTCGGCGGGGGG

ACCCAGCTGACCGTCACAGCTAGCACCACGACGCCAGCGCCGCGACCACCAACACCGGCGCCCACCATCGCGTCGCAGCCCCTGTCCCTG

CGCCCAGAGGCGTGCCGGCCAGCGGCGGGGGGCGCAGTGCACACGAGGGGGCTGGACTTCGCCTGTGATTCCGGAATCTACATCTGGGCC

CCTCTGGCCGGCACCTGTGGCGTGCTGCTGCTGTCCCTGGTCATCACCCTGTACTGCAAGCGGGGCAGAAAGAAGCTGCTGTACATCTTC

AAGCAGCCCTTCATGCGGCCTGTGCAGACCACACAGGAAGAGGACGGCTGTAGCTGTAGATTCCCCGAGGAAGAGGAAGGCGGCTGCGAG

-continued

CTGAGAGTGAAGTTCAGCAGAAGCGCCGACGCCCCTGCCTATCAGCAGGGCCAGAACCAGCTGTACAACGAGCTGAACCTGGGCAGACGG

GAGGAATACGACGTGCTGGACAAGAGAAGAGGCCGGGACCCTGAGATGGGCGGCAAGCCCAGACGGAAGAACCCCCAGGAAGGCCTGTAT

AACGAACTGCAGAAAGACAAGATGGCCGAGGCCTACAGCGAGATCGGCATGAAGGGCGAGCGGAGAAGAGGCAAGGGCCATGACGGCCTG

TACCAGGGCCTGAGCACCGCCACCAAGGACACCTACGACGCCCTGCACATGCAGGCCCTGCCTCCAAGATGAGTCGACAATCAACCTCTG

GATTACAAAATTTGTGAAAGATTGACTGGTATTCTTAACTATGTTGCTCCTTTTACGCTATGTGGATACGCTGCTTTAATGCCTTTGTAT

CATGCTATTGCTTCCCGTATGGCTTTCATTTTCTCCTCCTTGTATAAATCCTGGTTGCTGTCTCTTTATGAGGAGTTGTGGCCCGTTGTC

AGGCAACGTGGCGTGGTGTGCACTGTGTTTGCTGACGCAACCCCCACTGGTTGGGGCATTGCCACCACCTGTCAGCTCCTTTCCGGGACT

TTCGCTTTCCCCCTCCCTATTGCCACGGCGGAACTCATCGCCGCCTGCCTTGCCCGCTGCTGGACAGGGGCTCGGCTGTTGGGCACTGAC

AATTCCGTGGTGTTGTCGGGGAAGCTGACGTCCTTTCCTTGGCTGCTCGCCTGTGTTGCCACCTGGATTCTGCGCGGGACGTCCTTCTGC

TACGTCCCTTCGGCCCTCAATCCAGCGGACCTTCCTTCCCGCGGCCTGCTGCCGGCTCTGCGGCCTCTTCCGCGTCTTCGCCTTCGCCCT

CAGACGAGTCGGATCTCCCTTTGGGCCGCCTCCCCGCCTGGAATTCGAGCTCGGTACCTTTAAGACCAATGACTTACAAGGCAGCTGTAG

ATCTTAGCCACTTTTTAAAAGAAAAGGGGGGACTGGAAGGGCTAATTCACTCCCAACGAAGACAAGATCTGCTTTTTGCTTGTACTGGGT

CTCTCTGGTTAGACCAGATCTGAGCCTGGGAGCTCTCTGGCTAACTAGGGAACCCACTGCTTAAGCCTCAATAAAGCTTGCCTTGAGTGC

TTCAAGTAGTGTGTGCCCGTCTGTTGTGTGACTCTGGTAACTAGAGATCCCTCAGACCCTTTTAGTCAGTGTGGAAAATCTCTAGCAGTA

GTAGTTCATGTCATCTTATTATTCAGTATTTATAACTTGCAAAGAAATGAATATCAGAGAGTGAGAGGAACTTGTTTATTGCAGCTTATA

ATGGTTACAAATAAAGCAATAGCATCACAAATTTCACAAATAAAGCATTTTTTTCACTGCATTCTAGTTGTGGTTTGTCCAAACTCATCA

ATGTATCTTATCATGTCTGGCTCTAGCTATCCCGCCCCTAACTCCGCCCAGTTCCGCCCATTCTCCGCCCCATGGCTGACTAATTTTTTT

TATTTATGCAGAGGCCGAGGCCGCCTCGGCCTCTGAGCTATTCCAGAAGTAGTGAGGAGGCTTTTTTGGAGGCCTAGCTAGGGACGTACC

CAATTCGCCCTATAGTGAGTCGTATTACGCGCGCTCACTGGCCGTCGTTTTACAACGTCGTGACTGGGAAAACCCTGGCGTTACCCAACT

TAATCGCCTTGCAGCACATCCCCCTTTCGCCAGCTGGCGTAATAGCGAAGAGGCCCGCACCGATCGCCCTTCCCAACAGTTGCGCAGCCT

GAATGGCGAATGGGACGCGCCCTGTAGCGGCGCATTAAGCGCGGCGGGTGTGGTGGTTACGCGCAGCGTGACCGCTACACTTGCCAGCGC

CCTAGCGCCCGCTCCTTTCGCTTTCTTCCCTTCCTTTCTCGCCACGTTCGCCGGCTTTCCCCGTCAAGCTCTAAATCGGGGGCTCCCTTT

AGGGTTCCGATTTAGTGCTTTACGGCACCTCGACCCCAAAAAACTTGATTAGGGTGATGGTTCACGTAGTGGGCCATCGCCCTGATAGAC

GGTTTTTCGCCCTTTGACGTTGGAGTCCACGTTCTTTAATAGTGGACTCTTGTTCCAAACTGGAACAACACTCAACCCTATCTCGGTCTA

TTCTTTTGATTTATAAGGGATTTTGCCGATTTCGGCCTATTGGTTAAAAAATGAGCTGATTTAACAAAAATTTAACGCGAATTTTAACAA

AATATTAACGCTTACAATTTAGGTGGCACTTTTCGGGGAAATGTGCGCGGAACCCCTATTTGTTTATTTTTCTAAATACATTCAAATATG

TATCCGCTCATGAGACAATAACCCTGATAAATGCTTCAATAATATTGAAAAAGGAAGAGTATGAGTATTCAACATTTCCGTGTCGCCCTT

ATTCCCTTTTTTGCGGCATTTTGCCTTCCTGTTTTTGCTCACCCAGAAACGCTGGTGAAAGTAAAAGATGCTGAAGATCAGTTGG

Vector P4-10cd8 encoding CAR (SEQ ID NO: 108):

GTGCACGAGTGGGTTACATCGAACTGGATCTCAACAGCGGTAAGATCCTTGAGAGTTTTCGCCCCGAAGAACGTTTTCCAATGATGAGCA

CTTTTAAAGTTCTGCTATGTGGCGCGGTATTATCCCGTATTGACGCCGGGCAAGAGCAACTCGGTCGCCGCATACACTATTCTCAGAATG

ACTTGGTTGAGTACTCACCAGTCACAGAAAAGCATCTTACGGATGGCATGACAGTAAGAGAATTATGCAGTGCTGCCATAACCATGAGTG

ATAACACTGCGGCCAACTTACTTCTGACAACGATCGGAGGACCGAAGGAGCTAACCGCTTTTTTGCACAACATGGGGGATCATGTAACTC

GCCTTGATCGTTGGGAACCGGAGCTGAATGAAGCCATACCAAACGACGAGCGTGACACCACGATGCCTGTAGCAATGGCAACAACGTTGC

GCAAACTATTAACTGGCGAACTACTTACTCTAGCTTCCCGGCAACAATTAATAGACTGGATGGAGGCGGATAAAGTTGCAGGACCACTTC

TGCGCTCGGCCCTTCCGGCTGGCTGGTTTATTGCTGATAAATCTGGAGCCGGTGAGCGTGGGTCTCGCGGTATCATTGCAGCACTGGGGC

CAGATGGTAAGCCCTCCCGTATCGTAGTTATCTACACGACGGGGAGTCAGGCAACTATGGATGAACGAAATAGACAGATCGCTGAGATAG

GTGCCTCACTGATTAAGCATTGGTAACTGTCAGACCAAGTTTACTCATATATACTTTAGATTGATTTAAAACTTCATTTTTAATTTAAAA

GGATCTAGGTGAAGATCCTTTTTGATAATCTCATGACCAAAATCCCTTAACGTGAGTTTTCGTTCCACTGAGCGTCAGACCCCGTAGAAA

AGATCAAAGGATCTTCTTGAGATCCTTTTTTTCTGCGCGTAATCTGCTGCTTGCAAACAAAAAAACCACCGCTACCAGCGGTGGTTTGTT

TGCCGGATCAAGAGCTACCAACTCTTTTTCCGAAGGTAACTGGCTTCAGCAGAGCGCAGATACCAAATACTGTTCTTCTAGTGTAGCCGT

-continued
AGTTAGGCCACCACTTCAAGAACTCTGTAGCACCGCCTACATACCTCGCTCTGCTAATCCTGTTACCAGTGGCTGCTGCCAGTGGCGATA AGTCGTGTCTTACCGGGTTGGACTCAAGACGATAGTTACCGGATAAGGCGCAGCGGTCGGGCTGAACGGGGGGTTCGTGCACACAGCCCA GCTTGGAGCGAACGACCTACACCGAACTGAGATACCTACAGCGTGAGCTATGAGAAAGCGCCACGCTTCCCGAAGGGAGAAAGGCGGACA GGTATCCGGTAAGCGGCAGGGTCGGAACAGGAGAGCGCACGAGGGAGCTTCCAGGGGGAAACGCCTGGTATCTTTATAGTCCTGTCGGGT TTCGCCACCTCTGACTTGAGCGTCGATTTTTGTGATGCTCGTCAGGGGGGCGGAGCCTATGGAAAAACGCCAGCAACGCGGCCTTTTTAC GGTTCCTGGCCTTTTGCTGGCCTTTTGCTCACATGTTCTTTCCTGCGTTATCCCCTGATTCTGTGGATAACCGTATTACCGCCTTTGAGT GAGCTGATACCGCTCGCCGCAGCCGAACGACCGAGCGCAGCGAGTCAGTGAGCGAGGAAGCGGAAGAGCGCCCAATACGCAAACCGCCTC TCCCCGCGCGTTGGCCGATTCATTAATGCAGCTGGCACGACAGGTTTCCCGACTGGAAAGCGGGCAGTGAGCGCAACGCAATTAATGTGA GTTAGCTCACTCATTAGGCACCCCAGGCTTTACACTTTATGCTTCCGGCTCGTATGTTGTGTGGAATTGTGAGCGGATAACAATTTCACA CAGGAAACAGCTATGACCATGATTACGCCAAGCGCGCAATTAACCCTCACTAAAGGGAACAAAAGCTGGAGCTGCAAGCTTAATGTAGTC TTATGCAATACTCTTGTAGTCTTGCAACATGGTAACGATGAGTTAGCAACATGCCTTACAAGGAGAGAAAAAGCACCGTGCATGCCGATT GGTGGAAGTAAGGTGGTACGATCGTGCCTTATTAGGAAGGCAACAGACGGGTCTGACATGGATTGGACGAACCACTGAATTGCCGCATTG CAGAGATATTGTATTTAAGTGCCTAGCTCGATACATAAACGGGTCTCTCTGGTTAGACCAGATCTGAGCCTGGGAGCTCTCTGGCTAACT AGGGAACCCACTGCTTAAGCCTCAATAAAGCTTGCCTTGAGTGCTTCAAGTAGTGTGTGCCCGTCTGTTGTGTGACTCTGGTAACTAGAG ATCCCTCAGACCCTTTTAGTCAGTGTGGAAAATCTCTAGCAGTGGCGCCCGAACAGGGACTTGAAAGCGAAAGGGAAACCAGAGGAGCTC TCTCGACGCAGGACTCGGCTTGCTGAAGCGCGCACGGCAAGAGGCGAGGGGCGGCGACTGGTGAGTACGCCAAAAATTTTGACTAGCGGA GGCTAGAAGGAGAGAGATGGGTGCGAGAGCGTCAGTATTAAGCGGGGGAGAATTAGATCGCGATGGGAAAAAATTCGGTTAAGGCCAGGG GGAAAGAAAAAATATAAATTAAAACATATAGTATGGGCAAGCAGGGAGCTAGAACGATTCGCAGTTAATCCTGGCCTGTTAGAAACATCA GAAGGCTGTAGACAAATACTGGGACAGCTACAACCATCCCTTCAGACAGGATCAGAAGAACTTAGATCATTATATAATACAGTAGCAACC CTCTATTGTGTGCATCAAAGGATAGAGATAAAAGACACCAAGGAAGCTTTAGACAAGATAGAGGAAGAGCAAAACAAAAGTAAGACCACC GCACAGCAAGCGGCCGCTGATCTTCAGACCTGGAGGAGGAGATATGAGGGACAATTGGAGAAGTGAATTATATAAATATAAAGTAGTAAA AATTGAACCATTAGGAGTAGCACCCACCAAGGCAAAGAGAAGAGTGGTGCAGAGAGAAAAAAGAGCAGTGGGAATAGGAGCTTTGTTCCT TGGGTTCTTGGGAGCAGCAGGAAGCACTATGGGCGCAGCGTCAATGACGCTGACGGTACAGGCCAGACAATTATTGTCTGGTATAGTGCA GCAGCAGAACAATTTGCTGAGGGCTATTGAGGCGCAACAGCATCTGTTGCAACTCACAGTCTGGGGCATCAAGCAGCTCCAGGCAAGAAT CCTGGCTGTGGAAAGATACCTAAAGGATCAACAGCTCCTGGGGATTTGGGGTTGCTCTGGAAAACTCATTTGCACCACTGCTGTGCCTTG GAATGCTAGTTGGAGTAATAAATCTCTGGAACAGATTTGGAATCACACGACCTGGATGGAGTGGGACAGAGAAATTAACAATTACACAAG CTTAATACACTCCTTAATTGAAGAATCGCAAAACCAGCAAGAAAAGAATGAACAAGAATTATTGGAATTAGATAAATGGGCAAGTTTGTG GAATTGGTTTAACATAACAAATTGGCTGTGGTATATAAAATTATTCATAATGATAGTAGGAGGCTTGGTAGGTTTAAGAATAGTTTTTGC TGTACTTTCTATAGTGAATAGAGTTAGGCAGGGATATTCACCATTATCGTTTCAGACCCACCTCCCAACCCCGAGGGGACCCGACAGGCC CGAAGGAATAGAAGAAGAAGGTGGAGAGAGAGACAGAGACAGATCCATTCGATTAGTGAACGGATCTCGACGGTATCGATTAGACTGTAG CCCAGGAATATGGCAGCTAGATTGTACACATTTAGAAGGAAAAGTTATCTTGGTAGCAGTTCATGTAGCCAGTGGATATATAGAAGCAGA AGTAATTCCAGCAGAGACAGGGCAAGAAACAGCATACTTCCTCTTAAAATTAGCAGGAAGATGGCCAGTAAAAACAGTACATACAGACAA TGGCAGCAATTTCACCAGTACTACAGTTAAGGCCGCCTGTTGGTGGGCGGGGATCAAGCAGGAATTTGGCATTCCCTACAATCCCCAAAG TCAAGGAGTAATAGAATCTATGAATAAAGAATTAAAGAAAATTATAGGACAGGTAAGAGATCAGGCTGAACATCTTAAGACAGCAGTACA AATGGCAGTATTCATCCACAATTTTAAAAGAAAAGGGGGGATTGGGGGGTACAGTGCAGGGGAAAGAATAGTAGACATAATAGCAACAGA CATACAAACTAAAGAATTACAAAAACAAATTACAAAAATTCAAAATTTTCGGGTTTATTACAGGGACAGCAGAGATCCAGTTTGGCTGCA TACGCGTCGTGAGGCTCCGGTGCCCGTCAGTGGGCAGAGCGCACATCGCCCACAGTCCCCGAGAAGTTGGGGGGAGGGGTCGGCAATTGA ACCGGTGCCTAGAGAAGGTGGCGCGGGGTAAACTGGGAAAGTGATGTCGTGTACTGGCTCCGCCTTTTTCCCGAGGGTGGGGGAGAACCG TATATAAGTGCAGTAGTCGCCGTGAACGTTCTTTTTCGCAACGGGTTTGCCGCCAGAACACAGGTAAGTGCCGTGTGTGGTTCCCGCGGG CCTGGCCTCTTTACGGGTTATGGCCCTTGCGTGCCTTGAATTACTTCCACCTGGCTGCAGTACGTGATTCTTGATCCCGAGCTTCGGGTT GGAAGTGGGTGGGAGAGTTCGAGGCCTTGCGCTTAAGGAGCCCCTTCGCCTCGTGCTTGAGTTGAGGCCTGGCCTGGGCGCTGGGGCCGC -continued CGCGTGCGAATCTGGTGGCACCTTCGCGCCTGTCTCGCTGCTTTCGATAAGTCTCTAGCCATTTAAAATTTTTGATGACCTGCTGCGACG CTTTTTTTCTGGCAAGATAGTCTTGTAAATGCGGGCCAAGATCTGCACACTGGTATTTCGGTTTTTGGGGCCGCGGGCGGCGACGGGGCC CGTGCGTCCCAGCGCACATGTTCGGCGAGGCGGGGCCTGCGAGCGCGGCCACCGAGAATCGGACGGGGGTAGTCTCAAGCTGGCCGGCCT GCTCTGGTGCCTGGCCTCGCGCCGCCGTGTATCGCCCCGCCCTGGGCGGCAAGGCTGGCCCGGTCGGCACCAGTTGCGTGAGCGGAAAGA TGGCCGCTTCCCGGCCCTGCTGCAGGGAGCTCAAAATGGAGGACGCGGCGCTCGGGAGAGCGGGCGGGTGAGTCACCCACACAAAGGAAA AGGGCCTTTCCGTCCTCAGCCGTCGCTTCATGTGACTCCACTGAGTACCGGGCGCCGTCCAGGCACCTCGATTAGTTCTCGTGCTTTTGG AGTACGTCGTCTTTAGGTTGGGGGGAGGGGTTTTATGCGATGGAGTTTCCCCACACTGAGTGGGTGGAGACTGAAGTTAGGCCAGCTTGG CACTTGATGTAATTCTCCTTGGAATTTGCCCTTTTTGAGTTTGGATCTTGGTTCATTCTCAAGCCTCAGACAGTGGTTCAAAGTTTTTTT CTTCCATTTCAGGTGTCGTGAGCTAGAGCCACCATGGAGTTTGGGCTGAGCTGGCTTTTTCTTGTGGCTATTTTAAAAGGTGTCCAGTGC GGATCCCAGTCAGTGAAGGAGTCCGAGGGAGGTCTCTTCAAGCCAACGGATACCCTGACACTCACCTGCACGGTCTCTGGATTCTCCCTC AGTAGACATGCACTGACCTGGGTCCGCCAGGCTCCAGGGAACGGGCTGGAATGGATCGGAGCCATTGATAACGCTGGTACCACATACTAC GCGAGCTGGGCGAAAAGCCGCTCCACCATCACCAGAAACACCGACCTGCACACGGTGACTCTGAAAATGACCAGTCTGACAGCCTCGGAC ACGGCTACCTATTTCTGTGCGAGAGTCTTTTATGATATTAATAGTGGTTATTATCTGGACGGCATGGACCTCTGGGGCCCAGGGACCCTC GTCACCGTCTCTTCAGGTGGAGGCGGTTCAGGCGGCGGTGGCTCTAGCGGTGGTGGATCGCAGTTTGTGCTGACTCAGTCGCCCTCTGTG TCTGCCGCCCTGGGAGCCTCTGCCAAGCTCACCTGCACCCTGAGCAGTGCCCACAAGACCTACACCATTGACTGGTATCAGCAGCAGCAA GGGGAGGCCCCTCGGTACCTGATGCAAGTTAAGAGTGATGGAAGCTACACCAAGGGGACCGGGGTCCCTGATCGCTTCTCGGGCTCCAGC TCTGGGGCTGACCGCTACTTGATCATCCCCAGCGTCCAGGCTGATGACGAAGCCGGCTACGTTTGTGGTGCAGATGATAACGGTGGGTAT GTGTTCGGCGGAGGGACCCAGCTGACCGTCACAGCTAGCACCACGACGCCAGCGCCGCGACCACCAACACCGGCGCCCACCATCGCGTCG CAGCCCCTGTCCCTGCGCCCAGAGGCGTGCCGGCCAGCGGCGGGGGGCGCAGTGCACACGAGGGGGCTGGACTTCGCCTGTGATTCCGGA ATCTACATCTGGGCCCCTCTGGCCGGCACCTGTGGCGTGCTGCTGCTGTCCCTGGTCATCACCCTGTACTGCAAGCGGGGCAGAAAGAAG CTGCTGTACATCTTCAAGCAGCCCTTCATGCGGCCTGTGCAGACCACACAGGAAGAGGACGGCTGTAGCTGTAGATTCCCCGAGGAAGAG GAAGGCGGCTGCGAGCTGAGAGTGAAGTTCAGCAGAAGCGCCGACGCCCCTGCCTATCAGCAGGGCCAGAACCAGCTGTACAACGAGCTG AACCTGGGCAGACGGGAGGAATACGACGTGCTGGACAAGAGAAGAGGCCGGGACCCTGAGATGGGCGGCAAGCCCAGACGGAAGAACCCC CAGGAAGGCCTGTATAACGAACTGCAGAAAGACAAGATGGCCGAGGCCTACAGCGAGATCGGCATGAAGGGCGAGCGGAGAAGAGGCAAG GGCCATGACGGCCTGTACCAGGGCCTGAGCACCGCCACCAAGGACACCTACGACGCCCTGCACATGCAGGCCCTGCCTCCAAGATGAGTC GACAATCAACCTCTGGATTACAAAATTTGTGAAAGATTGACTGGTATTCTTAACTATGTTGCTCCTTTTACGCTATGTGGATACGCTGCT TTAATGCCTTTGTATCATGCTATTGCTTCCCGTATGGCTTTCATTTTCTCCTCCTTGTATAAATCCTGGTTGCTGTCTCTTTATGAGGAG TTGTGGCCCGTTGTCAGGCAACGTGGCGTGGTGTGCACTGTGTTTGCTGACGCAACCCCCACTGGTTGGGGCATTGCCACCACCTGTCAG CTCCTTTCCGGGACTTTCGCTTTCCCCCTCCCTATTGCCACGGCGGAACTCATCGCCGCCTGCCTTGCCCGCTGCTGGACAGGGGCTCGG CTGTTGGGCACTGACAATTCCGTGGTGTTGTCGGGGAAGCTGACGTCCTTTCCTTGGCTGCTCGCCTGTGTTGCCACCTGGATTCTGCGC GGGACGTCCTTCTGCTACGTCCCTTCGGCCCTCAATCCAGCGGACCTTCCTTCCCGCGGCCTGCTGCCGGCTCTGCGGCCTCTTCCGCGT CTTCGCCTTCGCCCTCAGACGAGTCGGATCTCCCTTTGGGCCGCCTCCCCGCCTGGAATTCGAGCTCGGTACCTTTAAGACCAATGACTT ACAAGGCAGCTGTAGATCTTAGCCACTTTTTAAAAGAAAAGGGGGGACTGGAAGGGCTAATTCACTCCCAACGAAGACAAGATCTGCTTT TTGCTTGTACTGGGTCTCTCTGGTTAGACCAGATCTGAGCCTGGGAGCTCTCTGGCTAACTAGGGAACCCACTGCTTAAGCCTCAATAAA GCTTGCCTTGAGTGCTTCAAGTAGTGTGTGCCCGTCTGTTGTGTGACTCTGGTAACTAGAGATCCCTCAGACCCTTTTAGTCAGTGTGGA AAATCTCTAGCAGTAGTAGTTCATGTCATCTTATTATTCAGTATTTATAACTTGCAAAGAAATGAATATCAGAGAGTGAGAGGAACTTGT TTATTGCAGCTTATAATGGTTACAAATAAAGCAATAGCATCACAAATTTCACAAATAAAGCATTTTTTTCACTGCATTCTAGTTGTGGTT TGTCCAAACTCATCAATGTATCTTATCATGTCTGGCTCTAGCTATCCCGCCCCTAACTCCGCCCAGTTCCGCCCATTCTCCGCCCCATGG CTGACTAATTTTTTTTATTTATGCAGAGGCCGAGGCCGCCTCGGCCTCTGAGCTATTCCAGAAGTAGTGAGGAGGCTTTTTTGGAGGCCT AGCTAGGGACGTACCCAATTCGCCCTATAGTGAGTCGTATTACGCGCGCTCACTGGCCGTCGTTTTACAACGTCGTGACTGGGAAAACCC -continued

```
TGGCGTTACCCAACTTAATCGCCTTGCAGCACATCCCCCTTTCGCCAGCTGGCGTAATAGCGAAGAGGCCCGCACCGATCGCCCTTCCCA

ACAGTTGCGCAGCCTGAATGGCGAATGGGACGCGCCCTGTAGCGGCGCATTAAGCGCGGCGGGTGTGGTGGTTACGCGCAGCGTGACCGC

TACACTTGCCAGCGCCCTAGCGCCCGCTCCTTTCGCTTTCTTCCCTTCCTTTCTCGCCACGTTCGCCGGCTTTCCCCGTCAAGCTCTAAA

TCGGGGGCTCCCTTTAGGGTTCCGATTTAGTGCTTTACGGCACCTCGACCCCAAAAAACTTGATTAGGGTGATGGTTCACGTAGTGGGCC

ATCGCCCTGATAGACGGTTTTTCGCCCTTTGACGTTGGAGTCCACGTTCTTTAATAGTGGACTCTTGTTCCAAACTGGAACAACACTCAA

CCCTATCTCGGTCTATTCTTTTGATTTATAAGGGATTTTGCCGATTTCGGCCTATTGGTTAAAAAATGAGCTGATTTAACAAAAATTTAA

CGCGAATTTTAACAAAATATTAACGCTTACAATTTAGGTGGCACTTTTCGGGGAAATGTGCGCGGAACCCCTATTTGTTTATTTTTCTAA

ATACATTCAAATATGTATCCGCTCATGAGACAATAACCCTGATAAATGCTTCAATAATATTGAAAAAGGAAGAGTATGAGTATTCAACAT

TTCCGTGTCGCCCTTATTCCCTTTTTTGCGGCATTTTGCCTTCCTGTTTTTGCTCACCCAGAAACGCTGGTGAAAGTAAAAGATGCTGAA

GATCAGTTGG
```

Bispecific CARs

In an embodiment a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv, or fragment thereof, have binding specificity for a first epitope and a scFv, or fragment thereof, have binding specificity for a second epitope.

In certain embodiments, the antibody molecule is a multispecific (e.g., a bispecific or a trispecific) antibody molecule. Protocols for generating bispecific or heterodimeric antibody molecules are known in the art; including but not limited to, for example, the "knob in a hole" approach described in, e.g., U.S. Pat. No. 5,731,168; the electrostatic steering Fc pairing as described in, e.g., WO 09/089004, WO 06/106905 and WO 2010/129304; Strand Exchange Engineered Domains (SEED) heterodimer formation as described in, e.g., WO 07/110205; Fab arm exchange as described in, e.g., WO 08/119353, WO 2011/131746, and WO 2013/060867; double antibody conjugate, e.g., by antibody cross-linking to generate a bi-specific structure using a heterobifunctional reagent having an amine-reactive group and a sulfhydryl reactive group as described in, e.g., U.S. Pat. No. 4,433,059; bispecific antibody determinants generated by recombining half antibodies (heavy-light chain pairs or Fabs) from different antibodies through cycle of reduction and oxidation of disulfide bonds between the two heavy chains, as described in, e.g., U.S. Pat. No. 4,444,878; trifunctional antibodies, e.g., three Fab' fragments cross-linked through sulfhdryl reactive groups, as described in, e.g., U.S. Pat. No. 5,273,743; biosynthetic binding proteins, e.g., pair of scFvs cross-linked through C-terminal tails preferably through disulfide or amine-reactive chemical cross-linking, as described in, e.g., U.S. Pat. No. 5,534,254; bifunctional antibodies, e.g., Fab fragments with different binding specificities dimerized through leucine zippers (e.g., c-fos and c-jun) that have replaced the constant domain, as described in, e.g., U.S. Pat. No. 5,582,996; bispecific and oligospecific mono- and oligovalent receptors, e.g., VH-CH1 regions of two antibodies (two Fab fragments) linked through a polypeptide spacer between the CH1 region of one antibody and the VH region of the other antibody typically with associated light chains, as described in, e.g., U.S. Pat. No. 5,591,828; bispecific DNA-antibody conjugates, e.g., crosslinking of antibodies or Fab fragments through a double stranded piece of DNA, as described in, e.g., U.S. Pat. No. 5,635,602; bispecific fusion proteins, e.g., an expression construct containing two scFvs with a hydrophilic helical peptide linker between them and a full constant region, as described in, e.g., U.S. Pat. No. 5,637,481; multivalent and multispecific binding proteins, e.g., dimer of polypeptides having first domain with binding region of Ig heavy chain variable region, and second domain with binding region of Ig light chain variable region, generally termed diabodies (higher order structures are also encompassed creating for bispecifc, trispecific, or tetraspecific molecules, as described in, e.g., U.S. Pat. No. 5,837,242; minibody constructs with linked VL and VH chains further connected with peptide spacers to an antibody hinge region and CH3 region, which can be dimerized to form bispecific/multivalent molecules, as described in, e.g., U.S. Pat. No. 5,837,821; VH and VL domains linked with a short peptide linker (e.g., 5 or 10 amino acids) or no linker at all in either orientation, which can form dimers to form bispecific diabodies; trimers and tetramers, as described in, e.g., U.S. Pat. No. 5,844,094; String of VH domains (or VL domains in family members) connected by peptide linkages with cross-linkable groups at the C-terminus further associated with VL domains to form a series of FVs (or scFvs), as described in, e.g., U.S. Pat. No. 5,864,019; and single chain binding polypeptides with both a VH and a VL domain linked through a peptide linker are combined into multivalent structures through non-covalent or chemical crosslinking to form, e.g., homobivalent, heterobivalent, trivalent, and tetravalent structures using both scFV or diabody type format, as described in, e.g., U.S. Pat. No. 5,869,620. Additional exemplary multispecific and bispecific molecules and methods of making the same are found, for example, in U.S. Pat. Nos. 5,910,573, 5,932,448, 5,959,083, 5,989,830, 6,005,079, 6,239,259, 6,294,353, 6,333,396, 6,476,198, 6,511,663, 6,670,453, 6,743,896, 6,809,185, 6,833,441, 7,129,330, 7,183,076, 7,521,056, 7,527,787, 7,534,866, 7,612,181, US2002004587A1, US2002076406A1, US2002103345A1, US2003207346A1, US2003211078A1, US2004219643A1, US2004220388A1, US2004242847A1, US2005003403A1, US2005004352A1, US2005069552A1, US2005079170A1, US2005100543A1, US2005136049A1, US2005136051A1, US2005163782A1, US2005266425A1, US2006083747A1, US2006120960A1, US2006204493A1, US2006263367A1, US2007004909A1, US2007087381A1, US2007128150A1, US2007141049A1, US2007154901A1, US2007274985A1, US2008050370A1, US2008069820A1, US2008152645A1, US2008171855A1, US2008241884A1, US2008254512A1, US2008260738A1, US2009130106A1, US2009148905A1, US2009155275A1, US2009162359A1, US2009162360A1, US2009175851A1, US2009175867A1, US2009232811A1, US2009234105A1, US2009263392A1, US2009274649A1, EP346087A2, WO0006605A2, WO02072635A2, WO04081051A1, WO06020258A2, WO2007044887A2, WO2007095338A2, WO2007137760A2, WO2008119353A1, WO2009021754A2, WO2009068630A1, WO9103493A1, WO9323537A1, WO9409131A1, WO9412625A2, WO9509917A1, WO9637621A2, WO9964460A1. The contents of the above-referenced applications are incorporated herein by reference in their entireties.

Within each antibody or antibody fragment (e.g., scFv) of a bispecific antibody molecule, the VH can be upstream or downstream of the VL. In some embodiments, the upstream antibody or antibody fragment (e.g., scFv) is arranged with its VH ($VH_1$) upstream of its VL ($VL_1$) and the downstream antibody or antibody fragment (e.g., scFv) is arranged with its VL ($VL_2$) upstream of its VH ($VH_2$), such that the overall bispecific antibody molecule has the arrangement $VH_1$-$VL_1$-$VL_2$-$VH_2$. In other embodiments, the upstream antibody or antibody fragment (e.g., scFv) is arranged with its VL ($VL_1$) upstream of its VH ($VH_1$) and the downstream antibody or antibody fragment (e.g., scFv) is arranged with its VH ($VH_2$) upstream of its $V_L$ ($VL_2$), such that the overall bispecific antibody molecule has the arrangement $VL_1$-$VH_1$-$VH_2$-$VL_2$. Optionally, a linker is disposed between the two antibodies or antibody fragments (e.g., scFvs), e.g., between $VL_1$ and $VL_2$ if the construct is arranged as $VH_1$-$VL_1$-$VL_2$-$VH_2$, or between $VH_1$ and $VH_2$ if the construct is arranged as $VL_1$-$VH_1$-$VH_2$-$VL_2$. The linker may be a linker as described herein, e.g., a ($Gly_4$-Ser)n linker, wherein n is 1, 2, 3, 4, 5, or 6, preferably 4 (SEQ ID NO: 39). In general, the linker between the two scFvs should be long enough to avoid mispairing between the domains of the two scFvs.

Optionally, a linker is disposed between the VL and VH of the first scFv. Optionally, a linker is disposed between the VL and VH of the second scFv. In constructs that have multiple linkers, any two or more of the linkers can be the same or different. Accordingly, in some embodiments, a bispecific CAR comprises VLs, VHs, and optionally one or more linkers in an arrangement as described herein.

In one aspect, the bispecific antibody molecule is characterized by a first immunoglobulin variable domain sequence, e.g., a scFv, which has binding specificity for GFRα4, e.g., comprises a scFv as described herein, e.g., as described in Table 2, or comprises the light chain CDRs and/or heavy chain CDRs from a GFRα4 scFv described herein, and a second immunoglobulin variable domain sequence that has binding specificity for a second epitope on a different antigen. In some aspects the second immunoglobulin variable domain sequence has binding specificity for an antigen expressed on medullary thyroid cancer cells, e.g., an antigen other than GFRα4.

Chimeric TCR

In one aspect, the GFRα4 antibodies and antibody fragments of the present invention (for example, those disclosed in Tables 2) can be grafted to one or more constant domain of a T cell receptor ("TCR") chain, for example, a TCR alpha or TCR beta chain, to create an chimeric TCR that binds specificity to GFRα4. Without being bound by theory, it is believed that chimeric TCRs will signal through the TCR complex upon antigen binding. For example, a GFRα4 scFv as disclosed herein, can be grafted to the constant domain, e.g., at least a portion of the extracellular constant domain, the transmembrane domain and the cytoplasmic domain, of a TCR chain, for example, the TCR alpha chain and/or the TCR beta chain. As another example, a GFRα4 antibody fragment, for example a VL domain as described herein, can be grafted to the constant domain of a TCR alpha chain, and a GFRα4 antibody fragment, for example a VH domain as described herein, can be grafted to the constant domain of a TCR beta chain (or alternatively, a VL domain may be grafted to the constant domain of the TCR beta chain and a VH domain may be grafted to a TCR alpha chain). As another example, the CDRs of a GFRα4 antibody or antibody fragment, e.g., the CDRs of a GFRα4 antibody or antibody fragment as described in Table 2 may be grafted into a TCR alpha and/or beta chain to create a chimeric TCR that binds specifically to GFRα4. For example, the LCDRs disclosed herein may be grafted into the variable domain of a TCR alpha chain and the HCDRs disclosed herein may be grafted to the variable domain of a TCR beta chain, or vice versa. Such chimeric TCRs may be produced by methods known in the art (For example, Willemsen R A et al, Gene Therapy 2000; 7: 1369-1377; Zhang T et al, Cancer Gene Ther 2004; 11: 487-496; Aggen et al, Gene Ther. 2012 April; 19(4):365-74).

Transmembrane Domain

With respect to the transmembrane domain, in various embodiments, the CAR can be designed to comprise a transmembrane domain that is fused to the extracellular domain of the CAR. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In one aspect, the transmembrane domain is one that is associated with one of the other domains of the CAR is used. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another CAR on the CART cell surface. In a different aspect the amino acid sequence of the transmembrane domain may be modified or substituted so as to minimize interactions with the binding domains of the native binding partner present in the same CART.

In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. In one aspect the transmembrane domain is capable of signaling to the intracellular domain(s) whenever the CAR has bound to a target. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. In some instances, a variety of human hinges can be employed as well including the human Ig (immunoglobulin) hinge. In some embodiments, a transmembrane domain may include at least the transmembrane region(s) of a costimulatory molecule, e.g., a MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

In some instances, the transmembrane domain can be attached to the extracellular region of the CAR, e.g., the antigen binding domain of the CAR, via a hinge, e.g., a hinge from a human protein. For example, in one embodiment, the hinge can be a human Ig (immunoglobulin) hinge, e.g., an IgG4 hinge, or a CD8a hinge. In one embodiment, the hinge or spacer comprises (e.g., consists of) the amino acid sequence of SEQ ID NO:2. In one aspect, the transmembrane domain comprises (e.g., consists of) a transmembrane domain of SEQ ID NO: 6.

In one aspect, the hinge or spacer comprises an IgG4 hinge. For example, in one embodiment, the hinge or spacer comprises a hinge of the amino acid sequence ESKYGPPCPPCPAPEFLGGPSVFLFPPKPKDTLMISRTPEVTCVVVDVSQEDPEVQFN WYVDGVEVHNAKTKPREEQFNSTYRVVSVLTVLHQDWLNGKEYKCKVSNKGLPSS IEKTISKAKGQPREPQVYTLPPSQEEMTKNQVSLTCLVKGFYPSDIAVEWESNGQPEN NYKTTPPVLDSDGSFFLYSRLTVDKSRWQEGNVFSCSVMHEALHNHYTQKSLSLSL GKM (SEQ ID NO:3). In some embodiments, the hinge or spacer comprises a hinge encoded by a nucleotide sequence of (SEQ ID NO: 14)

GAGAGCAAGTACGGCCCTCCCTGCCCCCCTTGCCCTGCCCCCGAGTTCCT

GGGCGGACCCAGCGTGTTCCTGTTCCCCCCCAAGCCCAAGGACACCCTGA

TGATCAGCCGGACCCCCGAGGTGACCTGTGTGGTGGTGGACGTGTCCCAG

GAGGACCCCGAGGTCCAGTTCAACTGGTACGTGGACGGCGTGGAGGTGCA

CAACGCCAAGACCAAGCCCCGGGAGGAGCAGTTCAATAGCACCTACCGGG

TGGTGTCCGTGCTGACCGTGCTGCACCAGGACTGGCTGAACGGCAAGGAA

TACAAGTGTAAGGTGTCCAACAAGGGCCTGCCCAGCAGCATCGAGAAAAC

CATCAGCAAGGCCAAGGGCCAGCCTCGGGAGCCCCAGGTGTACACCCTGC

CCCCTAGCCAAGAGGAGATGACCAAGAACCAGGTGTCCCTGACCTGCCTG

GTGAAGGGCTTCTACCCCAGCGACATCGCCGTGGAGTGGGAGAGCAACGG

CCAGCCCGAGAACAACTACAAGACCACCCCCCCTGTGCTGGACAGCGACG

GCAGCTTCTTCCTGTACAGCCGGCTGACCGTGGACAAGAGCCGGTGGCAG

GAGGGCAACGTCTTTAGCTGCTCCGTGATGCACGAGGCCCTGCACAACCA

CTACACCCAGAAGAGCCTGAGCCTGTCCCTGGGCAAGATG.

In one aspect, the hinge or spacer comprises an IgD hinge. For example, in one embodiment, the hinge or spacer comprises a hinge of the amino acid sequence RWPESPKAQASSVPTAQPQAEGSLAKATTAPATTRNTGRGGEEKKKEKEKEEQEER ETKTPECPSHTQPLGVYLLTPAVQDLWLRDKATFTCFVVGSDLKDAHLTWEVAGKV PTGGVEEGLLERHSNGSQSQHSRLTLPRSLWNAGTSVTCTLNHPSLPPQRLMALREP AAQAPVKLSLNLLASSDPPEAASWLLCEVSGFSPPNILLMWLEDQREVNTSGFAPAR PPPQPGSTTFWAWSVLRVPAPPSPQPATYTCVVSHEDSRTLLNASRSLEVSYVTDH (SEQ ID NO:4). In some embodiments, the hinge or spacer comprises a hinge encoded by a nucleotide sequence of (SEQ ID NO: 15)

AGGTGGCCCGAAAGTCCCAAGGCCCAGGCATCTAGTGTTCCTACTGCACA

GCCCCAGGCAGAAGGCAGCCTAGCCAAAGCTACTACTGCACCTGCCACTA

CGCGCAATACTGGCCGTGGCGGGGAGGAGAAGAAAAAGGAGAAAGAGAAA

GAAGAACAGGAAGAGAGGGAGACCAAGACCCCTGAATGTCCATCCCATAC

CCAGCCGCTGGGCGTCTATCTCTTGACTCCCGCAGTACAGGACTTGTGGC

TTAGAGATAAGGCCACCTTTACATGTTTCGTCGTGGGCTCTGACCTGAAG

GATGCCCATTTGACTTGGGAGGTTGCCGGAAAGGTACCCACAGGGGGGGT

TGAGGAAGGGTTGCTGGAGCGCCATTCCAATGGCTCTCAGAGCCAGCACT

CAAGACTCACCCTTCCGAGATCCCTGTGGAACGCCGGGACCTCTGTCACA

TGTACTCTAAATCATCCTAGCCTGCCCCCACAGCGTCTGATGGCCCTTAG

AGAGCCAGCCGCCCAGGCACCAGTTAAGCTTAGCCTGAATCTGCTCGCCA

GTAGTGATCCCCCAGAGGCCGCCAGCTGGCTCTTATGCGAAGTGTCCGGC

-continued

```
TTTAGCCCGCCCAACATCTTGCTCATGTGGCTGGAGGACCAGCGAGAAGT

GAACACCAGCGGCTTCGCTCCAGCCCGGCCCCCACCCCAGCCGGGTTCTA

CCACATTCTGGGCCTGGAGTGTCTTAAGGGTCCCAGCACCACCTAGCCCC

CAGCCAGCCACATACACCTGTGTTGTGTCCCATGAAGATAGCAGGACCCT

GCTAAATGCTTCTAGGAGTCTGGAGGTTTCCTACGTGACTGACCATT.
```

In one embodiment, the transmembrane domain may be synthetic, in which case it will comprise predominantly hydrophobic residues such as leucine and valine. Preferably a triplet of phenylalanine, tryptophan and valine will be found at each end of a synthetic transmembrane domain.

Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker. For example, in one aspect, the linker comprises the amino acid sequence of GGGGSGGGGS (SEQ ID NO:5). In some embodiments, the linker is encoded by a nucleotide sequence of GGTGGCGGAGGTTCTGGAGGTGGAGGTTCC (SEQ ID NO:16).

In one aspect, the hinge or spacer comprises a KIR2DS2 hinge.

Cytoplasmic Domain

The cytoplasmic domain of a CAR of the present invention includes an intracellular signaling domain. The intracellular signaling domain of the CAR of the invention is generally responsible for activation of at least one of the normal effector functions of the immune cell in which the CAR has been introduced.

Examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary intracellular signaling domain) and those that act in an antigen-independent manner to provide a secondary or co-stimulatory signal (secondary cytoplasmic domain, e.g., a costimulatory signaling domain).

A primary intracellular signaling domain regulates primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, FcεRI, DAP10, DAP12, and CD66d. In one embodiment, a CAR of the invention comprises an intracellular signaling domain, e.g., a primary signaling domain of CD3-zeta.

In one embodiment, a primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs.

Further examples of molecules containing a primary intracellular signaling domain that are of particular use in the invention include those of DAP10, DAP12, and CD32.

In a one embodiment, the intracellular signaling domain of the CAR can comprise the primary signaling domain, e.g., CD3-zeta signaling domain, by itself or it can be combined with any other desired intracellular signaling domain(s) useful in the context of the CAR of the invention. For example, the intracellular signaling domain of the CAR can comprise a primary signaling domain, e.g., CD3 zeta chain portion, and a costimulatory signaling domain. The costimulatory signaling domain refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include a MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83, and the like.

For example, CD27 costimulation has been demonstrated to enhance expansion, effector function, and survival of human CART cells in vitro and augments human T cell persistence and antitumor activity in vivo (Song et al. Blood. 2012; 119(3):696-706). The intracellular signaling sequences within the cytoplasmic portion of the CAR of the invention may be linked to each other in a random or specified order. Optionally, a short oligo- or polypeptide linker, for example, between 2 and 10 amino acids (e.g., 2, 3, 4, 5, 6, 7, 8, 9, or 10 amino acids) in length may form the linkage between intracellular signaling sequence. In one embodiment, a glycine-serine doublet can be used as a suitable linker. In one embodiment, a single amino acid, e.g., an alanine, a glycine, can be used as a suitable linker.

In one aspect, the intracellular signaling domain is designed to comprise two or more, e.g., 2, 3, 4, 5, or more, costimulatory signaling domains. In an embodiment, the two or more, e.g., 2, 3, 4, 5, or more, costimulatory signaling domains, are separated by a linker molecule, e.g., a linker molecule described herein. In one embodiment, the intracellular signaling domain comprises two costimulatory signaling domains. In some embodiments, the linker molecule is a glycine residue. In some embodiments, the linker is an alanine residue.

In one aspect, the intracellular signaling domain is designed to comprise the signaling domain of CD3-zeta and the signaling domain of CD28. In one aspect, the intracellular signaling domain is designed to comprise the signaling domain of CD3-zeta and the signaling domain of 4-1BB. In one aspect, the signaling domain of 4-1BB is a signaling domain of SEQ ID NO: 7. In one aspect, the signaling domain of CD3-zeta is a signaling domain of SEQ ID NO: 9 (mutant CD3 zeta) or SEQ ID NO: 10 (wild-type human CD3 zeta).

In one aspect, the intracellular signaling domain is designed to comprise the signaling domain of CD3-zeta and the signaling domain of CD27. In one aspect, the signaling domain of CD27 comprises an amino acid sequence of (SEQ ID NO: 8)
QRRKYRSNKGESPVEPAEPCRYSCPREEEGSTIPIQEDYRKPEPACSP.

In one aspect, the signaling domain of CD27 is encoded by a nucleic acid sequence of (SEQ ID NO: 19)
AGGAGTAAGAGGAGCAGGCTCCTGCACAGTGACTACATGAACATGACTCC

CCGCCGCCCCGGGCCCACCCGCAAGCATTACCAGCCCTATGCCCCACCAC

GCGACTTCGCAGCCTATCGCTCC.

In one aspect, the intracellular is designed to comprise the signaling domain of CD3-zeta and the signaling domain of CD28. In one aspect, the signaling domain of CD28 comprises an amino acid sequence of SEQ ID NO: 80. In one aspect, the signaling domain of CD28 is encoded by a nucleic acid sequence of SEQ ID NO: 81.

In one aspect, the intracellular is designed to comprise the signaling domain of CD3-zeta and the signaling domain of ICOS. In one aspect, the signaling domain of CD28 comprises an amino acid sequence of SEQ ID NO: 82. In one aspect, the signaling domain of ICOS is encoded by a nucleic acid sequence of SEQ ID NO: 83.

In one aspect, the CAR-expressing cell described herein can further comprise a second CAR, e.g., a second CAR that includes a different antigen binding domain, e.g., to the same target (GFRα4) or a different target. In one embodiment, the second CAR includes an antigen binding domain to a target expressed on medullary thyroid cancer cells. In one embodiment, the CAR-expressing cell comprises a first CAR that specifically binds a first antigen and includes an intracellular signaling domain having a costimulatory signaling domain but not a primary signaling domain, and a second CAR that specifically binds a second, different, antigen and includes an intracellular signaling domain having a primary signaling domain but not a costimulatory signaling domain. While not wishing to be bound by theory, placement of a costimulatory signaling domain, e.g., 4-1BB, CD28, CD27, ICOS, or OX-40, onto the first CAR, and the primary signaling domain, e.g., CD3 zeta, on the second CAR can limit the CAR activity to cells where both targets are expressed. In one embodiment, the CAR expressing cell comprises a first GFRα4 CAR that includes a GFRα4 binding domain, a transmembrane domain and a costimulatory domain and a second CAR that specifically binds an antigen other than GFRα4

In one embodiment, the CAR-expressing cell comprises a GFRα4CAR described herein and an inhibitory CAR. In one embodiment, the inhibitory CAR comprises an antigen binding domain that binds an antigen found on normal cells but not cancer cells, e.g., normal cells that also express GFRα4. In one embodiment, the inhibitory CAR comprises the antigen binding domain, a transmembrane domain and an intracellular domain of an inhibitory molecule. For example, the intracellular domain of the inhibitory CAR can be an intracellular domain of PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, and TGFR beta.

In one embodiment, when the CAR-expressing cell comprises two or more different CARs, the antigen binding domains of the different CARs can be such that the antigen binding domains do not interact with one another. For example, a cell expressing a first and second CAR can have an antigen binding domain of the first CAR, e.g., as a fragment, e.g., an scFv, that does not form an association with the antigen binding domain of the second CAR, e.g., the antigen binding domain of the second CAR is a VHH.

In some embodiments, the antigen binding domain comprises a single domain antigen binding (SDAB) molecules include molecules whose complementary determining regions are part of a single domain polypeptide. Examples include, but are not limited to, heavy chain variable domains, binding molecules naturally devoid of light chains, single domains derived from conventional 4-chain antibodies, engineered domains and single domain scaffolds other than those derived from antibodies. SDAB molecules may be any of the art, or any future single domain molecules. SDAB molecules may be derived from any species including, but not limited to mouse, human, camel, llama, lamprey, fish, shark, goat, rabbit, and bovine. This term also includes naturally occurring single domain antibody molecules from species other than Camelidae and sharks.

In one aspect, an SDAB molecule can be derived from a variable region of the immunoglobulin found in fish, such as, for example, that which is derived from the immunoglobulin isotype known as Novel Antigen Receptor (NAR) found in the serum of shark. Methods of producing single domain molecules derived from a variable region of NAR ("IgNARs") are described in WO 03/014161 and Streltsov (2005) Protein Sci. 14:2901-2909.

According to another aspect, an SDAB molecule is a naturally occurring single domain antigen binding molecule known as heavy chain devoid of light chains. Such single domain molecules are disclosed in WO 9404678 and Hamers-Casterman, C. et al. (1993) Nature 363:446-448, for example. For clarity reasons, this variable domain derived from a heavy chain molecule naturally devoid of light chain is known herein as a VHH or nanobody to distinguish it from the conventional VH of four chain immunoglobulins. Such a VHH molecule can be derived from Camelidae species, for example in camel, llama, dromedary, alpaca and guanaco. Other species besides Camelidae may produce heavy chain molecules naturally devoid of light chain; such VHHs are within the scope of the invention.

The SDAB molecules can be recombinant, CDR-grafted, humanized, camelized, de-immunized and/or in vitro generated (e.g., selected by phage display).

It has also been discovered, that cells having a plurality of chimeric membrane embedded receptors comprising an antigen binding domain that interactions between the antigen binding domain of the receptors can be undesirable, e.g., because it inhibits the ability of one or more of the antigen binding domains to bind its cognate antigen. Accordingly, disclosed herein are cells having a first and a second non-naturally occurring chimeric membrane embedded receptor comprising antigen binding domains that minimize such interactions. Also disclosed herein are nucleic acids encoding a first and a second non-naturally occurring chimeric membrane embedded receptor comprising a antigen binding domains that minimize such interactions, as well as methods of making and using such cells and nucleic acids. In an embodiment the antigen binding domain of one of said first said second non-naturally occurring chimeric membrane embedded receptor, comprises an scFv, and the other comprises a single VH domain, e.g., a camelid, shark, or lamprey single VH domain, or a single VH domain derived from a human or mouse sequence.

In some embodiments, the claimed invention comprises a first and second CAR, wherein the antigen binding domain of one of said first CAR said second CAR does not comprise a variable light domain and a variable heavy domain. In some embodiments, the antigen binding domain of one of said first CAR said second CAR is an scFv, and the other is not an scFv. In some embodiments, the antigen binding domain of one of said first CAR said second CAR comprises a single VH domain, e.g., a camelid, shark, or lamprey single VH domain, or a single VH domain derived from a human or mouse sequence. In some embodiments, the antigen binding domain of one of said first CAR said second CAR comprises a nanobody. In some embodiments, the antigen binding domain of one of said first CAR said second CAR comprises a camelid VHH domain.

In some embodiments, the antigen binding domain of one of said first CAR said second CAR comprises an scFv, and the other comprises a single VH domain, e.g., a camelid, shark, or lamprey single VH domain, or a single VH domain derived from a human or mouse sequence. In some embodiments, the antigen binding domain of one of said first CAR said second CAR comprises an scFv, and the other comprises a nanobody. In some embodiments, the antigen binding domain of one of the first CAR or the second CAR comprises an scFv, and the other comprises a camelid VHH domain.

In some embodiments, when present on the surface of a cell, binding of the antigen binding domain of said first CAR to its cognate antigen is not substantially reduced by the presence of said second CAR. In some embodiments, binding of the antigen binding domain of said first CAR to its cognate antigen in the presence of said second CAR is 85%, 90%, 95%, 96%, 97%, 98% or 99% of binding of the antigen binding domain of said first CAR to its cognate antigen in the absence of said second CAR.

In some embodiments, when present on the surface of a cell, the antigen binding domains of said first CAR said second CAR, associate with one another less than if both were scFv antigen binding domains. In some embodiments, the antigen binding domains of said first CAR said second CAR, associate with one another 85%, 90%, 95%, 96%, 97%, 98% or 99% less than if both were scFv antigen binding domains.

In another aspect, the CAR-expressing cell described herein can further express another agent, e.g., an agent which enhances the activity of a CAR-expressing cell. For example, in one embodiment, the agent can be an agent which inhibits an inhibitory molecule. Inhibitory molecules, e.g., PD1, can, in some embodiments, decrease the ability of a CAR-expressing cell to mount an immune effector response. Examples of inhibitory molecules include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. In one embodiment, the agent which inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta, or a fragment of any of these (e.g., at least a portion of an extracellular domain of any of these), and a second polypeptide which is an intracellular signaling domain described herein (e.g., comprising a costimulatory domain (e.g., 4-1BB, CD27, ICOS, or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of an extracellular domain of PD1), and a second polypeptide of an intracellular signaling domain described herein (e.g., a CD28 signaling domain described herein and/or a CD3 zeta signaling domain described herein). In embodiments, the CAR-expressing cell described herein comprises a switch costimulatory receptor, e.g., as described in WO 2013/019615, which is incorporated herein by reference in its entirety. PD1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD1, PD-L1 and PD-L2 have been shown to downregulate T cell activation upon binding to PD1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD1 with PD-L1.

In one embodiment, the agent comprises the extracellular domain (ECD) of an inhibitory molecule, e.g., Programmed Death 1 (PD1), can be fused to a transmembrane domain and intracellular signaling domains such as 41BB and CD3 zeta (also referred to herein as a PD1 CAR). In one embodiment, the PD1 CAR, when used in combinations with a GFRα4 CAR described herein, improves the persistence of the CAR-expressing cell, e.g., T cell or NK cell. In one embodiment, the CAR is a PD1 CAR comprising the extracellular domain of PD1 indicated as underlined in SEQ ID NO: 24. In one embodiment, the PD1 CAR comprises the amino acid sequence of SEQ ID NO:24.

(SEQ ID NO: 24)

Malpvtalllplalllhaarppgwfldspdrpwnpptfspallvvtegdn atftcsfsntsesfvlnwyrmspsnqtdklaafpedrsqpgqdcrfrvtq lpngrdfhmsvvrarrndsgtylcgaislapkaqikeslraelrvterra evptahpspsprpagqfqtlvtttpaprpptpaptiasqplslrpeacrp -continued aaggavhtrgldfacdiyiwaplagtcgvlllslvitlyckrgrkkllyi fkqpfmrpvqttqeedgcscrfpeeeeggcelrvkfsrsadapaykqgqn qlynelnlgrreeydvldkrrgrdpemggkprrknpqeglynelqkdkma eayseigmkgerrrgkghdglyqglstatkdtydalhmqalppr.

In one embodiment, the PD1 CAR comprises the amino acid sequence provided below (SEQ ID NO:22).

(SEQ ID NO: 22)

pgwfldspdrpwnpptfspallvvtegdnatftcsfsntsesfvinwyrm spsnqtdklaafpedrsqpgqdcrfrvtqlpngrdfhmsvvrarrndsgt ylcgaislapkaqikeslraelrvterraevptahpsprpagqfqtiv tttpaprpptpaptiasqplslrpeacrpaaggavhtrgldfacdiyiwa plagtcgvillslvitlyckrgrkkllyifkqpfmrpvqttqeedgcscr fpeeeeggcelrvkfsrsadapaykqgqnqlynelnlgrreeydvldkrr grdpemggkprrknpqeglynelqkdkmaeayseigmkgerrrgkghdgl yqglstatkdtydalhmqalppr.

In one embodiment, the agent comprises a nucleic acid sequence encoding the PD1 CAR, e.g., the PD1 CAR described herein. In one embodiment, the nucleic acid sequence for the PD1 CAR is shown below, with the PD1 ECD underlined below in SEQ ID NO: 23

(SEQ ID NO: 23)

atggccctccctgtcactgccctgcttctccccctcgcactcctgctcca cgccgctagaccacccggatggtttctggactctccggatcgcccgtgga atcccccaaccttctcaccggcactcttggttgtgactgagggcgataat gcgaccttcacgtgctcgttctccaacacctccgaatcattcgtgctgaa ctggtaccgcatgagcccgtcaaaccagaccgacaagctcgccgcgtttc cggaagatcggtcgcaaccgggacaggattgtcggttccgcgtgactcaa ctgccgaatggcagagacttccacatgagcgtggtccgcgctaggcgaaa cgactccgggacctacctgtgcggagccatctcgctggcgcctaaggccc aaatcaaagagagcttgagggccgaactgagagtgaccgagcgcagagct gaggtgccaactgcacatccatccccatcgcctcggcctgcggggcagtt tcagaccctggtcacgaccactccggcgccgcgcccaccgactccggccc caactatcgcgagccagcccctgtcgctgaggccggaagcatgccgccct gccgccggaggtgctgtgcatacccggggattggacttcgcatgcgacat ctacatttgggctcctctcgccggaacttgtggcgtgctccttctgtccc tggtcatcaccctgtactgcaagcggggtcggaaaaagcttctgtacatt ttcaagcagcccttcatgaggcccgtgcaaaccacccaggaggaggacgg ttgctcctgccggttccccgaagaggaagaaggaggttgcgagctgcgcg tgaagttctcccggagcgccgacgcccccgcctataagcagggccagaac cagctgtacaacgaactgaacctgggacggcgggaagagtacgatgtgct ggacaagcggcgcggccgggaccccgaaatgggcgggaagcctagaagaa agaaccctcaggaaggcctgtataacgagctgcagaaggacaagatggcc -continued gaggcctactccgaaattgggatgaagggagagcggcggaggggaaaggg gcacgacggcctgtaccaaggactgtccaccgccaccaaggacacatacg atgccctgcacatgcaggcccttccccctcgc.

In another aspect, the present invention provides a population of CAR-expressing cells, e.g., CART cells or CAR-expressing NK cells. In some embodiments, the population of CAR-expressing cells comprises a mixture of cells expressing different CARs. For example, in one embodiment, the population of CAR-expressing cells (e.g., CART cells or CAR-expressing NK cells) can include a first cell expressing a CAR having a GFRα4 binding domain described herein, and a second cell expressing a CAR having a different GFRα4 binding domain, e.g., a GFRα4 binding domain described herein that differs from the GFRα4 binding domain in the CAR expressed by the first cell. As another example, the population of CAR-expressing cells can include a first cell expressing a CAR that includes an GFRα4 binding domain, e.g., as described herein, and a second cell expressing a CAR that includes an antigen binding domain to a target other than GFRα4. In one embodiment, the population of CAR-expressing cells includes, e.g., a first cell expressing a CAR that includes a primary intracellular signaling domain, and a second cell expressing a CAR that includes a secondary signaling domain, e.g., a costimulatory signaling domain.

In another aspect, the present invention provides a population of cells wherein at least one cell in the population expresses a CAR having a GFRα4 domain described herein, and a second cell expressing another agent, e.g., an agent which enhances the activity of a CAR-expressing cell. For example, in one embodiment, the agent can be an agent which inhibits an inhibitory molecule. Inhibitory molecules, e.g., can, in some embodiments, decrease the ability of a CAR-expressing cell to mount an immune effector response. Examples of inhibitory molecules include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. In one embodiment, the agent which inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta, or a fragment of any of these (e.g., at least a portion of an extracellular domain of any of these), and a second polypeptide which is an intracellular signaling domain described herein (e.g., comprising a costimulatory domain (e.g., 4-1BB, CD27 ICOS, or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of the extracellular domain of PD1), and a second polypeptide of an intracellular signaling domain described herein (e.g., a CD28 signaling domain described herein and/or a CD3 zeta signaling domain described herein).

In one aspect, the present invention provides methods comprising administering a population of CAR-expressing cells (e.g., CART cells or CAR-expressing NK cells), e.g., a mixture of cells expressing different CARs, in combination with another agent, e.g., a kinase inhibitor, such as a kinase inhibitor described herein. In another aspect, the present invention provides methods comprising administering a population of cells wherein at least one cell in the population expresses a CAR having an anti-cancer associated antigen binding domain as described herein, and a second cell expressing another agent, e.g., an agent which enhances the activity of a CAR-expressing cell, in combination with another agent, e.g., a kinase inhibitor, such as a kinase inhibitor described herein.

Natural Killer Cell Receptor (NKR) CARs

In an embodiment, the CAR molecule described herein comprises one or more components of a natural killer cell receptor (NKR), thereby forming an NKR-CAR. The NKR component can be a transmembrane domain, a hinge domain, or a cytoplasmic domain from any of the following natural killer cell receptors: killer cell immunoglobulin-like receptor (KIR), e.g., KIR2DL1, KIR2DL2/L3, KIR2DL4, KIR2DL5A, KIR2DL5B, KIR2DS1, KIR2DS2, KIR2DS3, KIR2DS4, DIR2DS5, KIR3DL1/S1, KIR3DL2, KIR3DL3, KIR2DP1, and KIR3DP1; natural cyotoxicity receptor (NCR), e.g., NKp30, NKp44, NKp46; signaling lymphocyte activation molecule (SLAM) family of immune cell receptors, e.g., CD48, CD229, 2B4, CD84, NTB-A, CRACC, BLAME, and CD2F-10; Fc receptor (FcR), e.g., CD16, and CD64; and Ly49 receptors, e.g., LY49A, LY49C. The NKR-CAR molecules described herein may interact with an adaptor molecule or intracellular signaling domain, e.g., DAP12. Exemplary configurations and sequences of CAR molecules comprising NKR components are described in International Publication No. WO2014/145252, the contents of which are hereby incorporated by reference.

Strategies for Regulating Chimeric Antigen Receptors

There are many ways CAR activities can be regulated. In some embodiments, a regulatable CAR (RCAR) where the CAR activity can be controlled is desirable to optimize the safety and efficacy of a CAR therapy. For example, inducing apoptosis using, e.g., a caspase fused to a dimerization domain (see, e.g., Di et al., N Engl. J. Med. 2011 Nov. 3; 365(18):1673-1683), can be used as a safety switch in the CAR therapy of the instant invention. In another example, CAR-expressing cells can also express an inducible Caspase-9 (iCaspase-9) molecule that, upon administration of a dimerizer drug (e.g., rimiducid (also called AP1903 (Bellicum Pharmaceuticals) or AP20187 (Ariad)) leads to activation of the Caspase-9 and apoptosis of the cells. The iCaspase-9 molecule contains a chemical inducer of dimerization (CID) binding domain that mediates dimerization in the presence of a CID. This results in inducible and selective depletion of CAR-expressing cells. In some cases, the iCaspase-9 molecule is encoded by a nucleic acid molecule separate from the CAR-encoding vector(s). In some cases, the iCaspase-9 molecule is encoded by the same nucleic acid molecule as the CAR-encoding vector. The iCaspase-9 can provide a safety switch to avoid any toxicity of CAR-expressing cells. See, e.g., Song et al. Cancer Gene Ther. 2008; 15(10):667-75; Clinical Trial Id. No. NCT02107963; and Di Stasi et al. N. Engl. J. Med. 2011; 365:1673-83.

Alternative strategies for regulating the CAR therapy of the instant invention include utilizing small molecules or antibodies that deactivate or turn off CAR activity, e.g., by deleting CAR-expressing cells, e.g., by inducing antibody dependent cell-mediated cytotoxicity (ADCC). For example, CAR-expressing cells described herein may also express an antigen that is recognized by molecules capable of inducing cell death, e.g., ADCC or compliment-induced cell death. For example, CAR expressing cells described herein may also express a receptor capable of being targeted by an antibody or antibody fragment. Examples of such receptors include EpCAM, VEGFR, integrins (e.g., integrins αvβ3, α4, αI¾β3, α4β7, α5β1, αvβ3, αv), members of the TNF receptor superfamily (e.g., TRAIL-R1, TRAIL-R2), PDGF Receptor, interferon receptor, folate receptor, GPNMB, ICAM-1, HLA-DR, CEA, CA-125, MUC1, TAG-72, IL-6 receptor, 5T4, GD2, GD3, CD2, CD3, CD4, CD5, CD11, CD11 a/LFA-1, CD15, CD18/ITGB2, CD19, CD20, CD22, CD23/IgE Receptor, CD25, CD28, CD30, CD33, CD38, CD40, CD41, CD44, CD51, CD52, CD62L, CD74, CD80, CD125, CD147/basigin, CD152/CTLA-4, CD154/CD40L, CD195/CCR5, CD319/SLAMF7, and EGFR, and truncated versions thereof (e.g., versions preserving one or more extracellular epitopes but lacking one or more regions within the cytoplasmic domain). For example, CAR-expressing cells described herein may also express a truncated epidermal growth factor receptor (EGFR) which lacks signaling capacity but retains the epitope that is recognized by molecules capable of inducing ADCC, e.g., cetuximab (ERBITUX®), such that administration of cetuximab induces ADCC and subsequent depletion of the CAR-expressing cells (see, e.g., WO2011/056894, and Jonnalagadda et al., Gene Ther. 2013; 20(8)853-860). Another strategy includes expressing a highly compact marker/suicide gene that combines target epitopes from both CD32 and CD20 antigens in the CAR-expressing cells described herein, which binds rituximab, resulting in selective depletion of the CAR-expressing cells, e.g., by ADCC (see, e.g., Philip et al., Blood. 2014; 124(8)1277-1287). Other methods for depleting CAR-expressing cells described herein include administration of CAMPATH, a monoclonal anti-CD52 antibody that selectively binds and targets mature lymphocytes, e.g., CAR-expressing cells, for destruction, e.g., by inducing ADCC. In other embodiments, the CAR-expressing cell can be selectively targeted using a CAR ligand, e.g., an anti-idiotypic antibody. In some embodiments, the anti-idiotypic antibody can cause effector cell activity, e.g, ADCC or ADC activities, thereby reducing the number of CAR-expressing cells. In other embodiments, the CAR ligand, e.g., the anti-idiotypic antibody, can be coupled to an agent that induces cell killing, e.g., a toxin, thereby reducing the number of CAR-expressing cells. Alternatively, the CAR molecules themselves can be configured such that the activity can be regulated, e.g., turned on and off, as described below.

In some embodiments, a RCAR comprises a set of polypeptides, typically two in the simplest embodiments, in which the components of a standard CAR described herein, e.g., an antigen binding domain and an intracellular signaling domain, are partitioned on separate polypeptides or members. In some embodiments, the set of polypeptides include a dimerization switch that, upon the presence of a dimerization molecule, can couple the polypeptides to one another, e.g., can couple an antigen binding domain to an intracellular signaling domain. Additional description and exemplary configurations of such regulatable CARs are provided herein and in International Publication No. WO 2015/090229, hereby incorporated by reference in its entirety.

In an aspect, an RCAR comprises two polypeptides or members: 1) an intracellular signaling member comprising an intracellular signaling domain, e.g., a primary intracellular signaling domain described herein, and a first switch domain; 2) an antigen binding member comprising an antigen binding domain, e.g., that specifically binds a tumor antigen described herein, as described herein and a second switch domain. Optionally, the RCAR comprises a transmembrane domain described herein. In an embodiment, a transmembrane domain can be disposed on the intracellular signaling member, on the antigen binding member, or on both. (Unless otherwise indicated, when members or elements of an RCAR are described herein, the order can be as provided, but other orders are included as well. In other words, in an embodiment, the order is as set out in the text, but in other embodiments, the order can be different. E.g., the order of elements on one side of a transmembrane region can be different from the example, e.g., the placement of a switch domain relative to a intracellular signaling domain can be different, e.g., reversed).

In an embodiment, the first and second switch domains can form an intracellular or an extracellular dimerization switch. In an embodiment, the dimerization switch can be a homodimerization switch, e.g., where the first and second switch domain are the same, or a heterodimerization switch, e.g., where the first and second switch domain are different from one another.

In embodiments, an RCAR can comprise a "multi switch." A multi switch can comprise heterodimerization switch domains or homodimerization switch domains. A multi switch comprises a plurality of, e.g., 2, 3, 4, 5, 6, 7, 8, 9, or 10, switch domains, independently, on a first member, e.g., an antigen binding member, and a second member, e.g., an intracellular signaling member. In an embodiment, the first member can comprise a plurality of first switch domains, e.g., FKBP-based switch domains, and the second member can comprise a plurality of second switch domains, e.g., FRB-based switch domains. In an embodiment, the first member can comprise a first and a second switch domain, e.g., a FKBP-based switch domain and a FRB-based switch domain, and the second member can comprise a first and a second switch domain, e.g., a FKBP-based switch domain and a FRB-based switch domain.

In an embodiment, the intracellular signaling member comprises one or more intracellular signaling domains, e.g., a primary intracellular signaling domain and one or more costimulatory signaling domains.

In an embodiment, the antigen binding member may comprise one or more intracellular signaling domains, e.g., one or more costimulatory signaling domains. In an embodiment, the antigen binding member comprises a plurality, e.g., 2 or 3 costimulatory signaling domains described herein, e.g., selected from 4-1BB, CD28, CD27, ICOS, and OX40, and in embodiments, no primary intracellular signaling domain. In an embodiment, the antigen binding member comprises the following costimulatory signaling domains, from the extracellular to intracellular direction: 4-1BB-CD27; 4-1BB-CD27; CD27-4-1BB; 4-1BB-CD28; CD28-4-1BB; OX40-CD28; CD28-OX40; CD28-4-1BB; or 4-1BB-CD28. In such embodiments, the intracellular binding member comprises a CD3zeta domain. In one such embodiment the RCAR comprises (1) an antigen binding member comprising, an antigen binding domain, a transmembrane domain, and two costimulatory domains and a first switch domain; and (2) an intracellular signaling domain comprising a transmembrane domain or membrane tethering domain and at least one primary intracellular signaling domain, and a second switch domain.

An embodiment provides RCARs wherein the antigen binding member is not tethered to the surface of the CAR cell. This allows a cell having an intracellular signaling member to be conveniently paired with one or more antigen binding domains, without transforming the cell with a sequence that encodes the antigen binding member. In such embodiments, the RCAR comprises: 1) an intracellular signaling member comprising: a first switch domain, a transmembrane domain, an intracellular signaling domain, e.g., a primary intracellular signaling domain, and a first switch domain; and 2) an antigen binding member comprising: an antigen binding domain, and a second switch domain, wherein the antigen binding member does not comprise a transmembrane domain or membrane tethering domain, and, optionally, does not comprise an intracellular signaling domain. In some embodiments, the RCAR may further comprise 3) a second antigen binding member comprising: a second antigen binding domain, e.g., a second antigen binding domain that binds a different antigen than is bound by the antigen binding domain; and a second switch domain.

Also provided herein are RCARs wherein the antigen binding member comprises bispecific activation and targeting capacity. In this embodiment, the antigen binding member can comprise a plurality, e.g., 2, 3, 4, or 5 antigen binding domains, e.g., scFvs, wherein each antigen binding domain binds to a target antigen, e.g. different antigens or the same antigen, e.g., the same or different epitopes on the same antigen. In an embodiment, the plurality of antigen binding domains are in tandem, and optionally, a linker or hinge region is disposed between each of the antigen binding domains. Suitable linkers and hinge regions are described herein.

An embodiment provides RCARs having a configuration that allows switching of proliferation. In this embodiment, the RCAR comprises: 1) an intracellular signaling member comprising: optionally, a transmembrane domain or membrane tethering domain; one or more co-stimulatory signaling domain, e.g., selected from 4-1BB, CD28, CD27, ICOS, and OX40, and a switch domain; and 2) an antigen binding member comprising: an antigen binding domain, a transmembrane domain, and a primary intracellular signaling domain, e.g., a CD3zeta domain, wherein the antigen binding member does not comprise a switch domain, or does not comprise a switch domain that dimerizes with a switch domain on the intracellular signaling member. In an embodiment, the antigen binding member does not comprise a co-stimulatory signaling domain. In an embodiment, the intracellular signaling member comprises a switch domain from a homodimerization switch. In an embodiment, the intracellular signaling member comprises a first switch domain of a heterodimerization switch and the RCAR comprises a second intracellular signaling member which comprises a second switch domain of the heterodimerization switch. In such embodiments, the second intracellular signaling member comprises the same intracellular signaling domains as the intracellular signaling member. In an embodiment, the dimerization switch is intracellular. In an embodiment, the dimerization switch is extracellular.

In any of the RCAR configurations described here, the first and second switch domains comprise a FKBP-FRB based switch as described herein.

Also provided herein are cells comprising an RCAR described herein. Any cell that is engineered to express a RCAR can be used as a RCARX cell. In an embodiment the RCARX cell is a T cell, and is referred to as a RCART cell. In an embodiment the RCARX cell is an NK cell, and is referred to as a RCARN cell.

Also provided herein are nucleic acids and vectors comprising RCAR encoding sequences. Sequence encoding various elements of an RCAR can be disposed on the same nucleic acid molecule, e.g., the same plasmid or vector, e.g., viral vector, e.g., lentiviral vector. In an embodiment, (i) sequence encoding an antigen binding member and (ii) sequence encoding an intracellular signaling member, can be present on the same nucleic acid, e.g., vector. Production of the corresponding proteins can be achieved, e.g., by the use of separate promoters, or by the use of a bicistronic transcription product (which can result in the production of two proteins by cleavage of a single translation product or by the translation of two separate protein products). In an embodiment, a sequence encoding a cleavable peptide, e.g., a P2A or F2A sequence, is disposed between (i) and (ii). In an embodiment, a sequence encoding an IRES, e.g., an EMCV or EV71 IRES, is disposed between (i) and (ii). In these embodiments, (i) and (ii) are transcribed as a single RNA. In an embodiment, a first promoter is operably linked to (i) and a second promoter is operably linked to (ii), such that (i) and (ii) are transcribed as separate mRNAs.

Alternatively, the sequence encoding various elements of an RCAR can be disposed on the different nucleic acid molecules, e.g., different plasmids or vectors, e.g., viral vector, e.g., lentiviral vector. E.g., the (i) sequence encoding an antigen binding member can be present on a first nucleic acid, e.g., a first vector, and the (ii) sequence encoding an intracellular signaling member can be present on the second nucleic acid, e.g., the second vector.

Dimerization Switches

Dimerization switches can be non-covalent or covalent. In a non-covalent dimerization switch, the dimerization molecule promotes a non-covalent interaction between the switch domains. In a covalent dimerization switch, the dimerization molecule promotes a covalent interaction between the switch domains.

In an embodiment, the RCAR comprises a FKBP/FRAP, or FKBP/FRB-based dimerization switch. FKBP12 (FKBP, or FK506 binding protein) is an abundant cytoplasmic protein that serves as the initial intracellular target for the natural product immunosuppressive drug, rapamycin. Rapamycin binds to FKBP and to the large PI3K homolog FRAP (RAFT, mTOR). FRB is a 93 amino acid portion of FRAP, that is sufficient for binding the FKBP-rapamycin complex (Chen, J., Zheng, X. F., Brown, E. J. & Schreiber, S. L. (1995) *Identification of an 11-kDa FKBP12-rapamycin-binding domain within the 289-kDa FKBP12-rapamycin-associated protein and characterization of a critical serine residue*. Proc Natl Acad Sci USA 92: 4947-51.)

In embodiments, an FKBP/FRAP, e.g., an FKBP/FRB, based switch can use a dimerization molecule, e.g., rapamycin or a rapamycin analog.

The amino acid sequence of FKBP is as follows:

(SEQ ID NO: 214)
```
D V P D Y A S L G G P S S P K K K R K V S R G V Q

V E T I S P G D G R T F P K R G Q T C V V H Y T G

M L E D G K K F D S S R D R N K P F K F M L G K Q

E V I R G W E E G V A Q M S V G Q R A K L T I S P

D Y A Y G A T G H P G I I P P H A T L V FD V E L

L K L E T S Y
```

In embodiments, an FKBP switch domain can comprise a fragment of FKBP having the ability to bind with FRB, or a fragment or analog thereof, in the presence of rapamycin or a rapalog, e.g., the underlined portion of SEQ ID NO: 214, which is:

(SEQ ID NO: 215)
```
V Q V E T I S PG D G R T F P K R G Q T C V V H Y

T G M L E D G K K F D S S R D R N K P F K F M L G

K Q E V I R G W E E G V A Q M S V G Q R A K L T I

S P D Y A Y G A T G H P G I I P P H A T L V F D V

E L L K L E T S
```

The amino acid sequence of FRB is as follows:

(SEQ ID NO: 216)
```
ILWHEMWHEG LEEASRLYFG ERNVKGMFEV LEPLHAMMER

GPQTLKETSFNQAYGRDLME AQEWCRKYMK SGNVKDLTQA

WDLYYHVFRR ISK
```

"FKBP/FRAP, e.g., an FKBP/FRB, based switch" as that term is used herein, refers to a dimerization switch comprising: a first switch domain, which comprises an FKBP fragment or analog thereof having the ability to bind with FRB, or a fragment or analog thereof, in the presence of rapamycin or a rapalog, e.g., RAD001, and has at least 70, 75, 80, 85, 90, 95, 96, 97, 98, or 99% identity with, or differs by no more than 30, 25, 20, 15, 10, 5, 4, 3, 2, or 1 amino acid residues from, the FKBP sequence of SEQ ID NO: 214 or 215; and a second switch domain, which comprises an FRB fragment or analog thereof having the ability to bind with FRB, or a fragment or analog thereof, in the presence of rapamycin or a rapalog, and has at least 70, 75, 80, 85, 90, 95, 96, 97, 98, or 99% identity with, or differs by no more than 30, 25, 20, 15, 10, 5, 4, 3, 2, or 1 amino acid residues from, the FRB sequence of SEQ ID NO: 216. In an embodiment, a RCAR described herein comprises one switch domain comprises amino acid residues disclosed in SEQ ID NO: 214 (or SEQ ID NO: 215), and one switch domain comprises amino acid residues disclosed in SEQ ID NO: 216.

In embodiments, the FKBP/FRB dimerization switch comprises a modified FRB switch domain that exhibits altered, e.g., enhanced, complex formation between an FRB-based switch domain, e.g., the modified FRB switch domain, a FKBP-based switch domain, and the dimerization molecule, e.g., rapamycin or a rapalogue, e.g., RAD001. In an embodiment, the modified FRB switch domain comprises one or more mutations, e.g., 2, 3, 4, 5, 6, 7, 8, 9, 10 or more, selected from mutations at amino acid position(s) L2031, E2032, 52035, R2036, F2039, G2040, T2098, W2101, D2102, Y2105, and F2108, where the wild-type amino acid is mutated to any other naturally-occurring amino acid. In an embodiment, a mutant FRB comprises a mutation at E2032, where E2032 is mutated to phenylalanine (E2032F), methionine (E2032M), arginine (E2032R), valine (E2032V), tyrosine (E2032Y), isoleucine (E20321), e.g., SEQ ID NO: 217, or leucine (E2032L), e.g., SEQ ID NO: 109. In an embodiment, a mutant FRB comprises a mutation at T2098, where T2098 is mutated to phenylalanine (T2098F) or leucine (T2098L), e.g., SEQ ID NO: 110. In an embodiment, a mutant FRB comprises a mutation at E2032 and at T2098, where E2032 is mutated to any amino acid, and where T2098 is mutated to any amino acid, e.g., SEQ ID NO: 111. In an embodiment, a mutant FRB comprises an E20321 and a T2098L mutation, e.g., SEQ ID NO: 112. In an embodiment, a mutant FRB comprises an E2032L and a T2098L mutation, e.g., SEQ ID NO: 113.

TABLE 3

Exemplary mutant FR having increased affinity for a dimerization molecule.

| FRB mutant | Amino Acid Sequence | SEQ ID NO: |
|---|---|---|
| E2032I mutant | ILWHEMWHEGLIEASRLYFGERNVKGMFEVLEPLHAMMERGPQTLKETSFNQAY GRDLMEAQEWCRKYMKSGNVKDLTQAWDLYYHVFRRISKTS | 217 |
| E2032L mutant | ILWHEMWHEGLLEASRLYFGERNVKGMFEVLEPLHAMMERGPQTLKETSFNQAY GRDLMEAQEWCRKYMKSGNVKDLTQAWDLYYHVFRRISKTS | 109 |
| T2098L mutant | ILWHEMWHEGLEEASRLYFGERNVKGMFEVLEPLHAMMERGPQTLKETSFNQAY GRDLMEAQEWCRKYMKSGNVKDLLQAWDLYYHVFRRISKTS | 110 |
| E2032, T2098 mutant | ILWHEMWHEGLXEASRLYFGERNVKGMFEVLEPLHAMMERGPQTLKETSFNQAY GRDLMEAQEWCRKYMKSGNVKDLXQAWDLYYHVFRRISKTS | 111 |
| E2032I, T2098L mutant | ILWHEMWHEGLIEASRLYFGERNVKGMFEVLEPLHAMMERGPQTLKETSFNQAY GRDLMEAQEWDRKYMKSGNVKDLLQAWDLYYHVFRRISKTS | 112 |
| E2032L, T2098L mutant | ILWHEMWHEGLLEASRLYFGERNVKGMFEVLEPLHAMMERGPQTLKETSFNQAY GRDLMEAQEWCRKYMKSGNVKDLLQAWDLYYHVFRRISKTS | 113 |

Other suitable dimerization switches include a GyrB-GyrB based dimerization switch, a Gibberellin-based dimerization switch, a tag/binder dimerization switch, and a halo-tag/snap-tag dimerization switch. Following the guidance provided herein, such switches and relevant dimerization molecules will be apparent to one of ordinary skill.

Dimerization Molecule

Association between the switch domains is promoted by the dimerization molecule. In the presence of dimerization molecule interaction or association between switch domains allows for signal transduction between a polypeptide associated with, e.g., fused to, a first switch domain, and a polypeptide associated with, e.g., fused to, a second switch domain. In the presence of non-limiting levels of dimerization molecule signal transduction is increased by 1.1, 1.2, 1.3, 1.4, 1.5, 1.6, 1.7, 1.8, 1.9, 2, 5, 10, 50, 100 fold, e.g., as measured in a system described herein.

Rapamycin and rapamycin analogs (sometimes referred to as rapalogues), e.g., RAD001, can be used as dimerization molecules in a FKBP/FRB-based dimerization switch described herein. In an embodiment the dimerization molecule can be selected from rapamycin (sirolimus), RAD001 (everolimus), zotarolimus, temsirolimus, AP-23573 (ridaforolimus), biolimus and AP21967. Additional rapamycin analogs suitable for use with FKBP/FRB-based dimerization switches are further described in the section entitled "Combination Therapies", or in the subsection entitled "Combination with a low dose mTOR inhibitor".

Split CAR

In some embodiments, the CAR-expressing cell uses a split CAR. The split CAR approach is described in more detail in publications WO2014/055442 and WO2014/055657, incorporated herein by reference. Briefly, a split CAR system comprises a cell expressing a first CAR having a first antigen binding domain and a costimulatory domain (e.g., 41BB), and the cell also expresses a second CAR having a second antigen binding domain and an intracellular signaling domain (e.g., CD3 zeta). When the cell encounters the first antigen, the costimulatory domain is activated, and the cell proliferates. When the cell encounters the second antigen, the intracellular signaling domain is activated and cell-killing activity begins. Thus, the CAR-expressing cell is only fully activated in the presence of both antigens. In embodiments the first antigen binding domain recognizes GFRα4, e.g., comprises an antigen binding domain described herein, and the second antigen binding domain recognizes an antigen expressed on cancer cells, e.g., medullary thyroid cancer.

Stability and Mutations

The stability of a GFRα4 binding domain, e.g., scFv molecules (e.g., soluble scFv) can be evaluated in reference to the biophysical properties (e.g., thermal stability) of a conventional control scFv molecule or a full length antibody. In one embodiment, the human scFv has a thermal stability that is greater than about 0.1, about 0.25, about 0.5, about 0.75, about 1, about 1.25, about 1.5, about 1.75, about 2, about 2.5, about 3, about 3.5, about 4, about 4.5, about 5, about 5.5, about 6, about 6.5, about 7, about 7.5, about 8, about 8.5, about 9, about 9.5, about 10 degrees, about 11 degrees, about 12 degrees, about 13 degrees, about 14 degrees, or about 15 degrees Celsius than a control binding molecule (e.g. a conventional scFv molecule) in the described assays.

The improved thermal stability of the GFRα4 binding domain, e.g., scFv is subsequently conferred to the entire GFRα4 CAR construct, leading to improved therapeutic properties of the GFRα4 CAR construct. The thermal stability of the GFRα4 binding domain, e.g., scFv can be improved by at least about 2° C. or 3° C. as compared to a conventional antibody. In one embodiment, the GFRα4 binding domain, e.g., scFv has a 1° C. improved thermal stability as compared to a conventional antibody. In another embodiment, the GFRα4 binding domain, e.g., scFv has a 2° C. improved thermal stability as compared to a conventional antibody. In another embodiment, the scFv has a 4, 5, 6, 7, 8, 9, 10, 11, 12, 13, 14, 15° C. improved thermal stability as compared to a conventional antibody. Comparisons can be made, for example, between the scFv molecules disclosed herein and full length antibodies. Thermal stability can be measured using methods known in the art. For example, in one embodiment, Tm can be measured. Methods for measuring Tm and other methods of determining protein stability are described in more detail below.

Mutations in scFv alter the stability of the scFv and improve the overall stability of the scFv and the GFRα4 CART construct. Stability of the human scFv is determined using measurements such as Tm, temperature denaturation and temperature aggregation.

The binding capacity of the mutant scFvs can be determined using assays described in the Examples.

In one embodiment, the GFRα4 binding domain, e.g., scFv comprises at least one mutation such that the mutated scFv confers improved stability to the GFRα4 CAR construct. In another embodiment, the GFRα4 binding domain, e.g., scFv comprises at least 1, 2, 3, 4, 5, 6, 7, 8, 9, 10 mutations arising from the humanization process such that the mutated scFv confers improved stability to the GFRα4 CAR construct.

Methods of Evaluating Protein Stability

The stability of an antigen binding domain may be assessed using, e.g., the methods described below. Such methods allow for the determination of multiple thermal unfolding transitions where the least stable domain either unfolds first or limits the overall stability threshold of a multidomain unit that unfolds cooperatively (e.g., a multidomain protein which exhibits a single unfolding transition). The least stable domain can be identified in a number of additional ways. Mutagenesis can be performed to probe which domain limits the overall stability. Additionally, protease resistance of a multidomain protein can be performed under conditions where the least stable domain is known to be intrinsically unfolded via DSC or other spectroscopic methods (Fontana, et al., (1997) Fold. Des., 2: R17-26; Dimasi et al. (2009) J. Mol. Biol. 393: 672-692). Once the least stable domain is identified, the sequence encoding this domain (or a portion thereof) may be employed as a test sequence in the methods.

a) Thermal Stability

The thermal stability of the compositions may be analyzed using a number of non-limiting biophysical or biochemical techniques known in the art. In certain embodiments, thermal stability is evaluated by analytical spectroscopy.

An exemplary analytical spectroscopy method is Differential Scanning calorimetry (DSC). DSC employs a calorimeter which is sensitive to the heat absorbances that accompany the unfolding of most proteins or protein domains (see, e.g. Sanchez-Ruiz, et al., Biochemistry, 27: 1648-52, 1988). To determine the thermal stability of a protein, a sample of the protein is inserted into the calorimeter and the temperature is raised until the Fab or scFv unfolds. The temperature at which the protein unfolds is indicative of overall protein stability.

Another exemplary analytical spectroscopy method is Circular Dichroism (CD) spectroscopy. CD spectrometry measures the optical activity of a composition as a function of increasing temperature. Circular dichroism (CD) spectroscopy measures differences in the absorption of left-handed polarized light versus right-handed polarized light which arise due to structural asymmetry. A disordered or unfolded structure results in a CD spectrum very different from that of an ordered or folded structure. The CD spectrum reflects the sensitivity of the proteins to the denaturing effects of increasing temperature and is therefore indicative of a protein's thermal stability (see van Mierlo and Steemsma, J. Biotechnol., 79(3):281-98, 2000).

Another exemplary analytical spectroscopy method for measuring thermal stability is Fluorescence Emission Spectroscopy (see van Mierlo and Steemsma, supra). Yet another exemplary analytical spectroscopy method for measuring thermal stability is Nuclear Magnetic Resonance (NMR) spectroscopy (see, e.g. van Mierlo and Steemsma, supra).

The thermal stability of a composition can be measured biochemically. An exemplary biochemical method for assessing thermal stability is a thermal challenge assay. In a "thermal challenge assay", a composition is subjected to a range of elevated temperatures for a set period of time. For example, in one embodiment, test scFv molecules or molecules comprising scFv molecules are subject to a range of increasing temperatures, e.g., for 1-1.5 hours. The activity of the protein is then assayed by a relevant biochemical assay. For example, if the protein is a binding protein (e.g. an scFv or scFv-containing polypeptide) the binding activity of the binding protein may be determined by a functional or quantitative ELISA.

Such an assay may be done in a high-throughput format and those disclosed in the Examples using *E. coli* and high throughput screening. A library of GFRα4 binding domain, e.g., scFv variants may be created using methods known in the art. GFRα4 binding domain, e.g., scFv expression may be induced and the GFRα4 binding domain, e.g., scFv may be subjected to thermal challenge. The challenged test samples may be assayed for binding and those GFRα4 binding domain, e.g., scFvs which are stable may be scaled up and further characterized.

Thermal stability is evaluated by measuring the melting temperature (Tm) of a composition using any of the above techniques (e.g. analytical spectroscopy techniques). The melting temperature is the temperature at the midpoint of a thermal transition curve wherein 50% of molecules of a composition are in a folded state (See e.g., Dimasi et al. (2009) J. Mol Biol. 393: 672-692). In one embodiment, Tm values for an GFRα4 binding domain, e.g., scFv are about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C. In one embodiment, Tm values for an IgG is about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C. In one embodiment, Tm values for an multivalent antibody is about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C.

Thermal stability is also evaluated by measuring the specific heat or heat capacity (Cp) of a composition using an analytical calorimetric technique (e.g. DSC). The specific heat of a composition is the energy (e.g. in kcal/mol) is required to rise by 1° C., the temperature of 1 mol of water. As large Cp is a hallmark of a denatured or inactive protein composition. The change in heat capacity (ΔCp) of a composition is measured by determining the specific heat of a composition before and after its thermal transition. Thermal stability may also be evaluated by measuring or determining other parameters of thermodynamic stability including Gibbs free energy of unfolding (ΔG), enthalpy of unfolding (ΔH), or entropy of unfolding (ΔS). One or more of the above biochemical assays (e.g. a thermal challenge assay) are used to determine the temperature (i.e. the Tc value) at which 50% of the composition retains its activity (e.g. binding activity).

In addition, mutations to the GFRα4 binding domain, e.g., scFv alter the thermal stability of the GFRα4 binding domain, e.g., scFv compared with the unmutated GFRα4 binding domain, e.g., scFv. In one embodiment, the GFRα4 binding domain, e.g., scFv comprises a single mutation that confers thermal stability to the GFRα4 binding domain, e.g., scFv. In another embodiment, the GFRα4 binding domain, e.g., scFv comprises multiple mutations that confer thermal stability to the GFRα4 binding domain, e.g., scFv. In one embodiment, the multiple mutations in the GFRα4 binding domain, e.g., scFv have an additive effect on thermal stability of the GFRα4 binding domain, e.g., scFv.

b) % Aggregation

The stability of a composition can be determined by measuring its propensity to aggregate. Aggregation can be measured by a number of non-limiting biochemical or biophysical techniques. For example, the aggregation of a composition may be evaluated using chromatography, e.g. Size-Exclusion Chromatography (SEC). SEC separates molecules on the basis of size. A column is filled with semi-solid beads of a polymeric gel that will admit ions and small molecules into their interior but not large ones. When a protein composition is applied to the top of the column, the compact folded proteins (i.e. non-aggregated proteins) are distributed through a larger volume of solvent than is available to the large protein aggregates. Consequently, the large aggregates move more rapidly through the column, and in this way the mixture can be separated or fractionated into its components. Each fraction can be separately quantified (e.g. by light scattering) as it elutes from the gel. Accordingly, the % aggregation of a composition can be determined by comparing the concentration of a fraction with the total concentration of protein applied to the gel. Stable compositions elute from the column as essentially a single fraction and appear as essentially a single peak in the elution profile or chromatogram.

c) Binding Affinity

The stability of a composition can be assessed by determining its target binding affinity. A wide variety of methods for determining binding affinity are known in the art. An exemplary method for determining binding affinity employs surface plasmon resonance. Surface plasmon resonance is an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al. (1993) Ann. Biol. Clin. 51:19-26; Jonsson, U., i (1991) Biotechniques 11:620-627; Johnsson, B., et al. (1995) J. Mol. Recognit. 8:125-131; and Johnnson, B., et al. (1991) Anal. Biochem. 198:268-277.

In one aspect, the antigen binding domain of the CAR comprises an amino acid sequence that is homologous to an antigen binding domain amino acid sequence described herein, and the antigen binding domain retains the desired functional properties of the GFRα4 antibody fragments described herein. In one specific aspect, the CAR composition of the invention comprises an antibody fragment. In a further aspect, that antibody fragment comprises an scFv.

In various aspects, the antigen binding domain of the CAR is engineered by modifying one or more amino acids within one or both variable regions (e.g., VH and/or VL), for example within one or more CDR regions and/or within one or more framework regions. In one specific aspect, the CAR composition of the invention comprises an antibody fragment. In a further aspect, that antibody fragment comprises an scFv.

It will be understood by one of ordinary skill in the art that the antibody or antibody fragment of the invention may further be modified such that they vary in amino acid sequence (e.g., from wild-type), but not in desired activity. For example, additional nucleotide substitutions leading to amino acid substitutions at "non-essential" amino acid residues may be made to the protein For example, a nonessential amino acid residue in a molecule may be replaced with another amino acid residue from the same side chain family. In another embodiment, a string of amino acids can be replaced with a structurally similar string that differs in order and/or composition of side chain family members, e.g., a conservative substitution, in which an amino acid residue is replaced with an amino acid residue having a similar side chain, may be made.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Percent identity in the context of two or more nucleic acids or polypeptide sequences, refers to two or more sequences that are the same. Two sequences are "substantially identical" if two sequences have a specified percentage of amino acid residues or nucleotides that are the same (e.g., 60% identity, optionally 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well known in the art. Optimal alignment of sequences for comparison can be conducted, e.g., by the local homology algorithm of Smith and Waterman, (1970) Adv. Appl. Math. 2:482c, by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Brent et al., (2003) Current Protocols in Molecular Biology).

Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information.

The percent identity between two amino acid sequences can also be determined using the algorithm of E. Meyers and W. Miller, (1988) Comput. Appl. Biosci. 4:11-17) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (1970) J. Mol. Biol. 48:444-453) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

In one aspect, the present invention contemplates modifications of the starting antibody or fragment (e.g., scFv) amino acid sequence that generate functionally equivalent molecules. For example, the VH or VL of an GFRα4 binding domain, e.g., scFv, comprised in the CAR can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting VH or VL framework region of the GFRα4 binding domain, e.g., scFv. The present invention contemplates modifications of the entire CAR construct, e.g., modifications in one or more amino acid sequences of the various domains of the CAR construct in order to generate functionally equivalent molecules. The CAR construct can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting CAR construct.

RNA Transfection

Disclosed herein are methods for producing an in vitro transcribed RNA CAR. The present invention also includes a CAR encoding RNA construct that can be directly transfected into a cell. A method for generating mRNA for use in transfection can involve in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length (SEQ ID NO:35). RNA so produced can efficiently transfect different kinds of cells. In one aspect, the template includes sequences for the CAR.

In one aspect the GFRα4 CAR is encoded by a messenger RNA (mRNA). In one aspect the mRNA encoding the GFRα4 CAR is introduced into a T cell for production of a CART cell.

In one embodiment, the in vitro transcribed RNA CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired temple for in vitro transcription is a CAR of the present invention. For example, the template for the RNA CAR comprises an extracellular region comprising a single chain variable domain of an anti-tumor antibody; a hinge region, a transmembrane domain (e.g., a transmembrane domain of CD8a); and a cytoplasmic region that includes an intracellular signaling domain, e.g., comprising the signaling domain of CD3-zeta and the signaling domain of 4-1BB.

In one embodiment, the DNA to be used for PCR contains an open reading frame. The DNA can be from a naturally occurring DNA sequence from the genome of an organism. In one embodiment, the nucleic acid can include some or all of the 5' and/or 3' untranslated regions (UTRs). The nucleic acid can include exons and introns. In one embodiment, the DNA to be used for PCR is a human nucleic acid sequence. In another embodiment, the DNA to be used for PCR is a human nucleic acid sequence including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary," as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a nucleic acid that is normally transcribed in cells (the open reading frame), including 5' and 3' UTRs. The primers can also be designed to amplify a portion of a nucleic acid that encodes a particular domain of interest. In one embodiment, the primers are designed to amplify the coding region of a human cDNA, including all or portions of the 5' and 3' UTRs. Primers useful for PCR can be generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between one and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the nucleic acid of interest. Alternatively, UTR sequences that are not endogenous to the nucleic acid of interest can be added by incorporating the UTR sequences into the forward and reverse primers or by any other modifications of the template. The use of UTR sequences that are not endogenous to the nucleic acid of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous nucleic acid. Alternatively, when a 5' UTR that is not endogenous to the nucleic acid of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be 5'UTR of an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (SEQ ID NO: 31) (size can be 50-5000 T (SEQ ID NO: 32)), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines (SEQ ID NO: 33).

Poly(A) tails of RNAs can be further extended following in vitro transcription with the use of a poly(A) polymerase, such as *E. coli* polyA polymerase (E-PAP). In one embodiment, increasing the length of a poly(A) tail from 100 nucleotides to between 300 and 400 nucleotides (SEQ ID NO: 34) results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as “gene guns” (see, for example, Nishikawa, et al. Hum Gene Ther., 12(8):861-70 (2001).

Non-Viral Delivery Methods

In some aspects, non-viral methods can be used to deliver a nucleic acid encoding a CAR described herein into a cell or tissue or a subject.

In some embodiments, the non-viral method includes the use of a transposon (also called a transposable element). In some embodiments, a transposon is a piece of DNA that can insert itself at a location in a genome, for example, a piece of DNA that is capable of self-replicating and inserting its copy into a genome, or a piece of DNA that can be spliced out of a longer nucleic acid and inserted into another place in a genome. For example, a transposon comprises a DNA sequence made up of inverted repeats flanking genes for transposition.

Exemplary methods of nucleic acid delivery using a transposon include a Sleeping Beauty transposon system (SBTS) and a piggyBac (PB) transposon system. See, e.g., Aronovich et al. Hum. Mol. Genet. 20.R1(2011):R14-20; Singh et al. Cancer Res. 15(2008):2961-2971; Huang et al. Mol. Ther. 16(2008):580-589; Grabundzija et al. Mol. Ther. 18(2010):1200-1209; Kebriaei et al. Blood. 122.21(2013): 166; Williams. Molecular Therapy 16.9(2008):1515-16; Bell et al. Nat. Protoc. 2.12(2007):3153-65; and Ding et al. Cell. 122.3(2005):473-83, all of which are incorporated herein by reference.

The SBTS includes two components: 1) a transposon containing a transgene and 2) a source of transposase enzyme. The transposase can transpose the transposon from a carrier plasmid (or other donor DNA) to a target DNA, such as a host cell chromosome/genome. For example, the transposase binds to the carrier plasmid/donor DNA, cuts the transposon (including transgene(s)) out of the plasmid, and inserts it into the genome of the host cell. See, e.g., Aronovich et al. supra.

Exemplary transposons include a pT2-based transposon. See, e.g., Grabundzija et al. Nucleic Acids Res. 41.3(2013): 1829-47; and Singh et al. Cancer Res. 68.8(2008): 2961-2971, all of which are incorporated herein by reference. Exemplary transposases include a Tc1/mariner-type transposase, e.g., the SB10 transposase or the SB11 transposase (a hyperactive transposase which can be expressed, e.g., from a cytomegalovirus promoter). See, e.g., Aronovich et al.; Kebriaei et al.; and Grabundzija et al., all of which are incorporated herein by reference.

Use of the SBTS permits efficient integration and expression of a transgene, e.g., a nucleic acid encoding a CAR described herein. Provided herein are methods of generating a cell, e.g., T cell or NK cell, that stably expresses a CAR described herein, e.g., using a transposon system such as SBTS.

In accordance with methods described herein, in some embodiments, one or more nucleic acids, e.g., plasmids, containing the SBTS components are delivered to a cell (e.g., T or NK cell). For example, the nucleic acid(s) are delivered by standard methods of nucleic acid (e.g., plasmid DNA) delivery, e.g., methods described herein, e.g., electroporation, transfection, or lipofection. In some embodiments, the nucleic acid contains a transposon comprising a transgene, e.g., a nucleic acid encoding a CAR described herein. In some embodiments, the nucleic acid contains a transposon comprising a transgene (e.g., a nucleic acid encoding a CAR described herein) as well as a nucleic acid sequence encoding a transposase enzyme. In other embodiments, a system with two nucleic acids is provided, e.g., a dual-plasmid system, e.g., where a first plasmid contains a transposon comprising a transgene, and a second plasmid contains a nucleic acid sequence encoding a transposase enzyme. For example, the first and the second nucleic acids are co-delivered into a host cell.

In some embodiments, cells, e.g., T or NK cells, are generated that express a CAR described herein by using a combination of gene insertion using the SBTS and genetic editing using a nuclease (e.g., Zinc finger nucleases (ZFNs), Transcription Activator-Like Effector Nucleases (TALENs), the CRISPR/Cas system, or engineered meganuclease re-engineered homing endonucleases).

In some embodiments, use of a non-viral method of delivery permits reprogramming of cells, e.g., T or NK cells, and direct infusion of the cells into a subject. Advantages of non-viral vectors include but are not limited to the ease and relatively low cost of producing sufficient amounts required to meet a patient population, stability during storage, and lack of immunogenicity.

Nucleic Acid Constructs Encoding a CAR

The present invention also provides nucleic acid molecules encoding one or more CAR constructs described herein. In one aspect, the nucleic acid molecule is provided as a messenger RNA transcript. In one aspect, the nucleic acid molecule is provided as a DNA construct.

Accordingly, in one aspect, the invention pertains to an isolated nucleic acid molecule encoding a chimeric antigen receptor (CAR), wherein the CAR comprises a GFRα4 binding domain (e.g., a human GFRα4 binding domain), a transmembrane domain, and an intracellular signaling domain comprising a stimulatory domain, e.g., a costimulatory signaling domain and/or a primary signaling domain, e.g., zeta chain. In one embodiment, the GFRα4 binding domain is a GFRα4 binding domain described herein, e.g., a GFRα4 binding domain which comprises a sequence selected from SEQ ID NO:59 or 79, or a sequence with 95-99% identity thereof. In one embodiment, the transmembrane domain is transmembrane domain of a protein described herein, e.g., selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment, the transmembrane domain comprises a sequence of SEQ ID NO: 6, or a sequence with 95-99% identity thereof. In one embodiment, the GFRα4 binding domain is connected to the transmembrane domain by a hinge region, e.g., a hinge described herein. In one embodiment, the hinge region comprises SEQ ID NO:2 or SEQ ID NO:3 or SEQ ID NO:4 or SEQ ID NO:5, or a sequence with 95-99% identity thereof. In one embodiment, the isolated nucleic acid molecule further comprises a sequence encoding a costimulatory domain. In one embodiment, the costimulatory domain is a functional signaling domain of a protein described herein, e.g., selected from the group consisting of a MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

In one embodiment, the costimulatory domain comprises a sequence of SEQ ID NO:7, or a sequence with 95-99% identity thereof. In one embodiment, the intracellular signaling domain comprises a functional signaling domain of 4-1BB and a functional signaling domain of CD3 zeta. In one embodiment, the intracellular signaling domain comprises the sequence of SEQ ID NO: 7 or SEQ ID NO:8, or a sequence with 95-99% identity thereof, and the sequence of SEQ ID NO: 9 or SEQ ID NO:10, or a sequence with 95-99% identity thereof, wherein the sequences comprising the intracellular signaling domain are expressed in the same frame and as a single polypeptide chain.

In another aspect, the invention pertains to an isolated nucleic acid molecule encoding a CAR construct comprising a leader sequence of SEQ ID NO: 1, a scFv domain having a sequence selected from SEQ ID NO:59 or 79 (or a sequence with 95-99% identity thereof), a hinge region of SEQ ID NO:2 or SEQ ID NO:3 or SEQ ID NO:4 or SEQ ID NO:5 (or a sequence with 95-99% identity thereof), a transmembrane domain having a sequence of SEQ ID NO: 6 (or a sequence with 95-99% identity thereof), a 4-1BB costimulatory domain having a sequence of SEQ ID NO:7 or a CD27 costimulatory domain having a sequence of SEQ ID NO:8 (or a sequence with 95-99% identity thereof) or a CD28 costimulatory domain having a sequence of SEQ ID NO:80 (or a sequence with 95-99% identity thereof) or a ICOS costimulatory domain having a sequence of SEQ ID NO: 82 (or a sequence with 95-99% identity thereof), and a CD3 zeta stimulatory domain having a sequence of SEQ ID NO:9 or SEQ ID NO:10 (or a sequence with 95-99% identity thereof).

In another aspect, the invention pertains to an isolated polypeptide molecule encoded by the nucleic acid molecule. In one embodiment, the isolated polypeptide molecule comprises a sequence selected from the group consisting of SEQ ID NO:85, 86, 90, 92, 94, 96, 98, 100, 102, and 104, or a sequence with 95-99% identity thereof.

In another aspect, the invention pertains to a nucleic acid molecule encoding a chimeric antigen receptor (CAR) molecule that comprises a GFRα4 binding domain, a transmembrane domain, and an intracellular signaling domain comprising a stimulatory domain, and wherein said GFRα4 binding domain comprises a sequence selected from SEQ ID NO: 59 or 79, or a sequence with 95-99% identity thereof.

In one embodiment, the encoded CAR molecule further comprises a sequence encoding a costimulatory domain. In one embodiment, the costimulatory domain is a functional signaling domain of a protein selected from the group consisting of a MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83. In one embodiment, the 4-1BB costimulatory domain comprises an amino acid sequence of SEQ ID NO:7. In one embodiment, the CD27 costimulatory domain comprises an amino acid sequence of SEQ ID NO:8. In one embodiment, the CD28 costimulatory domain comprises an amino acid sequence of SEQ ID NO:80. In one embodiment, the ICOS costimulatory domain comprises an amino acid sequence of SEQ ID NO:82.

In one embodiment, the transmembrane domain is a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, a MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83. In one embodiment, the transmembrane domain comprises a sequence of SEQ ID NO:6. In one embodiment, the intracellular signaling domain comprises a functional signaling domain of 4-1BB and a functional signaling domain of zeta. In one embodiment, the intracellular signaling domain comprises the sequence of SEQ ID NO: 7 and the sequence of SEQ ID NO: 9, wherein the sequences comprising the intracellular signaling domain are expressed in the same frame and as a single polypeptide chain. In one embodiment, the GFRα4 binding domain is connected to the transmembrane domain by a hinge region. In one embodiment, the hinge region comprises SEQ ID NO:2. In one embodiment, the hinge region comprises SEQ ID NO:3 or SEQ ID NO:4 or SEQ ID NO:5.

In another aspect, the invention pertains to an encoded CAR molecule comprising a leader sequence of SEQ ID NO: 1, a scFv domain having a sequence selected from SEQ ID NO: 59 or 79, or a sequence with 95-99% identity thereof, a hinge region of SEQ ID NO:2 or SEQ ID NO:3 or SEQ ID NO:4 or SEQ ID NO:5, a transmembrane domain having a sequence of SEQ ID NO: 6, a 4-1BB costimulatory domain having a sequence of SEQ ID NO:7 or a CD27 costimulatory domain having a sequence of SEQ ID NO:8, and a CD3 zeta stimulatory domain having a sequence of SEQ ID NO:9 or SEQ ID NO:10. In one embodiment, the encoded CAR molecule comprises a sequence selected from a group consisting of SEQ ID NO:85, 86, 90, 92, 94, 96, 98, 100, 103, and 104, or a sequence with 95-99% identity thereof.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

Vectors

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. A retroviral vector may also be, e.g., a gammaretroviral vector. A gammaretroviral vector may include, e.g., a promoter, a packaging signal (w), a primer binding site (PBS), one or more (e.g., two) long terminal repeats (LTR), and a transgene of interest, e.g., a gene encoding a CAR. A gammaretroviral vector may lack viral structural gens such as gag, pol, and env. Exemplary gammaretroviral vectors include Murine Leukemia Virus (MLV), Spleen-Focus Forming Virus (SFFV), and Myeloproliferative Sarcoma Virus (MPSV), and vectors derived therefrom. Other gammaretroviral vectors are described, e.g., in Tobias Maetzig et al., "Gammaretroviral Vectors: Biology, Technology and Application" Viruses. 2011 June; 3(6): 677-713.

In another embodiment, the vector comprising the nucleic acid encoding the desired CAR of the invention is an adenoviral vector (A5/35). In another embodiment, the expression of nucleic acids encoding CARs can be accomplished using of transposons such as sleeping beauty, crisper, CAS9, and zinc finger nucleases. See below June et al. 2009 Nature Reviews Immunology 9.10: 704-716, is incorporated herein by reference.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., Molecular Cloning: A Laboratory Manual, volumes 1-3 (3$^{rd}$ ed., Cold Spring Harbor Press, NY 2001), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter that is capable of expressing a CAR transgene in an immune effector cell is the EF1alpha promoter. The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving CAR expression from transgenes cloned into a lentiviral vector. See, e.g., Milone et al., Mol. Ther. 17(8): 1453-1464 (2009). In one aspect, the EF1a promoter comprises the sequence provided as SEQ ID NO:11.

An additional example includes the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Another example of a promoter is the phosphoglycerate kinase (PGK) promoter. In embodiments, a truncated PGK promoter (e.g., a PGK promoter with one or more, e.g., 1, 2, 5, 10, 100, 200, 300, or 400, nucleotide deletions when compared to the wild-type PGK promoter sequence) may be desired. The nucleotide sequences of exemplary PGK promoters are provided below.

```
WT PGK Promoter
                                          (SEQ ID NO: 218)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACGAGGGACCGCGACAGGCAGACGCTCCCATG

ATCACTCTGCACGCCGAAGGCAAATAGTGCAGGCCGTGCGGCGCTTGGCG

TTCCTTGGAAGGGCTGAATCCCCGCCTCGTCCTTCGCAGCGGCCCCCCGG

GTGTTCCCATCGCCGCTTCTAGGCCCACTGCGACGCTTGCCTGCACTTCT

TACACGCTCTGGGTCCCAGCCGCGGCGACGCAAAGGGCCTTGGTGCGGGT

CTCGTCGGCGCAGGGACGCGTTTGGGTCCCGACGGAACCTTTTCCGCGTT

GGGGTTGGGGCACCATAAGCT

Exemplary truncated PGK Promoters:
PGK100:
                                          (SEQ ID NO: 219)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTG

PGK200:
                                          (SEQ ID NO: 220)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACG

PGK300:
                                          (SEQ ID NO: 221)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACGAGGGACCGCGACAGGCAGACGCTCCCATG

ATCACTCTGCACGCCGAAGGCAAATAGTGCAGGCCGTGCGGCGCTTGGCG

TTCCTTGGAAGGGCTGAATCCCCG
```

-continued

```
PGK400:
                                          (SEQ ID NO: 222)
ACCCCTCTCTCCAGCCACTAAGCCAGTTGCTCCCTCGGCTGACGGCTGCA

CGCGAGGCCTCCGAACGTCTTACGCCTTGTGGCGCGCCCGTCCTTGTCCC

GGGTGTGATGGCGGGGTGTGGGGCGGAGGGCGTGGCGGGGAAGGGCCGGC

GACGAGAGCCGCGCGGGACGACTCGTCGGCGATAACCGGTGTCGGGTAGC

GCCAGCCGCGCGACGGTAACGAGGGACCGCGACAGGCAGACGCTCCCATG

ATCACTCTGCACGCCGAAGGCAAATAGTGCAGGCCGTGCGGCGCTTGGCG

TTCCTTGGAAGGGCTGAATCCCCGCCTCGTCCTTCGCAGCGGCCCCCCGG

GTGTTCCCATCGCCGCTTCTAGGCCCACTGCGACGCTTGCCTGCACTTCT

TACACGCTCTGGGTCCCAGCCG
```

A vector may also include, e.g., a signal sequence to facilitate secretion, a polyadenylation signal and transcription terminator (e.g., from Bovine Growth Hormone (BGH) gene), an element allowing episomal replication and replication in prokaryotes (e.g. SV40 origin and ColE1 or others known in the art) and/or elements to allow selection (e.g., ampicillin resistance gene and/or zeocin marker).

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In one embodiment, the vector can further comprise a nucleic acid encoding a second CAR. In one embodiment, the vector comprises a nucleic acid sequence encoding a first CAR that specifically binds a first antigen and includes an intracellular signaling domain having a costimulatory signaling domain but not a primary signaling domain, and a nucleic acid encoding a second CAR that specifically binds a second, different, antigen and includes an intracellular signaling domain having a primary signaling domain but not a costimulatory signaling domain. In one embodiment, the vector comprises a nucleic acid encoding a first GFRα4

CAR that includes a GFRα4 binding domain, a transmembrane domain and a costimulatory domain and a nucleic acid encoding a second CAR that specifically binds an antigen other than GFRα4 (e.g., an antigen expressed on medullary thyroid cancer cells) and includes an antigen binding domain, a transmembrane domain and a primary signaling domain.

In one embodiment, the vector comprises a nucleic acid encoding a GFRα4 CAR described herein and a nucleic acid encoding an inhibitory CAR. In one embodiment, the inhibitory CAR comprises an antigen binding domain that binds an antigen found on normal cells but not cancer cells, e.g., normal cells that also express GFRα4. In one embodiment, the inhibitory CAR comprises the antigen binding domain, a transmembrane domain and an intracellular domain of an inhibitory molecule. For example, the intracellular domain of the inhibitory CAR can be an intracellular domain of PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, and TGFR beta.

In embodiments, the vector may comprise two or more nucleic acid sequences encoding a CAR, e.g., a GFRα4 CAR described herein and a second CAR, e.g., an inhibitory CAR or a CAR that specifically binds to an antigen other than GFRα4 (e.g., an antigen expressed on medullary thyroid cancer cells). In such embodiments, the two or more nucleic acid sequences encoding the CAR are encoded by a single nucleic molecule in the same frame and as a single polypeptide chain. In this aspect, the two or more CARs, can, e.g., be separated by one or more peptide cleavage sites. (e.g., an auto-cleavage site or a substrate for an intracellular protease). Examples of peptide cleavage sites include the following, wherein the GSG residues are optional:

```
                                       (SEQ ID NO: 223)
T2A:          (GSG) EGRGSLLTCGDVEENPGP

                                       (SEQ ID NO: 224)
P2A:          (GSG) ATNFSLLKQAGDVEENPGP

                                       (SEQ ID NO: 225)
E2A:          (GSG) QCTNYALLKLAGDVESNPGP

                                       (SEQ ID NO: 226)
F2A:          (GSG) VKQTLNFDLLKLAGDVESNPGP
```

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., Molecular Cloning: A Laboratory Manual, volumes 1-3 ($3^{rd}$ ed., Cold Spring Harbor Press, NY 2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Sources of Cells

Prior to expansion and genetic modification, a source of cells (e.g., immune effector cells, e.g., T cells or NK cells) is obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors.

In certain embodiments of the present invention, any number of immune effector cell (e.g., T cell or NK cell) lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

It is recognized that the methods of the application can utilize culture media conditions comprising 5% or less, for example 2%, human AB serum, and employ known culture media conditions and compositions, for example those described in Smith et al., "Ex vivo expansion of human T cells for adoptive immunotherapy using the novel Xeno-free CTS Immune Cell Serum Replacement" *Clinical & Translational Immunology* (2015) 4, e31; doi:10.1038/cti.2014.31.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-C25 conjugated beads or other similar method of selection.

The methods described herein can include, e.g., selection of a specific subpopulation of immune effector cells, e.g., T cells, that are a T regulatory cell-depleted population, CD25+ depleted cells, using, e.g., a negative selection technique, e.g., described herein. Preferably, the population of T regulatory depleted cells contains less than 30%, 25%, 20%, 15%, 10%, 5%, 4%, 3%, 2%, 1% of CD25+ cells.

In one embodiment, T regulatory cells, e.g., CD25+ T cells, are removed from the population using an anti-CD25 antibody, or fragment thereof, or a CD25-binding ligand, IL-2. In one embodiment, the anti-CD25 antibody, or fragment thereof, or CD25-binding ligand is conjugated to a substrate, e.g., a bead, or is otherwise coated on a substrate, e.g., a bead. In one embodiment, the anti-CD25 antibody, or fragment thereof, is conjugated to a substrate as described herein.

In one embodiment, the T regulatory cells, e.g., CD25+ T cells, are removed from the population using CD25 depletion reagent from Miltenyi™. In one embodiment, the ratio of cells to CD25 depletion reagent is 1e7 cells to 20 uL, or 1e7 cells to 15 uL, or 1e7 cells to 10 uL, or 1e7 cells to 5 uL, or 1e7 cells to 2.5 uL, or 1e7 cells to 1.25 uL. In one embodiment, e.g., for T regulatory cells, e.g., CD25+ depletion, greater than 500 million cells/ml is used. In a further aspect, a concentration of cells of 600, 700, 800, or 900 million cells/ml is used.

In one embodiment, the population of immune effector cells to be depleted includes about $6\times10^9$ CD25+ T cells. In other aspects, the population of immune effector cells to be depleted include about $1\times10^9$ to $1\times10^{10}$ CD25+ T cell, and any integer value in between. In one embodiment, the resulting population T regulatory depleted cells has $2\times10^9$ T regulatory cells, e.g., CD25+ cells, or less (e.g., $1\times10^9$, $5\times10^8$, $1\times10^8$, $5\times10^7$, $1\times10^7$, or less CD25+ cells).

In one embodiment, the T regulatory cells, e.g., CD25+ cells, are removed from the population using the CliniMAC system with a depletion tubing set, such as, e.g., tubing 162-01. In one embodiment, the CliniMAC system is run on a depletion setting such as, e.g., DEPLETION2.1.

Without wishing to be bound by a particular theory, decreasing the level of negative regulators of immune cells (e.g., decreasing the number of unwanted immune cells, e.g., $T_{REG}$ cells), in a subject prior to apheresis or during manufacturing of a CAR-expressing cell product can reduce the risk of subject relapse. For example, methods of depleting $T_{REG}$ cells are known in the art. Methods of decreasing $T_{REG}$ cells include, but are not limited to, cyclophosphamide, anti-GITR antibody (an anti-GITR antibody described herein), CD25-depletion, and combinations thereof.

In some embodiments, the manufacturing methods comprise reducing the number of (e.g., depleting) $T_{REG}$ cells prior to manufacturing of the CAR-expressing cell. For example, manufacturing methods comprise contacting the sample, e.g., the apheresis sample, with an anti-GITR antibody and/or an anti-CD25 antibody (or fragment thereof, or a CD25-binding ligand), e.g., to deplete $T_{REG}$ cells prior to manufacturing of the CAR-expressing cell (e.g., T cell, NK cell) product.

In an embodiment, a subject is pre-treated with one or more therapies that reduce $T_{REG}$ cells prior to collection of cells for CAR-expressing cell product manufacturing, thereby reducing the risk of subject relapse to CAR-expressing cell treatment. In an embodiment, methods of decreasing $T_{REG}$ cells include, but are not limited to, administration to the subject of one or more of cyclophosphamide, anti-GITR antibody, CD25-depletion, or a combination thereof. Administration of one or more of cyclophosphamide, anti-GITR antibody, CD25-depletion, or a combination thereof, can occur before, during or after an infusion of the CAR-expressing cell product.

In an embodiment, a subject is pre-treated with cyclophosphamide prior to collection of cells for CAR-expressing cell product manufacturing, thereby reducing the risk of subject relapse to CAR-expressing cell treatment. In an embodiment, a subject is pre-treated with an anti-GITR antibody prior to collection of cells for CAR-expressing cell product manufacturing, thereby reducing the risk of subject relapse to CAR-expressing cell treatment.

In one embodiment, the population of cells to be removed are neither the regulatory T cells or tumor cells, but cells that otherwise negatively affect the expansion and/or function of CART cells, e.g. cells expressing CD14, CD11b, CD33, CD15, or other markers expressed by potentially immune suppressive cells. In one embodiment, such cells are envisioned to be removed concurrently with regulatory T cells and/or tumor cells, or following said depletion, or in another order.

The methods described herein can include more than one selection step, e.g., more than one depletion step. Enrichment of a T cell population by negative selection can be accomplished, e.g., with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail can include antibodies to CD14, CD20, CD11b, CD16, HLA-DR, and CD8.

The methods described herein can further include removing cells from the population which express a tumor antigen, e.g., a tumor antigen that does not comprise CD25, e.g., CD19, CD30, CD38, CD123, CD20, CD14 or CD11b, to thereby provide a population of T regulatory depleted, e.g., CD25+ depleted, and tumor antigen depleted cells that are suitable for expression of a CAR, e.g., a CAR described herein. In one embodiment, tumor antigen expressing cells are removed simultaneously with the T regulatory, e.g., CD25+ cells. For example, an anti-CD25 antibody, or fragment thereof, and an anti-tumor antigen antibody, or fragment thereof, can be attached to the same substrate, e.g., bead, which can be used to remove the cells or an anti-CD25 antibody, or fragment thereof, or the anti-tumor antigen antibody, or fragment thereof, can be attached to separate beads, a mixture of which can be used to remove the cells. In other embodiments, the removal of T regulatory cells, e.g., CD25+ cells, and the removal of the tumor antigen expressing cells is sequential, and can occur, e.g., in either order.

Also provided are methods that include removing cells from the population which express a check point inhibitor, e.g., a check point inhibitor described herein, e.g., one or more of PD1+ cells, LAG3+ cells, and TIM3+ cells, to thereby provide a population of T regulatory depleted, e.g., CD25+ depleted cells, and check point inhibitor depleted cells, e.g., PD1+, LAG3+ and/or TIM3+ depleted cells. Exemplary check point inhibitors include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, and TGFR beta. In one embodiment, check point inhibitor expressing cells are removed simultaneously with the T regulatory, e.g., CD25+ cells. For example, an anti-CD25 antibody, or fragment thereof, and an anti-check point inhibitor antibody, or fragment thereof, can be attached to the same bead which can be used to remove the cells, or an anti-CD25 antibody, or fragment thereof, and the anti-check point inhibitor antibody, or fragment there, can be attached to separate beads, a mixture of which can be used to remove the cells. In other embodiments, the removal of T regulatory cells, e.g., CD25+ cells, and the removal of the check point inhibitor expressing cells is sequential, and can occur, e.g., in either order.

In one embodiment, a T cell population can be selected that expresses one or more of IFN-7, TNFα, IL-17A, IL-2, IL-3, IL-4, GM-CSF, IL-10, IL-13, granzyme B, and perforin, or other appropriate molecules, e.g., other cytokines. Methods for screening for cell expression can be determined, e.g., by the methods described in PCT Publication No.: WO 2013/126712.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

In one embodiment, the immune effector cells expressing a CAR molecule, e.g., a CAR molecule described herein, are obtained from a subject that has received a low, immune enhancing dose of an mTOR inhibitor. In an embodiment, the population of immune effector cells, e.g., T cells, to be engineered to express a CAR, are harvested after a sufficient time, or after sufficient dosing of the low, immune enhancing, dose of an mTOR inhibitor, such that the level of PD1 negative immune effector cells, e.g., T cells, or the ratio of PD1 negative immune effector cells, e.g., T cells/PD1 positive immune effector cells, e.g., T cells, in the subject or harvested from the subject has been, at least transiently, increased.

In other embodiments, population of immune effector cells, e.g., T cells, which have, or will be engineered to express a CAR, can be treated ex vivo by contact with an amount of an mTOR inhibitor that increases the number of PD1 negative immune effector cells, e.g., T cells or increases the ratio of PD1 negative immune effector cells, e.g., T cells/PD1 positive immune effector cells, e.g., T cells.

In one embodiment, a T cell population is diaglycerol kinase (DGK)-deficient. DGK-deficient cells include cells that do not express DGK RNA or protein, or have reduced or inhibited DGK activity. DGK-deficient cells can be generated by genetic approaches, e.g., administering RNA-interfering agents, e.g., siRNA, shRNA, miRNA, to reduce or prevent DGK expression. Alternatively, DGK-deficient cells can be generated by treatment with DGK inhibitors described herein.

In one embodiment, a T cell population is Ikaros-deficient. Ikaros-deficient cells include cells that do not express Ikaros RNA or protein, or have reduced or inhibited Ikaros activity, Ikaros-deficient cells can be generated by genetic approaches, e.g., administering RNA-interfering agents, e.g., siRNA, shRNA, miRNA, to reduce or prevent Ikaros expression. Alternatively, Ikaros-deficient cells can be generated by treatment with Ikaros inhibitors, e.g., lenalidomide.

In embodiments, a T cell population is DGK-deficient and Ikaros-deficient, e.g., does not express DGK and Ikaros, or has reduced or inhibited DGK and Ikaros activity. Such DGK and Ikaros-deficient cells can be generated by any of the methods described herein.

In an embodiment, the NK cells are obtained from the subject. In another embodiment, the NK cells are an NK cell line, e.g., NK-92 cell line (Conkwest).

Allogeneic CAR

In embodiments described herein, the immune effector cell can be an allogeneic immune effector cell, e.g., T cell or NK cell. For example, the cell can be an allogeneic T cell, e.g., an allogeneic T cell lacking expression of a functional T cell receptor (TCR) and/or human leukocyte antigen (HLA), e.g., HLA class I and/or HLA class II.

A T cell lacking a functional TCR can be, e.g., engineered such that it does not express any functional TCR on its surface, engineered such that it does not express one or more subunits that comprise a functional TCR (e.g., engineered such that it does not express (or exhibits reduced expression) of TCR alpha, TCR beta, TCR gamma, TCR delta, TCR epsilon, or TCR zeta) or engineered such that it produces very little functional TCR on its surface. Alternatively, the T cell can express a substantially impaired TCR, e.g., by expression of mutated or truncated forms of one or more of the subunits of the TCR. The term "substantially impaired TCR" means that this TCR will not elicit an adverse immune reaction in a host.

A T cell described herein can be, e.g., engineered such that it does not express a functional HLA on its surface. For example, a T cell described herein, can be engineered such that cell surface expression HLA, e.g., HLA class 1 and/or HLA class II, is downregulated. In some aspects, downregulation of HLA may be accomplished by reducing or eliminating expression of beta-2 microglobulin (B2M).

In some embodiments, the T cell can lack a functional TCR and a functional HLA, e.g., HLA class I and/or HLA class II.

Modified T cells that lack expression of a functional TCR and/or HLA can be obtained by any suitable means, including a knock out or knock down of one or more subunit of TCR or HLA. For example, the T cell can include a knock down of TCR and/or HLA using siRNA, shRNA, clustered regularly interspaced short palindromic repeats (CRISPR) transcription-activator like effector nuclease (TALEN), or zinc finger endonuclease (ZFN).

In some embodiments, the allogeneic cell can be a cell which does not expresses or expresses at low levels an inhibitory molecule, e.g., a cell engineered by any method described herein. For example, the cell can be a cell that does not express or expresses at low levels an inhibitory molecule, e.g., that can decrease the ability of a CAR-expressing cell to mount an immune effector response. Examples of inhibitory molecules include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MEW class I, MHC class II, GALS, adenosine, and TGFR beta. Inhibition of an inhibitory molecule, e.g., by inhibition at the DNA, RNA or protein level, can optimize a CAR-expressing cell performance. In embodiments, an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), e.g., as described herein, can be used.

siRNA and shRNA to Inhibit TCR or HLA

In some embodiments, TCR expression and/or HLA expression can be inhibited using siRNA or shRNA that targets a nucleic acid encoding a TCR and/or HLA, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MEW class I, MEW class II, GAL9, adenosine, and TGFR beta), in a cell.

Expression of siRNA and shRNAs in T cells can be achieved using any conventional expression system, e.g., such as a lentiviral expression system.

Exemplary shRNAs that downregulate expression of components of the TCR are described, e.g., in US Publication No.: 2012/0321667. Exemplary siRNA and shRNA that downregulate expression of HLA class I and/or HLA class II genes are described, e.g., in U.S. publication No.: US 2007/0036773.

CRISPR to Inhibit TCR or HLA

"CRISPR" or "CRISPR to TCR and/or HLA" or "CRISPR to inhibit TCR and/or HLA" as used herein refers to a set of clustered regularly interspaced short palindromic repeats, or a system comprising such a set of repeats. "Cas", as used herein, refers to a CRISPR-associated protein. A "CRISPR/Cas" system refers to a system derived from CRISPR and Cas which can be used to silence or mutate a TCR and/or HLA gene, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4

(VTCN1), HVEM (TNFRSF14 or CD270), KIR, A2aR, MEW class I, MEW class II, GAL9, adenosine, and TGFR beta).

Naturally-occurring CRISPR/Cas systems are found in approximately 40% of sequenced eubacteria genomes and 90% of sequenced archaea. Grissa et al. (2007) *BMC Bioinformatics* 8: 172. This system is a type of prokaryotic immune system that confers resistance to foreign genetic elements such as plasmids and phages and provides a form of acquired immunity. Barrangou et al. (2007) *Science* 315: 1709-1712; Marragini et al. (2008) *Science* 322: 1843-1845.

The CRISPR/Cas system has been modified for use in gene editing (silencing, enhancing or changing specific genes) in eukaryotes such as mice or primates. Wiedenheft et al. (2012) *Nature* 482: 331-8. This is accomplished by introducing into the eukaryotic cell a plasmid containing a specifically designed CRISPR and one or more appropriate Cas.

The CRISPR sequence, sometimes called a CRISPR locus, comprises alternating repeats and spacers. In a naturally-occurring CRISPR, the spacers usually comprise sequences foreign to the bacterium such as a plasmid or phage sequence; in the TCR and/or HLA CRISPR/Cas system, the spacers are derived from the TCR or HLA gene sequence.

RNA from the CRISPR locus is constitutively expressed and processed by Cas proteins into small RNAs. These comprise a spacer flanked by a repeat sequence. The RNAs guide other Cas proteins to silence exogenous genetic elements at the RNA or DNA level. Horvath et al. (2010) *Science* 327: 167-170; Makarova et al. (2006) *Biology Direct* 1: 7. The spacers thus serve as templates for RNA molecules, analogously to siRNAs. Pennisi (2013) *Science* 341: 833-836.

As these naturally occur in many different types of bacteria, the exact arrangements of the CRISPR and structure, function and number of Cas genes and their product differ somewhat from species to species. Haft et al. (2005) *PLoS Comput. Biol.* 1: e60; Kunin et al. (2007) *Genome Biol.* 8: R61; Mojica et al. (2005) *J Mol. Evol.* 60: 174-182; Bolotin et al. (2005) *Microbiol.* 151: 2551-2561; Pourcel et al. (2005) *Microbiol.* 151: 653-663; and Stern et al. (2010) *Trends. Genet.* 28: 335-340. For example, the Cse (Cas subtype, *E. coli*) proteins (e.g., CasA) form a functional complex, Cascade, that processes CRISPR RNA transcripts into spacer-repeat units that Cascade retains. Brouns et al. (2008) *Science* 321: 960-964. In other prokaryotes, Cas6 processes the CRISPR transcript. The CRISPR-based phage inactivation in *E. coli* requires Cascade and Cas3, but not Cas1 or Cas2. The Cmr (Cas RAMP module) proteins in *Pyrococcus furiosus* and other prokaryotes form a functional complex with small CRISPR RNAs that recognizes and cleaves complementary target RNAs. A simpler CRISPR system relies on the protein Cas9, which is a nuclease with two active cutting sites, one for each strand of the double helix. Combining Cas9 and modified CRISPR locus RNA can be used in a system for gene editing. Pennisi (2013) *Science* 341: 833-836.

The CRISPR/Cas system can thus be used to edit a TCR and/or HLA gene (adding or deleting a basepair), or introducing a premature stop which thus decreases expression of a TCR and/or HLA. The CRISPR/Cas system can alternatively be used like RNA interference, turning off TCR and/or HLA gene in a reversible fashion. In a mammalian cell, for example, the RNA can guide the Cas protein to a TCR and/or HLA promoter, sterically blocking RNA polymerases.

Artificial CRISPR/Cas systems can be generated which inhibit TCR and/or HLA, using technology known in the art, e.g., that described in U.S. Publication No. 20140068797 and Cong (2013) Science 339: 819-823. Other artificial CRISPR/Cas systems that are known in the art may also be generated which inhibit TCR and/or HLA, e.g., that described in Tsai (2014) Nature Biotechnol., 32:6 569-576, U.S. Pat. Nos. 8,871,445; 8,865,406; 8,795,965; 8,771,945; and 8,697,359.

TALEN to Inhibit TCR and/or HLA

"TALEN" or "TALEN to HLA and/or TCR" or "TALEN to inhibit HLA and/or TCR" refers to a transcription activator-like effector nuclease, an artificial nuclease which can be used to edit the HLA and/or TCR gene, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, and TGFR beta).

TALENs are produced artificially by fusing a TAL effector DNA binding domain to a DNA cleavage domain. Transcription activator-like effects (TALEs) can be engineered to bind any desired DNA sequence, including a portion of the HLA or TCR gene. By combining an engineered TALE with a DNA cleavage domain, a restriction enzyme can be produced which is specific to any desired DNA sequence, including a HLA or TCR sequence. These can then be introduced into a cell, wherein they can be used for genome editing. Boch (2011) *Nature Biotech.* 29: 135-6; and Boch et al. (2009) *Science* 326: 1509-12; Moscou et al. (2009) *Science* 326: 3501.

TALEs are proteins secreted by *Xanthomonas* bacteria. The DNA binding domain contains a repeated, highly conserved 33-34 amino acid sequence, with the exception of the 12th and 13th amino acids. These two positions are highly variable, showing a strong correlation with specific nucleotide recognition. They can thus be engineered to bind to a desired DNA sequence.

To produce a TALEN, a TALE protein is fused to a nuclease (N), which is a wild-type or mutated FokI endonuclease. Several mutations to FokI have been made for its use in TALENs; these, for example, improve cleavage specificity or activity. Cermak et al. (2011) *Nucl. Acids Res.* 39: e82; Miller et al. (2011) *Nature Biotech.* 29: 143-8; Hockemeyer et al. (2011) *Nature Biotech.* 29: 731-734; Wood et al. (2011) *Science* 333: 307; Doyon et al. (2010) *Nature Methods* 8: 74-79; Szczepek et al. (2007) *Nature Biotech.* 25: 786-793; and Guo et al. (2010) *J Mol. Biol.* 200: 96.

The FokI domain functions as a dimer, requiring two constructs with unique DNA binding domains for sites in the target genome with proper orientation and spacing. Both the number of amino acid residues between the TALE DNA binding domain and the FokI cleavage domain and the number of bases between the two individual TALEN binding sites appear to be important parameters for achieving high levels of activity. Miller et al. (2011) *Nature Biotech.* 29: 143-8.

A HLA or TCR TALEN can be used inside a cell to produce a double-stranded break (DSB). A mutation can be introduced at the break site if the repair mechanisms improperly repair the break via non-homologous end joining. For example, improper repair may introduce a frame shift mutation. Alternatively, foreign DNA can be introduced into the cell along with the TALEN; depending on the sequences of the foreign DNA and chromosomal sequence, this process can be used to correct a defect in the HLA or TCR gene or introduce such a defect into a wt HLA or TCR gene, thus decreasing expression of HLA or TCR.

TALENs specific to sequences in HLA or TCR can be constructed using any method known in the art, including various schemes using modular components. Zhang et al. (2011) *Nature Biotech.* 29: 149-53; Geibler et al. (2011) *PLoS ONE* 6: e19509.

Zinc Finger Nuclease to Inhibit HLA and/or TCR

"ZFN" or "Zinc Finger Nuclease" or "ZFN to HLA and/or TCR" or "ZFN to inhibit HLA and/or TCR" refer to a zinc finger nuclease, an artificial nuclease which can be used to edit the HLA and/or TCR gene, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MEW class I, MHC class II, GALS, adenosine, and TGFR beta).

Like a TALEN, a ZFN comprises a FokI nuclease domain (or derivative thereof) fused to a DNA-binding domain. In the case of a ZFN, the DNA-binding domain comprises one or more zinc fingers. Carroll et al. (2011) *Genetics Society of America* 188: 773-782; and Kim et al. (1996) *Proc. Natl. Acad. Sci. USA* 93: 1156-1160.

A zinc finger is a small protein structural motif stabilized by one or more zinc ions. A zinc finger can comprise, for example, Cys2His2, and can recognize an approximately 3-bp sequence. Various zinc fingers of known specificity can be combined to produce multi-finger polypeptides which recognize about 6, 9, 12, 15 or 18-bp sequences. Various selection and modular assembly techniques are available to generate zinc fingers (and combinations thereof) recognizing specific sequences, including phage display, yeast one-hybrid systems, bacterial one-hybrid and two-hybrid systems, and mammalian cells.

Like a TALEN, a ZFN must dimerize to cleave DNA. Thus, a pair of ZFNs are required to target non-palindromic DNA sites. The two individual ZFNs must bind opposite strands of the DNA with their nucleases properly spaced apart. Bitinaite et al. (1998) *Proc. Natl. Acad. Sci. USA* 95: 10570-5.

Also like a TALEN, a ZFN can create a double-stranded break in the DNA, which can create a frame-shift mutation if improperly repaired, leading to a decrease in the expression and amount of HLA and/or TCR in a cell. ZFNs can also be used with homologous recombination to mutate in the HLA or TCR gene.

ZFNs specific to sequences in HLA and/or TCR can be constructed using any method known in the art. See, e.g., Provasi (2011) Nature Med. 18: 807-815; Torikai (2013) Blood 122: 1341-1349; Cathomen et al. (2008) *Mol. Ther.* 16: 1200-7; Guo et al. (2010) *J. Mol. Biol.* 400: 96; U.S. Patent Publication 2011/0158957; and U.S. Patent Publication 2012/0060230.

Telomerase Expression

While not wishing to be bound by any particular theory, in some embodiments, a therapeutic T cell has short term persistence in a patient, due to shortened telomeres in the T cell; accordingly, transfection with a telomerase gene can lengthen the telomeres of the T cell and improve persistence of the T cell in the patient. See Carl June, "Adoptive T cell therapy for cancer in the clinic", Journal of Clinical Investigation, 117:1466-1476 (2007). Thus, in an embodiment, an immune effector cell, e.g., a T cell, ectopically expresses a telomerase subunit, e.g., the catalytic subunit of telomerase, e.g., TERT, e.g., hTERT. In some aspects, this disclosure provides a method of producing a CAR-expressing cell, comprising contacting a cell with a nucleic acid encoding a telomerase subunit, e.g., the catalytic subunit of telomerase, e.g., TERT, e.g., hTERT. The cell may be contacted with the nucleic acid before, simultaneous with, or after being contacted with a construct encoding a CAR.

In one aspect, the disclosure features a method of making a population of immune effector cells (e.g., T cells, NK cells). In an embodiment, the method comprises: providing a population of immune effector cells (e.g., T cells or NK cells), contacting the population of immune effector cells with a nucleic acid encoding a CAR; and contacting the population of immune effector cells with a nucleic acid encoding a telomerase subunit, e.g., hTERT, under conditions that allow for CAR and telomerase expression.

In an embodiment, the nucleic acid encoding the telomerase subunit is DNA. In an embodiment, the nucleic acid encoding the telomerase subunit comprises a promoter capable of driving expression of the telomerase subunit.

In an embodiment, hTERT has the amino acid sequence of GenBank Protein ID AAC51724.1 (Meyerson et al., "hEST2, the Putative Human Telomerase Catalytic Subunit Gene, Is Up-Regulated in Tumor Cells and during Immortalization" Cell Volume 90, Issue 4, 22 Aug. 1997, Pages 785-795) as follows:

```
                                             (SEQ ID NO: 114)
MPRAPRCRAVRSLLRSHYREVLPLATFVRRLGPQGWRLVQRGDPAAFRAL

VAQCLVCVPWDARPPPAAPSFRQVSCLKELVARVLQRLCERGAKNVLAFG

FALLDGARGGPPEAFTTSVRSYLPNTVTDALRGSGAWGLLLRRVGDDVLV

HLLARCALFVLVAPSCAYQVCGPPLYQLGAATQARPPPHASGPRRRLGCE

RAWNHSVREAGVPLGLPAPGARRRGGSASRSLPLPKRPRRGAAPEPERTP

VGQGSWAHPGRTRGPSDRGFCVVSPARPAEEATSLEGALSGTRHSHPSVG

RQHHAGPPSTSRPPRPWDTPCPPVYAETKHFLYSSGDKEQLRPSFLLSSL

RPSLTGARRLVETIFLGSRPWMPGTPRRLPRLPQRYWQMRPLFLELLGNH

AQCPYGVLLKTHCPLRAAVTPAAGVCAREKPQGSVAAPEEEDTDPRRLVQ

LLRQHSSPWQVYGFVRACLRRLVPPGLWGSRHNERRFLRNTKKFISLGKH

AKLSLQELTWKMSVRGCAWLRRSPGVGCVPAAEHRLREEILAKFLHWLMS

VYVVELLRSFFYVTETTFQKNRLFFYRKSVWSKLQSIGIRQHLKRVQLRE

LSEAEVRQHREARPALLTSRLRFIPKPDGLRPIVNMDYVVGARTFRREKR

AERLTSRVKALFSVLNYERARRPGLLGASVLGLDDIHRAWRTFVLRVRAQ

DPPPELYFVKVDVTGAYDTIPQDRLTEVIASIIKPQNTYCVRRYAVVQKA

AHGHVRKAFKSHVSTLTDLQPYMRQFVAHLQETSPLRDAVVIEQSSSLNE

ASSGLFDVFLRFMCHHAVRIRGKSYVQCQGIPQGSILSTLLCSLCYGDME

NKLFAGIRRDGLLLRLVDDFLLVTPHLTHAKTFLRTLVRGVPEYGCVVNL

RKTVVNFPVEDEALGGTAFVQMPAHGLFPWCGLLLDTRTLEVQSDYSSYA

RTSIRASLTFNRGFKAGRNMRRKLFGVLRLKCHSLFLDLQVNSLQTVCTN

IYKILLLQAYRFHACVLQLPFHQQVWKNPTFFLRVISDTASLCYSILKAK

NAGMSLGAKGAAGPLPSEAVQWLCHQAFLLKLTRHRVTYVPLLGSLRTAQ

TQLSRKLPGTTLTALEAAANPALPSDFKTILD
```

In an embodiment, the hTERT has a sequence at least 80%, 85%, 90%, 95%, 96%, 97%, 98%, or 99% identical to the sequence of SEQ ID NO: 114. In an embodiment, the hTERT has a sequence of SEQ ID NO: 114. In an embodiment, the hTERT comprises a deletion (e.g., of no more than 5, 10, 15, 20, or 30 amino acids) at the N-terminus, the C-terminus, or both. In an embodiment, the hTERT comprises a transgenic amino acid sequence (e.g., of no more than 5, 10, 15, 20, or 30 amino acids) at the N-terminus, the C-terminus, or both.

In an embodiment, the hTERT is encoded by the nucleic acid sequence of GenBank Accession No. AF018167 (Meyerson et al., "hEST2, the Putative Human Telomerase Catalytic Subunit Gene, Is Up-Regulated in Tumor Cells and during Immortalization" Cell Volume 90, Issue 4, 22 Aug. 1997, Pages 785-795):

(SEQ ID NO: 115)

```
   1 caggcagcgt ggtcctgctg cgcacgtggg aagccctggc cccggccacc cccgcgatgc
  61 cgcgcgctcc ccgctgccga gccgtgcgct ccctgctgcg cagccactac cgcgaggtgc
 121 tgccgctggc cacgttcgtg cggcgcctgg ggccccaggg ctggcggctg gtgcagcgcg
 181 gggacccggc ggctttccgc gcgctggtgg cccagtgcct ggtgtgcgtg ccctgggacg
 241 cacggccgcc ccccgccgcc ccctccttcc gccaggtgtc ctgcctgaag gagctggtgg
 301 cccgagtgct gcagaggctg tgcgagcgcg gcgcgaagaa cgtgctggcc ttcggcttcg
 361 cgctgctgga cggggcccgc gggggccccc ccgaggcctt caccaccagc gtgcgcagct
 421 acctgcccaa cacggtgacc gacgcactgc gggggagcgg ggcgtggggg ctgctgttgc
 481 gccgcgtggg cgacgacgtg ctggttcacc tgctggcacg ctgcgcgctc tttgtgctgg
 541 tggctcccag ctgcgcctac caggtgtgcg ggccgccgct gtaccagctc ggcgctgcca
 601 ctcaggcccg gcccccgcca cacgctagtg gaccccgaag gcgtctggga tgcgaacggg
 661 cctggaacca tagcgtcagg gaggccgggg tcccccctggg cctgccagcc ccgggtgcga
 721 ggaggcgcgg gggcagtgcc agccgaagtc tgccgttgcc caagaggccc aggcgtggcg
 781 ctgcccctga gccggagcgg acgcccgttg ggcaggggtc ctgggcccac ccgggcagga
 841 cgcgtggacc gagtgaccgt ggtttctgtg tggtgtcacc tgccagaccc gccgaagaag
 901 ccacctcttt ggagggtgcg ctctctggca cgcgccactc ccacccatcc gtgggccgcc
 961 agcaccacgc gggcccccca tccacatcgc ggccaccacg tccctgggac acgccttgtc
1021 ccccggtgta cgccgagacc aagcacttcc tctactcctc aggcgacaag gagcagctgc
1081 ggccctcctt cctactcagc tctctgaggc ccagcctgac tggcgctcgg aggctcgtgg
1141 agaccatctt tctgggttcc aggccctgga tgccagggac tccccgcagg ttgccccgcc
1201 tgccccagcg ctactggcaa atgcggcccc tgtttctgga gctgcttggg aaccacgcgc
1261 agtgccccta cggggtgctc ctcaagacgc actgcccgct gcgagctgcg gtcaccccag
1321 cagccggtgt ctgtgcccgg gagaagcccc agggctctgt ggcggccccc gaggaggagg
1381 acacagaccc ccgtcgcctg gtgcagctgc tccgccagca cagcagcccc tggcaggtgt
1441 acggcttcgt gcgggcctgc ctgcgccggc tggtgccccc aggcctctgg ggctccaggc
1501 acaacgaacg ccgcttcctc aggaacacca agaagttcat ctccctgggg aagcatgcca
1561 agctctcgct gcaggagctg acgtggaaga tgagcgtgcg gggctgcgct tggctgcgca
1621 ggagcccagg ggttggctgt gttccggccg cagagcaccg tctgcgtgag gagatcctgg
1681 ccaagttcct gcactggctg atgagtgtgt acgtcgtcga gctgctcagg tetttetttt
1741 atgtcacgga gaccacgttt caaaagaaca ggctcttttt ctaccggaag agtgtctgga
1801 gcaagttgca aagcattgga atcagacagc acttgaagag ggtgcagctg cgggagctgt
1861 cggaagcaga ggtcaggcag catcgggaag ccaggcccgc cctgctgacg tccagactcc
1921 gcttcatccc caagcctgac gggctgcggc cgattgtgaa catggactac gtcgtgggag
1981 ccagaacgtt ccgcagagaa aagagggccg agcgtctcac ctcgagggtg aaggcactgt
```

-continued

```
2041 tcagcgtgct caactacgag cgggcgcggc gccccggcct cctgggcgcc tctgtgctgg
2101 gcctggacga tatccacagg gcctggcgca ccttcgtgct gcgtgtgcgg gcccaggacc
2161 cgccgcctga gctgtacttt gtcaaggtgg atgtgacggg cgcgtacgac accatccccc
2221 aggacaggct cacggaggtc atcgccagca tcatcaaacc ccagaacacg tactgcgtgc
2281 gtcggtatgc cgtggtccag aaggccgccc atgggcacgt ccgcaaggcc ttcaagagcc
2341 acgtctctac cttgacagac ctccagccgt acatgcgaca gttcgtggct cacctgcagg
2401 agaccagccc gctgagggat gccgtcgtca tcgagcagag ctcctccctg aatgaggcca
2461 gcagtggcct cttcgacgtc ttcctacgct tcatgtgcca ccacgccgtg cgcatcaggg
2521 gcaagtccta cgtccagtgc caggggatcc cgcagggctc catcctctcc acgctgctct
2581 gcagcctgtg ctacggcgac atggagaaca agctgtttgc ggggattcgg cgggacgggc
2641 tgctcctgcg tttggtggat gatttcttgt tggtgacacc tcacctcacc cacgcgaaaa
2701 ccttcctcag gaccctggtc cgaggtgtcc ctgagtatgg ctgcgtggtg aacttgcgga
2761 agacagtggt gaacttccct gtagaagacg aggccctggg tggcacggct tttgttcaga
2821 tgccggccca cggcctattc ccctggtgcg gcctgctgct ggatacccgg accctggagg
2881 tgcagagcga ctactccagc tatgcccgga cctccatcag agccagtctc accttcaacc
2941 geggettcaa ggctgggagg aacatgcgtc gcaaactctt tggggtcttg cggctgaagt
3001 gtcacagcct gifictggat ttgcaggtga acagcctcca gacggtgtgc accaacatct
3061 acaagatcct cctgctgcag gcgtacaggt ttcacgcatg tgtgctgcag ctcccatttc
3121 atcagcaagt ttggaagaac cccacatttt tcctgcgcgt catctctgac acggcctccc
3181 tctgctactc catcctgaaa gccaagaacg cagggatgtc gctgggggcc aagggcgccg
3241 ccggccctct gccctccgag gccgtgcagt ggctgtgcca ccaagcattc ctgctcaagc
3301 tgactcgaca ccgtgtcacc tacgtgccac tcctggggtc actcaggaca gcccagacgc
3361 agctgagtcg gaagctcccg gggacgacgc tgactgccct ggaggccgca gccaacccgg
3421 cactgccctc agacttcaag accatcctgg actgatggcc acccgcccac agccaggccg
3481 agagcagaca ccagcagccc tgtcacgccg ggctctacgt cccagggagg gaggggcggc
3541 ccacacccag gcccgcaccg ctgggagtct gaggcctgag tgagtgtttg gccgaggcct
3601 gcatgtccgg ctgaaggctg agtgtccggc tgaggcctga gcgagtgtcc agccaagggc
3661 tgagtgtcca gcacacctgc cgtcttcact tccccacagg ctggcgctcg gctccacccc
3721 agggccagct tttcctcacc aggagcccgg cttccactcc ccacatagga atagtccatc
3781 cccagattcg ccattgttca cccctcgccc tgccctcctt tgccttccac ccccaccatc
3841 caggtggaga ccctgagaag gaccctggga gctctgggaa tttggagtga ccaaaggtgt
3901 gccctgtaca caggcgagga ccctgcacct ggatgggggt ccctgtgggt caaattgggg
3961 ggaggtgctg tgggagtaaa atactgaata tatgagtttt tcagttttga aaaaaaaaaa
4021 aaaaaaa
```

In an embodiment, the hTERT is encoded by a nucleic acid having a sequence at least 80%, 85%, 90%, 95%, 96, 97%, 98%, or 99% identical to the sequence of SEQ ID NO: 115. In an embodiment, the hTERT is encoded by a nucleic acid of SEQ ID NO: 115.

Activation and Expansion of T Cells

T cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention may be expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besançon, France) can be used as can other methods commonly known in the art (Berg et al., *Transplant Proc.* 30(8):3975-3977, 1998; Haanen et al., *J. Exp. Med.* 190(9):13191328, 1999; Garland et al., *J. Immunol Meth.* 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle:cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type. In one aspect, the most typical ratios for use are in the neighborhood of 1:1, 2:1 and 3:1 on the first day.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest.

Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 10 billion cells/ml, 9 billion/ml, 8 billion/ml, 7 billion/ml, 6 billion/ml, 5 billion/ml, or 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment, cells transduced with a nucleic acid encoding a CAR, e.g., a CAR described herein, are expanded, e.g., by a method described herein. In one embodiment, the cells are expanded in culture for a period of several hours (e.g., about 2, 3, 4, 5, 6, 7, 8, 9, 10, 15, 18, 21 hours) to about 14 days (e.g., 1, 2, 3, 4, 5, 6, 7, 8, 9, 10, 11, 12, 13 or 14 days). In one embodiment, the cells are expanded for a period of 4 to 9 days. In one embodiment, the cells are expanded for a period of 8 days or less, e.g., 7, 6 or 5 days. In one embodiment, the cells, e.g., a GFRα4 CAR cell described herein, are expanded in culture for 5 days, and the resulting cells are more potent than the same cells expanded in culture for 9 days under the same culture conditions. Potency can be defined, e.g., by various T cell functions, e.g. proliferation, target cell killing, cytokine production, activation, migration, or combinations thereof. In one embodiment, the cells, e.g., a GFRα4 CAR cell described herein, expanded for 5 days show at least a one, two, three or four fold increase in cells doublings upon antigen stimulation as compared to the same cells expanded in culture for 9 days under the same culture conditions. In one embodiment, the cells, e.g., the cells expressing a GFRα4 CAR described herein, are expanded in culture for 5 days, and the resulting cells exhibit higher proinflammatory cytokine production, e.g., IFN-γ and/or GM-CSF levels, as compared to the same cells expanded in culture for 9 days under the same culture conditions. In one embodiment, the cells, e.g., a GFRα4 CAR cell described herein, expanded for 5 days show at least a one, two, three, four, five, ten fold or more increase in pg/ml of proinflammatory cytokine production, e.g., IFN-γ and/or GM-CSF levels, as compared to the same cells expanded in culture for 9 days under the same culture conditions.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

In one embodiment, the cells are expanded in an appropriate media (e.g., media described herein) that includes one or more interleukin that result in at least a 200-fold (e.g., 200-fold, 250-fold, 300-fold, 350-fold) increase in cells over a 14 day expansion period, e.g., as measured by a method described herein such as flow cytometry. In one embodiment, the cells are expanded in the presence of IL-15 and/or IL-7 (e.g., IL-15 and IL-7).

In embodiments, methods described herein, e.g., CAR-expressing cell manufacturing methods, comprise removing T regulatory cells, e.g., CD25+ T cells, from a cell population, e.g., using an anti-CD25 antibody, or fragment thereof, or a CD25-binding ligand, IL-2. Methods of removing T regulatory cells, e.g., CD25+ T cells, from a cell population are described herein. In embodiments, the methods, e.g., manufacturing methods, further comprise contacting a cell population (e.g., a cell population in which T regulatory cells, such as CD25+ T cells, have been depleted; or a cell population that has previously contacted an anti-CD25 antibody, fragment thereof, or CD25-binding ligand) with IL-15 and/or IL-7. For example, the cell population (e.g., that has previously contacted an anti-CD25 antibody, fragment thereof, or CD25-binding ligand) is expanded in the presence of IL-15 and/or IL-7.

In some embodiments a CAR-expressing cell described herein is contacted with a composition comprising a interleukin-15 (IL-15) polypeptide, a interleukin-15 receptor alpha (IL-15Ra) polypeptide, or a combination of both a IL-15 polypeptide and a IL-15Ra polypeptide e.g., hetIL-15, during the manufacturing of the CAR-expressing cell, e.g., ex vivo. In embodiments, a CAR-expressing cell described herein is contacted with a composition comprising a IL-15 polypeptide during the manufacturing of the CAR-expressing cell, e.g., ex vivo. In embodiments, a CAR-expressing cell described herein is contacted with a composition comprising a combination of both a IL-15 polypeptide and a IL-15 Ra polypeptide during the manufacturing of the CAR-expressing cell, e.g., ex vivo. In embodiments, a CAR-expressing cell described herein is contacted with a composition comprising hetIL-15 during the manufacturing of the CAR-expressing cell, e.g., ex vivo.

In one embodiment the CAR-expressing cell described herein is contacted with a composition comprising hetIL-15 during ex vivo expansion. In an embodiment, the CAR-expressing cell described herein is contacted with a composition comprising an IL-15 polypeptide during ex vivo expansion. In an embodiment, the CAR-expressing cell described herein is contacted with a composition comprising both an IL-15 polypeptide and an IL-15Ra polypeptide during ex vivo expansion. In one embodiment the contacting results in the survival and proliferation of a lymphocyte subpopulation, e.g., CD8+ T cells.

T cells that have been exposed to varied stimulation times may exhibit different characteristics. For example, typical blood or apheresed peripheral blood mononuclear cell products have a helper T cell population ($T_H$, $CD4^+$) that is greater than the cytotoxic or suppressor T cell population ($T_C$, $CD8^+$). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of Tc cells. Accordingly, depending on the purpose of treatment, infusing a subject with a T cell population comprising predominately predominantly of $T_H$ cells may be advantageous. Similarly, if an antigen-specific subset of Tc cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Once a GFRα4 CAR is constructed, various assays can be used to evaluate the activity of the molecule, such as but not limited to, the ability to expand T cells following antigen stimulation, sustain T cell expansion in the absence of re-stimulation, and anti-cancer activities in appropriate in vitro and animal models. Assays to evaluate the effects of a GFRα4 CAR are described in further detail below Western blot analysis of CAR expression in primary T cells can be used to detect the presence of monomers and dimers. See, e.g., Milone et al., Molecular Therapy 17(8): 1453-1464 (2009). Very briefly, T cells (1:1 mixture of $CD4^+$ and $CD8^+$ T cells) expressing the CARs are expanded in vitro for more than 10 days followed by lysis and SDS-PAGE under reducing conditions. CARs containing the full length TCR-cytoplasmic domain and the endogenous TCR-ζ chain are detected by western blotting using an antibody to the TCR-ζ chain. The same T cell subsets are used for SDS-PAGE analysis under non-reducing conditions to permit evaluation of covalent dimer formation.

In vitro expansion of $CAR^+$ T cells following antigen stimulation can be measured by flow cytometry. For example, a mixture of $CD4^+$ and $CD8^+$ T cells are stimulated with αCD3/αCD28 aAPCs followed by transduction with lentiviral vectors expressing GFP under the control of the promoters to be analyzed. Exemplary promoters include the CMV IE gene, EF-1α, ubiquitin C, or phosphoglycerokinase (PGK) promoters. GFP fluorescence is evaluated on day 6 of culture in the $CD4^+$ and/or $CD8^+$ T cell subsets by flow cytometry. See, e.g., Milone et al., Molecular Therapy 17(8): 1453-1464 (2009). Alternatively, a mixture of $CD4^+$ and $CD8^+$ T cells are stimulated with αCD3/αCD28 coated magnetic beads on day 0, and transduced with CAR on day 1 using a bicistronic lentiviral vector expressing CAR along with eGFP using a 2A ribosomal skipping sequence. Cultures can be re-stimulated with GFRα4 expressing cells.

Sustained $CAR^+$ T cell expansion in the absence of re-stimulation can also be measured. See, e.g., Milone et al., Molecular Therapy 17(8): 1453-1464 (2009). Briefly, mean T cell volume (fl) is measured on day 8 of culture using a Coulter Multisizer III particle counter, a Nexcelom Cellometer Vision or Millipore Scepter, following stimulation with αCD3/αCD28 coated magnetic beads on day 0, and transduction with the indicated CAR on day 1.

Animal models can also be used to measure a CART activity. For example, xenograft model using human GFRα4-specific CAR' T cells to treat a cancer, e.g., a medullary thyroid cancer, in immunodeficient mice can be used. Very briefly, after establishment of the tumors, mice are randomized as to treatment groups. GFRα4 CART cells are injected into the immunodeficient mice, e.g., intravenously. Animals are assessed for cancer cells at weekly intervals. GFRα4-expressing tumor cells can be measured in mice that are injected with GFRα4 CART cells or mock-transduced T cells. Survival curves for the groups are compared using the log-rank test.

Cytotoxicity can be assessed by a standard 51Cr-release assay. See, e.g., Milone et al., Molecular Therapy 17(8): 1453-1464 (2009). Briefly, target cells are loaded with 51Cr (as NaCrO4, New England Nuclear, Boston, MA) at 37° C. for 2 hours with frequent agitation, washed twice in complete RPMI and plated into microtiter plates. Effector T cells are mixed with target cells in the wells in complete RPMI at varying ratios of effector cell:target cell (E:T). Additional wells containing media only (spontaneous release, SR) or a 1% solution of triton-X 100 detergent (total release, TR) are also prepared. After 4 hours of incubation at 37° C., supernatant from each well is harvested. Released 51Cr is then measured using a gamma particle counter (Packard Instrument Co., Waltham, MA). Each condition is performed in at least triplicate, and the percentage of lysis is calculated using the formula: % Lysis=(ER−SR)/(TR−SR), where ER represents the average 51Cr released for each experimental condition.

Imaging technologies can be used to evaluate specific trafficking and proliferation of CARs in tumor-bearing animal models. Such assays have been described, for example, in Barrett et al., Human Gene Therapy 22:1575-1586 (2011). Briefly, NOD/SCID/$\gamma c^{-/-}$ (NSG) mice are injected IV with Nalm-6 cells followed 7 days later with T cells 4 hour after electroporation with the CAR constructs. The T cells are stably transfected with a lentiviral construct to express firefly luciferase, and mice are imaged for bioluminescence. Alternatively, therapeutic efficacy and specificity of a single injection of $CAR^+$ T cells in Nalm-6 xenograft model can be measured as the following: NSG mice are injected with Nalm-6 transduced to stably express firefly luciferase, followed by a single tail-vein injection of T cells electroporated with GFRα4 CAR 7 days later. Animals are imaged at various time points post injection. For example, photon-density heat maps of firefly luciferasepositive leukemia in representative mice at day 5 (2 days before treatment) and day 8 (24 hr post CARP PBLs) can be generated.

Other assays, including those described in the Example section herein as well as those that are known in the art can also be used to evaluate the GFRα4 CAR constructs of the invention.

Alternatively, or in combination to the methods disclosed herein, methods and compositions for one or more of: detection and/or quantification of CAR-expressing cells (e.g., in vitro or in vivo (e.g., clinical monitoring)); immune cell expansion and/or activation; and/or CAR-specific selection, that involve the use of a CAR ligand, are disclosed. In one exemplary embodiment, the CAR ligand is an antibody that binds to the CAR molecule, e.g., binds to the extracellular antigen binding domain of CAR (e.g., an antibody that binds to the antigen binding domain, e.g., an anti-idiotypic antibody; or an antibody that binds to a constant region of the extracellular binding domain). In other embodiments, the CAR ligand is a CAR antigen molecule (e.g., a CAR antigen molecule as described herein).

In one aspect, a method for detecting and/or quantifying CAR-expressing cells is disclosed. For example, the CAR ligand can be used to detect and/or quantify CAR-expressing cells in vitro or in vivo (e.g., clinical monitoring of CAR-expressing cells in a patient, or dosing a patient). The method includes:

providing the CAR ligand (optionally, a labelled CAR ligand, e.g., a CAR ligand that includes a tag, a bead, a radioactive or fluorescent label);

acquiring the CAR-expressing cell (e.g., acquiring a sample containing CAR-expressing cells, such as a manufacturing sample or a clinical sample);

contacting the CAR-expressing cell with the CAR ligand under conditions where binding occurs, thereby detecting the level (e.g., amount) of the CAR-expressing cells present. Binding of the CAR-expressing cell with the CAR ligand can be detected using standard techniques such as FACS, ELISA and the like.

In another aspect, a method of expanding and/or activating cells (e.g., immune effector cells) is disclosed. The method includes:

providing a CAR-expressing cell (e.g., a first CAR-expressing cell or a transiently expressing CAR cell);

contacting said CAR-expressing cell with a CAR ligand, e.g., a CAR ligand as described herein), under conditions where immune cell expansion and/or proliferation occurs, thereby producing the activated and/or expanded cell population.

In certain embodiments, the CAR ligand is present on (e.g., is immobilized or attached to a substrate, e.g., a non-naturally occurring substrate). In some embodiments, the substrate is a non-cellular substrate. The non-cellular substrate can be a solid support chosen from, e.g., a plate (e.g., a microtiter plate), a membrane (e.g., a nitrocellulose membrane), a matrix, a chip or a bead. In embodiments, the CAR ligand is present in the substrate (e.g., on the substrate surface). The CAR ligand can be immobilized, attached, or associated covalently or non-covalently (e.g., cross-linked) to the substrate. In one embodiment, the CAR ligand is attached (e.g., covalently attached) to a bead. In the aforesaid embodiments, the immune cell population can be expanded in vitro or ex vivo. The method can further include culturing the population of immune cells in the presence of the ligand of the CAR molecule, e.g., using any of the methods described herein.

In other embodiments, the method of expanding and/or activating the cells further comprises addition of a second stimulatory molecule, e.g., CD28. For example, the CAR ligand and the second stimulatory molecule can be immobilized to a substrate, e.g., one or more beads, thereby providing increased cell expansion and/or activation.

In yet another aspect, a method for selecting or enriching for a CAR expressing cell is provided. The method includes contacting the CAR expressing cell with a CAR ligand as described herein; and selecting the cell on the basis of binding of the CAR ligand.

In yet other embodiments, a method for depleting, reducing and/or killing a CAR expressing cell is provided. The method includes contacting the CAR expressing cell with a CAR ligand as described herein; and targeting the cell on the basis of binding of the CAR ligand, thereby reducing the number, and/or killing, the CAR-expressing cell. In one embodiment, the CAR ligand is coupled to a toxic agent (e.g., a toxin or a cell ablative drug). In another embodiment, the anti-idiotypic antibody can cause effector cell activity, e.g., ADCC or ADC activities.

Exemplary anti-CAR antibodies that can be used in the methods disclosed herein are described, e.g., in WO 2014/190273 and by Jena et al., "Chimeric Antigen Receptor (CAR)-Specific Monoclonal Antibody to Detect CD19-Specific T cells in Clinical Trials", PLOS March 2013 8:3 e57838, the contents of which are incorporated by reference. In one embodiment, the anti-idiotypic antibody molecule recognizes an anti-CD19 antibody molecule, e.g., an anti-CD19 scFv. For instance, the anti-idiotypic antibody molecule can compete for binding with the CD19-specific CAR mAb clone no. 136.20.1 described in Jena et al., PLOS March 2013 8:3 e57838; may have the same CDRs (e.g., one or more of, e.g., all of, VH CDR1, VH CDR2, CH CDR3, VL CDR1, VL CDR2, and VL CDR3, using the Kabat definition, the Chothia definition, or a combination of the Kabat and Chothia definitions) as the CD19-specific CAR mAb clone no. 136.20.1; may have one or more (e.g., 2) variable regions as the CD19-specific CAR mAb clone no. 136.20.1, or may comprise the CD19-specific CAR mAb clone no. 136.20.1. In some embodiments, the anti-idiotypic antibody was made according to a method described in Jena et al. In another embodiment, the anti-idiotypic antibody molecule is an anti-idiotypic antibody molecule described in WO 2014/190273. In some embodiments, the anti-idiotypic antibody molecule has the same CDRs (e.g., one or more of, e.g., all of, VH CDR1, VH CDR2, CH CDR3, VL CDR1, VL CDR2, and VL CDR3) as an antibody molecule of WO 2014/190273 such as 136.20.1; may have one or more (e.g., 2) variable regions of an antibody molecule of WO 2014/190273, or may comprise an antibody molecule of WO 2014/190273 such as 136.20.1. In other embodiments, the anti-CAR antibody binds to a constant region of the extracellular binding domain of the CAR molecule, e.g., as described in WO 2014/190273. In some embodiments, the anti-CAR antibody binds to a constant region of the extracellular binding domain of the CAR molecule, e.g., a heavy chain constant region (e.g., a CH2-CH3 hinge region) or light chain constant region. For instance, in some embodiments the anti-CAR antibody competes for binding with the 2D3 monoclonal antibody described in WO 2014/190273, has the same CDRs (e.g., one or more of, e.g., all of, VH CDR1, VH CDR2, CH CDR3, VL CDR1, VL CDR2, and VL CDR3) as 2D3, or has one or more (e.g., 2) variable regions of 2D3, or comprises 2D3 as described in WO 2014/190273.

In some aspects and embodiments, the compositions and methods herein are optimized for a specific subset of T cells, e.g., as described in U.S. Ser. No. 62/031,699 filed Jul. 31, 2014, the contents of which are incorporated herein by reference in their entirety. In some embodiments, the optimized subsets of T cells display an enhanced persistence compared to a control T cell, e.g., a T cell of a different type (e.g., $CD8^+$ or $CD4^+$) expressing the same construct.

In some embodiments, a $CD4^+$ T cell comprises a CAR described herein, which CAR comprises an intracellular signaling domain suitable for (e.g., optimized for, e.g., leading to enhanced persistence in) a $CD4^+$ T cell, e.g., an ICOS domain. In some embodiments, a $CD8^+$ T cell comprises a CAR described herein, which CAR comprises an intracellular signaling domain suitable for (e.g., optimized for, e.g., leading to enhanced persistence of) a $CD8^+$ T cell, e.g., a 4-1BB domain, a CD28 domain, or another costimulatory domain other than an ICOS domain. In some embodiments, the CAR described herein comprises an antigen binding domain described herein, e.g., a CAR comprising an antigen binding domain that specifically binds GFRα4.

In an aspect, described herein is a method of treating a subject, e.g., a subject having cancer. The method includes administering to said subject, an effective amount of:

1) a $CD4^+$ T cell comprising a CAR (the $CAR^{CD4+}$) comprising:

an antigen binding domain, e.g., an antigen binding domain described herein, e.g., an antigen binding domain that specifically binds GFRα4, e.g., an antigen-binding domain of Table 2;

a transmembrane domain; and an intracellular signaling domain, e.g., a first costimulatory domain, e.g., an ICOS domain; and 2) a $CD8^+$ T cell comprising a CAR (the $CAR^{CD8+}$) comprising:

an antigen binding domain, e.g., an antigen binding domain described herein, e.g., an antigen binding domain that specifically binds GFRα4, e.g., an antigen-binding domain of Table 2;

a transmembrane domain; and an intracellular signaling domain, e.g., a second costimulatory domain, e.g., a 4-1BB domain, a CD28 domain, or another costimulatory domain other than an ICOS domain;

wherein the $CAR^{CD4+}$ and the $CAR^{CD8+}$ differ from one another.

Optionally, the method further includes administering:

3) a second CD8+ T cell comprising a CAR (the second $CAR^{CD8+}$) comprising:

an antigen binding domain, e.g., an antigen binding domain described herein, e.g., an antigen binding domain that specifically binds GFRα4, e.g., an antigen-binding domain of Table 2;

a transmembrane domain; and an intracellular signaling domain, wherein the second $CAR^{CD8+}$ comprises an intracellular signaling domain, e.g., a costimulatory signaling domain, not present on the $CAR^{CD8+}$, and, optionally, does not comprise an ICOS signaling domain.

Therapeutic Application

GFRα4 Associated Diseases and/or Disorders

In one aspect, the invention provides methods for treating a disease associated with GFRα4 expression. The method includes administering to a mammal at least one antibody or a fragment thereof of the invention, or a GFRα4 CAR-expressing cell (e.g., GFRα4 CART or GFRα4 CAR-expressing NK cell) of the present invention.

In one aspect, the invention provides methods for treating a disease wherein part of the tumor is negative for GFRα4 and part of the tumor is positive for GFRα4. For example, the antibodies or CAR of the invention are useful for treating subjects that have undergone treatment for a disease associated with elevated expression of GFRα4, wherein the subject that has undergone treatment for elevated levels of GFRα4 exhibits a disease associated with elevated levels of GFRα4.

In one embodiment, the disease associated with expression of GFRα4 is an endocrine cancer. An endocrine cancer can arise from cells that secrete hormones. Examples of endocrine cancers include adrenal gland tumors, parathyroid tumors, pituitary gland tumors, and thyroid cancer. In one embodiment, the disease associated with expression of GFRα4 is medullary thyroid cancer, or a metastasis that originated from a medullary thyroid tumor. In another embodiment, the disease associated with expression of GFRα4 is a pheochromacytoma. In another embodiment, the disease associated with expression of GFRα4 is T-cell acute lymphoblastic leukemia (T-cell ALL) or Wilms kidney tumor.

In one embodiment, the invention pertains to a nucleic acid, e.g., a vector, comprising GFRα4 CAR operably linked to promoter for expression in mammalian immune effector cells, e.g., T cells or NK cells.

In one embodiment, the invention provides a recombinant immune effector cells, e.g., T cells or NK cells expressing the GFRα4 CAR for use in treating GFRα4-expressing tumors, wherein the recombinant immune effector cells, e.g., T cells or NK cells expressing the GFRα4 CAR is termed a GFRα4 CAR-expressing cell (e.g., GFRα4 CART or GFRα4 CAR-expressing NK cell). In one embodiment, the GFRα4 CAR-expressing cell (e.g., GFRα4 CART or GFRαA4 CAR-expressing NK cell) is capable of contacting a tumor cell with at least one GFRα4 CAR of the invention expressed on its surface such that the GFRα4 CAR-expressing cell (e.g., GFRα4 CART or GFRα4 CAR-expressing NK cell) targets the tumor cell and growth of the tumor is inhibited.

In one embodiment, the invention pertains to a method of inhibiting growth of a GFRα4-expressing tumor cell, comprising contacting the tumor cell with at least one antibody or a fragment thereof of the invention, or a GFRα4 CAR-expressing cell (e.g., GFRα4 CART or GFRα4 CAR-expressing NK cell) of the present invention such that growth of the tumor cell is inhibited.

In one aspect, the invention pertains to a method of treating cancer in a subject. The method comprises administering to the subject a GFRα4 CAR-expressing cell (e.g., GFRα4 CART or GFRα4 CAR-expressing NK cell) such that the cancer is treated in the subject. An example of a cancer that is treatable by the GFRα4 CAR-expressing cell (e.g., GFRα4 CART or GFRα4 CAR-expressing NK cell) is a cancer associated with expression of GFRα4. In one aspect, the cancer associated with expression of GFRα4 is medullary thyroid cancer.

The invention includes a type of cellular therapy where immune effector cell, e.g., T cells or NK cells, are genetically modified to express a chimeric antigen receptor (CAR) and the GFRα4 CAR-expressing cell (e.g., GFRα4 CART or GFRα4 CAR-expressing NK cell) is infused to a recipient in need thereof. The infused cell is able to kill tumor cells in the recipient. Unlike antibody therapies, CAR-modified cells (e.g., T cells or NK cells) are able to replicate in vivo resulting in long-term persistence that can lead to sustained tumor control. In various aspects, the immune effector cells (e.g., T cells or NK cells), administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the immune effector cell (e.g., T cell or NK cell) to the patient.

The invention also includes a type of cellular therapy where immune effector cells (e.g., T cells or NK cells) are modified, e.g., by in vitro transcribed RNA, to transiently express a chimeric antigen receptor (CAR) and the GFRα4 CAR expressing cell (e.g., GFRα4 CAR T cell or GFRα4 CAR-expressing NK cell) is infused to a recipient in need thereof. The infused cell is able to kill tumor cells in the recipient. Thus, in various aspects, the immune effector cells (e.g., T cells or NK cells) administered to the patient, is present for less than one month, e.g., three weeks, two weeks, one week, after administration of the immune effector cells (e.g., T cells or NK cells) to the patient.

Without wishing to be bound by any particular theory, the anti-tumor immunity response elicited by the GFRα4 antibody of this invention may be an active or a passive immune response. The GFRα4 antibody of the invention may be used in some type of vaccine for ex vivo immunization and/or in vivo therapy in a mammal. Preferably, the mammal is a human.

In one aspect, the fully-human CAR-modified immune effector cells (e.g., T cells or NK cells) of the invention may be a type of vaccine for ex vivo immunization and/or in vivo therapy in a mammal. In one embodiment, the mammal is a human.

With respect to ex vivo immunization, at least one of the following occurs in vitro prior to administering the cell into a mammal: i) expansion of the cells, ii) introducing a nucleic acid encoding a CAR to the cells or iii) cryopreservation of the cells.

Ex vivo procedures are well known in the art and are discussed more fully below. Briefly, cells are isolated from a mammal (e.g., a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified immune effector cells (e.g., T cells or NK cells) of the invention are used in the treatment of diseases, disorders and conditions associated with expression of GFRα4. In certain aspects, the cells of the invention are used in the treatment of patients at risk for developing diseases, disorders and conditions associated with expression of FRα4. Thus, the present invention provides methods for the treatment or prevention of diseases, disorders and conditions associated with expression of GFRα4 comprising administering to a subject in need thereof, a therapeutically effective amount of the CAR-modified immune effector cells (e.g., T cells or NK cells). In one aspect the CAR-expressing cells, e.g., CART cells or CAR-expressing NK cells) may be used to treat a proliferative disease such as a cancer or malignancy or is a precancerous condition such as medullary thyroid cancer.

The present invention also provides methods for inhibiting the proliferation or reducing a GFRα4-expressing cell population, the methods comprising contacting a population of cells comprising a GFRα4-expressing cell with a GFRα4 CAR-expressing cell (e.g., GFRα4 CART cell or GFRα4 CAR-expressing NK cell) of the invention that binds to the GFRα4-expressing cell. In a specific aspect, the present invention provides methods for inhibiting the proliferation or reducing the population of cancer cells expressing GFRα4, the methods comprising contacting the GFRα4-expressing cancer cell population with a GFRα4 CAR-expressing cell (e.g., GFRα4 CART cell or GFRα4 CAR-expressing NK cell) of the invention that binds to the GFRα4 expressing cell. In one aspect, the present invention provides methods for inhibiting the proliferation or reducing the population of cancer cells expressing GFRα4, the methods comprising contacting the GFRα4 expressing cancer cell population with a GFRα4 CAR-expressing cell (e.g., GFRα4 CART cell or GFRα4 CAR-expressing NK cell) of the invention that binds to the GFRα4-expressing cell. In certain aspects, the GFRα4 CAR-expressing cell (e.g., GFRα4 CART cell or GFRα4 CAR-expressing NK cell) cell of the invention reduces the quantity, number, amount or percentage of cells and/or cancer cells by at least 25%, at least 30%, at least 40%, at least 50%, at least 65%, at least 75%, at least 85%, at least 95%, or at least 99% in a subject with or animal model for myeloid leukemia or another cancer associated with GFRα4-expressing cells relative to a negative control. In one aspect, the subject is a human.

The present invention also provides methods for preventing, treating and/or managing a disease associated with GFRα4-expressing cells (e.g., a hematologic cancer or atypical cancer expressing GFRα4), the methods comprising administering to a subject in need a GFRα4 CAR-expressing cell (e.g., GFRα4 CART cell or GFRα4 CAR-expressing NK cell) of the invention that binds to the GFRα4-expressing cell. In one aspect, the subject is a human. Non-limiting examples of disorders associated with GFRα4-expressing cells include autoimmune disorders (such as lupus), inflammatory disorders (such as allergies and asthma) and cancers (such as hematological cancers or atypical cancers expressing GFRα4).

The present invention also provides methods for preventing, treating and/or managing a disease associated with GFRα4-expressing cells, the methods comprising administering to a subject in need an a GFRα4 CAR-expressing cell (e.g., GFRα4 CART cell or GFRα4 CAR-expressing NK cell) of the invention that binds to the GFRα4-expressing cell. In one aspect, the subject is a human.

The present invention provides methods for preventing relapse of cancer associated with GFRα4-expressing cells, the methods comprising administering to a subject in need thereof a GFRα4 CAR-expressing cell (e.g., GFRα4 CART cell or GFRα4 CAR-expressing NK cell) of the invention that binds to the GFRα4-expressing cell. In one aspect, the methods comprise administering to the subject in need thereof an effective amount of a GFRα4 CAR-expressing cell (e.g., GFRα4 CART cell or GFRα4 CAR-expressing NK cell) described herein that binds to the GFRα4-expressing cell in combination with an effective amount of another therapy.

Combination Therapies

A CAR-expressing cell described herein may be used in combination with other known agents and therapies. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

A CAR-expressing cell described herein and the at least one additional therapeutic agent can be administered simultaneously, in the same or in separate compositions, or sequentially. For sequential administration, the CAR-expressing cell described herein can be administered first, and the additional agent can be administered second, or the order of administration can be reversed.

The CAR therapy and/or other therapeutic agents, procedures or modalities can be administered during periods of active disorder, or during a period of remission or less active disease. The CAR therapy can be administered before the other treatment, concurrently with the treatment, post-treatment, or during remission of the disorder.

When administered in combination, the CAR therapy and the additional agent (e.g., second or third agent), or all, can be administered in an amount or dose that is higher, lower or the same than the amount or dosage of each agent used individually, e.g., as a monotherapy. In certain embodiments, the administered amount or dosage of the CAR therapy, the additional agent (e.g., second or third agent), or all, is lower (e.g., at least 20%, at least 30%, at least 40%, or at least 50%) than the amount or dosage of each agent used individually, e.g., as a monotherapy. In other embodiments, the amount or dosage of the CAR therapy, the additional agent (e.g., second or third agent), or all, that results in a desired effect (e.g., treatment of cancer) is lower (e.g., at least 20%, at least 30%, at least 40%, or at least 50% lower) than the amount or dosage of each agent used individually, e.g., as a monotherapy, required to achieve the same therapeutic effect.

In further aspects, a CAR-expressing cell described herein may be used in a treatment regimen in combination with surgery, chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and irradiation. peptide vaccine, such as that described in Izumoto et al. 2008 J Neurosurg 108:963-971.

In certain instances, compounds of the present invention are combined with other therapeutic agents, such as other anti-cancer agents, anti-allergic agents, anti-nausea agents (or anti-emetics), pain relievers, cytoprotective agents, and combinations thereof.

In one embodiment, a CAR-expressing cell described herein can be used in combination with surgery and/or radiation therapy. In an embodiment, the surgery or radiation therapy is performed or administered prior to, after, or concurrent with administration of the cell expressing a CAR molecule, e.g., a CAR molecule described herein.

In one embodiment, a CAR-expressing cell described herein can be used in combination with a tyrosine kinase inhibitor. Examples of tyrosine kinase inhibitors include vandetanib (CAPRELSA®) and cabozantinib (COMETRIQ®). In an embodiment, the tyrosine kinase inhibitor is administered prior to, after, or concurrently with administration of the cell expressing a CAR molecule, e.g., a CAR molecule described herein. In treatment regimens where more than one dose of a tyrosine kinase inhibitor is administered, the cell expressing a CAR molecule described herein is administered before initiation of the tyrosine kinase inhibitor regimen, during the tyrosine kinase inhibitor regimen, overlapping with the tyrosine kinase inhibitor regimen, or after completion of the tyroskin kinase inhibitor regimen.

In one embodiment, a CAR-expressing cell described herein can be used in combination with a chemotherapeutic agent. Exemplary chemotherapeutic agents include an anthracycline (e.g., doxorubicin (e.g., liposomal doxorubicin)). a vinca alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, ofatumumab, tositumomab, brentuximab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide).

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

In an embodiment, the chemotherapeutic agent is administered prior to administration of the cell expressing a CAR molecule, e.g., a CAR molecule described herein. In chemotherapeutic regimens where more than one administration of the chemotherapeutic agent is desired, the chemotherapeutic regimen is initiated or completed prior to administration of a cell expressing a CAR molecule, e.g., a CAR molecule described herein. In embodiments, the chemotherapeutic agent is administered at least 1 day, 2 days, 3 days, 4 days, 5 days, 6 days, 7 days, 8 days, 9 days, 10 days, 11 days, 12 days, 13 days, 14 days, 15 days, 20 days, 25 days, or 30 days prior to administration of the cell expressing the CAR molecule. In embodiments, the chemotherapeutic regimen is initiated or completed at least 1 day, 2 days, 3 days, 4 days, 5 days, 6 days, 7 days, 8 days, 9 days, 10 days, 11 days, 12 days, 13 days, 14 days, 15 days, 20 days, 25 days, or 30 days prior to administration of the cell expressing the CAR molecule. In embodiments, the chemotherapeutic agent is a chemotherapeutic agent that increases GFRα4 expression on the cancer cells, e.g., the tumor cells, e.g., as compared to GFRα4 expression on normal or non-cancer cells. GFRα4 expression can be determined, for example, by immunohistochemical staining or flow cytometry analysis. For example, the chemotherapeutic agent is cytarabine (Ara-C).

Anti-cancer agents of particular interest for combinations with the compounds of the present invention include: anti-metabolites; drugs that inhibit either the calcium dependent phosphatase calcineurin or the p70S6 kinase FK506) or inhibit the p70S6 kinase; alkylating agents; mTOR inhibitors; immunomodulators; anthracyclines; vinca alkaloids; proteosome inhibitors; GITR agonists; protein tyrosine phosphatase inhibitors; a CDK4 kinase inhibitor; a BTK kinase inhibitor; a MKN kinase inhibitor; a DGK kinase inhibitor; or an oncolytic virus.

Exemplary antimetabolites include, without limitation, folic acid antagonists (also referred to herein as antifolates), pyrimidine analogs, purine analogs and adenosine deaminase inhibitors): methotrexate (Rheumatrex®, Trexall®), 5-fluorouracil (Adrucil®, Efudex®, Fluoroplex®), floxuridine (FUDF®), cytarabine (Cytosar-U®, Tarabine PFS), 6-mercaptopurine (Puri-Nethol®)), 6-thioguanine (Thioguanine Tabloid®), fludarabine phosphate (Fludara®), pentostatin (Nipent®), pemetrexed (Alimta®), raltitrexed (Tomudex®), cladribine (Leustatin®), clofarabine (Clofarex®, Clolar®), mercaptopurine (Puri-Nethol®), capecitabine (Xeloda®), nelarabine (Arranon®), azacitidine (Vidaza®) and gemcitabine (Gemzar®). Preferred antimetabolites include, e.g., 5-fluorouracil (Adrucil®, Efudex®, Fluoroplex®), floxuridine (FUDF®), capecitabine (Xeloda®), pemetrexed (Alimta®), raltitrexed (Tomudex®) and gemcitabine (Gemzar®).

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

In embodiments, a CAR-expressing cell described herein is administered to a subject in combination with fludarabine, cyclophosphamide, and/or rituximab. In embodiments, a CAR-expressing cell described herein is administered to a subject in combination with fludarabine, cyclophosphamide, and rituximab (FCR). In embodiments, the subject has a cancer. In embodiments, the fludarabine is administered at a dosage of about 10-50 mg/m$^2$ (e.g., about 10-15, 15-20, 20-25, 25-30, 30-35, 35-40, 40-45, or 45-50 mg/m$^2$), e.g., intravenously. In embodiments, the cyclophosphamide is administered at a dosage of about 200-300 mg/m$^2$ (e.g., about 200-225, 225-250, 250-275, or 275-300 mg/m$^2$), e.g., intravenously. In embodiments, the rituximab is administered at a dosage of about 400-600 mg/m2 (e.g., 400-450, 450-500, 500-550, or 550-600 mg/m$^2$), e.g., intravenously.

In embodiments, a CAR-expressing cell described herein is administered to a subject in combination with bendamustine and rituximab. In embodiments, the subject has a cancer. In embodiments, the bendamustine is administered at a dosage of about 70-110 mg/m2 (e.g., 70-80, 80-90, 90-100, or 100-110 mg/m2), e.g., intravenously. In embodiments, the rituximab is administered at a dosage of about 400-600 mg/m2 (e.g., 400-450, 450-500, 500-550, or 550-600 mg/m$^2$), e.g., intravenously.

In embodiments, a CAR-expressing cell described herein is administered to a subject in combination with rituximab, cyclophosphamide, doxorubicine, vincristine, and/or a corticosteroid (e.g., prednisone). In embodiments, a CAR-expressing cell described herein is administered to a subject in combination with rituximab, cyclophosphamide, doxorubicine, vincristine, and prednisone (R-CHOP). In embodiments, the subject has diffuse large B-cell lymphoma (DLBCL). In embodiments, the subject has nonbulky limited-stage DLBCL (e.g., comprises a tumor having a size/diameter of less than 7 cm). In embodiments, the subject is treated with radiation in combination with the R-CHOP. For example, the subject is administered R-CHOP (e.g., 1-6 cycles, e.g., 1, 2, 3, 4, 5, or 6 cycles of R-CHOP), followed by radiation. In some cases, the subject is administered R-CHOP (e.g., 1-6 cycles, e.g., 1, 2, 3, 4, 5, or 6 cycles of R-CHOP) following radiation.

In embodiments, a CAR-expressing cell described herein is administered to a subject in combination with etoposide, prednisone, vincristine, cyclophosphamide, doxorubicin, and/or rituximab. In embodiments, a CAR-expressing cell described herein is administered to a subject in combination with etoposide, prednisone, vincristine, cyclophosphamide, doxorubicin, and rituximab (EPOCH-R). In embodiments, a CAR-expressing cell described herein is administered to a subject in combination with dose-adjusted EPOCH-R (DA-EPOCH-R). In embodiments, the subject has a B cell lymphoma, e.g., a Myc-rearranged aggressive B cell lymphoma.

In embodiments, a CAR-expressing cell described herein is administered to a subject in combination with rituximab and/or lenalidomide. Lenalidomide ((RS)-3-(4-Amino-1-oxo 1,3-dihydro-2H-isoindol-2-yl)piperidine-2,6-dione) is an immunomodulator. In embodiments, a CAR-expressing cell described herein is administered to a subject in combination with rituximab and lenalidomide. In embodiments, the subject has follicular lymphoma (FL) or mantle cell lymphoma (MCL). In embodiments, the subject has FL and has not previously been treated with a cancer therapy. In embodiments, lenalidomide is administered at a dosage of about 10-20 mg (e.g., 10-15 or 15-20 mg), e.g., daily. In embodiments, rituximab is administered at a dosage of about 350-550 $mg/m^2$ (e.g., 350-375, 375-400, 400-425, 425-450, 450-475, or 475-500 $mg/m^2$), e.g., intravenously.

Exemplary mTOR inhibitors include, e.g., temsirolimus; ridaforolimus (formally known as deferolimus, (1R,2R,4S)-4-[(2R)-2 [(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.$0^{4,9}$]hexatriaconta-16,24,26,28-tetraen-12-yl]propyl]-2-methoxycyclohexyl dimethylphosphinate, also known as AP23573 and MK8669, and described in PCT Publication No. WO 03/064383); everolimus (Afinitor® or RAD001); rapamycin (AY22989, Sirolimus®); simapimod (CAS 164301-51-3); emsirolimus, (5-{2,4-Bis[(3S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502, CAS 1013101-36-4); and $N^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine, inner salt (SF1126, CAS 936487-67-1), and XL765.

Exemplary immunomodulators include, e.g., afutuzumab (available from Roche®); pegfilgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon γ, CAS 951209-71-5, available from IRX Therapeutics).

Exemplary anthracyclines include, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids include, e.g., vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteosome inhibitors include bortezomib (Velcade®); carfilzomib (PX-171-007, (S)-4-Methyl-N-((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912).

In embodiments, a CAR-expressing cell described herein is administered to a subject in combination with brentuximab. Brentuximab is an antibody-drug conjugate of anti-CD30 antibody and monomethyl auristatin E. In embodiments, the subject has Hodgkin's lymphoma (HL), e.g., relapsed or refractory HL. In embodiments, the subject comprises CD30+ HL. In embodiments, the subject has undergone an autologous stem cell transplant (ASCT). In embodiments, the subject has not undergone an ASCT. In embodiments, brentuximab is administered at a dosage of about 1-3 mg/kg (e.g., about 1-1.5, 1.5-2, 2-2.5, or 2.5-3 mg/kg), e.g., intravenously, e.g., every 3 weeks.

In embodiments, a CAR-expressing cell described herein is administered to a subject in combination with brentuximab and dacarbazine or in combination with brentuximab and bendamustine. Dacarbazine is an alkylating agent with a chemical name of 5-(3,3-Dimethyl-1-triazenyl)imidazole-4-carboxamide. Bendamustine is an alkylating agent with a chemical name of 4-[5-[Bis(2-chloroethyl)amino]-1-methylbenzimidazol-2-yl]butanoic acid. In embodiments, the subject has Hodgkin's lymphoma (HL). In embodiments, the subject has not previously been treated with a cancer therapy. In embodiments, the subject is at least 60 years of age, e.g., 60, 65, 70, 75, 80, 85, or older. In embodiments, dacarbazine is administered at a dosage of about 300-450 $mg/m^2$ (e.g., about 300-325, 325-350, 350-375, 375-400, 400-425, or 425-450 $mg/m^2$), e.g., intravenously. In embodiments, bendamustine is administered at a dosage of about 75-125 mg/m2 (e.g., 75-100 or 100-125 $mg/m^2$, e.g., about 90 $mg/m^2$), e.g., intravenously. In embodiments, brentuximab is administered at a dosage of about 1-3 mg/kg (e.g., about 1-1.5, 1.5-2, 2-2.5, or 2.5-3 mg/kg), e.g., intravenously, e.g., every 3 weeks.

In some embodiments, a CAR-expressing cell described herein is administered to a subject in combination with a CD20 inhibitor, e.g., an anti-CD20 antibody (e.g., an anti-CD20 mono- or bispecific antibody) or a fragment thereof. Exemplary anti-CD20 antibodies include but are not limited to rituximab, ofatumumab, ocrelizumab, veltuzumab, obinutuzumab, TRU-015 (Trubion Pharmaceuticals), ocaratuzumab, and Pro131921 (Genentech). See, e.g., Lim et al. Haematologica. 95.1(2010):135-43.

In some embodiments, the anti-CD20 antibody comprises rituximab. Rituximab is a chimeric mouse/human monoclonal antibody IgG1 kappa that binds to CD20 and causes cytolysis of a CD20 expressing cell, e.g., as described in www.accessdata.fda.gov/drugsatfda_docs/label/2010/103705s5311lbl.pdf. In embodiments, a CAR-expressing cell described herein is administered to a subject in combination with rituximab. In embodiments, the subject has CLL or SLL.

In some embodiments, rituximab is administered intravenously, e.g., as an intravenous infusion. For example, each infusion provides about 500-2000 mg (e.g., about 500-550, 550-600, 600-650, 650-700, 700-750, 750-800, 800-850, 850-900, 900-950, 950-1000, 1000-1100, 1100-1200, 1200-1300, 1300-1400, 1400-1500, 1500-1600, 1600-1700, 1700-1800, 1800-1900, or 1900-2000 mg) of rituximab. In some embodiments, rituximab is administered at a dose of 150 $mg/m^2$ to 750 $mg/m^2$, e.g., about 150-175 $mg/m^2$, 175-200 $mg/m^2$, 200-225 $mg/m^2$, 225-250 $mg/m^2$, 250-300 $mg/m^2$, 300-325 $mg/m^2$, 325-350 $mg/m^2$, 350-375 $mg/m^2$, 375-400 $mg/m^2$, 400-425 $mg/m^2$, 425-450 $mg/m^2$, 450-475 $mg/m^2$, 475-500 $mg/m^2$, 500-525 $mg/m^2$, 525-550 $mg/m^2$, 550-575 $mg/m^2$, 575-600 $mg/m^2$, 600-625 $mg/m^2$, 625-650 $mg/m^2$, 650-675 $mg/m^2$, or 675-700 $mg/m^2$, where $m^2$ indicates the body surface area of the subject. In some embodiments, rituximab is administered at a dosing interval of at least 4 days, e.g., 4, 7, 14, 21, 28, 35 days, or more. For example, rituximab is administered at a dosing interval of at least 0.5 weeks, e.g., 0.5, 1, 2, 3, 4, 5, 6, 7, 8 weeks, or more. In some embodiments, rituximab is administered at a dose and dosing interval described herein for a period of time, e.g., at least 2 weeks, e.g., at least 2, 3, 4, 5, 6, 7, 8, 9, 10, 11, 12, 13, 14, 15, 16, 17, 18, 19, 20 weeks, or greater. For example, rituximab is administered at a dose and dosing interval described herein for a total of at least 4 doses per treatment cycle (e.g., at least 4, 5, 6, 7, 8, 9, 10, 11, 12, 13, 14, 15, 16, or more doses per treatment cycle).

In some embodiments, the anti-CD20 antibody comprises ofatumumab. Ofatumumab is an anti-CD20 IgG1κ human monoclonal antibody with a molecular weight of approximately 149 kDa. For example, ofatumumab is generated using transgenic mouse and hybridoma technology and is expressed and purified from a recombinant murine cell line (NSO). See, e.g., www.accessdata.fda.gov/drugsatfda_docs/label/2009/125326lbl.pdf; and Clinical Trial Identifier number NCT01363128, NCT01515176, NCT01626352, and NCT01397591. In embodiments, a CAR-expressing cell described herein is administered to a subject in combination with ofatumumab. In embodiments, the subject has CLL or SLL.

In some embodiments, ofatumumab is administered as an intravenous infusion. For example, each infusion provides about 150-3000 mg (e.g., about 150-200, 200-250, 250-300, 300-350, 350-400, 400-450, 450-500, 500-550, 550-600, 600-650, 650-700, 700-750, 750-800, 800-850, 850-900, 900-950, 950-1000, 1000-1200, 1200-1400, 1400-1600, 1600-1800, 1800-2000, 2000-2200, 2200-2400, 2400-2600, 2600-2800, or 2800-3000 mg) of ofatumumab. In embodiments, ofatumumab is administered at a starting dosage of about 300 mg, followed by 2000 mg, e.g., for about 11 doses, e.g., for 24 weeks. In some embodiments, ofatumumab is administered at a dosing interval of at least 4 days, e.g., 4, 7, 14, 21, 28, 35 days, or more. For example, ofatumumab is administered at a dosing interval of at least 1 week, e.g., 1, 2, 3, 4, 5, 6, 7, 8, 9, 10, 11, 12, 24, 26, 28, 20, 22, 24, 26, 28, 30 weeks, or more. In some embodiments, ofatumumab is administered at a dose and dosing interval described herein for a period of time, e.g., at least 1 week, e.g., 1, 2, 3, 4, 5, 6, 7, 8, 9, 10, 11, 12, 13, 14, 15, 16, 17, 18, 19, 20, 22, 24, 26, 28, 30, 40, 50, 60 weeks or greater, or 1, 2, 3, 4, 5, 6, 7, 8, 9, 10, 11, 12 months or greater, or 1, 2, 3, 4, 5 years or greater. For example, ofatumumab is administered at a dose and dosing interval described herein for a total of at least 2 doses per treatment cycle (e.g., at least 2, 3, 4, 5, 6, 7, 8, 9, 10, 11, 12, 13, 14, 15, 16, 18, 20, or more doses per treatment cycle).

In some cases, the anti-CD20 antibody comprises ocrelizumab. Ocrelizumab is a humanized anti-CD20 monoclonal antibody, e.g., as described in Clinical Trials Identifier Nos. NCT00077870, NCT01412333, NCT00779220, NCT00673920, NCT01194570, and Kappos et al. Lancet. 19.378(2011):1779-87.

In some cases, the anti-CD20 antibody comprises veltuzumab. Veltuzumab is a humanized monoclonal antibody against CD20. See, e.g., Clinical Trial Identifier No. NCT00547066, NCT00546793, NCT01101581, and Goldenberg et al. Leuk Lymphoma. 51(5)(2010):747-55.

In some cases, the anti-CD20 antibody comprises GA101. GA101 (also called obinutuzumab or RO5072759) is a humanized and glyco-engineered anti-CD20 monoclonal antibody. See, e.g., Robak. Curr. Opin. Investig. Drugs. 10.6(2009):588-96; Clinical Trial Identifier Numbers: NCT01995669, NCT01889797, NCT02229422, and NCT01414205; and www.accessdata.fda.gov/drugsatfda_docs/label/2013/125486s0001bl.pdf.

In some cases, the anti-CD20 antibody comprises AME-133v. AME-133v (also called LY2469298 or ocaratuzumab) is a humanized IgG1 monoclonal antibody against CD20 with increased affinity for the FcγRIIIa receptor and an enhanced antibody dependent cellular cytotoxicity (ADCC) activity compared with rituximab. See, e.g., Robak et al. BioDrugs 25.1(2011):13-25; and Forero-Torres et al. Clin Cancer Res. 18.5(2012):1395-403.

In some cases, the anti-CD20 antibody comprises PRO131921. PRO131921 is a humanized anti-CD20 monoclonal antibody engineered to have better binding to FcγRIIIa and enhanced ADCC compared with rituximab. See, e.g., Robak et al. BioDrugs 25.1(2011):13-25; and Casulo et al. Clin Immunol. 154.1(2014):37-46; and Clinical Trial Identifier No. NCT00452127.

In some cases, the anti-CD20 antibody comprises TRU-015. TRU-015 is an anti-CD20 fusion protein derived from domains of an antibody against CD20. TRU-015 is smaller than monoclonal antibodies, but retains Fc-mediated effector functions. See, e.g., Robak et al. BioDrugs 25.1(2011):13-25. TRU-015 contains an anti-CD20 single-chain variable fragment (scFv) linked to human IgG1 hinge, CH2, and CH3 domains but lacks CH1 and CL domains.

In some embodiments, an anti-CD20 antibody described herein is conjugated or otherwise bound to a therapeutic agent, e.g., a chemotherapeutic agent (e.g., cytoxan, fludarabine, histone deacetylase inhibitor, demethylating agent, peptide vaccine, anti-tumor antibiotic, tyrosine kinase inhibitor, alkylating agent, anti-microtubule or anti-mitotic agent), anti-allergic agent, anti-nausea agent (or anti-emetic), pain reliever, or cytoprotective agent described herein.

In embodiments, a CAR-expressing cell described herein is administered to a subject in combination with a B-cell lymphoma 2 (BCL-2) inhibitor (e.g., venetoclax, also called ABT-199 or GDC-0199;) and/or rituximab. In embodiments, a CAR-expressing cell described herein is administered to a subject in combination with venetoclax and rituximab. Venetoclax is a small molecule that inhibits the anti-apoptotic protein, BCL-2. The structure of venetoclax (4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide) is shown below.

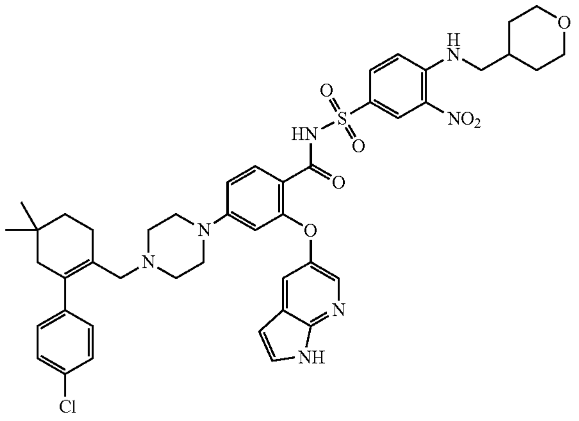 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1]

In embodiments, the subject has CLL. In embodiments, the subject has relapsed CLL, e.g., the subject has previously been administered a cancer therapy. In embodiments, venetoclax is administered at a dosage of about 15-600 mg (e.g., 15-20, 20-50, 50-75, 75-100, 100-200, 200-300, 300-400, 400-500, or 500-600 mg), e.g., daily. In embodiments, rituximab is administered at a dosage of about 350-550 mg/m2 (e.g., 350-375, 375-400, 400-425, 425-450, 450-475, or 475-500 mg/m2), e.g., intravenously, e.g., monthly.

In some embodiments, a CAR-expressing cell described herein is administered in combination with an oncolytic virus. In embodiments, oncolytic viruses are capable of selectively replicating in and triggering the death of or slowing the growth of a cancer cell. In some cases, oncolytic viruses have no effect or a minimal effect on non-cancer cells. An oncolytic virus includes but is not limited to an oncolytic adenovirus, oncolytic Herpes Simplex Viruses, oncolytic retrovirus, oncolytic parvovirus, oncolytic vaccinia virus, oncolytic Sinbis virus, oncolytic influenza virus, or oncolytic RNA virus (e.g., oncolytic reovirus, oncolytic Newcastle Disease Virus (NDV), oncolytic measles virus, or oncolytic vesicular stomatitis virus (VSV)).

In some embodiments, the oncolytic virus is a virus, e.g., recombinant oncolytic virus, described in US2010/0178684 A1, which is incorporated herein by reference in its entirety. In some embodiments, a recombinant oncolytic virus comprises a nucleic acid sequence (e.g., heterologous nucleic acid sequence) encoding an inhibitor of an immune or inflammatory response, e.g., as described in US2010/0178684 A1, incorporated herein by reference in its entirety. In embodiments, the recombinant oncolytic virus, e.g., oncolytic NDV, comprises a pro-apoptotic protein (e.g., apoptin), a cytokine (e.g., GM-CSF, interferon-gamma, interleukin-2 (IL-2), tumor necrosis factor-alpha), an immunoglobulin (e.g., an antibody against ED-B firbonectin), tumor associated antigen, a bispecific adapter protein (e.g., bispecific antibody or antibody fragment directed against NDV HN protein and a T cell co-stimulatory receptor, such as CD3 or CD28; or fusion protein between human IL-2 and single chain antibody directed against NDV HN protein). See, e.g., Zamarin et al. Future Microbiol. 7.3(2012):347-67, incorporated herein by reference in its entirety. In some embodiments, the oncolytic virus is a chimeric oncolytic NDV described in U.S. Pat. No. 8,591,881 B2, US 2012/0122185 A1, or US 2014/0271677 A1, each of which is incorporated herein by reference in their entireties.

In some embodiments, the oncolytic virus comprises a conditionally replicative adenovirus (CRAd), which is designed to replicate exclusively in cancer cells. See, e.g., Alemany et al. Nature Biotechnol. 18(2000):723-27. In some embodiments, an oncolytic adenovirus comprises one described in Table 1 on page 725 of Alemany et al., incorporated herein by reference in its entirety.

Exemplary oncolytic viruses include but are not limited to the following:

Group B Oncolytic Adenovirus (ColoAd1) (PsiOxus Therapeutics Ltd.) (see, e.g., Clinical Trial Identifier: NCT02053220);

ONCOS-102 (previously called CGTG-102), which is an adenovirus comprising granulocyte-macrophage colony stimulating factor (GM-CSF) (Oncos Therapeutics) (see, e.g., Clinical Trial Identifier: NCT01598129);

VCN-01, which is a genetically modified oncolytic human adenovirus encoding human PH20 hyaluronidase (VCN Biosciences, S.L.) (see, e.g., Clinical Trial Identifiers: NCT02045602 and NCT02045589);

Conditionally Replicative Adenovirus ICOVIR-5, which is a virus derived from wild-type human adenovirus serotype 5 (Had5) that has been modified to selectively replicate in cancer cells with a deregulated retinoblastoma/E2F pathway (Institut Catala d'Oncologia) (see, e.g., Clinical Trial Identifier: NCT01864759);

Celyvir, which comprises bone marrow-derived autologous mesenchymal stem cells (MSCs) infected with ICOVIR5, an oncolytic adenovirus (Hospital Infantil Universitario Niño Jesús, Madrid, Spain/Ramon Alemany) (see, e.g., Clinical Trial Identifier: NCT01844661);

CG0070, which is a conditionally replicating oncolytic serotype 5 adenovirus (Ad5) in which human E2F-1 promoter drives expression of the essential Ela viral genes, thereby restricting viral replication and cytotoxicity to Rb pathway-defective tumor cells (Cold Genesys, Inc.) (see, e.g., Clinical Trial Identifier: NCT02143804); or DNX-2401 (formerly named Delta-24-RGD), which is an adenovirus that has been engineered to replicate selectively in retinoblastoma (Rb)-pathway deficient cells and to infect cells that express certain RGD-binding integrins more efficiently (Clinica Universidad de Navarra, Universidad de Navarra/DNAtrix, Inc.) (see, e.g., Clinical Trial Identifier: NCT01956734).

In some embodiments, an oncolytic virus described herein is administering by injection, e.g., subcutaneous, intra-arterial, intravenous, intramuscular, intrathecal, or intraperitoneal injection. In embodiments, an oncolytic virus described herein is administered intratumorally, transdermally, transmucosally, orally, intranasally, or via pulmonary administration.

In an embodiment, cells expressing a CAR described herein are administered to a subject in combination with a molecule that decreases the Treg cell population. Methods that decrease the number of (e.g., deplete) Treg cells are known in the art and include, e.g., CD25 depletion, cyclophosphamide administration, modulating GITR function. Without wishing to be bound by theory, it is believed that reducing the number of Treg cells in a subject prior to apheresis or prior to administration of a CAR-expressing cell described herein reduces the number of unwanted immune cells (e.g., Tregs) in the tumor microenvironment and reduces the subject's risk of relapse.

In one embodiment, a CAR expressing cell described herein is administered to a subject in combination with a molecule targeting GITR and/or modulating GITR functions, such as a GITR agonist and/or a GITR antibody that depletes regulatory T cells (Tregs). In embodiments, cells expressing a CAR described herein are administered to a subject in combination with cyclophosphamide. In one embodiment, the GITR binding molecules and/or molecules modulating GITR functions (e.g., GITR agonist and/or Treg depleting GITR antibodies) are administered prior to administration of the CAR-expressing cell. For example, in one embodiment, the GITR agonist can be administered prior to apheresis of the cells. In embodiments, cyclophosphamide is administered to the subject prior to administration (e.g., infusion or re-infusion) of the CAR-expressing cell or prior to aphersis of the cells. In embodiments, cyclophosphamide and an anti-GITR antibody are administered to the subject prior to administration (e.g., infusion or re-infusion) of the CAR-expressing cell or prior to apheresis of the cells. In one embodiment, the subject has cancer (e.g., a solid cancer or a hematological cancer such as ALL or CLL). In an embodiment, the subject has CLL. In embodiments, the subject has ALL. In embodiments, the subject has a solid cancer, e.g., a solid cancer described herein. Exemplary GITR agonists include, e.g., GITR fusion proteins and anti-GITR antibodies (e.g., bivalent anti-GITR antibodies) such as, e.g., a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In one embodiment, a CAR expressing cell described herein is administered to a subject in combination with an mTOR inhibitor, e.g., an mTOR inhibitor described herein, e.g., a rapalog such as everolimus. In one embodiment, the mTOR inhibitor is administered prior to the CAR-expressing cell. For example, in one embodiment, the mTOR inhibitor can be administered prior to apheresis of the cells.

In one embodiment, a CAR expressing cell described herein is administered to a subject in combination with a GITR agonist, e.g., a GITR agonist described herein. In one embodiment, the GITR agonist is administered prior to the CAR-expressing cell. For example, in one embodiment, the GITR agonist can be administered prior to apheresis of the cells.

In one embodiment, a CAR expressing cell described herein is administered to a subject in combination with a protein tyrosine phosphatase inhibitor, e.g., a protein tyrosine phosphatase inhibitor described herein. In one embodiment, the protein tyrosine phosphatase inhibitor is an SHP-1 inhibitor, e.g., an SHP-1 inhibitor described herein, such as, e.g., sodium stibogluconate. In one embodiment, the protein tyrosine phosphatase inhibitor is an SHP-2 inhibitor, e.g., an SHP-2 inhibitor described herein.

In one embodiment, a CAR-expressing cell described herein can be used in combination with a kinase inhibitor. In one embodiment, the kinase inhibitor is a CDK4 inhibitor, e.g., a CDK4 inhibitor described herein, e.g., a CDK4/6 inhibitor, such as, e.g., 6-Acetyl-8-cyclopentyl-5-methyl-2-(5-piperazin-1-yl-pyridin-2-ylamino)-8H-pyrido[2,3-d]pyrimidin-7-one, hydrochloride (also referred to as palbociclib or PD0332991). In one embodiment, the kinase inhibitor is a BTK inhibitor, e.g., a BTK inhibitor described herein, such as, e.g., ibrutinib. In one embodiment, the kinase inhibitor is an mTOR inhibitor, e.g., an mTOR inhibitor described herein, such as, e.g., rapamycin, a rapamycin analog, OSI-027. The mTOR inhibitor can be, e.g., an mTORC1 inhibitor and/or an mTORC2 inhibitor, e.g., an mTORC1 inhibitor and/or mTORC2 inhibitor described herein. In one embodiment, the kinase inhibitor is a MNK inhibitor, e.g., a MNK inhibitor described herein, such as, e.g., 4-amino-5-(4-fluoroanilino)-pyrazolo [3,4-d] pyrimidine. The MNK inhibitor can be, e.g., a MNK1a, MNK1b, MNK2a and/or MNK2b inhibitor. In one embodiment, the kinase inhibitor is a dual PI3K/mTOR inhibitor described herein, such as, e.g., PF-04695102. In one embodiment, the kinase inhibitor is a DGK inhibitor, e.g., a DGK inhibitor described herein, such as, e.g., DGKinh1 (D5919) or DGKinh2 (D5794). In one embodiment, the kinase inhibitor is a CDK4 inhibitor selected from aloisine A; flavopiridol or HMR-1275, 2-(2-chlorophenyl)-5,7-dihydroxy-8-[(3 S,4R)-3-hydroxy-1-methyl-4-piperidinyl]-4-chromenone; crizotinib (PF-02341066; 2-(2-Chlorophenyl)-5,7-dihydroxy-8-[(2R,3S)-2-(hydroxymethyl)-1-methyl-3-pyrrolidinyl]-4H-1-benzopyran-4-one, hydrochloride (P276-00); 1-methyl-5-[[2-[5-(trifluoromethyl)-1H-imidazol-2-yl]-4-pyridinyl]oxy]-N-[4-(trifluoromethyl)phenyl]-1H-benzimidazol-2-amine (RAF265); indisulam (E7070); roscovitine (CYC202); palbociclib (PD0332991); dinaciclib (SCH727965); N-[5-[[(5-tert-butyloxazol-2-yl)methyl]thio]thiazol-2-yl]piperidine-4-carboxamide (BMS 387032); 4-[[9-chloro-7-(2,6-difluorophenyl)-5H-pyrimido[5,4-d][2]benzazepin-2-yl]amino]-benzoic acid (MLN8054); 5-[3-(4,6-difluoro-1H-benzimidazol-2-yl)-1H-indazol-5-yl]-N-ethyl-4-methyl-3-pyridinemethanamine (AG-024322); 4-(2,6-dichlorobenzoylamino)-1H-pyrazole-3-carboxylic acid N-(piperidin-4-yl)amide (AT7519); 4-[2-methyl-1-(1-methylethyl)-1H-imidazol-5-yl]-N-[4-(methylsulfonyl)phenyl]-2-pyrimidinamine (AZD5438); and XL281 (BMS908662).

In one embodiment, the kinase inhibitor is a CDK4 inhibitor, e.g., palbociclib (PD0332991), and the palbociclib is administered at a dose of about 50 mg, 60 mg, 70 mg, 75 mg, 80 mg, 90 mg, 100 mg, 105 mg, 110 mg, 115 mg, 120 mg, 125 mg, 130 mg, 135 mg (e.g., 75 mg, 100 mg or 125 mg) daily for a period of time, e.g., daily for 14-21 days of a 28 day cycle, or daily for 7-12 days of a 21 day cycle. In one embodiment, 1, 2, 3, 4, 5, 6, 7, 8, 9, 10, 11, 12 or more cycles of palbociclib are administered.

In embodiments, a CAR-expressing cell described herein is administered to a subject in combination with a cyclin-dependent kinase (CDK) 4 or 6 inhibitor, e.g., a CDK4 inhibitor or a CDK6 inhibitor described herein. In embodiments, a CAR-expressing cell described herein is administered to a subject in combination with a CDK4/6 inhibitor (e.g., an inhibitor that targets both CDK4 and CDK6), e.g., a CDK4/6 inhibitor described herein. In an embodiment, the subject has MCL. MCL is an aggressive cancer that is poorly responsive to currently available therapies, i.e., essentially incurable. In many cases of MCL, cyclin D1 (a regulator of CDK4/6) is expressed (e.g., due to chromosomal translocation involving immunoglobulin and Cyclin D1 genes) in MCL cells. Thus, without being bound by theory, it is thought that MCL cells are highly sensitive to CDK4/6 inhibition with high specificity (i.e., minimal effect on normal immune cells). CDK4/6 inhibitors alone have had some efficacy in treating MCL, but have only achieved partial remission with a high relapse rate. An exemplary CDK4/6 inhibitor is LEE011 (also called ribociclib), the structure of which is shown below.

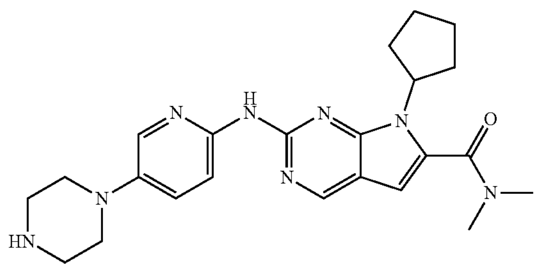 [SMILES: CN(C)C(=O)c1cc2cnc(Nc3ccc(N4CCNCC4)cn3)nc2n1C1CCCC1]

Without being bound by theory, it is believed that administration of a CAR-expressing cell described herein with a CDK4/6 inhibitor (e.g., LEE011 or other CDK4/6 inhibitor described herein) can achieve higher responsiveness, e.g., with higher remission rates and/or lower relapse rates, e.g., compared to a CDK4/6 inhibitor alone.

In one embodiment, the kinase inhibitor is a BTK inhibitor selected from ibrutinib (PCI-32765); GDC-0834; RN-486; CGI-560; CGI-1764; HM-71224; CC-292; ONO-4059; CNX-774; and LFM-A13. In a preferred embodiment, the BTK inhibitor does not reduce or inhibit the kinase activity of interleukin-2-inducible kinase (ITK), and is selected from GDC-0834; RN-486; CGI-560; CGI-1764; HM-71224; CC-292; ONO-4059; CNX-774; and LFM-A13.

In one embodiment, the kinase inhibitor is a BTK inhibitor, e.g., ibrutinib (PCI-32765). In embodiments, a CAR-expressing cell described herein is administered to a subject in combination with a BTK inhibitor (e.g., ibrutinib). In embodiments, a CAR-expressing cell described herein is administered to a subject in combination with ibrutinib (also called PCI-32765). The structure of ibrutinib (1-[(3R)-3-[4-Amino-3-(4-phenoxyphenyl)-1H-pyrazolo[3,4-d]pyrimidin-1-yl]piperidin-1-yl]prop-2-en-1-one) is shown below.

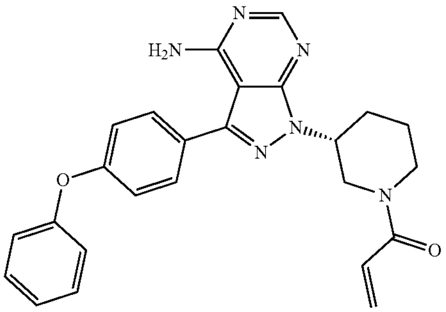 [SMILES: C=CC(=O)N1CCC[C@@H](n2nc(-c3ccc(Oc4ccccc4)cc3)c3c(N)ncnc32)C1]

In embodiments, the subject has CLL, mantle cell lymphoma (MCL), or small lymphocytic lymphoma (SLL). For example, the subject has a deletion in the short arm of chromosome 17 (del(17p), e.g., in a leukemic cell). In other examples, the subject does not have a del(17p). In embodiments, the subject has relapsed CLL or SLL, e.g., the subject has previously been administered a cancer therapy (e.g., previously been administered one, two, three, or four prior cancer therapies). In embodiments, the subject has refractory CLL or SLL. In other embodiments, the subject has follicular lymphoma, e.g., relapse or refractory follicular lymphoma. In some embodiments, ibrutinib is administered at a dosage of about 300-600 mg/day (e.g., about 300-350, 350-400, 400-450, 450-500, 500-550, or 550-600 mg/day, e.g., about 420 mg/day or about 560 mg/day), e.g., orally. In embodiments, the ibrutinib is administered at a dose of about 250 mg, 300 mg, 350 mg, 400 mg, 420 mg, 440 mg, 460 mg, 480 mg, 500 mg, 520 mg, 540 mg, 560 mg, 580 mg, 600 mg (e.g., 250 mg, 420 mg or 560 mg) daily for a period of time, e.g., daily for 21 day cycle cycle, or daily for 28 day cycle. In one embodiment, 1, 2, 3, 4, 5, 6, 7, 8, 9, 10, 11, 12 or more cycles of ibrutinib are administered. In some embodiments, ibrutinib is administered in combination with rituximab. See, e.g., Burger et al. (2013) Ibrutinib In Combination With Rituximab (iR) Is Well Tolerated and Induces a High Rate Of Durable Remissions In Patients With High-Risk Chronic Lymphocytic Leukemia (CLL): New, Updated Results Of a Phase II Trial In 40 Patients, Abstract 675 presented at $55^{th}$ ASH Annual Meeting and Exposition, New Orleans, LA 7-10 December Without being bound by theory, it is thought that the addition of ibrutinib enhances the T cell proliferative response and may shift T cells from a T-helper-2 (Th2) to T-helper-1 (Th1) phenotype. Th1 and Th2 are phenotypes of helper T cells, with Th1 versus Th2 directing different immune response pathways. A Th1 phenotype is associated with proinflammatory responses, e.g., for killing cells, such as intracellular pathogens/viruses or cancerous cells, or perpetuating autoimmune responses. A Th2 phenotype is associated with eosinophil accumulation and anti-inflammatory responses.

In some embodiments of the methods, uses, and compositions herein, the BTK inhibitor is a BTK inhibitor described in International Application WO/2015/079417, which is herein incorporated by reference in its entirety. For instance, in some embodiments, the BTK inhibitor is a compound of formula (I) or a pharmaceutically acceptable salt thereof;

(I)

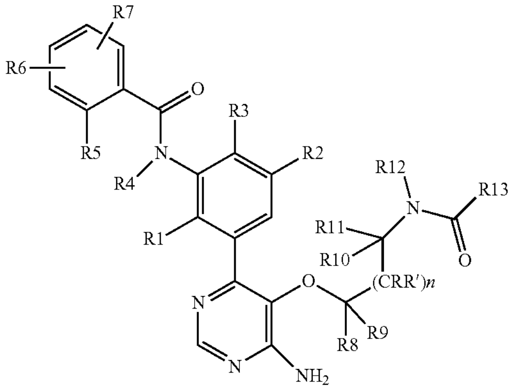

wherein,

R1 is hydrogen, C1-C6 alkyl optionally substituted by hydroxy;

R2 is hydrogen or halogen;

R3 is hydrogen or halogen;

R4 is hydrogen;

R5 is hydrogen or halogen;

or R4 and R5 are attached to each other and stand for a bond, —CH2-, —CH2-CH2-, —CH═CH—, —CH═CH—CH2-; —CH2-CH═CH—; or —CH2-CH2-CH2-;

R6 and R7 stand independently from each other for H, C1-C6 alkyl optionally substituted by hydroxyl, C3-C6 cycloalkyl optionally substituted by halogen or hydroxy, or halogen;

R8, R9, R, R', R10 and R11 independently from each other stand for H, or C1-C6 alkyl optionally substituted by C1-C6 alkoxy; or any two of R8, R9, R, R', R10 and R11 together with the carbon atom to which they are bound may form a 3-6 membered saturated carbocyclic ring;

R12 is hydrogen or C1-C6 alkyl optionally substituted by halogen or C1-C6 alkoxy;

or R12 and any one of R8, R9, R, R', R10 or R11 together with the atoms to which they are bound may form a 4, 5, 6 or 7 membered azacyclic ring, which ring may optionally be substituted by halogen, cyano, hydroxyl, C1-C6 alkyl or C1-C6 alkoxy;

n is 0 or 1; and

R13 is C2-C6 alkenyl optionally substituted by C1-C6 alkyl, C1-C6 alkoxy or N,N-di-C1-C6 alkyl amino; C2-C6 alkynyl optionally substituted by C1-C6 alkyl or C1-C6 alkoxy; or C2-C6 alkylenyl oxide optionally substituted by C1-C6 alkyl.

In some embodiments, the BTK inhibitor of Formula I is chosen from: N-(3-(5-((1-Acryloylazetidin-3-yl)oxy)-6-aminopyrimidin-4-yl)-5-fluoro-2-methylphenyl)-4-cyclopropyl-2-fluorobenzamide; (E)-N-(3-(6-Amino-5-((1-(but-2-enoyl)azetidin-3-yl)oxy)pyrimidin-4-yl)-5-fluoro-2-methylphenyl)-4-cyclopropyl-2-fluorobenzamide; N-(3-(6-Amino-5-((1-propioloylazetidin-3-yl)oxy)pyrimidin-4-yl)-5-fluoro-2-methylphenyl)-4-cyclopropyl-2-fluorobenzamide; N-(3-(6-Amino-5-((1-(but-2-ynoyl)azetidin-3-yl)oxy)pyrimidin-4-yl)-5-fluoro-2-methylphenyl)-4-cyclopropyl-2-fluorobenzamide; N-(3-(5-((1-Acryloylpiperidin-4-yl)oxy)-6-aminopyrimidin-4-yl)-5-fluoro-2-methylphenyl)-4-cyclopropyl-2-fluorobenzamide; N-(3-(6-Amino-5-(2-(N-methylacrylamido)ethoxy)pyrimidin-4-yl)-5-fluoro-2-methylphenyl)-4-cyclopropyl-2-fluorobenzamide; (E)-N-(3-(6-Amino-5-(2-(N-methylbut-2-enamido)ethoxy)pyrimidin-4-yl)-5-fluoro-2-methylphenyl)-4-cyclopropyl-2-fluorobenzamide; N-(3-(6-Amino-5-(2-(N-methylpropiolamido)ethoxy)pyrimidin-4-yl)-5-fluoro-2-methylphenyl)-4-cyclopropyl-2-fluorobenzamide; (E)-N-(3-(6-Amino-5-(2-(4-methoxy-N-methylbut-2-enamido)ethoxy)pyrimidin-4-yl)-5-fluoro-2-methylphenyl)-4-cyclopropyl-2-fluorobenzamide; N-(3-(6-Amino-5-(2-(N-methylbut-2-ynamido)ethoxy)pyrimidin-4-yl)-5-fluoro-2-methylphenyl)-4-cyclopropyl-2-fluorobenzamide; N-(2-((4-Amino-6-(3-(4-cyclopropyl-2-fluorobenzamido)-5-fluoro-2-methylphenyl)pyrimidin-5-yl)oxy)ethyl)-N-methyloxirane-2-carboxamide; N-(2-((4-Amino-6-(3-(6-cyclopropyl-8-fluoro-1-oxoisoquinolin-2(1H)-yl)phenyl)pyrimidin-5-yl)oxy)ethyl)-N-methylacrylamide; N-(3-(5-(2-Acrylamidoethoxy)-6-aminopyrimidin-4-yl)-5-fluoro-2-methylphenyl)-4-cyclopropyl-2-fluorobenzamide; N-(3-(6-Amino-5-(2-(N-ethylacrylamido)ethoxy)pyrimidin-4-yl)-5-fluoro-2-methylphenyl)-4-cyclopropyl-2-fluorobenzamide; N-(3-(6-Amino-5-(2-(N-(2-fluoroethyl)acrylamido)ethoxy)pyrimidin-4-yl)-5-fluoro-2-methylphenyl)-4-cyclopropyl-2-fluorobenzamide; N-(3-(5-((1-Acrylamidocyclopropyl)methoxy)-6-aminopyrimidin-4-yl)-5-fluoro-2-methylphenyl)-4-cyclopropyl-2-fluorobenzamide; (S)-N-(3-(5-(2-Acrylamidopropoxy)-6-aminopyrimidin-4-yl)-5-fluoro-2-methylphenyl)-4-cyclopropyl-2-fluorobenzamide; (S)-N-(3-(6-Amino-5-(2-(but-2-ynamido)propoxy)pyrimidin-4-yl)-5-fluoro-2-methylphenyl)-4-cyclopropyl-2-fluorobenzamide; (S)-N-(3-(6-Amino-5-(2-(N-methylacrylamido)propoxy)pyrimidin-4-yl)-5-fluoro-2-methylphenyl)-4-cyclopropyl-2-fluorobenzamide; (S)-N-(3-(6-Amino-5-(2-(N-methylbut-2-ynamido)propoxy)pyrimidin-4-yl)-5-fluoro-2-methylphenyl)-4-cyclopropyl-2-fluorobenzamide; N-(3-(6-Amino-5-(3-(N-methylacrylamido)propoxy)pyrimidin-4-yl)-5-fluoro-2-methylphenyl)-4-cyclopropyl-2-fluorobenzamide; (S)-N-(3-(5-((1-Acryloylpyrrolidin-2-yl)methoxy)-6-aminopyrimidin-4-yl)-5-fluoro-2-methylphenyl)-4-cyclopropyl-2-fluorobenzamide; (S)-N-(3-(6-Amino-5-((1-(but-2-ynoyl)pyrrolidin-2-yl)methoxy)pyrimidin-4-yl)-5-fluoro-2-methylphenyl)-4-cyclopropyl-2-fluorobenzamide; (S)-2-(3-(5-((1-Acryloylpyrrolidin-2-yl)methoxy)-6-aminopyrimidin-4-yl)-5-fluoro-2-(hydroxymethyl)phenyl)-6-cyclopropyl-3,4-dihydroisoquinolin-1(2H)-one; N-(2-((4-Amino-6-(3-(6-cyclopropyl-1-oxo-3,4-dihydroisoquinolin-2(1H)-yl)-5-fluoro-2-(hydroxymethyl)phenyl)pyrimidin-5-yl)oxy)ethyl)-N-methylacrylamide; N-(3-(5-(((2S,4R)-1-Acryloyl-4-methoxypyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4R)-1-(but-2-ynoyl)-4-methoxypyrrolidin-2-yl)methoxy)pyrimidin-4-yl)-5-fluoro-2-methylphenyl)-4-cyclopropyl-2-fluorobenzamide; 2-(3-(5-(((2S,4R)-1-Acryloyl-4-methoxypyrrolidin-2-yl)methoxy)-6-aminopyrimidin-4-yl)-5-fluoro-2-(hydroxymethyl)phenyl)-6-cyclopropyl-3,4-dihydroisoquinolin-1(2H)-one; N-(3-(5-((2S,4S)-1-Acryloyl-4-methoxypyrrolidin-2-yl)methoxy)-6-aminopyrimidin-4-yl)-5-fluoro-2-methylphenyl)-4-cyclopropyl-2-fluorobenzamide; N-(3-(6-Amino-5-((2S,4S)-1-(but-2-ynoyl)-4-methoxypyrrolidin-2-yl)methoxy)pyrimidin-4-yl)-5-fluoro-2-methylphenyl)-4-cyclopropyl-2-fluorobenzamide; N-(3-(5-(((2S,4R)-1-Acryloyl-4-fluoropyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4R)-1-(but-2-ynoyl)-4-fluoropyrrolidin-2-yl)methoxy)pyrimidin-4-yl)-5-fluoro-2-methylphenyl)-4-cyclopropyl-2-fluorobenzamide; (S)-N-(3-(5-((1-Acryloylazetidin-2-yl)methoxy)-6-aminopyrimidin-4-yl)-5-fluoro-2-methylphenyl)-4-cyclopropyl-2-fluorobenzamide; (S)-N-(3-(6-Amino-5-((1-propioloylazetidin-2-yl)methoxy)pyrimidin-4-yl)-5-fluoro-2-methylphenyl)-4-cyclopropyl-2-fluorobenzamide; (S)-2-(3-(5-((1-Acryloylazetidin-2-yl)methoxy)-6-aminopyrimidin-4-yl)-5-fluoro-2-(hydroxymethyl)phenyl)-6-cyclopropyl-3,4-dihydroisoquinolin-1(2H)-one; (R)-N-(3-(5-((1-Acryloylazetidin-2-yl)methoxy)-6-aminopyrimidin-4-yl)-5-fluoro-2-methylphenyl)-4-cyclopropyl-2-fluorobenzamide; (R)-N-(3-(5-((1-Acryloylpiperidin-3-yl)methoxy)-6-aminopyrimidin-4-yl)-5-fluoro-2-methylphenyl)-4-cyclopropyl-2-fluorobenzamide; N-(3-(5-(((2R,3S)-1-Acryloyl-3-methoxypyrrolidin-2-yl)methoxy)-6-aminopyrimidin-4-yl)-5-fluoro-2-methylphenyl)-4-cyclopropyl-2-fluorobenzamide; N-(3-(5-(((2S,4R)-1-Acryloyl-4-cyanopyrrolidin-2-yl)methoxy)-6-aminopyrimidin-4-yl)-5-fluoro-2-methylphenyl)-4-cyclopropyl-2-fluorobenzamide; or N-(3-(5-(((2S,4S)-1-Acryloyl-4-cyanopyrrolidin-2-yl)methoxy)-6-aminopyrimidin-4-yl)-5-fluoro-2-methylphenyl)-4-cyclopropyl-2-fluorobenzamide.

Unless otherwise provided, the chemical terms used above in describing the BTK inhibitor of Formula I are used according to their meanings as set out in International Application WO/2015/079417, which is herein incorporated by reference in its entirety In one embodiment, the kinase inhibitor is an mTOR inhibitor selected from temsirolimus; ridaforolimus (1R,2R,4S)-4-[(2R)-2 [(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0$^{4,9}$]hexatriaconta-16,24,26,28-tetraen-12-yl]propyl]-2-methoxycyclohexyl dimethylphosphinate, also known as AP23573 and MK8669; everolimus (RAD001); rapamycin (AY22989); simapimod; (5-{2,4-bis[(3S)-3-methylmorpholin-4-yl]pyrido[2,3-d]pyrimidin-7-yl}-2-methoxyphenyl)methanol (AZD8055); 2-mmino-8-[trans-4-(2-hydroxyethoxy)cyclohexyl]-6-(6-methoxy-3-pyridinyl)-4-methyl-pyrido[2,3-d]pyrimidin-7(8H)-one (PF04691502); and N$^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine, inner salt (SF1126); and XL765.

In one embodiment, the kinase inhibitor is an mTOR inhibitor, e.g., rapamycin, and the rapamycin is administered at a dose of about 3 mg, 4 mg, 5 mg, 6 mg, 7 mg, 8 mg, 9 mg, 10 mg (e.g., 6 mg) daily for a period of time, e.g., daily for 21 day cycle cycle, or daily for 28 day cycle. In one embodiment, 1, 2, 3, 4, 5, 6, 7, 8, 9, 10, 11, 12 or more cycles of rapamycin are administered. In one embodiment, the kinase inhibitor is an mTOR inhibitor, e.g., everolimus and the everolimus is administered at a dose of about 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg (e.g., 10 mg) daily for a period of time, e.g., daily for 28 day cycle. In one embodiment, 1, 2, 3, 4, 5, 6, 7, 8, 9, 10, 11, 12 or more cycles of everolimus are administered.

In one embodiment, the kinase inhibitor is an MNK inhibitor selected from CGP052088; 4-amino-3-(p-fluorophenylamino)-pyrazolo [3,4-d] pyrimidine (CGP57380); cercosporamide; ETC-1780445-2; and 4-amino-5-(4-fluoroanilino)-pyrazolo [3,4-d] pyrimidine.

In embodiments, a CAR-expressing cell described herein is administered to a subject in combination with a phosphoinositide 3-kinase (PI3K) inhibitor (e.g., a PI3K inhibitor described herein, e.g., idelalisib or duvelisib) and/or rituximab. In embodiments, a CAR-expressing cell described herein is administered to a subject in combination with idelalisib and rituximab. In embodiments, a CAR-expressing cell described herein is administered to a subject in combination with duvelisib and rituximab. Idelalisib (also called GS-1101 or CAL-101; Gilead) is a small molecule that blocks the delta isoform of PI3K. The structure of idelalisib (5-Fluoro-3-phenyl-2-[(1S)-1-(7H-purin-6-ylamino)propyl]-4(3H)-quinazolinone) is shown below.

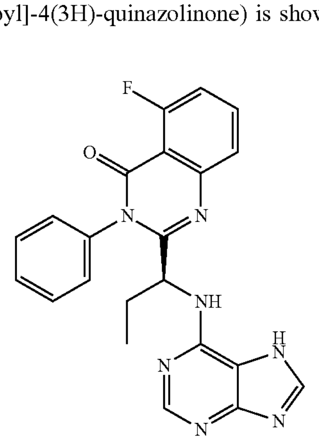

Duvelisib (also called IPI-145; Infinity Pharmaceuticals and Abbvie) is a small molecule that blocks PI3K-δ,γ. The structure of duvelisib (8-Chloro-2-phenyl-3-[(1S)-1-(9H-purin-6-ylamino)ethyl]-1(2H)-isoquinolinone) is shown below.

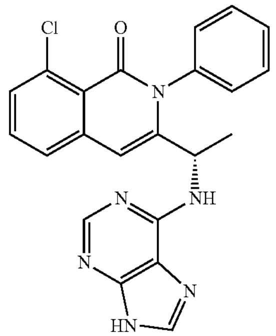 [SMILES: C[C@H](Nc1ncnc2[nH]cnc12)c1cc2cccc(Cl)c2c(=O)n1-c1ccccc1]

In embodiments, the subject has CLL. In embodiments, the subject has relapsed CLL, e.g., the subject has previously been administered a cancer therapy (e.g., previously been administered an anti-CD20 antibody or previously been administered ibrutinib). For example, the subject has a deletion in the short arm of chromosome 17 (del(17p), e.g., in a leukemic cell). In other examples, the subject does not have a del(17p). In embodiments, the subject comprises a leukemic cell comprising a mutation in the immunoglobulin heavy-chain variable-region (Ig$V_H$) gene. In other embodiments, the subject does not comprise a leukemic cell comprising a mutation in the immunoglobulin heavy-chain variable-region (Ig$V_H$) gene. In embodiments, the subject has a deletion in the long arm of chromosome 11 (del(11q)). In other embodiments, the subject does not have a del(11q). In embodiments, idelalisib is administered at a dosage of about 100-400 mg (e.g., 100-125, 125-150, 150-175, 175-200, 200-225, 225-250, 250-275, 275-300, 325-350, 350-375, or 375-400 mg), e.g., BID. In embodiments, duvelisib is administered at a dosage of about 15-100 mg (e.g., about 15-25, 25-50, 50-75, or 75-100 mg), e.g., twice a day. In embodiments, rituximab is administered at a dosage of about 350-550 mg/m$^2$ (e.g., 350-375, 375-400, 400-425, 425-450, 450-475, or 475-500 mg/m$^2$), e.g., intravenously.

In one embodiment, the kinase inhibitor is a dual phosphatidylinositol 3-kinase (PI3K) and mTOR inhibitor selected from 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF-04691502); N-[4-[[4-(Dimethylamino)-1-piperidinyl]carbonyl]phenyl]-N-[4-(4,6-di-4-morpholinyl-1,3,5-triazin-2-yl)phenyl]urea (PF-05212384, PKI-587); 2-Methyl-2-{4-[3-methyl-2-oxo-8-(quinolin-3-yl)-2,3-dihydro-1H-imidazo[4,5-c]quinolin-1-yl]phenyl}propanenitrile (BEZ-235); apitolisib (GDC-0980, RG7422); 2,4-Difluoro-N-{2-(methyloxy)-5-[4-(4-pyridazinyl)-6-quinolinyl]-3-pyridinyl}benzenesulfonamide (GSK2126458); 8-(6-methoxypyridin-3-yl)-3-methyl-1-(4-(piperazin-1-yl)-3-(trifluoromethyl)phenyl)-1H-imidazo[4,5-c]quinolin-2(3H)-one Maleic acid (NVP-BGT226); 3-[4-(4-Morpholinylpyrido[3',2':4,5]furo[3,2-d]pyrimidin-2-yl]phenol (PI-103); 5-(9-isopropyl-8-methyl-2-morpholino-9H-purin-6-yl)pyrimidin-2-amine (VS-5584, SB2343); and N-[2-[(3,5-Dimethoxyphenyl)amino]quinoxalin-3-yl]-4-[(4-methyl-3-methoxyphenyl)carbonyl]aminophenylsulfonamide (XL765).

In embodiments, a CAR-expressing cell described herein is administered to a subject in combination with an anaplastic lymphoma kinase (ALK) inhibitor. Exemplary ALK kinases include but are not limited to crizotinib (Pfizer), ceritinib (Novartis), alectinib (Chugai), brigatinib (also called AP26113; Ariad), entrectinib (Ignyta), PF-06463922

(Pfizer), TSR-011 (Tesaro) (see, e.g., Clinical Trial Identifier No. NCT02048488), CEP-37440 (Teva), and X-396 (Xcovery). In some embodiments, the subject has a solid cancer, e.g., a solid cancer described herein, e.g., lung cancer.

The chemical name of crizotinib is 3-[(1R)-1-(2,6-dichloro-3-fluorophenyl)ethoxy]-5-(1-piperidin-4-ylpyrazol-4-yl)pyridin-2-amine. The chemical name of ceritinib is 5-Chloro-$N^2$-[2-isopropoxy-5-methyl-4-(4-piperidinyl)phenyl]-N4-[2-(isopropylsulfonyl)phenyl]-2,4-pyrimidinediamine. The chemical name of alectinib is 9-ethyl-6,6-dimethyl-8-(4-morpholinopiperidin-1-yl)-11-oxo-6,11-dihydro-5H-benzo[b]carbazole-3-carbonitrile. The chemical name of brigatinib is 5-Chloro-$N^2$-{4-[4-(dimethylamino)-1-piperidinyl]-2-methoxyphenyl}-$N^4$-[2-(dimethylphosphoryl)phenyl]-2,4-pyrimidinediamine. The chemical name of entrectinib is N-(5-(3,5-difluorobenzyl)-1H-indazol-3-yl)-4-(4-methylpiperazin-1-yl)-2-((tetrahydro-2H-pyran-4-yl)amino)benzamide. The chemical name of PF-06463922 is (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile. The chemical structure of CEP-37440 is (S)-2-((5-chloro-2-((6-(4-(2-hydroxyethyl)piperazin-1-yl)-1-methoxy-6,7,8,9-tetrahydro-5H-benzo[7]annulen-2-yl)amino)pyrimidin-4-yl)amino)-N-methylbenzamide. The chemical name of X-396 is (R)-6-amino-5-(1-(2,6-dichloro-3-fluorophenyl)ethoxy)-N-(4-(4-methylpiperazine-1-carbonyl)phenyl)pyridazine-3-carboxamide.

Drugs that inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993) can also be used. In a further aspect, the cell compositions of the present invention may be administered to a patient in conjunction with (e.g., before, simultaneously or following) bone marrow transplantation, T cell ablative therapy using chemotherapy agents such as, fludarabine, external-beam radiation therapy (XRT), cyclophosphamide, and/or antibodies such as OKT3 or CAMPATH. In one aspect, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

In embodiments, a CAR-expressing cell described herein is administered to a subject in combination with an indoleamine 2,3-dioxygenase (IDO) inhibitor. IDO is an enzyme that catalyzes the degradation of the amino acid, L-tryptophan, to kynurenine. Many cancers overexpress IDO, e.g., prostatic, colorectal, pancreatic, cervical, gastric, ovarian, head, and lung cancer. pDCs, macrophages, and dendritic cells (DCs) can express IDO. Without being bound by theory, it is thought that a decrease in L-tryptophan (e.g., catalyzed by IDO) results in an immunosuppressive milieu by inducing T-cell anergy and apoptosis. Thus, without being bound by theory, it is thought that an IDO inhibitor can enhance the efficacy of a CAR-expressing cell described herein, e.g., by decreasing the suppression or death of a CAR-expressing immune cell. In embodiments, the subject has a solid tumor, e.g., a solid tumor described herein, e.g., prostatic, colorectal, pancreatic, cervical, gastric, ovarian, head, or lung cancer. Exemplary inhibitors of IDO include but are not limited to 1-methyl-tryptophan, indoximod (NewLink Genetics) (see, e.g., Clinical Trial Identifier Nos. NCT01191216; NCT01792050), and INCB024360 (Incyte Corp.) (see, e.g., Clinical Trial Identifier Nos. NCT01604889; NCT01685255)

In embodiments, a CAR-expressing cell described herein is administered to a subject in combination with a modulator of myeloid-derived suppressor cells (MDSCs). MDSCs accumulate in the periphery and at the tumor site of many solid tumors. These cells suppress T cell responses, thereby hindering the efficacy of CAR-expressing cell therapy. Without being bound by theory, it is thought that administration of a MDSC modulator enhances the efficacy of a CAR-expressing cell described herein. In an embodiment, the subject has a solid tumor, e.g., a solid tumor described herein, e.g., glioblastoma. Exemplary modulators of MDSCs include but are not limited to MCS110 and BLZ945. MCS110 is a monoclonal antibody (mAb) against macrophage colony-stimulating factor (M-CSF). See, e.g., Clinical Trial Identifier No. NCT00757757. BLZ945 is a small molecule inhibitor of colony stimulating factor 1 receptor (CSF1R). See, e.g., Pyonteck et al. Nat. Med. 19(2013): 1264-72. The structure of BLZ945 is shown below.

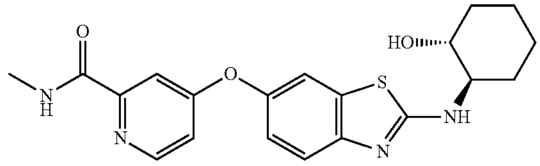 [SMILES: CNC(=O)c1cc(Oc2ccc3nc(N[C@@H]4CCCC[C@H]4O)sc3c2)ccn1]

In embodiments, a CAR-expressing cell described herein is administered to a subject in combination with a CD19 CART cell (e.g., CTL019, e.g., as described in WO2012/079000, incorporated herein by reference). In embodiments, the subject has acute myeloid leukemia (AML), e.g., a CD19 positive AML or a CD19 negative AML. In embodiments, the subject has a CD19+ lymphoma, e.g., a CD19+ Non-Hodgkin's Lymphoma (NHL), a CD19+FL, or a CD19+ DLBCL. In embodiments, the subject has a relapsed or refractory CD19+ lymphoma. In embodiments, a lymphodepleting chemotherapy is administered to the subject prior to, concurrently with, or after administration (e.g., infusion) of CD19 CART cells. In an example, the lymphodepleting chemotherapy is administered to the subject prior to administration of CD19 CART cells. For example, the lymphodepleting chemotherapy ends 1-4 days (e.g., 1, 2, 3, or 4 days) prior to CD19 CART cell infusion. In embodiments, multiple doses of CD19 CART cells are administered, e.g., as described herein. For example, a single dose comprises about $5\times10^8$ CD19 CART cells. In embodiments, a lymphodepleting chemotherapy is administered to the subject prior to, concurrently with, or after administration (e.g., infusion) of a CAR-expressing cell described herein, e.g., a non-CD19 CAR-expressing cell. In embodiments, a CD19 CART is administered to the subject prior to, concurrently with, or after administration (e.g., infusion) of a non-CD19 CAR-expressing cell, e.g., a non-CD19 CAR-expressing cell described herein.

In some embodiments, a CAR-expressing cell described herein is administered to a subject in combination with a CD19 CAR-expressing cell, e.g., CTL019, e.g., as described in WO2012/079000, incorporated herein by reference, for treatment of a disease associated with the expression of GFRα4, e.g., a cancer described herein. Without being bound by theory, it is believed that administering a CD19 CAR-expressing cell in combination with a CAR-expressing cell improves the efficacy of a CAR-expressing cell described herein by targeting early lineage cancer cells, e.g., cancer stem cells, modulating the immune response, depleting regulatory B cells, and/or improving the tumor microenvironment. For example, a CD19 CAR-expressing cell targets cancer cells that express early lineage markers, e.g., cancer stem cells and CD19-expressing cells, while the CAR-expressing cell described herein targets cancer cells that express later lineage markers, e.g., GFRα4. This preconditioning approach can improve the efficacy of the CAR-expressing cell described herein. In such embodiments, the CD19 CAR-expressing cell is administered prior to, concurrently with, or after administration (e.g., infusion) of a CAR-expressing cell described herein.

In embodiments, a CAR-expressing cell described herein also expresses a CAR targeting CD19, e.g., a CD19 CAR. In an embodiment, the cell expressing a CAR described herein and a CD19 CAR is administered to a subject for treatment of a cancer described herein. In an embodiment, the configurations of one or both of the CAR molecules comprise a primary intracellular signaling domain and a costimulatory signaling domain. In another embodiment, the configurations of one or both of the CAR molecules comprise a primary intracellular signaling domain and two or more, e.g., 2, 3, 4, or 5 or more, costimulatory signaling domains. In such embodiments, the CAR molecule described herein and the CD19 CAR may have the same or a different primary intracellular signaling domain, the same or different costimulatory signaling domains, or the same number or a different number of costimulatory signaling domains. Alternatively, the CAR described herein and the CD19 CAR are configured as a split CAR, in which one of the CAR molecules comprises an antigen binding domain and a costimulatory domain (e.g., 4-1BB), while the other CAR molecule comprises an antigen binding domain and a primary intracellular signaling domain (e.g., CD3 zeta).

In some embodiments, a CAR-expressing cell described herein is administered to a subject in combination with a interleukin-15 (IL-15) polypeptide, a interleukin-15 receptor alpha (IL-15Ra) polypeptide, or a combination of both a IL-15 polypeptide and a IL-15Ra polypeptide e.g., hetIL-15 (Admune Therapeutics, LLC). hetIL-15 is a heterodimeric non-covalent complex of IL-15 and IL-15Ra. hetIL-15 is described in, e.g., U.S. Pat. No. 8,124,084, U.S. 2012/0177598, U.S. 2009/0082299, U.S. 2012/0141413, and U.S. 2011/0081311, incorporated herein by reference. In embodiments, het-IL-15 is administered subcutaneously. In embodiments, the subject has a cancer, e.g., solid cancer, e.g., melanoma or colon cancer. In embodiments, the subject has a metastatic cancer.

In embodiments, a subject having a disease described herein, e.g., a hematological disorder, e.g., AML or MDS, is administered a CAR-expressing cell described herein in combination with an agent, e.g., cytotoxic or chemotherapy agent, a biologic therapy (e.g., antibody, e.g., monoclonal antibody, or cellular therapy), or an inhibitor (e.g., kinase inhibitor). In embodiments, the subject is administered a CAR-expressing cell described herein in combination with a cytotoxic agent, e.g., CPX-351 (Celator Pharmaceuticals), cytarabine, daunorubicin, vosaroxin (Sunesis Pharmaceuticals), sapacitabine (Cyclacel Pharmaceuticals), idarubicin, or mitoxantrone. CPX-351 is a liposomal formulation comprising cytarabine and daunorubicin at a 5:1 molar ratio. In embodiments, the subject is administered a CAR-expressing cell described herein in combination with a hypomethylating agent, e.g., a DNA methyltransferase inhibitor, e.g., azacitidine or decitabine. In embodiments, the subject is administered a CAR-expressing cell described herein in combination with a biologic therapy, e.g., an antibody or cellular therapy, e.g., 225Ac-lintuzumab (Actimab-A; Actinium Pharmaceuticals), IPH2102 (Innate Pharma/Bristol Myers Squibb), SGN-CD33A (Seattle Genetics), or gemtuzumab ozogamicin (Mylotarg; Pfizer). SGN-CD33A is an antibody-drug conjugate (ADC) comprising a pyrrolobenzodiazepine dimer that is attached to an anti-CD33 antibody. Actimab-A is an anti-CD33 antibody (lintuzumab) labeled with actinium. IPH2102 is a monoclonal antibody that targets killer immunoglobulin-like receptors (KIRs). In embodiments, the subject is administered a CAR-expressing cell described herein in combination a FLT3 inhibitor, e.g., sorafenib (Bayer), midostaurin (Novartis), quizartinib (Daiichi Sankyo), crenolanib (Arog Pharmaceuticals), PLX3397 (Daiichi Sankyo), AKN-028 (Akinion Pharmaceuticals), or ASP2215 (Astellas). In embodiments, the subject is administered a CAR-expressing cell described herein in combination with an isocitrate dehydrogenase (IDH) inhibitor, e.g., AG-221 (Celgene/Agios) or AG-120 (Agios/Celgene). In embodiments, the subject is administered a CAR-expressing cell described herein in combination with a cell cycle regulator, e.g., inhibitor of polo-like kinase 1 (Plk1), e.g., volasertib (Boehringer Ingelheim); or an inhibitor of cyclin-dependent kinase 9 (Cdk9), e.g., alvocidib (Tolero Pharmaceuticals/Sanofi Aventis). In embodiments, the subject is administered a CAR-expressing cell described herein in combination with a B cell receptor signaling network inhibitor, e.g., an inihibitor of B-cell lymphoma 2 (Bcl-2), e.g., venetoclax (Abbvie/Roche); or an inhibitor of Bruton's tyrosine kinase (Btk), e.g., ibrutinib (Pharmacyclics/Johnson & Johnson Janssen Pharmaceutical). In embodiments, the subject is administered a CAR-expressing cell described herein in combination with an inhibitor of M1 aminopeptidase, e.g., tosedostat (CTI BioPharma/Vernalis); an inhibitor of histone deacetylase (HDAC), e.g., pracinostat (MEI Pharma); a multi-kinase inhibitor, e.g., rigosertib (Onconova Therapeutics/Baxter/SymBio); or a peptidic CXCR4 inverse agonist, e.g., BL-8040 (BioLineRx). In embodiments, the subject is administered a GFRα4 CAR-expressing cell in combination with a CAR-expressing cell that specifically binds an antigen other than GFRα4.

In another embodiment, the subjects receive an infusion of the GFRα4 expressing cell compositions of the present invention prior to transplantation, e.g., allogeneic stem cell transplant, of cells. In a preferred embodiment, GFRα4 expressing cells transiently express GFRα4 CAR, e.g., by electroporation of an mRNA GFRα4 CAR, whereby the expression of the GFRα4 is terminated prior to infusion of donor stem cells to avoid engraftment failure.

Some patients may experience allergic reactions to the compounds of the present invention and/or other anti-cancer agent(s) during or after administration; therefore, anti-allergic agents are often administered to minimize the risk of an allergic reaction. Suitable anti-allergic agents include corticosteroids, such as dexamethasone (e.g., Decadron®), beclomethasone (e.g., Beclovent®), hydrocortisone (also known as cortisone, hydrocortisone sodium succinate, hydrocortisone sodium phosphate, and sold under the tradenames Ala-Cort®, hydrocortisone phosphate, Solu-Cortef®, Hydrocort Acetate® and Lanacort®), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-methylprednisolone, methylprednisolone acetate, methylprednisolone sodium succinate, sold under the tradenames Duralone®, Medralone®, Medrol®, M-Prednisol® and Solu-Medrol®); antihistamines, such as diphenhydramine (e.g., Benadryl®), hydroxyzine, and cyproheptadine; and bronchodilators, such as the beta-adrenergic receptor agonists, albuterol (e.g., Proventil®), and terbutaline (Brethine®).

Some patients may experience nausea during and after administration of the compound of the present invention and/or other anti-cancer agent(s); therefore, anti-emetics are used in preventing nausea (upper stomach) and vomiting. Suitable anti-emetics include aprepitant (Emend®), ondansetron (Zofran®), granisetron HCl (Kytril®), lorazepam (Ativan®. dexamethasone (Decadron®), prochlorperazine (Compazine®), casopitant (Rezonic® and Zunrisa®), and combinations thereof.

Medication to alleviate the pain experienced during the treatment period is often prescribed to make the patient more comfortable. Common over-the-counter analgesics, such Tylenol®, are often used. However, opioid analgesic drugs such as hydrocodone/paracetamol or hydrocodone/acetaminophen (e.g., Vicodin®), morphine (e.g., Astramorph® or Avinza®), oxycodone (e.g., OxyContin® or Percocet®), oxymorphone hydrochloride (Opana®), and fentanyl (e.g., Duragesic®) are also useful for moderate or severe pain.

In an effort to protect normal cells from treatment toxicity and to limit organ toxicities, cytoprotective agents (such as neuroprotectants, free-radical scavengers, cardioprotectors, anthracycline extravasation neutralizers, nutrients and the like) may be used as an adjunct therapy. Suitable cytoprotective agents include Amifostine (Ethyol®), glutamine, dimesna (Tavocept®), mesna (Mesnex®), dexrazoxane (Zinecard® or Totect®), xaliproden (Xaprila®), and leucovorin (also known as calcium leucovorin, citrovorum factor and folinic acid).

The structure of the active compounds identified by code numbers, generic or trade names may be taken from the actual edition of the standard compendium "The Merck Index" or from databases, e.g. Patents International (e.g. IMS World Publications).

The above-mentioned compounds, which can be used in combination with a compound of the present invention, can be prepared and administered as described in the art, such as in the documents cited above.

In one embodiment, the present invention provides pharmaceutical compositions comprising at least one compound of the present invention (e.g., a compound of the present invention) or a pharmaceutically acceptable salt thereof together with a pharmaceutically acceptable carrier suitable for administration to a human or animal subject, either alone or together with other anti-cancer agents.

In one embodiment, the present invention provides methods of treating human or animal subjects suffering from a cellular proliferative disease, such as cancer. The present invention provides methods of treating a human or animal subject in need of such treatment, comprising administering to the subject a therapeutically effective amount of a compound of the present invention (e.g., a compound of the present invention) or a pharmaceutically acceptable salt thereof, either alone or in combination with other anti-cancer agents.

In particular, compositions will either be formulated together as a combination therapeutic or administered separately.

In combination therapy, the compound of the present invention and other anti-cancer agent(s) may be administered either simultaneously, concurrently or sequentially with no specific time limits, wherein such administration provides therapeutically effective levels of the two compounds in the body of the patient.

In a preferred embodiment, the compound of the present invention and the other anti-cancer agent(s) is generally administered sequentially in any order by infusion or orally. The dosing regimen may vary depending upon the stage of the disease, physical fitness of the patient, safety profiles of the individual drugs, and tolerance of the individual drugs, as well as other criteria well-known to the attending physician and medical practitioner(s) administering the combination. The compound of the present invention and other anti-cancer agent(s) may be administered within minutes of each other, hours, days, or even weeks apart depending upon the particular cycle being used for treatment. In addition, the cycle could include administration of one drug more often than the other during the treatment cycle and at different doses per administration of the drug.

In another aspect of the present invention, kits that include one or more compound of the present invention and a combination partner as disclosed herein are provided. Representative kits include (a) a compound of the present invention or a pharmaceutically acceptable salt thereof, (b) at least one combination partner, e.g., as indicated above, whereby such kit may comprise a package insert or other labeling including directions for administration.

A compound of the present invention may also be used to advantage in combination with known therapeutic processes, for example, the administration of hormones or especially radiation. A compound of the present invention may in particular be used as a radiosensitizer, especially for the treatment of tumors which exhibit poor sensitivity to radiotherapy.

In one embodiment, the subject can be administered an agent which reduces or ameliorates a side effect associated with the administration of a CAR-expressing cell. Side effects associated with the administration of a CAR-expressing cell include, but are not limited to CRS, and hemophagocytic lymphohistiocytosis (HLH), also termed Macrophage Activation Syndrome (MAS). Symptoms of CRS include high fevers, nausea, transient hypotension, hypoxia, and the like. CRS may include clinical constitutional signs and symptoms such as fever, fatigue, anorexia, myalgias, arthalgias, nausea, vomiting, and headache. CRS may include clinical skin signs and symptoms such as rash. CRS may include clinical gastrointestinal signs and symptoms such as nausea, vomiting and diarrhea. CRS may include clinical respiratory signs and symptoms such as tachypnea and hypoxemia. CRS may include clinical cardiovascular signs and symptoms such as tachycardia, widened pulse pressure, hypotension, increased cardac output (early) and potentially diminished cardiac output (late). CRS may include clinical coagulation signs and symptoms such as elevated d-dimer, hypofibrinogenemia with or without bleeding. CRS may include clinical renal signs and symptoms such as azotemia. CRS may include clinical hepatic signs and symptoms such as transaminitis and hyperbilirubinemia. CRS may include clinical neurologic signs and symptoms such as headache, mental status changes, confusion, delirium, word finding difficulty or frank aphasia, hallucinations, tremor, dymetria, altered gait, and seizures. Accordingly, the methods described herein can comprise administering a CAR-expressing cell described herein to a subject and further administering one or more agents to manage elevated levels of a soluble factor resulting from treatment with a CAR-expressing cell. In one embodiment, the soluble factor elevated in the subject is one or more of IFN-γ, TNFα, IL-2 and IL-6. In an embodiment, the factor elevated in the subject is one or more of IL-1, GM-CSF, IL-10, IL-8, IL-5 and fraktalkine. Therefore, an agent administered to treat this side effect can be an agent that neutralizes one or more of these soluble factors. In one embodiment, the agent that neutralizes one or more of these soluble forms is an antibody or antibody thereof. Examples of such agents include, but are not limited to a steroid (e.g., corticosteroid), an inhibitor of TNFα, and an inhibitor of IL-6. An example of a TNFα inhibitor is an anti-TNFα antibody molecule such as, infliximab, adalimumab, certolizumab pegol, and golimumab. Another example of a TNFα inhibitor is a fusion protein such as entanercept. Small molecule inhibitor of TNFα include, but are not limited to, xanthine derivatives (e.g. pentoxifylline) and bupropion. An example of an IL-6 inhibitor is an anti-IL-6 antibody molecule such as tocilizumab (toc), sarilumab, elsilimomab, CNTO 328, ALD518/BMS-945429, CNTO 136, CPSI-2364, CDP6038, VX30, ARGX-109, FE301, and FM101. In one embodiment, the anti-IL-6 antibody molecule is tocilizumab. An example of an IL-1R based inhibitor is anakinra.

In one embodiment, the subject can be administered an agent which enhances the activity of a CAR-expressing cell. For example, in one embodiment, the agent can be an agent which inhibits an inhibitory molecule, e.g., the agent is a checkpoint inhibitor. Inhibitory molecules, e.g., Programmed Death 1 (PD1), can, in some embodiments, decrease the ability of a CAR-expressing cell to mount an immune effector response. Examples of inhibitory molecules include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. Inhibition of an inhibitory molecule, e.g., by inhibition at the DNA, RNA or protein level, can optimize a CAR-expressing cell performance. In embodiments, an inhibitory nucleic acid, e.g., an inhibitory nucleic acid, e.g., a dsRNA, e.g., an siRNA or shRNA, can be used to inhibit expression of an inhibitory molecule in the CAR-expressing cell. In an embodiment the inhibitor is an shRNA. In an embodiment, the inhibitory molecule is inhibited within a CAR-expressing cell. In these embodiments, a dsRNA molecule that inhibits expression of the inhibitory molecule is linked to the nucleic acid that encodes a component, e.g., all of the components, of the CAR.

In an embodiment, a nucleic acid molecule that encodes a dsRNA molecule that inhibits expression of the molecule that modulates or regulates, e.g., inhibits, T-cell function is operably linked to a promoter, e.g., a H1- or a U6-derived promoter such that the dsRNA molecule that inhibits expression of the molecule that modulates or regulates, e.g., inhibits, T-cell function is expressed, e.g., is expressed within a CAR-expressing cell. See e.g., Tiscornia G., "Development of Lentiviral Vectors Expressing siRNA," Chapter 3, in *Gene Transfer: Delivery and Expression of DNA and RNA* (eds. Friedmann and Rossi). Cold Spring Harbor Laboratory Press, Cold Spring Harbor, NY, USA, 2007; Brummelkamp T R, et al. (2002) *Science* 296: 550-553; Miyagishi M, et al. (2002) *Nat. Biotechnol.* 19: 497-500. In an embodiment the nucleic acid molecule that encodes a dsRNA molecule that inhibits expression of the molecule that modulates or regulates, e.g., inhibits, T-cell function is present on the same vector, e.g., a lentiviral vector, that comprises a nucleic acid molecule that encodes a component, e.g., all of the components, of the CAR. In such an embodiment, the nucleic acid molecule that encodes a dsRNA molecule that inhibits expression of the molecule that modulates or regulates, e.g., inhibits, T-cell function is located on the vector, e.g., the lentiviral vector, 5'- or 3'- to the nucleic acid that encodes a component, e.g., all of the components, of the CAR. The nucleic acid molecule that encodes a dsRNA molecule that inhibits expression of the molecule that modulates or regulates, e.g., inhibits, T-cell function can be transcribed in the same or different direction as the nucleic acid that encodes a component, e.g., all of the components, of the CAR. In an embodiment the nucleic acid molecule that encodes a dsRNA molecule that inhibits expression of the molecule that modulates or regulates, e.g., inhibits, T-cell function is present on a vector other than the vector that comprises a nucleic acid molecule that encodes a component, e.g., all of the components, of the CAR. In an embodiment, the nucleic acid molecule that encodes a dsRNA molecule that inhibits expression of the molecule that modulates or regulates, e.g., inhibits, T-cell function it transiently expressed within a CAR-expressing cell. In an embodiment, the nucleic acid molecule that encodes a dsRNA molecule that inhibits expression of the molecule that modulates or regulates, e.g., inhibits, T-cell function is stably integrated into the genome of a CAR-expressing cell. FIGS. 29A-29E depicts examples of vectors for expressing a component, e.g., all of the components, of the CAR with a dsRNA molecule that inhibits expression of the molecule that modulates or regulates, e.g., inhibits, T-cell function.

Examples of dsRNA molecules useful for inhibiting expression of a molecule that modulates or regulates, e.g., inhibits, T-cell function, wherein the molecule that modulates or regulates, e.g., inhibits, T-cell function is PD-1 are provided below.

Provided in Table 4 below are the names of PDCD1 (PD1) RNAi agents (derived from their position in the mouse PDCD1 gene sequence NM_008798.2), along with the SEQ ID NOs: 116-163 representing the DNA sequence. Both sense (S) and antisense (AS) sequences are presented as 19mer and 21mer sequences are in this table. Also note that the position (PoS, e.g., 176) is derived from the position number in the mouse PDCD1 gene sequence NM_008798.2. SEQ ID NOs are indicated in groups of 12 that correspond with "sense 19" SEQ ID NOs: 116-127; "sense 21" SEQ ID NOs: 128-139; "asense 21" SEQ ID NOs: 140-151; "asense 19" SEQ ID NOs: 152-163.

Mouse PDCD1 (PD1) shRNA sequences

| Position on NM_008798.2 | Target region | Sense19 | Sense21 | Asense21 | Asense19 |
|---|---|---|---|---|---|
| 176 | CDS | GGAGGTCCCTCACCTTCTA (SEQ ID NO: 116) | CTGGAGGTCCCTCACCTTCTA (SEQ ID NO: 128) | TAGAAGGTGAGGGACCTCCAG (SEQ ID NO: 140) | TAGAAGGTGAGGGACCTCC (SEQ ID NO: 152) |

-continued

| Mouse PDCD1 (PD1) shRNA sequences | | | | | |
|---|---|---|---|---|---|
| Position on NM_008798.2 | Target region | Sense19 | Sense21 | Asense21 | Asense19 |
| 260 | CDS | CGGAGGATCTTATGCTGAA (SEQ ID NO: 117) | GTCGGAGGATCTTATGCTGAA (SEQ ID NO: 129) | TTCAGCATAAGATCCTCCGAC (SEQ ID NO: 141) | TTCAGCATAAGATCCTCCG (SEQ ID NO: 153) |
| 359 | CDS | CCCGCTTCCAGATCATACA (SEQ ID NO: 118) | TGCCCGCTTCCAGATCATACA (SEQ ID NO: 130) | TGTATGATCTGGAAGCGGGCA (SEQ ID NO: 142) | TGTATGATCTGGAAGCGGG (SEQ ID NO: 154) |
| 528 | CDS | GGAGACCTCAACAAGATAT (SEQ ID NO: 119) | CTGGAGACCTCAACAAGATAT (SEQ ID NO: 131) | ATATCTTGTTGAGGTCTCCAG (SEQ ID NO: 143) | ATATCTTGTTGAGGTCTCC (SEQ ID NO: 155) |
| 581 | CDS | AAGGCATGGTCATTGGTAT (SEQ ID NO: 120) | TCAAGGCATGGTCATTGGTAT (SEQ ID NO: 132) | ATACCAATGACCATGCCTTGA (SEQ ID NO: 144) | ATACCAATGACCATGCCTT (SEQ ID NO: 156) |
| 584 | CDS | GCATGGTCATTGGTATCAT (SEQ ID NO: 121) | AGGCATGGTCATTGGTATCAT (SEQ ID NO: 133) | ATGATACCAATGACCATGCCT (SEQ ID NO: 145) | ATGATACCAATGACCATGC (SEQ ID NO: 157) |
| 588 | CDS | GGTCATTGGTATCATGAGT (SEQ ID NO: 122) | ATGGTCATTGGTATCATGAGT (SEQ ID NO: 134) | ATGGTCATTGGTATCATGAGT (SEQ ID NO: 146) | ATGGTCATTGGTATCATGA (SEQ ID NO: 158) |
| 609 | CDS | CCTAGTGGGTATCCCTGTA (SEQ ID NO: 123) | GCCCTAGTGGGTATCCCTGTA (SEQ ID NO: 135) | GCCCTAGTGGGTATCCCTGTA (SEQ ID NO: 147) | GCCCTAGTGGGTATCCTG (SEQ ID NO: 159) |
| 919 | CDS | GAGGATGGACATTGTTCTT (SEQ ID NO: 124) | ATGAGGATGGACATTGTTCTT (SEQ ID NO: 136) | ATGAGGATGGACATTGTTCTT (SEQ ID NO: 148) | ATGAGGATGGACATTGTTC (SEQ ID NO: 160) |
| 1021 | 3'UTR | GCATGCAGGCTACAGTTCA (SEQ ID NO: 125) | GAGCATGCAGGCTACAGTTCA (SEQ ID NO: 137) | GAGCATGCAGGCTACAGTTCA (SEQ ID NO: 149) | GAGCATGCAGGCTACAGTT (SEQ ID NO: 161) |
| 1097 | 3'UTR | CCAGCACATGCACTGTTGA (SEQ ID NO: 126) | TTCCAGCACATGCACTGTTGA (SEQ ID NO: 138) | TTCCAGCACATGCACTGTTGA (SEQ ID NO: 150) | TTCCAGCACATGCACTGTT (SEQ ID NO: 162) |
| 1101 | 3'UTR | CACATGCACTGTTGAGTGA (SEQ ID NO: 127) | AGCACATGCACTGTTGAGTGA (SEQ ID NO: 139) | AGCACATGCACTGTTGAGTGA (SEQ ID NO: 151) | AGCACATGCACTGTTGAGT (SEQ ID NO: 163) |

Provided in Table 5 below are the names of PDCD1 (PD1) RNAi agents (derived from their position in the human PDCD1 gene sequence, along with the SEQ ID NOs. 164-211 representing the DNA sequence. Both sense (5) and antisense (AS) sequences are presented as 19mer and 21mer sequences. SEQ ID NOs are indicated in groups of 12 that correspond with "sense 19" SEQ ID NOs: 164-175; "sense 21" SEQ ID NOs: 176-187; "asense 21" SEQ ID NOs: 188-199; "asense 19" SEQ ID NOs: 200-211.

TABLE 5

| Human PDCD1 (PD1) shRNA sequences | | | | | |
|---|---|---|---|---|---|
| Position on NM_005018.2 | Target region | Sense19 | Asense19 | Sense21 | Asense21 |
| 145 | CDS | GGCCAGGATGGTTCTTAGA (SEQ ID NO: 164) | TCTAAGAACCATCCTGGCC (SEQ ID NO: 176) | GCGGCCAGGATGGTTCTTAGA (SEQ ID NO: 188) | TCTAAGAACCATCCTGGCCGC (SEQ ID NO: 200) |
| 271 | CDS | GCTTCGTGCTAAACTGGTA (SEQ ID NO: 165) | TACCAGTTTAGCACGAAGC (SEQ ID NO: 177) | GAGCTTCGTGCTAAACTGGTA (SEQ ID NO: 189) | TACCAGTTTAGCACGAAGCTC (SEQ ID NO: 201) |
| 393 | CDS | GGGCGTGACTTCCACATGA (SEQ ID NO: 166) | TCATGTGGAAGTCACGCCC (SEQ ID NO: 178) | ACGGGCGTGACTTCCACATGA (SEQ ID NO: 190) | TCATGTGGAAGTCACGCCCGT (SEQ ID NO: 202) |

TABLE 5-continued

Human PDCD1 (PD1) shRNA sequences

| Position on NM_005018.2 | Target region | Sense19 | Asense19 | Sense21 | Asense21 |
|---|---|---|---|---|---|
| 1497 | 3'UTR | CAGGCCTAGAGAAGTT TCA (SEQ ID NO: 167) | TGAAACTTCTCTAGGC CTG (SEQ ID NO: 179) | TGCAGGCCTAGAGAAG TTTCA (SEQ ID NO: 191) | TGAAACTTCTCTAGGC CTGCA (SEQ ID NO: 203) |
| 1863 | 3'UTR | CTTGGAACCCATTCCT GAA (SEQ ID NO: 168) | TTCAGGAATGGGTTCC AAG (SEQ ID NO: 180) | TCCTTGGAACCCATTC CTGAA (SEQ ID NO: 192) | TTCAGGAATGGGTTCC AAGGA (SEQ ID NO: 204) |
| 1866 | 3'UTR | GGAACCCATTCCTGAA ATT (SEQ ID NO: 169) | AATTTCAGGAATGGGT TCC (SEQ ID NO: 181) | TTGGAACCCATTCCTG AAATT (SEQ ID NO: 193) | AATTTCAGGAATGGGT TCCAA (SEQ ID NO: 205) |
| 1867 | 3'UTR | GAACCCATTCCTGAAA TTA (SEQ ID NO: 170) | TAATTTCAGGAATGGG TTC (SEQ ID NO: 182) | TGGAACCCATTCCTGA AATTA (SEQ ID NO: 194) | TAATTTCAGGAATGGG TTCCA (SEQ ID NO: 206) |
| 1868 | 3'UTR | AACCCATTCCTGAAAT TAT (SEQ ID NO: 171) | ATAATTTCAGGAATGG GTT (SEQ ID NO: 184) | GGAACCCATTCCTGAA ATTAT (SEQ ID NO: 195) | ATAATTTCAGGAATGG GTTCC (SEQ ID NO: 207) |
| 1869 | 3'UTR | ACCCATTCCTGAAATT ATT (SEQ ID NO: 172) | AATAATTTCAGGAATG GGT (SEQ ID NO: 184) | GAACCCATTCCTGAAA TTATT (SEQ ID NO: 196) | AATAATTTCAGGAATG GGTTC (SEQ ID NO: 208) |
| 1870 | 3'UTR | CCCATTCCTGAAATTA TTT (SEQ ID NO: 173) | AAATAATTTCAGGAAT GGG (SEQ ID NO: 185) | AACCCATTCCTGAAAT TATTT (SEQ ID NO: 197) | AAATAATTTCAGGAAT GGGTT (SEQ ID NO: 209) |
| 2079 | 3'UTR | CTGTGGTTCTATTATA TTA (SEQ ID NO: 174) | TAATATAATAGAACCA CAG (SEQ ID NO:186 ) | CCCTGTGGTTCTATTA TATTA (SEQ ID NO: 198) | TAATATAATAGAACCA CAGGG (SEQ ID NO: 210) |
| 2109 | 3'UTR | AAATATGAGAGCATGC TAA (SEQ ID NO: 175) | TTAGCATGCTCTCATA TTT (SEQ ID NO: 187) | TTAAATATGAGAGCAT GCTAA (SEQ ID NO: 199) | TTAGCATGCTCTCATA TTTAA (SEQ ID NO: 211) |

In one embodiment, the inhibitor of an inhibitory signal can be, e.g., an antibody or antibody fragment that binds to an inhibitory molecule. For example, the agent can be an antibody or antibody fragment that binds to PD1, PD-L1, PD-L2 or CTLA4 (e.g., ipilimumab (also referred to as MDX-010 and MDX-101, and marketed as Yervoy®; Bristol-Myers Squibb; Tremelimumab (IgG2 monoclonal antibody available from Pfizer, formerly known as ticilimumab, CP-675,206).). In an embodiment, the agent is an antibody or antibody fragment that binds to TIM3. In an embodiment, the agent is an antibody or antibody fragment that binds to LAG3. In embodiments, the agent that enhances the activity of a CAR-expressing cell, e.g., inhibitor of an inhibitory molecule, is administered in combination with an allogeneic CAR, e.g., an allogeneic CAR described herein (e.g., described in the Allogeneic CAR section herein).

PD-1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD-1, PD-L1 and PD-L2 have been shown to downregulate T cell activation upon binding to PD-1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD-1 with PD-L1. Antibodies, antibody fragments, and other inhibitors of PD-1, PD-L1 and PD-L2 are available in the art and may be used combination with a cars of the present invention described herein. For example, nivolumab (also referred to as BMS-936558 or MDX1106; Bristol-Myers Squibb) is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449 and WO2006/121168. Pidilizumab (CT-011; Cure Tech) is a humanized IgG1k monoclonal antibody that binds to PD-1. Pidilizumab and other humanized anti-PD-1 monoclonal antibodies are disclosed in WO2009/101611. Pembrolizumab (formerly known as lambrolizumab, and also referred to as MK03475; Merck) is a humanized IgG4 monoclonal antibody that binds to PD-1. Pembrolizumab and other humanized anti-PD-1 antibodies are disclosed in U.S. Pat. No. 8,354,509 and WO2009/114335. MEDI4736 (Medimmune) is a human monoclonal antibody that binds to PDL1, and inhibits interaction of the ligand with PD1. MDPL3280A (Genentech/Roche) is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906. Other anti-PD-L1 binding agents include YW243.55.70 (heavy and light chain variable regions are shown in SEQ ID NOs 20 and 21 in WO2010/077634) and MDX-1 105 (also referred to as BMS-936559, and, e.g., anti-PD-L1 binding agents disclosed in WO2007/005874). AMP-224 (B7-DCIg;

Amplimmune; e.g., disclosed in WO2010/027827 and WO2011/066342), is a PD-L2 Fc fusion soluble receptor that blocks the interaction between PD-1 and B7-H1. Other anti-PD-1 antibodies include AMP 514 (Amplimmune), among others, e.g., anti-PD-1 antibodies disclosed in U.S. Pat. No. 8,609,089, US 2010028330, and/or US 20120114649.

In an embodiment, the CAR-expressing cell described herein can be administered in combination with a PD-1 antibody molecule as described in US2015/0210769, hereby incorporated by reference in its entirety.

TIM3 (T cell immunoglobulin-3) also negatively regulates T cell function, particularly in IFN-g-secreting CD4+ T helper 1 and CD8+ T cytotoxic 1 cells, and plays a critical role in T cell exhaustion. Inhibition of the interaction between TIM3 and its ligands, e.g., galectin-9 (Gal9), phosphotidylserine (PS), and HMGB1, can increase immune response. Antibodies, antibody fragments, and other inhibitors of TIM3 and its ligands are available in the art and may be used combination with a CD19 CAR described herein. For example, antibodies, antibody fragments, small molecules, or peptide inhibitors that target TIM3 binds to the IgV domain of TIM3 to inhibit interaction with its ligands. Antibodies and peptides that inhibit TIM3 are disclosed in WO2013/006490 and US20100247521. Other anti-TIM3 antibodies include humanized versions of RMT3-23 (disclosed in Ngiow et al., 2011, Cancer Res, 71:3540-3551), and clone 8B.2C12 (disclosed in Monney et al., 2002, Nature, 415:536-541). Bi-specific antibodies that inhibit TIM3 and PD-1 are disclosed in US20130156774.

In an embodiment, the CAR-expressing cell described herein can be administered in combination with a TIM3 antibody molecule as described in US2015/0218274, hereby incorporated by reference in its entirety.

In other embodiments, the agent which enhances the activity of a CAR-expressing cell is a CEACAM inhibitor (e.g., CEACAM-1, CEACAM-3, and/or CEACAM-5 inhibitor). In one embodiment, the inhibitor of CEACAM is an anti-CEACAM antibody molecule. Exemplary anti-CEACAM-1 antibodies are described in WO 2010/125571, WO 2013/082366 WO 2014/059251 and WO 2014/022332, e.g., a monoclonal antibody 34B1, 26H7, and 5F4; or a recombinant form thereof, as described in, e.g., US 2004/0047858, U.S. Pat. No. 7,132,255 and WO 99/052552. In other embodiments, the anti-CEACAM antibody binds to CEACAM-5 as described in, e.g., Zheng et al. *PLoS One.* 2010 Sep. 2; 5(9). pii: e12529 (DOI:10:1371/journal.pone.0021146), or crossreacts with CEACAM-1 and CEACAM-5 as described in, e.g., WO 2013/054331 and US 2014/0271618.

Without wishing to be bound by theory, carcinoembryonic antigen cell adhesion molecules (CEACAM), such as CEACAM-1 and CEACAM-5, are believed to mediate, at least in part, inhibition of an anti-tumor immune response (see e.g., Markel et al. *J Immunol.* 2002 Mar. 15; 168(6): 2803-10; Markel et al. *Jmmunol.* 2006 Nov. 1; 177(9):6062-71; Markel et al. *Immunology.* 2009 February; 126(2):186-200; Markel et al. *Cancer Immunol Immunother.* 2010 February; 59(2):215-30; Ortenberg et al. *Mol Cancer Ther.* 2012 June; 11(6):1300-10; Stern et al. *J Immunol.* 2005 Jun. 1; 174(11):6692-701; Zheng et al. *PLoS One.* 2010 Sep. 2; 5(9). pii: e12529). For example, CEACAM-1 has been described as a heterophilic ligand for TIM-3 and as playing a role in TIM-3-mediated T cell tolerance and exhaustion (see e.g., WO 2014/022332; Huang, et al. (2014) *Nature* doi:10.1038/nature13848). In embodiments, co-blockade of CEACAM-1 and TIM-3 has been shown to enhance an anti-tumor immune response in xenograft colorectal cancer models (see e.g., WO 2014/022332; Huang, et al. (2014), supra). In other embodiments, co-blockade of CEACAM-1 and PD-1 reduce T cell tolerance as described, e.g., in WO 2014/059251. Thus, CEACAM inhibitors can be used with the other immunomodulators described herein (e.g., anti-PD-1 and/or anti-TIM-3 inhibitors) to enhance an immune response against a cancer, e.g., a melanoma, a lung cancer (e.g., NSCLC), a bladder cancer, a colon cancer an ovarian cancer, and other cancers as described herein.

LAG3 (lymphocyte activation gene-3 or CD223) is a cell surface molecule expressed on activated T cells and B cells that has been shown to play a role in CD8+ T cell exhaustion. Antibodies, antibody fragments, and other inhibitors of LAG3 and its ligands are available in the art and may be used combination with a CD19 CAR described herein. For example, 3MS-986016 (Bristol-Myers Squib) is a monoclonal antibody that targets LAG3. IMP701 (Immutep) is an antagonist LAG3 antibody and IMP173 (Immutep and GlaxoSmithKline) is a depleting LAG3 antibody. Other LAG3 inhibitors include IMP321 (Immutep), which is a recombinant fusion protein of a soluble portion of LAG3 and Ig that binds to MHC class II molecules and activates antigen presenting cells (APC). Other antibodies are disclosed, e.g., in WO2010/019570.

In some embodiments, the agent which enhances the activity of a CAR-expressing cell can be, e.g., a fusion protein comprising a first domain and a second domain, wherein the first domain is an inhibitory molecule, or fragment thereof, and the second domain is a polypeptide that is associated with a positive signal, e.g., a polypeptide comprising an antracellular signaling domain as described herein. In some embodiments, the polypeptide that is associated with a positive signal can include a costimulatory domain of CD28, CD27, ICOS, e.g., an intracellular signaling domain of CD28, CD27 and/or ICOS, and/or a primary signaling domain, e.g., of CD3 zeta, e.g., described herein. In one embodiment, the fusion protein is expressed by the same cell that expressed the CAR. In another embodiment, the fusion protein is expressed by a cell, e.g., a T cell that does not express a GFRα4 CAR.

In one embodiment, the agent which enhances activity of a CAR-expressing cell described herein is miR-17-92.

In one embodiment, the agent which enhances activity of a CAR-described herein is a cytokine. Cytokines have important functions related to T cell expansion, differentiation, survival, and homeostatis. Cytokines that can be administered to the subject receiving a CAR-expressing cell described herein include: IL-2, IL-4, IL-7, IL-9, IL-15, IL-18, and IL-21, or a combination thereof. In preferred embodiments, the cytokine administered is IL-7, IL-15, or IL-21, or a combination thereof. The cytokine can be administered once a day or more than once a day, e.g., twice a day, three times a day, or four times a day. The cytokine can be administered for more than one day, e.g. the cytokine is administered for 2 days, 3 days, 4 days, 5 days, 6 days, 1 week, 2 weeks, 3 weeks, or 4 weeks. For example, the cytokine is administered once a day for 7 days.

In embodiments, the cytokine is administered in combination with CAR-expressing T cells. The cytokine can be administered simultaneously or concurrently with the CAR-expressing T cells, e.g., administered on the same day. The cytokine may be prepared in the same pharmaceutical composition as the CAR-expressing T cells, or may be prepared in a separate pharmaceutical composition. Alternatively, the cytokine can be administered shortly after administration of the CAR-expressing T cells, e.g., 1 day, 2 days, 3 days, 4 days, 5 days, 6 days, or 7 days after administration of the CAR-expressing T cells. In embodiments where the cytokine is administered in a dosing regimen that occurs over more than one day, the first day of the cytokine dosing regimen can be on the same day as administration with the CAR-expressing T cells, or the first day of the cytokine dosing regimen can be 1 day, 2 days, 3 days, 4 days, 5 days, 6 days, or 7 days after administration of the CAR-expressing T cells. In one embodiment, on the first day, the CAR-expressing T cells are administered to the subject, and on the second day, a cytokine is administered once a day for the next 7 days. In a preferred embodiment, the cytokine to be administered in combination with CAR-expressing T cells is IL-7, IL-15, or IL-21.

In other embodiments, the cytokine is administered a period of time after administration of CAR-expressing cells, e.g., at least 2 weeks, 3 weeks, 4 weeks, 6 weeks, 8 weeks, 10 weeks, 12 weeks, 4 months, 5 months, 6 months, 7 months, 8 months, 9 months, 10 months, 11 months, or 1 year or more after administration of CAR-expressing cells. In one embodiment, the cytokine is administered after assessment of the subject's response to the CAR-expressing cells. For example, the subject is administered CAR-expressing cells according to the dosage and regimens described herein. The response of the subject to CAR-expressing cell therapy is assessed at 2 weeks, 3 weeks, 4 weeks, 6 weeks, 8 weeks, 10 weeks, 12 weeks, 4 months, 5 months, 6 months, 7 months, 8 months, 9 months, 10 months, 11 months, or 1 year or more after administration of CAR-expressing cells, using any of the methods described herein, including inhibition of tumor growth, reduction of circulating tumor cells, or tumor regression. Subjects that do not exhibit a sufficient response to CAR-expressing cell therapy can be administered a cytokine. Administration of the cytokine to the subject that has sub-optimal response to the CAR-expressing cell therapy improves CAR-expressing cell efficacy or anti-cancer activity. In a preferred embodiment, the cytokine administered after administration of CAR-expressing cells is IL-7.

Combination with a Low, Immune Enhancing, Dose of an mTOR Inhibitor

Methods described herein use low, immune enhancing, doses of mTOR inhibitors, e.g., allosteric mTOR inhibitors, including rapalogs such as RAD001. Administration of a low, immune enhancing, dose of an mTOR inhibitor (e.g., a dose that is insufficient to completely suppress the immune system, but sufficient to improve immune function) can optimize the performance of immune effector cells, e.g., T cells or CAR-expressing cells, in the subject. Methods for measuring mTOR inhibition, dosages, treatment regimens, and suitable pharmaceutical compositions are described in U.S. Patent Application No. 2015/01240036, hereby incorporated by reference.

In an embodiment, administration of a low, immune enhancing, dose of an mTOR inhibitor can result in one or more of the following:

i) a decrease in the number of PD-1 positive immune effector cells;

ii) an increase in the number of PD-1 negative immune effector cells;

iii) an increase in the ratio of PD-1 negative immune effector cells/PD-1 positive immune effector cells;

iv) an increase in the number of naive T cells;

v) an increase in the expression of one or more of the following markers: $CD62L^{high}$, $CD127^{high}$, $C27^{+}$, and BCL2, e.g., on memory T cells, e.g., memory T cell precursors;

vi) a decrease in the expression of KLRG1, e.g., on memory T cells, e.g., memory T cell precursors; or vii) an increase in the number of memory T cell precursors, e.g., cells with any one or combination of the following characteristics: increased $CD62L^{high}$, increased $CD127^{high}$, increased $CD27^{+}$, decreased KLRG1, and increased BCL2;

and wherein any of the foregoing, e.g., i), ii), iii), iv), v), vi), or vii), occurs e.g., at least transiently, e.g., as compared to a non-treated subject.

In another embodiment, administration of a low, immune enhancing, dose of an mTOR inhibitor results in increased or prolonged proliferation or persistence of CAR-expressing cells, e.g., in culture or in a subject, e.g., as compared to non-treated CAR-expressing cells or a non-treated subject. In embodiments, increased proliferation is associated with in an increase in the number of CAR-expressing cells. Methods for measuring increased or prolonged proliferation are described in Examples 8 and 9. In another embodiment, administration of a low, immune enhancing, dose of an mTOR inhibitor results in increased killing of cancer cells by CAR-expressing cells, e.g., in culture or in a subject, e.g., as compared to non-treated CAR-expressing cells or a non-treated subject. In embodiments, increased killing of cancer cells is associated with in a decrease in tumor volume.

In one embodiment, the cells expressing a CAR molecule, e.g., a CAR molecule described herein, are administered in combination with a low, immune enhancing dose of an mTOR inhibitor, e.g., an allosteric mTOR inhibitor, e.g., RAD001, or a catalytic mTOR inhibitor. For example, administration of the low, immune enhancing, dose of the mTOR inhibitor can be initiated prior to administration of a CAR-expressing cell described herein; completed prior to administration of a CAR-expressing cell described herein; initiated at the same time as administration of a CAR-expressing cell described herein; overlapping with administration of a CAR-expressing cell described herein; or continuing after administration of a CAR-expressing cell described herein.

Alternatively or in addition, administration of a low, immune enhancing, dose of an mTOR inhibitor can optimize immune effector cells to be engineered to express a CAR molecule described herein. In such embodiments, administration of a low, immune enhancing, dose of an mTOR inhibitor, e.g., an allosteric inhibitor, e.g., RAD001, or a catalytic inhibitor, is initiated or completed prior to harvest of immune effector cells, e.g., T cells or NK cells, to be engineered to express a CAR molecule described herein, from a subject.

In another embodiment, immune effector cells, e.g., T cells or NK cells, to be engineered to express a CAR molecule described herein, e.g., after harvest from a subject, or CAR-expressing immune effector cells, e.g., T cells or NK cells, e.g., prior to administration to a subject, can be cultured in the presence of a low, immune enhancing, dose of an mTOR inhibitor.

In an embodiment, administering to the subject a low, immune enhancing, dose of an mTOR inhibitor comprises administering, e.g., once per week, e.g., in an immediate release dosage form, 0.1 to 20, 0.5 to 10, 2.5 to 7.5, 3 to 6, or about 5, mgs of RAD001, or a bioequivalent dose thereof. In an embodiment, administering to the subject a low, immune enhancing, dose of an mTOR inhibitor comprises administering, e.g., once per week, e.g., in a sustained release dosage form, 0.3 to 60, 1.5 to 30, 7.5 to 22.5, 9 to 18, or about 15 mgs of RAD001, or a bioequivalent dose thereof.

In an embodiment, a dose of an mTOR inhibitor is associated with, or provides, mTOR inhibition of at least 5 but no more than 90%, at least 10 but no more than 90%, at least 15, but no more than 90%, at least 20 but no more than 90%, at least 30 but no more than 90%, at least 40 but no more than 90%, at least 50 but no more than 90%, at least 60 but no more than 90%, at least 70 but no more than 90%, at least 5 but no more than 80%, at least 10 but no more than 80%, at least 15, but no more than 80%, at least 20 but no more than 80%, at least 30 but no more than 80%, at least 40 but no more than 80%, at least 50 but no more than 80%, at least 60 but no more than 80%, at least 5 but no more than 70%, at least 10 but no more than 70%, at least 15, but no more than 70%, at least 20 but no more than 70%, at least 30 but no more than 70%, at least 40 but no more than 70%, at least 50 but no more than 70%, at least 5 but no more than 60%, at least 10 but no more than 60%, at least 15, but no more than 60%, at least 20 but no more than 60%, at least 30 but no more than 60%, at least 40 but no more than 60%, at least 5 but no more than 50%, at least 10 but no more than 50%, at least 15, but no more than 50%, at least 20 but no more than 50%, at least 30 but no more than 50%, at least 40 but no more than 50%, at least 5 but no more than 40%, at least 10 but no more than 40%, at least 15, but no more than 40%, at least 20 but no more than 40%, at least 30 but no more than 40%, at least 35 but no more than 40%, at least 5 but no more than 30%, at least 10 but no more than 30%, at least 15, but no more than 30%, at least 20 but no more than 30%, or at least 25 but no more than 30%.

The extent of mTOR inhibition can be conveyed as, or corresponds to, the extent of P70 S6 kinase inhibition, e.g., the extent of mTOR inhibition can be determined by the level of decrease in P70 S6 kinase activity, e.g., by the decrease in phosphorylation of a P70 S6 kinase substrate. The level of mTOR inhibition can be evaluated by various methods, such as measuring P70 S6 kinase activity by the Boulay assay, as described in U.S. Patent Application No. 2015/01240036, hereby incorporated by reference, or as described in U.S. Pat. No. 7,727,950, hereby incorporated by reference; measuring the level of phosphorylated S6 by western blot; or evaluating a change in the ratio of PD1 negative immune effector cells to PD1 positive immune effector cells.

As used herein, the term "mTOR inhibitor" refers to a compound or ligand, or a pharmaceutically acceptable salt thereof, which inhibits the mTOR kinase in a cell. In an embodiment, an mTOR inhibitor is an allosteric inhibitor. Allosteric mTOR inhibitors include the neutral tricyclic compound rapamycin (sirolimus), rapamycin-related compounds, that is compounds having structural and functional similarity to rapamycin including, e.g., rapamycin derivatives, rapamycin analogs (also referred to as rapalogs) and other macrolide compounds that inhibit mTOR activity. In an embodiment, an mTOR inhibitor is a catalytic inhibitor.

Rapamycin is a known macrolide antibiotic produced by *Streptomyces hygroscopicus* having the structure shown in Formula A.

(A)

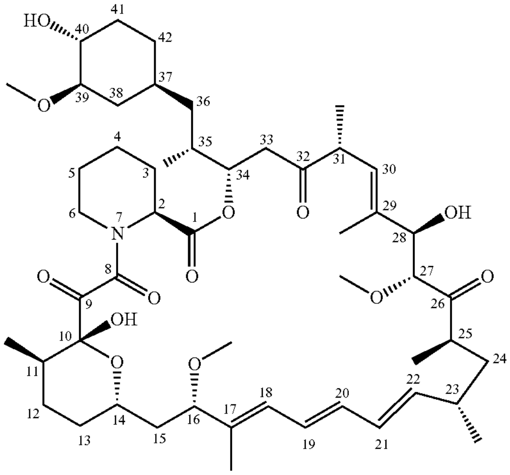

See, e.g., McAlpine, J. B., et al., J. Antibiotics (1991) 44: 688; Schreiber, S. L., et al., J. Am. Chem. Soc. (1991) 113: 7433; U.S. Pat. No. 3,929,992. There are various numbering schemes proposed for rapamycin. To avoid confusion, when specific rapamycin analogs are named herein, the names are given with reference to rapamycin using the numbering scheme of formula A.

Rapamycin analogs useful in the invention are, for example, O-substituted analogs in which the hydroxyl group on the cyclohexyl ring of rapamycin is replaced by $OR_1$ in which $R_1$ is hydroxyalkyl, hydroxyalkoxyalkyl, acylaminoalkyl, or aminoalkyl; e.g. RAD001, also known as, everolimus as described in U.S. Pat. No. 5,665,772 and WO94/09010 the contents of which are incorporated by reference. Other suitable rapamycin analogs include those substituted at the 26- or 28-position. The rapamycin analog may be an epimer of an analog mentioned above, particularly an epimer of an analog substituted in position 40, 28 or 26, and may optionally be further hydrogenated, e.g. as described in U.S. Pat. No. 6,015,815, WO95/14023 and WO99/15530 the contents of which are incorporated by reference, e.g. ABT578 also known as zotarolimus or a rapamycin analog described in U.S. Pat. No. 7,091,213, WO98/02441 and WO01/14387 the contents of which are incorporated by reference, e.g. AP23573 also known as ridaforolimus.

Examples of rapamycin analogs suitable for use in the present invention from U.S. Pat. No. 5,665,772 include, but are not limited to, 40-O-benzyl-rapamycin, 40-O-(4'-hydroxymethyl)benzyl-rapamycin, 40-O-[4'-(1,2-dihydroxyethyl)]benzyl-rapamycin, 40-O-allyl-rapamycin, 40-O-[3'-(2,2-dimethyl-1,3-dioxolan-4(S)-yl)-prop-2'-en-1'-yl]-rapamycin, (2'E,4'S)-40-O-(4',5'-dihydroxypent-2'-en-1'-yl)-rapamycin, 40-O-(2-hydroxy)ethoxycarbonylmethyl-rapamycin, 40-O-(2-hydroxy)ethyl-rapamycin, 40-O-(3-hydroxy)propyl-rapamycin, 40-O-(6-hydroxy)hexyl-rapamycin, 40-O-[2-(2-hydroxy)ethoxy]ethyl-rapamycin, 40-O-[(3 S)-2,2-dimethyldioxolan-3-yl]methyl-rapamycin, 40-O-[(2S)-2,3-dihydroxyprop-1-yl]-rapamycin, 40-O-(2-acetoxy)ethyl-rapamycin, 40-O-(2-nicotinoyloxy)ethyl-rapamycin, 40-O-[2-(N-morpholino)acetoxy]ethyl-rapamycin, 40-O-(2-N-imidazolylacetoxy)ethyl-rapamycin, 40-O-[2-(N-methyl-N'-piperazinyl)acetoxy]ethyl-rapamycin, 39-O-desmethyl-39,40-O,O-ethylene-rapamycin, (26R)-26-dihydro-40-O-(2-hydroxy)ethyl-rapamycin, 40-O-(2-aminoethyl)-rapamycin, 40-O-(2-acetaminoethyl)-rapamycin, 40-O-(2-nicotinamidoethyl)-rapamycin, 40-O-(2-(N-methyl-imidazo-2'-ylcarbethoxamido)ethyl)-rapamycin, 40-O-(2-ethoxycarbonylaminoethyl)-rapamycin, 40-O-(2-tolylsulfonamidoethyl)-rapamycin and 40-O-[2-(4',5'-dicarboethoxy-1',2',3'-triazol-1'-yl)-ethyl]-rapamycin.

Other rapamycin analogs useful in the present invention are analogs where the hydroxyl group on the cyclohexyl ring of rapamycin and/or the hydroxy group at the 28 position is replaced with an hydroxyester group are known, for example, rapamycin analogs found in U.S. RE44,768, e.g. temsirolimus.

Other rapamycin analogs useful in the preset invention include those wherein the methoxy group at the 16 position is replaced with another substituent, preferably (optionally hydroxy-substituted) alkynyloxy, benzyl, orthomethoxybenzyl or chlorobenzyl and/or wherein the mexthoxy group at the 39 position is deleted together with the 39 carbon so that the cyclohexyl ring of rapamycin becomes a cyclopentyl ring lacking the 39 position methyoxy group; e.g. as described in WO95/16691 and WO96/41807 the contents of which are incorporated by reference. The analogs can be further modified such that the hydroxy at the 40-position of rapamycin is alkylated and/or the 32-carbonyl is reduced.

Rapamycin analogs from WO95/16691 include, but are not limited to, 16-demthoxy-16-(pent-2-ynyl)oxy-rapamycin, 16-demthoxy-16-(but-2-ynyl)oxy-rapamycin, 16-demthoxy-16-(propargyl)oxy-rapamycin, 16-demethoxy-16-(4-hydroxy-but-2-ynyl)oxy-rapamycin, 16-demthoxy-16-benzyloxy-40-O-(2-hydroxyethyl)-rapamycin, 16-demthoxy-16-benzyloxy-rapamycin, 16-demethoxy-16-ortho-methoxybenzyl-rapamycin, 16-demethoxy-40-O-(2-methoxyethyl)-16-pent-2-ynyl)oxy-rapamycin, 39-demethoxy-40-desoxy-39-formyl-42-nor-rapamycin, 39-demethoxy-40-desoxy-39-hydroxymethyl-42-nor-rapamycin, 39-demethoxy-40-desoxy-39-carboxy-42-nor-rapamycin, 39-demethoxy-40-desoxy-39-(4-methyl-piperazin-1-yl)carbonyl-42-nor-rapamycin, 39-demethoxy-40-desoxy-39-(morpholin-4-yl)carbonyl-42-nor-rapamycin, 39-demethoxy-40-desoxy-39-[N-methyl, N-(2-pyridin-2-yl-ethyl)]carbamoyl-42-nor-rapamycin and 39-demethoxy-40-desoxy-39-(p-toluenesulfonylhydrazonomethyl)-42-nor-rapamycin.

Rapamycin analogs from WO96/41807 include, but are not limited to, 32-deoxo-rapamycin, 16-O-pent-2-ynyl-32-deoxo-rapamycin, 16-O-pent-2-ynyl-32-deoxo-40-O-(2-hydroxy-ethyl)-rapamycin, 16-O-pent-2-ynyl-32-(S)-dihydro-40-O-(2-hydroxyethyl)-rapamycin, 32(S)-dihydro-40-O-(2-methoxy)ethyl-rapamycin and 32(S)-dihydro-40-O-(2-hydroxyethyl)-rapamycin.

Another suitable rapamycin analog is umirolimus as described in US2005/0101624 the contents of which are incorporated by reference.

RAD001, otherwise known as everolimus (Afinitor®), has the chemical name (1R,9S,12S,15R,16E,18R,19R,21R,23S,24E,26E,28E,30S,32S,35R)-1,18-dihydroxy-12-{(1R)-2-[(1S,3R,4R)-4-(2-hydroxyethoxy)-3-methoxycyclohexyl]-1-methylethyl}-19,30-dimethoxy-15,17,21,23,29,35-hexamethyl-11,36-dioxa-4-aza-tricyclo[30.3.1.04,9]hexatriaconta-16,24,26,28-tetraene-2,3,10,14,20-pentaone, as described in U.S. Pat. No. 5,665,772 and WO94/09010, the contents of each are incorporated by reference.

Further examples of allosteric mTOR inhibitors include sirolimus (rapamycin, AY-22989), 40-[3-hydroxy-2-(hydroxymethyl)-2-methylpropanoate]-rapamycin (also called temsirolimus or CCI-779) and ridaforolimus (AP-23573/MK-8669). Other examples of allosteric mTor inhibitors include zotarolimus (ABT578) and umirolimus.

Alternatively or additionally, catalytic, ATP-competitive mTOR inhibitors have been found to target the mTOR kinase domain directly and target both mTORC1 and mTORC2. These are also more effective inhibitors of mTORC1 than such allosteric mTOR inhibitors as rapamycin, because they modulate rapamycin-resistant mTORC1 outputs such as 4EBP1-T37/46 phosphorylation and cap-dependent translation.

Catalytic inhibitors include: BEZ235 or 2-methyl-2-[4-(3-methyl-2-oxo-8-quinolin-3-yl-2,3-dihydro-imidazo[4,5-c]quinolin-1-yl)-phenyl]-propionitrile, or the monotosylate salt form. the synthesis of BEZ235 is described in W2006/122806; CCG168 (otherwise known as AZD-8055, Chresta, C. M., et al., Cancer Res, 2010, 70(1), 288-298) which has the chemical name {5-[2,4-bis-((S)-3-methyl-morpholin-4-yl)-pyrido[2,3d]pyrimidin-7-yl]-2-methoxy-phenyl}-methanol; 3-[2,4-bis[(3S)-3-methylmorpholin-4-yl]pyrido[2,3-d]pyrimidin-7-yl]-N-methylbenzamide (WO09104019); 3-(2-aminobenzo[d]oxazol-5-yl)-1-isopropyl-1H-pyrazolo[3,4-d]pyrimidin-4-amine (WO10051043 and WO2013023184); A N-(3-(N-(3-((3,5-dimethoxyphenyl)amino)quinoxaline-2-yl)sulfamoyl)phenyl)-3-methoxy-4-methylbenzamide (WO07044729 and WO12006552); PKI-587 (Venkatesan, A. M., J. Med. Chem., 2010, 53, 2636-2645) which has the chemical name 1-[4-[4-(dimethylamino)piperidine-1-carbonyl]phenyl]-3-[4-(4,6-dimorpholino-1,3,5-triazin-2-yl)phenyl]urea; GSK-2126458 (ACS Med. Chem. Lett., 2010, 1, 39-43) which has the chemical name 2,4-difluoro-N-{2-methoxy-5-[4-(4-pyridazinyl)-6-quinolinyl]-3-pyridinyl}benzenesulfonamide; 5-(9-isopropyl-8-methyl-2-morpholino-9H-purin-6-yl)pyrimidin-2-amine (WO10114484); (E)-N-(8-(6-amino-5-(trifluoromethyl)pyridin-3-yl)-1-(6-(2-cyanopropan-2-yl)pyridin-3-yl)-3-methyl-1H-imidazo[4,5-c]quinolin-2(3H)-ylidene)cyanamide (WO12007926).

Further examples of catalytic mTOR inhibitors include 8-(6-methoxy-pyridin-3-yl)-3-methyl-1-(4-piperazin-1-yl-3-trifluoromethyl-phenyl)-1,3-dihydro-imidazo[4,5-c]quinolin-2-one (WO2006/122806) and Ku-0063794 (Garcia-Martinez J M, et al., Biochem J., 2009, 421(1), 29-42. Ku-0063794 is a specific inhibitor of the mammalian target of rapamycin (mTOR).) WYE-354 is another example of a catalytic mTor inhibitor (Yu K, et al. (2009). Biochemical, Cellular, and In vivo Activity of Novel ATP-Competitive and Selective Inhibitors of the Mammalian Target of Rapamycin. Cancer Res. 69(15): 6232-6240).

mTOR inhibitors useful according to the present invention also include prodrugs, derivatives, pharmaceutically acceptable salts, or analogs thereof of any of the foregoing.

mTOR inhibitors, such as RAD001, may be formulated for delivery based on well-established methods in the art based on the particular dosages described herein. In particular, U.S. Pat. No. 6,004,973 (incorporated herein by reference) provides examples of formulations useable with the mTOR inhibitors described herein.

Methods and Biomarkers for Evaluating CAR-Effectiveness or Sample Suitability

In another aspect, the invention features a method of evaluating or monitoring the effectiveness of a CAR-expressing cell therapy (e.g., a GFRα4 CAR therapy), in a subject (e.g., a subject having a cancer, e.g., a hematological cancer), or the suitability of a sample (e.g., an apheresis sample) for a CAR therapy (e.g., a GFRα4 CAR therapy). The method includes acquiring a value of effectiveness to the CAR therapy, or sample suitability, wherein said value is indicative of the effectiveness or suitability of the CAR-expressing cell therapy.

In embodiments, the value of effectiveness to the CAR therapy, or sample suitability, comprises a measure of one, two, three, four, five, six or more (all) of the following:

(i) the level or activity of one, two, three, or more (e.g., all) of resting $T_{EFF}$ cells, resting $T_{REG}$ cells, younger T cells (e.g., younger CD4 or CD8 cells, or gamma/delta T cells), or early memory T cells, or a combination thereof, in a sample (e.g., an apheresis sample or a manufactured CAR-expressing cell product sample);

(ii) the level or activity of one, two, three, or more (e.g., all) of activated $T_{EFF}$ cells, activated $T_{REG}$ cells, older T cells (e.g., older CD4 or CD8 cells), or late memory T cells, or a combination thereof, in a sample (e.g., an apheresis sample or a manufactured CAR-expressing cell product sample);

(iii) the level or activity of an immune cell exhaustion marker, e.g., one, two or more immune checkpoint inhibitors (e.g., PD-1, PD-L1, TIM-3 and/or LAG-3) in a sample (e.g., an apheresis sample or a manufactured CAR-expressing cell product sample). In one embodiment, an immune cell has an exhausted phenotype, e.g., co-expresses at least two exhaustion markers, e.g., co-expresses PD-1 and TIM-3. In other embodiments, an immune cell has an exhausted phenotype, e.g., co-expresses at least two exhaustion markers, e.g., co-expresses PD-1 and LAG-3;

(iv) the level or activity of CD27 and/or CD45RO− (e.g., CD27+ CD45RO−) immune effector cells, e.g., in a CD4+ or a CD8+ T cell population, in a sample (e.g., an apheresis sample or a manufactured CAR-expressing cell product sample);

(v) the level or activity of one, two, three, four, five, ten, twenty or more of the biomarkers chosen from CCL20, IL-17a and/or IL-6, PD-1, PD-L1, LAG-3, TIM-3, CD57, CD27, CD122, CD62L, KLRG1;

(vi) a cytokine level or activity (e.g., quality of cytokine reportoire) in a CAR-expressing cell product sample, e.g., GFRα4-expressing cell product sample; or (vii) a transduction efficiency of a CAR-expressing cell in a manufactured CAR-expressing cell product sample.

In some embodiments of any of the methods disclosed herein, the CAR-expressing cell therapy comprises a plurality (e.g., a population) of CAR-expressing immune effector cells, e.g., a plurality (e.g., a population) of T cells or NK cells, or a combination thereof. In one embodiment, the CAR-expressing cell therapy is a GFRα4 CAR therapy.

In some embodiments of any of the methods disclosed herein, the measure of one or more of (i)-(vii) is obtained from an apheresis sample acquired from the subject. The apheresis sample can be evaluated prior to infusion or re-infusion.

In some embodiments of any of the methods disclosed herein, the measure of one or more of (i)-(vii) is obtained from a manufactured CAR-expressing cell product sample, e.g., GFRα4 CAR-expressing cell product sample. The manufactured CAR-expressing cell product can be evaluated prior to infusion or re-infusion.

In some embodiments of any of the methods disclosed herein, the subject is evaluated prior to receiving, during, or after receiving, the CAR-expressing cell therapy.

In some embodiments of any of the methods disclosed herein, the measure of one or more of (i)-(vii) evaluates a profile for one or more of gene expression, flow cytometry or protein expression.

In some embodiments of any of the methods disclosed herein, the method further comprises identifying the subject as a responder, a non-responder, a relapser or a non-relapser, based on a measure of one or more of (i)-(vii).

In some embodiments of any of the methods disclosed herein, a responder (e.g., a complete responder) has, or is identified as having, a greater level or activity of one, two, or more (all) of GZMK, PPF1BP2, or naïve T cells as compared to a non-responder.

In some embodiments of any of the methods disclosed herein, a non-responder has, or is identified as having, a greater level or activity of one, two, three, four, five, six, seven, or more (e.g., all) of IL22, IL-2RA, IL-21, IRF8, IL8, CCL17, CCL22, effector T cells, or regulatory T cells, as compared to a responder.

In an embodiment, a relapser is a patient having, or who is identified as having, an increased level of expression of one or more of (e.g., 2, 3, 4, or all of) the following genes, compared to non relapsers: MIR199A1, MIR1203, uc021ovp, ITM2C, and HLA-DQB1 and/or a decreased levels of expression of one or more of (e.g., 2, 3, 4, 5, 6, 7, 8, 9, 10, 11, or all of) the following genes, compared to non relapsers: PPIAL4D, TTTY10, TXLNG2P, MIR4650-1, KDM5D, USP9Y, PRKY, RPS4Y2, RPS4Y1, NCRNA00185, SULT1E1, and EIF1AY.

In some embodiments of any of the methods disclosed herein, a complete responder has, or is identified as having, a greater, e.g., a statistically significant greater, percentage of CD8+ T cells compared to a reference value, e.g., a non-responder percentage of CD8+ T cells.

In some embodiments of any of the methods disclosed herein, a complete responder has, or is identified as having, a greater percentage of CD27+ CD45RO-immune effector cells, e.g., in the CD8+ population, compared to a reference value, e.g., a non-responder number of CD27+ CD45RO-immune effector cells.

In some embodiments of any of the methods disclosed herein, a complete responder or a partial responder has, or is identified as having, a greater, e.g., a statistically significant greater, percentage of CD4+ T cells compared to a reference value, e.g., a non-responder percentage of CD4+ T cells.

In some embodiments of any of the methods disclosed herein, a complete responder has, or is identified as having, a greater percentage of one, two, three, or more (e.g., all) of resting $T_{EFF}$ cells, resting $T_{REG}$ cells, younger T cells (e.g., younger CD4 or CD8 cells, or gamma/delta T cells), or early memory T cells, or a combination thereof, compared to a reference value, e.g., a non-responder number of resting $T_{EFF}$ cells, resting $T_{REG}$ cells, younger T cells (e.g., younger CD4 or CD8 cells), or early memory T cells.

In some embodiments of any of the methods disclosed herein, a non-responder has, or is identified as having, a greater percentage of one, two, three, or more (e.g., all) of activated $T_{EFF}$ cells, activated $T_{REG}$ cells, older T cells (e.g., older CD4 or CD8 cells), or late memory T cells, or a combination thereof, compared to a reference value, e.g., a responder number of activated $T_{EFF}$ cells, activated $T_{REG}$ cells, older T cells (e.g., older CD4 or CD8 cells), or late memory T cells.

In some embodiments of any of the methods disclosed herein, a non-responder has, or is identified as having, a greater percentage of an immune cell exhaustion marker, e.g., one, two or more immune checkpoint inhibitors (e.g., PD-1, PD-L1, TIM-3 and/or LAG-3). In one embodiment, a non-responder has, or is identified as having, a greater percentage of PD-1, PD-L1, or LAG-3 expressing immune effector cells (e.g., CD4+ T cells and/or CD8+ T cells) (e.g., CAR-expressing CD4+ cells and/or CD8+ T cells) compared to the percentage of PD-1 or LAG-3 expressing immune effector cells from a responder.

In one embodiment, a non-responder has, or is identified as having, a greater percentage of immune cells having an exhausted phenotype, e.g., immune cells that co-express at least two exhaustion markers, e.g., co-expresses PD-1, PD-L1 and/or TIM-3. In other embodiments, a non-responder has, or is identified as having, a greater percentage of immune cells having an exhausted phenotype, e.g., immune cells that co-express at least two exhaustion markers, e.g., co-expresses PD-1 and LAG-3.

In some embodiments of any of the methods disclosed herein, a non-responder has, or is identified as having, a greater percentage of PD-1/PD-L1+/LAG-3+ cells in the CAR-expressing cell population (e.g., a GFRα4 CAR+ cell population) compared to a responder (e.g., a complete responder) to the CAR-expressing cell therapy.

In some embodiments of any of the methods disclosed herein, a partial responder has, or is identified as having, a higher percentages of PD-1/PD-L1+/LAG-3+ cells, than a responder, in the CAR-expressing cell population (e.g., a GFRα4 CAR+ cell population).

In some embodiments of any of the methods disclosed herein, a non-responder has, or is identified as having, an exhausted phenotype of PD1/PD-L1+ CAR+ and co-expression of LAG3 in the CAR-expressing cell population (e.g., a GFRα4 CAR+ cell population).

In some embodiments of any of the methods disclosed herein, a non-responder has, or is identified as having, a greater percentage of PD-1/PD-L1+/TIM-3+ cells in the CAR-expressing cell population (e.g., a GFRα4 CAR+ cell population) compared to the responder (e.g., a complete responder).

In some embodiments of any of the methods disclosed herein, a partial responders has, or is identified as having, a higher percentage of PD-1/PD-L1+/TIM-3+ cells, than responders, in the CAR-expressing cell population (e.g., a GFRα4 CAR+ cell population).

In some embodiments of any of the methods disclosed herein, the presence of CD8+ CD27+ CD45RO-T cells in an apheresis sample is a positive predictor of the subject response to a CAR-expressing cell therapy (e.g., a GFRα4 CAR therapy).

In some embodiments of any of the methods disclosed herein, a high percentage of PD1+ CAR+ and LAG3+ or TIM3+ T cells in an apheresis sample is a poor prognostic predictor of the subject response to a CAR-expressing cell therapy (e.g., a GFRα4 CAR therapy).

In some embodiments of any of the methods disclosed herein, the responder (e.g., the complete or partial responder) has one, two, three or more (or all) of the following profile:

(i) has a greater number of CD27+ immune effector cells compared to a reference value, e.g., a non-responder number of CD27+ immune effector cells;

(ii) (i) has a greater number of CD8+ T cells compared to a reference value, e.g., a non-responder number of CD8+ T cells;

(iii) has a lower number of immune cells expressing one or more checkpoint inhibitors, e.g., a checkpoint inhibitor chosen from PD-1, PD-L1, LAG-3, TIM-3, or KLRG-1, or a combination, compared to a reference value, e.g., a non-responder number of cells expressing one or more checkpoint inhibitors; or (iv) has a greater number of one, two, three, four or more (all) of resting $T_{EFF}$ cells, resting $T_{REG}$ cells, naïve CD4 cells, unstimulated memory cells or early memory T cells, or a combination thereof, compared to a reference value, e.g., a non-responder number of resting $T_{EFF}$ cells, resting $T_{REG}$ cells, naïve CD4 cells, unstimulated memory cells or early memory T cells.

In some embodiments of any of the methods disclosed herein, the cytokine level or activity of (vi) is chosen from one, two, three, four, five, six, seven, eight, or more (or all) of cytokine CCL20/MIP3a, IL17A, IL6, GM-CSF, IFNγ, IL10, IL13, IL2, IL21, IL4, IL5, IL9 or TNFα, or a combination thereof. The cytokine can be chosen from one, two, three, four or more (all) of IL-17a, CCL20, IL2, IL6, or TNFa. In one embodiment, an increased level or activity of a cytokine is chosen from one or both of IL-17a and CCL20, is indicative of increased responsiveness or decreased relapse.

In some embodiments of any of the methods disclosed herein, a transduction efficiency of 15% or higher in (vii) is indicative of increased responsiveness or decreased relapse.

In some embodiments of any of the methods disclosed herein, a transduction efficiency of less than 15% in (vii) is indicative of decreased responsiveness or increased relapse.

In embodiments, the responder, a non-responder, a relapser or a non-relapser identified by the methods herein can be further evaluated according to clinical criteria. For example, a complete responder has, or is identified as, a subject having a disease, e.g., a cancer, who exhibits a complete response, e.g., a complete remission, to a treatment. A complete response may be identified, e.g., using the NCCN Guidelines®, or Cheson et al, J Clin Oncol 17:1244 (1999) and Cheson et al., "Revised Response Criteria for Malignant Lymphoma", J Clin Oncol 25:579-586 (2007) (both of which are incorporated by reference herein in their entireties), as described herein. A partial responder has, or is identified as, a subject having a disease, e.g., a cancer, who exhibits a partial response, e.g., a partial remission, to a treatment. A partial response may be identified, e.g., using the NCCN Guidelines®, or Cheson criteria as described herein. A non-responder has, or is identified as, a subject having a disease, e.g., a cancer, who does not exhibit a response to a treatment, e.g., the patient has stable disease or progressive disease. A non-responder may be identified, e.g., using the NCCN Guidelines®, or Cheson criteria as described herein.

Alternatively, or in combination with the methods disclosed herein, responsive to said value, performing one, two, three four or more of:

administering e.g., to a responder or a non-relapser, a CAR-expressing cell therapy;

administered an altered dosing of a CAR-expressing cell therapy;

altering the schedule or time course of a CAR-expressing cell therapy;

administering, e.g., to a non-responder or a partial responder, an additional agent in combination with a CAR-expressing cell therapy, e.g., a checkpoint inhibitor, e.g., a checkpoint inhibitor described herein;

administering to a non-responder or partial responder a therapy that increases the number of younger T cells in the subject prior to treatment with a CAR-expressing cell therapy;

modifying a manufacturing process of a CAR-expressing cell therapy, e.g., enriching for younger T cells prior to introducing a nucleic acid encoding a CAR, or increasing the transduction efficiency, e.g., for a subject identified as a non-responder or a partial responder;

administering an alternative therapy, e.g., for a non-responder or partial responder or relapser; or if the subject is, or is identified as, a non-responder or a relapser, decreasing the $T_{REG}$ cell population and/or $T_{REG}$ gene signature, e.g., by one or more of CD25 depletion, administration of cyclophosphamide, anti-GITR antibody, or a combination thereof.

In certain embodiments, the subject is pre-treated with an anti-GITR antibody. In certain embodiment, the subject is treated with an anti-GITR antibody prior to infusion or re-infusion.

Biopolymer Delivery Methods

In some embodiments, one or more CAR-expressing cells as disclosed herein can be administered or delivered to the subject via a biopolymer scaffold, e.g., a biopolymer implant. Biopolymer scaffolds can support or enhance the delivery, expansion, and/or dispersion of the CAR-expressing cells described herein. A biopolymer scaffold comprises a biocompatible (e.g., does not substantially induce an inflammatory or immune response) and/or a biodegradable polymer that can be naturally occurring or synthetic.

Examples of suitable biopolymers include, but are not limited to, agar, agarose, alginate, alginate/calcium phosphate cement (CPC), beta-galactosidase (β-GAL), (1,2,3,4,6-pentaacetyl a-D-galactose), cellulose, chitin, chitosan, collagen, elastin, gelatin, hyaluronic acid collagen, hydroxyapatite, poly(3-hydroxybutyrate-co-3-hydroxy-hexanoate) (PHBHHx), poly(lactide), poly(caprolactone) (PCL), poly(lactide-co-glycolide) (PLG), polyethylene oxide (PEO), poly(lactic-co-glycolic acid) (PLGA), polypropylene oxide (PPO), polyvinyl alcohol) (PVA), silk, soy protein, and soy protein isolate, alone or in combination with any other polymer composition, in any concentration and in any ratio. The biopolymer can be augmented or modified with adhesion- or migration-promoting molecules, e.g., collagen-mimetic peptides that bind to the collagen receptor of lymphocytes, and/or stimulatory molecules to enhance the delivery, expansion, or function, e.g., anti-cancer activity, of the cells to be delivered. The biopolymer scaffold can be an injectable, e.g., a gel or a semi-solid, or a solid composition.

In some embodiments, CAR-expressing cells described herein are seeded onto the biopolymer scaffold prior to delivery to the subject. In embodiments, the biopolymer scaffold further comprises one or more additional therapeutic agents described herein (e.g., another CAR-expressing cell, an antibody, or a small molecule) or agents that enhance the activity of a CAR-expressing cell, e.g., incorporated or conjugated to the biopolymers of the scaffold. In embodiments, the biopolymer scaffold is injected, e.g., intratumorally, or surgically implanted at the tumor or within a proximity of the tumor sufficient to mediate an anti-tumor effect. Additional examples of biopolymer compositions and methods for their delivery are described in Stephan et al., *Nature Biotechnology*, 2015, 33:97-101; and WO2014/110591.

Pharmaceutical Compositions

Pharmaceutical compositions of the present invention may comprise a CAR-expressing cell, e.g., a plurality of CAR-expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

In one embodiment, the pharmaceutical composition is substantially free of, e.g., there are no detectable levels of a contaminant, e.g., selected from the group consisting of endotoxin, mycoplasma, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus. In one embodiment, the bacterium is at least one selected from the group consisting of *Alcaligenes faecalis, Candida albicans, Escherichia coli, Haemophilus influenza, Neisseria meningitides, Pseudomonas aeruginosa, Staphylococcus aureus, Streptococcus pneumonia*, and *Streptococcus pyogenes* group A.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol, may select out certain populations of T cells.

The administration of the subject compositions may be carried out in any convenient manner, including by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

In a particular exemplary aspect, subjects may undergo leukapheresis, wherein leukocytes are collected, enriched, or depleted ex vivo to select and/or isolate the cells of interest, e.g., immune effector cells (e.g., T cells or NK cells). These immune effector cells (e.g., T cells or NK cells) isolates may be expanded by methods known in the art and treated such that one or more CAR constructs of the invention may be introduced, thereby creating a CAR-expressing cell (e.g., CAR T cell or CAR-expressing NK cell) of the invention. Subjects in need thereof may subsequently undergo standard treatment with high dose chemotherapy followed by peripheral blood stem cell transplantation. In certain aspects, following or concurrent with the transplant, subjects receive an infusion of the expanded CAR-expressing cell (e.g., CAR T cell or CAR-expressing NK cell) of the present invention. In an additional aspect, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

In one embodiment, the CAR is introduced into immune effector cells (e.g., T cells or NK cells), e.g., using in vitro transcription, and the subject (e.g., human) receives an initial administration of CAR-expressing immune effector cells (e.g., T cells, NK cells) cells of the invention, and one or more subsequent administrations of the CAR-expressing immune effector cells (e.g., T cells, NK cells) cells of the invention, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of the CAR-expressing immune effector cells (e.g., T cells, NK cells) of the invention are administered to the subject (e.g., human) per week, e.g., 2, 3, or 4 administrations of the CAR-expressing immune effector cells (e.g., T cells, NK cells) of the invention are administered per week. In one embodiment, the subject (e.g., human subject) receives more than one administration of the CAR-expressing immune effector cells (e.g., T cells, NK cells) cells per week (e.g., 2, 3 or 4 administrations per week) (also referred to herein as a cycle), followed by a week of no CAR-expressing immune effector cells (e.g., T cells, NK cells) administrations, and then one or more additional administration of the CAR-expressing immune effector cells (e.g., T cells, NK cells) (e.g., more than one administration of the CAR-expressing immune effector cells (e.g., T cells, NK cells) per week) is administered to the subject. In another embodiment, the subject (e.g., human subject) receives more than one cycle of CAR-expressing immune effector cells (e.g., T cells, NK cells), and the time between each cycle is less than 10, 9, 8, 7, 6, 5, 4, or 3 days. In one embodiment, the CAR-expressing immune effector cells (e.g., T cells, NK cells) are administered every other day for 3 administrations per week. In one embodiment, the CAR-expressing immune effector cells (e.g., T cells, NK cells) of the invention are administered for at least two, three, four, five, six, seven, eight or more weeks.

In one aspect, GFRα4 CAR-expressing cells, e.g., GFRα4 CARTs or GFRα4 CAR-expressing NK cells) are generated using lentiviral viral vectors, such as lentivirus. CAR-expressing cells, e.g., GFRα4 CARTs or CAR expressing NK cells, generated that way will have stable CAR expression.

In one aspect, CAR-expressing cells, e.g., CARTs or CAR-expressing NK cells, are generated using a viral vector such as a gammaretroviral vector, e.g., a gammaretroviral vector described herein. CAR-expressing cells, e.g., CARTs or CAR-expressing NK cells, generated using these vectors can have stable CAR expression.

In one aspect, CAR-expressing cells, e.g., CARTs or CAR-expressing NK cells, transiently express CAR vectors for 4, 5, 6, 7, 8, 9, 10, 11, 12, 13, 14, 15 days after transduction. Transient expression of CARs can be effected by RNA CAR vector delivery. In one aspect, the CAR RNA is transduced into the T cell by electroporation.

A potential issue that can arise in patients being treated using transiently expressing CAR-expressing cells, e.g., CARTs or CAR-expressing NK cells, (particularly with murine scFv bearing CARTs) is anaphylaxis after multiple treatments.

Without being bound by this theory, it is believed that such an anaphylactic response might be caused by a patient developing humoral anti-CAR response, i.e., anti-CAR antibodies having an anti-IgE isotype. It is thought that a patient's antibody producing cells undergo a class switch from IgG isotype (that does not cause anaphylaxis) to IgE isotype when there is a ten to fourteen day break in exposure to antigen.

If a patient is at high risk of generating an anti-CAR antibody response during the course of transient CAR therapy (such as those generated by RNA transductions), CART infusion breaks should not last more than ten to fourteen days.

Diagnostic Methods

In another aspect, the present invention provides a method of diagnosing a disease such as cancer by detecting GFRα4 protein in a test sample with the use of the antibody of the present invention. Because GFRα4 is present in normal thyroid tissue this method is useful when the patient expresses GFRα4 in either non-thyroid tissue or has already undergone a thyroidectomy.

The detection used herein includes quantitative detection and non-quantitative detection. The non-quantitative detection include, for example, determination of merely whether or not GFRα4 protein is present, determination of whether or not a specific amount or more of GFRα4 protein is present, determination for comparison of the amount of GFRα4 protein with that of another sample (e.g., a control sample). The quantitative detection includes determination of the concentration of GFRα4 protein, determination of the amount of GFRα4 protein.

The test sample is not particularly limited as long as it is a sample that may contain GFRα4 protein. Specific examples of the test sample may include biopsy from the thyroid, biopsy from the medullary thyroid, blood, serum and/or plasma. In addition, a sample obtained from the test sample such as culture solution of cells collected from the body of the living organism is also included in the test sample of the present invention.

The cancer to be diagnosed preferably limited to medullary thyroid cancer (MTC). Other thyroid cancer could potentially be diagnosed such as papillary thyroid cancer, follicular thyroid cancer, and anaplastic thyroid cancer.

GFRα4 to be detected is not particularly limited, and may be either full-length GFRα4 (i.e. GFRa4 isoform "a" and/or GFRa4 isoform "b") or a fragment thereof. In the case where a fragment of GFRα4 is detected, it may be either the N-terminal fragment or the C-terminal fragment.

The method of detecting GFRα4 protein contained in a test sample is not particularly limited, however, detection is preferably performed by an immunological method with the use of an anti-GFRα4 antibody. Examples of the immunological method include, for example, a radioimmunoassay, an enzyme immunoassay, a fluorescence immunoassay, a luminescence immunoassay, immunoprecipitation, a turbidimetric immunoassay. Preferred is an enzyme immunoassay, and particularly preferred is an enzyme-linked immunosorbent assay (ELISA) (e.g., a sandwich ELISA). The above-mentioned immunological method such as an ELISA can be carried out by a method known to those skilled in the art.

A general detection method with the use of an anti-GFRα4 antibody comprises immobilizing an anti-GFRα4 antibody on a support, adding a test sample thereto, incubating the support to allow the anti-GFRα4 antibody and GFRα4 protein to bind to each other, washing the support, and detecting the GFRα4 protein binding to the support via the anti-GFRα4 antibody to detect GFRα4 protein in a test sample.

The binding between the anti-GFRα4 antibody and the GFRα4 protein is generally carried out in a buffer. Buffers used in the invention include, for example, a phosphate buffer, a Tris buffer. Incubation is carried out under the conditions generally employed in the art, for example, at 4° C. to room temperature for 1 hour to 24 hours. The washing after incubation can be carried out by any method as long as it does not inhibit the binding between the GFRα4 protein and the anti-GFRα4 antibody, using for example a buffer containing a surfactant such as Tween 20.

In the method of detecting GFRα4 protein of the present invention, a control sample may be provided in addition to a test sample to be tested for GFRα4 protein. The control samples include a negative control sample that does not contain GFRα4 protein and a positive control sample that contains GFRα4 protein. In this case, it is possible to detect GFRα4 protein in the test sample by comparing the result obtained with the negative control sample that does not contain GFRα4 protein with the result obtained with the positive control sample that contains GFRα4 protein. It is also possible to quantitatively detect GFRα4 protein contained in the test sample by obtaining the detection results of the control samples and the test sample as numerical values, and comparing these numerical values.

One method for detecting GFRα4 protein binding to the support via an anti-GFRα4 antibody is a method that employs an anti-GFRα4 antibody labeled with a detectable label. For example, GFRα4 protein may be detected by contacting the test sample with an anti-GFRα4 antibody immobilized on the support, washing the support, and then detecting GFRα4 with the use of the labeled antibody that specifically binds to GFRα4 protein.

The labeling of an anti-GFRα4 antibody can be carried out by any method known in the art. Examples of the detectable label known to those skilled in the art include a fluorescent dye, an enzyme, a coenzyme, a chemiluminescent substance or a radioactive substance. Specific examples may include radioisotopes ($^{32}P$, $^{14}C$, $^{125}I$, $^{3}H$, $^{131}I$ and the like), fluorescein, rhodamine, dansyl chloride, umbelliferone, luciferase, peroxidase, alkaline phosphatase, beta-galactosidase, beta-glucosidase, horseradish peroxidase, glucoamylase, lysozyme, saccharide oxidase, microperoxidase, biotin and the like. In the case where biotin is used as a detectable label, it is preferred that a biotin-labeled antibody is added, and then avidin conjugated to an enzyme such as alkaline phosphatase is further added.

Specifically, a solution containing an anti-GFRα4 antibody is added to a support such as a plate to allow the anti-GFRα4 antibody to be immobilized. After washing, the plate is blocked with, for example, BSA in order to prevent the nonspecific binding of a protein. The plate is washed again, and then the test sample is added to the plate. After being incubated, the plate is washed, and then the labeled anti-GFRα4 antibody is added. After being incubated appropriately, the plate is washed, and then the labeled anti-GFRα4 antibody remaining on the plate is detected (e.g.

GFRα4 ELISA kit, mybiosource.com Product_id=939378). The detection of the protein can be carried out by a method known to those skilled in the art. For example, in the case where the antibody is labeled with a radioactive substance, the protein may be detected by liquid scintillation or the RIA method. In the case where the antibody is labeled with an enzyme, the protein may be detected by adding a substrate and detecting an enzymatic change of the substrate such as color development with an absorbance reader. In the case where the antibody is labeled with a fluorescent substance, the protein may be detected with the use of a fluorometer.

A particularly preferred embodiment of the method of detecting GFRα4 protein of the present invention is a method using an anti-GFRα4 antibody labeled with biotin and avidin. Specifically, a solution containing an anti-GFRα4 antibody is added to a support such as a plate to allow the anti-GFRα4 antibody to be immobilized thereon. After washing, the plate is blocked with, for example, BSA in order to prevent the nonspecific binding of a protein. The plate is washed again, and then the test sample is added to the plate. After being incubated, the plate is washed, and then the biotin-labeled anti-GFRα4 antibody is added. After being incubated appropriately, the plate is washed, and then avidin conjugated to an enzyme such as alkaline phosphatase or peroxidase is added. After being incubated, the plate is washed, and then a substrate of the enzyme conjugated to avidin is added. Then, GFRα4 protein is detected by means of the enzymatic change of the substrate as an indicator.

Another embodiment of the method of detecting GFRα4 protein of the present invention is a method using a primary antibody that specifically binds to GFRα4 protein and a secondary antibody that specifically binds to the primary antibody. For example, the test sample is brought into contact with an anti-GFRα4 antibody immobilized on the support, the support is incubated and washed, and the bound GFRα4 protein after washing is detected with a primary anti-GFRα4 antibody and a secondary antibody that specifically binds to the primary antibody. In this case, the secondary antibody is preferably labeled with a detectable label.

Specifically, a solution containing an anti-GFRα4 antibody is added to a support such as a plate to allow the anti-GFRα4 antibody to be immobilized thereon. After washing, the plate is blocked with, for example, BSA in order to prevent the nonspecific binding of a protein. The plate is washed again, and then the test sample is added to the plate. After being incubated, the plate is washed, and then a primary anti-GFRα4 antibody is added. After being incubated appropriately, the plate is washed, and then a secondary antibody that specifically binds to the primary antibody is added. After being incubated appropriately, the plate is washed, and then the secondary antibody remaining on the plate is detected. The detection of the secondary antibody can be carried out by the above-mentioned method.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The following experiments were designed to develop and validate GFRα4-specific antibodies, GFRα4 CAR molecules, and GFRα4 CART therapy. The results of the experiments are now described.

Example 1: Isolation of 2 Unique Human/Rabbit Chimeric Fab Antibodies to GFRα4

Antibody phage display was performed utilizing a naïve chimeric human/rabbit Fab library and solid phase antibody selection against immobilized human GFRα4. For construction of the library, rabbit spleen and bone marrow for the preparation of B-cell RNA was provided by Pocono Rabbit Farm & Laboratory (PRF&L, Canadensis, PA) and R & R Research (Stanwood, WA). A total of nine rabbits (ages 3-4 months) were used. Five of these rabbits were of the New Zealand White (NZW) strain, with three obtained from PRF&L and two obtained from R & R Research. Four b9 wild-type rabbits were also used and obtained from a separate R & R Research colony (Popkov et al., J. Mol. Biol. 325, 325-335, 2003). Total RNA was prepared from spleen and bone marrow from each rabbit and RT-PCR amplification of rabbit $V_κ$, $V_λ$, and $V_H$ encoding sequences was performed using established protocols (Rader, et al., Methods Mol. Biol. 525, 101-128, 2009). Rabbit (rb) $V_κ$/human (hu) $C_κ$/rb$V_H$ and rb$V_λ$/hu$C_λ$/rb$V_H$ segments, respectively, were assembled in one fusion step based on 3-fragment overlap extension PCR as described. VL derived from b9 rabbits were also assembled with $V_H$ from NZW rabbits. The Fab-encoding fragments (less the heavy chain $C_{H1}$ constant domain) were digested with SfiI and ligated at 16° C. for 24 h with SfiI-digested phage display vector pC3C that provided the $C_{H1}$ domain to complete the Fab construct (Hofer et al., J. Immunol. Methods 318, 75-87, 2007). Subsequently, 15 g of purified pC3C-rb$V_κ$/h$C_κ$/rb$V_H$/h$C_{H1}$ ligated products were transformed into *E. coli* strain SR320 by 30 separate electroporations (each using 0.5 μg DNA in 50 μl electrocompetent cells) and yielded $7.5×10^9$ independent transformants for the γ/κ-light chain sub-library. For the γ/λ-light chain sub-library, $4.8×10^9$ independent transformants were obtained using the same procedure. Using VCSM13 helper phage (Stratagene, La Jolla, CA), the phagemid libraries were converted to phage particle libraries and stored at −80° C. The day prior to selecting anti-GFRα4 antibodies from the κ and λ libraries, reamplification of phagemids in XL1-Blue strain of *E. coli* (Stratagene) was performed and equal volumes of each library were combined.

Library selections against human Fc-fusion constructs of immobilized GFRα4 isoforms a (GFRα4a) and b (GFRα4b) were performed in separate experiments and carried out as described in Rader and colleagues (Rader et al., Selection from antibody libraries in Phage Display: A Laboratory Manual (Chapter 10), eds. Barbas, C. F., Burton, D. R., Scott, J. K., and Silverman, G. J., 10.1-10.20; 2001) with the following modifications. For each round of panning, 8 wells of an ELISA plate (½-area wells, Costar #3690, Corning Life Sciences, Tewksbury, MA) were each coated overnight at 4° C. with 50 μl of a 10 μg/ml PBS solution of either GFRα4a (R&D Systems, Inc.) or GFRα4b (LakePharma, Inc.) and blocked with 2% nonfat dry milk in PBS (MPBS) for 1 hour at 37° C. In order to target the capture of GFRα4-specific antibodies, phage were initially incubated with a mixture of soluble human GFRα1, GFRα2, and GFRα3 (R&D Systems, Inc., 6 μg/ml final concentration) in MPBS and blocked for 1 hour at room temperature. Addition of phage (with GFRα's 1, 2, and 3) to antigen-coated wells, incubation, washing, low pH buffer elution of bound phage, and overnight phage amplification were performed as described (Steinberger et al., Analysis of Selected Antibodies in Phage Display: A Laboratory Manual (Chapter 11), eds Barbas, C. F., Burton, D. R., Scott, J. K., and Silverman, G. J., 11.1-11.24; 2001).

GFRalpha4 isoform "a" (GFRα4a) was purchased from R&D Systems (Minneapolis, MN) and comprises a portion of GFRα 4a (Asn24-Ser245, UniProt accession Q9GZZ7-2), followed by a Factor Xa cleavage site/linker, a portion of optimized human IgG1 Fc domain (Pro100-Lys330), and 6 His residues (SEQ ID NO: 212) for purification (FIG. 1).

```
GFRα4a construct Amino acid sequence
                                        (SEQ ID NO: 212)
NRCVDAAEACTADARCQRLRSEYVAQCLGRAAQGGCPRARCRRALRRFFA

RGPPALTHALLFCPCAGPACAERRRQTFVPSCAFSGPGPAPPSCLEPLNF

CERSRVCRPRLLAFQVSCTPAPSAPDGCLLDQGARCLRAYAGLVGTAVTP

NYVDNVSARVAPWCDCGASGNRREDCEAFRGLFTRNRCLDGAIQAFASGW

PPVLLDQLNPQGDPEHSLLQVSIEGRMDPKSCDKTHTCPPCPAPEAEGAP

SVFLEPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISK

AKGQPREPQVYTLPPSRDELTKNQVSLTCLVKGEYPSDIAVEWESNGQPE

NNYKATPPVLDSDGSFFLYSKLTVDKSRWQQGNVFSCSVMHEALHNHYTQ

KSLSLSPGKHREIRHH
```

GFRalpha4 isoform "b" (GFRα4b) was purchased from LakePharma, Inc. (Belmont, CA) and comprises a portion of GFRα 4b (Asn24-Val274, UniProt #Q9GZZ7-1), followed by a TEV cleavage site linker, and a portion of human IgG1 Fc domain (Asp104-Lys330) (FIG. 2).

```
GFRa4b construct Amino acid sequence
                                        (SEQ ID NO: 213)
NRCVDAAEACTADARCQRLRSEYVAQCLGRAAQGGCPRARCRRALRRFFA

RGPPALTHALLFCPCAGPACAERRRQTFVPSCAFSGPGPAPPSCLEPLNF

CERSRVCRCARAAAGPWRGWGRGLSPAHRPPAAQASPPGLSGLVHPSAQR

PRRLPAGPGRPLPARLRGPRGVPAGTAVTPNYVDNVSARVAPWCDCGASG

NRREDCEAFRGLFTRNRCLDGAIQAFASGWPPVLLDQLNPQGDPEHSLLQ

VGGGENLYFQGGGGGAGGGGDKTHTCPPCPAPELLGGPSVFLEPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK
```

After 4 rounds of selection of the phage display library on either GFRα4a or GFRα4b, phage ELISAs were performed to assess enrichment in the capture of anti-GFRα4-binding phage (Steinberger et al., Analysis of Selected Antibodies in Phage Display: A Laboratory Manual (Chapter 11), eds Barbas, C. F., Burton, D. R., Scott, J. K., and Silverman, G. J. 11.1-11.24; 2001). Significant enrichment was observed beginning in panning round 3 with only background reactivity to wells coated with GFRα1, GFRα2, or GFRα3. Individual monoclonal phage preparations were prepared from rounds 3 and 4 of selection for the GFRα4a and GFRα4b libraries, and phage ELISAs were performed to identify positive clones. For the GFRα4a library, 18 of 19 randomly selected phage clones were positive against wells coated with GFRα4a. Nucleotide sequencing of antibody heavy and light chains of positive clones revealed 2 unique antibodies designated P4-6 and P4-10. Subsequently, these 2 phage antibodies were also found to bind to GFRα4b even though they were the result of a panning experiment selecting against GFRα4a. For the GFRα4b-panned library, 8 of 8 randomly selected phage clones were positive against GFRα4b, and all of these clones cross-reacted with GFRα4a. Nucleotide sequencing of theses clones showed them to all be the same antibody and to be identical to antibody P4-10 originally identified in the GFRα4a selection experiment.

The amino acid and nucleotide sequences for the P4-6 and P4-10 antibodies identified are provided in Table 2 (in the Detailed Description).

To verify that human/rabbit Fabs P4-6 and P4-10 retain their binding to both isoforms of GFRα4 but do not cross-react with GFRα1, GFRα2, and GFRα3 when expressed as soluble Fabs (i.e. unlinked to phage particles), Fabs were expressed in *E. coli* without helper phage rescue and harvested from the periplasmic space as described (Elia et al., Production and purification of Fab and scFv in Phage Display: A Laboratory Manual (Chapter 12), eds Barbas, C. F., Burton, D. R., Scott, J. K., and Silverman, G. J. 12.1-12.26; 2001) (FIG. 3).

In sum, this example demonstrates the isolation of 2 novel and unique human/rabbit chimeric monoclonal Fab antibodies (P4-6 and P4-10) to be used for development of potential humoral or cellular therapies for the treatment of medullary thyroid carcinoma.

Example 2—Expression of P4-6 and P4-10 scFv's as CARs

Figure 4A:
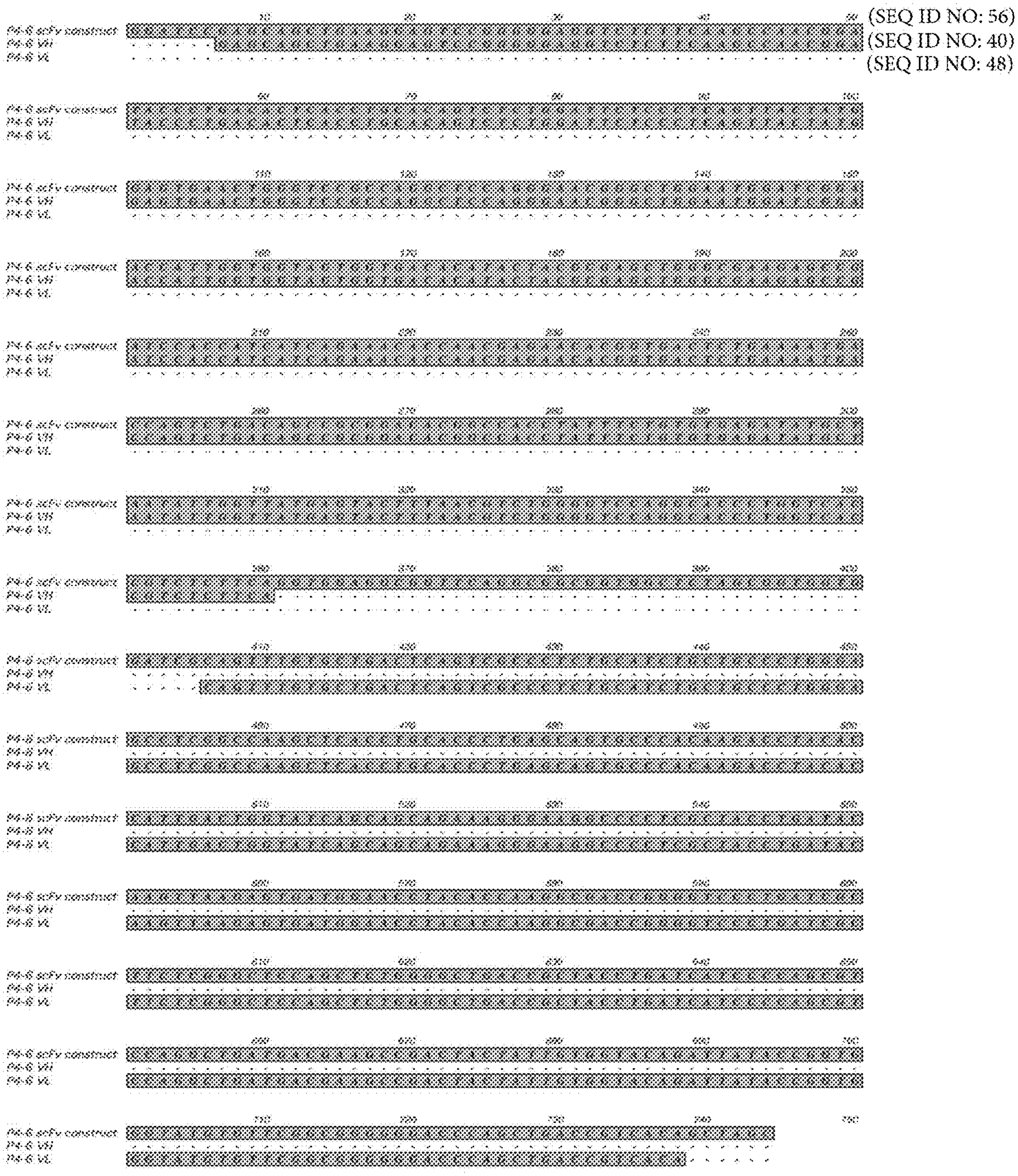
FIGS. 4A and 4B, is a sequence alignment showing how the P4-6 scFv construct with restriction sites and linker was pieced together from P4-6 $V_H$ and $V_L$ segments.
Figure 4B:
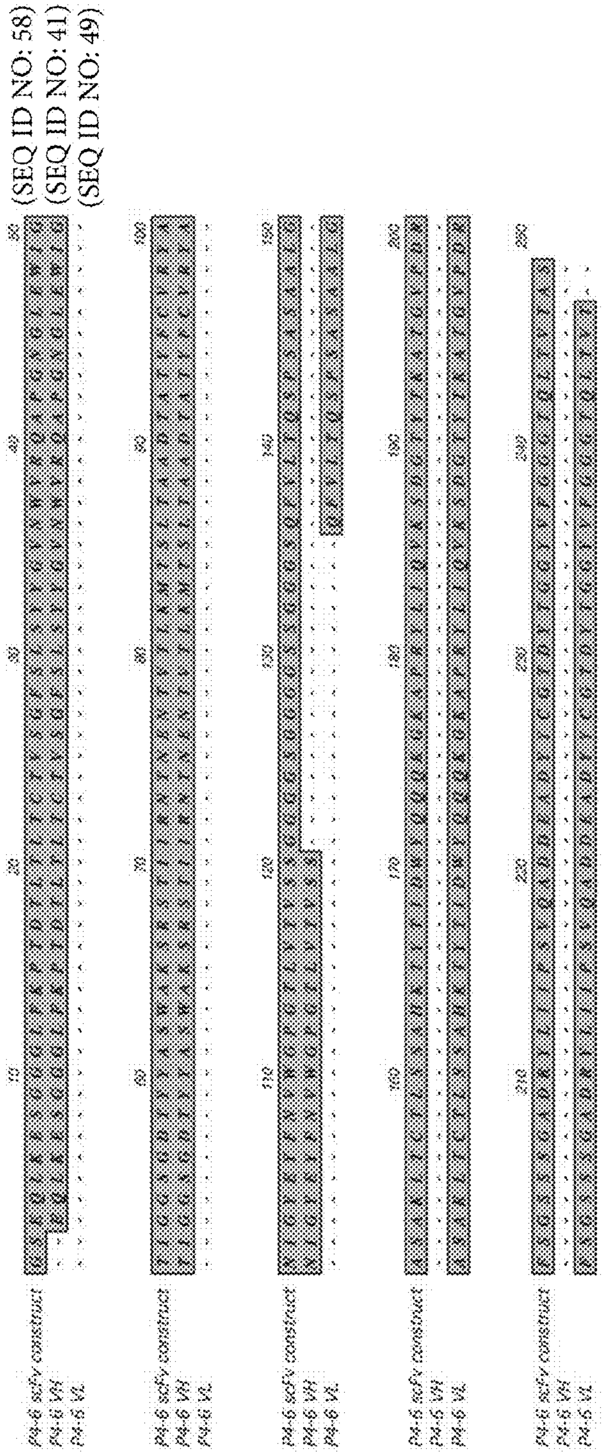
Figure 5A:
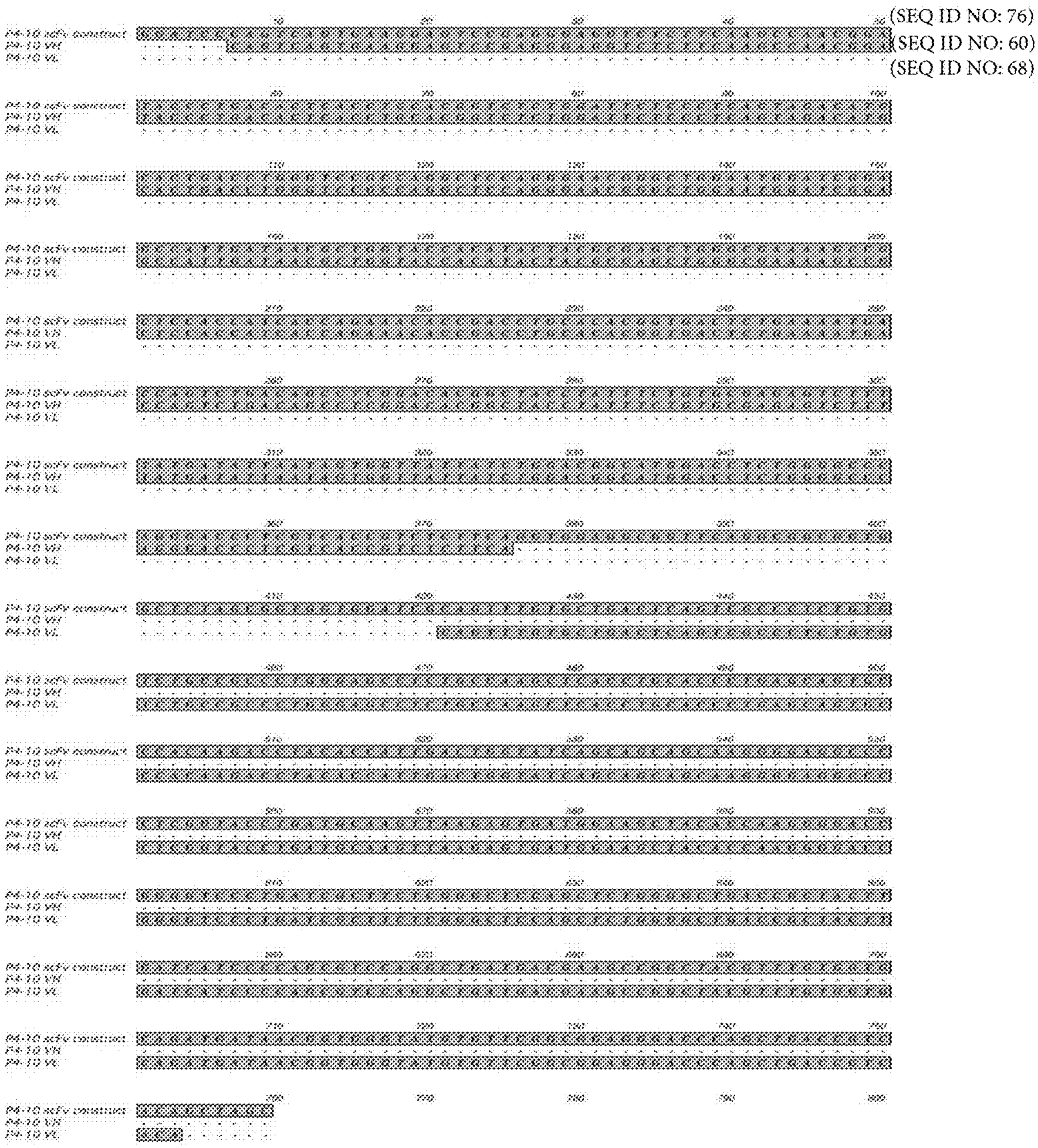
FIGS. 5A and 5B, is a sequence alignment showing how the P4-10 scFv construct with restriction sites and linker was pieced together from P4-10 $V_H$ and $V_L$ segments.
Figure 5B:
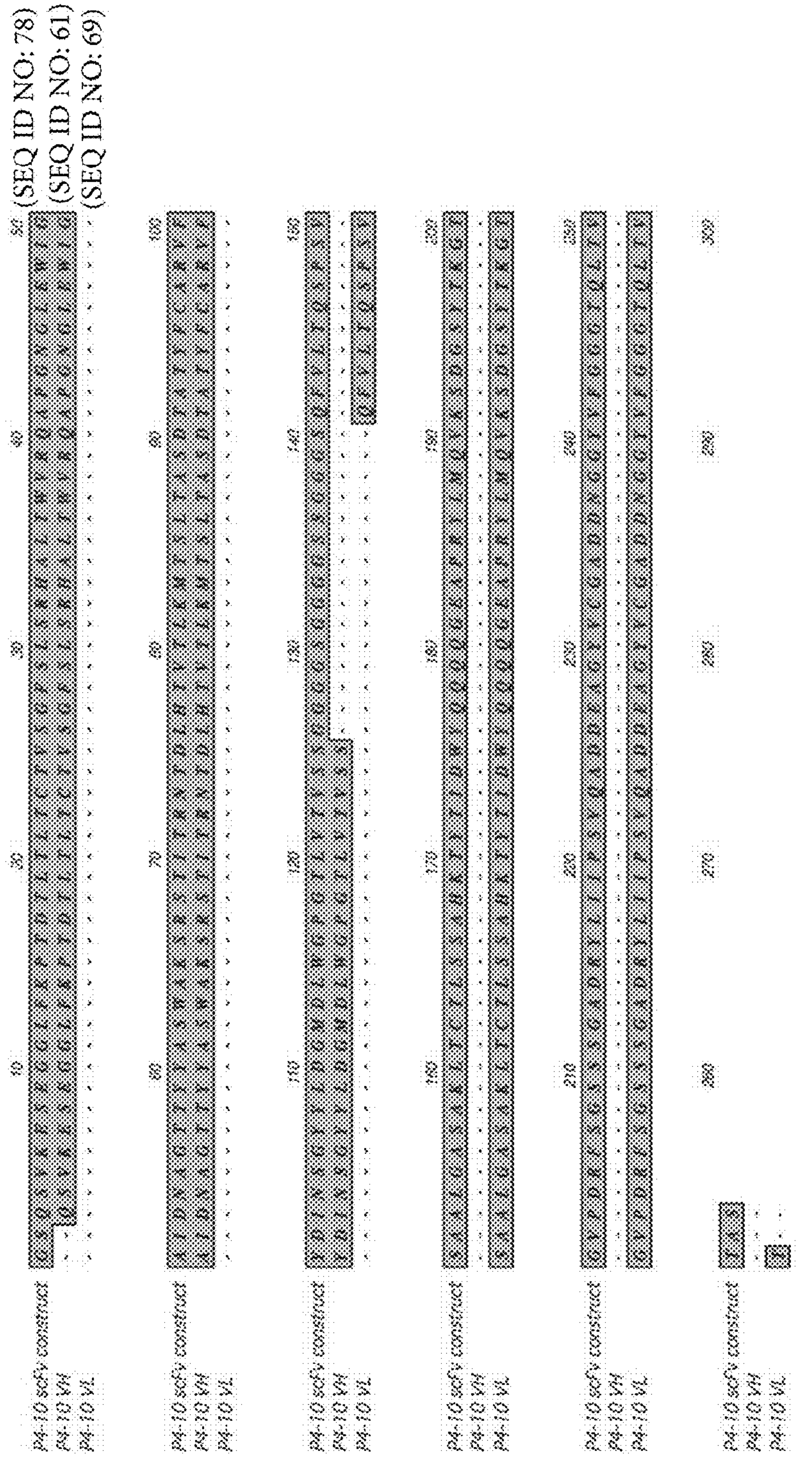
Figure 6:
FIG. 6 is a sequence alignment comparing the nucleotide bases between the original P4-6 scFv construct (SEQ ID NO: 56) and the human codon optimized P4-6 scFv construct (SEQ ID NO: 57) used for CAR construction.
Figure 7:
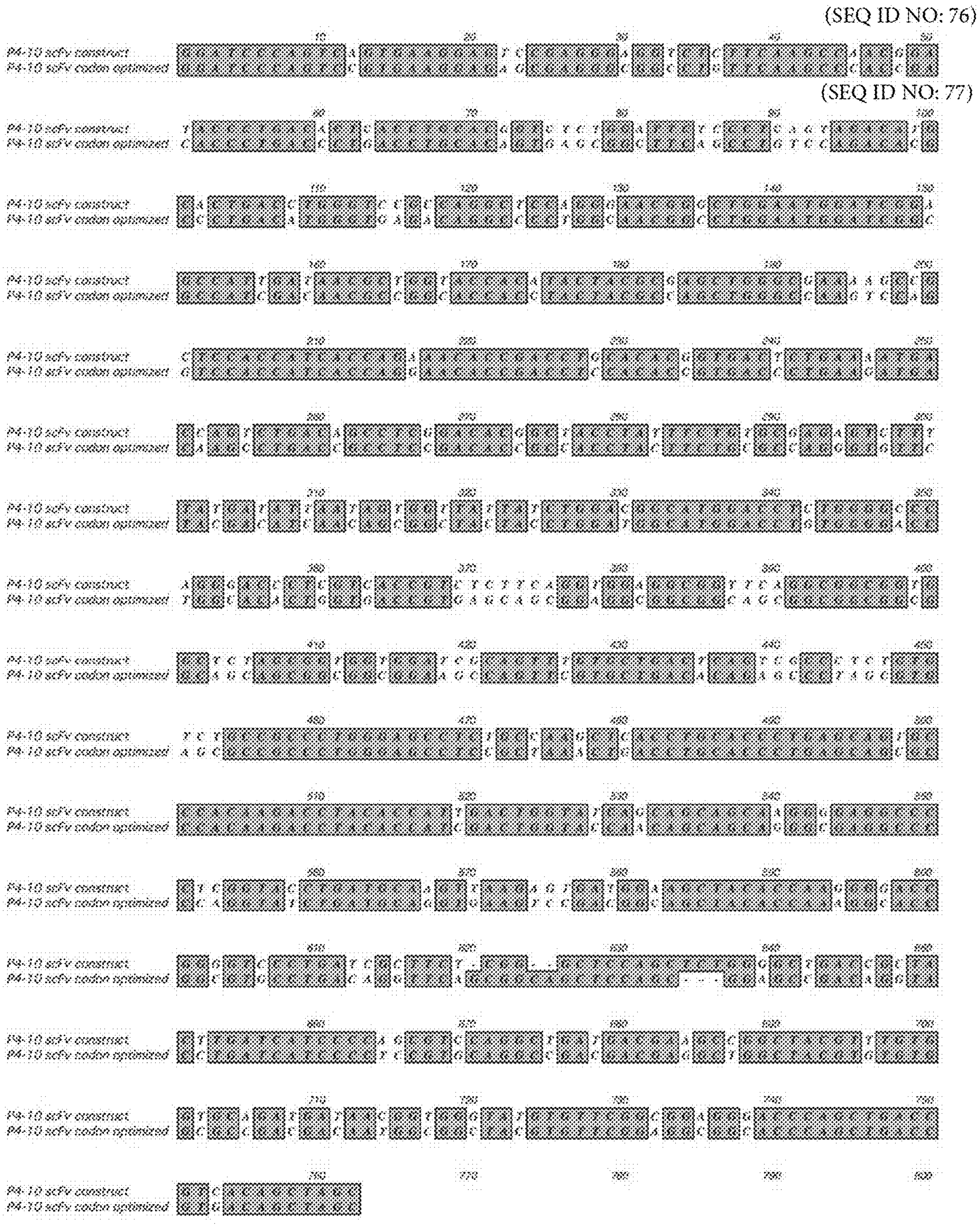
FIG. 7 is a sequence alignment comparing the nucleotide bases between the original P4-10 scFv construct (SEQ ID NO: 76) and the human codon optimized P4-10 scFv construct (SEQ ID NO: 77) used for CAR construction.
Figure 8:
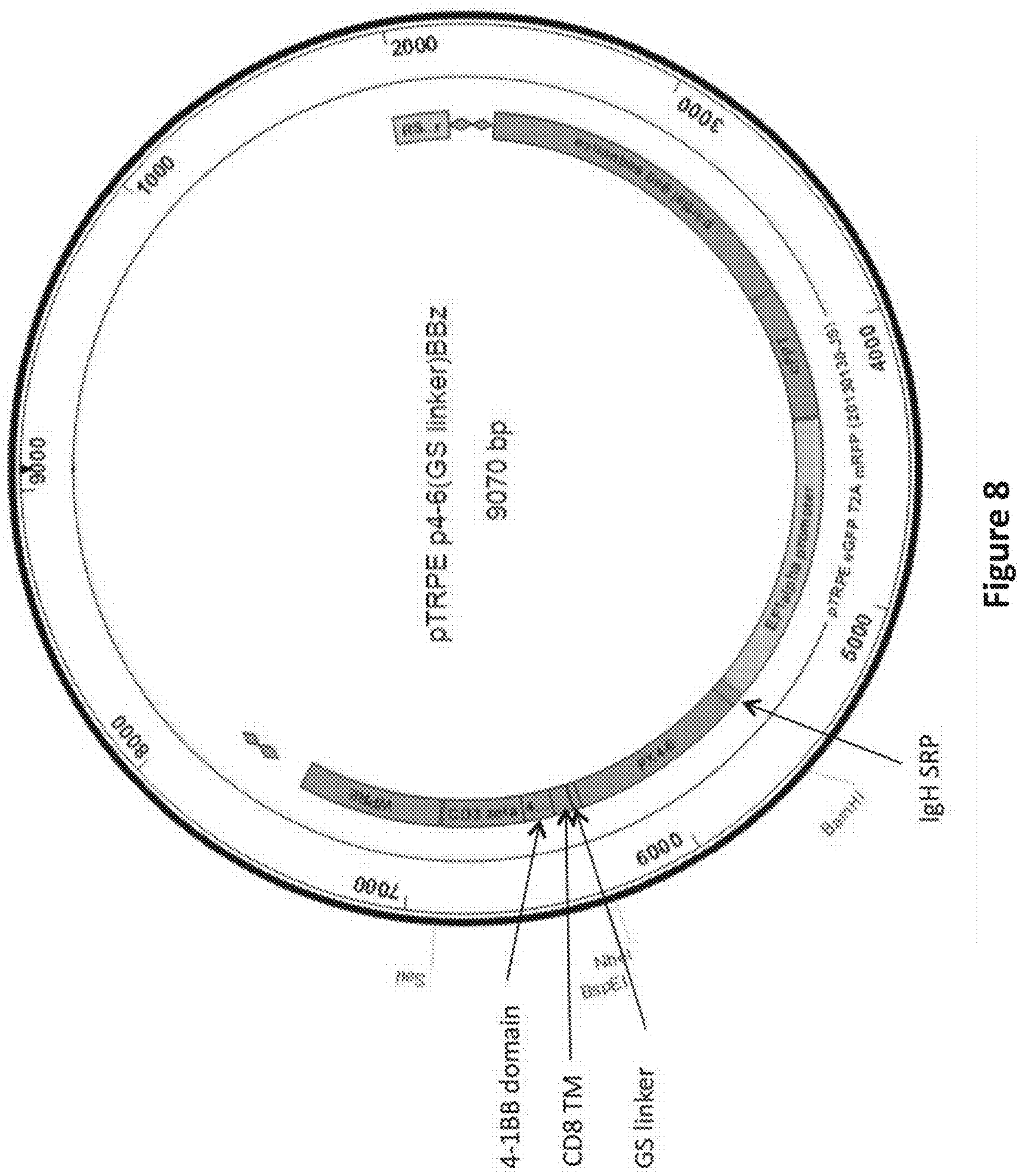
FIG. 8 illustrates the map of the P4-6 CAR GS linker BBz plasmid. Map indicates the position of anti-GFRα4 scFv P4-6, glycine/serine rich linker, CD8 transmembrane domain, and the cytoplasmic fragment of the 4-1BB domain. In addition, the drawing depicts the positions of other components necessary for lentiviral construction as described in WO/2012/079000.
Figure 9:
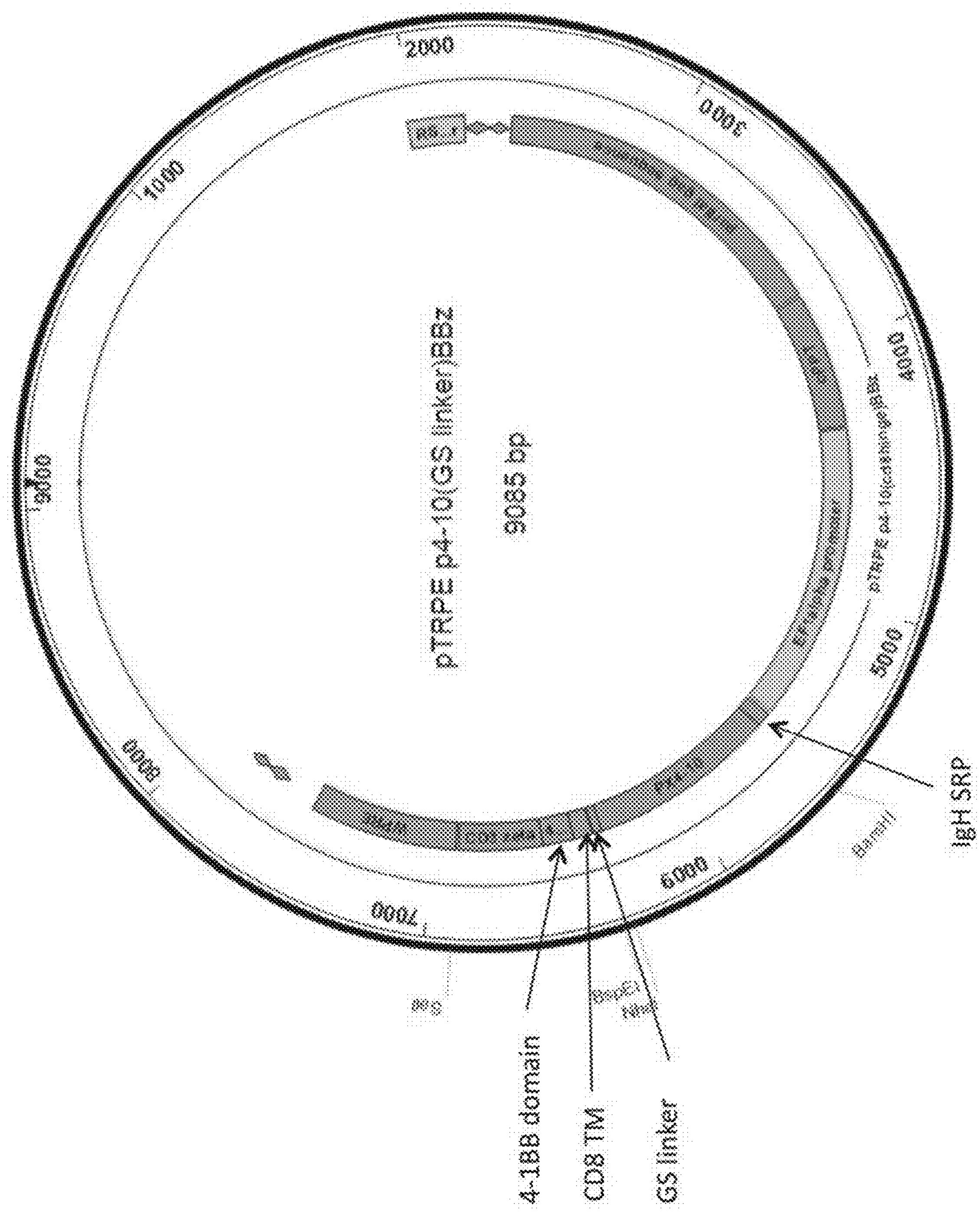
FIG. 9 illustrates the map of the P4-10 CAR GS linker BBz plasmid. Map indicates the position of anti-GFRα4 scFv P4-10, glycine/serine rich linker, CD8 transmembrane domain, and the cytoplasmic fragment of the 4-1BB domain. In addition, the drawing depicts the positions of other components necessary for lentiviral construction.

ScFv constructs for P4-6 and P4-10 based on the rabbit Fab $V_H/V_L$ nucleotide sequences were designed in the orientation $V_H$-linker-$V_L$ with the linker comprising nucleotides to encode a 15-amino acid glycine/serine rich peptide and with 5' and 3' BamH1 and Nhe1 restriction sites, respectively (SEQ ID NOs: 56, 58, 76, and 79). FIG. 4 shows nucleotide (FIG. 4A) and amino acid (FIG. 4B) alignments of the individual $V_H$ and $V_L$ segments to the scFv P4-6 construct. FIG. 5 shows nucleotide (FIG. 5A) and amino acid alignments (FIG. 5B) of the individual $V_H$ and $V_L$ segments to the scFv P4-10 construct. Optimization for human codon usage (except for restriction sites) was performed by Genewiz, Inc. (South Plainfield, NJ). FIGS. 6 and 7 show nucleotide sequences of optimized P4-6 (SEQ ID NO: 57) and P4-10 (SEQ ID NO: 77) scFv constructs. FIGS. 6 and 7 compare original and optimized nucleotide sequences for P4-6 and P4-10.

Figure 10:
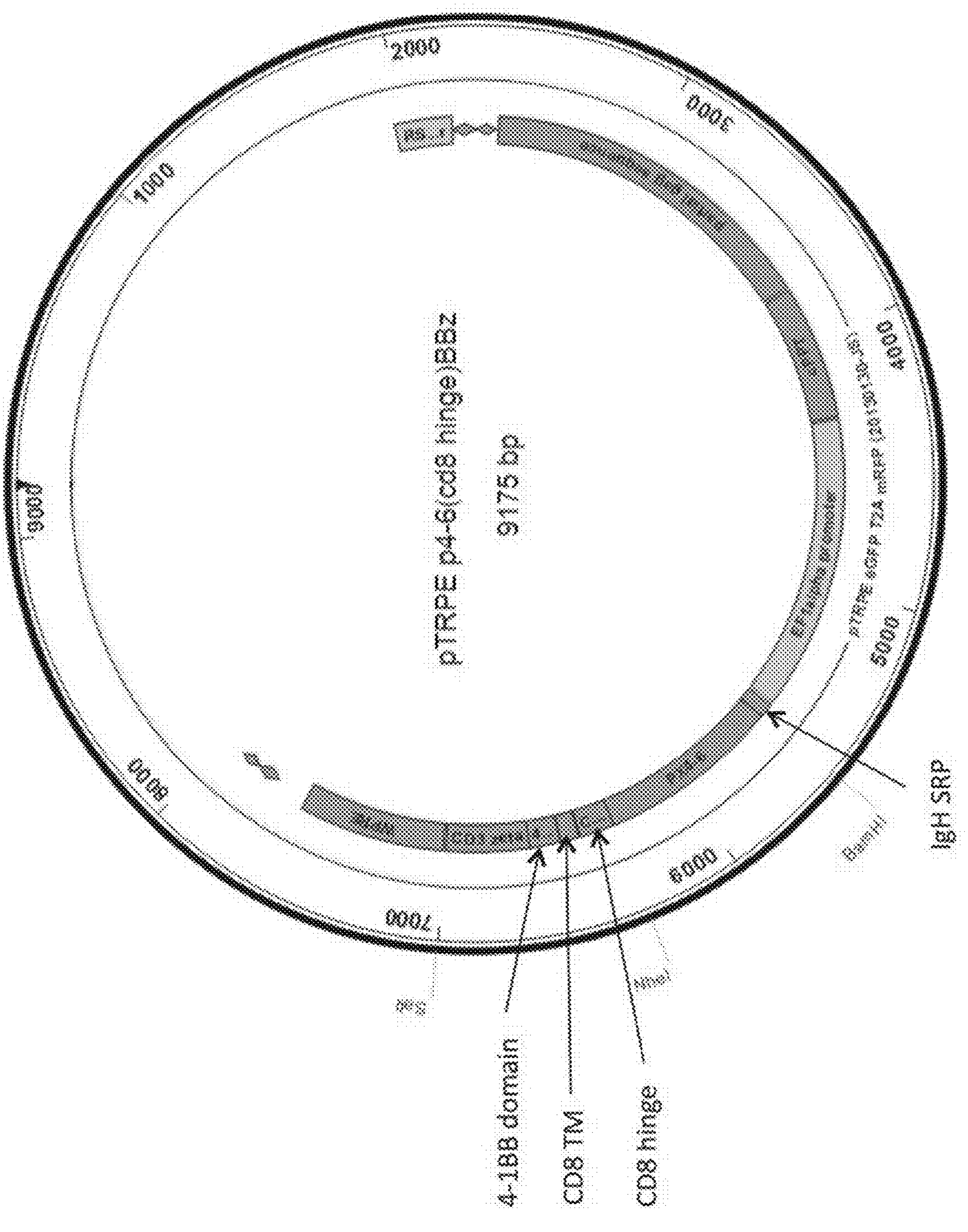
FIG. 10 illustrates the map of the P4-6 CD8 linker BBz plasmid. Map indicates the position of anti-GFRα4 scFv P4-6, CD8 hinge linker, CD8 transmembrane domain, and the cytoplasmic fragment of the 4-1BB domain. In addition, the drawing depicts the positions of other components necessary for lentiviral construction.
Figure 11:
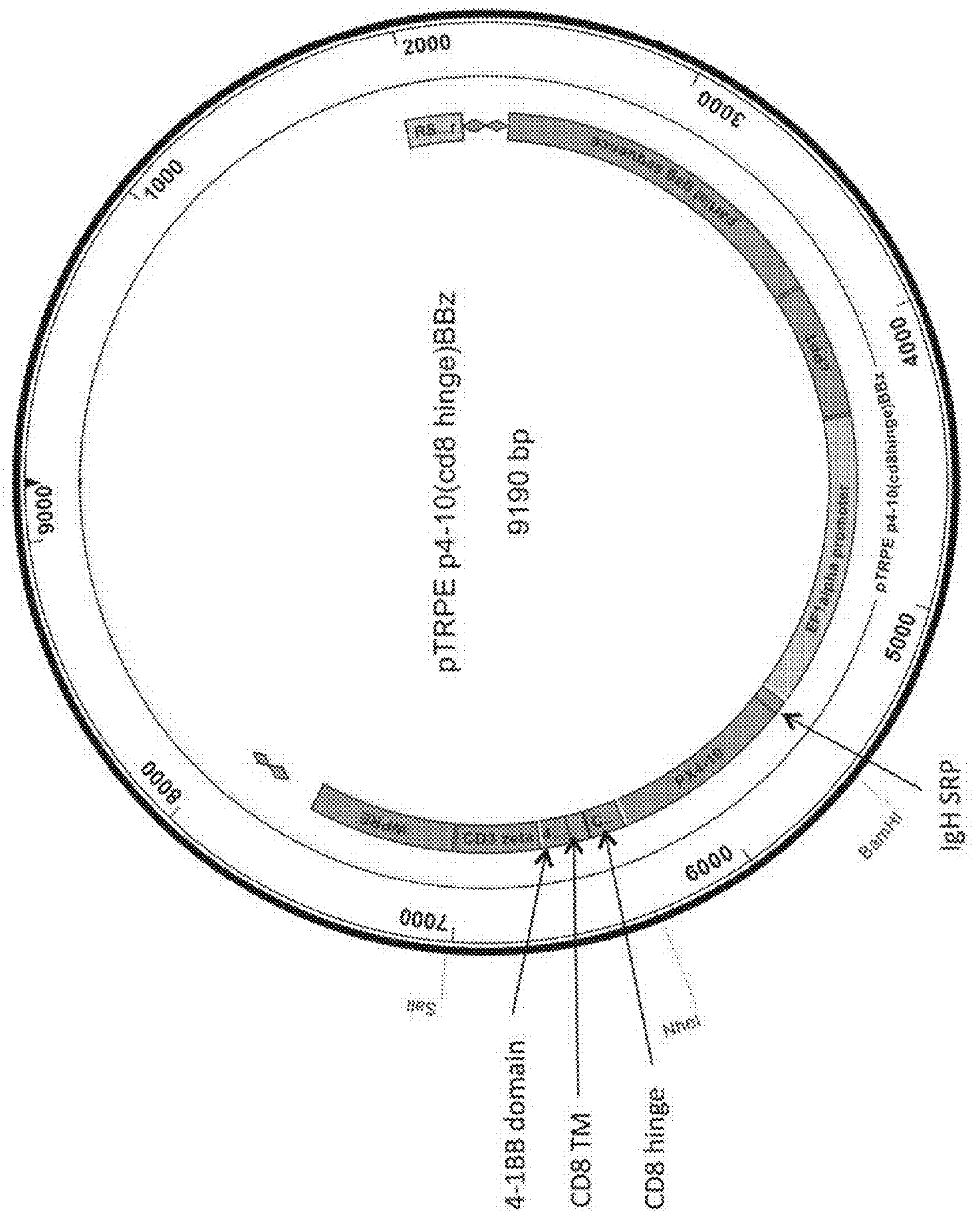
FIG. 11 illustrates the map of the P4-10 CD8 linker BBz plasmid. Map indicates the position of anti-GFRα4 scFv P4-10, CD8 hinge linker, CD8 transmembrane domain, and the cytoplasmic fragment of the 4-1BB domain. In addition, the drawing depicts the positions of other components necessary for lentiviral construction.

ScFv constructs for P4-6 and P4-10 were restriction digested with BamH1 and NheI and ligated into the corresponding restriction sites of plasmid vectors that provide a 10-amino acid glycine/serine (GS)-rich linker (GGGGSGGGGS (SEQ ID NO: 5)) at the carboxy terminus of the scFv, followed by the transmembrane domain of human CD8, a 4-1BB domain and CD3zeta domain sequentially (plasmids pTRPE p4-6(GS linker)BBz, and pTRPE p4-10(GS linker)BBz, FIGS. 10 and 11 respectively). The resulting vectors encode CARs termed P4-6gs or P4-6(gs) bbz (SEQ ID NO: 105) and P4-10gs or P4-10(gs)bbz (SEQ ID NO: 106). Additionally, scFv constructs for P4-6 and P4-10 were similarly ligated into vectors identical except that the 10-amino acid GS-rich linker was replaced with a 47-amino acid peptide derived from the human CD8a hinge region (plasmids pTRPE p4-6(CD8 hinge)BBz, and pTRPE p4-10(CD8 hinge)BBz, FIGS. 14 and 15 respectively). The resulting vectors encode CARs termed P4-6(cd8)bbz (SEQ ID NO: 107) and P4-10(cd8)bbz (SEQ ID NO: 108).

To generate lentiviral supernatants, LentiX-293T cells (Clontech, Inc., Mountain View, CA) were seeded on Day 0 and transfected using Lipofectamine 2000 (Life Technologies, Grand Island, NY) on Day 1 as described (Milone et al., Molec. Ther., 17, 1453-1464, 2009). For each construct, the plasmids used were pVSV-G (VSV glycoprotein expression plasmid), pRSV.REV (Rev expression plasmid), pMDLg/p-1.RRE (Gag/Pol expression plasmid), and the CAR transfer vector (pTRPE). Lentiviral-supernatants were filtered through 0.45 um pore size filters and concentrated by centrifugation at 12,000×g at 4° C. for 12-18 hours.

Reporter Jurkat T cells with a stably integrated NFAT promoter driven EGFP construct (Lin et al., J. Cell Biol., 162, 673-682., 2003; Hooijberg et al., Blood, 96, 459-466, 2003) were transduced with lentiviral supernatant to express the P4-6- and P4-10-containing CARs or a mesothelin-specific CAR control (SS1-KIRS2, Dr. V. Bhoj, unpublished) at a MOI of approximately 5. Primary T-cells were isolated, expanded and transduced as previously described (Milone et al., Molec. Ther., 17, 1453-1464, 2009).

Figure 12:
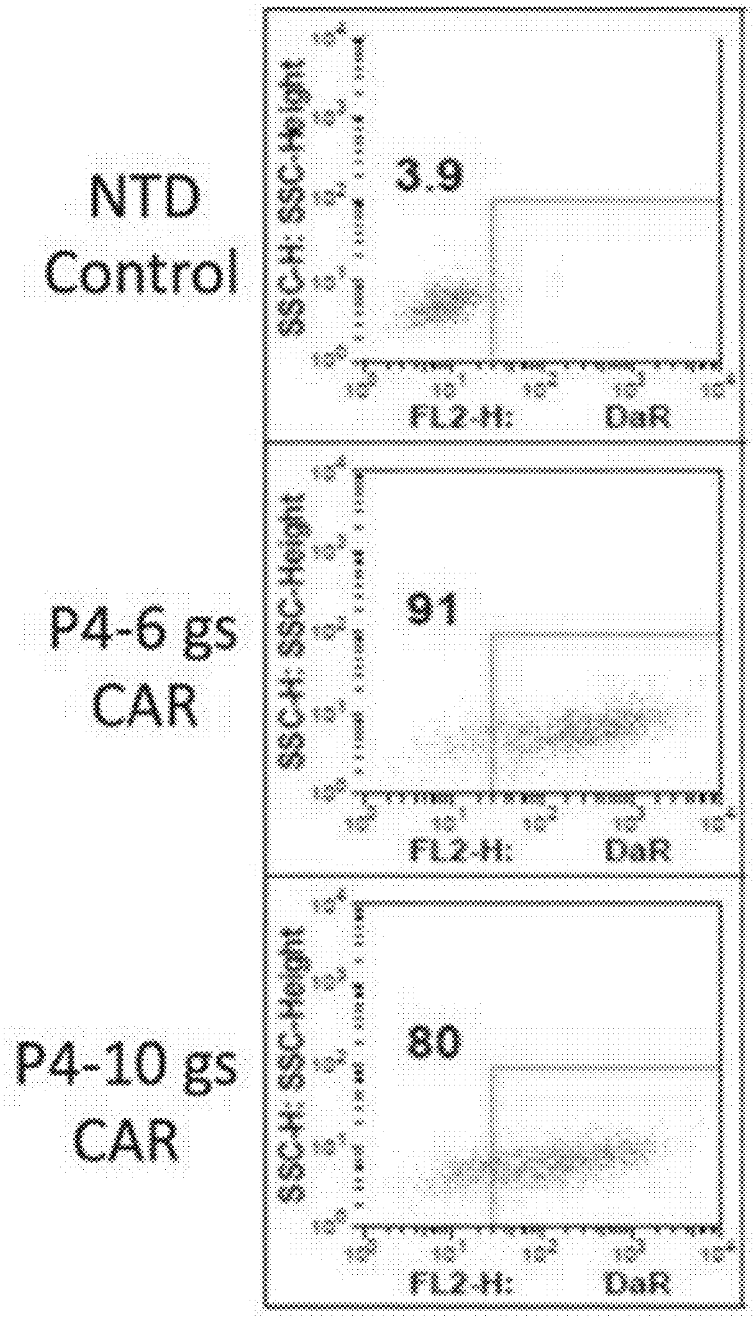
FIG. 12 is an image of the results of a flow cytometry experiment demonstrating the expression of the P4-6 and P4-10 scFv T bodies (CARs) on the T-cell surface. T bodies were detected with biotinylated donkey anti-rabbit IgG followed by phycoerythrin-conjugated streptavidin. Numbers on each panel adjacent to flow gate represent % cells positive for T body.

Expression of P4-6 and P4-10 scFv's on the extracellular portion of the CARs is illustrated for the GS linker set of scFv's along with non-transduced cells ("NTD") in FIG. 12 by flow cytometry (FACSCalibur (BD Biosciences, Franklin Lakes, NJ)) of cells stained with biotin-labeled F(ab')$_2$ fragment donkey anti-rabbit IgG (H+L) followed by streptavidin-conjugated-phycoerythrin (Jackson ImmunoResearch, West Grove, PA).

The nucleotide and amino acid sequences of the P4-6 and P4-10 scFv constructs are provided in Table 2 (in the Detailed Description).

Example 3—Reporter T Cells Expressing CART-P4-6 and CART-P4-10 are Specifically Activated by GFRα4

Figure 13:
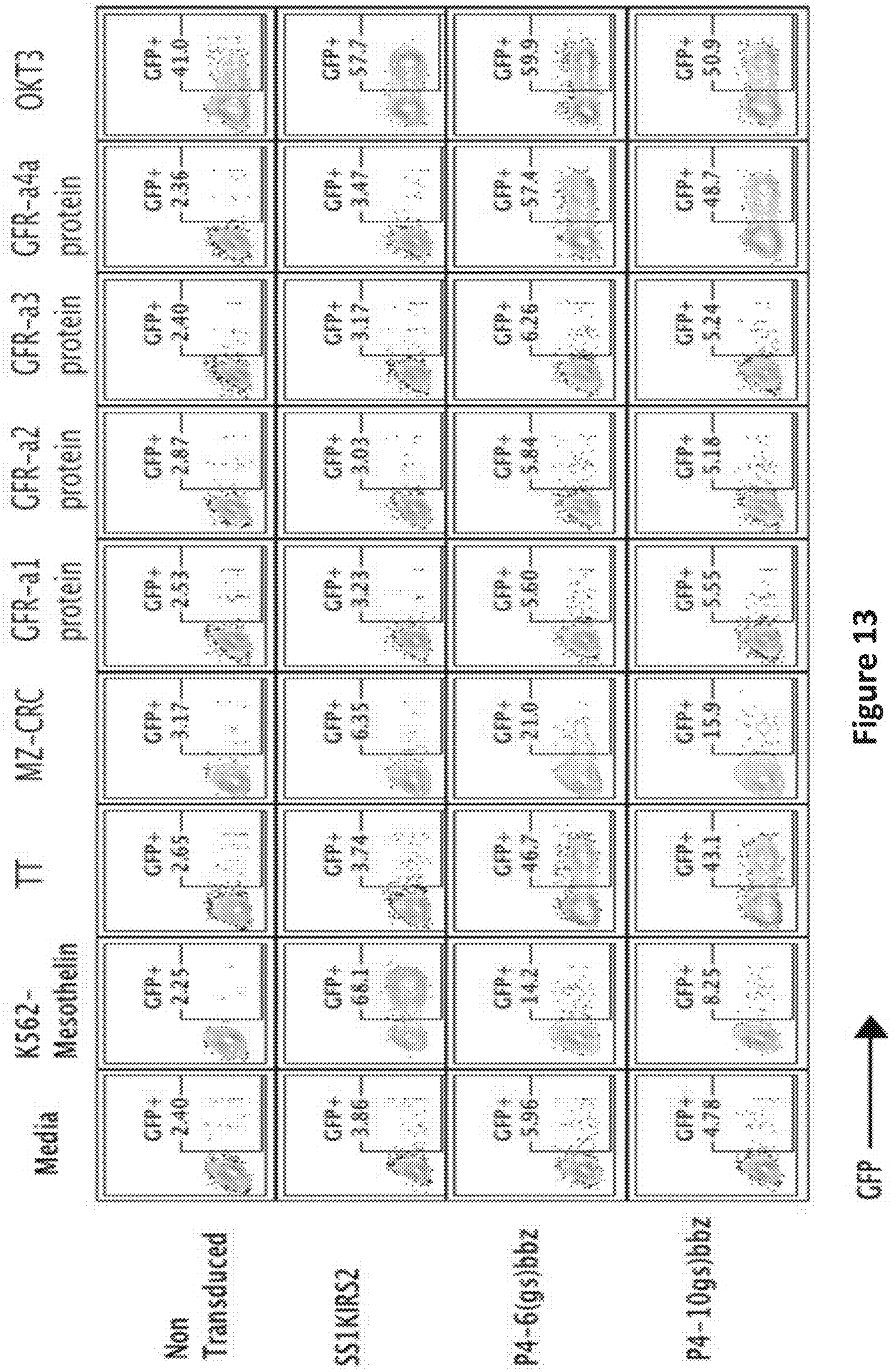
FIG. 13 is an image of a series of flow cytometric measurements demonstrating the specificity of anti-GFRα4 CARs. Reporter Jurkat cells expressing GFP under an NFAT-responsive promoter were transduced with P4-6(gs) or P4-10(gs) CAR's and incubated with various immobilized Fc-fusion proteins or cell lines. Figure shows that Jurkat cells are activated by immobilized GFRα4a protein, but not by its homologs GFRα1, GFRα2, and GFRα3. Figure also shows that TT cells as well as MZ-CRC-1 cells (both MTC cell lines) also activate the Jurkat cells, but not K562 cells expressing mesothelin. Jurkat cells expressing the mesothelin-specific CAR (SS1KIRS2) were activated by K562 mesothelin-expressing cells, but not by TT or MZ-CRC-1 cells or by the immobilized GFRα proteins, including GFRα4a. Wells coated with the anti-CD3 antibody OKT3 represent positive control. Numerical values in figure above GFP-positive cell gate represent percentage of total Jurkat reporter cells in the positive gate.

Reporter Jurkat cells expressing GFP under an NFAT-responsive promoter (Lin et al., J. Cell Biol., 162, 673-682., 2003; Hooijberg et al., Blood, 96, 459-466, 2003) transduced with P4-6gs and P4-10gs CARs were incubated with GFRα4-expressing cells and control cells, as well as with immobilized Fc-fusion proteins in order to assess the ability of GFRα4 to specifically activate reporter cells and trigger GFP expression. Fc-fusion proteins GFRα1, GFRα2, GFRα3 and GFRα4a were captured in tissue culture wells by first coating wells overnight with mouse anti-human-Fc (10 ug/ml) followed by 3 washes with PBS, blocking with 5% BSA/PBS for 1 hour, washing with PBS 3 times and then incubating overnight again with each of the GFRα-Fc fusion proteins in 1% BSA/PBS (5 ug/ml). OKT3 antibody was directly coated on wells by overnight incubation (10 ug/ml). Wells were then washed 3 times with PBS before Jurkat reporter cells containing no CAR, a mesothelin-specific CAR (SS1-KIRS2), or P4-6 and P4-10 GS linker CARs. Reporter Jurkats were incubated in the GFRα-Fc fusion proteins and OKT3-coated wells overnight. Reporter Jurkats were also co-incubated with K562 cells expressing mesothelin (Carpenito et al., Proc. Natl. Acad. Sci (USA), 106, 3360-3365; 2009), and medullary thyroid cancer cell lines TT (ATCC CRL-1803, Manassas, VA) and MZ-CRC-1 (Plaza-Menacho et al., Cancer Res., 65, 1729-1737, 2005) cells at a 1:1 ratio overnight. After overnight incubation, cells were analyzed by flow cytometry. Jurkat cells were gated based on forward- and side-light scatter characteristics and GFP expression was measured. As shown in FIG. 13, the Jurkat cells are activated by immobilized GFRα4a protein, but not by its homologs GFRα1, GFRα2, and GFRα3. TT cells as well as MZ-CRC-1 cells also activated the Jurkat cells (TT>MZ-CRC-1), but not K562 cells expressing mesothelin. Jurkat cells expressing the mesothelin-specific CAR (SS1KIRS2) were activated by K562 mesothelin-expressing cells, but not by TT or MZ-CRC-1 cells or by the immobilized GFRα proteins, including GFRα4a. Wells coated with the anti-CD3 antibody OKT3 served as a positive control. Numerical values in figure above GFP-positive cell gate represent % of total Jurkat reporter cells in the positive gate.

Figure 16:
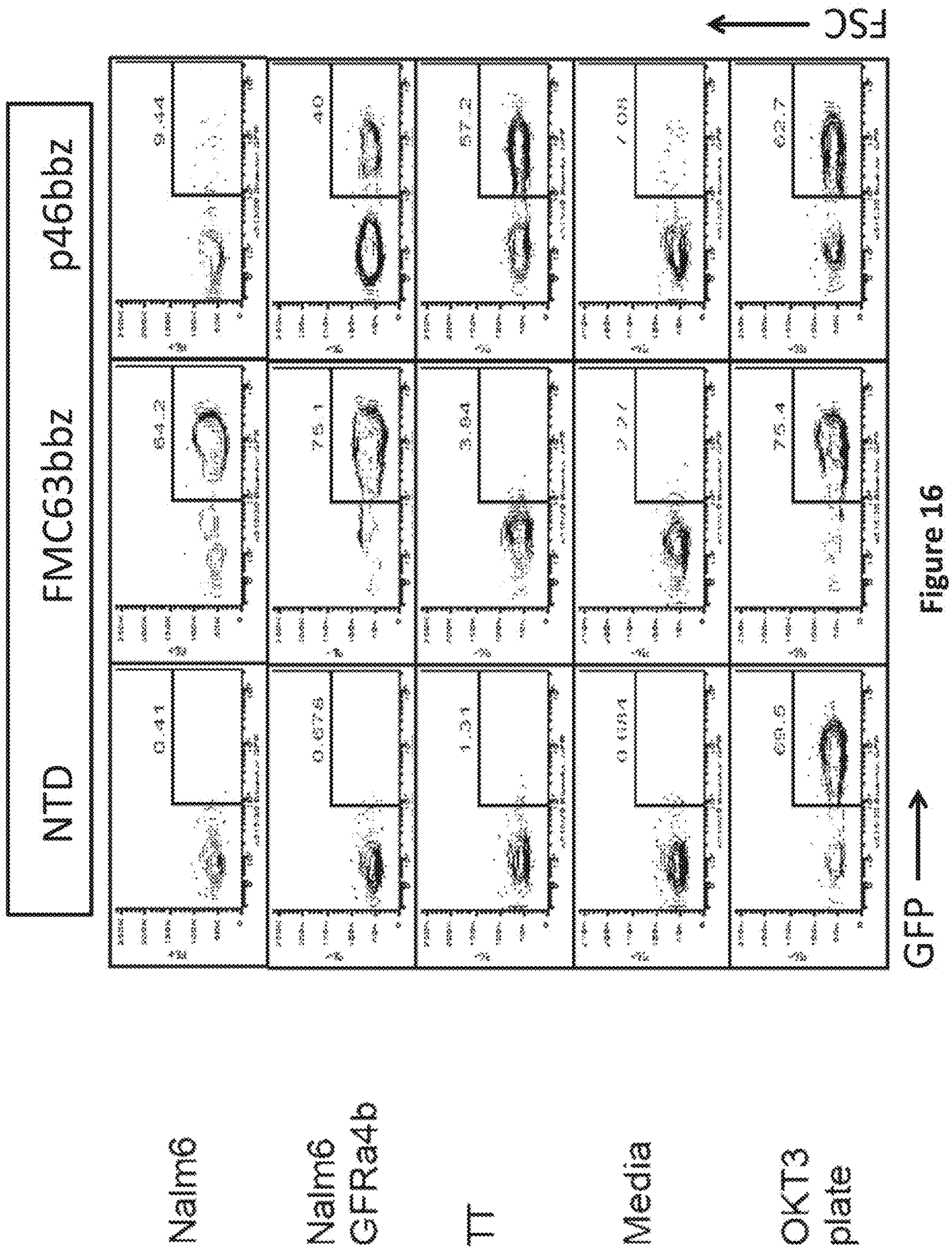
FIG. 16 is an image of a series of flow cytometric measurements demonstrating the specificity of GFRα4-expressing CAR-T cells.

To further show specificity of CAR, additional assays were performed. Jurkat cells stably expressing the coding sequence for green fluorescence protein (GFP) under the control of a promoter containing four NFAT/AP1 binding sites from the IL-2 promoter (NFAT-GFP Jurkat) were transduced by lentiviral vector to express a CD19-specific chimeric antigen receptor (FMC63bbz, comprising a human CD8 hinge, 4-1BB, and CD3zeta) or the GFRα4-specific CAR, P4-6bbz (comprising a gs-linker, 4-1BB, and CD3 zeta), or were left non-transduced (NTD). The Jurkat cells were then mixed in a 1:1 ratio with wild-type Nalm6 cells (an acute lymphoblastic leukemia cell line that expresses CD19), Nalm6 cells engineered to express GFRα4 isoform b, or wild-type TT cells. As a positive control for reporter activation, NFAT-GFP Jurkat cells were also plated into wells of polystyrene microtiter plates that were pre-coated overnight with the anti-CD3 agonist antibody, clone OKT3 (10 ug/ml), which stimulates GFP expression through the endogenous TCR/CD3 complex. After overnight incubation, GFP expression in the cells was analyzed by flow cytometry. Numbers in each plot indicate the percentage of GFP positive Jurkat cells. Results show specificity of the GFRα4-directed P4-6bbz CAR: wild-type Nalm6 cells only stimulated GFP expression in FMC63bbz cells; Nalm6 cells co-expressing GFRα4 activated both FMC63bbz and the GFRα4-directed P4-6bbz cells; and wild-type TT cells that expressed GFRα4 but lacked CD19 only induce dGFP in GFRα4-directed P4-6bbz cells (FIG. 16).

Figure 17:
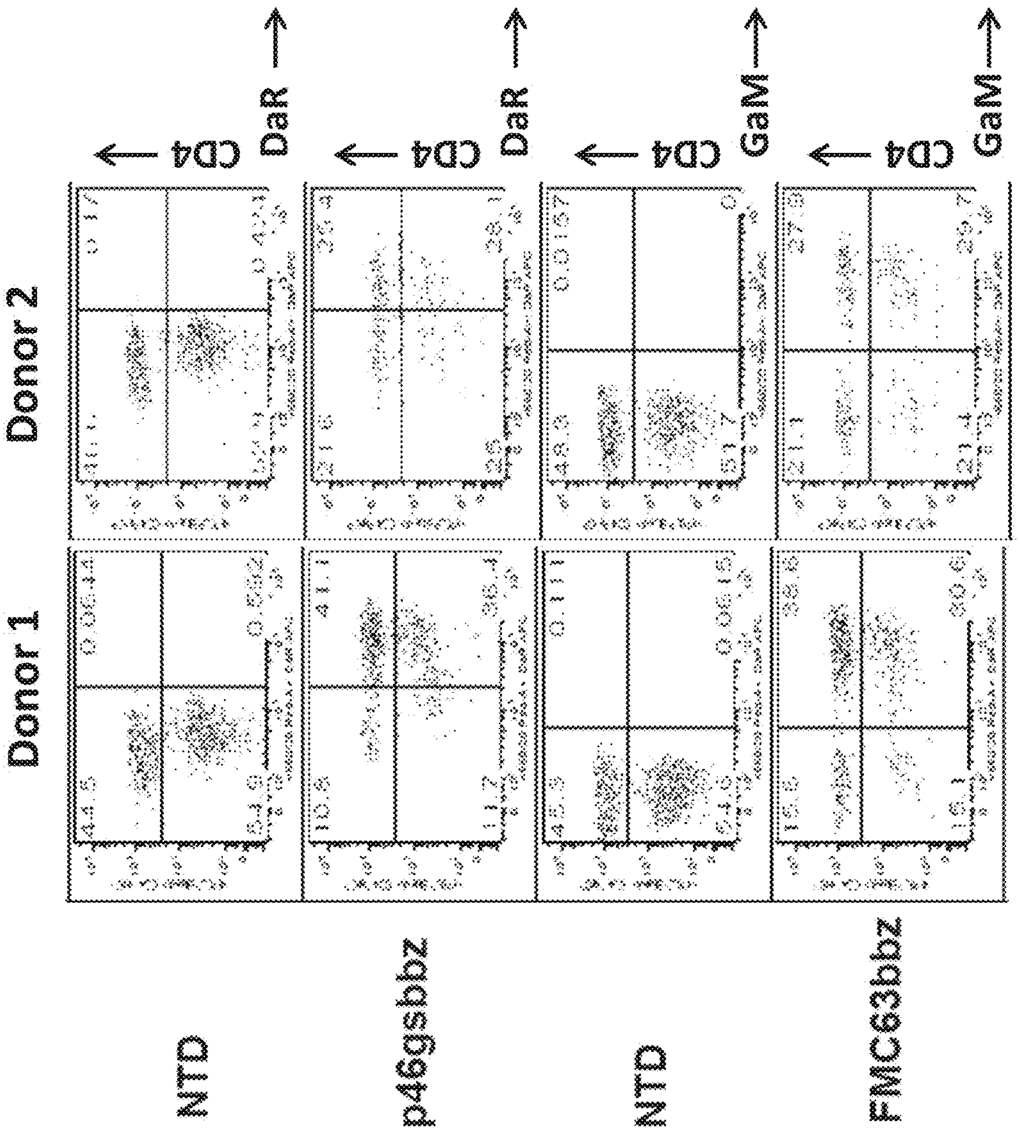
FIG. 17 is an image of a series of flow cytometric measurements demonstrating the expression of GFRα4-specific CAR-T protein in CD4-positive and CD4-negative T cells from multiple healthy donors.

Example 4—Expression of GFRα4-Specific CAR-T Protein in CD4-Positive and CD4-Negative T Cells from Multiple Healthy Donors Human T cells from two healthy donors were activated with anti-CD3 and anti-CD28 coated paramagnetic beads (DYNABEADS©Human T-Activator CD3/CD28, Life Technologies). One day following activation, cells were transduced with lentiviral vector encoding either the CD19-specific FMC63(cd8)bbz CAR or the GFRα4-specific P4-6 (gs)bbz CAR, or were left non-transduced (NTD). Cells were expanded and on day 7, were stained with anti-CD4-PerCP and either biotinylated-donkey anti-rabbit (DaR, top two panels for each donor) or biotinylated-goat anti-mouse (GaM, bottom two panels for each donor) followed by a secondary stain with streptavidin-APC after thorough washing. Cells were fixed in 2% paraformaldehyde prior to analysis by flow cytometry. Results show similar expression of the CARs on the surface of CD4-positive and CD4-negative T cells indicating that there are no differences in transduction efficiency for either CAR-encoding lentiviral vector in the CD4-positive and CD4-negative, presumably CD8+, T cell subsets (FIG. 17).

Figure 14:
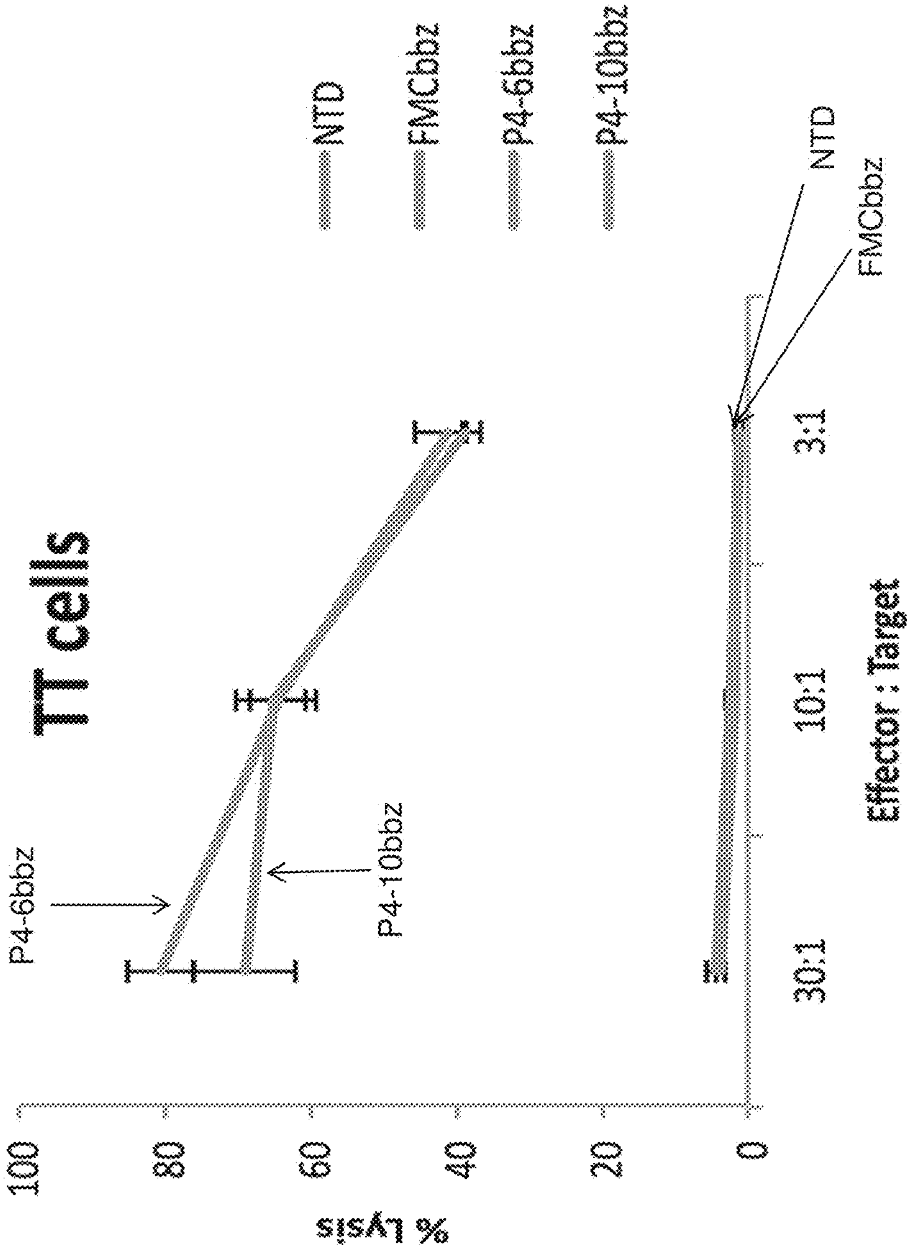
FIG. 14 is a graph demonstrating that T cells expressing P4-6(gs) and P4-10(gs) scFv T bodies (P4-6bbz and P4-10bbz, respectively) are capable of killing a calcitonin-secreting MTC cell line cells (TT cells) when these are incubated in vitro at several effector to target ratios. FMCbbz cells, a CD19/mesothelin-specific CAR-T cell, serves as a negative control along with non-transduced (NTD) T cells.
Figure 15:
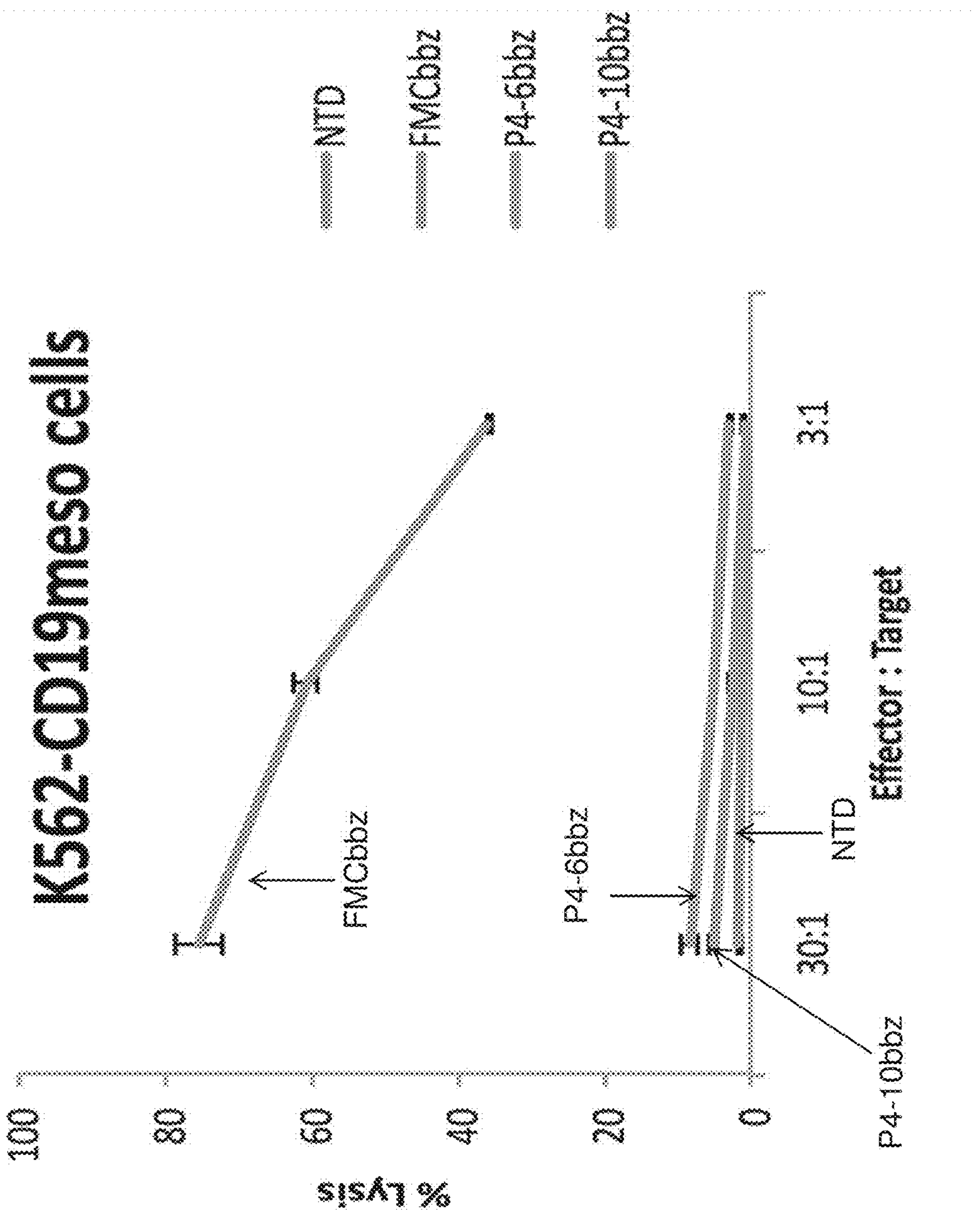
FIG. 15 is a control experiment showing that CD19/mesothelin-specific CAR-T cells (FMCbbz) lysed CD19/mesothelin-expressing K562 cells (K562-CD19meso) while the P4-6 and P4-10 CAR-T cells do not.

Example 5—Primary T Cells Expressing CART-P4-6 and CART-P4-10 Kill a Thyroid Medullary Cancer Cell Line In Vitro Cytotoxicity of target cells by P4-6gs and P4-10gs CARs was evaluated using a $^{51}$Cr release-assay. Target TT cells were labeled with $^{51}$Cr (sodium dichromate salt), washed and co-cultured with effector CAR T cells at effector:target ratios of 30:1, 10:1, and 3:1. Ten thousand target cells were co-cultured with the appropriate number of effector T cells in each well. Supernatants were collected after overnight co-culture and placed into 96-well Lumaplates (Perkin Elmer, Inc., Walthan MA). The amount of $^{51}$Cr released from the labeled target cells was measured on a liquid scintillation counter (MicroBeta Trilux, Perkin Elmer). Target cells incubated in medium alone or with 1% SDS were used to determine spontaneous (S) or maximum (M) $^{51}$Cr release. Percentage of specific lysis was calculated as follow: [(cpm experimental release-cpm S release)/(cpm M release-cpm S release)]×100. As shown in FIG. 14, T cells transduced to express P4-6 and P4-10 GS linker CARs lysed TT cells while non-transduced T cells (NTD) and CD19/mesothelin-specific CAR-T cells (FMCbbz) did not. As shown in control FIG. 15, FMCbbz cells lysed CD19/mesothelin-expressing K562 cells (K562-CD19meso) while the P4-6 and P4-10 CAR-T cells do not.

Figure 18A:
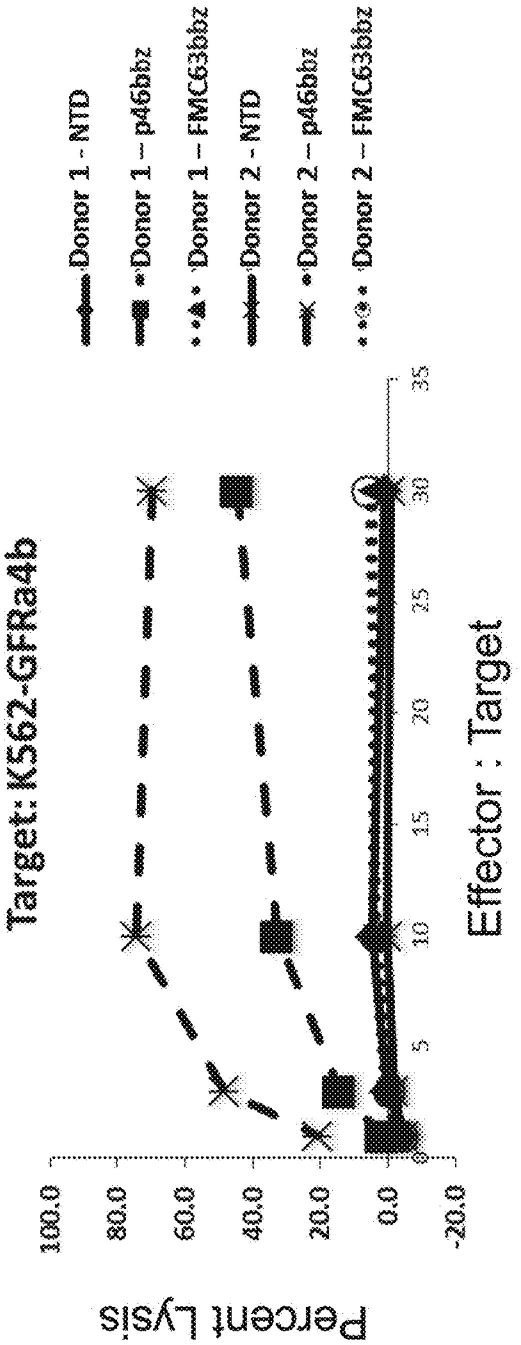
FIGS. 18A and 18B, is two graphs demonstrating specific lysis of GFRα4-expressing cells by anti-GFRα4-specific CAR-transduced T cells. Human T cells from two healthy donors transfected with either the FMC63bbz anti-CD19 CAR or the P4-6bbz GFRα4-specific CAR were mixed at the indicated effector to target ratios with K562 cells (ATCC) expressing either GFRα4 isoform b (FIG. 18A) or human CD19 (FIG. 18B) pre-loaded with $^{51}Cr$.
Figure 18B:
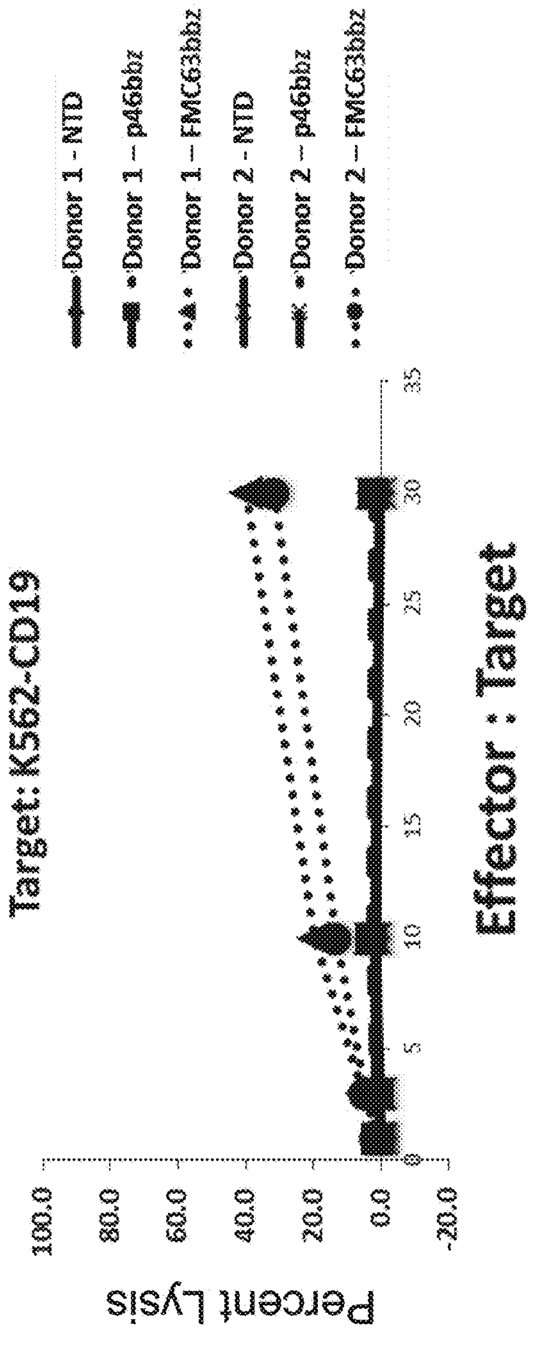

Example 6—Specific Lysis of GFRα4-Expressing Cells by Anti-GFRα4-Specific CAR-Transduced T Cells Human T cells from two healthy donors transfected with either the FMC63(cd8)bbz anti-CD19 CAR or the P4-6(gs) bbz GFRα4-specific CAR (from Example 4) were mixed at the indicated effector to target ratios with K562 cells (ATCC) expressing either GFRα4 isoform b (FIG. 18A) or human CD19 (FIG. 18B) pre-loaded with 51Cr. K562 cell lines expressing GFRα4b or CD19 were generated by lentiviral vector-mediated transduction. Lentiviral vectors expressing these proteins were generated by cloning of cDNA from PMBC or synthesized DNA (Genewiz, South Plainfield, NJ) through PCR and standard molecular biology techniques. All plasmids were confirmed by sequencing. Expression of the antigens on the surface of the transduced K562 cells was confirmed by flow cytometry. The procedures for generation of high-titer lentiviral vectors have been previously described (Parry, R. V JI 2003). Briefly, 293T cells grown in RPMI with 10% FBS were co-transfected with lentiviral vector plasmids along with the pMDL.g/p, pRSV.rev and pVSVg packaging plasmids using Lipofectamine 2000 (Life Technologies, Carlsbad, CA) transfection reagent. Vector containing supernatants were harvested at 24 and 48 hours after transfection, and concentrated by centrifugation at 12,000 rpm for 2 hrs. Concentrated vector was stored at −70° C. until use. Lysis of target cells was measured as described in Example 5. CAR expression percentages were as follows: Donor 1 P4-6bbz were 77% CAR+; Donor 1 FMC63bbz were 69% CAR+; Donor 2 P4-6bbz were 53% CAR+; Donor 2 FMC63bbz were 57% CAR+. The results demonstrate a requirement for GFRα4-expression on cells for cytotoxicity by T cells expressing the GFRα4-specific P4-6bbz CAR.

Figure 19A:
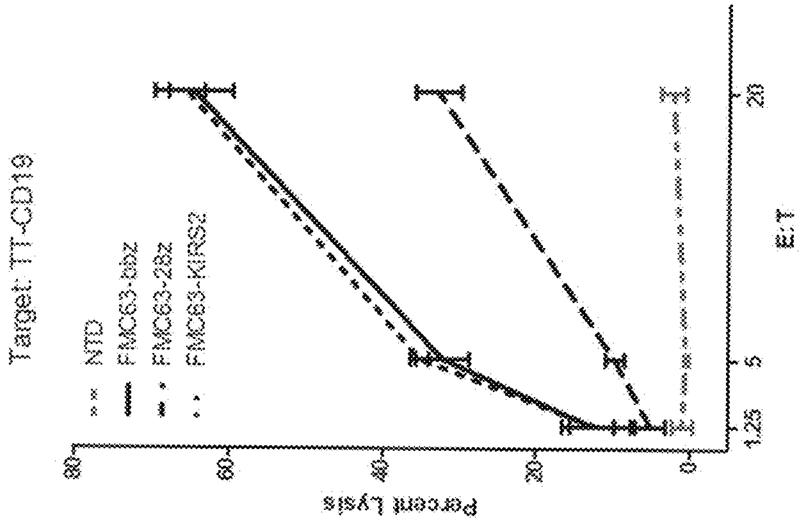
FIGS. 19A, 19B, and 19C, is three graphs showing specific lysis of GFRα4-expressing tumor cells by T cells expressing anti-GFRα4-CARs with different cytoplasmic signaling domains.
Figure 19B:
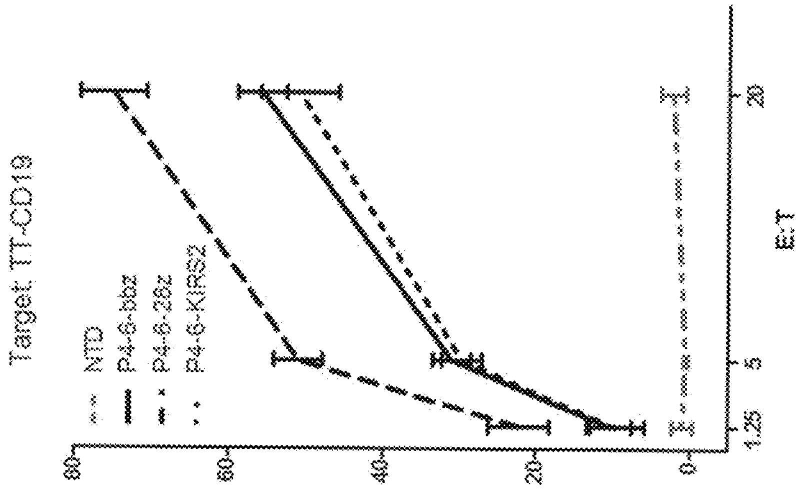
Figure 19C:
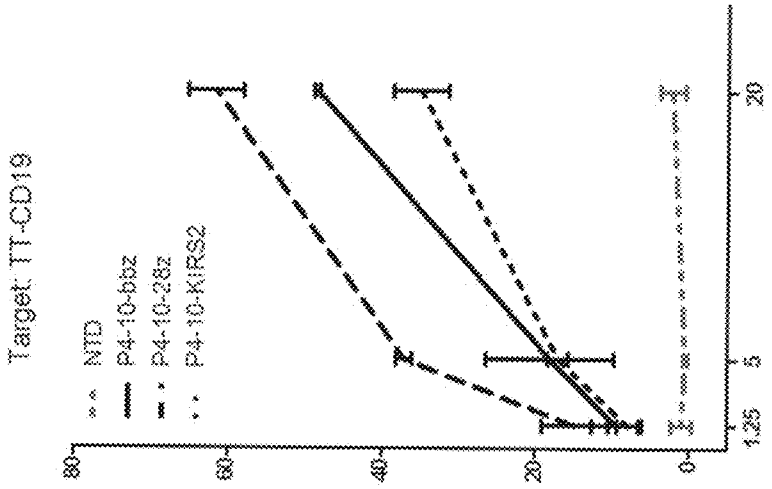

Example 7—Specific Lysis of GFRα4-Expressing Tumor Cells by T Cells Expressing Anti-GFRα4-CARs with Different Cytoplasmic Signaling Domains Human T cells were activated with anti-CD3 and anti-CD28 coated paramagnetic beads (DYNABEADS® Human T-Activator CD3/CD28, Life Technologies). One day following activation, cells were transduced with lentiviral vector encoding CARs constructed with either the CD19-specific scFv FMC63 or the GFRα4-specific scFvs, P4-6 or P4-10. Non-transduced T cells were used as a negative control (NTD). For each scFv, CARs were further constructed to contain the either the GS-linker (for the GFRα4 CAR) or a human CD8 hinge (for the CD19 CAR), and signaling domains as follows: 4-1bb and CD3-zeta cytoplasmic domains (FMC63bbz, P4-6bbz or P4-10bbz), the CD28 and CD3-zeta cytoplasmic domains (FMC6328z, P4-6-28z (SEQ ID NO: 98) or P4-10-28z (SEQ ID NO: 100)) or a KIR2DS2 transmembrane and cytoplasmic domain with human DAP12 co-delivered using the T2A ribosomal skipping sequence from the *Thosea asigna* virus (19KIRS2, P4-6-KIRS2 (SEQ ID NO: 102) or P4-10-KIRS2 (SEQ ID NO: 104)). The transduced T cells were mixed at the indicated effector to targets ratios (E:T) with $^{51}$Cr-labeled TT-CD19 cells, a medullary thyroid carcinoma cell line that expresses endogenous GFRα4 and was engineered to also express human CD19. Engineering of TT cells to express CD19 was carried out as described above for K562 cells. After a 4-hour co-incubation, culture supernatants were harvested and percent of target cells lysis (percent lysis) was calculated as in the previous examples. CAR expression for each of the CAR bearing T cells was in the range of 61% to 79% with the exception of FMC63-28z that were approximately 9% CAR+. Results show the ability of FMC63 CD19-specific CAR-expressing T cells to lyse TT target cells utilizing several different signaling configurations (FIG. 19A). Results show the ability of both P4-6gs and P4-10gs GFRα4-specific CAR-expressing T cells to lyse TT target cells utilizing several different signaling configurations (FIGS. 19B and 19C). Error bars indicate standard deviations.

Example 8—T Cells Expressing a GFRα4-Specific P4-6bbz and P4-10bbz CARs Show GFRα4-Dependent Secretion of the Cytokines IFN-γ and IL-2

Figure 20A:
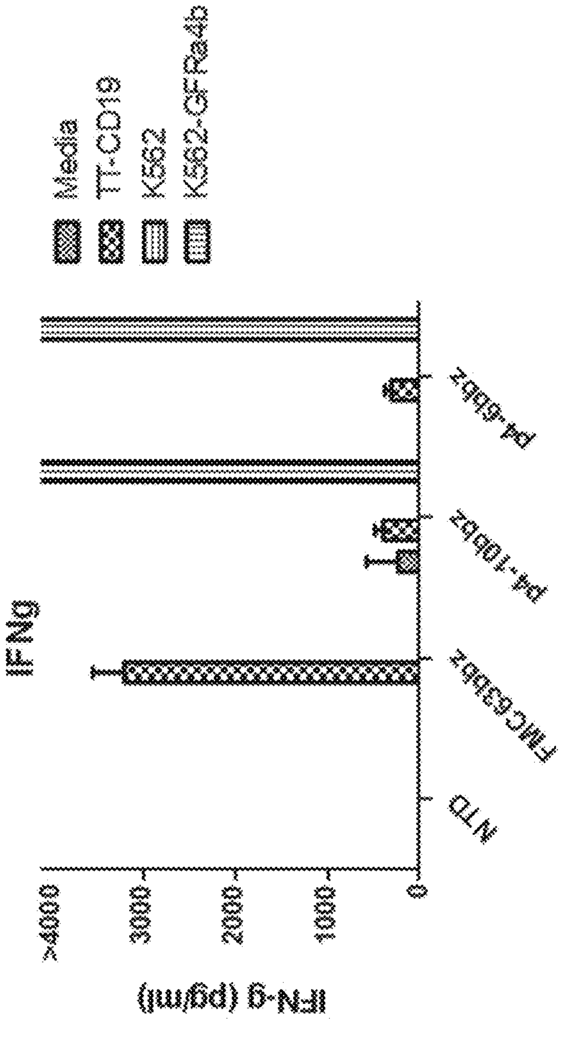
FIGS. 20A and 20B, is two graphs demonstrating that T cells expressing a GFRα4-specific P4-6bbz and P4-10bbz CARs show GFRα4-dependent secretion of the cytokines IFN-γ (FIG. 20A) and IL-2 (FIG. 20B).
Figure 20B:
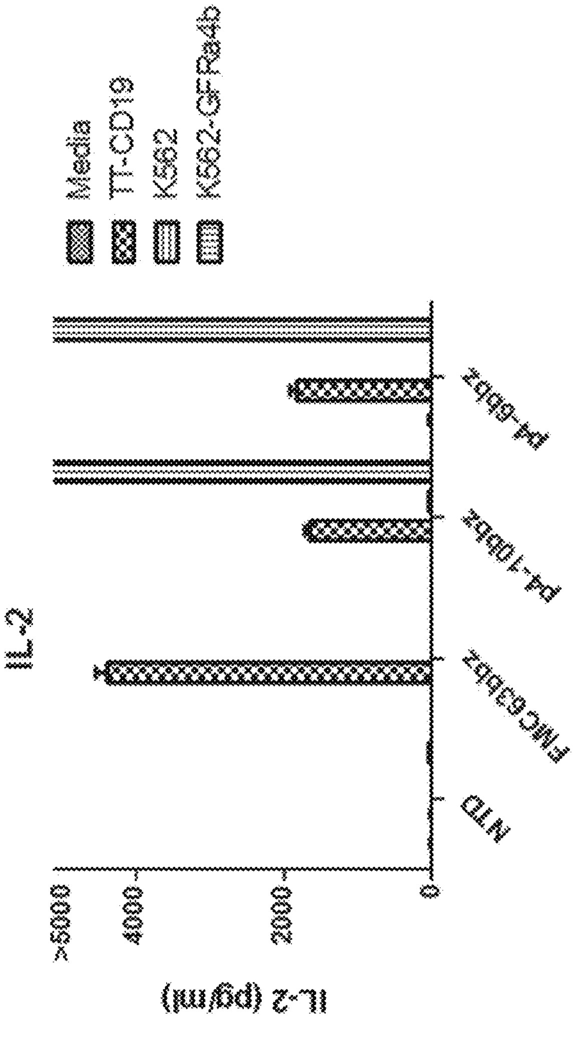

Human T cells were activated with anti-CD3 and anti-CD28 coated paramagnetic beads (DYNABEADS® Human T-Activator CD3/CD28, Life Technologies). One day following activation, cells were transduced with lentiviral vector encoding either the CD19-specific FMC63(cd8)bbz CAR, the GFRα4-specific P4-6(gs) bbz or P4-10(gs)bbz CARs, or were left non-transduced (NTD). Expanded T cells were co-cultured with TT-CD19 cells or K562 cells engineered to express GFRα4 isoform b by lentiviral transduction at a T cell to target cell ratio of 1:1. After overnight incubation, culture supernatants were harvested and analyzed by ELISA for interferon-gamma (IFN-γ)(FIG. 20A) and interleukin-2 (IL-2)(FIG. 20B). Results demonstrate secretion of cytokines by T cells expressing the GFRα4- specific P4-6(gs)bbz and P4-10(gs)bbz CARs when incubated with target cells expressing GFRα4, but not with target cells lacking GFRα4 expression. Error bars indicate standard deviations.

Example 9—T Cells Expressing a GFRα4-Specific p4-10-28z CAR Show GFRα4-Dependent Secretion of the Cytokines IFN-γ and IL-2

Figure 21A:
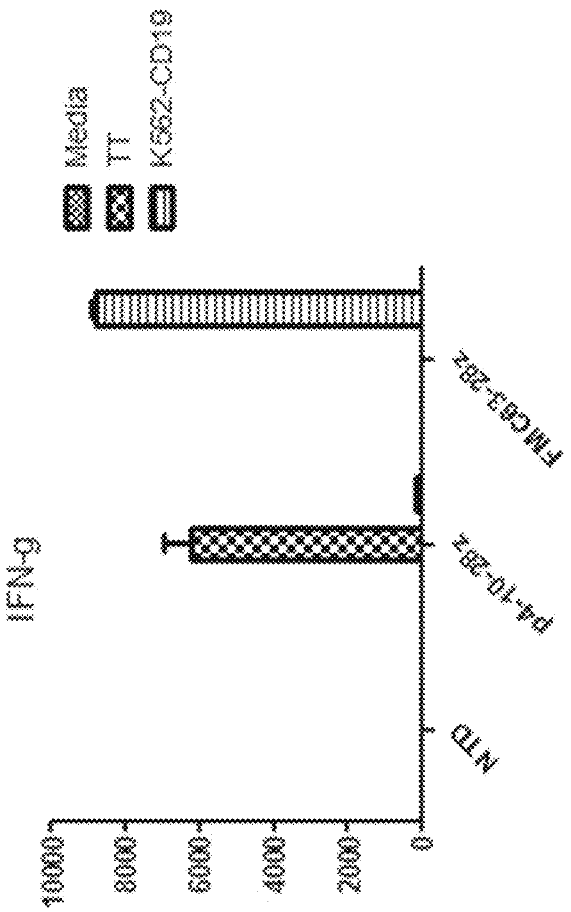
FIGS. 21A and 21B, is two graphs demonstrating that cells expressing a GFRα4-specific p4-10-28z CAR show GFRα4-dependent secretion of the cytokines IFN-γ (FIG. 21A) and IL-2 (FIG. 21B).
Figure 21B:
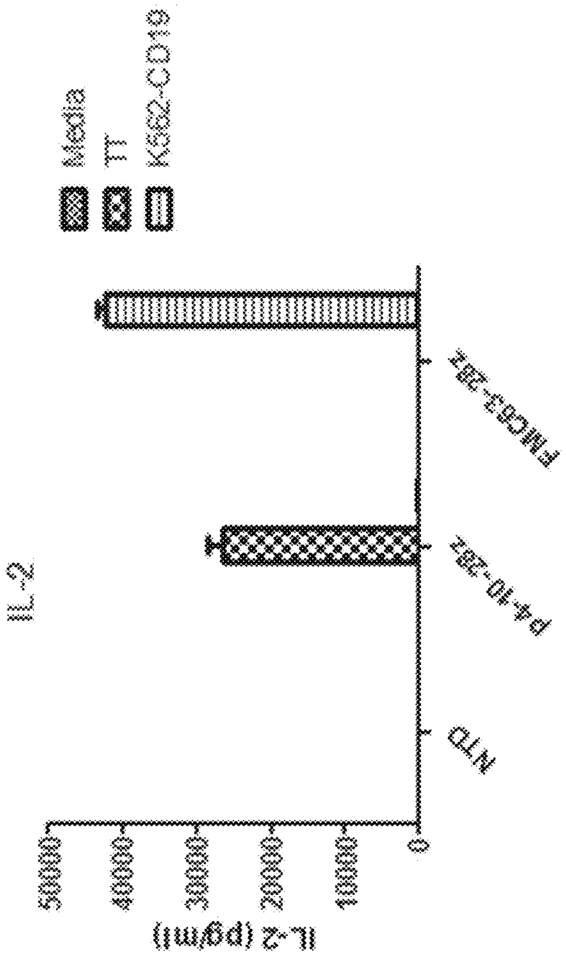

Human T cells were activated with anti-CD3 and anti-CD28 coated paramagnetic beads (DYNABEADS® Human T-Activator CD3/CD28, Life Technologies). One day following activation, cells were transduced with lentiviral vector encoding either the CD19-specific FMC63(cd8)-28z CAR, the GFRα4-specific p4-10(gs)-28z CAR, or were left non-transduced (NTD). Expanded T cells were co-incubated with wild-type TT cells or K562 cells engineered to express CD19 by lentiviral transduction at a T cell to target cell ratio of 1:1. After overnight co-culture, culture supernatants were harvested and analyzed by ELISA for interferon-gamma (IFN-γ)(FIG. 21A) and interleukin-2 (IL-2)(FIG. 21B). Results show secretion of cytokines by T cells expressing P4-10(gs)-28z CAR only in the presence of target cells expressing GFRα4. Error bars indicate standard deviations.

Example 10—GFRα4 CART Kill MTC Cells in Mouse Model

Figure 22A:
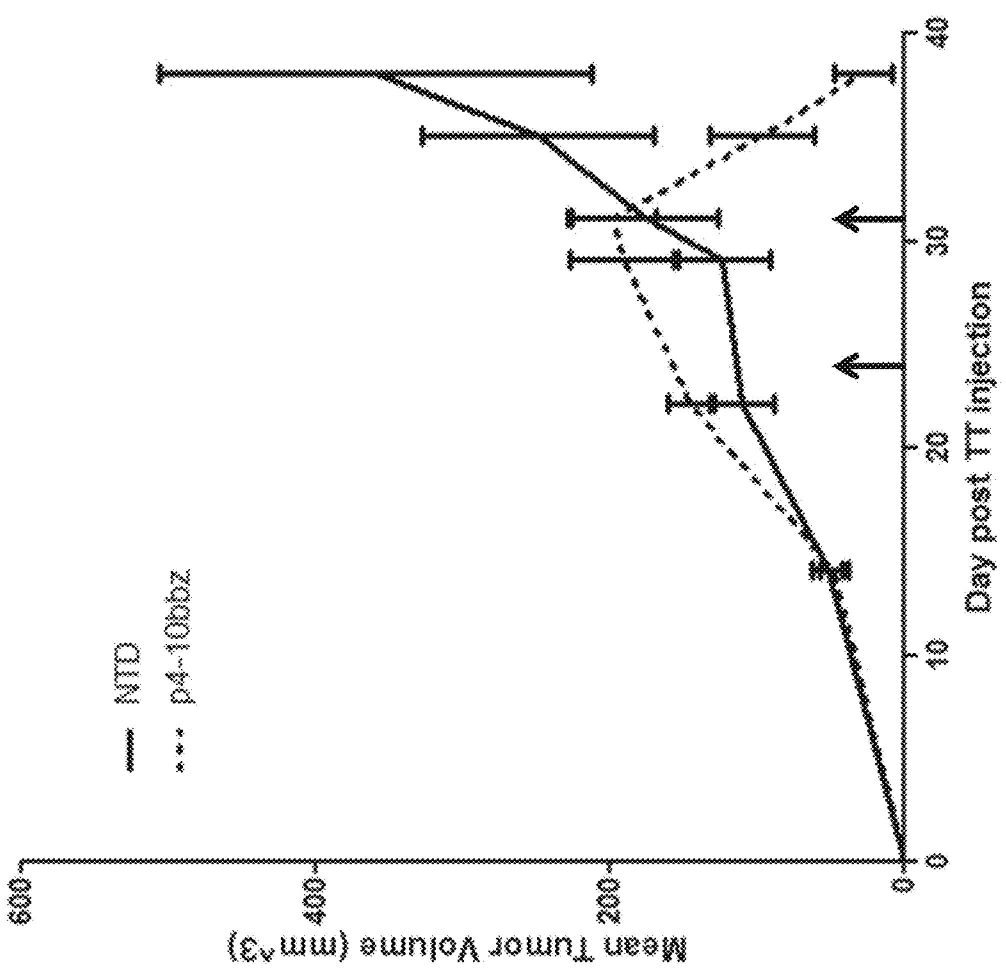
FIGS. 22A and 22B, are two graphs demonstrating that T cells expressing a GFRα4 CAR reduce the size of medullary thyroid carcinoma-derived TT cell tumors in vivo when TT cells were implanted sub-cutaneously and T-cells were injected intra-tumorally.
Figure 22B:
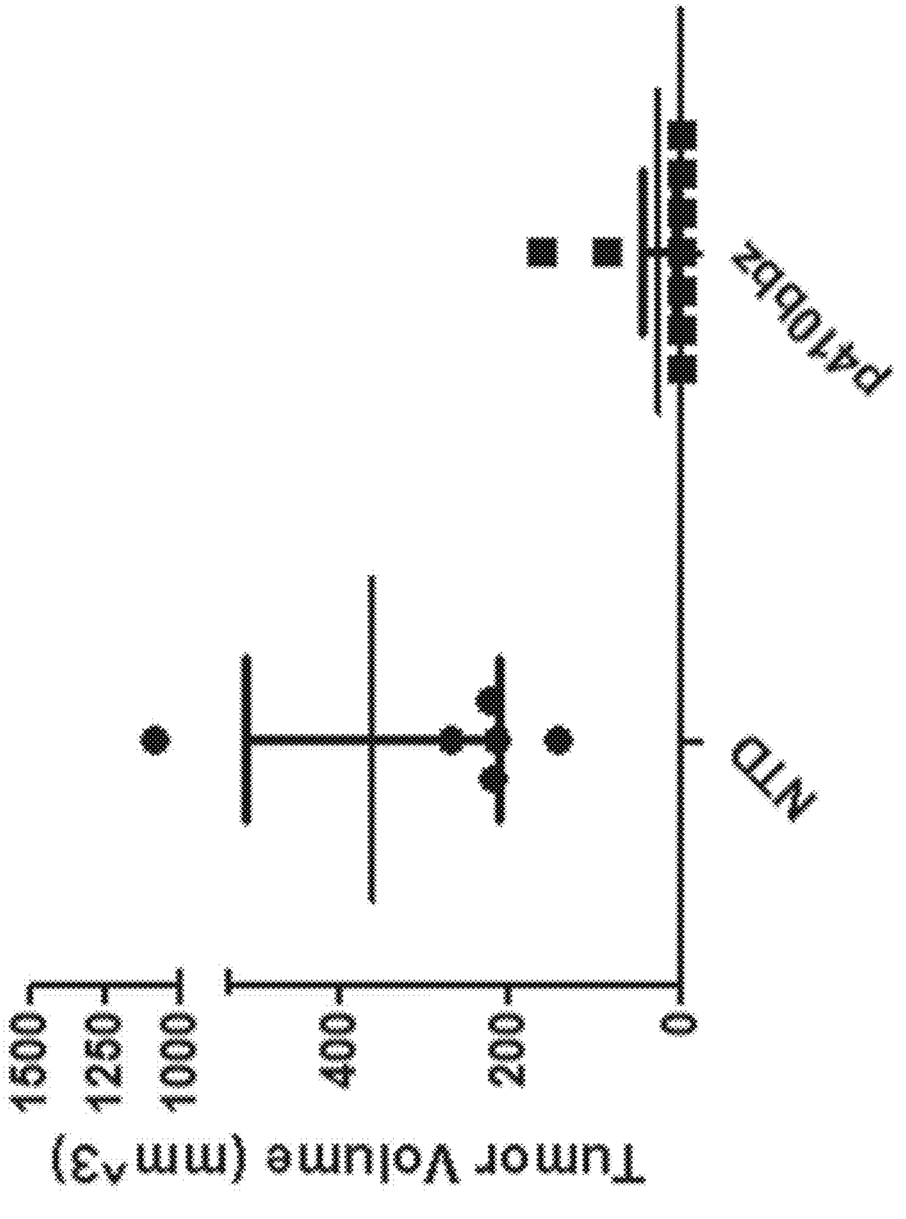

In vivo experiment on a mouse model demonstrated that CART-P4-10 has the capacity of killing MTC cells and treating cancer. On day 0, $5\times10^6$ TT cells were implanted sub-cutaneously in the flank of NOD-SCID-$\gamma_c^{-/-}$ (NSG) mice. On day 24, $1\times10^7$ non-transduced (NTD, n=6) or P4-10(gs)bbz-transduced (n=9) human T cells were injected intra-tumorally. On day 31, $6\times10^6$ non-transduced or P4-10bbz-transduced T cells from the same donor were again injected intra-tumorally. Tumor volume was measured by caliper measurement over time. FIG. 22A shows the mean with standard error of the mean of tumor volume over time. Arrows indicate times of T cell injection. FIG. 22B shows tumor size of individual mice at day 38 for each group (P=0.0008 by Mann-Whitney test). Mean and standard error of the mean are indicated for each group. Results show the continued growth of tumors in mice treated intra-tumorally with non-transduced T cells compared with a reduction in tumor volume in mice treated intra-tumorally with T cells transduced with the GFRα4-specific P4-10(gs)bbz CAR.

On day 0, $5\times10^6$ TT cells engineered to express click-beetle-green luceriferase were implanted sub-cutaneously in the flank of NSG mice. Lentiviral transduction of TT cells with click-beetle green luciferase was performed by using a vector encoding GFP followed by the T2A ribosomal skipping sequence from the *Thosea asigna* virus, followed by click-beetle green luciferase, all under the regulation of the EF-alpha promoter. The use of luciferase expressing TT cells permitted imaging by bioluminescence.

Figure 23A:
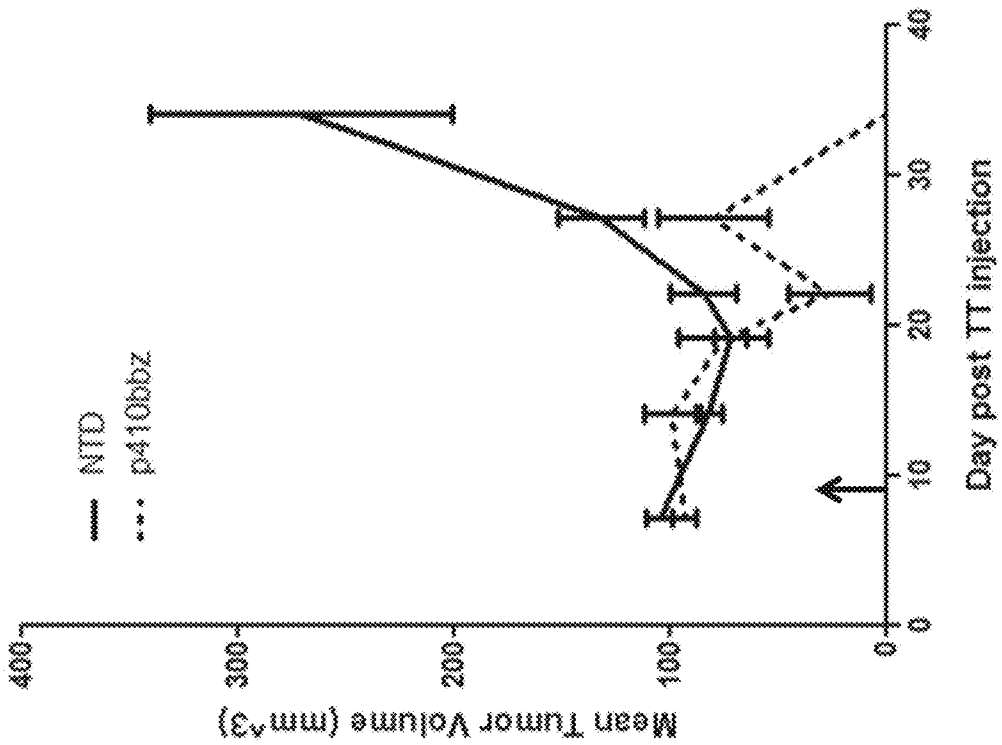
FIGS. 23A and 23B, are two graphs showing reduction in medullary thyroid carcinoma cell tumor size in mice treated intravenously with T cells expressing a GFRα4-specific CAR.
Figure 23B:
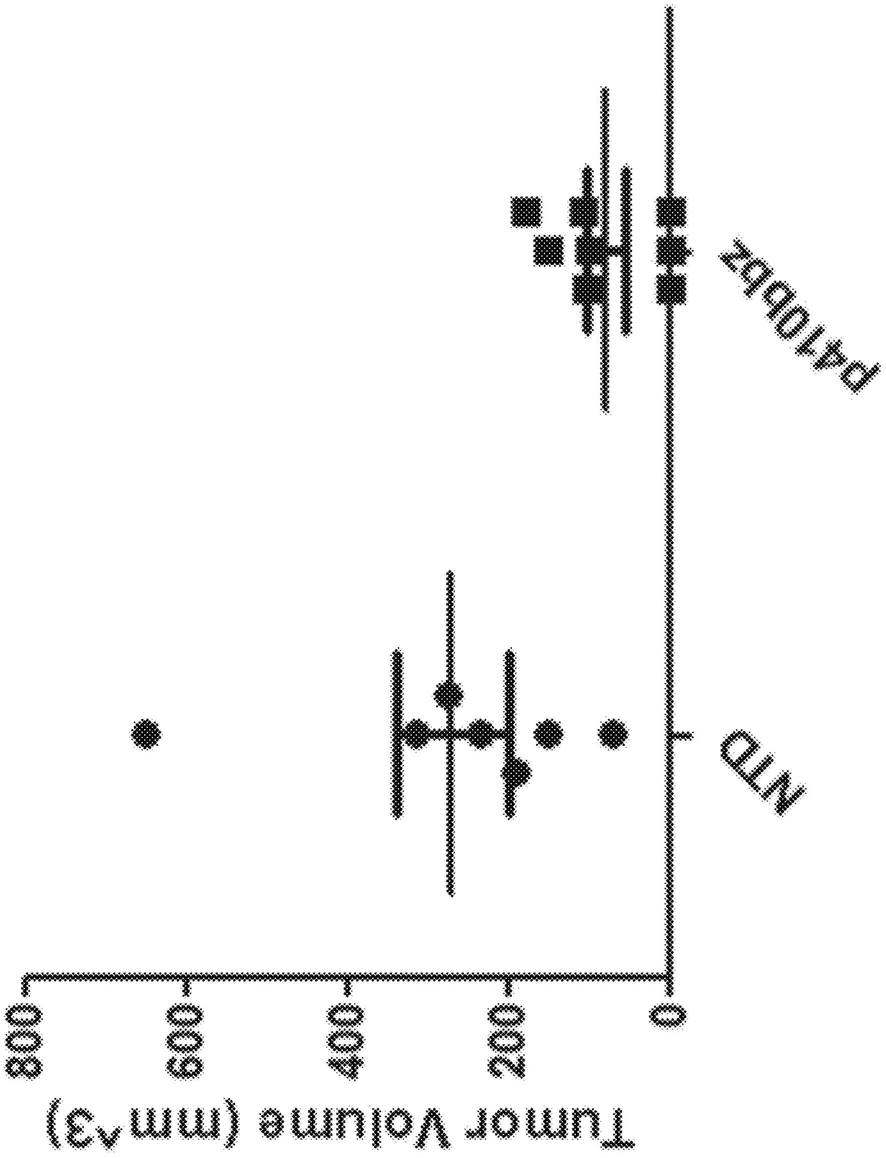

On day 9, $1\times10^7$ non-transduced (NTD, n=7) or P4-10bbz-transduced (n=8) human T cells were injected intravenously. Tumor volume was measured with calipers over time. FIG. 23A shows the mean with standard error of the mean of tumor volume over time. The arrow indicates time of T cell injection. FIG. 23B shows tumor size of individual mice at day 27 for each group (P=0.0093 by Mann-Whitney test). Mean and standard error of the mean are indicated for each group. Statistical analysis was performed for day 27 as this was the last time point containing all mice as some were then euthanized due to graft-versus-host effects. Results show continued growth of tumors in mice treated intravenously with non-transduced T cells and reduction in tumor volume in mice treated intravenously with T cells transduced with P4-10bbz CAR-T construct.

Figures 24A, 24B, 24C:
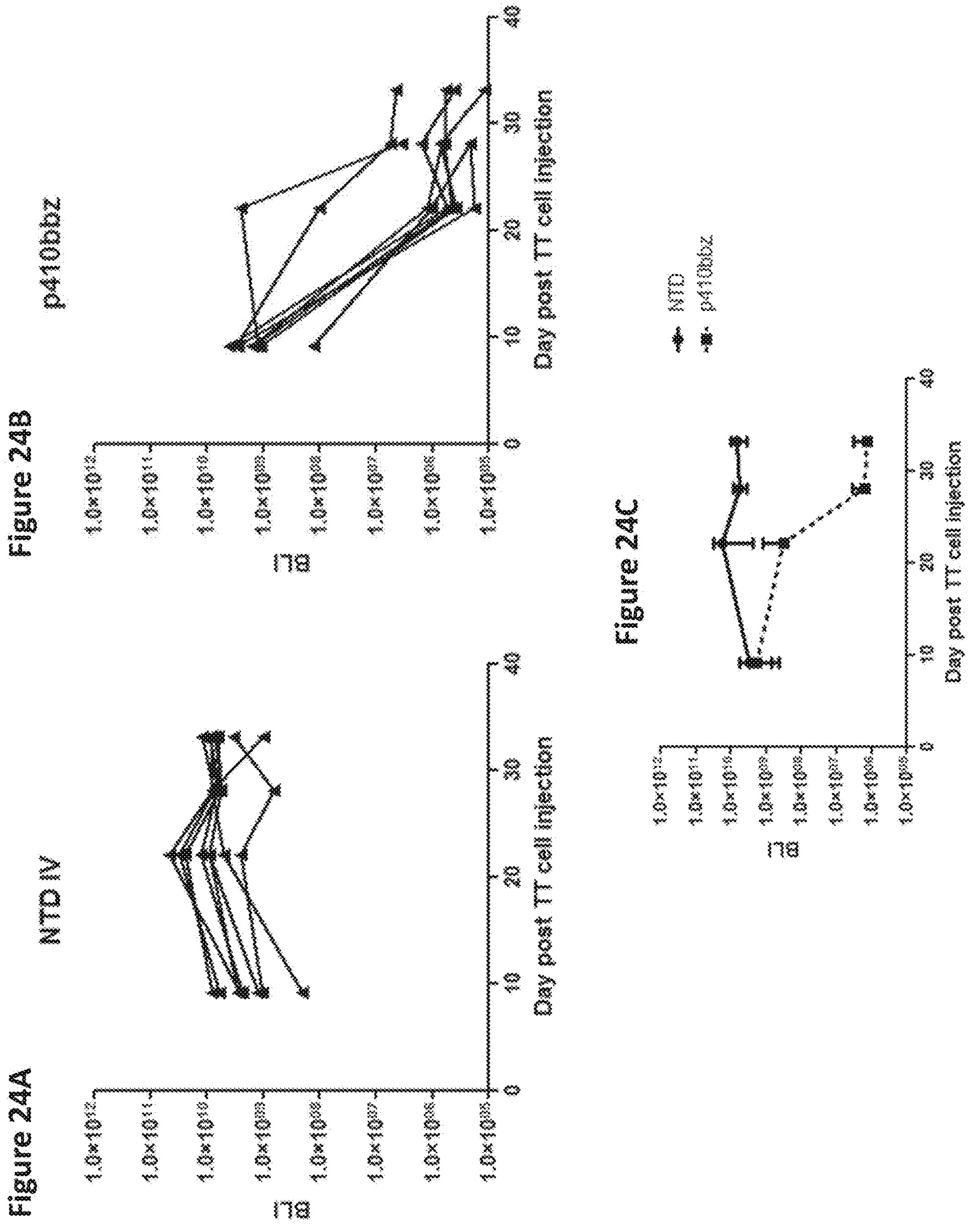
FIGS. 24A, 24B, and 24C, show the reduction in medullary thyroid carcinoma cell tumor burden in mice treated intravenously with GFRα4 CAR-T cells. Each line in FIGS. 24A and B shows the bioluminescence intensity (BLI) of an individual mouse over time.

The mice shown above that had been injected with TT cells engineered to expressed luciferase were imaged using an IVIS Spectrum bioluminescence imaging system (Perkin Elmer) following the intravenous injection of luciferin to determine the bioluminescence intensity (BLI) of the sub-cutaneous tumors in each mouse. Each line in FIGS. 24A and 24B shows the BLI of an individual mouse over time. FIG. 24C shows the mean with standard deviation of BLI over time. These results show the reduction in tumor burden in mice treated intravenously with GFRα4-specific P4-10 (gs)bbz CAR T cells, but not with the NTD negative control T cells.

Example 11—GFRα4 RNA is Expressed by Medullary Thyroid Carcinoma

Figure 25:
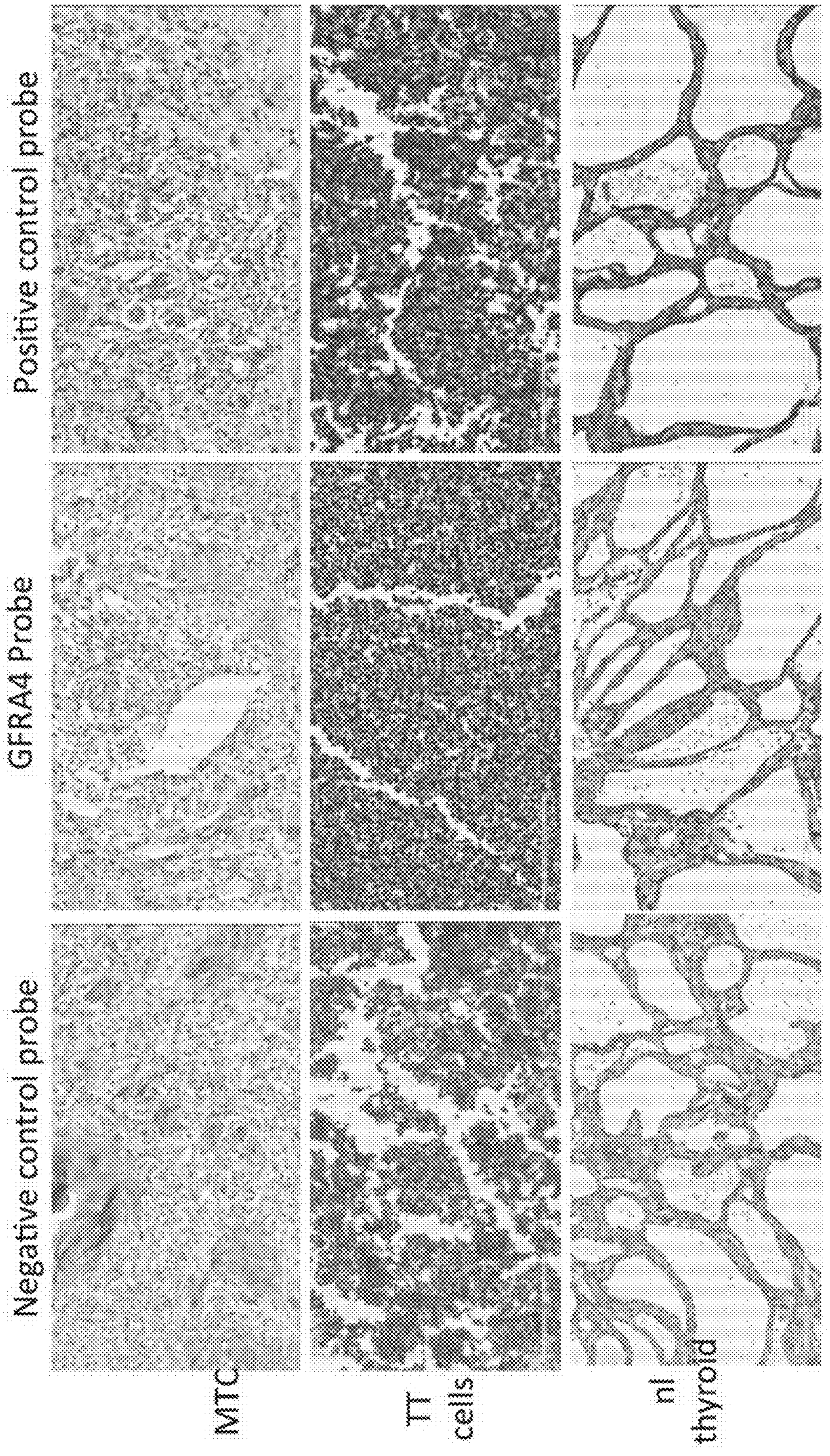
FIG. 25 shows images demonstrating that GFRα4 RNA is expressed by medullary thyroid carcinoma.

Formalin-fixed, paraffin-embedded (FFPE) sections from a surgically resected, medullary thyroid carcinoma (MTC), from normal thyroid tissue, or from a cell pellet of the TT cell line (obtained from ATCC) were analyzed by RNA in situ hybridization using proprietary RNAscope technology (Advanced Cell Diagnostics, Hayward, CA). Sections were probed using a negative control probe targeting the bacterial RNA for the bacterial gene, DapB, a positive control probe for the RNA derived from the human PPIB gene, or a probe targeting the GFRα4 gene that binds to RNA sequences shared by both isoforms a and b of human GFRα4. The results show specific hybridization of the GFRα4 probe to malignant cells within the resected MTC tissue and TT cells, but no hybridization to normal thyroid follicular epithelial cells (FIG. 25). Hybridization to normal parafollicular C-cells was observed but not shown.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A chimeric antigen receptor (CAR) polypeptide comprising an antigen binding domain, a transmembrane domain, and an intracellular signaling domain, wherein the antigen binding domain binds to isoform a or isoform b of human Glycosyl-phosphatidylinositol (GPI)-linked GDNF family α-receptor 4 (GFRα4) cell-surface receptor and comprises:

(a) (i) a heavy chain variable region comprising a heavy chain complementary determining region 1 (HC CDR1) comprising the amino acid sequence set forth in SEQ ID NO: 63, a heavy chain complementary determining region 2 (HC CDR2) comprising the amino acid sequence set forth in SEQ ID NO: 65, and a heavy chain complementary determining region 3 (HC CDR3) comprising the amino acid sequence set forth in SEQ ID NO: 67; and (ii) a light chain complementary determining region 1 (LC CDR1) comprising the amino acid sequence set forth in SEQ ID NO: 71, a light chain complementary determining region 2 (LC CDR2) comprising the amino acid sequence set forth in SEQ ID NO: 73, and a light chain complementary determining region 3 (LC CDR3) comprising the amino acid sequence set forth in SEQ ID NO: 75; or (b) (i) a heavy chain variable region comprising a heavy chain complementary determining region 1 (HC CDR1) comprising the amino acid sequence set forth in SEQ ID NO: 43, a heavy chain complementary determining region 2 (HC CDR2) comprising the amino acid sequence set forth in SEQ ID NO: 45, and a heavy chain complementary determining region 3 (HC CDR3) comprising the amino acid sequence set forth in SEQ ID NO: 47; and (ii) a light chain complementary determining region 1 (LC CDR1) comprising the amino acid sequence set forth in SEQ ID NO: 51, a light chain complementary determining region 2 (LC CDR2) comprising the amino acid sequence set forth in SEQ ID NO: 53, and a light chain complementary determining region 3 (LC CDR3) comprising the amino acid sequence set forth in SEQ ID NO: 55.

2. The CAR polypeptide of claim 1, wherein the antigen binding domain is an antibody or an antigen-binding fragment thereof.

3. The CAR polypeptide of claim 2, wherein the antigen-binding fragment is a scFv.

4. The CAR polypeptide of claim 2, wherein the antibody or antigen-binding fragment is a human antibody or a fragment thereof.

5. The CAR polypeptide of claim 1, wherein the CAR comprises:

a light chain variable region comprising an amino acid sequence having at least one, two or three modifications but not more than 20 or 10 modifications of the amino acid sequence set forth in SEQ ID NO: 69 or SEQ ID NO: 49; or a light chain variable region comprising an amino acid sequence with about 95% up to about 99% identity to the amino acid sequence set forth in SEQ ID NO: 69 or SEQ ID NO: 49.

6. The CAR polypeptide of claim 1, wherein the CAR comprises:

a heavy chain variable region comprising an amino acid sequence having at least one, two or three modifications but not more than 20 or 10 modifications of the amino acid sequence set forth in SEQ ID NO: 61 or SEQ ID NO: 41: or a heavy chain variable region comprising an amino acid sequence with about 95 up to about 99% identity to the amino acid sequence set forth in SEQ ID NO: 61 or SEQ ID NO: 41.

7. The CAR polypeptide of claim 1, wherein the CAR comprises (a) the amino acid sequences set forth in SEQ ID NO: 61 and SEQ ID NO: 69; or (b) the amino acid sequences set forth in SEQ ID NO: 41 and SEQ ID NO: 49.

8. The CAR polypeptide of claim 1, wherein the antigen binding domain comprises:

(a) the amino acid sequence selected from SEQ ID NO: 58, SEQ ID NO: 59, SEQ ID NO: 78, or SEQ ID NO: 79;

(b) an amino acid sequence having at least one, two or three modifications but not more than 30, 20, or 10 modifications of SEQ ID NO: 58, SEQ ID NO: 59, SEQ ID NO: 78, or SEQ ID NO: 79; or (c) an amino acid sequence with about 95 up to about 99% identity to SEQ ID NO: 58, SEQ ID NO: 59, SEQ ID NO: 78, or SEQ ID NO: 79.

9. The CAR polypeptide of claim 1, wherein the transmembrane domain comprises a transmembrane domain from a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154.

10. The CAR polypeptide of claim 1, wherein the transmembrane domain comprises:

(a) the amino acid sequence of SEQ ID NO: 6;

(b) an amino acid sequence comprising at least one, two or three modifications but not more than 5 modifications of the amino acid sequence of SEQ ID NO: 6; or (c) a sequence with about 95 up to about 99% identity to the amino acid sequence of SEQ ID NO: 6.

11. The CAR polypeptide of claim 1, wherein the antigen binding domain is connected to the transmembrane domain by a hinge region.

12. The CAR polypeptide of claim 11, wherein the hinge region comprises the amino acid sequence of SEQ ID NO: 2, or a sequence with about 95 up to about 99% identity to SEQ ID NO: 2.

13. The CAR polypeptide of claim 1, wherein the intracellular signaling domain comprises a functional signaling domain from a protein selected from the group consisting of an MHC class I molecule, a TNF receptor protein, an immunoglobulin-like proteins, a cytokine receptor, an integrin, a signaling lymphocytic activation molecule (SLAM protein), an activating NK cell receptor, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

14. The CAR polypeptide of claim 1, wherein the intracellular signaling domain comprises the amino acid sequence of SEQ ID NO: 7, or an amino acid sequence having at least one, two or three modifications but not more than 10 or 5 modifications of the amino acid sequence of SEQ ID NO: 7, or a sequence with about 95 up to about 99% identity to the amino acid sequence of SEQ ID NO: 7.

15. The CAR polypeptide of claim 1, wherein the intracellular signaling domain comprises a functional signaling domain of 4-1BB and/or a functional signaling domain of CD3 zeta.

16. The CAR polypeptide of claim 1, wherein the intracellular signaling domain comprises:

(a) the amino acid sequence of SEQ ID NO: 7 and/or the sequence of SEQ ID NO: 9 or SEQ ID NO: 10; or (b) an amino acid sequence having at least 1, one, two or three modifications but not more than 10 or 5 modifications of the amino acid sequence of SEQ ID NO: 7 and/or the amino acid sequence of SEQ ID NO: 9 or SEQ ID NO: 10; or (c) a sequence with about 95 up to about 99% identity to the amino acid sequence of SEQ ID NO: 7 and/or the amino acid sequence of SEQ ID NO: 9 or SEQ ID NO: 10.

17. The CAR polypeptide of claim 1, wherein the intracellular signaling domain comprises the sequence of SEQ ID NO: 7 and the sequence of SEQ ID NO: 9 or SEQ ID NO: 10, wherein the sequences comprising the intracellular signaling domain are expressed as a single polypeptide chain.

18. The CAR polypeptide of claim 1, further comprising a leader sequence comprising the amino acid sequence of SEQ ID NO: 1.

19. The CAR polypeptide of claim 1, wherein the CAR comprises:

(a) the amino acid sequence of any of SEQ ID NOs: 85, 86, 90, 92, 94, 96, 98, 100, 102, or 104;

(b) an amino acid sequence having at least one, two or three modifications but not more than 30, 20 or 10 modifications to any of SEQ ID NOs: 85, 86, 90, 92, 94, 96, 98, 100, 102, or 104; or (c) an amino acid sequence with about 95 up to about 99% identity to any of SEQ ID NOs: 85, 86, 90, 92, 94, 96, 98, 100, 102, or 104.

20. A chimeric antigen receptor (CAR) polypeptide, wherein the CAR comprises an antigen binding domain, a transmembrane domain, and an intracellular signaling domain, and wherein the antigen binding domain binds to both isoforms a and b of human Glycosyl-phosphatidylinositol (GPI)-linked GDNF family α-receptor 4 (GFRα4) cell-surface receptor and comprises:

(a) (i) a heavy chain variable region comprising a heavy chain complementary determining region 1 (HC CDR1) comprising the amino acid sequence set forth in SEQ ID NO: 63, a heavy chain complementary determining region 2 (HC CDR2) comprising the amino acid sequence set forth in SEQ ID NO: 65, and a heavy chain complementary determining region 3 (HC CDR3) comprising the amino acid sequence set forth in SEQ ID NO: 67; and (ii) a light chain complementary determining region 1 (LC CDR1) comprising the amino acid sequence set forth in SEQ ID NO: 71, a light chain complementary determining region 2 (LC CDR2) comprising the amino acid sequence set forth in SEQ ID NO: 73, and a light chain complementary determining region 3 (LC CDR3) comprising the amino acid sequence set forth in SEQ ID NO: 75; or (b) (i) a heavy chain variable region comprising a heavy chain complementary determining region 1 (HC CDR1) comprising the amino acid sequence set forth in SEQ ID NO: 43, a heavy chain complementary determining region 2 (HC CDR2) comprising the amino acid sequence set forth in SEQ ID NO: 45, and a heavy chain complementary determining region 3 (HC CDR3) comprising the amino acid sequence set forth in SEQ ID NO: 47; and (ii) a light chain complementary determining region 1 (LC CDR1) comprising the amino acid sequence set forth in SEQ ID NO: 51, a light chain complementary determining region 2 (LC CDR2) comprising the amino acid sequence set forth in SEQ ID NO: 53, and a light chain complementary determining region 3 (LC CDR3) comprising the amino acid sequence set forth in SEQ ID NO: 55.

* * * * *

SEQUENCE LISTING

```
<160> NUMBER OF SEQ ID NOS: 226

<210> SEQ ID NO 1
<211> LENGTH: 21
<212> TYPE: PRT
<213> ORGANISM: Artificial Sequence
<220> FEATURE:
```

<223> OTHER INFORMATION: Artifically generated sequence

<400> SEQUENCE: 1

Met Ala Leu Pro Val Thr Ala Leu Leu Leu Pro Leu Ala Leu Leu Leu
1               5                   10                  15

His Ala Ala Arg Pro
            20

<210> SEQ ID NO 2
<211> LENGTH: 45
<212> TYPE: PRT
<213> ORGANISM: Artificial Sequence
<220> FEATURE:
<223> OTHER INFORMATION: Artifically generated sequence

<400> SEQUENCE: 2

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 3
<211> LENGTH: 230
<212> TYPE: PRT
<213> ORGANISM: Artificial Sequence
<220> FEATURE:
<223> OTHER INFORMATION: Artifically generated sequence

<400> SEQUENCE: 3

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser

```
    210                 215                 220

Leu Ser Leu Gly Lys Met
225                 230


<210> SEQ ID NO 4
<211> LENGTH: 282
<212> TYPE: PRT
<213> ORGANISM: Artificial Sequence
<220> FEATURE:
<223> OTHER INFORMATION: Artifically generated sequence

<400> SEQUENCE: 4

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
        35                  40                  45

Glu Lys Glu Glu Gln Glu Glu Arg Glu Thr Lys Thr Pro Glu Cys Pro
    50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
        115                 120                 125

Ser Gln Ser Gln His Ser Arg Leu Thr Leu Pro Arg Ser Leu Trp Asn
    130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
    210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
            260                 265                 270

Ser Leu Glu Val Ser Tyr Val Thr Asp His
        275                 280


<210> SEQ ID NO 5
<211> LENGTH: 10
<212> TYPE: PRT
<213> ORGANISM: Artificial Sequence
<220> FEATURE:
<223> OTHER INFORMATION: Artifically generated sequence

<400> SEQUENCE: 5
```

Gly Gly Gly Gly Ser Gly Gly Gly Gly Ser
1 5 10

<210> SEQ ID NO 6
<211> LENGTH: 24
<212> TYPE: PRT
<213> ORGANISM: Artificial Sequence
<220> FEATURE:
<223> OTHER INFORMATION: Artifically generated sequence

<400> SEQUENCE: 6

Ile Tyr Ile Trp Ala Pro Leu Ala Gly Thr Cys Gly Val Leu Leu Leu
1 5 10 15

Ser Leu Val Ile Thr Leu Tyr Cys
20

<210> SEQ ID NO 7
<211> LENGTH: 42
<212> TYPE: PRT
<213> ORGANISM: Artificial Sequence
<220> FEATURE:
<223> OTHER INFORMATION: Artifically generated sequence

<400> SEQUENCE: 7

Lys Arg Gly Arg Lys Lys Leu Leu Tyr Ile Phe Lys Gln Pro Phe Met
1 5 10 15

Arg Pro Val Gln Thr Thr Gln Glu Glu Asp Gly Cys Ser Cys Arg Phe
20 25 30

Pro Glu Glu Glu Glu Gly Gly Cys Glu Leu
35 40

<210> SEQ ID NO 8
<211> LENGTH: 48
<212> TYPE: PRT
<213> ORGANISM: Artificial Sequence
<220> FEATURE:
<223> OTHER INFORMATION: Artifically generated sequence

<400> SEQUENCE: 8

Gln Arg Arg Lys Tyr Arg Ser Asn Lys Gly Glu Ser Pro Val Glu Pro
1 5 10 15

Ala Glu Pro Cys Arg Tyr Ser Cys Pro Arg Glu Glu Glu Gly Ser Thr
20 25 30

Ile Pro Ile Gln Glu Asp Tyr Arg Lys Pro Glu Pro Ala Cys Ser Pro
35 40 45

<210> SEQ ID NO 9
<211> LENGTH: 112
<212> TYPE: PRT
<213> ORGANISM: Artificial Sequence
<220> FEATURE:
<223> OTHER INFORMATION: Artifically generated sequence

<400> SEQUENCE: 9

Arg Val Lys Phe Ser Arg Ser Ala Asp Ala Pro Ala Tyr Lys Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 10
<211> LENGTH: 112
<212> TYPE: PRT
<213> ORGANISM: Homo sapiens

<400> SEQUENCE: 10

Arg Val Lys Phe Ser Arg Ser Ala Asp Ala Pro Ala Tyr Gln Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 11
<211> LENGTH: 1184
<212> TYPE: DNA
<213> ORGANISM: Artificial Sequence
<220> FEATURE:
<223> OTHER INFORMATION: Artifically generated sequence

<400> SEQUENCE: 11
cgtgaggctc cggtgcccgt cagtgggcag agcgcacatc gcccacagtc cccgagaagt 60
tggggggagg ggtcggcaat tgaaccggtg cctagagaag gtggcgcggg gtaaactggg 120
aaagtgatgt cgtgtactgg ctccgccttt ttcccgaggg tgggggagaa ccgtatataa 180
gtgcagtagt cgccgtgaac gttctttttc gcaacgggtt tgccgccaga acacaggtaa 240
gtgccgtgtg tggttcccgc gggcctggcc tctttacggg ttatggccct tgcgtgcctt 300
gaattacttc cacctggctg cagtacgtga ttcttgatcc cgagcttcgg gttggaagtg 360
ggtgggagag ttcgaggcct tgcgcttaag gagccccttc gcctcgtgct tgagttgagg 420
cctggcctgg gcgctggggc cgccgcgtgc gaatctggtg gcaccttcgc gcctgtctcg 480
ctgctttcga taagtctcta gccatttaaa atttttgatg acctgctgcg acgctttttt 540
tctggcaaga tagtcttgta aatgcgggcc aagatctgca cactggtatt tcggtttttg 600
gggccgcggg cggcgacggg gcccgtgcgt cccagcgcac atgttcggcg aggcggggcc 660
tgcgagcgcg gccaccgaga atcggacggg ggtagtctca agctggccgg cctgctctgg 720
tgcctggcct cgcgccgccg tgtatcgccc cgccctgggc ggcaaggctg gcccggtcgg 780
caccagttgc gtgagcggaa agatggccgc ttcccggccc tgctgcaggg agctcaaaat 840
ggaggacgcg gcgctcggga gagcgggcgg gtgagtcacc cacacaaagg aaaagggcct 900
ttccgtcctc agccgtcgct tcatgtgact ccacggagta ccgggcgccg tccaggcacc 960
tcgattagtt ctcgagcttt tggagtacgt cgtctttagg ttggggggag ggttttatg 1020 cgatggagtt tccccacact gagtgggtgg agactgaagt taggccagct tggcacttga 1080
tgtaattctc cttggaattt gcccttttg agtttggatc ttggttcatt ctcaagcctc 1140
agacagtggt tcaaagtttt tttcttccat ttcaggtgtc gtga 1184

<210> SEQ ID NO 12
<211> LENGTH: 63
<212> TYPE: DNA
<213> ORGANISM: Artificial Sequence
<220> FEATURE:
<223> OTHER INFORMATION: Artifically generated sequence

<400> SEQUENCE: 12
atggccctgc ctgtgacagc cctgctgctg cctctggctc tgctgctgca tgccgctaga 60
ccc 63

<210> SEQ ID NO 13
<211> LENGTH: 134
<212> TYPE: DNA
<213> ORGANISM: Artificial Sequence
<220> FEATURE:
<223> OTHER INFORMATION: Artifically generated sequence

<400> SEQUENCE: 13
accacgacgc cagcgccgcg accaccaaca ccggcgccca ccatcgcgtc gcagcccctg 60
tccctgcgcc cagaggcgtg ccggccagcg gcggggggcg cagtgcacac gagggggctg 120
gacttcgcct gtga 134

<210> SEQ ID NO 14
<211> LENGTH: 690
<212> TYPE: DNA
<213> ORGANISM: Artificial Sequence
<220> FEATURE:
<223> OTHER INFORMATION: Artifically generated sequence

<400> SEQUENCE: 14
gagagcaagt acggccctcc ctgccccct tgccctgccc ccgagttcct gggcggaccc 60
agcgtgttcc tgttcccccc caagcccaag gacaccctga tgatcagccg gacccccgag 120
gtgacctgtg tggtggtgga cgtgtcccag gaggaccccg aggtccagtt caactggtac 180
gtggacggcg tggaggtgca caacgccaag accaagcccc gggaggagca gttcaatagc 240
acctaccggg tggtgtccgt gctgaccgtg ctgcaccagg actggctgaa cggcaaggaa 300
tacaagtgta aggtgtccaa caagggcctg cccagcagca tcgagaaaac catcagcaag 360
gccaagggcc agcctcggga gccccaggtg tacaccctgc cccctagcca agaggagatg 420
accaagaacc aggtgtccct gacctgcctg gtgaagggct tctaccccag cgacatcgcc 480
gtggagtggg agagcaacgg ccagcccgag aacaactaca agaccacccc ccctgtgctg 540
gacagcgacg gcagcttctt cctgtacagc cggctgaccg tggacaagag ccggtggcag 600
gagggcaacg tctttagctg ctccgtgatg cacgaggccc tgcacaacca ctacacccag 660
aagagcctga gcctgtccct gggcaagatg 690

<210> SEQ ID NO 15
<211> LENGTH: 847
<212> TYPE: DNA
<213> ORGANISM: Artificial Sequence
<220> FEATURE:

<223> OTHER INFORMATION: Artifically generated sequence

<400> SEQUENCE: 15
aggtggcccg aaagtcccaa ggcccaggca tctagtgttc ctactgcaca gccccaggca 60
gaaggcagcc tagccaaagc tactactgca cctgccacta cgcgcaatac tggccgtggc 120
ggggaggaga agaaaaagga gaaagagaaa gaagaacagg aagagaggga gaccaagacc 180
cctgaatgtc catcccatac ccagccgctg ggcgtctatc tcttgactcc cgcagtacag 240
gacttgtggc ttagagataa ggccaccttt acatgtttcg tcgtgggctc tgacctgaag 300
gatgcccatt tgacttggga ggttgccgga aaggtaccca caggggggt tgaggaaggg 360 ttgctggagc gccattccaa tggctctcag agccagcact caagactcac ccttccgaga 420
tccctgtgga acgccgggac ctctgtcaca tgtactctaa atcatcctag cctgccccca 480
cagcgtctga tggcccttag agagccagcc gcccaggcac cagttaagct tagcctgaat 540
ctgctcgcca gtagtgatcc cccagaggcc gccagctggc tcttatgcga agtgtccggc 600
tttagcccgc ccaacatctt gctcatgtgg ctggaggacc agcgagaagt gaacaccagc 660
ggcttcgctc cagcccggcc cccaccccag ccgggttcta ccacattctg ggcctggagt 720
gtcttaaggg tcccagcacc acctagcccc cagccagcca catacacctg tgttgtgtcc 780
catgaagata gcaggaccct gctaaatgct tctaggagtc tggaggtttc ctacgtgact 840
gaccatt 847

<210> SEQ ID NO 16
<211> LENGTH: 30
<212> TYPE: DNA
<213> ORGANISM: Artificial Sequence
<220> FEATURE:
<223> OTHER INFORMATION: Artifically generated sequence

<400> SEQUENCE: 16
ggtggcggag gttctggagg tggaggttcc 30

<210> SEQ ID NO 17
<211> LENGTH: 72
<212> TYPE: DNA
<213> ORGANISM: Artificial Sequence
<220> FEATURE:
<223> OTHER INFORMATION: Artifically generated sequence

<400> SEQUENCE: 17
atctacatct gggcgccctt ggccgggact tgtggggtcc ttctcctgtc actggttatc 60
accctttact gc 72

<210> SEQ ID NO 18
<211> LENGTH: 126
<212> TYPE: DNA
<213> ORGANISM: Artificial Sequence
<220> FEATURE:
<223> OTHER INFORMATION: Artifically generated sequence

<400> SEQUENCE: 18
aaacggggca gaaagaaact cctgtatata ttcaaacaac catttatgag accagtacaa 60
actactcaag aggaagatgg ctgtagctgc cgatttccag aagaagaaga aggaggatgt 120
gaactg 126

<210> SEQ ID NO 19
<211> LENGTH: 123

<212> TYPE: DNA
<213> ORGANISM: Artificial Sequence
<220> FEATURE:
<223> OTHER INFORMATION: Artifically generated sequence

<400> SEQUENCE: 19
aggagtaaga ggagcaggct cctgcacagt gactacatga acatgactcc ccgccgcccc 60
gggcccaccc gcaagcatta ccagccctat gccccaccac gcgacttcgc agcctatcgc 120
tcc 123

<210> SEQ ID NO 20
<211> LENGTH: 336
<212> TYPE: DNA
<213> ORGANISM: Artificial Sequence
<220> FEATURE:
<223> OTHER INFORMATION: Artifically generated sequence

<400> SEQUENCE: 20
agagtgaagt tcagcaggag cgcagacgcc cccgcgtaca agcagggcca gaaccagctc 60
tataacgagc tcaatctagg acgaagagag gagtacgatg ttttggacaa gagacgtggc 120
cgggaccctg agatgggggg aaagccgaga aggaagaacc ctcaggaagg cctgtacaat 180
gaactgcaga aagataagat ggcggaggcc tacagtgaga ttgggatgaa aggcgagcgc 240
cggaggggca aggggcacga tggcctttac cagggtctca gtacagccac caaggacacc 300
tacgacgccc ttcacatgca ggccctgccc cctcgc 336

<210> SEQ ID NO 21
<211> LENGTH: 336
<212> TYPE: DNA
<213> ORGANISM: Homo sapiens

<400> SEQUENCE: 21
agagtgaagt tcagcaggag cgcagacgcc cccgcgtacc agcagggcca gaaccagctc 60
tataacgagc tcaatctagg acgaagagag gagtacgatg ttttggacaa gagacgtggc 120
cgggaccctg agatgggggg aaagccgaga aggaagaacc ctcaggaagg cctgtacaat 180
gaactgcaga aagataagat ggcggaggcc tacagtgaga ttgggatgaa aggcgagcgc 240
cggaggggca aggggcacga tggcctttac cagggtctca gtacagccac caaggacacc 300
tacgacgccc ttcacatgca ggccctgccc cctcgc 336

<210> SEQ ID NO 22
<211> LENGTH: 373
<212> TYPE: PRT
<213> ORGANISM: Artificial Sequence
<220> FEATURE:
<223> OTHER INFORMATION: Artifically generated sequence

<400> SEQUENCE: 22

Pro Gly Trp Phe Leu Asp Ser Pro Asp Arg Pro Trp Asn Pro Pro Thr
1 5 10 15

Phe Ser Pro Ala Leu Leu Val Val Thr Glu Gly Asp Asn Ala Thr Phe
20 25 30

Thr Cys Ser Phe Ser Asn Thr Ser Glu Ser Phe Val Leu Asn Trp Tyr
35 40 45

Arg Met Ser Pro Ser Asn Gln Thr Asp Lys Leu Ala Ala Phe Pro Glu
50 55 60

Asp Arg Ser Gln Pro Gly Gln Asp Cys Arg Phe Arg Val Thr Gln Leu
65 70 75 80

```
Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Cys Asp Ile Tyr Ile Trp Ala Pro Leu Ala Gly Thr Cys Gly Val
        195                 200                 205

Leu Leu Leu Ser Leu Val Ile Thr Leu Tyr Cys Lys Arg Gly Arg Lys
    210                 215                 220

Lys Leu Leu Tyr Ile Phe Lys Gln Pro Phe Met Arg Pro Val Gln Thr
225                 230                 235                 240

Thr Gln Glu Glu Asp Gly Cys Ser Cys Arg Phe Pro Glu Glu Glu Glu
                245                 250                 255

Gly Gly Cys Glu Leu Arg Val Lys Phe Ser Arg Ser Ala Asp Ala Pro
            260                 265                 270

Ala Tyr Lys Gln Gly Gln Asn Gln Leu Tyr Asn Glu Leu Asn Leu Gly
        275                 280                 285

Arg Arg Glu Glu Tyr Asp Val Leu Asp Lys Arg Arg Gly Arg Asp Pro
    290                 295                 300

Glu Met Gly Gly Lys Pro Arg Arg Lys Asn Pro Gln Glu Gly Leu Tyr
305                 310                 315                 320

Asn Glu Leu Gln Lys Asp Lys Met Ala Glu Ala Tyr Ser Glu Ile Gly
                325                 330                 335

Met Lys Gly Glu Arg Arg Arg Gly Lys Gly His Asp Gly Leu Tyr Gln
            340                 345                 350

Gly Leu Ser Thr Ala Thr Lys Asp Thr Tyr Asp Ala Leu His Met Gln
        355                 360                 365

Ala Leu Pro Pro Arg
    370
```

<210> SEQ ID NO 23
<211> LENGTH: 1182
<212> TYPE: DNA
<213> ORGANISM: Artificial Sequence
<220> FEATURE:
<223> OTHER INFORMATION: Artifically generated sequence

<400> SEQUENCE: 23

```
atggccctcc ctgtcactgc cctgcttctc cccctcgcac tcctgctcca cgccgctaga     60

ccacccggat ggtttctgga ctctccggat cgcccgtgga atcccccaac cttctcaccg    120

gcactcttgg ttgtgactga gggcgataat gcgaccttca cgtgctcgtt ctccaacacc    180

tccgaatcat tcgtgctgaa ctggtaccgc atgagcccgt caaaccagac cgacaagctc    240

gccgcgtttc cggaagatcg gtcgcaaccg ggacaggatt gtcggttccg cgtgactcaa    300

ctgccgaatg gcagagactt ccacatgagc gtggtccgcg ctaggcgaaa cgactccggg    360
```

```
acctacctgt gcggagccat ctcgctggcg cctaaggccc aaatcaaaga gagcttgagg    420

gccgaactga gagtgaccga gcgcagagct gaggtgccaa ctgcacatcc atccccatcg    480

cctcggcctg cggggcagtt tcagaccctg gtcacgacca ctccggcgcc gcgcccaccg    540

actccggccc caactatcgc gagccagccc ctgtcgctga ggccggaagc atgccgccct    600

gccgccggag gtgctgtgca tacccgggga ttggacttcg catgcgacat ctacatttgg    660

gctcctctcg ccggaacttg tggcgtgctc cttctgtccc tggtcatcac cctgtactgc    720

aagcggggtc ggaaaaagct tctgtacatt ttcaagcagc ccttcatgag gcccgtgcaa    780

accacccagg aggaggacgg ttgctcctgc cggttccccg aagaggaaga aggaggttgc    840

gagctgcgcg tgaagttctc ccggagcgcc gacgcccccg cctataagca gggccagaac    900

cagctgtaca acgaactgaa cctgggacgg cgggaagagt acgatgtgct ggacaagcgg    960

cgcggccggg accccgaaat gggcgggaag cctagaagaa agaaccctca ggaaggcctg   1020

tataacgagc tgcagaagga caagatggcc gaggcctact ccgaaattgg gatgaaggga   1080

gagcggcgga ggggaaaggg gcacgacggc ctgtaccaag gactgtccac cgccaccaag   1140

gacacatacg atgccctgca catgcaggcc cttccccctc gc                      1182


<210> SEQ ID NO 24
<211> LENGTH: 394
<212> TYPE: PRT
<213> ORGANISM: Artificial Sequence
<220> FEATURE:
<223> OTHER INFORMATION: Artifically generated sequence

<400> SEQUENCE: 24

Met Ala Leu Pro Val Thr Ala Leu Leu Leu Pro Leu Ala Leu Leu Leu
1               5                   10                  15

His Ala Ala Arg Pro Pro Gly Trp Phe Leu Asp Ser Pro Asp Arg Pro
            20                  25                  30

Trp Asn Pro Pro Thr Phe Ser Pro Ala Leu Leu Val Val Thr Glu Gly
        35                  40                  45

Asp Asn Ala Thr Phe Thr Cys Ser Phe Ser Asn Thr Ser Glu Ser Phe
    50                  55                  60

Val Leu Asn Trp Tyr Arg Met Ser Pro Ser Asn Gln Thr Asp Lys Leu
65                  70                  75                  80

Ala Ala Phe Pro Glu Asp Arg Ser Gln Pro Gly Gln Asp Cys Arg Phe
                85                  90                  95

Arg Val Thr Gln Leu Pro Asn Gly Arg Asp Phe His Met Ser Val Val
            100                 105                 110

Arg Ala Arg Arg Asn Asp Ser Gly Thr Tyr Leu Cys Gly Ala Ile Ser
        115                 120                 125

Leu Ala Pro Lys Ala Gln Ile Lys Glu Ser Leu Arg Ala Glu Leu Arg
    130                 135                 140

Val Thr Glu Arg Arg Ala Glu Val Pro Thr Ala His Pro Ser Pro Ser
145                 150                 155                 160

Pro Arg Pro Ala Gly Gln Phe Gln Thr Leu Val Thr Thr Thr Pro Ala
                165                 170                 175

Pro Arg Pro Pro Thr Pro Ala Pro Thr Ile Ala Ser Gln Pro Leu Ser
            180                 185                 190

Leu Arg Pro Glu Ala Cys Arg Pro Ala Ala Gly Gly Ala Val His Thr
        195                 200                 205

Arg Gly Leu Asp Phe Ala Cys Asp Ile Tyr Ile Trp Ala Pro Leu Ala
```

```
    210                 215                 220

Gly Thr Cys Gly Val Leu Leu Leu Ser Leu Val Ile Thr Leu Tyr Cys
225                 230                 235                 240

Lys Arg Gly Arg Lys Lys Leu Leu Tyr Ile Phe Lys Gln Pro Phe Met
                245                 250                 255

Arg Pro Val Gln Thr Thr Gln Glu Glu Asp Gly Cys Ser Cys Arg Phe
            260                 265                 270

Pro Glu Glu Glu Glu Gly Gly Cys Glu Leu Arg Val Lys Phe Ser Arg
        275                 280                 285

Ser Ala Asp Ala Pro Ala Tyr Lys Gln Gly Gln Asn Gln Leu Tyr Asn
    290                 295                 300

Glu Leu Asn Leu Gly Arg Arg Glu Glu Tyr Asp Val Leu Asp Lys Arg
305                 310                 315                 320

Arg Gly Arg Asp Pro Glu Met Gly Gly Lys Pro Arg Arg Lys Asn Pro
                325                 330                 335

Gln Glu Gly Leu Tyr Asn Glu Leu Gln Lys Asp Lys Met Ala Glu Ala
            340                 345                 350

Tyr Ser Glu Ile Gly Met Lys Gly Glu Arg Arg Arg Gly Lys Gly His
        355                 360                 365

Asp Gly Leu Tyr Gln Gly Leu Ser Thr Ala Thr Lys Asp Thr Tyr Asp
    370                 375                 380

Ala Leu His Met Gln Ala Leu Pro Pro Arg
385                 390


<210> SEQ ID NO 25
<211> LENGTH: 5
<212> TYPE: PRT
<213> ORGANISM: Artificial Sequence
<220> FEATURE:
<223> OTHER INFORMATION: Artifically generated sequence

<400> SEQUENCE: 25

Gly Gly Gly Gly Ser
1               5


<210> SEQ ID NO 26
<211> LENGTH: 30
<212> TYPE: PRT
<213> ORGANISM: Artificial Sequence
<220> FEATURE:
<223> OTHER INFORMATION: Artifically generated sequence

<400> SEQUENCE: 26

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30


<210> SEQ ID NO 27
<211> LENGTH: 20
<212> TYPE: PRT
<213> ORGANISM: Artificial Sequence
<220> FEATURE:
<223> OTHER INFORMATION: Artifically generated sequence

<400> SEQUENCE: 27

Gly Gly Gly Gly Ser Gly Gly Gly Gly Ser Gly Gly Gly Gly Ser Gly
1               5                   10                  15

Gly Gly Gly Ser
            20
```

<210> SEQ ID NO 28
<211> LENGTH: 15
<212> TYPE: PRT
<213> ORGANISM: Artificial Sequence
<220> FEATURE:
<223> OTHER INFORMATION: Artifically generated sequence

<400> SEQUENCE: 28

Gly Gly Gly Gly Ser Gly Gly Gly Gly Ser Gly Gly Gly Gly Ser
1 5 10 15

<210> SEQ ID NO 29
<211> LENGTH: 4
<212> TYPE: PRT
<213> ORGANISM: Artificial Sequence
<220> FEATURE:
<223> OTHER INFORMATION: Artifically generated sequence

<400> SEQUENCE: 29

Gly Gly Gly Ser
1

<210> SEQ ID NO 30
<211> LENGTH: 50
<212> TYPE: DNA
<213> ORGANISM: Artificial Sequence
<220> FEATURE:
<223> OTHER INFORMATION: Artifically generated sequence
<220> FEATURE:
<221> NAME/KEY: Repeated_Feature
<222> LOCATION: (1)..(50)
<223> OTHER INFORMATION: Sequence pattern repeated n times (n= 1-10)

<400> SEQUENCE: 30
aaaaaaaaaa aaaaaaaaaa aaaaaaaaaa aaaaaaaaaa aaaaaaaaaa 50

<210> SEQ ID NO 31
<211> LENGTH: 100
<212> TYPE: DNA
<213> ORGANISM: Artificial Sequence
<220> FEATURE:
<223> OTHER INFORMATION: Artifically generated sequence

<400> SEQUENCE: 31
tttttttttt tttttttttt tttttttttt tttttttttt tttttttttt tttttttttt 60
tttttttttt tttttttttt tttttttttt tttttttttt 100

<210> SEQ ID NO 32
<211> LENGTH: 50
<212> TYPE: DNA
<213> ORGANISM: Artificial Sequence
<220> FEATURE:
<223> OTHER INFORMATION: Artifically generated sequence
<220> FEATURE:
<221> NAME/KEY: Repeated_Feature
<222> LOCATION: (1)..(50)
<223> OTHER INFORMATION: Sequence pattern repeated n times (n= 1-10)

<400> SEQUENCE: 32
tttttttttt tttttttttt tttttttttt tttttttttt tttttttttt 50

<210> SEQ ID NO 33
<211> LENGTH: 100
<212> TYPE: DNA
<213> ORGANISM: Artificial Sequence
<220> FEATURE:

<223> OTHER INFORMATION: Artifically generated sequence
<220> FEATURE:
<221> NAME/KEY: Repeated_Feature
<222> LOCATION: (1)..(100)
<223> OTHER INFORMATION: Sequence pattern repeated n times (n= 1-50)

<400> SEQUENCE: 33
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa 100

<210> SEQ ID NO 34
<211> LENGTH: 400
<212> TYPE: DNA
<213> ORGANISM: Artificial Sequence
<220> FEATURE:
<223> OTHER INFORMATION: Artifically generated sequence

<400> SEQUENCE: 34
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360
aaaaaaaaaa aaaaaaaaaa aaaaaaaaaa aaaaaaaaaa 400

<210> SEQ ID NO 35
<211> LENGTH: 2000
<212> TYPE: DNA
<213> ORGANISM: Artificial Sequence
<220> FEATURE:
<223> OTHER INFORMATION: Artifically generated sequence

<400> SEQUENCE: 35
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360
aaaaaaaaaa aaaaaaaaaa aaaaaaaaaa aaaaaaaaaa aaaaaaaaaa aaaaaaaaaa 420
aaaaaaaaaa aaaaaaaaaa aaaaaaaaaa aaaaaaaaaa aaaaaaaaaa aaaaaaaaaa 480
aaaaaaaaaa aaaaaaaaaa aaaaaaaaaa aaaaaaaaaa aaaaaaaaaa aaaaaaaaaa 540
aaaaaaaaaa aaaaaaaaaa aaaaaaaaaa aaaaaaaaaa aaaaaaaaaa aaaaaaaaaa 600
aaaaaaaaaa aaaaaaaaaa aaaaaaaaaa aaaaaaaaaa aaaaaaaaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa aaaaaaaaaa 780
aaaaaaaaaa aaaaaaaaaa aaaaaaaaaa aaaaaaaaaa aaaaaaaaaa aaaaaaaaaa 840
aaaaaaaaaa aaaaaaaaaa aaaaaaaaaa aaaaaaaaaa aaaaaaaaaa aaaaaaaaaa 900
aaaaaaaaaa aaaaaaaaaa aaaaaaaaaa aaaaaaaaaa aaaaaaaaaa aaaaaaaaaa 960
aaaaaaaaaa aaaaaaaaaa aaaaaaaaaa aaaaaaaaaa aaaaaaaaaa aaaaaaaaaa 1020

```
aaaaaaaaaa aaaaaaaaaa aaaaaaaaaa aaaaaaaaaa aaaaaaaaaa aaaaaaaaaa   1080

aaaaaaaaaa aaaaaaaaaa aaaaaaaaaa aaaaaaaaaa aaaaaaaaaa aaaaaaaaaa   1140

aaaaaaaaaa aaaaaaaaaa aaaaaaaaaa aaaaaaaaaa aaaaaaaaaa aaaaaaaaaa   1200

aaaaaaaaaa aaaaaaaaaa aaaaaaaaaa aaaaaaaaaa aaaaaaaaaa aaaaaaaaaa   1260

aaaaaaaaaa aaaaaaaaaa aaaaaaaaaa aaaaaaaaaa aaaaaaaaaa aaaaaaaaaa   1320

aaaaaaaaaa aaaaaaaaaa aaaaaaaaaa aaaaaaaaaa aaaaaaaaaa aaaaaaaaaa   1380

aaaaaaaaaa aaaaaaaaaa aaaaaaaaaa aaaaaaaaaa aaaaaaaaaa aaaaaaaaaa   1440

aaaaaaaaaa aaaaaaaaaa aaaaaaaaaa aaaaaaaaaa aaaaaaaaaa aaaaaaaaaa   1500

aaaaaaaaaa aaaaaaaaaa aaaaaaaaaa aaaaaaaaaa aaaaaaaaaa aaaaaaaaaa   1560

aaaaaaaaaa aaaaaaaaaa aaaaaaaaaa aaaaaaaaaa aaaaaaaaaa aaaaaaaaaa   1620

aaaaaaaaaa aaaaaaaaaa aaaaaaaaaa aaaaaaaaaa aaaaaaaaaa aaaaaaaaaa   1680

aaaaaaaaaa aaaaaaaaaa aaaaaaaaaa aaaaaaaaaa aaaaaaaaaa aaaaaaaaaa   1740

aaaaaaaaaa aaaaaaaaaa aaaaaaaaaa aaaaaaaaaa aaaaaaaaaa aaaaaaaaaa   1800

aaaaaaaaaa aaaaaaaaaa aaaaaaaaaa aaaaaaaaaa aaaaaaaaaa aaaaaaaaaa   1860

aaaaaaaaaa aaaaaaaaaa aaaaaaaaaa aaaaaaaaaa aaaaaaaaaa aaaaaaaaaa   1920

aaaaaaaaaa aaaaaaaaaa aaaaaaaaaa aaaaaaaaaa aaaaaaaaaa aaaaaaaaaa   1980

aaaaaaaaaa aaaaaaaaaa                                               2000
```

<210> SEQ ID NO 36
<211> LENGTH: 230
<212> TYPE: PRT
<213> ORGANISM: Homo sapiens

<400> SEQUENCE: 36

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190
```

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Lys Met
225 230

<210> SEQ ID NO 37
<211> LENGTH: 690
<212> TYPE: DNA
<213> ORGANISM: Homo sapiens

<400> SEQUENCE: 37
gagagcaagt acggccctcc ctgcccccct tgccctgccc ccgagttcct gggcggaccc 60
agcgtgttcc tgttcccccc caagcccaag gacaccctga tgatcagccg gacccccgag 120
gtgacctgtg tggtggtgga cgtgtcccag gaggaccccg aggtccagtt caactggtac 180
gtggacggcg tggaggtgca caacgccaag accaagcccc gggaggagca gttcaatagc 240
acctaccggg tggtgtccgt gctgaccgtg ctgcaccagg actggctgaa cggcaaggaa 300
tacaagtgta aggtgtccaa caagggcctg cccagcagca tcgagaaaac catcagcaag 360
gccaagggcc agcctcggga gccccaggtg tacaccctgc cccctagcca agaggagatg 420
accaagaacc aggtgtccct gacctgcctg gtgaagggct tctaccccag cgacatcgcc 480
gtggagtggg agagcaacgg ccagcccgag aacaactaca agaccacccc ccctgtgctg 540
gacagcgacg gcagcttctt cctgtacagc cggctgaccg tggacaagag ccggtggcag 600
gagggcaacg tctttagctg ctccgtgatg cacgaggccc tgcacaacca ctacacccag 660
aagagcctga gcctgtccct gggcaagatg 690

<210> SEQ ID NO 38
<211> LENGTH: 40
<212> TYPE: PRT
<213> ORGANISM: Artificial Sequence
<220> FEATURE:
<223> OTHER INFORMATION: Artifically generated sequence

<400> SEQUENCE: 38

Gly Gly Gly Ser Gly Gly Gly Ser Gly Gly Gly Ser Gly Gly Gly Ser
1 5 10 15

Gly Gly Gly Ser Gly Gly Gly Ser Gly Gly Gly Ser Gly Gly Gly Ser
20 25 30

Gly Gly Gly Ser Gly Gly Gly Ser
35 40

<210> SEQ ID NO 39
<211> LENGTH: 10
<212> TYPE: DNA
<213> ORGANISM: Artificial Sequence
<220> FEATURE:
<223> OTHER INFORMATION: Artifically generated sequence
<220> FEATURE:
<221> NAME/KEY: Repeated_Feature
<222> LOCATION: (1)..(5)
<223> OTHER INFORMATION: Sequence pattern repeated n times (n= 1-10)

<400> SEQUENCE: 39 ggggsggggs 10

<210> SEQ ID NO 40
<211> LENGTH: 354

```
<212> TYPE: DNA
<213> ORGANISM: Artificial Sequence
<220> FEATURE:
<223> OTHER INFORMATION: Artifically generated sequence

<400> SEQUENCE: 40

gagcagctga aggagtccgg gggaggtctc ttcaagccaa cggataccct gacactcacc      60

tgcacagtct ctggattctc cctcagttac tatggagtga actgggtccg ccaggctcca     120

gggaacgggc tggaatggat cggaaccatt ggtggtagtg gtgacacata ctacgcgagc     180

tgggcgaaga gccgatccac catcatcaga aacaccaacg agaacacggt gactctgaaa     240

atgaccagtc tgacagccgc ggacacggcc acctatttct gtgtgagata tgctaatatt     300

ggttatgagt actttaacgt ctggggtcca ggcaccctgg tcaccgtctc ttca           354


<210> SEQ ID NO 41
<211> LENGTH: 118
<212> TYPE: PRT
<213> ORGANISM: Artificial Sequence
<220> FEATURE:
<223> OTHER INFORMATION: Artifically generated sequence

<400> SEQUENCE: 41

Glu Gln Leu Lys Glu Ser Gly Gly Gly Leu Phe Lys Pro Thr Asp Thr
1               5                   10                  15

Leu Thr Leu Thr Cys Thr Val Ser Gly Phe Ser Leu Ser Tyr Tyr Gly
            20                  25                  30

Val Asn Trp Val Arg Gln Ala Pro Gly Asn Gly Leu Glu Trp Ile Gly
        35                  40                  45

Thr Ile Gly Gly Ser Gly Asp Thr Tyr Tyr Ala Ser Trp Ala Lys Ser
    50                  55                  60

Arg Ser Thr Ile Ile Arg Asn Thr Asn Glu Asn Thr Val Thr Leu Lys
65                  70                  75                  80

Met Thr Ser Leu Thr Ala Ala Asp Thr Ala Thr Tyr Phe Cys Val Arg
                85                  90                  95

Tyr Ala Asn Ile Gly Tyr Glu Tyr Phe Asn Val Trp Gly Pro Gly Thr
            100                 105                 110

Leu Val Thr Val Ser Ser
        115


<210> SEQ ID NO 42
<211> LENGTH: 24
<212> TYPE: DNA
<213> ORGANISM: Artificial Sequence
<220> FEATURE:
<223> OTHER INFORMATION: Artifically generated sequence

<400> SEQUENCE: 42

ggattctccc tcagttacta tgga                                             24


<210> SEQ ID NO 43
<211> LENGTH: 8
<212> TYPE: PRT
<213> ORGANISM: Artificial Sequence
<220> FEATURE:
<223> OTHER INFORMATION: Artifically generated sequence

<400> SEQUENCE: 43

Gly Phe Ser Leu Ser Tyr Tyr Gly
1               5
```

<210> SEQ ID NO 44
<211> LENGTH: 21
<212> TYPE: DNA
<213> ORGANISM: Artificial Sequence
<220> FEATURE:
<223> OTHER INFORMATION: Artifically generated sequence

<400> SEQUENCE: 44
attggtggta gtggtgacac a 21

<210> SEQ ID NO 45
<211> LENGTH: 7
<212> TYPE: PRT
<213> ORGANISM: Artificial Sequence
<220> FEATURE:
<223> OTHER INFORMATION: Artifically generated sequence

<400> SEQUENCE: 45

Ile Gly Gly Ser Gly Asp Thr
1 5

<210> SEQ ID NO 46
<211> LENGTH: 39
<212> TYPE: DNA
<213> ORGANISM: Artificial Sequence
<220> FEATURE:
<223> OTHER INFORMATION: Artifically generated sequence

<400> SEQUENCE: 46
gtgagatatg ctaatattgg ttatgagtac tttaacgtc 39

<210> SEQ ID NO 47
<211> LENGTH: 13
<212> TYPE: PRT
<213> ORGANISM: Artificial Sequence
<220> FEATURE:
<223> OTHER INFORMATION: Artifically generated sequence

<400> SEQUENCE: 47

Val Arg Tyr Ala Asn Ile Gly Tyr Glu Tyr Phe Asn Val
1 5 10

<210> SEQ ID NO 48
<211> LENGTH: 333
<212> TYPE: DNA
<213> ORGANISM: Artificial Sequence
<220> FEATURE:
<223> OTHER INFORMATION: Artifically generated sequence

<400> SEQUENCE: 48
cagtttgtgc tgactcagtc gccctctgca tctgctgccc tgggagcctc ggccaagctc 60
acctgcaccc tgagcagtgc ccacaagacc tacaccattg actggtatca gcagcagaaa 120
gggaaggccc ctcgctacct gatacaagtt aagagtgatg gaacctacac caaggcgacc 180
ggggtccctg atcgcttctc gggctccagc tctggggctg accgctacct gatcatcccc 240
agcgtccagg ctgatgacga agccgactac tattgtggta cagattatac cggtgggtat 300
gtgttcggcg gggggaccca gctgaccgtc aca 333

<210> SEQ ID NO 49
<211> LENGTH: 111
<212> TYPE: PRT
<213> ORGANISM: Artificial Sequence
<220> FEATURE:
<223> OTHER INFORMATION: Artifically generated sequence

<400> SEQUENCE: 49

Gln Phe Val Leu Thr Gln Ser Pro Ser Ala Ser Ala Ala Leu Gly Ala
1 5 10 15

Ser Ala Lys Leu Thr Cys Thr Leu Ser Ser Ala His Lys Thr Tyr Thr
20 25 30

Ile Asp Trp Tyr Gln Gln Gln Lys Gly Lys Ala Pro Arg Tyr Leu Ile
35 40 45

Gln Val Lys Ser Asp Gly Thr Tyr Thr Lys Ala Thr Gly Val Pro Asp
50 55 60

Arg Phe Ser Gly Ser Ser Ser Gly Ala Asp Arg Tyr Leu Ile Ile Pro
65 70 75 80

Ser Val Gln Ala Asp Asp Glu Ala Asp Tyr Tyr Cys Gly Thr Asp Tyr
85 90 95

Thr Gly Gly Tyr Val Phe Gly Gly Gly Thr Gln Leu Thr Val Thr
100 105 110

<210> SEQ ID NO 50
<211> LENGTH: 21
<212> TYPE: DNA
<213> ORGANISM: Artificial Sequence
<220> FEATURE:
<223> OTHER INFORMATION: Artifically generated sequence

<400> SEQUENCE: 50
agtgcccaca agacctacac c 21

<210> SEQ ID NO 51
<211> LENGTH: 7
<212> TYPE: PRT
<213> ORGANISM: Artificial Sequence
<220> FEATURE:
<223> OTHER INFORMATION: Artifically generated sequence

<400> SEQUENCE: 51

Ser Ala His Lys Thr Tyr Thr
1 5

<210> SEQ ID NO 52
<211> LENGTH: 21
<212> TYPE: DNA
<213> ORGANISM: Artificial Sequence
<220> FEATURE:
<223> OTHER INFORMATION: Artifically generated sequence

<400> SEQUENCE: 52
gttaagagtg atggaaccta c 21

<210> SEQ ID NO 53
<211> LENGTH: 7
<212> TYPE: PRT
<213> ORGANISM: Artificial Sequence
<220> FEATURE:
<223> OTHER INFORMATION: Artifically generated sequence

<400> SEQUENCE: 53

Val Lys Ser Asp Gly Thr Tyr
1 5

<210> SEQ ID NO 54
<211> LENGTH: 27
<212> TYPE: DNA
<213> ORGANISM: Artificial Sequence
<220> FEATURE:

<223> OTHER INFORMATION: Artifically generated sequence

<400> SEQUENCE: 54
ggtacagatt ataccggtgg gtatgtg 27

<210> SEQ ID NO 55
<211> LENGTH: 9
<212> TYPE: PRT
<213> ORGANISM: Artificial Sequence
<220> FEATURE:
<223> OTHER INFORMATION: Artifically generated sequence

<400> SEQUENCE: 55

Gly Thr Asp Tyr Thr Gly Gly Tyr Val
1 5

<210> SEQ ID NO 56
<211> LENGTH: 744
<212> TYPE: DNA
<213> ORGANISM: Artificial Sequence
<220> FEATURE:
<223> OTHER INFORMATION: Artifically generated sequence

<400> SEQUENCE: 56
ggatccgagc agctgaagga gtccgggga ggtctcttca agccaacgga taccctgaca 60
ctcacctgca cagtctctgg attctccctc agttactatg gagtgaactg ggtccgccag 120
gctccaggga acgggctgga atggatcgga accattggtg gtagtggtga cacatactac 180
gcgagctggg cgaagagccg atccaccatc atcagaaaca ccaacgagaa cacggtgact 240
ctgaaaatga ccagtctgac agccgcggac acggccacct atttctgtgt gagatatgct 300
aatattggtt atgagtactt taacgtctgg ggtccaggca ccctggtcac cgtctcttca 360
ggtggaggcg gttcaggcgg cggtggctct agcggtggtg gatcgcagtt tgtgctgact 420
cagtcgccct ctgcatctgc tgccctggga gcctcggcca agctcacctg caccctgagc 480
agtgcccaca agacctacac cattgactgg tatcagcagc agaaagggaa ggcccctcgc 540
tacctgatac aagttaagag tgatggaacc tacaccaagg cgaccggggt ccctgatcgc 600
ttctcgggct ccagctctgg ggctgaccgc tacctgatca tccccagcgt ccaggctgat 660
gacgaagccg actactattg tggtacagat tataccggtg ggtatgtgtt cggcgggggg 720
acccagctga ccgtcacagc tagc 744

<210> SEQ ID NO 57
<211> LENGTH: 744
<212> TYPE: DNA
<213> ORGANISM: Artificial Sequence
<220> FEATURE:
<223> OTHER INFORMATION: Artifically generated sequence

<400> SEQUENCE: 57
ggatccgagc agctgaagga gtccggcgga ggcctgttta agcccaccga caccctgaca 60
ctgacctgca cagtgtccgg cttcagcctg agctactatg gcgtgaactg ggtgagacag 120
gcccctggca acggactgga gtggatcggc accattggcg gcagcggaga cacctactac 180
gccagctggg ccaagtccag gagcaccatc atcagaaaca ccaacgagaa caccgtgacc 240
ctgaagatga cctccctgac agccgccgac accgccacct acttctgcgt gaggtacgcc 300
aacatcggct acgagtactt caacgtgtgg ggccctggca ccctggtgac agtgtccagc 360
ggcggaggag gaagcggcgg cggcggctcc agcggaggcg gcagccagtt tgtgctgacc 420

-continued

```
cagagcccta gcgcttccgc cgccctgggc gccagcgcca agctcacctg taccctgagc    480

agcgcccaca agacctatac catcgactgg taccagcagc agaagggcaa ggcccccagg    540

tacctgatcc aggtgaagtc cgacggcacc tacaccaaag ccaccggcgt gcccgacaga    600

tttagcggca gcagctccgg cgccgacagg tatctgatca tcccttccgt gcaggccgac    660

gacgaggccg actactactg cggaaccgac tacaccggcg gatacgtgtt cggaggcggc    720

acccagctga ccgtgaccgc tagc                                           744


<210> SEQ ID NO 58
<211> LENGTH: 248
<212> TYPE: PRT
<213> ORGANISM: Artificial Sequence
<220> FEATURE:
<223> OTHER INFORMATION: Artifically generated sequence

<400> SEQUENCE: 58

Gly Ser Glu Gln Leu Lys Glu Ser Gly Gly Gly Leu Phe Lys Pro Thr
1               5                   10                  15

Asp Thr Leu Thr Leu Thr Cys Thr Val Ser Gly Phe Ser Leu Ser Tyr
            20                  25                  30

Tyr Gly Val Asn Trp Val Arg Gln Ala Pro Gly Asn Gly Leu Glu Trp
        35                  40                  45

Ile Gly Thr Ile Gly Gly Ser Gly Asp Thr Tyr Tyr Ala Ser Trp Ala
    50                  55                  60

Lys Ser Arg Ser Thr Ile Ile Arg Asn Thr Asn Glu Asn Thr Val Thr
65                  70                  75                  80

Leu Lys Met Thr Ser Leu Thr Ala Ala Asp Thr Ala Thr Tyr Phe Cys
                85                  90                  95

Val Arg Tyr Ala Asn Ile Gly Tyr Glu Tyr Phe Asn Val Trp Gly Pro
            100                 105                 110

Gly Thr Leu Val Thr Val Ser Ser Gly Gly Gly Gly Ser Gly Gly Gly
        115                 120                 125

Gly Ser Ser Gly Gly Gly Ser Gln Phe Val Leu Thr Gln Ser Pro Ser
    130                 135                 140

Ala Ser Ala Ala Leu Gly Ala Ser Ala Lys Leu Thr Cys Thr Leu Ser
145                 150                 155                 160

Ser Ala His Lys Thr Tyr Thr Ile Asp Trp Tyr Gln Gln Gln Lys Gly
                165                 170                 175

Lys Ala Pro Arg Tyr Leu Ile Gln Val Lys Ser Asp Gly Thr Tyr Thr
            180                 185                 190

Lys Ala Thr Gly Val Pro Asp Arg Phe Ser Gly Ser Ser Ser Gly Ala
        195                 200                 205

Asp Arg Tyr Leu Ile Ile Pro Ser Val Gln Ala Asp Asp Glu Ala Asp
    210                 215                 220

Tyr Tyr Cys Gly Thr Asp Tyr Thr Gly Gly Tyr Val Phe Gly Gly Gly
225                 230                 235                 240

Thr Gln Leu Thr Val Thr Ala Ser
                245


<210> SEQ ID NO 59
<211> LENGTH: 244
<212> TYPE: PRT
<213> ORGANISM: Artificial Sequence
<220> FEATURE:
<223> OTHER INFORMATION: Artifically generated sequence

<400> SEQUENCE: 59
```

```
Glu Gln Leu Lys Glu Ser Gly Gly Gly Leu Phe Lys Pro Thr Asp Thr
1               5                   10                  15

Leu Thr Leu Thr Cys Thr Val Ser Gly Phe Ser Leu Ser Tyr Tyr Gly
            20                  25                  30

Val Asn Trp Val Arg Gln Ala Pro Gly Asn Gly Leu Glu Trp Ile Gly
        35                  40                  45

Thr Ile Gly Gly Ser Gly Asp Thr Tyr Tyr Ala Ser Trp Ala Lys Ser
    50                  55                  60

Arg Ser Thr Ile Ile Arg Asn Thr Asn Glu Asn Thr Val Thr Leu Lys
65                  70                  75                  80

Met Thr Ser Leu Thr Ala Ala Asp Thr Ala Thr Tyr Phe Cys Val Arg
                85                  90                  95

Tyr Ala Asn Ile Gly Tyr Glu Tyr Phe Asn Val Trp Gly Pro Gly Thr
            100                 105                 110

Leu Val Thr Val Ser Ser Gly Gly Gly Gly Ser Gly Gly Gly Gly Ser
        115                 120                 125

Ser Gly Gly Gly Ser Gln Phe Val Leu Thr Gln Ser Pro Ser Ala Ser
    130                 135                 140

Ala Ala Leu Gly Ala Ser Ala Lys Leu Thr Cys Thr Leu Ser Ser Ala
145                 150                 155                 160

His Lys Thr Tyr Thr Ile Asp Trp Tyr Gln Gln Gln Lys Gly Lys Ala
                165                 170                 175

Pro Arg Tyr Leu Ile Gln Val Lys Ser Asp Gly Thr Tyr Thr Lys Ala
            180                 185                 190

Thr Gly Val Pro Asp Arg Phe Ser Gly Ser Ser Ser Gly Ala Asp Arg
        195                 200                 205

Tyr Leu Ile Ile Pro Ser Val Gln Ala Asp Asp Glu Ala Asp Tyr Tyr
    210                 215                 220

Cys Gly Thr Asp Tyr Thr Gly Gly Tyr Val Phe Gly Gly Gly Thr Gln
225                 230                 235                 240

Leu Thr Val Thr
```

<210> SEQ ID NO 60
<211> LENGTH: 369
<212> TYPE: DNA
<213> ORGANISM: Artificial Sequence
<220> FEATURE:
<223> OTHER INFORMATION: Artifically generated sequence

<400> SEQUENCE: 60

```
cagtcagtga aggagtccga gggaggtctc ttcaagccaa cggataccct gacactcacc     60

tgcacggtct ctggattctc cctcagtaga catgcactga cctgggtccg ccaggctcca    120

gggaacgggc tggaatggat cggagccatt gataacgctg gtaccacata ctacgcgagc    180

tgggcgaaaa gccgctccac catcaccaga aacaccgacc tgcacacggt gactctgaaa    240

atgaccagtc tgacagcctc ggacacggct acctatttct gtgcgagagt cttttatgat    300

attaatagtg gttattatct ggacggcatg gacctctggg gcccagggac cctcgtcacc    360

gtctcttca                                                            369
```

<210> SEQ ID NO 61
<211> LENGTH: 123
<212> TYPE: PRT
<213> ORGANISM: Artificial Sequence
<220> FEATURE:
<223> OTHER INFORMATION: Artifically generated sequence

<400> SEQUENCE: 61

Gln Ser Val Lys Glu Ser Glu Gly Gly Leu Phe Lys Pro Thr Asp Thr
1               5                   10                  15

Leu Thr Leu Thr Cys Thr Val Ser Gly Phe Ser Leu Ser Arg His Ala
            20                  25                  30

Leu Thr Trp Val Arg Gln Ala Pro Gly Asn Gly Leu Glu Trp Ile Gly
        35                  40                  45

Ala Ile Asp Asn Ala Gly Thr Thr Tyr Tyr Ala Ser Trp Ala Lys Ser
    50                  55                  60

Arg Ser Thr Ile Thr Arg Asn Thr Asp Leu His Thr Val Thr Leu Lys
65                  70                  75                  80

Met Thr Ser Leu Thr Ala Ser Asp Thr Ala Thr Tyr Phe Cys Ala Arg
                85                  90                  95

Val Phe Tyr Asp Ile Asn Ser Gly Tyr Tyr Leu Asp Gly Met Asp Leu
            100                 105                 110

Trp Gly Pro Gly Thr Leu Val Thr Val Ser Ser
        115                 120

<210> SEQ ID NO 62
<211> LENGTH: 24
<212> TYPE: DNA
<213> ORGANISM: Artificial Sequence
<220> FEATURE:
<223> OTHER INFORMATION: Artifically generated sequence

<400> SEQUENCE: 62
ggattctccc tcagtagaca tgca 24

<210> SEQ ID NO 63
<211> LENGTH: 8
<212> TYPE: PRT
<213> ORGANISM: Artificial Sequence
<220> FEATURE:
<223> OTHER INFORMATION: Artifically generated sequence

<400> SEQUENCE: 63

Gly Phe Ser Leu Ser Arg His Ala
1               5

<210> SEQ ID NO 64
<211> LENGTH: 21
<212> TYPE: DNA
<213> ORGANISM: Artificial Sequence
<220> FEATURE:
<223> OTHER INFORMATION: Artifically generated sequence

<400> SEQUENCE: 64
attgataacg ctggtaccac a 21

<210> SEQ ID NO 65
<211> LENGTH: 7
<212> TYPE: PRT
<213> ORGANISM: Artificial Sequence
<220> FEATURE:
<223> OTHER INFORMATION: Artifically generated sequence

<400> SEQUENCE: 65

Ile Asp Asn Ala Gly Thr Thr
1               5

<210> SEQ ID NO 66

<211> LENGTH: 54
<212> TYPE: DNA
<213> ORGANISM: Artificial Sequence
<220> FEATURE:
<223> OTHER INFORMATION: Artifically generated sequence

<400> SEQUENCE: 66
gcgagagtct tttatgatat taatagtggt tattatctgg acggcatgga cctc 54

<210> SEQ ID NO 67
<211> LENGTH: 18
<212> TYPE: PRT
<213> ORGANISM: Artificial Sequence
<220> FEATURE:
<223> OTHER INFORMATION: Artifically generated sequence

<400> SEQUENCE: 67

Ala Arg Val Phe Tyr Asp Ile Asn Ser Gly Tyr Tyr Leu Asp Gly Met
1 5 10 15

Asp Leu

<210> SEQ ID NO 68
<211> LENGTH: 333
<212> TYPE: DNA
<213> ORGANISM: Artificial Sequence
<220> FEATURE:
<223> OTHER INFORMATION: Artifically generated sequence

<400> SEQUENCE: 68
cagtttgtgc tgactcagtc gccctctgtg tctgccgccc tgggagcctc tgccaagctc 60
acctgcaccc tgagcagtgc ccacaagacc tacaccattg actggtatca gcagcagcaa 120
ggggaggccc ctcggtacct gatgcaagtt aagagtgatg gaagctacac caaggggacc 180
ggggtccctg atcgcttctc gggctccagc tctggggctg accgctactt gatcatcccc 240
agcgtccagg ctgatgacga agccggctac gtttgtggtg cagatgataa cggtgggtat 300
gtgttcggcg gagggaccca gctgaccgtc aca 333

<210> SEQ ID NO 69
<211> LENGTH: 111
<212> TYPE: PRT
<213> ORGANISM: Artificial Sequence
<220> FEATURE:
<223> OTHER INFORMATION: Artifically generated sequence

<400> SEQUENCE: 69

Gln Phe Val Leu Thr Gln Ser Pro Ser Val Ser Ala Ala Leu Gly Ala
1 5 10 15

Ser Ala Lys Leu Thr Cys Thr Leu Ser Ser Ala His Lys Thr Tyr Thr
20 25 30

Ile Asp Trp Tyr Gln Gln Gln Gln Gly Glu Ala Pro Arg Tyr Leu Met
35 40 45

Gln Val Lys Ser Asp Gly Ser Tyr Thr Lys Gly Thr Gly Val Pro Asp
50 55 60

Arg Phe Ser Gly Ser Ser Ser Gly Ala Asp Arg Tyr Leu Ile Ile Pro
65 70 75 80

Ser Val Gln Ala Asp Asp Glu Ala Gly Tyr Val Cys Gly Ala Asp Asp
85 90 95

Asn Gly Gly Tyr Val Phe Gly Gly Gly Thr Gln Leu Thr Val Thr
100 105 110

<210> SEQ ID NO 70
<211> LENGTH: 21
<212> TYPE: DNA
<213> ORGANISM: Artificial Sequence
<220> FEATURE:
<223> OTHER INFORMATION: Artifically generated sequence

<400> SEQUENCE: 70
agtgcccaca agacctacac c 21

<210> SEQ ID NO 71
<211> LENGTH: 7
<212> TYPE: PRT
<213> ORGANISM: Artificial Sequence
<220> FEATURE:
<223> OTHER INFORMATION: Artifically generated sequence

<400> SEQUENCE: 71

Ser Ala His Lys Thr Tyr Thr
1 5

<210> SEQ ID NO 72
<211> LENGTH: 21
<212> TYPE: DNA
<213> ORGANISM: Artificial Sequence
<220> FEATURE:
<223> OTHER INFORMATION: Artifically generated sequence

<400> SEQUENCE: 72
gttaagagtg atggaagcta c 21

<210> SEQ ID NO 73
<211> LENGTH: 7
<212> TYPE: PRT
<213> ORGANISM: Artificial Sequence
<220> FEATURE:
<223> OTHER INFORMATION: Artifically generated sequence

<400> SEQUENCE: 73

Val Lys Ser Asp Gly Ser Tyr
1 5

<210> SEQ ID NO 74
<211> LENGTH: 27
<212> TYPE: DNA
<213> ORGANISM: Artificial Sequence
<220> FEATURE:
<223> OTHER INFORMATION: Artifically generated sequence

<400> SEQUENCE: 74
ggtgcagatg ataacggtgg gtatgtg 27

<210> SEQ ID NO 75
<211> LENGTH: 9
<212> TYPE: PRT
<213> ORGANISM: Artificial Sequence
<220> FEATURE:
<223> OTHER INFORMATION: Artifically generated sequence

<400> SEQUENCE: 75

Gly Ala Asp Asp Asn Gly Gly Tyr Val
1 5

<210> SEQ ID NO 76
<211> LENGTH: 759
<212> TYPE: DNA
<213> ORGANISM: Artificial Sequence

```
<220> FEATURE:
<223> OTHER INFORMATION: Artifically generated sequence

<400> SEQUENCE: 76

ggatcccagt cagtgaagga gtccgaggga ggtctcttca agccaacgga taccctgaca     60

ctcacctgca cggtctctgg attctccctc agtagacatg cactgacctg ggtccgccag    120

gctccaggga acgggctgga atggatcgga gccattgata acgctggtac cacatactac    180

gcgagctggg cgaaaagccg ctccaccatc accagaaaca ccgacctgca cacggtgact    240

ctgaaaatga ccagtctgac agcctcggac acggctacct atttctgtgc gagagtcttt    300

tatgatatta atagtggtta ttatctggac ggcatggacc tctggggccc agggaccctc    360

gtcaccgtct cttcaggtgg aggcggttca ggcggcggtg gctctagcgg tggtggatcg    420

cagtttgtgc tgactcagtc gccctctgtg tctgccgccc tgggagcctc tgccaagctc    480

acctgcaccc tgagcagtgc ccacaagacc tacaccattg actggtatca gcagcagcaa    540

ggggaggccc ctcggtacct gatgcaagtt aagagtgatg gaagctacac caaggggacc    600

ggggtccctg atcgcttctc gggctccagc tctggggctg accgctactt gatcatcccc    660

agcgtccagg ctgatgacga agccggctac gtttgtggtg cagatgataa cggtgggtat    720

gtgttcggcg gagggaccca gctgaccgtc acagctagc                          759


<210> SEQ ID NO 77
<211> LENGTH: 759
<212> TYPE: DNA
<213> ORGANISM: Artificial Sequence
<220> FEATURE:
<223> OTHER INFORMATION: Artifically generated sequence

<400> SEQUENCE: 77

ggatcccagt ccgtgaagga gagcgagggc ggcctgttca agcccaccga caccctgacc     60

ctgacctgca cagtgagcgg cttcagcctg tccagacacg ccctgacatg ggtgagacag    120

gcccctggca acggcctgga atggatcggc gccatcgaca acgccggcac cacctactac    180

gccagctggg ccaagtccag gtccaccatc accaggaaca ccgacctcca caccgtgacc    240

ctgaagatga caagcctgac cgcctccgac accgccacct acttctgcgc cagggtgttc    300

tacgacatca acagcggcta ctacctggat ggcatggacc tgtggggacc tggcacactg    360

gtgaccgtga gcagcggagg cggcggcagc ggcggcggcg gcagcagcgg cggcggaagc    420

cagttcgtgc tgacacagag ccctagcgtg agcgccgccc tgggagcctc cgctaaactg    480

acctgcaccc tgagcagcgc ccacaagacc tacaccatcg actggtacca acagcagcag    540

ggcgaggccc ccaggtatct gatgcaggtg aagtccgacg gcagctacac caaaggcacc    600

ggcgtgcctg acaggttcag cggcagctcc agcggagccg acaggtacct gatcatcccc    660

tccgtgcagg ccgacgacga ggctggctac gtgtgtggcg ccgacgacaa tggcggctac    720

gtgttcggag gcggcaccca gctgaccgtg acagctagc                          759


<210> SEQ ID NO 78
<211> LENGTH: 253
<212> TYPE: PRT
<213> ORGANISM: Artificial Sequence
<220> FEATURE:
<223> OTHER INFORMATION: Artifically generated sequence

<400> SEQUENCE: 78

Gly Ser Gln Ser Val Lys Glu Ser Glu Gly Gly Leu Phe Lys Pro Thr
1               5                   10                  15
```

```
Asp Thr Leu Thr Leu Thr Cys Thr Val Ser Gly Phe Ser Leu Ser Arg
            20                  25                  30

His Ala Leu Thr Trp Val Arg Gln Ala Pro Gly Asn Gly Leu Glu Trp
        35                  40                  45

Ile Gly Ala Ile Asp Asn Ala Gly Thr Thr Tyr Tyr Ala Ser Trp Ala
    50                  55                  60

Lys Ser Arg Ser Thr Ile Thr Arg Asn Thr Asp Leu His Thr Val Thr
65                  70                  75                  80

Leu Lys Met Thr Ser Leu Thr Ala Ser Asp Thr Ala Thr Tyr Phe Cys
                85                  90                  95

Ala Arg Val Phe Tyr Asp Ile Asn Ser Gly Tyr Tyr Leu Asp Gly Met
            100                 105                 110

Asp Leu Trp Gly Pro Gly Thr Leu Val Thr Val Ser Ser Gly Gly Gly
        115                 120                 125

Gly Ser Gly Gly Gly Gly Ser Ser Gly Gly Gly Ser Gln Phe Val Leu
    130                 135                 140

Thr Gln Ser Pro Ser Val Ser Ala Ala Leu Gly Ala Ser Ala Lys Leu
145                 150                 155                 160

Thr Cys Thr Leu Ser Ser Ala His Lys Thr Tyr Thr Ile Asp Trp Tyr
                165                 170                 175

Gln Gln Gln Gln Gly Glu Ala Pro Arg Tyr Leu Met Gln Val Lys Ser
            180                 185                 190

Asp Gly Ser Tyr Thr Lys Gly Thr Gly Val Pro Asp Arg Phe Ser Gly
        195                 200                 205

Ser Ser Ser Gly Ala Asp Arg Tyr Leu Ile Ile Pro Ser Val Gln Ala
    210                 215                 220

Asp Asp Glu Ala Gly Tyr Val Cys Gly Ala Asp Asp Asn Gly Gly Tyr
225                 230                 235                 240

Val Phe Gly Gly Gly Thr Gln Leu Thr Val Thr Ala Ser
                245                 250


<210> SEQ ID NO 79
<211> LENGTH: 249
<212> TYPE: PRT
<213> ORGANISM: Artificial Sequence
<220> FEATURE:
<223> OTHER INFORMATION: Artifically generated sequence

<400> SEQUENCE: 79

Gln Ser Val Lys Glu Ser Glu Gly Gly Leu Phe Lys Pro Thr Asp Thr
1               5                   10                  15

Leu Thr Leu Thr Cys Thr Val Ser Gly Phe Ser Leu Ser Arg His Ala
            20                  25                  30

Leu Thr Trp Val Arg Gln Ala Pro Gly Asn Gly Leu Glu Trp Ile Gly
        35                  40                  45

Ala Ile Asp Asn Ala Gly Thr Thr Tyr Tyr Ala Ser Trp Ala Lys Ser
    50                  55                  60

Arg Ser Thr Ile Thr Arg Asn Thr Asp Leu His Thr Val Thr Leu Lys
65                  70                  75                  80

Met Thr Ser Leu Thr Ala Ser Asp Thr Ala Thr Tyr Phe Cys Ala Arg
                85                  90                  95

Val Phe Tyr Asp Ile Asn Ser Gly Tyr Tyr Leu Asp Gly Met Asp Leu
            100                 105                 110

Trp Gly Pro Gly Thr Leu Val Thr Val Ser Ser Gly Gly Gly Gly Ser
        115                 120                 125
```

```
Gly Gly Gly Gly Ser Ser Gly Gly Gly Ser Gln Phe Val Leu Thr Gln
    130                 135                 140

Ser Pro Ser Val Ser Ala Ala Leu Gly Ala Ser Ala Lys Leu Thr Cys
145                 150                 155                 160

Thr Leu Ser Ser Ala His Lys Thr Tyr Thr Ile Asp Trp Tyr Gln Gln
                165                 170                 175

Gln Gln Gly Glu Ala Pro Arg Tyr Leu Met Gln Val Lys Ser Asp Gly
            180                 185                 190

Ser Tyr Thr Lys Gly Thr Gly Val Pro Asp Arg Phe Ser Gly Ser Ser
        195                 200                 205

Ser Gly Ala Asp Arg Tyr Leu Ile Ile Pro Ser Val Gln Ala Asp Asp
    210                 215                 220

Glu Ala Gly Tyr Val Cys Gly Ala Asp Asp Asn Gly Gly Tyr Val Phe
225                 230                 235                 240

Gly Gly Gly Thr Gln Leu Thr Val Thr
                245


<210> SEQ ID NO 80
<211> LENGTH: 41
<212> TYPE: PRT
<213> ORGANISM: Artificial Sequence
<220> FEATURE:
<223> OTHER INFORMATION: Artifically generated sequence

<400> SEQUENCE: 80

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40


<210> SEQ ID NO 81
<211> LENGTH: 123
<212> TYPE: DNA
<213> ORGANISM: Artificial Sequence
<220> FEATURE:
<223> OTHER INFORMATION: Artifically generated sequence

<400> SEQUENCE: 81

aggagtaaga ggagcaggct cctgcacagt gactacatga acatgactcc ccgccgcccc      60

gggcccaccc gcaagcatta ccagccctat gccccaccac gcgacttcgc agcctatcgc     120

tcc                                                                   123


<210> SEQ ID NO 82
<211> LENGTH: 35
<212> TYPE: PRT
<213> ORGANISM: Artificial Sequence
<220> FEATURE:
<223> OTHER INFORMATION: Artifically generated sequence

<400> SEQUENCE: 82

Thr Lys Lys Lys Tyr Ser Ser Ser Val His Asp Pro Asn Gly Glu Tyr
1               5                   10                  15

Met Phe Met Arg Ala Val Asn Thr Ala Lys Lys Ser Arg Leu Thr Asp
            20                  25                  30

Val Thr Leu
        35
```

<210> SEQ ID NO 83
<211> LENGTH: 105
<212> TYPE: DNA
<213> ORGANISM: Artificial Sequence
<220> FEATURE:
<223> OTHER INFORMATION: Artifically generated sequence

<400> SEQUENCE: 83
acaaaaaaga agtattcatc cagtgtgcac gaccctaacg gtgaatacat gttcatgaga 60
gcagtgaaca cagccaaaaa atccagactc acagatgtga cccta 105

<210> SEQ ID NO 84
<211> LENGTH: 18
<212> TYPE: PRT
<213> ORGANISM: Artificial Sequence
<220> FEATURE:
<223> OTHER INFORMATION: Artifically generated sequence

<400> SEQUENCE: 84

Gly Ser Thr Ser Gly Ser Gly Lys Pro Gly Ser Gly Glu Gly Ser Thr
1 5 10 15

Lys Gly

<210> SEQ ID NO 85
<211> LENGTH: 488
<212> TYPE: PRT
<213> ORGANISM: Artificial Sequence
<220> FEATURE:
<223> OTHER INFORMATION: Artifically generated sequence

<400> SEQUENCE: 85

Met Ala Leu Pro Val Thr Ala Leu Leu Leu Pro Leu Ala Leu Leu Leu
1 5 10 15

His Ala Ala Arg Pro Glu Gln Leu Lys Glu Ser Gly Gly Gly Leu Phe
20 25 30

Lys Pro Thr Asp Thr Leu Thr Leu Thr Cys Thr Val Ser Gly Phe Ser
35 40 45

Leu Ser Tyr Tyr Gly Val Asn Trp Val Arg Gln Ala Pro Gly Asn Gly
50 55 60

Leu Glu Trp Ile Gly Thr Ile Gly Gly Ser Gly Asp Thr Tyr Tyr Ala
65 70 75 80

Ser Trp Ala Lys Ser Arg Ser Thr Ile Ile Arg Asn Thr Asn Glu Asn
85 90 95

Thr Val Thr Leu Lys Met Thr Ser Leu Thr Ala Ala Asp Thr Ala Thr
100 105 110

Tyr Phe Cys Val Arg Tyr Ala Asn Ile Gly Tyr Glu Tyr Phe Asn Val
115 120 125

Trp Gly Pro Gly Thr Leu Val Thr Val Ser Ser Gly Gly Gly Gly Ser
130 135 140

Gly Gly Gly Gly Ser Gly Gly Gly Gly Ser Gln Phe Val Leu Thr Gln
145 150 155 160

Ser Pro Ser Ala Ser Ala Ala Leu Gly Ala Ser Ala Lys Leu Thr Cys
165 170 175

Thr Leu Ser Ser Ala His Lys Thr Tyr Thr Ile Asp Trp Tyr Gln Gln
180 185 190

Gln Lys Gly Lys Ala Pro Arg Tyr Leu Ile Gln Val Lys Ser Asp Gly
195 200 205

Thr Tyr Thr Lys Ala Thr Gly Val Pro Asp Arg Phe Ser Gly Ser Ser 210 215 220

Ser Gly Ala Asp Arg Tyr Leu Ile Ile Pro Ser Val Gln Ala Asp Asp
225 230 235 240

Glu Ala Asp Tyr Tyr Cys Gly Thr Asp Tyr Thr Gly Gly Tyr Val Phe
245 250 255

Gly Gly Gly Thr Gln Leu Thr Val Thr Thr Thr Thr Pro Ala Pro Arg
260 265 270

Pro Pro Thr Pro Ala Pro Thr Ile Ala Ser Gln Pro Leu Ser Leu Arg
275 280 285

Pro Glu Ala Cys Arg Pro Ala Ala Gly Gly Ala Val His Thr Arg Gly
290 295 300

Leu Asp Phe Ala Cys Asp Ile Tyr Ile Trp Ala Pro Leu Ala Gly Thr
305 310 315 320

Cys Gly Val Leu Leu Leu Ser Leu Val Ile Thr Leu Tyr Cys Lys Arg
325 330 335

Gly Arg Lys Lys Leu Leu Tyr Ile Phe Lys Gln Pro Phe Met Arg Pro
340 345 350

Val Gln Thr Thr Gln Glu Glu Asp Gly Cys Ser Cys Arg Phe Pro Glu
355 360 365

Glu Glu Glu Gly Gly Cys Glu Leu Arg Val Lys Phe Ser Arg Ser Ala
370 375 380

Asp Ala Pro Ala Tyr Lys Gln Gly Gln Asn Gln Leu Tyr Asn Glu Leu
385 390 395 400

Asn Leu Gly Arg Arg Glu Glu Tyr Asp Val Leu Asp Lys Arg Arg Gly
405 410 415

Arg Asp Pro Glu Met Gly Gly Lys Pro Arg Arg Lys Asn Pro Gln Glu
420 425 430

Gly Leu Tyr Asn Glu Leu Gln Lys Asp Lys Met Ala Glu Ala Tyr Ser
435 440 445

Glu Ile Gly Met Lys Gly Glu Arg Arg Arg Gly Lys Gly His Asp Gly
450 455 460

Leu Tyr Gln Gly Leu Ser Thr Ala Thr Lys Asp Thr Tyr Asp Ala Leu
465 470 475 480

His Met Gln Ala Leu Pro Pro Arg
485

<210> SEQ ID NO 86
<211> LENGTH: 493
<212> TYPE: PRT
<213> ORGANISM: Artificial Sequence
<220> FEATURE:
<223> OTHER INFORMATION: Artifically generated sequence

<400> SEQUENCE: 86

Met Ala Leu Pro Val Thr Ala Leu Leu Leu Pro Leu Ala Leu Leu Leu
1 5 10 15

His Ala Ala Arg Pro Gln Ser Val Lys Glu Ser Glu Gly Gly Leu Phe
20 25 30

Lys Pro Thr Asp Thr Leu Thr Leu Thr Cys Thr Val Ser Gly Phe Ser
35 40 45

Leu Ser Arg His Ala Leu Thr Trp Val Arg Gln Ala Pro Gly Asn Gly
50 55 60

Leu Glu Trp Ile Gly Ala Ile Asp Asn Ala Gly Thr Thr Tyr Tyr Ala
65 70 75 80

Ser Trp Ala Lys Ser Arg Ser Thr Ile Thr Arg Asn Thr Asp Leu His

```
                85                  90                  95

Thr Val Thr Leu Lys Met Thr Ser Leu Thr Ala Ser Asp Thr Ala Thr
            100                 105                 110

Tyr Phe Cys Ala Arg Val Phe Tyr Asp Ile Asn Ser Gly Tyr Tyr Leu
        115                 120                 125

Asp Gly Met Asp Leu Trp Gly Pro Gly Thr Leu Val Thr Val Ser Ser
    130                 135                 140

Gly Gly Gly Gly Ser Gly Gly Gly Gly Ser Gly Gly Gly Gly Ser Gln
145                 150                 155                 160

Phe Val Leu Thr Gln Ser Pro Ser Val Ser Ala Ala Leu Gly Ala Ser
                165                 170                 175

Ala Lys Leu Thr Cys Thr Leu Ser Ser Ala His Lys Thr Tyr Thr Ile
            180                 185                 190

Asp Trp Tyr Gln Gln Gln Gln Gly Glu Ala Pro Arg Tyr Leu Met Gln
        195                 200                 205

Val Lys Ser Asp Gly Ser Tyr Thr Lys Gly Thr Gly Val Pro Asp Arg
    210                 215                 220

Phe Ser Gly Ser Ser Ser Gly Ala Asp Arg Tyr Leu Ile Ile Pro Ser
225                 230                 235                 240

Val Gln Ala Asp Asp Glu Ala Gly Tyr Val Cys Gly Ala Asp Asp Asn
                245                 250                 255

Gly Gly Tyr Val Phe Gly Gly Gly Thr Gln Leu Thr Val Thr Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

<210> SEQ ID NO 87

<211> LENGTH: 19
<212> TYPE: PRT
<213> ORGANISM: Artificial Sequence
<220> FEATURE:
<223> OTHER INFORMATION: Artifically generated sequence

<400> SEQUENCE: 87

Met Glu Phe Gly Leu Ser Trp Leu Phe Leu Val Ala Ile Leu Lys Gly
1 5 10 15

Val Gln Cys

<210> SEQ ID NO 88
<211> LENGTH: 57
<212> TYPE: DNA
<213> ORGANISM: Artificial Sequence
<220> FEATURE:
<223> OTHER INFORMATION: Artifically generated sequence

<400> SEQUENCE: 88
atggagtttg ggctgagctg gctttttctt gtggctattt taaaaggtgt ccagtgc 57

<210> SEQ ID NO 89
<211> LENGTH: 1317
<212> TYPE: DNA
<213> ORGANISM: Artificial Sequence
<220> FEATURE:
<223> OTHER INFORMATION: Artifically generated sequence

<400> SEQUENCE: 89
ggatccgagc agctgaagga gtccggggga ggtctcttca agccaacgga taccctgaca 60
ctcacctgca cagtctctgg attctccctc agttactatg gagtgaactg ggtccgccag 120
gctccaggga acgggctgga atggatcgga accattggtg gtagtggtga cacatactac 180
gcgagctggg cgaagagccg atccaccatc atcagaaaca ccaacgagaa cacggtgact 240
ctgaaaatga ccagtctgac agccgcggac acggccacct atttctgtgt gagatatgct 300
aatattggtt atgagtactt taacgtctgg ggtccaggca ccctggtcac cgtctcttca 360
ggtggaggcg gttcaggcgg cggtggctct agcggtggtg gatcgcagtt tgtgctgact 420
cagtcgccct ctgcatctgc tgccctggga gcctcggcca agctcacctg caccctgagc 480
agtgcccaca agacctacac cattgactgg tatcagcagc agaaagggaa ggcccctcgc 540
tacctgatac aagttaagag tgatggaacc tacaccaagg cgaccggggt ccctgatcgc 600
ttctcgggct ccagctctgg ggctgaccgc tacctgatca tccccagcgt ccaggctgat 660
gacgaagccg actactattg tggtacagat tataccggtg ggtatgtgtt cggcgggggg 720
acccagctga ccgtcacagc tagcggtggc ggaggttctg gaggtggagg ttcctccgga 780
atctacatct gggcccctct ggccggcacc tgtggcgtgc tgctgctgtc cctggtcatc 840
accctgtact gcaagcgggg cagaaagaag ctgctgtaca tcttcaagca gcccttcatg 900
cggcctgtgc agaccacaca ggaagaggac ggctgtagct gtagattccc cgaggaagag 960
gaaggcggct gcgagctgag agtgaagttc agcagaagcg ccgacgcccc tgcctatcag 1020
cagggccaga accagctgta caacgagctg aacctgggca gacgggagga atacgacgtg 1080
ctggacaaga gaagaggccg ggaccctgag atgggcggca agcccagacg gaagaacccc 1140
caggaaggcc tgtataacga actgcagaaa gacaagatgg ccgaggccta cagcgagatc 1200
ggcatgaagg gcgagcggag aagaggcaag ggccatgacg gcctgtacca gggcctgagc 1260
accgccacca aggacaccta cgacgccctg cacatgcagg ccctgcctcc aagatga 1317

<210> SEQ ID NO 90
<211> LENGTH: 438
<212> TYPE: PRT
<213> ORGANISM: Artificial Sequence
<220> FEATURE:
<223> OTHER INFORMATION: Artifically generated sequence

<400> SEQUENCE: 90

```
Gly Ser Glu Gln Leu Lys Glu Ser Gly Gly Gly Leu Phe Lys Pro Thr
1               5                   10                  15

Asp Thr Leu Thr Leu Thr Cys Thr Val Ser Gly Phe Ser Leu Ser Tyr
            20                  25                  30

Tyr Gly Val Asn Trp Val Arg Gln Ala Pro Gly Asn Gly Leu Glu Trp
        35                  40                  45

Ile Gly Thr Ile Gly Gly Ser Gly Asp Thr Tyr Tyr Ala Ser Trp Ala
    50                  55                  60

Lys Ser Arg Ser Thr Ile Ile Arg Asn Thr Asn Glu Asn Thr Val Thr
65                  70                  75                  80

Leu Lys Met Thr Ser Leu Thr Ala Ala Asp Thr Ala Thr Tyr Phe Cys
                85                  90                  95

Val Arg Tyr Ala Asn Ile Gly Tyr Glu Tyr Phe Asn Val Trp Gly Pro
            100                 105                 110

Gly Thr Leu Val Thr Val Ser Ser Gly Gly Gly Gly Ser Gly Gly Gly
        115                 120                 125

Gly Ser Ser Gly Gly Gly Ser Gln Phe Val Leu Thr Gln Ser Pro Ser
    130                 135                 140

Ala Ser Ala Ala Leu Gly Ala Ser Ala Lys Leu Thr Cys Thr Leu Ser
145                 150                 155                 160

Ser Ala His Lys Thr Tyr Thr Ile Asp Trp Tyr Gln Gln Gln Lys Gly
                165                 170                 175

Lys Ala Pro Arg Tyr Leu Ile Gln Val Lys Ser Asp Gly Thr Tyr Thr
            180                 185                 190

Lys Ala Thr Gly Val Pro Asp Arg Phe Ser Gly Ser Ser Ser Gly Ala
        195                 200                 205

Asp Arg Tyr Leu Ile Ile Pro Ser Val Gln Ala Asp Asp Glu Ala Asp
    210                 215                 220

Tyr Tyr Cys Gly Thr Asp Tyr Thr Gly Gly Tyr Val Phe Gly Gly Gly
225                 230                 235                 240

Thr Gln Leu Thr Val Thr Ala Ser Gly Gly Gly Gly Ser Gly Gly Gly
                245                 250                 255

Gly Ser Ser Gly Ile Tyr Ile Trp Ala Pro Leu Ala Gly Thr Cys Gly
            260                 265                 270

Val Leu Leu Leu Ser Leu Val Ile Thr Leu Tyr Cys Lys Arg Gly Arg
        275                 280                 285

Lys Lys Leu Leu Tyr Ile Phe Lys Gln Pro Phe Met Arg Pro Val Gln
    290                 295                 300

Thr Thr Gln Glu Glu Asp Gly Cys Ser Cys Arg Phe Pro Glu Glu Glu
305                 310                 315                 320

Glu Gly Gly Cys Glu Leu Arg Val Lys Phe Ser Arg Ser Ala Asp Ala
                325                 330                 335

Pro Ala Tyr Gln Gln Gly Gln Asn Gln Leu Tyr Asn Glu Leu Asn Leu
            340                 345                 350

Gly Arg Arg Glu Glu Tyr Asp Val Leu Asp Lys Arg Arg Gly Arg Asp
        355                 360                 365
```

-continued

```
Pro Glu Met Gly Gly Lys Pro Arg Arg Lys Asn Pro Gln Glu Gly Leu
    370                 375                 380

Tyr Asn Glu Leu Gln Lys Asp Lys Met Ala Glu Ala Tyr Ser Glu Ile
385                 390                 395                 400

Gly Met Lys Gly Glu Arg Arg Arg Gly Lys Gly His Asp Gly Leu Tyr
                405                 410                 415

Gln Gly Leu Ser Thr Ala Thr Lys Asp Thr Tyr Asp Ala Leu His Met
            420                 425                 430

Gln Ala Leu Pro Pro Arg
        435
```

<210> SEQ ID NO 91
<211> LENGTH: 1332
<212> TYPE: DNA
<213> ORGANISM: Artificial Sequence
<220> FEATURE:
<223> OTHER INFORMATION: Artifically generated sequence

<400> SEQUENCE: 91

```
ggatcccagt cagtgaagga gtccgaggga ggtctcttca agccaacgga taccctgaca     60

ctcacctgca cggtctctgg attctccctc agtagacatg cactgacctg ggtccgccag    120

gctccaggga acgggctgga atggatcgga gccattgata acgctggtac cacatactac    180

gcgagctggg cgaaaagccg ctccaccatc accagaaaca ccgacctgca cacggtgact    240

ctgaaaatga ccagtctgac agcctcggac acggctacct atttctgtgc gagagtcttt    300

tatgatatta atagtggtta ttatctggac ggcatggacc tctggggccc agggaccctc    360

gtcaccgtct cttcaggtgg aggcggttca ggcggcggtg gctctagcgg tggtggatcg    420

cagtttgtgc tgactcagtc gccctctgtg tctgccgccc tgggagcctc tgccaagctc    480

acctgcaccc tgagcagtgc ccacaagacc tacaccattg actggtatca gcagcagcaa    540

ggggaggccc ctcggtacct gatgcaagtt aagagtgatg gaagctacac caaggggacc    600

ggggtccctg atcgcttctc gggctccagc tctggggctg accgctactt gatcatcccc    660

agcgtccagg ctgatgacga agccggctac gtttgtggtg cagatgataa cggtgggtat    720

gtgttcggcg gagggaccca gctgaccgtc acagctagcg gtggcggagg ttctggaggt    780

ggaggttcct ccggaatcta catctgggcc cctctggccg gcacctgtgg cgtgctgctg    840

ctgtccctgg tcatcaccct gtactgcaag cggggcagaa agaagctgct gtacatcttc    900

aagcagccct tcatgcggcc tgtgcagacc acacaggaag aggacggctg tagctgtaga    960

ttccccgagg aagaggaagg cggctgcgag ctgagagtga agttcagcag aagcgccgac   1020

gcccctgcct atcagcaggg ccagaaccag ctgtacaacg agctgaacct gggcagacgg   1080

gaggaatacg acgtgctgga caagagaaga ggccgggacc ctgagatggg cggcaagccc   1140

agacggaaga acccccagga aggcctgtat aacgaactgc agaaagacaa gatggccgag   1200

gcctacagcg agatcggcat gaagggcgag cggagaagag gcaagggcca tgacggcctg   1260

taccagggcc tgagcaccgc caccaaggac acctacgacg ccctgcacat gcaggccctg   1320

cctccaagat ga                                                       1332
```

<210> SEQ ID NO 92
<211> LENGTH: 443
<212> TYPE: PRT
<213> ORGANISM: Artificial Sequence
<220> FEATURE:
<223> OTHER INFORMATION: Artifically generated sequence

<400> SEQUENCE: 92

Gly Ser Gln Ser Val Lys Glu Ser Glu Gly Gly Leu Phe Lys Pro Thr
1 5 10 15

Asp Thr Leu Thr Leu Thr Cys Thr Val Ser Gly Phe Ser Leu Ser Arg
20 25 30

His Ala Leu Thr Trp Val Arg Gln Ala Pro Gly Asn Gly Leu Glu Trp
35 40 45

Ile Gly Ala Ile Asp Asn Ala Gly Thr Thr Tyr Tyr Ala Ser Trp Ala
50 55 60

Lys Ser Arg Ser Thr Ile Thr Arg Asn Thr Asp Leu His Thr Val Thr
65 70 75 80

Leu Lys Met Thr Ser Leu Thr Ala Ser Asp Thr Ala Thr Tyr Phe Cys
85 90 95

Ala Arg Val Phe Tyr Asp Ile Asn Ser Gly Tyr Tyr Leu Asp Gly Met
100 105 110

Asp Leu Trp Gly Pro Gly Thr Leu Val Thr Val Ser Ser Gly Gly Gly
115 120 125

Gly Ser Gly Gly Gly Gly Ser Ser Gly Gly Gly Ser Gln Phe Val Leu
130 135 140

Thr Gln Ser Pro Ser Val Ser Ala Ala Leu Gly Ala Ser Ala Lys Leu
145 150 155 160

Thr Cys Thr Leu Ser Ser Ala His Lys Thr Tyr Thr Ile Asp Trp Tyr
165 170 175

Gln Gln Gln Gln Gly Glu Ala Pro Arg Tyr Leu Met Gln Val Lys Ser
180 185 190

Asp Gly Ser Tyr Thr Lys Gly Thr Gly Val Pro Asp Arg Phe Ser Gly
195 200 205

Ser Ser Ser Gly Ala Asp Arg Tyr Leu Ile Ile Pro Ser Val Gln Ala
210 215 220

Asp Asp Glu Ala Gly Tyr Val Cys Gly Ala Asp Asp Asn Gly Gly Tyr
225 230 235 240

Val Phe Gly Gly Gly Thr Gln Leu Thr Val Thr Ala Ser Gly Gly Gly
245 250 255

Gly Ser Gly Gly Gly Gly Ser Ser Gly Ile Tyr Ile Trp Ala Pro Leu
260 265 270

Ala Gly Thr Cys Gly Val Leu Leu Leu Ser Leu Val Ile Thr Leu Tyr
275 280 285

Cys Lys Arg Gly Arg Lys Lys Leu Leu Tyr Ile Phe Lys Gln Pro Phe
290 295 300

Met Arg Pro Val Gln Thr Thr Gln Glu Glu Asp Gly Cys Ser Cys Arg
305 310 315 320

Phe Pro Glu Glu Glu Glu Gly Gly Cys Glu Leu Arg Val Lys Phe Ser
325 330 335

Arg Ser Ala Asp Ala Pro Ala Tyr Gln Gln Gly Gln Asn Gln Leu Tyr
340 345 350

Asn Glu Leu Asn Leu Gly Arg Arg Glu Glu Tyr Asp Val Leu Asp Lys
355 360 365

Arg Arg Gly Arg Asp Pro Glu Met Gly Gly Lys Pro Arg Arg Lys Asn
370 375 380

Pro Gln Glu Gly Leu Tyr Asn Glu Leu Gln Lys Asp Lys Met Ala Glu
385 390 395 400

Ala Tyr Ser Glu Ile Gly Met Lys Gly Glu Arg Arg Arg Gly Lys Gly
405 410 415

```
His Asp Gly Leu Tyr Gln Gly Leu Ser Thr Ala Thr Lys Asp Thr Tyr
            420                 425                 430

Asp Ala Leu His Met Gln Ala Leu Pro Pro Arg
        435                 440


<210> SEQ ID NO 93
<211> LENGTH: 1422
<212> TYPE: DNA
<213> ORGANISM: Artificial Sequence
<220> FEATURE:
<223> OTHER INFORMATION: Artifically generated sequence

<400> SEQUENCE: 93

ggatccgagc agctgaagga gtccggggga ggtctcttca agccaacgga taccctgaca      60

ctcacctgca cagtctctgg attctccctc agttactatg gagtgaactg ggtccgccag     120

gctccaggga acgggctgga atggatcgga accattggtg gtagtggtga cacatactac     180

gcgagctggg cgaagagccg atccaccatc atcagaaaca ccaacgagaa cacggtgact     240

ctgaaaatga ccagtctgac agccgcggac acggccacct atttctgtgt gagatatgct     300

aatattggtt atgagtactt taacgtctgg ggtccaggca ccctggtcac cgtctcttca     360

ggtggaggcg gttcaggcgg cggtggctct agcggtggtg gatcgcagtt tgtgctgact     420

cagtcgccct ctgcatctgc tgccctggga gcctcggcca agctcacctg caccctgagc     480

agtgcccaca agacctacac cattgactgg tatcagcagc agaaagggaa ggcccctcgc     540

tacctgatac aagttaagag tgatggaacc tacaccaagg cgaccggggt ccctgatcgc     600

ttctcgggct ccagctctgg ggctgaccgc tacctgatca tccccagcgt ccaggctgat     660

gacgaagccg actactattg tggtacagat tataccggtg ggtatgtgtt cggcgggggg     720

acccagctga ccgtcacagc tagcaccacg acgccagcgc cgcgaccacc aacaccggcg     780

cccaccatcg cgtcgcagcc cctgtccctg cgcccagagg cgtgccggcc agcggcgggg     840

ggcgcagtgc acacgagggg gctggacttc gcctgtgatt ccggaatcta catctgggcc     900

cctctggccg gcacctgtgg cgtgctgctg ctgtccctgg tcatcaccct gtactgcaag     960

cggggcagaa agaagctgct gtacatcttc aagcagccct tcatgcggcc tgtgcagacc    1020

acacaggaag aggacggctg tagctgtaga ttccccgagg aagaggaagg cggctgcgag    1080

ctgagagtga agttcagcag aagcgccgac gcccctgcct atcagcaggg ccagaaccag    1140

ctgtacaacg agctgaacct gggcagacgg gaggaatacg acgtgctgga caagagaaga    1200

ggccgggacc ctgagatggg cggcaagccc agacggaaga acccccagga aggcctgtat    1260

aacgaactgc agaaagacaa gatggccgag gcctacagcg agatcggcat gaagggcgag    1320

cggagaagag gcaagggcca tgacggcctg taccagggcc tgagcaccgc caccaaggac    1380

acctacgacg ccctgcacat gcaggccctg cctccaagat ga                       1422


<210> SEQ ID NO 94
<211> LENGTH: 473
<212> TYPE: PRT
<213> ORGANISM: Artificial Sequence
<220> FEATURE:
<223> OTHER INFORMATION: Artifically generated sequence

<400> SEQUENCE: 94

Gly Ser Glu Gln Leu Lys Glu Ser Gly Gly Gly Leu Phe Lys Pro Thr
1               5                   10                  15

Asp Thr Leu Thr Leu Thr Cys Thr Val Ser Gly Phe Ser Leu Ser Tyr
```

-continued

```
            20                  25                  30

Tyr Gly Val Asn Trp Val Arg Gln Ala Pro Gly Asn Gly Leu Glu Trp
        35                  40                  45

Ile Gly Thr Ile Gly Gly Ser Gly Asp Thr Tyr Tyr Ala Ser Trp Ala
    50                  55                  60

Lys Ser Arg Ser Thr Ile Ile Arg Asn Thr Asn Glu Asn Thr Val Thr
65                  70                  75                  80

Leu Lys Met Thr Ser Leu Thr Ala Ala Asp Thr Ala Thr Tyr Phe Cys
                85                  90                  95

Val Arg Tyr Ala Asn Ile Gly Tyr Glu Tyr Phe Asn Val Trp Gly Pro
            100                 105                 110

Gly Thr Leu Val Thr Val Ser Ser Gly Gly Gly Gly Ser Gly Gly Gly
        115                 120                 125

Gly Ser Ser Gly Gly Gly Ser Gln Phe Val Leu Thr Gln Ser Pro Ser
    130                 135                 140

Ala Ser Ala Ala Leu Gly Ala Ser Ala Lys Leu Thr Cys Thr Leu Ser
145                 150                 155                 160

Ser Ala His Lys Thr Tyr Thr Ile Asp Trp Tyr Gln Gln Gln Lys Gly
                165                 170                 175

Lys Ala Pro Arg Tyr Leu Ile Gln Val Lys Ser Asp Gly Thr Tyr Thr
            180                 185                 190

Lys Ala Thr Gly Val Pro Asp Arg Phe Ser Gly Ser Ser Ser Gly Ala
        195                 200                 205

Asp Arg Tyr Leu Ile Ile Pro Ser Val Gln Ala Asp Asp Glu Ala Asp
    210                 215                 220

Tyr Tyr Cys Gly Thr Asp Tyr Thr Gly Gly Tyr Val Phe Gly Gly Gly
225                 230                 235                 240

Thr Gln Leu Thr Val Thr Ala Ser Thr Thr Thr Pro Ala Pro Arg Pro
                245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Gly Ala Val His Thr Arg Gly Leu
        275                 280                 285

Asp Phe Ala Cys Asp Ser Gly Ile Tyr Ile Trp Ala Pro Leu Ala Gly
    290                 295                 300

Thr Cys Gly Val Leu Leu Leu Ser Leu Val Ile Thr Leu Tyr Cys Lys
305                 310                 315                 320

Arg Gly Arg Lys Lys Leu Leu Tyr Ile Phe Lys Gln Pro Phe Met Arg
                325                 330                 335

Pro Val Gln Thr Thr Gln Glu Glu Asp Gly Cys Ser Cys Arg Phe Pro
            340                 345                 350

Glu Glu Glu Glu Gly Gly Cys Glu Leu Arg Val Lys Phe Ser Arg Ser
        355                 360                 365

Ala Asp Ala Pro Ala Tyr Gln Gln Gly Gln Asn Gln Leu Tyr Asn Glu
    370                 375                 380

Leu Asn Leu Gly Arg Arg Glu Glu Tyr Asp Val Leu Asp Lys Arg Arg
385                 390                 395                 400

Gly Arg Asp Pro Glu Met Gly Gly Lys Pro Arg Arg Lys Asn Pro Gln
                405                 410                 415

Glu Gly Leu Tyr Asn Glu Leu Gln Lys Asp Lys Met Ala Glu Ala Tyr
            420                 425                 430

Ser Glu Ile Gly Met Lys Gly Glu Arg Arg Arg Gly Lys Gly His Asp
        435                 440                 445
```

Gly Leu Tyr Gln Gly Leu Ser Thr Ala Thr Lys Asp Thr Tyr Asp Ala
450 455 460

Leu His Met Gln Ala Leu Pro Pro Arg
465 470

<210> SEQ ID NO 95
<211> LENGTH: 1437
<212> TYPE: DNA
<213> ORGANISM: Artificial Sequence
<220> FEATURE:
<223> OTHER INFORMATION: Artifically generated sequence

<400> SEQUENCE: 95
ggatcccagt cagtgaagga gtccgaggga ggtctcttca agccaacgga taccctgaca 60
ctcacctgca cggtctctgg attctccctc agtagacatg cactgacctg ggtccgccag 120
gctccaggga acgggctgga atggatcgga gccattgata acgctggtac cacatactac 180
gcgagctggg cgaaaagccg ctccaccatc accagaaaca ccgacctgca cacggtgact 240
ctgaaaatga ccagtctgac agcctcggac acggctacct atttctgtgc gagagtcttt 300
tatgatatta atagtggtta ttatctggac ggcatggacc tctggggccc agggaccctc 360
gtcaccgtct cttcaggtgg aggcggttca ggcggcggtg gctctagcgg tggtggatcg 420
cagtttgtgc tgactcagtc gccctctgtg tctgccgccc tgggagcctc tgccaagctc 480
acctgcaccc tgagcagtgc ccacaagacc tacaccattg actggtatca gcagcagcaa 540
ggggaggccc ctcggtacct gatgcaagtt aagagtgatg gaagctacac caaggggacc 600
ggggtccctg atcgcttctc gggctccagc tctggggctg accgctactt gatcatcccc 660
agcgtccagg ctgatgacga agccggctac gtttgtggtg cagatgataa cggtgggtat 720
gtgttcggcg gagggaccca gctgaccgtc acagctagca ccacgacgcc agcgccgcga 780
ccaccaacac cggcgcccac catcgcgtcg cagcccctgt ccctgcgccc agaggcgtgc 840
cggccagcgg cggggggcgc agtgcacacg agggggctgg acttcgcctg tgattccgga 900
atctacatct gggcccctct ggccggcacc tgtggcgtgc tgctgctgtc cctggtcatc 960
accctgtact gcaagcgggg cagaaagaag ctgctgtaca tcttcaagca gcccttcatg 1020
cggcctgtgc agaccacaca ggaagaggac ggctgtagct gtagattccc cgaggaagag 1080
gaaggcggct gcgagctgag agtgaagttc agcagaagcg ccgacgcccc tgcctatcag 1140
cagggccaga accagctgta caacgagctg aacctgggca gacgggagga atacgacgtg 1200
ctggacaaga gaagaggccg ggaccctgag atgggcggca agcccagacg gaagaacccc 1260
caggaaggcc tgtataacga actgcagaaa gacaagatgg ccgaggccta cagcgagatc 1320
ggcatgaagg gcgagcggag aagaggcaag ggccatgacg gcctgtacca gggcctgagc 1380
accgccacca aggacaccta cgacgccctg cacatgcagg ccctgcctcc aagatga 1437

<210> SEQ ID NO 96
<211> LENGTH: 478
<212> TYPE: PRT
<213> ORGANISM: Artificial Sequence
<220> FEATURE:
<223> OTHER INFORMATION: Artifically generated sequence

<400> SEQUENCE: 96

Gly Ser Gln Ser Val Lys Glu Ser Glu Gly Gly Leu Phe Lys Pro Thr
1 5 10 15

Asp Thr Leu Thr Leu Thr Cys Thr Val Ser Gly Phe Ser Leu Ser Arg

-continued

```
            20                  25                  30

His Ala Leu Thr Trp Val Arg Gln Ala Pro Gly Asn Gly Leu Glu Trp
        35                  40                  45

Ile Gly Ala Ile Asp Asn Ala Gly Thr Thr Tyr Tyr Ala Ser Trp Ala
    50                  55                  60

Lys Ser Arg Ser Thr Ile Thr Arg Asn Thr Asp Leu His Thr Val Thr
65                  70                  75                  80

Leu Lys Met Thr Ser Leu Thr Ala Ser Asp Thr Ala Thr Tyr Phe Cys
                85                  90                  95

Ala Arg Val Phe Tyr Asp Ile Asn Ser Gly Tyr Tyr Leu Asp Gly Met
            100                 105                 110

Asp Leu Trp Gly Pro Gly Thr Leu Val Thr Val Ser Ser Gly Gly Gly
        115                 120                 125

Gly Ser Gly Gly Gly Gly Ser Ser Gly Gly Gly Ser Gln Phe Val Leu
    130                 135                 140

Thr Gln Ser Pro Ser Val Ser Ala Ala Leu Gly Ala Ser Ala Lys Leu
145                 150                 155                 160

Thr Cys Thr Leu Ser Ser Ala His Lys Thr Tyr Thr Ile Asp Trp Tyr
                165                 170                 175

Gln Gln Gln Gln Gly Glu Ala Pro Arg Tyr Leu Met Gln Val Lys Ser
            180                 185                 190

Asp Gly Ser Tyr Thr Lys Gly Thr Gly Val Pro Asp Arg Phe Ser Gly
        195                 200                 205

Ser Ser Ser Gly Ala Asp Arg Tyr Leu Ile Ile Pro Ser Val Gln Ala
    210                 215                 220

Asp Asp Glu Ala Gly Tyr Val Cys Gly Ala Asp Asp Asn Gly Gly Tyr
225                 230                 235                 240

Val Phe Gly Gly Gly Thr Gln Leu Thr Val Thr Ala Ser Thr Thr Thr
                245                 250                 255

Pro Ala Pro Arg Pro Pro Thr Pro Ala Pro Thr Ile Ala Ser Gln Pro
            260                 265                 270

Leu Ser Leu Arg Pro Glu Ala Cys Arg Pro Ala Ala Gly Gly Ala Val
        275                 280                 285

His Thr Arg Gly Leu Asp Phe Ala Cys Asp Ser Gly Ile Tyr Ile Trp
    290                 295                 300

Ala Pro Leu Ala Gly Thr Cys Gly Val Leu Leu Leu Ser Leu Val Ile
305                 310                 315                 320

Thr Leu Tyr Cys Lys Arg Gly Arg Lys Lys Leu Leu Tyr Ile Phe Lys
                325                 330                 335

Gln Pro Phe Met Arg Pro Val Gln Thr Thr Gln Glu Glu Asp Gly Cys
            340                 345                 350

Ser Cys Arg Phe Pro Glu Glu Glu Glu Gly Gly Cys Glu Leu Arg Val
        355                 360                 365

Lys Phe Ser Arg Ser Ala Asp Ala Pro Ala Tyr Gln Gln Gly Gln Asn
    370                 375                 380

Gln Leu Tyr Asn Glu Leu Asn Leu Gly Arg Arg Glu Glu Tyr Asp Val
385                 390                 395                 400

Leu Asp Lys Arg Arg Gly Arg Asp Pro Glu Met Gly Gly Lys Pro Arg
                405                 410                 415

Arg Lys Asn Pro Gln Glu Gly Leu Tyr Asn Glu Leu Gln Lys Asp Lys
            420                 425                 430

Met Ala Glu Ala Tyr Ser Glu Ile Gly Met Lys Gly Glu Arg Arg Arg
        435                 440                 445
```

Gly Lys Gly His Asp Gly Leu Tyr Gln Gly Leu Ser Thr Ala Thr Lys
450 455 460

Asp Thr Tyr Asp Ala Leu His Met Gln Ala Leu Pro Pro Arg
465 470 475

<210> SEQ ID NO 97
<211> LENGTH: 1329
<212> TYPE: DNA
<213> ORGANISM: Artificial Sequence
<220> FEATURE:
<223> OTHER INFORMATION: Artifically generated sequence

<400> SEQUENCE: 97
ggatccgagc agctgaagga gtccggggga ggtctcttca agccaacgga taccctgaca 60
ctcacctgca cagtctctgg attctccctc agttactatg gagtgaactg ggtccgccag 120
gctccaggga acgggctgga atggatcgga accattggtg gtagtggtga cacatactac 180
gcgagctggg cgaagagccg atccaccatc atcagaaaca ccaacgagaa cacggtgact 240
ctgaaaatga ccagtctgac agccgcggac acggccacct atttctgtgt gagatatgct 300
aatattggtt atgagtactt taacgtctgg ggtccaggca ccctggtcac cgtctcttca 360
ggtggaggcg gttcaggcgg cggtggctct agcggtggtg gatcgcagtt tgtgctgact 420
cagtcgccct ctgcatctgc tgccctggga gcctcggcca agctcacctg caccctgagc 480
agtgcccaca agacctacac cattgactgg tatcagcagc agaaagggaa ggcccctcgc 540
tacctgatac aagttaagag tgatggaacc tacaccaagg cgaccggggt ccctgatcgc 600
ttctcgggct ccagctctgg ggctgaccgc tacctgatca tccccagcgt ccaggctgat 660
gacgaagccg actactattg tggtacagat tataccggtg ggtatgtgtt cggcgggggg 720
acccagctga ccgtcacagc tagcggtggc ggaggttctg gaggtggagg ttcctccgga 780
ttttgggtgc tggtggtggt tggtggagtc ctggcttgct atagcttgct agtaacagtg 840
gcctttatta ttttctgggt gaggagtaag aggagcaggc tcctgcacag tgactacatg 900
aacatgactc cccgccgccc cgggcccacc cgcaagcatt accagcccta tgccccacca 960
cgcgacttcg cagcctatcg ctccctgaga gtgaagttca gcaggagcgc agacgccccc 1020
gcgtaccagc agggccagaa ccagctctat aacgagctca atctaggacg aagagaggag 1080
tacgatgttt tggacaagag acgtggccgg gaccctgaga tgggggggaaa gccgagaagg 1140 aagaaccctc aggaaggcct gtacaatgaa ctgcagaaag ataagatggc ggaggcctac 1200
agtgagattg ggatgaaagg cgagcgccgg aggggcaagg ggcacgatgg cctttaccag 1260
ggtctcagta cagccaccaa ggacacctac gacgcccttc acatgcaggc cctgccccct 1320
cgctaataa 1329

<210> SEQ ID NO 98
<211> LENGTH: 441
<212> TYPE: PRT
<213> ORGANISM: Artificial Sequence
<220> FEATURE:
<223> OTHER INFORMATION: Artifically generated sequence

<400> SEQUENCE: 98

Gly Ser Glu Gln Leu Lys Glu Ser Gly Gly Gly Leu Phe Lys Pro Thr
1 5 10 15

Asp Thr Leu Thr Leu Thr Cys Thr Val Ser Gly Phe Ser Leu Ser Tyr
20 25 30

```
Tyr Gly Val Asn Trp Val Arg Gln Ala Pro Gly Asn Gly Leu Glu Trp
        35                  40                  45

Ile Gly Thr Ile Gly Gly Ser Gly Asp Thr Tyr Tyr Ala Ser Trp Ala
    50                  55                  60

Lys Ser Arg Ser Thr Ile Ile Arg Asn Thr Asn Glu Asn Thr Val Thr
65                  70                  75                  80

Leu Lys Met Thr Ser Leu Thr Ala Ala Asp Thr Ala Thr Tyr Phe Cys
                85                  90                  95

Val Arg Tyr Ala Asn Ile Gly Tyr Glu Tyr Phe Asn Val Trp Gly Pro
            100                 105                 110

Gly Thr Leu Val Thr Val Ser Ser Gly Gly Gly Gly Ser Gly Gly Gly
        115                 120                 125

Gly Ser Ser Gly Gly Gly Ser Gln Phe Val Leu Thr Gln Ser Pro Ser
    130                 135                 140

Ala Ser Ala Ala Leu Gly Ala Ser Ala Lys Leu Thr Cys Thr Leu Ser
145                 150                 155                 160

Ser Ala His Lys Thr Tyr Thr Ile Asp Trp Tyr Gln Gln Gln Lys Gly
                165                 170                 175

Lys Ala Pro Arg Tyr Leu Ile Gln Val Lys Ser Asp Gly Thr Tyr Thr
            180                 185                 190

Lys Ala Thr Gly Val Pro Asp Arg Phe Ser Gly Ser Ser Ser Gly Ala
        195                 200                 205

Asp Arg Tyr Leu Ile Ile Pro Ser Val Gln Ala Asp Asp Glu Ala Asp
    210                 215                 220

Tyr Tyr Cys Gly Thr Asp Tyr Thr Gly Gly Tyr Val Phe Gly Gly Gly
225                 230                 235                 240

Thr Gln Leu Thr Val Thr Ala Ser Gly Gly Gly Gly Ser Gly Gly Gly
                245                 250                 255

Gly Ser Ser Gly Phe Trp Val Leu Val Val Val Gly Gly Val Leu Ala
            260                 265                 270

Cys Tyr Ser Leu Leu Val Thr Val Ala Phe Ile Ile Phe Trp Val Arg
        275                 280                 285

Ser Lys Arg Ser Arg Leu Leu His Ser Asp Tyr Met Asn Met Thr Pro
    290                 295                 300

Arg Arg Pro Gly Pro Thr Arg Lys His Tyr Gln Pro Tyr Ala Pro Pro
305                 310                 315                 320

Arg Asp Phe Ala Ala Tyr Arg Ser Leu Arg Val Lys Phe Ser Arg Ser
                325                 330                 335

Ala Asp Ala Pro Ala Tyr Gln Gln Gly Gln Asn Gln Leu Tyr Asn Glu
            340                 345                 350

Leu Asn Leu Gly Arg Arg Glu Glu Tyr Asp Val Leu Asp Lys Arg Arg
        355                 360                 365

Gly Arg Asp Pro Glu Met Gly Gly Lys Pro Arg Arg Lys Asn Pro Gln
    370                 375                 380

Glu Gly Leu Tyr Asn Glu Leu Gln Lys Asp Lys Met Ala Glu Ala Tyr
385                 390                 395                 400

Ser Glu Ile Gly Met Lys Gly Glu Arg Arg Arg Gly Lys Gly His Asp
                405                 410                 415

Gly Leu Tyr Gln Gly Leu Ser Thr Ala Thr Lys Asp Thr Tyr Asp Ala
            420                 425                 430

Leu His Met Gln Ala Leu Pro Pro Arg
        435                 440
```

```
<210> SEQ ID NO 99
<211> LENGTH: 1344
<212> TYPE: DNA
<213> ORGANISM: Artificial Sequence
<220> FEATURE:
<223> OTHER INFORMATION: Artifically generated sequence

<400> SEQUENCE: 99

ggatcccagt cagtgaagga gtccgaggga ggtctcttca agccaacgga taccctgaca     60

ctcacctgca cggtctctgg attctccctc agtagacatg cactgacctg ggtccgccag    120

gctccaggga acgggctgga atggatcgga gccattgata acgctggtac cacatactac    180

gcgagctggg cgaaaagccg ctccaccatc accagaaaca ccgacctgca cacggtgact    240

ctgaaaatga ccagtctgac agcctcggac acggctacct atttctgtgc gagagtcttt    300

tatgatatta atagtggtta ttatctggac ggcatggacc tctggggccc agggaccctc    360

gtcaccgtct cttcaggtgg aggcggttca ggcggcggtg gctctagcgg tggtggatcg    420

cagtttgtgc tgactcagtc gccctctgtg tctgccgccc tgggagcctc tgccaagctc    480

acctgcaccc tgagcagtgc ccacaagacc tacaccattg actggtatca gcagcagcaa    540

ggggaggccc ctcggtacct gatgcaagtt aagagtgatg gaagctacac caaggggacc    600

ggggtccctg atcgcttctc gggctccagc tctggggctg accgctactt gatcatcccc    660

agcgtccagg ctgatgacga agccggctac gtttgtggtg cagatgataa cggtgggtat    720

gtgttcggcg gagggaccca gctgaccgtc acagctagcg gtggcggagg ttctggaggt    780

ggaggttcct ccggattttg ggtgctggtg gtggttggtg gagtcctggc ttgctatagc    840

ttgctagtaa cagtggcctt tattattttc tgggtgagga gtaagaggag caggctcctg    900

cacagtgact acatgaacat gactccccgc cgccccgggc ccacccgcaa gcattaccag    960

ccctatgccc caccacgcga cttcgcagcc tatcgctccc tgagagtgaa gttcagcagg   1020

agcgcagacg cccccgcgta ccagcagggc cagaaccagc tctataacga gctcaatcta   1080

ggacgaagag aggagtacga tgttttggac aagagacgtg gccgggaccc tgagatgggg   1140

ggaaagccga gaaggaagaa ccctcaggaa ggcctgtaca atgaactgca gaaagataag   1200

atggcggagg cctacagtga gattgggatg aaaggcgagc gccggagggg caaggggcac   1260

gatggccttt accagggtct cagtacagcc accaaggaca cctacgacgc ccttcacatg   1320

caggccctgc cccctcgcta ataa                                           1344


<210> SEQ ID NO 100
<211> LENGTH: 446
<212> TYPE: PRT
<213> ORGANISM: Artificial Sequence
<220> FEATURE:
<223> OTHER INFORMATION: Artifically generated sequence

<400> SEQUENCE: 100

Gly Ser Gln Ser Val Lys Glu Ser Glu Gly Gly Leu Phe Lys Pro Thr
1               5                   10                  15

Asp Thr Leu Thr Leu Thr Cys Thr Val Ser Gly Phe Ser Leu Ser Arg
            20                  25                  30

His Ala Leu Thr Trp Val Arg Gln Ala Pro Gly Asn Gly Leu Glu Trp
        35                  40                  45

Ile Gly Ala Ile Asp Asn Ala Gly Thr Thr Tyr Tyr Ala Ser Trp Ala
    50                  55                  60

Lys Ser Arg Ser Thr Ile Thr Arg Asn Thr Asp Leu His Thr Val Thr
65                  70                  75                  80
```

```
Leu Lys Met Thr Ser Leu Thr Ala Ser Asp Thr Ala Thr Tyr Phe Cys
                85                  90                  95

Ala Arg Val Phe Tyr Asp Ile Asn Ser Gly Tyr Tyr Leu Asp Gly Met
            100                 105                 110

Asp Leu Trp Gly Pro Gly Thr Leu Val Thr Val Ser Ser Gly Gly Gly
        115                 120                 125

Gly Ser Gly Gly Gly Gly Ser Ser Gly Gly Gly Ser Gln Phe Val Leu
    130                 135                 140

Thr Gln Ser Pro Ser Val Ser Ala Ala Leu Gly Ala Ser Ala Lys Leu
145                 150                 155                 160

Thr Cys Thr Leu Ser Ser Ala His Lys Thr Tyr Thr Ile Asp Trp Tyr
                165                 170                 175

Gln Gln Gln Gln Gly Glu Ala Pro Arg Tyr Leu Met Gln Val Lys Ser
            180                 185                 190

Asp Gly Ser Tyr Thr Lys Gly Thr Gly Val Pro Asp Arg Phe Ser Gly
        195                 200                 205

Ser Ser Ser Gly Ala Asp Arg Tyr Leu Ile Ile Pro Ser Val Gln Ala
    210                 215                 220

Asp Asp Glu Ala Gly Tyr Val Cys Gly Ala Asp Asp Asn Gly Gly Tyr
225                 230                 235                 240

Val Phe Gly Gly Gly Thr Gln Leu Thr Val Thr Ala Ser Gly Gly Gly
                245                 250                 255

Gly Ser Gly Gly Gly Gly Ser Ser Gly Phe Trp Val Leu Val Val Val
            260                 265                 270

Gly Gly Val Leu Ala Cys Tyr Ser Leu Leu Val Thr Val Ala Phe Ile
        275                 280                 285

Ile Phe Trp Val Arg Ser Lys Arg Ser Arg Leu Leu His Ser Asp Tyr
    290                 295                 300

Met Asn Met Thr Pro Arg Arg Pro Gly Pro Thr Arg Lys His Tyr Gln
305                 310                 315                 320

Pro Tyr Ala Pro Pro Arg Asp Phe Ala Ala Tyr Arg Ser Leu Arg Val
                325                 330                 335

Lys Phe Ser Arg Ser Ala Asp Ala Pro Ala Tyr Gln Gln Gly Gln Asn
            340                 345                 350

Gln Leu Tyr Asn Glu Leu Asn Leu Gly Arg Arg Glu Glu Tyr Asp Val
        355                 360                 365

Leu Asp Lys Arg Arg Gly Arg Asp Pro Glu Met Gly Gly Lys Pro Arg
    370                 375                 380

Arg Lys Asn Pro Gln Glu Gly Leu Tyr Asn Glu Leu Gln Lys Asp Lys
385                 390                 395                 400

Met Ala Glu Ala Tyr Ser Glu Ile Gly Met Lys Gly Glu Arg Arg Arg
                405                 410                 415

Gly Lys Gly His Asp Gly Leu Tyr Gln Gly Leu Ser Thr Ala Thr Lys
            420                 425                 430

Asp Thr Tyr Asp Ala Leu His Met Gln Ala Leu Pro Pro Arg
        435                 440                 445
```

<210> SEQ ID NO 101
<211> LENGTH: 1476
<212> TYPE: DNA
<213> ORGANISM: Artificial Sequence
<220> FEATURE:
<223> OTHER INFORMATION: Artifically generated sequence

<400> SEQUENCE: 101

```
atggggggac ttgaaccctg cagcaggttc ctgctcctgc ctctcctgct ggctgtaagt      60
ggtctccgtc ctgtccaggt ccaggcccag agcgattgca gttgctctac ggtgagcccg     120
ggcgtgctgg cagggatcgt gatgggagac ctggtgctga cagtgctcat tgccctggcc     180
gtgtacttcc tgggccggct ggtccctcgg gggcgagggg ctgcggaggc agcgacccgg     240
aaacagcgta tcactgagac cgagtcgcct tatcaggagc tccagggtca gaggtcggat     300
gtctacagcg acctcaacac acagaggccg tattacaaag tcgagggcgg cggagagggc     360
agaggaagtc ttctaacatg cggtgacgtg gaggagaatc ccggccctag gatggcctta     420
ccagtgaccg ccttgctcct gccgctggcc ttgctgctcc acgccgccag gccgggatcc     480
gagcagctga aggagtccgg gggaggtctc ttcaagccaa cggataccct gacactcacc     540
tgcacagtct ctggattctc cctcagttac tatggagtga actgggtccg ccaggctcca     600
gggaacgggc tggaatggat cggaaccatt ggtggtagtg gtgacacata ctacgcgagc     660
tgggcgaaga gccgatccac catcatcaga aacaccaacg agaacacggt gactctgaaa     720
atgaccagtc tgacagccgc ggacacggcc acctatttct gtgtgagata tgctaatatt     780
ggttatgagt actttaacgt ctggggtcca ggcaccctgg tcaccgtctc ttcaggtgga     840
ggcggttcag gcggcggtgg ctctagcggt ggtggatcgc agtttgtgct gactcagtcg     900
ccctctgcat ctgctgccct gggagcctcg gccaagctca cctgcaccct gagcagtgcc     960
cacaagacct acaccattga ctggtatcag cagcagaaag ggaaggcccc tcgctacctg    1020
atacaagtta agagtgatgg aacctacacc aaggcgaccg gggtccctga tcgcttctcg    1080
ggctccagct ctggggctga ccgctacctg atcatcccca gcgtccaggc tgatgacgaa    1140
gccgactact attgtggtac agattatacc ggtgggtatg tgttcggcgg ggggacccag    1200
ctgaccgtca cagctagcgg tggcggaggt tctggaggtg gggggttcctc acccactgaa    1260
ccaagctcca aaaccggtaa ccccagacac ctgcatgttc tgattgggac ctcagtggtc    1320
aaaatccctt tcaccatcct cctcttcttt ctccttcatc gctggtgctc caacaaaaaa    1380
aatgctgctg taatggacca agagcctgca gggaacagaa cagtgaacag cgaggattct    1440
gatgaacaag accatcagga ggtgtcatac gcataa                              1476
```

<210> SEQ ID NO 102
<211> LENGTH: 491
<212> TYPE: PRT
<213> ORGANISM: Artificial Sequence
<220> FEATURE:
<223> OTHER INFORMATION: Artifically generated sequence

<400> SEQUENCE: 102

```
Met Gly Gly Leu Glu Pro Cys Ser Arg Phe Leu Leu Leu Pro Leu Leu
1               5                   10                  15

Leu Ala Val Ser Gly Leu Arg Pro Val Gln Val Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Ala Glu Ala Ala Thr Arg
65                  70                  75                  80

Lys Gln Arg Ile Thr Glu Thr Glu Ser Pro Tyr Gln Glu Leu Gln Gly
                85                  90                  95
```

```
Gln Arg Ser Asp Val Tyr Ser Asp Leu Asn Thr Gln Arg Pro Tyr Tyr
            100                 105                 110

Lys Val Glu Gly Gly Gly Glu Gly Arg Gly Ser Leu Leu Thr Cys Gly
        115                 120                 125

Asp Val Glu Glu Asn Pro Gly Pro Arg Met Ala Leu Pro Val Thr Ala
    130                 135                 140

Leu Leu Leu Pro Leu Ala Leu Leu Leu His Ala Ala Arg Pro Gly Ser
145                 150                 155                 160

Glu Gln Leu Lys Glu Ser Gly Gly Gly Leu Phe Lys Pro Thr Asp Thr
                165                 170                 175

Leu Thr Leu Thr Cys Thr Val Ser Gly Phe Ser Leu Ser Tyr Tyr Gly
            180                 185                 190

Val Asn Trp Val Arg Gln Ala Pro Gly Asn Gly Leu Glu Trp Ile Gly
        195                 200                 205

Thr Ile Gly Gly Ser Gly Asp Thr Tyr Tyr Ala Ser Trp Ala Lys Ser
    210                 215                 220

Arg Ser Thr Ile Ile Arg Asn Thr Asn Glu Asn Thr Val Thr Leu Lys
225                 230                 235                 240

Met Thr Ser Leu Thr Ala Ala Asp Thr Ala Thr Tyr Phe Cys Val Arg
                245                 250                 255

Tyr Ala Asn Ile Gly Tyr Glu Tyr Phe Asn Val Trp Gly Pro Gly Thr
            260                 265                 270

Leu Val Thr Val Ser Ser Gly Gly Gly Gly Ser Gly Gly Gly Gly Ser
        275                 280                 285

Ser Gly Gly Gly Ser Gln Phe Val Leu Thr Gln Ser Pro Ser Ala Ser
    290                 295                 300

Ala Ala Leu Gly Ala Ser Ala Lys Leu Thr Cys Thr Leu Ser Ser Ala
305                 310                 315                 320

His Lys Thr Tyr Thr Ile Asp Trp Tyr Gln Gln Gln Lys Gly Lys Ala
                325                 330                 335

Pro Arg Tyr Leu Ile Gln Val Lys Ser Asp Gly Thr Tyr Thr Lys Ala
            340                 345                 350

Thr Gly Val Pro Asp Arg Phe Ser Gly Ser Ser Ser Gly Ala Asp Arg
        355                 360                 365

Tyr Leu Ile Ile Pro Ser Val Gln Ala Asp Asp Glu Ala Asp Tyr Tyr
    370                 375                 380

Cys Gly Thr Asp Tyr Thr Gly Gly Tyr Val Phe Gly Gly Gly Thr Gln
385                 390                 395                 400

Leu Thr Val Thr Ala Ser Gly Gly Gly Gly Ser Gly Gly Gly Gly Ser
                405                 410                 415

Ser Pro Thr Glu Pro Ser Ser Lys Thr Gly Asn Pro Arg His Leu His
            420                 425                 430

Val Leu Ile Gly Thr Ser Val Val Lys Ile Pro Phe Thr Ile Leu Leu
        435                 440                 445

Phe Phe Leu Leu His Arg Trp Cys Ser Asn Lys Lys Asn Ala Ala Val
    450                 455                 460

Met Asp Gln Glu Pro Ala Gly Asn Arg Thr Val Asn Ser Glu Asp Ser
465                 470                 475                 480

Asp Glu Gln Asp His Gln Glu Val Ser Tyr Ala
                485                 490
```

<210> SEQ ID NO 103
<211> LENGTH: 1491
<212> TYPE: DNA

<213> ORGANISM: Artificial Sequence
<220> FEATURE:
<223> OTHER INFORMATION: Artifically generated sequence

<400> SEQUENCE: 103
atggggggac ttgaaccctg cagcaggttc ctgctcctgc ctctcctgct ggctgtaagt 60
ggtctccgtc ctgtccaggt ccaggcccag agcgattgca gttgctctac ggtgagcccg 120
ggcgtgctgg cagggatcgt gatgggagac ctggtgctga cagtgctcat tgccctggcc 180
gtgtacttcc tgggccggct ggtccctcgg gggcgagggg ctgcggaggc agcgacccgg 240
aaacagcgta tcactgagac cgagtcgcct tatcaggagc tccagggtca gaggtcggat 300
gtctacagcg acctcaacac acagaggccg tattacaaag tcgagggcgg cggagagggc 360
agaggaagtc ttctaacatg cggtgacgtg gaggagaatc ccggccctag gatggcctta 420
ccagtgaccg ccttgctcct gccgctggcc ttgctgctcc acgccgccag gccgggatcc 480
cagtcagtga aggagtccga gggaggtctc ttcaagccaa cggataccct gacactcacc 540
tgcacggtct ctggattctc cctcagtaga catgcactga cctgggtccg ccaggctcca 600
gggaacgggc tggaatggat cggagccatt gataacgctg gtaccacata ctacgcgagc 660
tgggcgaaaa gccgctccac catcaccaga aacaccgacc tgcacacggt gactctgaaa 720
atgaccagtc tgacagcctc ggacacggct acctatttct gtgcgagagt cttttatgat 780
attaatagtg gttattatct ggacggcatg gacctctggg gcccagggac cctcgtcacc 840
gtctcttcag gtggaggcgg ttcaggcggc ggtggctcta gcggtggtgg atcgcagttt 900
gtgctgactc agtcgccctc tgtgtctgcc gccctgggag cctctgccaa gctcacctgc 960
accctgagca gtgcccacaa gacctacacc attgactggt atcagcagca gcaaggggag 1020
gcccctcggt acctgatgca agttaagagt gatggaagct acaccaaggg gaccggggtc 1080
cctgatcgct tctcgggctc cagctctggg gctgaccgct acttgatcat ccccagcgtc 1140
caggctgatg acgaagccgg ctacgtttgt ggtgcagatg ataacggtgg gtatgtgttc 1200
ggcggaggga cccagctgac cgtcacagct agcggtggcg gaggttctgg aggtgggggt 1260
tcctcaccca ctgaaccaag ctccaaaacc ggtaacccca gacacctgca tgttctgatt 1320
gggacctcag tggtcaaaat ccctttcacc atcctcctct tctttctcct tcatcgctgg 1380
tgctccaaca aaaaaaatgc tgctgtaatg gaccaagagc ctgcagggaa cagaacagtg 1440
aacagcgagg attctgatga acaagaccat caggaggtgt catacgcata a 1491

<210> SEQ ID NO 104
<211> LENGTH: 496
<212> TYPE: PRT
<213> ORGANISM: Artificial Sequence
<220> FEATURE:
<223> OTHER INFORMATION: Artifically generated sequence

<400> SEQUENCE: 104

Met Gly Gly Leu Glu Pro Cys Ser Arg Phe Leu Leu Leu Pro Leu Leu
1 5 10 15

Leu Ala Val Ser Gly Leu Arg Pro Val Gln Val Gln Ala Gln Ser Asp
20 25 30

Cys Ser Cys Ser Thr Val Ser Pro Gly Val Leu Ala Gly Ile Val Met
35 40 45

Gly Asp Leu Val Leu Thr Val Leu Ile Ala Leu Ala Val Tyr Phe Leu
50 55 60

Gly Arg Leu Val Pro Arg Gly Arg Gly Ala Ala Glu Ala Ala Thr Arg

-continued

```
65                  70                  75                  80

Lys Gln Arg Ile Thr Glu Thr Glu Ser Pro Tyr Gln Glu Leu Gln Gly
                85                  90                  95

Gln Arg Ser Asp Val Tyr Ser Asp Leu Asn Thr Gln Arg Pro Tyr Tyr
            100                 105                 110

Lys Val Glu Gly Gly Gly Glu Gly Arg Gly Ser Leu Leu Thr Cys Gly
        115                 120                 125

Asp Val Glu Glu Asn Pro Gly Pro Arg Met Ala Leu Pro Val Thr Ala
    130                 135                 140

Leu Leu Leu Pro Leu Ala Leu Leu Leu His Ala Ala Arg Pro Gly Ser
145                 150                 155                 160

Gln Ser Val Lys Glu Ser Glu Gly Gly Leu Phe Lys Pro Thr Asp Thr
                165                 170                 175

Leu Thr Leu Thr Cys Thr Val Ser Gly Phe Ser Leu Ser Arg His Ala
            180                 185                 190

Leu Thr Trp Val Arg Gln Ala Pro Gly Asn Gly Leu Glu Trp Ile Gly
        195                 200                 205

Ala Ile Asp Asn Ala Gly Thr Thr Tyr Tyr Ala Ser Trp Ala Lys Ser
    210                 215                 220

Arg Ser Thr Ile Thr Arg Asn Thr Asp Leu His Thr Val Thr Leu Lys
225                 230                 235                 240

Met Thr Ser Leu Thr Ala Ser Asp Thr Ala Thr Tyr Phe Cys Ala Arg
                245                 250                 255

Val Phe Tyr Asp Ile Asn Ser Gly Tyr Tyr Leu Asp Gly Met Asp Leu
            260                 265                 270

Trp Gly Pro Gly Thr Leu Val Thr Val Ser Ser Gly Gly Gly Gly Ser
        275                 280                 285

Gly Gly Gly Gly Ser Ser Gly Gly Gly Ser Gln Phe Val Leu Thr Gln
    290                 295                 300

Ser Pro Ser Val Ser Ala Ala Leu Gly Ala Ser Ala Lys Leu Thr Cys
305                 310                 315                 320

Thr Leu Ser Ser Ala His Lys Thr Tyr Thr Ile Asp Trp Tyr Gln Gln
                325                 330                 335

Gln Gln Gly Glu Ala Pro Arg Tyr Leu Met Gln Val Lys Ser Asp Gly
            340                 345                 350

Ser Tyr Thr Lys Gly Thr Gly Val Pro Asp Arg Phe Ser Gly Ser Ser
        355                 360                 365

Ser Gly Ala Asp Arg Tyr Leu Ile Ile Pro Ser Val Gln Ala Asp Asp
    370                 375                 380

Glu Ala Gly Tyr Val Cys Gly Ala Asp Asp Asn Gly Gly Tyr Val Phe
385                 390                 395                 400

Gly Gly Gly Thr Gln Leu Thr Val Thr Ala Ser Gly Gly Gly Gly Ser
                405                 410                 415

Gly Gly Gly Gly Ser Ser Pro Thr Glu Pro Ser Ser Lys Thr Gly Asn
            420                 425                 430

Pro Arg His Leu His Val Leu Ile Gly Thr Ser Val Val Lys Ile Pro
        435                 440                 445

Phe Thr Ile Leu Leu Phe Phe Leu Leu His Arg Trp Cys Ser Asn Lys
    450                 455                 460

Lys Asn Ala Ala Val Met Asp Gln Glu Pro Ala Gly Asn Arg Thr Val
465                 470                 475                 480

Asn Ser Glu Asp Ser Asp Glu Gln Asp His Gln Glu Val Ser Tyr Ala
                485                 490                 495
```

<210> SEQ ID NO 105
<211> LENGTH: 9070
<212> TYPE: DNA
<213> ORGANISM: Artificial Sequence
<220> FEATURE:
<223> OTHER INFORMATION: Artifically generated sequence

<400> SEQUENCE: 105
gtgcacgagt gggttacatc gaactggatc tcaacagcgg taagatcctt gagagttttc 60
gccccgaaga acgttttcca atgatgagca cttttaaagt tctgctatgt ggcgcggtat 120
tatcccgtat tgacgccggg caagagcaac tcggtcgccg catacactat tctcagaatg 180
acttggttga gtactcacca gtcacagaaa agcatcttac ggatggcatg acagtaagag 240
aattatgcag tgctgccata accatgagtg ataacactgc ggccaactta cttctgacaa 300
cgatcggagg accgaaggag ctaaccgctt ttttgcacaa catgggggat catgtaactc 360
gccttgatcg ttgggaaccg gagctgaatg aagccatacc aaacgacgag cgtgacacca 420
cgatgcctgt agcaatggca acaacgttgc gcaaactatt aactggcgaa ctacttactc 480
tagcttcccg gcaacaatta atagactgga tggaggcgga taaagttgca ggaccacttc 540
tgcgctcggc ccttccggct ggctggttta ttgctgataa atctggagcc ggtgagcgtg 600
ggtctcgcgg tatcattgca gcactggggc cagatggtaa gccctcccgt atcgtagtta 660
tctacacgac ggggagtcag gcaactatgg atgaacgaaa tagacagatc gctgagatag 720
gtgcctcact gattaagcat tggtaactgt cagaccaagt ttactcatat atactttaga 780
ttgatttaaa acttcatttt taatttaaaa ggatctaggt gaagatcctt tttgataatc 840
tcatgaccaa aatcccttaa cgtgagtttt cgttccactg agcgtcagac cccgtagaaa 900
agatcaaagg atcttcttga gatccttttt ttctgcgcgt aatctgctgc ttgcaaacaa 960
aaaaaccacc gctaccagcg gtggtttgtt tgccggatca agagctacca actctttttc 1020
cgaaggtaac tggcttcagc agagcgcaga taccaaatac tgttcttcta gtgtagccgt 1080
agttaggcca ccacttcaag aactctgtag caccgcctac atacctcgct ctgctaatcc 1140
tgttaccagt ggctgctgcc agtggcgata agtcgtgtct taccgggttg gactcaagac 1200
gatagttacc ggataaggcg cagcggtcgg gctgaacggg gggttcgtgc acacagccca 1260
gcttggagcg aacgacctac accgaactga gatacctaca gcgtgagcta tgagaaagcg 1320
ccacgcttcc cgaagggaga aaggcggaca ggtatccggt aagcggcagg gtcggaacag 1380
gagagcgcac gagggagctt ccagggggaa acgcctggta tctttatagt cctgtcgggt 1440
ttcgccacct ctgacttgag cgtcgatttt tgtgatgctc gtcagggggg cggagcctat 1500
ggaaaaacgc cagcaacgcg gcctttttac ggttcctggc cttttgctgg ccttttgctc 1560
acatgttctt tcctgcgtta tcccctgatt ctgtggataa ccgtattacc gcctttgagt 1620
gagctgatac cgctcgccgc agccgaacga ccgagcgcag cgagtcagtg agcgaggaag 1680
cggaagagcg cccaatacgc aaaccgcctc tccccgcgcg ttggccgatt cattaatgca 1740
gctggcacga caggtttccc gactggaaag cgggcagtga gcgcaacgca attaatgtga 1800
gttagctcac tcattaggca ccccaggctt tacactttat gcttccggct cgtatgttgt 1860
gtggaattgt gagcggataa caatttcaca caggaaacag ctatgaccat gattacgcca 1920
agcgcgcaat taaccctcac taaagggaac aaaagctgga gctgcaagct taatgtagtc 1980
ttatgcaata ctcttgtagt cttgcaacat ggtaacgatg agttagcaac atgccttaca 2040

-continued

```
aggagagaaa aagcaccgtg catgccgatt ggtggaagta aggtggtacg atcgtgcctt   2100
attaggaagg caacagacgg gtctgacatg gattggacga accactgaat tgccgcattg   2160
cagagatatt gtatttaagt gcctagctcg atacataaac gggtctctct ggttagacca   2220
gatctgagcc tgggagctct ctggctaact agggaaccca ctgcttaagc ctcaataaag   2280
cttgccttga gtgcttcaag tagtgtgtgc ccgtctgttg tgtgactctg gtaactagag   2340
atccctcaga cccttttagt cagtgtggaa aatctctagc agtggcgccc gaacagggac   2400
ttgaaagcga aagggaaacc agaggagctc tctcgacgca ggactcggct tgctgaagcg   2460
cgcacggcaa gaggcgaggg gcggcgactg gtgagtacgc caaaaatttt gactagcgga   2520
ggctagaagg agagagatgg gtgcgagagc gtcagtatta agcgggggag aattagatcg   2580
cgatgggaaa aaattcggtt aaggccaggg ggaaagaaaa aatataaatt aaaacatata   2640
gtatgggcaa gcagggagct agaacgattc gcagttaatc ctggcctgtt agaaacatca   2700
gaaggctgta gacaaatact gggacagcta caaccatccc ttcagacagg atcagaagaa   2760
cttagatcat tatataatac agtagcaacc ctctattgtg tgcatcaaag gatagagata   2820
aaagacacca aggaagcttt agacaagata gaggaagagc aaaacaaaag taagaccacc   2880
gcacagcaag cggccgctga tcttcagacc tggaggagga gatatgaggg acaattggag   2940
aagtgaatta tataaatata aagtagtaaa aattgaacca ttaggagtag cacccaccaa   3000
ggcaaagaga agagtggtgc agagagaaaa aagagcagtg ggaataggag ctttgttcct   3060
tgggttcttg ggagcagcag gaagcactat gggcgcagcg tcaatgacgc tgacggtaca   3120
ggccagacaa ttattgtctg gtatagtgca gcagcagaac aatttgctga gggctattga   3180
ggcgcaacag catctgttgc aactcacagt ctggggcatc aagcagctcc aggcaagaat   3240
cctggctgtg gaaagatacc taaaggatca acagctcctg gggatttggg gttgctctgg   3300
aaaactcatt tgcaccactg ctgtgccttg gaatgctagt tggagtaata aatctctgga   3360
acagatttgg aatcacacga cctggatgga gtgggacaga gaaattaaca attacacaag   3420
cttaatacac tccttaattg aagaatcgca aaaccagcaa gaaaagaatg aacaagaatt   3480
attggaatta gataaatggg caagtttgtg gaattggttt aacataacaa attggctgtg   3540
gtatataaaa ttattcataa tgatagtagg aggcttggta ggtttaagaa tagtttttgc   3600
tgtactttct atagtgaata gagttaggca gggatattca ccattatcgt ttcagaccca   3660
cctcccaacc ccgaggggac ccgacaggcc cgaaggaata gaagaagaag gtggagagag   3720
agacagagac agatccattc gattagtgaa cggatctcga cggtatcgat tagactgtag   3780
cccaggaata tggcagctag attgtacaca tttagaagga aaagttatct tggtagcagt   3840
tcatgtagcc agtggatata tagaagcaga agtaattcca gcagagacag ggcaagaaac   3900
agcatacttc ctcttaaaat tagcaggaag atggccagta aaaacagtac atacagacaa   3960
tggcagcaat ttcaccagta ctacagttaa ggccgcctgt tggtgggcgg ggatcaagca   4020
ggaatttggc attccctaca atccccaaag tcaaggagta atagaatcta tgaataaaga   4080
attaaagaaa attataggac aggtaagaga tcaggctgaa catcttaaga cagcagtaca   4140
aatggcagta ttcatccaca attttaaaag aaaagggggg attggggggt acagtgcagg   4200
ggaaagaata gtagacataa tagcaacaga catacaaact aaagaattac aaaaacaaat   4260
tacaaaaatt caaaattttc gggtttatta cagggacagc agagatccag tttggctgca   4320
tacgcgtcgt gaggctccgg tgcccgtcag tgggcagagc gcacatcgcc cacagtcccc   4380
gagaagttgg ggggaggggt cggcaattga accggtgcct agagaaggtg gcgcggggta   4440
```

aactgggaaa gtgatgtcgt gtactggctc cgcctttttc ccgagggtgg gggagaaccg 4500
tatataagtg cagtagtcgc cgtgaacgtt ctttttcgca acgggtttgc cgccagaaca 4560
caggtaagtg ccgtgtgtgg ttcccgcggg cctggcctct ttacgggtta tggcccttgc 4620
gtgccttgaa ttacttccac ctggctgcag tacgtgattc ttgatcccga gcttcgggtt 4680
ggaagtgggt gggagagttc gaggccttgc gcttaaggag ccccttcgcc tcgtgcttga 4740
gttgaggcct ggcctgggcg ctggggccgc cgcgtgcgaa tctggtggca ccttcgcgcc 4800
tgtctcgctg ctttcgataa gtctctagcc atttaaaatt tttgatgacc tgctgcgacg 4860
ctttttttct ggcaagatag tcttgtaaat gcgggccaag atctgcacac tggtatttcg 4920
gtttttgggg ccgcgggcgg cgacggggcc cgtgcgtccc agcgcacatg ttcggcgagg 4980
cggggcctgc gagcgcggcc accgagaatc ggacgggggt agtctcaagc tggccggcct 5040
gctctggtgc ctggcctcgc gccgccgtgt atcgccccgc cctgggcggc aaggctggcc 5100
cggtcggcac cagttgcgtg agcggaaaga tggccgcttc ccggccctgc tgcagggagc 5160
tcaaaatgga ggacgcggcg ctcgggagag cgggcgggtg agtcacccac acaaaggaaa 5220
agggcctttc cgtcctcagc cgtcgcttca tgtgactcca ctgagtaccg ggcgccgtcc 5280
aggcacctcg attagttctc gtgcttttgg agtacgtcgt ctttaggttg gggggagggg 5340
ttttatgcga tggagtttcc ccacactgag tgggtggaga ctgaagttag gccagcttgg 5400
cacttgatgt aattctcctt ggaatttgcc ctttttgagt ttggatcttg gttcattctc 5460
aagcctcaga cagtggttca aagttttttt cttccatttc aggtgtcgtg agctagagcc 5520
accatggagt ttgggctgag ctggcttttt cttgtggcta ttttaaaagg tgtccagtgc 5580
ggatccgagc agctgaagga gtccggggga ggtctcttca agccaacgga taccctgaca 5640
ctcacctgca cagtctctgg attctccctc agttactatg gagtgaactg ggtccgccag 5700
gctccaggga acgggctgga atggatcgga accattggtg gtagtggtga cacatactac 5760
gcgagctggg cgaagagccg atccaccatc atcagaaaca ccaacgagaa cacggtgact 5820
ctgaaaatga ccagtctgac agccgcggac acggccacct atttctgtgt gagatatgct 5880
aatattggtt atgagtactt taacgtctgg ggtccaggca ccctggtcac cgtctcttca 5940
ggtggaggcg gttcaggcgg cggtggctct agcggtggtg gatcgcagtt tgtgctgact 6000
cagtcgccct ctgcatctgc tgccctggga gcctcggcca agctcacctg caccctgagc 6060
agtgcccaca agacctacac cattgactgg tatcagcagc agaaagggaa ggcccctcgc 6120
tacctgatac aagttaagag tgatggaacc tacaccaagg cgaccggggt ccctgatcgc 6180
ttctcgggct ccagctctgg ggctgaccgc tacctgatca tccccagcgt ccaggctgat 6240
gacgaagccg actactattg tggtacagat tataccggtg ggtatgtgtt cggcgggggg 6300
acccagctga ccgtcacagc tagcggtggc ggaggttctg gaggtggagg ttcctccgga 6360
atctacatct gggcccctct ggccggcacc tgtggcgtgc tgctgctgtc cctggtcatc 6420
accctgtact gcaagcgggg cagaaagaag ctgctgtaca tcttcaagca gcccttcatg 6480
cggcctgtgc agaccacaca ggaagaggac ggctgtagct gtagattccc cgaggaagag 6540
gaaggcggct gcgagctgag agtgaagttc agcagaagcg ccgacgcccc tgcctatcag 6600
cagggccaga accagctgta caacgagctg aacctgggca gacgggagga atacgacgtg 6660
ctggacaaga gaagaggccg ggaccctgag atgggcggca agcccagacg gaagaacccc 6720
caggaaggcc tgtataacga actgcagaaa gacaagatgg ccgaggccta cagcgagatc 6780

-continued

```
ggcatgaagg gcgagcggag aagaggcaag ggccatgacg gcctgtacca gggcctgagc   6840
accgccacca aggacaccta cgacgccctg cacatgcagg ccctgcctcc aagatgagtc   6900
gacaatcaac ctctggatta caaaatttgt gaaagattga ctggtattct taactatgtt   6960
gctcctttta cgctatgtgg atacgctgct ttaatgcctt tgtatcatgc tattgcttcc   7020
cgtatggctt tcattttctc ctccttgtat aaatcctggt tgctgtctct ttatgaggag   7080
ttgtggcccg ttgtcaggca acgtggcgtg gtgtgcactg tgtttgctga cgcaaccccc   7140
actggttggg gcattgccac cacctgtcag ctcctttccg ggactttcgc tttccccctc   7200
cctattgcca cggcggaact catcgccgcc tgccttgccc gctgctggac aggggctcgg   7260
ctgttgggca ctgacaattc cgtggtgttg tcggggaagc tgacgtcctt tccttggctg   7320
ctcgcctgtg ttgccacctg gattctgcgc gggacgtcct tctgctacgt cccttcggcc   7380
ctcaatccag cggaccttcc ttcccgcggc ctgctgccgg ctctgcggcc tcttccgcgt   7440
cttcgccttc gccctcagac gagtcggatc tccctttggg ccgcctcccc gcctggaatt   7500
cgagctcggt acctttaaga ccaatgactt acaaggcagc tgtagatctt agccactttt   7560
taaaagaaaa ggggggactg gaagggctaa ttcactccca acgaagacaa gatctgcttt   7620
ttgcttgtac tgggtctctc tggttagacc agatctgagc ctgggagctc tctggctaac   7680
tagggaaccc actgcttaag cctcaataaa gcttgccttg agtgcttcaa gtagtgtgtg   7740
cccgtctgtt gtgtgactct ggtaactaga gatccctcag acccttttag tcagtgtgga   7800
aaatctctag cagtagtagt tcatgtcatc ttattattca gtatttataa cttgcaaaga   7860
aatgaatatc agagagtgag aggaacttgt ttattgcagc ttataatggt tacaaataaa   7920
gcaatagcat cacaaatttc acaaataaag catttttttc actgcattct agttgtggtt   7980
tgtccaaact catcaatgta tcttatcatg tctggctcta gctatcccgc ccctaactcc   8040
gcccagttcc gcccattctc cgccccatgg ctgactaatt ttttttattt atgcagaggc   8100
cgaggccgcc tcggcctctg agctattcca gaagtagtga ggaggctttt ttggaggcct   8160
agctagggac gtacccaatt cgccctatag tgagtcgtat tacgcgcgct cactggccgt   8220
cgttttacaa cgtcgtgact gggaaaaccc tggcgttacc caacttaatc gccttgcagc   8280
acatccccct ttcgccagct ggcgtaatag cgaagaggcc cgcaccgatc gcccttccca   8340
acagttgcgc agcctgaatg gcgaatggga cgcgccctgt agcggcgcat taagcgcggc   8400
gggtgtggtg gttacgcgca gcgtgaccgc tacacttgcc agcgccctag cgcccgctcc   8460
tttcgctttc ttcccttcct ttctcgccac gttcgccggc tttccccgtc aagctctaaa   8520
tcgggggctc cctttagggt tccgatttag tgctttacgg cacctcgacc ccaaaaaact   8580
tgattagggt gatggttcac gtagtgggcc atcgccctga tagacggttt ttcgcccttt   8640
gacgttggag tccacgttct ttaatagtgg actcttgttc caaactggaa caacactcaa   8700
ccctatctcg gtctattctt ttgatttata agggattttg ccgatttcgg cctattggtt   8760
aaaaaatgag ctgatttaac aaaaatttaa cgcgaatttt aacaaaatat taacgcttac   8820
aatttaggtg gcacttttcg gggaaatgtg cgcggaaccc ctatttgttt atttttctaa   8880
atacattcaa atatgtatcc gctcatgaga caataaccct gataaatgct tcaataatat   8940
tgaaaaagga agagtatgag tattcaacat ttccgtgtcg cccttattcc cttttttgcg   9000
gcattttgcc ttcctgtttt tgctcaccca gaaacgctgg tgaaagtaaa agatgctgaa   9060
gatcagttgg                                                          9070
```

<210> SEQ ID NO 106
<211> LENGTH: 9085
<212> TYPE: DNA
<213> ORGANISM: Artificial Sequence
<220> FEATURE:
<223> OTHER INFORMATION: Artifically generated sequence

<400> SEQUENCE: 106
gtgcacgagt gggttacatc gaactggatc tcaacagcgg taagatcctt gagagttttc 60
gccccgaaga acgttttcca atgatgagca cttttaaagt tctgctatgt ggcgcggtat 120
tatcccgtat tgacgccggg caagagcaac tcggtcgccg catacactat tctcagaatg 180
acttggttga gtactcacca gtcacagaaa agcatcttac ggatggcatg acagtaagag 240
aattatgcag tgctgccata accatgagtg ataacactgc ggccaactta cttctgacaa 300
cgatcggagg accgaaggag ctaaccgctt ttttgcacaa catgggggat catgtaactc 360
gccttgatcg ttgggaaccg gagctgaatg aagccatacc aaacgacgag cgtgacacca 420
cgatgcctgt agcaatggca acaacgttgc gcaaactatt aactggcgaa ctacttactc 480
tagcttcccg gcaacaatta atagactgga tggaggcgga taaagttgca ggaccacttc 540
tgcgctcggc ccttccggct ggctggttta ttgctgataa atctggagcc ggtgagcgtg 600
ggtctcgcgg tatcattgca gcactggggc cagatggtaa gccctcccgt atcgtagtta 660
tctacacgac ggggagtcag gcaactatgg atgaacgaaa tagacagatc gctgagatag 720
gtgcctcact gattaagcat tggtaactgt cagaccaagt ttactcatat atactttaga 780
ttgatttaaa acttcatttt taatttaaaa ggatctaggt gaagatcctt tttgataatc 840
tcatgaccaa aatcccttaa cgtgagtttt cgttccactg agcgtcagac cccgtagaaa 900
agatcaaagg atcttcttga gatccttttt ttctgcgcgt aatctgctgc ttgcaaacaa 960
aaaaaccacc gctaccagcg gtggtttgtt tgccggatca agagctacca actctttttc 1020
cgaaggtaac tggcttcagc agagcgcaga taccaaatac tgttcttcta gtgtagccgt 1080
agttaggcca ccacttcaag aactctgtag caccgcctac atacctcgct ctgctaatcc 1140
tgttaccagt ggctgctgcc agtggcgata agtcgtgtct taccgggttg gactcaagac 1200
gatagttacc ggataaggcg cagcggtcgg gctgaacggg gggttcgtgc acacagccca 1260
gcttggagcg aacgacctac accgaactga gatacctaca gcgtgagcta tgagaaagcg 1320
ccacgcttcc cgaagggaga aaggcggaca ggtatccggt aagcggcagg gtcggaacag 1380
gagagcgcac gagggagctt ccagggggaa acgcctggta tctttatagt cctgtcgggt 1440
ttcgccacct ctgacttgag cgtcgatttt tgtgatgctc gtcagggggg cggagcctat 1500
ggaaaaacgc cagcaacgcg gcctttttac ggttcctggc cttttgctgg ccttttgctc 1560
acatgttctt tcctgcgtta tcccctgatt ctgtggataa ccgtattacc gcctttgagt 1620
gagctgatac cgctcgccgc agccgaacga ccgagcgcag cgagtcagtg agcgaggaag 1680
cggaagagcg cccaatacgc aaaccgcctc tccccgcgcg ttggccgatt cattaatgca 1740
gctggcacga caggtttccc gactggaaag cgggcagtga gcgcaacgca attaatgtga 1800
gttagctcac tcattaggca ccccaggctt tacactttat gcttccggct cgtatgttgt 1860
gtggaattgt gagcggataa caatttcaca caggaaacag ctatgaccat gattacgcca 1920
agcgcgcaat taaccctcac taaagggaac aaaagctgga gctgcaagct taatgtagtc 1980
ttatgcaata ctcttgtagt cttgcaacat ggtaacgatg agttagcaac atgccttaca 2040
aggagagaaa aagcaccgtg catgccgatt ggtggaagta aggtggtacg atcgtgcctt 2100

-continued

```
attaggaagg caacagacgg gtctgacatg gattggacga accactgaat tgccgcattg   2160
cagagatatt gtatttaagt gcctagctcg atacataaac gggtctctct ggttagacca   2220
gatctgagcc tgggagctct ctggctaact agggaaccca ctgcttaagc ctcaataaag   2280
cttgccttga gtgcttcaag tagtgtgtgc ccgtctgttg tgtgactctg gtaactagag   2340
atccctcaga cccttttagt cagtgtggaa aatctctagc agtggcgccc gaacagggac   2400
ttgaaagcga aagggaaacc agaggagctc tctcgacgca ggactcggct tgctgaagcg   2460
cgcacggcaa gaggcgaggg gcggcgactg gtgagtacgc caaaaatttt gactagcgga   2520
ggctagaagg agagagatgg gtgcgagagc gtcagtatta agcgggggag aattagatcg   2580
cgatgggaaa aaattcggtt aaggccaggg ggaaagaaaa aatataaatt aaaacatata   2640
gtatgggcaa gcagggagct agaacgattc gcagttaatc ctggcctgtt agaaacatca   2700
gaaggctgta gacaaatact gggacagcta caaccatccc ttcagacagg atcagaagaa   2760
cttagatcat tatataatac agtagcaacc ctctattgtg tgcatcaaag gatagagata   2820
aaagacacca aggaagcttt agacaagata gaggaagagc aaaacaaaag taagaccacc   2880
gcacagcaag cggccgctga tcttcagacc tggaggagga gatatgaggg acaattggag   2940
aagtgaatta tataaatata aagtagtaaa aattgaacca ttaggagtag cacccaccaa   3000
ggcaaagaga agagtggtgc agagagaaaa aagagcagtg ggaataggag ctttgttcct   3060
tgggttcttg ggagcagcag gaagcactat gggcgcagcg tcaatgacgc tgacggtaca   3120
ggccagacaa ttattgtctg gtatagtgca gcagcagaac aatttgctga gggctattga   3180
ggcgcaacag catctgttgc aactcacagt ctggggcatc aagcagctcc aggcaagaat   3240
cctggctgtg gaaagatacc taaaggatca acagctcctg gggatttggg gttgctctgg   3300
aaaactcatt tgcaccactg ctgtgccttg gaatgctagt tggagtaata aatctctgga   3360
acagatttgg aatcacacga cctggatgga gtgggacaga gaaattaaca attacacaag   3420
cttaatacac tccttaattg aagaatcgca aaaccagcaa gaaaagaatg aacaagaatt   3480
attggaatta gataaatggg caagtttgtg gaattggttt aacataacaa attggctgtg   3540
gtatataaaa ttattcataa tgatagtagg aggcttggta ggtttaagaa tagtttttgc   3600
tgtactttct atagtgaata gagttaggca gggatattca ccattatcgt ttcagaccca   3660
cctcccaacc ccgaggggac ccgacaggcc cgaaggaata gaagaagaag gtggagagag   3720
agacagagac agatccattc gattagtgaa cggatctcga cggtatcgat tagactgtag   3780
cccaggaata tggcagctag attgtacaca tttagaagga aaagttatct tggtagcagt   3840
tcatgtagcc agtggatata tagaagcaga agtaattcca gcagagacag ggcaagaaac   3900
agcatacttc ctcttaaaat tagcaggaag atggccagta aaaacagtac atacagacaa   3960
tggcagcaat ttcaccagta ctacagttaa ggccgcctgt tggtgggcgg ggatcaagca   4020
ggaatttggc attccctaca atccccaaag tcaaggagta atagaatcta tgaataaaga   4080
attaaagaaa attataggac aggtaagaga tcaggctgaa catcttaaga cagcagtaca   4140
aatggcagta ttcatccaca attttaaaag aaaagggggg attggggggt acagtgcagg   4200
ggaaagaata gtagacataa tagcaacaga catacaaact aaagaattac aaaaacaaat   4260
tacaaaaatt caaaattttc gggtttatta cagggacagc agagatccag tttggctgca   4320
tacgcgtcgt gaggctccgg tgcccgtcag tgggcagagc gcacatcgcc cacagtcccc   4380
gagaagttgg ggggaggggt cggcaattga accggtgcct agagaaggtg gcgcggggta   4440
aactgggaaa gtgatgtcgt gtactggctc cgcctttttc ccgagggtgg gggagaaccg   4500
```

-continued

```
tatataagtg cagtagtcgc cgtgaacgtt ctttttcgca acgggtttgc cgccagaaca   4560
caggtaagtg ccgtgtgtgg ttcccgcggg cctggcctct ttacgggtta tggcccttgc   4620
gtgccttgaa ttacttccac ctggctgcag tacgtgattc ttgatcccga gcttcgggtt   4680
ggaagtgggt gggagagttc gaggccttgc gcttaaggag ccccttcgcc tcgtgcttga   4740
gttgaggcct ggcctgggcg ctggggccgc cgcgtgcgaa tctggtggca ccttcgcgcc   4800
tgtctcgctg ctttcgataa gtctctagcc atttaaaatt tttgatgacc tgctgcgacg   4860
ctttttttct ggcaagatag tcttgtaaat gcgggccaag atctgcacac tggtatttcg   4920
gtttttgggg ccgcgggcgg cgacggggcc cgtgcgtccc agcgcacatg ttcggcgagg   4980
cggggcctgc gagcgcggcc accgagaatc ggacgggggt agtctcaagc tggccggcct   5040
gctctggtgc ctggcctcgc gccgccgtgt atcgccccgc cctgggcggc aaggctggcc   5100
cggtcggcac cagttgcgtg agcggaaaga tggccgcttc ccggccctgc tgcagggagc   5160
tcaaaatgga ggacgcggcg ctcgggagag cgggcgggtg agtcacccac acaaaggaaa   5220
agggcctttc cgtcctcagc cgtcgcttca tgtgactcca ctgagtaccg ggcgccgtcc   5280
aggcacctcg attagttctc gtgcttttgg agtacgtcgt ctttaggttg gggggagggg   5340
ttttatgcga tggagtttcc ccacactgag tgggtggaga ctgaagttag gccagcttgg   5400
cacttgatgt aattctcctt ggaatttgcc ctttttgagt ttggatcttg gttcattctc   5460
aagcctcaga cagtggttca aagttttttt cttccatttc aggtgtcgtg agctagagcc   5520
accatggagt ttgggctgag ctggcttttt cttgtggcta ttttaaaagg tgtccagtgc   5580
ggatcccagt cagtgaagga gtccgaggga ggtctcttca agccaacgga taccctgaca   5640
ctcacctgca cggtctctgg attctccctc agtagacatg cactgacctg ggtccgccag   5700
gctccaggga acgggctgga atggatcgga gccattgata acgctggtac cacatactac   5760
gcgagctggg cgaaaagccg ctccaccatc accagaaaca ccgacctgca cacggtgact   5820
ctgaaaatga ccagtctgac agcctcggac acggctacct atttctgtgc gagagtcttt   5880
tatgatatta atagtggtta ttatctggac ggcatggacc tctggggccc agggaccctc   5940
gtcaccgtct cttcaggtgg aggcggttca ggcggcggtg gctctagcgg tggtggatcg   6000
cagtttgtgc tgactcagtc gccctctgtg tctgccgccc tgggagcctc tgccaagctc   6060
acctgcaccc tgagcagtgc ccacaagacc tacaccattg actggtatca gcagcagcaa   6120
ggggaggccc ctcggtacct gatgcaagtt aagagtgatg gaagctacac caaggggacc   6180
ggggtccctg atcgcttctc gggctccagc tctggggctg accgctactt gatcatcccc   6240
agcgtccagg ctgatgacga agccggctac gtttgtggtg cagatgataa cggtgggtat   6300
gtgttcggcg gagggaccca gctgaccgtc acagctagcg gtggcggagg ttctggaggt   6360
ggaggttcct ccggaatcta catctgggcc cctctggccg gcacctgtgg cgtgctgctg   6420
ctgtccctgg tcatcaccct gtactgcaag cggggcagaa agaagctgct gtacatcttc   6480
aagcagccct tcatgcggcc tgtgcagacc acacaggaag aggacggctg tagctgtaga   6540
ttccccgagg aagaggaagg cggctgcgag ctgagagtga agttcagcag aagcgccgac   6600
gcccctgcct atcagcaggg ccagaaccag ctgtacaacg agctgaacct gggcagacgg   6660
gaggaatacg acgtgctgga caagagaaga ggccgggacc ctgagatggg cggcaagccc   6720
agacggaaga acccccagga aggcctgtat aacgaactgc agaaagacaa gatggccgag   6780
gcctacagcg agatcggcat gaagggcgag cggagaagag gcaagggcca tgacggcctg   6840
```

```
taccagggcc tgagcaccgc caccaaggac acctacgacg ccctgcacat gcaggccctg   6900
cctccaagat gagtcgacaa tcaacctctg gattacaaaa tttgtgaaag attgactggt   6960
attcttaact atgttgctcc ttttacgcta tgtggatacg ctgctttaat gcctttgtat   7020
catgctattg cttcccgtat ggctttcatt ttctcctcct tgtataaatc ctggttgctg   7080
tctctttatg aggagttgtg gcccgttgtc aggcaacgtg gcgtggtgtg cactgtgttt   7140
gctgacgcaa cccccactgg ttggggcatt gccaccacct gtcagctcct ttccgggact   7200
ttcgctttcc ccctccctat tgccacggcg gaactcatcg ccgcctgcct tgcccgctgc   7260
tggacagggg ctcggctgtt gggcactgac aattccgtgg tgttgtcggg gaagctgacg   7320
tcctttcctt ggctgctcgc ctgtgttgcc acctggattc tgcgcgggac gtccttctgc   7380
tacgtccctt cggccctcaa tccagcggac cttccttccc gcggcctgct gccggctctg   7440
cggcctcttc cgcgtcttcg ccttcgccct cagacgagtc ggatctccct ttgggccgcc   7500
tccccgcctg gaattcgagc tcggtacctt taagaccaat gacttacaag gcagctgtag   7560
atcttagcca ctttttaaaa gaaaaggggg gactggaagg gctaattcac tcccaacgaa   7620
gacaagatct gctttttgct tgtactgggt ctctctggtt agaccagatc tgagcctggg   7680
agctctctgg ctaactaggg aacccactgc ttaagcctca ataaagcttg ccttgagtgc   7740
ttcaagtagt gtgtgcccgt ctgttgtgtg actctggtaa ctagagatcc ctcagaccct   7800
tttagtcagt gtggaaaatc tctagcagta gtagttcatg tcatcttatt attcagtatt   7860
tataacttgc aaagaaatga atatcagaga gtgagaggaa cttgtttatt gcagcttata   7920
atggttacaa ataaagcaat agcatcacaa atttcacaaa taaagcattt ttttcactgc   7980
attctagttg tggtttgtcc aaactcatca atgtatctta tcatgtctgg ctctagctat   8040
cccgccccta actccgccca gttccgccca ttctccgccc catggctgac taattttttt   8100
tatttatgca gaggccgagg ccgcctcggc ctctgagcta ttccagaagt agtgaggagg   8160
cttttttgga ggcctagcta gggacgtacc caattcgccc tatagtgagt cgtattacgc   8220
gcgctcactg gccgtcgttt tacaacgtcg tgactgggaa aaccctggcg ttacccaact   8280
taatcgcctt gcagcacatc ccccttttcgc cagctggcgt aatagcgaag aggcccgcac   8340
cgatcgccct tcccaacagt tgcgcagcct gaatggcgaa tgggacgcgc cctgtagcgg   8400
cgcattaagc gcggcgggtg tggtggttac gcgcagcgtg accgctacac ttgccagcgc   8460
cctagcgccc gctcctttcg ctttcttccc ttcctttctc gccacgttcg ccggctttcc   8520
ccgtcaagct ctaaatcggg ggctcccttt agggttccga tttagtgctt tacggcacct   8580
cgaccccaaa aaacttgatt agggtgatgg ttcacgtagt gggccatcgc cctgatagac   8640
ggtttttcgc cctttgacgt tggagtccac gttctttaat agtggactct tgttccaaac   8700
tggaacaaca ctcaacccta tctcggtcta ttcttttgat ttataaggga ttttgccgat   8760
ttcggcctat tggttaaaaa atgagctgat ttaacaaaaa tttaacgcga attttaacaa   8820
aatattaacg cttacaattt aggtggcact tttcggggaa atgtgcgcgg aacccctatt   8880
tgtttatttt tctaaataca ttcaaatatg tatccgctca tgagacaata accctgataa   8940
atgcttcaat aatattgaaa aaggaagagt atgagtattc aacatttccg tgtcgccctt   9000
attccctttt ttgcggcatt ttgccttcct gtttttgctc acccagaaac gctggtgaaa   9060
gtaaaagatg ctgaagatca gttgg                                          9085
```

<210> SEQ ID NO 107
<211> LENGTH: 9175

<212> TYPE: DNA
<213> ORGANISM: Artificial Sequence
<220> FEATURE:
<223> OTHER INFORMATION: Artifically generated sequence

<400> SEQUENCE: 107
gtgcacgagt gggttacatc gaactggatc tcaacagcgg taagatcctt gagagttttc 60
gccccgaaga acgttttcca atgatgagca cttttaaagt tctgctatgt ggcgcggtat 120
tatcccgtat tgacgccggg caagagcaac tcggtcgccg catacactat tctcagaatg 180
acttggttga gtactcacca gtcacagaaa agcatcttac ggatggcatg acagtaagag 240
aattatgcag tgctgccata accatgagtg ataacactgc ggccaactta cttctgacaa 300
cgatcggagg accgaaggag ctaaccgctt ttttgcacaa catgggggat catgtaactc 360
gccttgatcg ttgggaaccg gagctgaatg aagccatacc aaacgacgag cgtgacacca 420
cgatgcctgt agcaatggca acaacgttgc gcaaactatt aactggcgaa ctacttactc 480
tagcttcccg gcaacaatta atagactgga tggaggcgga taaagttgca ggaccacttc 540
tgcgctcggc ccttccggct ggctggttta ttgctgataa atctggagcc ggtgagcgtg 600
ggtctcgcgg tatcattgca gcactggggc cagatggtaa gccctcccgt atcgtagtta 660
tctacacgac ggggagtcag gcaactatgg atgaacgaaa tagacagatc gctgagatag 720
gtgcctcact gattaagcat tggtaactgt cagaccaagt ttactcatat atactttaga 780
ttgatttaaa acttcatttt taatttaaaa ggatctaggt gaagatcctt tttgataatc 840
tcatgaccaa aatcccttaa cgtgagtttt cgttccactg agcgtcagac cccgtagaaa 900
agatcaaagg atcttcttga gatccttttt ttctgcgcgt aatctgctgc ttgcaaacaa 960
aaaaaccacc gctaccagcg gtggtttgtt tgccggatca agagctacca actctttttc 1020
cgaaggtaac tggcttcagc agagcgcaga taccaaatac tgttcttcta gtgtagccgt 1080
agttaggcca ccacttcaag aactctgtag caccgcctac atacctcgct ctgctaatcc 1140
tgttaccagt ggctgctgcc agtggcgata agtcgtgtct taccgggttg gactcaagac 1200
gatagttacc ggataaggcg cagcggtcgg gctgaacggg gggttcgtgc acacagccca 1260
gcttggagcg aacgacctac accgaactga gatacctaca gcgtgagcta tgagaaagcg 1320
ccacgcttcc cgaagggaga aaggcggaca ggtatccggt aagcggcagg gtcggaacag 1380
gagagcgcac gagggagctt ccagggggaa acgcctggta tctttatagt cctgtcgggt 1440
ttcgccacct ctgacttgag cgtcgatttt tgtgatgctc gtcagggggg cggagcctat 1500
ggaaaaacgc cagcaacgcg gcctttttac ggttcctggc cttttgctgg ccttttgctc 1560
acatgttctt tcctgcgtta tcccctgatt ctgtggataa ccgtattacc gcctttgagt 1620
gagctgatac cgctcgccgc agccgaacga ccgagcgcag cgagtcagtg agcgaggaag 1680
cggaagagcg cccaatacgc aaaccgcctc tccccgcgcg ttggccgatt cattaatgca 1740
gctggcacga caggtttccc gactggaaag cgggcagtga gcgcaacgca attaatgtga 1800
gttagctcac tcattaggca ccccaggctt tacactttat gcttccggct cgtatgttgt 1860
gtggaattgt gagcggataa caatttcaca caggaaacag ctatgaccat gattacgcca 1920
agcgcgcaat taaccctcac taaagggaac aaaagctgga gctgcaagct taatgtagtc 1980
ttatgcaata ctcttgtagt cttgcaacat ggtaacgatg agttagcaac atgccttaca 2040
aggagagaaa aagcaccgtg catgccgatt ggtggaagta aggtggtacg atcgtgcctt 2100
attaggaagg caacagacgg gtctgacatg gattggacga accactgaat tgccgcattg 2160

-continued

```
cagagatatt gtatttaagt gcctagctcg atacataaac gggtctctct ggttagacca   2220
gatctgagcc tgggagctct ctggctaact agggaaccca ctgcttaagc ctcaataaag   2280
cttgccttga gtgcttcaag tagtgtgtgc ccgtctgttg tgtgactctg gtaactagag   2340
atccctcaga cccttttagt cagtgtggaa aatctctagc agtggcgccc gaacagggac   2400
ttgaaagcga aagggaaacc agaggagctc tctcgacgca ggactcggct tgctgaagcg   2460
cgcacggcaa gaggcgaggg gcggcgactg gtgagtacgc caaaaatttt gactagcgga   2520
ggctagaagg agagagatgg gtgcgagagc gtcagtatta agcgggggag aattagatcg   2580
cgatgggaaa aaattcggtt aaggccaggg ggaaagaaaa aatataaatt aaaacatata   2640
gtatgggcaa gcagggagct agaacgattc gcagttaatc ctggcctgtt agaaacatca   2700
gaaggctgta gacaaatact gggacagcta caaccatccc ttcagacagg atcagaagaa   2760
cttagatcat tatataatac agtagcaacc ctctattgtg tgcatcaaag gatagagata   2820
aaagacacca aggaagcttt agacaagata gaggaagagc aaaacaaaag taagaccacc   2880
gcacagcaag cggccgctga tcttcagacc tggaggagga gatatgaggg acaattggag   2940
aagtgaatta tataaatata aagtagtaaa aattgaacca ttaggagtag cacccaccaa   3000
ggcaaagaga agagtggtgc agagagaaaa aagagcagtg ggaataggag ctttgttcct   3060
tgggttcttg ggagcagcag gaagcactat gggcgcagcg tcaatgacgc tgacggtaca   3120
ggccagacaa ttattgtctg gtatagtgca gcagcagaac aatttgctga gggctattga   3180
ggcgcaacag catctgttgc aactcacagt ctggggcatc aagcagctcc aggcaagaat   3240
cctggctgtg gaaagatacc taaaggatca acagctcctg gggatttggg gttgctctgg   3300
aaaactcatt tgcaccactg ctgtgccttg gaatgctagt tggagtaata aatctctgga   3360
acagatttgg aatcacacga cctggatgga gtgggacaga gaaattaaca attacacaag   3420
cttaatacac tccttaattg aagaatcgca aaaccagcaa gaaaagaatg aacaagaatt   3480
attggaatta gataaatggg caagtttgtg gaattggttt aacataacaa attggctgtg   3540
gtatataaaa ttattcataa tgatagtagg aggcttggta ggtttaagaa tagtttttgc   3600
tgtactttct atagtgaata gagttaggca gggatattca ccattatcgt ttcagaccca   3660
cctcccaacc ccgaggggac ccgacaggcc cgaaggaata gaagaagaag gtggagagag   3720
agacagagac agatccattc gattagtgaa cggatctcga cggtatcgat tagactgtag   3780
cccaggaata tggcagctag attgtacaca tttagaagga aaagttatct tggtagcagt   3840
tcatgtagcc agtggatata tagaagcaga agtaattcca gcagagacag ggcaagaaac   3900
agcatacttc ctcttaaaat tagcaggaag atggccagta aaaacagtac atacagacaa   3960
tggcagcaat ttcaccagta ctacagttaa ggccgcctgt tggtgggcgg ggatcaagca   4020
ggaatttggc attccctaca atccccaaag tcaaggagta atagaatcta tgaataaaga   4080
attaaagaaa attataggac aggtaagaga tcaggctgaa catcttaaga cagcagtaca   4140
aatggcagta ttcatccaca attttaaaag aaaagggggg attggggggt acagtgcagg   4200
ggaaagaata gtagacataa tagcaacaga catacaaact aaagaattac aaaaacaaat   4260
tacaaaaatt caaaattttc gggtttatta cagggacagc agagatccag tttggctgca   4320
tacgcgtcgt gaggctccgg tgcccgtcag tgggcagagc gcacatcgcc cacagtcccc   4380
gagaagttgg ggggaggggt cggcaattga accggtgcct agagaaggtg gcgcggggta   4440
aactgggaaa gtgatgtcgt gtactggctc cgcctttttc ccgagggtgg gggagaaccg   4500
tatataagtg cagtagtcgc cgtgaacgtt ctttttcgca acgggtttgc cgccagaaca   4560
```

caggtaagtg ccgtgtgtgg ttcccgcggg cctggcctct ttacgggtta tggcccttgc 4620
gtgccttgaa ttacttccac ctggctgcag tacgtgattc ttgatcccga gcttcgggtt 4680
ggaagtgggt gggagagttc gaggccttgc gcttaaggag ccccttcgcc tcgtgcttga 4740
gttgaggcct ggcctgggcg ctggggccgc cgcgtgcgaa tctggtggca ccttcgcgcc 4800
tgtctcgctg ctttcgataa gtctctagcc atttaaaatt tttgatgacc tgctgcgacg 4860
ctttttttct ggcaagatag tcttgtaaat gcgggccaag atctgcacac tggtatttcg 4920
gtttttgggg ccgcgggcgg cgacggggcc cgtgcgtccc agcgcacatg ttcggcgagg 4980
cggggcctgc gagcgcggcc accgagaatc ggacgggggt agtctcaagc tggccggcct 5040
gctctggtgc ctggcctcgc gccgccgtgt atcgccccgc cctgggcggc aaggctggcc 5100
cggtcggcac cagttgcgtg agcggaaaga tggccgcttc ccggccctgc tgcagggagc 5160
tcaaaatgga ggacgcggcg ctcgggagag cgggcgggtg agtcacccac acaaaggaaa 5220
agggcctttc cgtcctcagc cgtcgcttca tgtgactcca ctgagtaccg ggcgccgtcc 5280
aggcacctcg attagttctc gtgcttttgg agtacgtcgt ctttaggttg gggggagggg 5340
ttttatgcga tggagtttcc ccacactgag tgggtggaga ctgaagttag gccagcttgg 5400
cacttgatgt aattctcctt ggaatttgcc ctttttgagt ttggatcttg gttcattctc 5460
aagcctcaga cagtggttca aagttttttt cttccatttc aggtgtcgtg agctagagcc 5520
accatggagt ttgggctgag ctggcttttt cttgtggcta ttttaaaagg tgtccagtgc 5580
ggatccgagc agctgaagga gtccggggga ggtctcttca agccaacgga taccctgaca 5640
ctcacctgca cagtctctgg attctccctc agttactatg gagtgaactg ggtccgccag 5700
gctccaggga acgggctgga atggatcgga accattggtg gtagtggtga cacatactac 5760
gcgagctggg cgaagagccg atccaccatc atcagaaaca ccaacgagaa cacggtgact 5820
ctgaaaatga ccagtctgac agccgcggac acggccacct atttctgtgt gagatatgct 5880
aatattggtt atgagtactt taacgtctgg ggtccaggca ccctggtcac cgtctcttca 5940
ggtggaggcg gttcaggcgg cggtggctct agcggtggtg gatcgcagtt tgtgctgact 6000
cagtcgccct ctgcatctgc tgccctggga gcctcggcca agctcacctg caccctgagc 6060
agtgcccaca agacctacac cattgactgg tatcagcagc agaaagggaa ggcccctcgc 6120
tacctgatac aagttaagag tgatggaacc tacaccaagg cgaccggggt ccctgatcgc 6180
ttctcgggct ccagctctgg ggctgaccgc tacctgatca tccccagcgt ccaggctgat 6240
gacgaagccg actactattg tggtacagat tataccggtg ggtatgtgtt cggcgggggg 6300
acccagctga ccgtcacagc tagcaccacg acgccagcgc cgcgaccacc aacaccggcg 6360
cccaccatcg cgtcgcagcc cctgtccctg cgcccagagg cgtgccggcc agcggcgggg 6420
ggcgcagtgc acacgagggg gctggacttc gcctgtgatt ccggaatcta catctgggcc 6480
cctctggccg gcacctgtgg cgtgctgctg ctgtccctgg tcatcaccct gtactgcaag 6540
cggggcagaa agaagctgct gtacatcttc aagcagccct tcatgcggcc tgtgcagacc 6600
acacaggaag aggacggctg tagctgtaga ttccccgagg aagaggaagg cggctgcgag 6660
ctgagagtga agttcagcag aagcgccgac gcccctgcct atcagcaggg ccagaaccag 6720
ctgtacaacg agctgaacct gggcagacgg gaggaatacg acgtgctgga caagagaaga 6780
ggccgggacc ctgagatggg cggcaagccc agacggaaga acccccagga aggcctgtat 6840
aacgaactgc agaaagacaa gatggccgag gcctacagcg agatcggcat gaagggcgag 6900

```
cggagaagag gcaagggcca tgacggcctg taccagggcc tgagcaccgc caccaaggac   6960
acctacgacg ccctgcacat gcaggccctg cctccaagat gagtcgacaa tcaacctctg   7020
gattacaaaa tttgtgaaag attgactggt attcttaact atgttgctcc ttttacgcta   7080
tgtggatacg ctgctttaat gcctttgtat catgctattg cttcccgtat ggctttcatt   7140
ttctcctcct tgtataaatc ctggttgctg tctctttatg aggagttgtg gcccgttgtc   7200
aggcaacgtg gcgtggtgtg cactgtgttt gctgacgcaa cccccactgg ttggggcatt   7260
gccaccacct gtcagctcct ttccgggact ttcgctttcc ccctccctat tgccacggcg   7320
gaactcatcg ccgcctgcct tgcccgctgc tggacagggg ctcggctgtt gggcactgac   7380
aattccgtgg tgttgtcggg gaagctgacg tcctttcctt ggctgctcgc ctgtgttgcc   7440
acctggattc tgcgcgggac gtccttctgc tacgtccctt cggccctcaa tccagcggac   7500
cttccttccc gcggcctgct gccggctctg cggcctcttc cgcgtcttcg ccttcgccct   7560
cagacgagtc ggatctccct ttgggccgcc tccccgcctg gaattcgagc tcggtacctt   7620
taagaccaat gacttacaag gcagctgtag atcttagcca ctttttaaaa gaaaaggggg   7680
gactggaagg gctaattcac tcccaacgaa gacaagatct gctttttgct tgtactgggt   7740
ctctctggtt agaccagatc tgagcctggg agctctctgg ctaactaggg aacccactgc   7800
ttaagcctca ataaagcttg ccttgagtgc ttcaagtagt gtgtgcccgt ctgttgtgtg   7860
actctggtaa ctagagatcc ctcagaccct tttagtcagt gtggaaaatc tctagcagta   7920
gtagttcatg tcatcttatt attcagtatt tataacttgc aaagaaatga atatcagaga   7980
gtgagaggaa cttgtttatt gcagcttata atggttacaa ataaagcaat agcatcacaa   8040
atttcacaaa taaagcattt ttttcactgc attctagttg tggtttgtcc aaactcatca   8100
atgtatctta tcatgtctgg ctctagctat cccgccccta actccgccca gttccgccca   8160
ttctccgccc catggctgac taattttttt tatttatgca gaggccgagg ccgcctcggc   8220
ctctgagcta ttccagaagt agtgaggagg cttttttgga ggcctagcta gggacgtacc   8280
caattcgccc tatagtgagt cgtattacgc gcgctcactg gccgtcgttt tacaacgtcg   8340
tgactgggaa aaccctggcg ttacccaact taatcgcctt gcagcacatc cccctttcgc   8400
cagctggcgt aatagcgaag aggcccgcac cgatcgccct tcccaacagt tgcgcagcct   8460
gaatggcgaa tgggacgcgc cctgtagcgg cgcattaagc gcggcgggtg tggtggttac   8520
gcgcagcgtg accgctacac ttgccagcgc cctagcgccc gctcctttcg ctttcttccc   8580
ttcctttctc gccacgttcg ccggctttcc ccgtcaagct ctaaatcggg ggctcccttt   8640
agggttccga tttagtgctt tacggcacct cgaccccaaa aaacttgatt agggtgatgg   8700
ttcacgtagt gggccatcgc cctgatagac ggtttttcgc cctttgacgt tggagtccac   8760
gttctttaat agtggactct tgttccaaac tggaacaaca ctcaacccta tctcggtcta   8820
ttcttttgat ttataaggga ttttgccgat ttcggcctat tggttaaaaa atgagctgat   8880
ttaacaaaaa tttaacgcga attttaacaa aatattaacg cttacaattt aggtggcact   8940
tttcggggaa atgtgcgcgg aacccctatt tgtttatttt tctaaataca ttcaaatatg   9000
tatccgctca tgagacaata accctgataa atgcttcaat aatattgaaa aaggaagagt   9060
atgagtattc aacatttccg tgtcgccctt attccctttt ttgcggcatt ttgccttcct   9120
gtttttgctc acccagaaac gctggtgaaa gtaaaagatg ctgaagatca gttgg        9175
```

<210> SEQ ID NO 108
<211> LENGTH: 9190

<212> TYPE: DNA
<213> ORGANISM: Artificial Sequence
<220> FEATURE:
<223> OTHER INFORMATION: Artifically generated sequence

<400> SEQUENCE: 108

```
gtgcacgagt gggttacatc gaactggatc tcaacagcgg taagatcctt gagagttttc     60
gccccgaaga acgttttcca atgatgagca cttttaaagt tctgctatgt ggcgcggtat    120
tatcccgtat tgacgccggg caagagcaac tcggtcgccg catacactat tctcagaatg    180
acttggttga gtactcacca gtcacagaaa agcatcttac ggatggcatg acagtaagag    240
aattatgcag tgctgccata accatgagtg ataacactgc ggccaactta cttctgacaa    300
cgatcggagg accgaaggag ctaaccgctt ttttgcacaa catgggggat catgtaactc    360
gccttgatcg ttgggaaccg gagctgaatg aagccatacc aaacgacgag cgtgacacca    420
cgatgcctgt agcaatggca acaacgttgc gcaaactatt aactggcgaa ctacttactc    480
tagcttcccg gcaacaatta atagactgga tggaggcgga taaagttgca ggaccacttc    540
tgcgctcggc ccttccggct ggctggttta ttgctgataa atctggagcc ggtgagcgtg    600
ggtctcgcgg tatcattgca gcactggggc cagatggtaa gccctcccgt atcgtagtta    660
tctacacgac ggggagtcag gcaactatgg atgaacgaaa tagacagatc gctgagatag    720
gtgcctcact gattaagcat tggtaactgt cagaccaagt ttactcatat atactttaga    780
ttgatttaaa acttcatttt taatttaaaa ggatctaggt gaagatcctt tttgataatc    840
tcatgaccaa aatcccttaa cgtgagtttt cgttccactg agcgtcagac cccgtagaaa    900
agatcaaagg atcttcttga gatccttttt ttctgcgcgt aatctgctgc ttgcaaacaa    960
aaaaaccacc gctaccagcg gtggtttgtt tgccggatca agagctacca actctttttc   1020
cgaaggtaac tggcttcagc agagcgcaga taccaaatac tgttcttcta gtgtagccgt   1080
agttaggcca ccacttcaag aactctgtag caccgcctac atacctcgct ctgctaatcc   1140
tgttaccagt ggctgctgcc agtggcgata agtcgtgtct taccgggttg gactcaagac   1200
gatagttacc ggataaggcg cagcggtcgg gctgaacggg gggttcgtgc acacagccca   1260
gcttggagcg aacgacctac accgaactga gatacctaca gcgtgagcta tgagaaagcg   1320
ccacgcttcc cgaagggaga aaggcggaca ggtatccggt aagcggcagg gtcggaacag   1380
gagagcgcac gagggagctt ccagggggaa acgcctggta tctttatagt cctgtcgggt   1440
ttcgccacct ctgacttgag cgtcgatttt tgtgatgctc gtcagggggg cggagcctat   1500
ggaaaaacgc cagcaacgcg gcctttttac ggttcctggc cttttgctgg ccttttgctc   1560
acatgttctt tcctgcgtta tcccctgatt ctgtggataa ccgtattacc gcctttgagt   1620
gagctgatac cgctcgccgc agccgaacga ccgagcgcag cgagtcagtg agcgaggaag   1680
cggaagagcg cccaatacgc aaaccgcctc tccccgcgcg ttggccgatt cattaatgca   1740
gctggcacga caggtttccc gactggaaag cgggcagtga gcgcaacgca attaatgtga   1800
gttagctcac tcattaggca ccccaggctt tacactttat gcttccggct cgtatgttgt   1860
gtggaattgt gagcggataa caatttcaca caggaaacag ctatgaccat gattacgcca   1920
agcgcgcaat taaccctcac taaagggaac aaaagctgga gctgcaagct taatgtagtc   1980
ttatgcaata ctcttgtagt cttgcaacat ggtaacgatg agttagcaac atgccttaca   2040
aggagagaaa aagcaccgtg catgccgatt ggtggaagta aggtggtacg atcgtgcctt   2100
attaggaagg caacagacgg gtctgacatg gattggacga accactgaat tgccgcattg   2160
```

-continued

```
cagagatatt gtatttaagt gcctagctcg atacataaac gggtctctct ggttagacca   2220
gatctgagcc tgggagctct ctggctaact agggaaccca ctgcttaagc ctcaataaag   2280
cttgccttga gtgcttcaag tagtgtgtgc ccgtctgttg tgtgactctg gtaactagag   2340
atccctcaga cccttttagt cagtgtggaa aatctctagc agtggcgccc gaacagggac   2400
ttgaaagcga aagggaaacc agaggagctc tctcgacgca ggactcggct tgctgaagcg   2460
cgcacggcaa gaggcgaggg gcggcgactg gtgagtacgc caaaaatttt gactagcgga   2520
ggctagaagg agagagatgg gtgcgagagc gtcagtatta agcgggggag aattagatcg   2580
cgatgggaaa aaattcggtt aaggccaggg ggaaagaaaa aatataaatt aaaacatata   2640
gtatgggcaa gcagggagct agaacgattc gcagttaatc ctggcctgtt agaaacatca   2700
gaaggctgta gacaaatact gggacagcta caaccatccc ttcagacagg atcagaagaa   2760
cttagatcat tatataatac agtagcaacc ctctattgtg tgcatcaaag gatagagata   2820
aaagacacca aggaagcttt agacaagata gaggaagagc aaaacaaaag taagaccacc   2880
gcacagcaag cggccgctga tcttcagacc tggaggagga gatatgaggg acaattggag   2940
aagtgaatta tataaatata aagtagtaaa aattgaacca ttaggagtag cacccaccaa   3000
ggcaaagaga agagtggtgc agagagaaaa aagagcagtg ggaataggag ctttgttcct   3060
tgggttcttg ggagcagcag gaagcactat gggcgcagcg tcaatgacgc tgacggtaca   3120
ggccagacaa ttattgtctg gtatagtgca gcagcagaac aatttgctga gggctattga   3180
ggcgcaacag catctgttgc aactcacagt ctggggcatc aagcagctcc aggcaagaat   3240
cctggctgtg gaaagatacc taaaggatca acagctcctg gggatttggg gttgctctgg   3300
aaaactcatt tgcaccactg ctgtgccttg gaatgctagt tggagtaata aatctctgga   3360
acagatttgg aatcacacga cctggatgga gtgggacaga gaaattaaca attacacaag   3420
cttaatacac tccttaattg aagaatcgca aaaccagcaa gaaaagaatg aacaagaatt   3480
attggaatta gataaatggg caagtttgtg gaattggttt aacataacaa attggctgtg   3540
gtatataaaa ttattcataa tgatagtagg aggcttggta ggtttaagaa tagtttttgc   3600
tgtactttct atagtgaata gagttaggca gggatattca ccattatcgt ttcagaccca   3660
cctcccaacc ccgaggggac ccgacaggcc cgaaggaata gaagaagaag gtggagagag   3720
agacagagac agatccattc gattagtgaa cggatctcga cggtatcgat tagactgtag   3780
cccaggaata tggcagctag attgtacaca tttagaagga aaagttatct tggtagcagt   3840
tcatgtagcc agtggatata tagaagcaga agtaattcca gcagagacag ggcaagaaac   3900
agcatacttc ctcttaaaat tagcaggaag atggccagta aaaacagtac atacagacaa   3960
tggcagcaat ttcaccagta ctacagttaa ggccgcctgt tggtgggcgg ggatcaagca   4020
ggaatttggc attccctaca atccccaaag tcaaggagta atagaatcta tgaataaaga   4080
attaaagaaa attataggac aggtaagaga tcaggctgaa catcttaaga cagcagtaca   4140
aatggcagta ttcatccaca attttaaaag aaaagggggg attggggggt acagtgcagg   4200
ggaaagaata gtagacataa tagcaacaga catacaaact aaagaattac aaaaacaaat   4260
tacaaaaatt caaaattttc gggtttatta cagggacagc agagatccag tttggctgca   4320
tacgcgtcgt gaggctccgg tgcccgtcag tgggcagagc gcacatcgcc cacagtcccc   4380
gagaagttgg ggggaggggt cggcaattga accggtgcct agagaaggtg gcgcggggta   4440
aactgggaaa gtgatgtcgt gtactggctc cgcctttttc ccgagggtgg gggagaaccg   4500
tatataagtg cagtagtcgc cgtgaacgtt ctttttcgca acgggtttgc cgccagaaca   4560
```

-continued

```
caggtaagtg ccgtgtgtgg ttcccgcggg cctggcctct ttacgggtta tggcccttgc   4620
gtgccttgaa ttacttccac ctggctgcag tacgtgattc ttgatcccga gcttcgggtt   4680
ggaagtgggt gggagagttc gaggccttgc gcttaaggag ccccttcgcc tcgtgcttga   4740
gttgaggcct ggcctgggcg ctggggccgc cgcgtgcgaa tctggtggca ccttcgcgcc   4800
tgtctcgctg ctttcgataa gtctctagcc atttaaaatt tttgatgacc tgctgcgacg   4860
ctttttttct ggcaagatag tcttgtaaat gcgggccaag atctgcacac tggtatttcg   4920
gtttttgggg ccgcgggcgg cgacggggcc cgtgcgtccc agcgcacatg ttcggcgagg   4980
cggggcctgc gagcgcggcc accgagaatc ggacgggggt agtctcaagc tggccggcct   5040
gctctggtgc ctggcctcgc gccgccgtgt atcgccccgc cctgggcggc aaggctggcc   5100
cggtcggcac cagttgcgtg agcggaaaga tggccgcttc ccggccctgc tgcagggagc   5160
tcaaaatgga ggacgcggcg ctcgggagag cgggcgggtg agtcacccac acaaaggaaa   5220
agggcctttc cgtcctcagc cgtcgcttca tgtgactcca ctgagtaccg ggcgccgtcc   5280
aggcacctcg attagttctc gtgcttttgg agtacgtcgt ctttaggttg gggggagggg   5340
ttttatgcga tggagtttcc ccacactgag tgggtggaga ctgaagttag gccagcttgg   5400
cacttgatgt aattctcctt ggaatttgcc ctttttgagt ttggatcttg gttcattctc   5460
aagcctcaga cagtggttca aagttttttt cttccatttc aggtgtcgtg agctagagcc   5520
accatggagt ttgggctgag ctggcttttt cttgtggcta ttttaaaagg tgtccagtgc   5580
ggatcccagt cagtgaagga gtccgaggga ggtctcttca agccaacgga taccctgaca   5640
ctcacctgca cggtctctgg attctccctc agtagacatg cactgacctg ggtccgccag   5700
gctccaggga acgggctgga atggatcgga gccattgata acgctggtac cacatactac   5760
gcgagctggg cgaaaagccg ctccaccatc accagaaaca ccgacctgca cacggtgact   5820
ctgaaaatga ccagtctgac agcctcggac acggctacct atttctgtgc gagagtcttt   5880
tatgatatta atagtggtta ttatctggac ggcatggacc tctggggccc agggaccctc   5940
gtcaccgtct cttcaggtgg aggcggttca ggcggcggtg gctctagcgg tggtggatcg   6000
cagtttgtgc tgactcagtc gccctctgtg tctgccgccc tgggagcctc tgccaagctc   6060
acctgcaccc tgagcagtgc ccacaagacc tacaccattg actggtatca gcagcagcaa   6120
ggggaggccc ctcggtacct gatgcaagtt aagagtgatg gaagctacac caaggggacc   6180
ggggtccctg atcgcttctc gggctccagc tctggggctg accgctactt gatcatcccc   6240
agcgtccagg ctgatgacga agccggctac gtttgtggtg cagatgataa cggtgggtat   6300
gtgttcggcg gagggaccca gctgaccgtc acagctagca ccacgacgcc agcgccgcga   6360
ccaccaacac cggcgcccac catcgcgtcg cagcccctgt ccctgcgccc agaggcgtgc   6420
cggccagcgg cggggggcgc agtgcacacg agggggctgg acttcgcctg tgattccgga   6480
atctacatct gggcccctct ggccggcacc tgtggcgtgc tgctgctgtc cctggtcatc   6540
accctgtact gcaagcgggg cagaaagaag ctgctgtaca tcttcaagca gcccttcatg   6600
cggcctgtgc agaccacaca ggaagaggac ggctgtagct gtagattccc cgaggaagag   6660
gaaggcggct gcgagctgag agtgaagttc agcagaagcg ccgacgcccc tgcctatcag   6720
cagggccaga accagctgta caacgagctg aacctgggca gacgggagga atacgacgtg   6780
ctggacaaga gaagaggccg ggaccctgag atgggcggca agcccagacg gaagaacccc   6840
caggaaggcc tgtataacga actgcagaaa gacaagatgg ccgaggccta cagcgagatc   6900
```

-continued

```
ggcatgaagg gcgagcggag aagaggcaag ggccatgacg gcctgtacca gggcctgagc   6960
accgccacca aggacaccta cgacgccctg cacatgcagg ccctgcctcc aagatgagtc   7020
gacaatcaac ctctggatta caaaatttgt gaaagattga ctggtattct taactatgtt   7080
gctcctttta cgctatgtgg atacgctgct ttaatgcctt tgtatcatgc tattgcttcc   7140
cgtatggctt tcattttctc ctccttgtat aaatcctggt tgctgtctct ttatgaggag   7200
ttgtggcccg ttgtcaggca acgtggcgtg gtgtgcactg tgtttgctga cgcaaccccc   7260
actggttggg gcattgccac cacctgtcag ctcctttccg ggactttcgc tttccccctc   7320
cctattgcca cggcggaact catcgccgcc tgccttgccc gctgctggac aggggctcgg   7380
ctgttgggca ctgacaattc cgtggtgttg tcggggaagc tgacgtcctt tccttggctg   7440
ctcgcctgtg ttgccacctg gattctgcgc gggacgtcct tctgctacgt cccttcggcc   7500
ctcaatccag cggaccttcc ttcccgcggc ctgctgccgg ctctgcggcc tcttccgcgt   7560
cttcgccttc gccctcagac gagtcggatc tccctttggg ccgcctcccc gcctggaatt   7620
cgagctcggt acctttaaga ccaatgactt acaaggcagc tgtagatctt agccactttt   7680
taaaagaaaa ggggggactg gaagggctaa ttcactccca acgaagacaa gatctgcttt   7740
ttgcttgtac tgggtctctc tggttagacc agatctgagc ctgggagctc tctggctaac   7800
tagggaaccc actgcttaag cctcaataaa gcttgccttg agtgcttcaa gtagtgtgtg   7860
cccgtctgtt gtgtgactct ggtaactaga gatccctcag acccttttag tcagtgtgga   7920
aaatctctag cagtagtagt tcatgtcatc ttattattca gtatttataa cttgcaaaga   7980
aatgaatatc agagagtgag aggaacttgt ttattgcagc ttataatggt tacaaataaa   8040
gcaatagcat cacaaatttc acaaataaag cattttttc actgcattct agttgtggtt    8100
tgtccaaact catcaatgta tcttatcatg tctggctcta gctatcccgc ccctaactcc   8160
gcccagttcc gcccattctc cgccccatgg ctgactaatt ttttttattt atgcagaggc   8220
cgaggccgcc tcggcctctg agctattcca gaagtagtga ggaggctttt ttggaggcct   8280
agctagggac gtacccaatt cgccctatag tgagtcgtat tacgcgcgct cactggccgt   8340
cgttttacaa cgtcgtgact gggaaaaccc tggcgttacc caacttaatc gccttgcagc   8400
acatccccct ttcgccagct ggcgtaatag cgaagaggcc cgcaccgatc gcccttccca   8460
acagttgcgc agcctgaatg gcgaatggga cgcgccctgt agcggcgcat taagcgcggc   8520
gggtgtggtg gttacgcgca gcgtgaccgc tacacttgcc agcgccctag cgcccgctcc   8580
tttcgctttc ttcccttcct ttctcgccac gttcgccggc tttccccgtc aagctctaaa   8640
tcgggggctc cctttagggt tccgatttag tgctttacgg cacctcgacc ccaaaaaact   8700
tgattagggt gatggttcac gtagtgggcc atcgccctga tagacggttt ttcgcccttt   8760
gacgttggag tccacgttct ttaatagtgg actcttgttc caaactggaa caacactcaa   8820
ccctatctcg gtctattctt ttgatttata agggattttg ccgatttcgg cctattggtt   8880
aaaaaatgag ctgatttaac aaaaatttaa cgcgaatttt aacaaaatat taacgcttac   8940
aatttaggtg gcacttttcg gggaaatgtg cgcggaaccc ctatttgttt atttttctaa   9000
atacattcaa atatgtatcc gctcatgaga caataaccct gataaatgct tcaataatat   9060
tgaaaaagga agagtatgag tattcaacat ttccgtgtcg cccttattcc cttttttgcg   9120
gcattttgcc ttcctgtttt tgctcaccca gaaacgctgg tgaaagtaaa agatgctgaa   9180
gatcagttgg                                                          9190
```

```
<210> SEQ ID NO 109
<211> LENGTH: 95
<212> TYPE: PRT
<213> ORGANISM: Artificial Sequence
<220> FEATURE:
<223> OTHER INFORMATION: Artifically generated sequence

<400> SEQUENCE: 109

Ile Leu Trp His Glu Met Trp His Glu Gly Leu Leu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys Thr Ser
                85                  90                  95


<210> SEQ ID NO 110
<211> LENGTH: 95
<212> TYPE: PRT
<213> ORGANISM: Artificial Sequence
<220> FEATURE:
<223> OTHER INFORMATION: Artifically generated sequence

<400> SEQUENCE: 110

Ile Leu Trp His Glu Met Trp His Glu Gly Leu Glu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Leu Gln Ala
65                  70                  75                  80

Trp Asp Leu Tyr Tyr His Val Phe Arg Arg Ile Ser Lys Thr Ser
                85                  90                  95


<210> SEQ ID NO 111
<211> LENGTH: 95
<212> TYPE: PRT
<213> ORGANISM: Artificial Sequence
<220> FEATURE:
<223> OTHER INFORMATION: Artifically generated sequence
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 111

Ile Leu Trp His Glu Met Trp His Glu Gly Leu Xaa Glu Ala Ser Arg
1               5                   10                  15

Leu Tyr Phe Gly Glu Arg Asn Val Lys Gly Met Phe Glu Val Leu Glu
            20                  25                  30
```

```
Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Xaa Gln Ala
65                  70                  75                  80

Trp Asp Leu Tyr Tyr His Val Phe Arg Arg Ile Ser Lys Thr Ser
                85                  90                  95


<210> SEQ ID NO 112
<211> LENGTH: 95
<212> TYPE: PRT
<213> ORGANISM: Artificial Sequence
<220> FEATURE:
<223> OTHER INFORMATION: Artifically generated sequence

<400> SEQUENCE: 112

Ile Leu Trp His Glu Met Trp His Glu Gly Leu Ile Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Leu Gln Ala
65                  70                  75                  80

Trp Asp Leu Tyr Tyr His Val Phe Arg Arg Ile Ser Lys Thr Ser
                85                  90                  95


<210> SEQ ID NO 113
<211> LENGTH: 95
<212> TYPE: PRT
<213> ORGANISM: Artificial Sequence
<220> FEATURE:
<223> OTHER INFORMATION: Artifically generated sequence

<400> SEQUENCE: 113

Ile Leu Trp His Glu Met Trp His Glu Gly Leu Leu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Leu Gln Ala
65                  70                  75                  80

Trp Asp Leu Tyr Tyr His Val Phe Arg Arg Ile Ser Lys Thr Ser
                85                  90                  95


<210> SEQ ID NO 114
<211> LENGTH: 1132
<212> TYPE: PRT
<213> ORGANISM: Homo sapiens

<400> SEQUENCE: 114

Met Pro Arg Ala Pro Arg Cys Arg Ala Val Arg Ser Leu Leu Arg Ser
1               5                   10                  15
```

-continued

His Tyr Arg Glu Val Leu Pro Leu Ala Thr Phe Val Arg Arg Leu Gly
20 25 30

Pro Gln Gly Trp Arg Leu Val Gln Arg Gly Asp Pro Ala Ala Phe Arg
35 40 45

Ala Leu Val Ala Gln Cys Leu Val Cys Val Pro Trp Asp Ala Arg Pro
50 55 60

Pro Pro Ala Ala Pro Ser Phe Arg Gln Val Ser Cys Leu Lys Glu Leu
65 70 75 80

Val Ala Arg Val Leu Gln Arg Leu Cys Glu Arg Gly Ala Lys Asn Val
85 90 95

Leu Ala Phe Gly Phe Ala Leu Leu Asp Gly Ala Arg Gly Gly Pro Pro
100 105 110

Glu Ala Phe Thr Thr Ser Val Arg Ser Tyr Leu Pro Asn Thr Val Thr
115 120 125

Asp Ala Leu Arg Gly Ser Gly Ala Trp Gly Leu Leu Leu Arg Arg Val
130 135 140

Gly Asp Asp Val Leu Val His Leu Leu Ala Arg Cys Ala Leu Phe Val
145 150 155 160

Leu Val Ala Pro Ser Cys Ala Tyr Gln Val Cys Gly Pro Pro Leu Tyr
165 170 175

Gln Leu Gly Ala Ala Thr Gln Ala Arg Pro Pro Pro His Ala Ser Gly
180 185 190

Pro Arg Arg Arg Leu Gly Cys Glu Arg Ala Trp Asn His Ser Val Arg
195 200 205

Glu Ala Gly Val Pro Leu Gly Leu Pro Ala Pro Gly Ala Arg Arg Arg
210 215 220

Gly Gly Ser Ala Ser Arg Ser Leu Pro Leu Pro Lys Arg Pro Arg Arg
225 230 235 240

Gly Ala Ala Pro Glu Pro Glu Arg Thr Pro Val Gly Gln Gly Ser Trp
245 250 255

Ala His Pro Gly Arg Thr Arg Gly Pro Ser Asp Arg Gly Phe Cys Val
260 265 270

Val Ser Pro Ala Arg Pro Ala Glu Glu Ala Thr Ser Leu Glu Gly Ala
275 280 285

Leu Ser Gly Thr Arg His Ser His Pro Ser Val Gly Arg Gln His His
290 295 300

Ala Gly Pro Pro Ser Thr Ser Arg Pro Pro Arg Pro Trp Asp Thr Pro
305 310 315 320

Cys Pro Pro Val Tyr Ala Glu Thr Lys His Phe Leu Tyr Ser Ser Gly
325 330 335

Asp Lys Glu Gln Leu Arg Pro Ser Phe Leu Leu Ser Ser Leu Arg Pro
340 345 350

Ser Leu Thr Gly Ala Arg Arg Leu Val Glu Thr Ile Phe Leu Gly Ser
355 360 365

Arg Pro Trp Met Pro Gly Thr Pro Arg Arg Leu Pro Arg Leu Pro Gln
370 375 380

Arg Tyr Trp Gln Met Arg Pro Leu Phe Leu Glu Leu Leu Gly Asn His
385 390 395 400

Ala Gln Cys Pro Tyr Gly Val Leu Leu Lys Thr His Cys Pro Leu Arg
405 410 415

Ala Ala Val Thr Pro Ala Ala Gly Val Cys Ala Arg Glu Lys Pro Gln
420 425 430

Gly Ser Val Ala Ala Pro Glu Glu Glu Asp Thr Asp Pro Arg Arg Leu

-continued

```
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Gly Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
        835                 840                 845

Met Glu Asn Lys Leu Phe Ala Gly Ile Arg Arg Asp Gly Leu Leu Leu
    850                 855                 860
```

```
Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
        915                 920                 925

Pro Trp Cys Gly Leu Leu Leu Asp Thr Arg Thr Leu Glu Val Gln Ser
    930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
            980                 985                 990

Ser Leu Gln Thr Val Cys Thr Asn  Ile Tyr Lys Ile Leu  Leu Leu Gln
        995                 1000                1005

Ala Tyr  Arg Phe His Ala Cys  Val Leu Gln Leu Pro  Phe His Gln
    1010                1015                1020

Gln Val  Trp Lys Asn Pro Thr  Phe Phe Leu Arg Val  Ile Ser Asp
    1025                1030                1035

Thr Ala  Ser Leu Cys Tyr Ser  Ile Leu Lys Ala Lys  Asn Ala Gly
    1040                1045                1050

Met Ser  Leu Gly Ala Lys Gly  Ala Ala Gly Pro Leu  Pro Ser Glu
    1055                1060                1065

Ala Val  Gln Trp Leu Cys His  Gln Ala Phe Leu Leu  Lys Leu Thr
    1070                1075                1080

Arg His  Arg Val Thr Tyr Val  Pro Leu Leu Gly Ser  Leu Arg Thr
    1085                1090                1095

Ala Gln  Thr Gln Leu Ser Arg  Lys Leu Pro Gly Thr  Thr Leu Thr
    1100                1105                1110

Ala Leu  Glu Ala Ala Ala Asn  Pro Ala Leu Pro Ser  Asp Phe Lys
    1115                1120                1125

Thr Ile  Leu Asp
    1130


<210> SEQ ID NO 115
<211> LENGTH: 4027
<212> TYPE: DNA
<213> ORGANISM: Homo sapiens

<400> SEQUENCE: 115

caggcagcgt ggtcctgctg cgcacgtggg aagccctggc cccggccacc cccgcgatgc      60

cgcgcgctcc ccgctgccga gccgtgcgct ccctgctgcg cagccactac cgcgaggtgc     120

tgccgctggc cacgttcgtg cggcgcctgg ggccccaggg ctggcggctg gtgcagcgcg     180

gggacccggc ggctttccgc gcgctggtgg cccagtgcct ggtgtgcgtg ccctgggacg     240

cacggccgcc ccccgccgcc ccctccttcc gccaggtgtc ctgcctgaag gagctggtgg     300

cccgagtgct gcagaggctg tgcgagcgcg gcgcgaagaa cgtgctggcc ttcggcttcg     360

cgctgctgga cggggcccgc gggggccccc ccgaggcctt caccaccagc gtgcgcagct     420

acctgcccaa cacggtgacc gacgcactgc gggggagcgg ggcgtggggg ctgctgttgc     480
```

-continued

```
gccgcgtggg cgacgacgtg ctggttcacc tgctggcacg ctgcgcgctc tttgtgctgg    540
tggctcccag ctgcgcctac caggtgtgcg ggccgccgct gtaccagctc ggcgctgcca    600
ctcaggcccg gcccccgcca cacgctagtg gaccccgaag gcgtctggga tgcgaacggg    660
cctggaacca tagcgtcagg gaggccgggg tccccctggg cctgccagcc ccgggtgcga    720
ggaggcgcgg gggcagtgcc agccgaagtc tgccgttgcc caagaggccc aggcgtggcg    780
ctgcccctga gccggagcgg acgcccgttg ggcaggggtc ctgggcccac ccgggcagga    840
cgcgtggacc gagtgaccgt ggtttctgtg tggtgtcacc tgccagaccc gccgaagaag    900
ccacctcttt ggagggtgcg ctctctggca cgcgccactc ccacccatcc gtgggccgcc    960
agcaccacgc gggcccccca tccacatcgc ggccaccacg tccctgggac acgccttgtc   1020
ccccggtgta cgccgagacc aagcacttcc tctactcctc aggcgacaag gagcagctgc   1080
ggccctcctt cctactcagc tctctgaggc ccagcctgac tggcgctcgg aggctcgtgg   1140
agaccatctt tctgggttcc aggccctgga tgccagggac tccccgcagg ttgccccgcc   1200
tgccccagcg ctactggcaa atgcggcccc tgtttctgga gctgcttggg aaccacgcgc   1260
agtgccccta cggggtgctc ctcaagacgc actgcccgct gcgagctgcg gtcaccccag   1320
cagccggtgt ctgtgcccgg gagaagcccc agggctctgt ggcggccccc gaggaggagg   1380
acacagaccc ccgtcgcctg gtgcagctgc tccgccagca cagcagcccc tggcaggtgt   1440
acggcttcgt gcgggcctgc ctgcgccggc tggtgcccc aggcctctgg ggctccaggc   1500
acaacgaacg ccgcttcctc aggaacacca agaagttcat ctccctgggg aagcatgcca   1560
agctctcgct gcaggagctg acgtggaaga tgagcgtgcg gggctgcgct tggctgcgca   1620
ggagcccagg ggttggctgt gttccggccg cagagcaccg tctgcgtgag gagatcctgg   1680
ccaagttcct gcactggctg atgagtgtgt acgtcgtcga gctgctcagg tctttctttt   1740
atgtcacgga gaccacgttt caaaagaaca ggctcttttt ctaccggaag agtgtctgga   1800
gcaagttgca aagcattgga atcagacagc acttgaagag ggtgcagctg cgggagctgt   1860
cggaagcaga ggtcaggcag catcgggaag ccaggcccgc cctgctgacg tccagactcc   1920
gcttcatccc caagcctgac gggctgcggc cgattgtgaa catggactac gtcgtgggag   1980
ccagaacgtt ccgcagagaa aagagggccg agcgtctcac ctcgagggtg aaggcactgt   2040
tcagcgtgct caactacgag cgggcgcggc gccccggcct cctgggcgcc tctgtgctgg   2100
gcctggacga tatccacagg gcctggcgca ccttcgtgct gcgtgtgcgg gcccaggacc   2160
cgccgcctga gctgtacttt gtcaaggtgg atgtgacggg cgcgtacgac accatccccc   2220
aggacaggct cacggaggtc atcgccagca tcatcaaacc ccagaacacg tactgcgtgc   2280
gtcggtatgc cgtggtccag aaggccgccc atgggcacgt ccgcaaggcc ttcaagagcc   2340
acgtctctac cttgacagac ctccagccgt acatgcgaca gttcgtggct cacctgcagg   2400
agaccagccc gctgagggat gccgtcgtca tcgagcagag ctcctccctg aatgaggcca   2460
gcagtggcct cttcgacgtc ttcctacgct tcatgtgcca ccacgccgtg cgcatcaggg   2520
gcaagtccta cgtccagtgc caggggatcc cgcagggctc catcctctcc acgctgctct   2580
gcagcctgtg ctacggcgac atggagaaca agctgtttgc ggggattcgg cgggacgggc   2640
tgctcctgcg tttggtggat gatttcttgt tggtgacacc tcacctcacc cacgcgaaaa   2700
ccttcctcag gaccctggtc cgaggtgtcc ctgagtatgg ctgcgtggtg aacttgcgga   2760
agacagtggt gaacttccct gtagaagacg aggccctggg tggcacggct tttgttcaga   2820
tgccggccca cggcctattc cctggtgcg gcctgctgct ggatacccgg accctggagg   2880
```

tgcagagcga ctactccagc tatgcccgga cctccatcag agccagtctc accttcaacc 2940
gcggcttcaa ggctgggagg aacatgcgtc gcaaactctt tggggtcttg cggctgaagt 3000
gtcacagcct gtttctggat ttgcaggtga acagcctcca gacggtgtgc accaacatct 3060
acaagatcct cctgctgcag gcgtacaggt ttcacgcatg tgtgctgcag ctcccatttc 3120
atcagcaagt ttggaagaac ccccacattt tcctgcgcgt catctctgac acggcctccc 3180
tctgctactc catcctgaaa gccaagaacg cagggatgtc gctgggggcc aagggcgccg 3240
ccggccctct gccctccgag gccgtgcagt ggctgtgcca ccaagcattc ctgctcaagc 3300
tgactcgaca ccgtgtcacc tacgtgccac tcctggggtc actcaggaca gcccagacgc 3360
agctgagtcg gaagctcccg gggacgacgc tgactgccct ggaggccgca gccaacccgg 3420
cactgccctc agacttcaag accatcctgg actgatggcc acccgcccac agccaggccg 3480
agagcagaca ccagcagccc tgtcacgccg ggctctacgt cccagggagg gaggggcggc 3540
ccacacccag gcccgcaccg ctgggagtct gaggcctgag tgagtgtttg gccgaggcct 3600
gcatgtccgg ctgaaggctg agtgtccggc tgaggcctga gcgagtgtcc agccaagggc 3660
tgagtgtcca gcacacctgc cgtcttcact tccccacagg ctggcgctcg gctccacccc 3720
agggccagct tttcctcacc aggagcccgg cttccactcc ccacatagga atagtccatc 3780
cccagattcg ccattgttca cccctcgccc tgccctcctt tgccttccac ccccaccatc 3840
caggtggaga ccctgagaag gaccctggga gctctgggaa tttggagtga ccaaaggtgt 3900
gccctgtaca caggcgagga ccctgcacct ggatgggggt ccctgtgggt caaattgggg 3960
ggaggtgctg tgggagtaaa atactgaata tatgagtttt tcagttttga aaaaaaaaaa 4020
aaaaaaa 4027

<210> SEQ ID NO 116
<211> LENGTH: 19
<212> TYPE: DNA
<213> ORGANISM: Mus musculus

<400> SEQUENCE: 116
ggaggtccct caccttcta 19

<210> SEQ ID NO 117
<211> LENGTH: 19
<212> TYPE: DNA
<213> ORGANISM: Mus musculus

<400> SEQUENCE: 117
cggaggatct tatgctgaa 19

<210> SEQ ID NO 118
<211> LENGTH: 19
<212> TYPE: DNA
<213> ORGANISM: Mus musculus

<400> SEQUENCE: 118
cccgcttcca gatcataca 19

<210> SEQ ID NO 119
<211> LENGTH: 19
<212> TYPE: DNA
<213> ORGANISM: Mus musculus

<400> SEQUENCE: 119
ggagacctca acaagatat 19

<210> SEQ ID NO 120
<211> LENGTH: 19
<212> TYPE: DNA
<213> ORGANISM: Mus musculus

<400> SEQUENCE: 120
aaggcatggt cattggtat 19

<210> SEQ ID NO 121
<211> LENGTH: 19
<212> TYPE: DNA
<213> ORGANISM: Mus musculus

<400> SEQUENCE: 121
gcatggtcat tggtatcat 19

<210> SEQ ID NO 122
<211> LENGTH: 19
<212> TYPE: DNA
<213> ORGANISM: Mus musculus

<400> SEQUENCE: 122
ggtcattggt atcatgagt 19

<210> SEQ ID NO 123
<211> LENGTH: 19
<212> TYPE: DNA
<213> ORGANISM: Mus musculus

<400> SEQUENCE: 123
cctagtgggt atccctgta 19

<210> SEQ ID NO 124
<211> LENGTH: 19
<212> TYPE: DNA
<213> ORGANISM: Mus musculus

<400> SEQUENCE: 124
gaggatggac attgttctt 19

<210> SEQ ID NO 125
<211> LENGTH: 19
<212> TYPE: DNA
<213> ORGANISM: Mus musculus

<400> SEQUENCE: 125
gcatgcaggc tacagttca 19

<210> SEQ ID NO 126
<211> LENGTH: 19
<212> TYPE: DNA
<213> ORGANISM: Mus musculus

<400> SEQUENCE: 126
ccagcacatg cactgttga 19

<210> SEQ ID NO 127
<211> LENGTH: 19
<212> TYPE: DNA
<213> ORGANISM: Mus musculus

<400> SEQUENCE: 127
cacatgcact gttgagtga 19

<210> SEQ ID NO 128
<211> LENGTH: 21
<212> TYPE: DNA
<213> ORGANISM: Mus musculus

<400> SEQUENCE: 128
ctggaggtcc ctcaccttct a 21

<210> SEQ ID NO 129
<211> LENGTH: 21
<212> TYPE: DNA
<213> ORGANISM: Mus musculus

<400> SEQUENCE: 129
gtcggaggat cttatgctga a 21

<210> SEQ ID NO 130
<211> LENGTH: 21
<212> TYPE: DNA
<213> ORGANISM: Mus musculus

<400> SEQUENCE: 130
tgcccgcttc cagatcatac a 21

<210> SEQ ID NO 131
<211> LENGTH: 21
<212> TYPE: DNA
<213> ORGANISM: Mus musculus

<400> SEQUENCE: 131
ctggagacct caacaagata t 21

<210> SEQ ID NO 132
<211> LENGTH: 21
<212> TYPE: DNA
<213> ORGANISM: Mus musculus

<400> SEQUENCE: 132
tcaaggcatg gtcattggta t 21

<210> SEQ ID NO 133
<211> LENGTH: 21
<212> TYPE: DNA
<213> ORGANISM: Mus musculus

<400> SEQUENCE: 133
aggcatggtc attggtatca t 21

<210> SEQ ID NO 134
<211> LENGTH: 21
<212> TYPE: DNA
<213> ORGANISM: Mus musculus

<400> SEQUENCE: 134
atggtcattg gtatcatgag t 21

<210> SEQ ID NO 135
<211> LENGTH: 21
<212> TYPE: DNA
<213> ORGANISM: Mus musculus

<400> SEQUENCE: 135
gccctagtgg gtatccctgt a 21

<210> SEQ ID NO 136
<211> LENGTH: 21
<212> TYPE: DNA
<213> ORGANISM: Mus musculus

<400> SEQUENCE: 136
atgaggatgg acattgttct t 21

<210> SEQ ID NO 137
<211> LENGTH: 21
<212> TYPE: DNA
<213> ORGANISM: Mus musculus

<400> SEQUENCE: 137
gagcatgcag gctacagttc a 21

<210> SEQ ID NO 138
<211> LENGTH: 21
<212> TYPE: DNA
<213> ORGANISM: Mus musculus

<400> SEQUENCE: 138
ttccagcaca tgcactgttg a 21

<210> SEQ ID NO 139
<211> LENGTH: 21
<212> TYPE: DNA
<213> ORGANISM: Mus musculus

<400> SEQUENCE: 139
agcacatgca ctgttgagtg a 21

<210> SEQ ID NO 140
<211> LENGTH: 21
<212> TYPE: DNA
<213> ORGANISM: Mus musculus

<400> SEQUENCE: 140
tagaaggtga gggacctcca g 21

<210> SEQ ID NO 141
<211> LENGTH: 21
<212> TYPE: DNA
<213> ORGANISM: Mus musculus

<400> SEQUENCE: 141
ttcagcataa gatcctccga c 21

<210> SEQ ID NO 142
<211> LENGTH: 21
<212> TYPE: DNA
<213> ORGANISM: Mus musculus

<400> SEQUENCE: 142
tgtatgatct ggaagcgggc a 21

<210> SEQ ID NO 143
<211> LENGTH: 21
<212> TYPE: DNA
<213> ORGANISM: Mus musculus

<400> SEQUENCE: 143
atatcttgtt gaggtctcca g 21

<210> SEQ ID NO 144
<211> LENGTH: 21
<212> TYPE: DNA
<213> ORGANISM: Mus musculus

<400> SEQUENCE: 144
ataccaatga ccatgccttg a 21

<210> SEQ ID NO 145
<211> LENGTH: 21
<212> TYPE: DNA
<213> ORGANISM: Mus musculus

<400> SEQUENCE: 145
atgataccaa tgaccatgcc t 21

<210> SEQ ID NO 146
<211> LENGTH: 21
<212> TYPE: DNA
<213> ORGANISM: Mus musculus

<400> SEQUENCE: 146
atggtcattg gtatcatgag t 21

<210> SEQ ID NO 147
<211> LENGTH: 21
<212> TYPE: DNA
<213> ORGANISM: Mus musculus

<400> SEQUENCE: 147
gccctagtgg gtatccctgt a 21

<210> SEQ ID NO 148
<211> LENGTH: 21
<212> TYPE: DNA
<213> ORGANISM: Mus musculus

<400> SEQUENCE: 148
atgaggatgg acattgttct t 21

<210> SEQ ID NO 149
<211> LENGTH: 21
<212> TYPE: DNA
<213> ORGANISM: Mus musculus

<400> SEQUENCE: 149
gagcatgcag gctacagttc a 21

<210> SEQ ID NO 150
<211> LENGTH: 21
<212> TYPE: DNA
<213> ORGANISM: Mus musculus

<400> SEQUENCE: 150
ttccagcaca tgcactgttg a 21

<210> SEQ ID NO 151
<211> LENGTH: 21
<212> TYPE: DNA

<213> ORGANISM: Mus musculus

<400> SEQUENCE: 151
agcacatgca ctgttgagtg a 21

<210> SEQ ID NO 152
<211> LENGTH: 19
<212> TYPE: DNA
<213> ORGANISM: Mus musculus

<400> SEQUENCE: 152
tagaaggtga gggacctcc 19

<210> SEQ ID NO 153
<211> LENGTH: 19
<212> TYPE: DNA
<213> ORGANISM: Mus musculus

<400> SEQUENCE: 153
ttcagcataa gatcctccg 19

<210> SEQ ID NO 154
<211> LENGTH: 19
<212> TYPE: DNA
<213> ORGANISM: Mus musculus

<400> SEQUENCE: 154
tgtatgatct ggaagcggg 19

<210> SEQ ID NO 155
<211> LENGTH: 19
<212> TYPE: DNA
<213> ORGANISM: Mus musculus

<400> SEQUENCE: 155
atatcttgtt gaggtctcc 19

<210> SEQ ID NO 156
<211> LENGTH: 19
<212> TYPE: DNA
<213> ORGANISM: Mus musculus

<400> SEQUENCE: 156
ataccaatga ccatgcctt 19

<210> SEQ ID NO 157
<211> LENGTH: 19
<212> TYPE: DNA
<213> ORGANISM: Mus musculus

<400> SEQUENCE: 157
atgataccaa tgaccatgc 19

<210> SEQ ID NO 158
<211> LENGTH: 19
<212> TYPE: DNA
<213> ORGANISM: Mus musculus

<400> SEQUENCE: 158
atggtcattg gtatcatga 19

<210> SEQ ID NO 159
<211> LENGTH: 19

<212> TYPE: DNA
<213> ORGANISM: Mus musculus

<400> SEQUENCE: 159
gccctagtgg gtatccctg 19

<210> SEQ ID NO 160
<211> LENGTH: 19
<212> TYPE: DNA
<213> ORGANISM: Mus musculus

<400> SEQUENCE: 160
atgaggatgg acattgttc 19

<210> SEQ ID NO 161
<211> LENGTH: 19
<212> TYPE: DNA
<213> ORGANISM: Mus musculus

<400> SEQUENCE: 161
gagcatgcag gctacagtt 19

<210> SEQ ID NO 162
<211> LENGTH: 19
<212> TYPE: DNA
<213> ORGANISM: Mus musculus

<400> SEQUENCE: 162
ttccagcaca tgcactgtt 19

<210> SEQ ID NO 163
<211> LENGTH: 19
<212> TYPE: DNA
<213> ORGANISM: Mus musculus

<400> SEQUENCE: 163
agcacatgca ctgttgagt 19

<210> SEQ ID NO 164
<211> LENGTH: 19
<212> TYPE: DNA
<213> ORGANISM: Mus musculus

<400> SEQUENCE: 164
ggccaggatg gttcttaga 19

<210> SEQ ID NO 165
<211> LENGTH: 19
<212> TYPE: DNA
<213> ORGANISM: Mus musculus

<400> SEQUENCE: 165
gcttcgtgct aaactggta 19

<210> SEQ ID NO 166
<211> LENGTH: 19
<212> TYPE: DNA
<213> ORGANISM: Mus musculus

<400> SEQUENCE: 166
gggcgtgact tccacatga 19

<210> SEQ ID NO 167

<211> LENGTH: 19
<212> TYPE: DNA
<213> ORGANISM: Mus musculus

<400> SEQUENCE: 167
caggcctaga gaagtttca 19

<210> SEQ ID NO 168
<211> LENGTH: 19
<212> TYPE: DNA
<213> ORGANISM: Mus musculus

<400> SEQUENCE: 168
cttggaaccc attcctgaa 19

<210> SEQ ID NO 169
<211> LENGTH: 19
<212> TYPE: DNA
<213> ORGANISM: Mus musculus

<400> SEQUENCE: 169
ggaacccatt cctgaaatt 19

<210> SEQ ID NO 170
<211> LENGTH: 19
<212> TYPE: DNA
<213> ORGANISM: Mus musculus

<400> SEQUENCE: 170
gaacccattc ctgaaatta 19

<210> SEQ ID NO 171
<211> LENGTH: 19
<212> TYPE: DNA
<213> ORGANISM: Mus musculus

<400> SEQUENCE: 171
aacccattcc tgaaattat 19

<210> SEQ ID NO 172
<211> LENGTH: 19
<212> TYPE: DNA
<213> ORGANISM: Mus musculus

<400> SEQUENCE: 172
acccattcct gaaattatt 19

<210> SEQ ID NO 173
<211> LENGTH: 19
<212> TYPE: DNA
<213> ORGANISM: Mus musculus

<400> SEQUENCE: 173
cccattcctg aaattattt 19

<210> SEQ ID NO 174
<211> LENGTH: 19
<212> TYPE: DNA
<213> ORGANISM: Mus musculus

<400> SEQUENCE: 174
ctgtggttct attatatta 19

<210> SEQ ID NO 175
<211> LENGTH: 19
<212> TYPE: DNA
<213> ORGANISM: Mus musculus

<400> SEQUENCE: 175
aaatatgaga gcatgctaa 19

<210> SEQ ID NO 176
<211> LENGTH: 19
<212> TYPE: DNA
<213> ORGANISM: Mus musculus

<400> SEQUENCE: 176
tctaagaacc atcctggcc 19

<210> SEQ ID NO 177
<211> LENGTH: 19
<212> TYPE: DNA
<213> ORGANISM: Mus musculus

<400> SEQUENCE: 177
taccagttta gcacgaagc 19

<210> SEQ ID NO 178
<211> LENGTH: 19
<212> TYPE: DNA
<213> ORGANISM: Mus musculus

<400> SEQUENCE: 178
tcatgtggaa gtcacgccc 19

<210> SEQ ID NO 179
<211> LENGTH: 19
<212> TYPE: DNA
<213> ORGANISM: Mus musculus

<400> SEQUENCE: 179
tgaaacttct ctaggcctg 19

<210> SEQ ID NO 180
<211> LENGTH: 19
<212> TYPE: DNA
<213> ORGANISM: Mus musculus

<400> SEQUENCE: 180
ttcaggaatg ggttccaag 19

<210> SEQ ID NO 181
<211> LENGTH: 19
<212> TYPE: DNA
<213> ORGANISM: Mus musculus

<400> SEQUENCE: 181
aatttcagga atgggttcc 19

<210> SEQ ID NO 182
<211> LENGTH: 19
<212> TYPE: DNA
<213> ORGANISM: Mus musculus

<400> SEQUENCE: 182
taatttcagg aatgggttc 19

<210> SEQ ID NO 183
<211> LENGTH: 19
<212> TYPE: DNA
<213> ORGANISM: Mus musculus

<400> SEQUENCE: 183
ataatttcag gaatgggtt 19

<210> SEQ ID NO 184
<211> LENGTH: 19
<212> TYPE: DNA
<213> ORGANISM: Mus musculus

<400> SEQUENCE: 184
aataatttca ggaatgggt 19

<210> SEQ ID NO 185
<211> LENGTH: 19
<212> TYPE: DNA
<213> ORGANISM: Mus musculus

<400> SEQUENCE: 185
aaataatttc aggaatggg 19

<210> SEQ ID NO 186
<211> LENGTH: 19
<212> TYPE: DNA
<213> ORGANISM: Mus musculus

<400> SEQUENCE: 186
taatataata gaaccacag 19

<210> SEQ ID NO 187
<211> LENGTH: 19
<212> TYPE: DNA
<213> ORGANISM: Mus musculus

<400> SEQUENCE: 187
ttagcatgct ctcatattt 19

<210> SEQ ID NO 188
<211> LENGTH: 21
<212> TYPE: DNA
<213> ORGANISM: Mus musculus

<400> SEQUENCE: 188
gcggccagga tggttcttag a 21

<210> SEQ ID NO 189
<211> LENGTH: 21
<212> TYPE: DNA
<213> ORGANISM: Mus musculus

<400> SEQUENCE: 189
gagcttcgtg ctaaactggt a 21

<210> SEQ ID NO 190
<211> LENGTH: 21
<212> TYPE: DNA
<213> ORGANISM: Mus musculus

<400> SEQUENCE: 190
acgggcgtga cttccacatg a 21

<210> SEQ ID NO 191
<211> LENGTH: 21
<212> TYPE: DNA
<213> ORGANISM: Mus musculus

<400> SEQUENCE: 191
tgcaggccta gagaagtttc a 21

<210> SEQ ID NO 192
<211> LENGTH: 21
<212> TYPE: DNA
<213> ORGANISM: Mus musculus

<400> SEQUENCE: 192
tccttggaac ccattcctga a 21

<210> SEQ ID NO 193
<211> LENGTH: 21
<212> TYPE: DNA
<213> ORGANISM: Mus musculus

<400> SEQUENCE: 193
ttggaaccca ttcctgaaat t 21

<210> SEQ ID NO 194
<211> LENGTH: 21
<212> TYPE: DNA
<213> ORGANISM: Mus musculus

<400> SEQUENCE: 194
tggaacccat tcctgaaatt a 21

<210> SEQ ID NO 195
<211> LENGTH: 21
<212> TYPE: DNA
<213> ORGANISM: Mus musculus

<400> SEQUENCE: 195
ggaacccatt cctgaaatta t 21

<210> SEQ ID NO 196
<211> LENGTH: 21
<212> TYPE: DNA
<213> ORGANISM: Mus musculus

<400> SEQUENCE: 196
gaacccattc ctgaaattat t 21

<210> SEQ ID NO 197
<211> LENGTH: 21
<212> TYPE: DNA
<213> ORGANISM: Mus musculus

<400> SEQUENCE: 197
aacccattcc tgaaattatt t 21

<210> SEQ ID NO 198
<211> LENGTH: 21
<212> TYPE: DNA
<213> ORGANISM: Mus musculus

<400> SEQUENCE: 198

-continued ccctgtggtt ctattatatt a 21

<210> SEQ ID NO 199
<211> LENGTH: 21
<212> TYPE: DNA
<213> ORGANISM: Mus musculus

<400> SEQUENCE: 199
ttaaatatga gagcatgcta a 21

<210> SEQ ID NO 200
<211> LENGTH: 21
<212> TYPE: DNA
<213> ORGANISM: Mus musculus

<400> SEQUENCE: 200
tctaagaacc atcctggccg c 21

<210> SEQ ID NO 201
<211> LENGTH: 21
<212> TYPE: DNA
<213> ORGANISM: Mus musculus

<400> SEQUENCE: 201
taccagttta gcacgaagct c 21

<210> SEQ ID NO 202
<211> LENGTH: 21
<212> TYPE: DNA
<213> ORGANISM: Mus musculus

<400> SEQUENCE: 202
tcatgtggaa gtcacgcccg t 21

<210> SEQ ID NO 203
<211> LENGTH: 21
<212> TYPE: DNA
<213> ORGANISM: Mus musculus

<400> SEQUENCE: 203
tgaaacttct ctaggcctgc a 21

<210> SEQ ID NO 204
<211> LENGTH: 21
<212> TYPE: DNA
<213> ORGANISM: Mus musculus

<400> SEQUENCE: 204
ttcaggaatg ggttccaagg a 21

<210> SEQ ID NO 205
<211> LENGTH: 21
<212> TYPE: DNA
<213> ORGANISM: Mus musculus

<400> SEQUENCE: 205
aatttcagga atgggttcca a 21

<210> SEQ ID NO 206
<211> LENGTH: 21
<212> TYPE: DNA
<213> ORGANISM: Mus musculus

<400> SEQUENCE: 206
taatttcagg aatgggttcc a 21

<210> SEQ ID NO 207
<211> LENGTH: 21
<212> TYPE: DNA
<213> ORGANISM: Mus musculus

<400> SEQUENCE: 207
ataatttcag gaatgggttc c 21

<210> SEQ ID NO 208
<211> LENGTH: 21
<212> TYPE: DNA
<213> ORGANISM: Mus musculus

<400> SEQUENCE: 208
aataatttca ggaatgggtt c 21

<210> SEQ ID NO 209
<211> LENGTH: 21
<212> TYPE: DNA
<213> ORGANISM: Mus musculus

<400> SEQUENCE: 209
aaataatttc aggaatgggt t 21

<210> SEQ ID NO 210
<211> LENGTH: 21
<212> TYPE: DNA
<213> ORGANISM: Mus musculus

<400> SEQUENCE: 210
taatataata gaaccacagg g 21

<210> SEQ ID NO 211
<211> LENGTH: 21
<212> TYPE: DNA
<213> ORGANISM: Mus musculus

<400> SEQUENCE: 211
ttagcatgct ctcatattta a 21

<210> SEQ ID NO 212
<211> LENGTH: 465
<212> TYPE: PRT
<213> ORGANISM: Homo sapiens

<400> SEQUENCE: 212

Asn Arg Cys Val Asp Ala Ala Glu Ala Cys Thr Ala Asp Ala Arg Cys
1 5 10 15

Gln Arg Leu Arg Ser Glu Tyr Val Ala Gln Cys Leu Gly Arg Ala Ala
20 25 30

Gln Gly Gly Cys Pro Arg Ala Arg Cys Arg Arg Ala Leu Arg Arg Phe
35 40 45

Phe Ala Arg Gly Pro Pro Ala Leu Thr His Ala Leu Leu Phe Cys Pro
50 55 60

Cys Ala Gly Pro Ala Cys Ala Glu Arg Arg Arg Gln Thr Phe Val Pro
65 70 75 80

Ser Cys Ala Phe Ser Gly Pro Gly Pro Ala Pro Pro Ser Cys Leu Glu
85 90 95

-continued

Pro Leu Asn Phe Cys Glu Arg Ser Arg Val Cys Arg Pro Arg Leu Leu
100 105 110

Ala Phe Gln Val Ser Cys Thr Pro Ala Pro Ser Ala Pro Asp Gly Cys
115 120 125

Leu Leu Asp Gln Gly Ala Arg Cys Leu Arg Ala Tyr Ala Gly Leu Val
130 135 140

Gly Thr Ala Val Thr Pro Asn Tyr Val Asp Asn Val Ser Ala Arg Val
145 150 155 160

Ala Pro Trp Cys Asp Cys Gly Ala Ser Gly Asn Arg Arg Glu Asp Cys
165 170 175

Glu Ala Phe Arg Gly Leu Phe Thr Arg Asn Arg Cys Leu Asp Gly Ala
180 185 190

Ile Gln Ala Phe Ala Ser Gly Trp Pro Pro Val Leu Leu Asp Gln Leu
195 200 205

Asn Pro Gln Gly Asp Pro Glu His Ser Leu Leu Gln Val Ser Ile Glu
210 215 220

Gly Arg Met Asp Pro Lys Ser Cys Asp Lys Thr His Thr Cys Pro Pro
225 230 235 240

Cys Pro Ala Pro Glu Ala Glu Gly Ala Pro Ser Val Phe Leu Phe Pro
245 250 255

Pro Lys Pro Lys Asp Thr Leu Met Ile Ser Arg Thr Pro Glu Val Thr
260 265 270

Cys Val Val Val Asp Val Ser His Glu Asp Pro Glu Val Lys Phe Asn
275 280 285

Trp Tyr Val Asp Gly Val Glu Val His Asn Ala Lys Thr Lys Pro Arg
290 295 300

Glu Glu Gln Tyr Asn Ser Thr Tyr Arg Val Val Ser Val Leu Thr Val
305 310 315 320

Leu His Gln Asp Trp Leu Asn Gly Lys Glu Tyr Lys Cys Lys Val Ser
325 330 335

Asn Lys Ala Leu Pro Ala Pro Ile Glu Lys Thr Ile Ser Lys Ala Lys
340 345 350

Gly Gln Pro Arg Glu Pro Gln Val Tyr Thr Leu Pro Pro Ser Arg Asp
355 360 365

Glu Leu Thr Lys Asn Gln Val Ser Leu Thr Cys Leu Val Lys Gly Phe
370 375 380

Tyr Pro Ser Asp Ile Ala Val Glu Trp Glu Ser Asn Gly Gln Pro Glu
385 390 395 400

Asn Asn Tyr Lys Ala Thr Pro Pro Val Leu Asp Ser Asp Gly Ser Phe
405 410 415

Phe Leu Tyr Ser Lys Leu Thr Val Asp Lys Ser Arg Trp Gln Gln Gly
420 425 430

Asn Val Phe Ser Cys Ser Val Met His Glu Ala Leu His Asn His Tyr
435 440 445

Thr Gln Lys Ser Leu Ser Leu Ser Pro Gly Lys His His His His His
450 455 460

His
465

<210> SEQ ID NO 213
<211> LENGTH: 497
<212> TYPE: PRT
<213> ORGANISM: Homo sapiens

<400> SEQUENCE: 213

```
Asn Arg Cys Val Asp Ala Ala Glu Ala Cys Thr Ala Asp Ala Arg Cys
1               5                   10                  15

Gln Arg Leu Arg Ser Glu Tyr Val Ala Gln Cys Leu Gly Arg Ala Ala
            20                  25                  30

Gln Gly Gly Cys Pro Arg Ala Arg Cys Arg Arg Ala Leu Arg Arg Phe
        35                  40                  45

Phe Ala Arg Gly Pro Pro Ala Leu Thr His Ala Leu Leu Phe Cys Pro
    50                  55                  60

Cys Ala Gly Pro Ala Cys Ala Glu Arg Arg Arg Gln Thr Phe Val Pro
65                  70                  75                  80

Ser Cys Ala Phe Ser Gly Pro Gly Pro Ala Pro Pro Ser Cys Leu Glu
                85                  90                  95

Pro Leu Asn Phe Cys Glu Arg Ser Arg Val Cys Arg Cys Ala Arg Ala
            100                 105                 110

Ala Ala Gly Pro Trp Arg Gly Trp Gly Arg Gly Leu Ser Pro Ala His
        115                 120                 125

Arg Pro Pro Ala Ala Gln Ala Ser Pro Pro Gly Leu Ser Gly Leu Val
    130                 135                 140

His Pro Ser Ala Gln Arg Pro Arg Arg Leu Pro Ala Gly Pro Gly Arg
145                 150                 155                 160

Pro Leu Pro Ala Arg Leu Arg Gly Pro Arg Gly Val Pro Ala Gly Thr
                165                 170                 175

Ala Val Thr Pro Asn Tyr Val Asp Asn Val Ser Ala Arg Val Ala Pro
            180                 185                 190

Trp Cys Asp Cys Gly Ala Ser Gly Asn Arg Arg Glu Asp Cys Glu Ala
        195                 200                 205

Phe Arg Gly Leu Phe Thr Arg Asn Arg Cys Leu Asp Gly Ala Ile Gln
    210                 215                 220

Ala Phe Ala Ser Gly Trp Pro Pro Val Leu Leu Asp Gln Leu Asn Pro
225                 230                 235                 240

Gln Gly Asp Pro Glu His Ser Leu Leu Gln Val Gly Gly Gly Glu Asn
                245                 250                 255

Leu Tyr Phe Gln Gly Gly Gly Gly Gly Ala Gly Gly Gly Gly Asp Lys
            260                 265                 270

Thr His Thr Cys Pro Pro Cys Pro Ala Pro Glu Leu Leu Gly Gly Pro
        275                 280                 285

Ser Val Phe Leu Phe Pro Pro Lys Pro Lys Asp Thr Leu Met Ile Ser
    290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
        355                 360                 365

Tyr Lys Cys Lys Val Ser Asn Lys Ala Leu Pro Ala Pro Ile Glu Lys
    370                 375                 380

Thr Ile Ser Lys Ala Lys Gly Gln Pro Arg Glu Pro Gln Val Tyr Thr
385                 390                 395                 400

Leu Pro Pro Ser Arg Asp Glu Leu Thr Lys Asn Gln Val Ser Leu Thr
                405                 410                 415
```

```
Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
        435                 440                 445

Asp Ser Asp Gly Ser Phe Phe Leu Tyr Ser Lys Leu Thr Val Asp Lys
    450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys


<210> SEQ ID NO 214
<211> LENGTH: 132
<212> TYPE: PRT
<213> ORGANISM: Homo sapiens

<400> SEQUENCE: 214

Asp Val Pro Asp Tyr Ala Ser Leu Gly Gly Pro Ser Ser Pro Lys Lys
1               5                   10                  15

Lys Arg Lys Val Ser Arg Gly Val Gln Val Glu Thr Ile Ser Pro Gly
            20                  25                  30

Asp Gly Arg Thr Phe Pro Lys Arg Gly Gln Thr Cys Val Val His Tyr
        35                  40                  45

Thr Gly Met Leu Glu Asp Gly Lys Lys Phe Asp Ser Ser Arg Asp Arg
    50                  55                  60

Asn Lys Pro Phe Lys Phe Met Leu Gly Lys Gln Glu Val Ile Arg Gly
65                  70                  75                  80

Trp Glu Glu Gly Val Ala Gln Met Ser Val Gly Gln Arg Ala Lys Leu
                85                  90                  95

Thr Ile Ser Pro Asp Tyr Ala Tyr Gly Ala Thr Gly His Pro Gly Ile
            100                 105                 110

Ile Pro Pro His Ala Thr Leu Val Phe Asp Val Glu Leu Leu Lys Leu
        115                 120                 125

Glu Thr Ser Tyr
    130


<210> SEQ ID NO 215
<211> LENGTH: 108
<212> TYPE: PRT
<213> ORGANISM: Homo sapiens

<400> SEQUENCE: 215

Val Gln Val Glu Thr Ile Ser Pro Gly Asp Gly Arg Thr Phe Pro Lys
1               5                   10                  15

Arg Gly Gln Thr Cys Val Val His Tyr Thr Gly Met Leu Glu Asp Gly
            20                  25                  30

Lys Lys Phe Asp Ser Ser Arg Asp Arg Asn Lys Pro Phe Lys Phe Met
        35                  40                  45

Leu Gly Lys Gln Glu Val Ile Arg Gly Trp Glu Glu Gly Val Ala Gln
    50                  55                  60

Met Ser Val Gly Gln Arg Ala Lys Leu Thr Ile Ser Pro Asp Tyr Ala
65                  70                  75                  80

Tyr Gly Ala Thr Gly His Pro Gly Ile Ile Pro Pro His Ala Thr Leu
                85                  90                  95

Val Phe Asp Val Glu Leu Leu Lys Leu Glu Thr Ser
```

100 105

<210> SEQ ID NO 216
<211> LENGTH: 93
<212> TYPE: PRT
<213> ORGANISM: Homo sapiens

<400> SEQUENCE: 216

Ile Leu Trp His Glu Met Trp His Glu Gly Leu Glu Glu Ala Ser Arg
1 5 10 15

Leu Tyr Phe Gly Glu Arg Asn Val Lys Gly Met Phe Glu Val Leu Glu
20 25 30

Pro Leu His Ala Met Met Glu Arg Gly Pro Gln Thr Leu Lys Glu Thr
35 40 45

Ser Phe Asn Gln Ala Tyr Gly Arg Asp Leu Met Glu Ala Gln Glu Trp
50 55 60

Cys Arg Lys Tyr Met Lys Ser Gly Asn Val Lys Asp Leu Thr Gln Ala
65 70 75 80

Trp Asp Leu Tyr Tyr His Val Phe Arg Arg Ile Ser Lys
85 90

<210> SEQ ID NO 217
<211> LENGTH: 95
<212> TYPE: PRT
<213> ORGANISM: Artificial Sequence
<220> FEATURE:
<223> OTHER INFORMATION: Artifically generated sequence

<400> SEQUENCE: 217

Ile Leu Trp His Glu Met Trp His Glu Gly Leu Ile Glu Ala Ser Arg
1 5 10 15

Leu Tyr Phe Gly Glu Arg Asn Val Lys Gly Met Phe Glu Val Leu Glu
20 25 30

Pro Leu His Ala Met Met Glu Arg Gly Pro Gln Thr Leu Lys Glu Thr
35 40 45

Ser Phe Asn Gln Ala Tyr Gly Arg Asp Leu Met Glu Ala Gln Glu Trp
50 55 60

Cys Arg Lys Tyr Met Lys Ser Gly Asn Val Lys Asp Leu Thr Gln Ala
65 70 75 80

Trp Asp Leu Tyr Tyr His Val Phe Arg Arg Ile Ser Lys Thr Ser
85 90 95

<210> SEQ ID NO 218
<211> LENGTH: 521
<212> TYPE: DNA
<213> ORGANISM: Artificial Sequence
<220> FEATURE:
<223> OTHER INFORMATION: Artifically generated sequence

<400> SEQUENCE: 218
acccctctct ccagccacta agccagttgc tccctcggct gacggctgca cgcgaggcct 60
ccgaacgtct tacgccttgt ggcgcgcccg tccttgtccc gggtgtgatg gcggggtgtg 120
gggcggaggg cgtggcgggg aagggccggc gacgagagcc gcgcgggacg actcgtcggc 180
gataaccggt gtcgggtagc gccagccgcg cgacggtaac gagggaccgc gacaggcaga 240
cgctcccatg atcactctgc acgccgaagg caaatagtgc aggccgtgcg gcgcttggcg 300
ttccttggaa gggctgaatc cccgcctcgt ccttcgcagc ggccccccgg gtgttcccat 360
cgccgcttct aggcccactg cgacgcttgc ctgcacttct tacacgctct gggtcccagc 420
cgcggcgacg caaagggcct tggtgcgggt ctcgtcggcg cagggacgcg tttgggtccc 480
gacggaacct tttccgcgtt ggggttgggg caccataagc t 521

<210> SEQ ID NO 219
<211> LENGTH: 118
<212> TYPE: DNA
<213> ORGANISM: Artificial Sequence
<220> FEATURE:
<223> OTHER INFORMATION: Artifically generated sequence

<400> SEQUENCE: 219
acccctctct ccagccacta agccagttgc tccctcggct gacggctgca cgcgaggcct 60
ccgaacgtct tacgccttgt ggcgcgcccg tccttgtccc gggtgtgatg gcggggtg 118

<210> SEQ ID NO 220
<211> LENGTH: 221
<212> TYPE: DNA
<213> ORGANISM: Artificial Sequence
<220> FEATURE:
<223> OTHER INFORMATION: Artifically generated sequence

<400> SEQUENCE: 220
acccctctct ccagccacta agccagttgc tccctcggct gacggctgca cgcgaggcct 60
ccgaacgtct tacgccttgt ggcgcgcccg tccttgtccc gggtgtgatg gcggggtgtg 120
gggcggaggg cgtggcgggg aagggccggc gacgagagcc gcgcgggacg actcgtcggc 180
gataaccggt gtcgggtagc gccagccgcg cgacggtaac g 221

<210> SEQ ID NO 221
<211> LENGTH: 324
<212> TYPE: DNA
<213> ORGANISM: Artificial Sequence
<220> FEATURE:
<223> OTHER INFORMATION: Artifically generated sequence

<400> SEQUENCE: 221
acccctctct ccagccacta agccagttgc tccctcggct gacggctgca cgcgaggcct 60
ccgaacgtct tacgccttgt ggcgcgcccg tccttgtccc gggtgtgatg gcggggtgtg 120
gggcggaggg cgtggcgggg aagggccggc gacgagagcc gcgcgggacg actcgtcggc 180
gataaccggt gtcgggtagc gccagccgcg cgacggtaac gagggaccgc gacaggcaga 240
cgctcccatg atcactctgc acgccgaagg caaatagtgc aggccgtgcg gcgcttggcg 300
ttccttggaa gggctgaatc cccg 324

<210> SEQ ID NO 222
<211> LENGTH: 422
<212> TYPE: DNA
<213> ORGANISM: Artificial Sequence
<220> FEATURE:
<223> OTHER INFORMATION: Artifically generated sequence

<400> SEQUENCE: 222
acccctctct ccagccacta agccagttgc tccctcggct gacggctgca cgcgaggcct 60
ccgaacgtct tacgccttgt ggcgcgcccg tccttgtccc gggtgtgatg gcggggtgtg 120
gggcggaggg cgtggcgggg aagggccggc gacgagagcc gcgcgggacg actcgtcggc 180
gataaccggt gtcgggtagc gccagccgcg cgacggtaac gagggaccgc gacaggcaga 240
cgctcccatg atcactctgc acgccgaagg caaatagtgc aggccgtgcg gcgcttggcg 300

-continued

```
ttccttggaa gggctgaatc cccgcctcgt ccttcgcagc ggccccccgg gtgttcccat    360

cgccgcttct aggcccactg cgacgcttgc ctgcacttct tacacgctct gggtcccagc    420

cg                                                                   422


<210> SEQ ID NO 223
<211> LENGTH: 21
<212> TYPE: PRT
<213> ORGANISM: Artificial Sequence
<220> FEATURE:
<223> OTHER INFORMATION: Artifically generated sequence

<400> SEQUENCE: 223

Gly Ser Gly Glu Gly Arg Gly Ser Leu Leu Thr Cys Gly Asp Val Glu
1               5                   10                  15

Glu Asn Pro Gly Pro
            20


<210> SEQ ID NO 224
<211> LENGTH: 22
<212> TYPE: PRT
<213> ORGANISM: Artificial Sequence
<220> FEATURE:
<223> OTHER INFORMATION: Artifically generated sequence

<400> SEQUENCE: 224

Gly Ser Gly Ala Thr Asn Phe Ser Leu Leu Lys Gln Ala Gly Asp Val
1               5                   10                  15

Glu Glu Asn Pro Gly Pro
            20


<210> SEQ ID NO 225
<211> LENGTH: 23
<212> TYPE: PRT
<213> ORGANISM: Artificial Sequence
<220> FEATURE:
<223> OTHER INFORMATION: Artifically generated sequence

<400> SEQUENCE: 225

Gly Ser Gly Gln Cys Thr Asn Tyr Ala Leu Leu Lys Leu Ala Gly Asp
1               5                   10                  15

Val Glu Ser Asn Pro Gly Pro
            20


<210> SEQ ID NO 226
<211> LENGTH: 25
<212> TYPE: PRT
<213> ORGANISM: Artificial Sequence
<220> FEATURE:
<223> OTHER INFORMATION: Artifically generated sequence

<400> SEQUENCE: 226

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25
```